US012502386B2

(12) United States Patent
Shi et al.

(10) Patent No.: US 12,502,386 B2
(45) **Date of Patent: *Dec. 23, 2025**

(54) NITROGEN-CONTAINING HETEROCYCLIC COMPOUND AND USE THEREOF

(71) Applicant: SHANGHAI SHIJIANG BIOTECHNOLOGY CO., LTD, Shanghai (CN)

(72) Inventors: Yufeng Shi, Nanjing (CN); Wenjiang Ma, Nanjing (CN); Gang Pei, Nanjing (CN); Peng Xia, Nanjing (CN); Yingcai Wang, Nanjing (CN)

(73) Assignee: Shanghai Shijiang Biotechnology Co., Ltd., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/847,298

(22) PCT Filed: Mar. 16, 2023

(86) PCT No.: PCT/CN2023/081983
§ 371 (c)(1),
(2) Date: Sep. 16, 2024

(87) PCT Pub. No.: WO2023/174381
PCT Pub. Date: Sep. 21, 2023

(65) Prior Publication Data

US 2025/0197415 A1 Jun. 19, 2025

(30) Foreign Application Priority Data

| | | |
|---|---|---|
| Mar. 16, 2022 | (CN) | 202210256272.2 |
| Mar. 16, 2022 | (CN) | 202210256355.1 |
| May 5, 2022 | (CN) | 202210481050.0 |
| May 5, 2022 | (CN) | 202210482528.1 |
| May 5, 2022 | (CN) | 202210482536.6 |
| Dec. 12, 2022 | (CN) | 202211590192.7 |

(51) Int. Cl.

| | |
|---|---|
| ***A61K 31/4745*** | (2006.01) |
| ***A61K 31/4741*** | (2006.01) |
| ***A61K 31/496*** | (2006.01) |
| ***A61K 31/55*** | (2006.01) |
| ***A61P 35/00*** | (2006.01) |
| ***C07B 59/00*** | (2006.01) |
| ***C07D 455/03*** | (2006.01) |
| ***C07D 491/147*** | (2006.01) |
| ***C07D 491/22*** | (2006.01) |

(52) U.S. Cl.
CPC ...... *A61K 31/4745* (2013.01); *A61K 31/4741* (2013.01); *A61K 31/496* (2013.01); *A61K 31/55* (2013.01); *A61P 35/00* (2018.01); *C07B 59/002* (2013.01); *C07D 455/03* (2013.01); *C07D 491/147* (2013.01); *C07D 491/22* (2013.01)

(58) Field of Classification Search
CPC ... C07D 491/147; C07D 491/22; A61P 35/00; A61K 31/4741; A61K 31/496; A61K 31/55
See application file for complete search history.

(56) References Cited

U.S. PATENT DOCUMENTS

| | | | |
|---|---|---|---|
| 6,239,139 B1 * | 5/2001 | Kim | C07D 471/04 546/71 |
| 6,255,317 B1 * | 7/2001 | Kim | C07D 471/04 514/282 |
| 2010/0120810 A1 | 5/2010 | Leblond | |

FOREIGN PATENT DOCUMENTS

| | | |
|---|---|---|
| CN | 102421774 A | 4/2012 |
| CN | 104211697 | 12/2014 |

(Continued)

OTHER PUBLICATIONS

Registry. "RN 1912438-08-4 etc." *STN Columbus*, May 17, 2016 (May 17, 2016), pp. 1-2.

(Continued)

*Primary Examiner* — Joseph K Mckane
*Assistant Examiner* — Quincy Mckoy
(74) *Attorney, Agent, or Firm* — Adam Warwick Bell; Matthew Rupert Kaser

(57) ABSTRACT

The present invention relates to a nitrogen-containing heterocyclic compound and the use thereof. Specifically, provided is a compound of formula I or an optical isomer thereof, or a racemate thereof, or a solvate thereof, or a pharmaceutically acceptable salt thereof, or a deuterated compound thereof. The compound has excellent and precise therapeutic effects on tumors with low expression or non-expression of the NNMT gene, high expression of DNA methylase, high expression of UHRF1, a high methylation level of nucleotide sites of the NNMT gene, and/or a high methylation level of DNACpG site in a NNMT gene region.

I

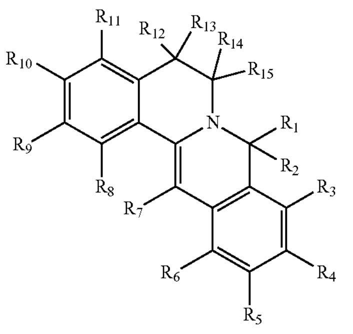

19 Claims, 9 Drawing Sheets

Specification includes a Sequence Listing.

(56) References Cited

FOREIGN PATENT DOCUMENTS

| | | | |
|---|---|---|---|
| CN | 104211697 | A | 12/2014 |
| CN | 104211709 | A | 12/2014 |
| CN | 113599380 | | 11/2021 |
| CN | 113599380 | A | 11/2021 |
| EP | 2789612 | A1 | 10/2014 |
| JP | S5019780 | | 3/1975 |
| JP | S5019780 | A | 3/1975 |
| JP | S5070397 | | 6/1975 |
| JP | S5070397 | A | 6/1975 |
| JP | 2012526077 | | 10/2012 |
| JP | 20144530883 | | 11/2014 |
| JP | 2023544226 | | 10/2023 |
| WO | WO2022063311 | A1 | 3/2011 |
| WO | WO2018068769 | | 4/2018 |
| WO | WO2018068769 | A1 | 4/2018 |
| WO | 2022063311 | A | 3/2022 |

OTHER PUBLICATIONS

钱平等 (Qian, Ping et al.). "左金方的生物碱类成分及其对肿瘤细胞的细胞毒活性 (Alkaloids from Zuojin Formula And Their Cytotoxicities against Proliferation of Cancer Cells)" *中草药* (*Chinese Traditional and Herbal Drugs*), vol. 45, No. 1, Jan. 31, 2014 (Jan. 31, 2014), pp. 8-15.

张岩等 (Zhang, Yan et al.). 用酿酒酵母全基因组DNA芯片研究盐酸小檗碱的药理作用机制 (Study on Pharmacological Action Mechanism of Berberine Chloride by Genome-wide Expression Profiling of *Saccharomyces cerevisiae*)" *中国中西医结合杂志* (Chinese Journal of Integrated Traditional and Western Medicine), vol. 23, No. 1, Dec. 31, 2003 (Dec. 31, 2003), pp. 48-53.

Du, Peifang et al. "Tumor microenvironment and NIR laser dualresponsive release of berberine 9-O-pyrazole alkyl derivative loaded in graphene oxide nanosheets for chemo-photothermal synergetic cancer therapy" *Journal of Materials Chemistry B*, vol. 8, Mar. 19, 2020 (Mar. 19, 2020), pp. 4046-4055.

Qian, Ping, Alkaloids from Zuojin Formula and their cytotoxicities against proliferation of cancer cells Zhongc aoyao 45(1) Aug. 15, 2014.

Zhang, Y. Study on Pharmacological Action Mechanism of Berberine Chloride by Genome-wide Expression. Profiling of Saccharomyces cerevisiae Chinese Journal of Integrated Traditional and Western Medicine 23(1) 48-53, (2011).

Du, Peifanga Tumor Microenvironment and NIR laser dual -responsive release of berberine 9-O-pyrazole alkyl. Derivative loaded in graphene oxide nanosheets for chemo-photothermal synergetic cancer therapy Journal of Materials Chemistry B: Materials for Biology and Medicine 18 (18) 4046-4055, (2020).

Jiang, Xiaofeido Binding interaction of 8-alkyl coptisine derivatives with lysozyme by fluorescence quenching method Hunan Nongye Daxue Xuebao 37(3) 0346-350, (2011) .

Tang, Xiaonan Butyric acid increases the therapeutic effect of ehlj7 on ulcerative colitis by inhibiting JAK2/STAT3/SOCS1 signaling pathway Frontiers in Pharmacology 10 1553, (2020) .

Dai, Bingling Dihydroberberine exhibits synergistic effects with sunitinib on NSCLC NCI-H460 cells by repressing MAP kinase pathways and inflammatory mediators Journal of Cellular and Molecular Medicine 21(10) 02 573-2585, (2017) .

Gu, Chunming Identification of berberine as a novel drug for the treatment of multiple myeloma via targeting UH RF10Bmc Biology 18(1) 033, (2020) .

Huang, Chao Effect of evodiamine and berberine on the interaction between DNMTs and target microRNAs during malignant transformation of the colon by TGF-β1 Oncology Reports, (2017).

DATABASE Registry, May 30, 2012, Anonymous: "4H-Bis[1,3]benzodioxolo[5,6-a.4,5-g]quinolizine, 4-hexyl-6,7- dihydro-(CA Index Name)", XP093091793, retrieved from STNext, Database accession No. 1374744-39-4, see the compound with the Registry No. 1374744-39-4.

Registry. "Rn 1912438-08-40" STN Columbus, May 17, 2016 (May 17, 2016) 1-2 1-2.

* cited by examiner

NITROGEN-CONTAINING HETEROCYCLIC COMPOUND AND USE THEREOF

FIELD OF THE INVENTION

The present invention relates to the field of medicine. Specifically, the present invention relates to nitrogen-containing heterocyclic compound and use thereof.

SEQUENCE LISTING

A sequence listing text (.txt) file is submitted herewith under 37 CFR. 1.821 (c) and is hereby incorporated by reference in its entirely. The details of the file as required under 37 CFR. 1.52(e)(5) and 37 CFR 1.77(b)(5) are as follows: Name of file is 100-P220024FWIsequencelist.xml; date of creation is Sep. 16, 2024; size is 5.28 KB (5,408 bytes). The content of the sequence listing information recorded in computer readable form is identical to the written sequence listing (if any) and identical to the sequence information provided with the original filed application and with the priority application, and contains no new matter. The information recorded in electronic form (if any) submitted (under Rule 13ter, if appropriate) with this application is identical to the sequence listing as contained in the application as filed.

BACKGROUND TECHNOLOGY

Tumor is a common disease that seriously endangers human health, and the mortality rate of malignant tumors is rising. Due to the heterogeneity of tumor, simply using the same treatment method or medication based on source or pathological characteristic of tumors can easily lead to improper treatment, which can delay valuable treatment time and opportunities for patient. Therefore, it is very necessary to take precision treatment according to the different features of tumor. With the development of biological technology, tumors are typed at the molecular level such as gene and protein level, etc, and more and more changes in tumor-related gene and the expression and activity of protein have been discovered, changes in tumor-related gene and the expression and activity of protein play an important role in the development of malignant tumors, the discovery and application of biomarkers can provide precise guidance for the application of related drug and make precision treatment of tumor possible, thereby achieving targeted administration of drug, significantly improving treatment effect, reducing the dose of drug and reducing toxic side effects.

Therefore, there is an urgent need in the art to develop a drug that can achieve precision treatment on tumor.

SUMMARY OF THE INVENTION

It is an object of the present invention to provide a compound, the compound has excellent precision treatment effect on tumor with low or no expression of NNMT gene, high expression of DNA methylase, high expression of UHRF1, high methylation level of nucleotide site of NNMT gene, and/or high methylation level of DNA CpG site of NNMT gene.

In the first aspect of the present invention, it provides a compound of formula I, or an optical isomer thereof, or a racemate thereof, or a solvate thereof, or a pharmaceutically acceptable salt thereof, or a deuterated compound thereof;

I

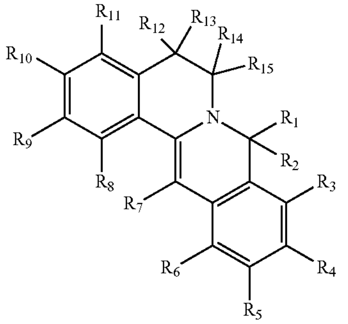

wherein, $R_1$ and $R_2$ are each independently hydrogen, deuterium, halogen, substituted or unsubstituted C1-C16 alkyl, substituted or unsubstituted C3-C16 cycloalkyl, substituted or unsubstituted 3-12 membered heterocycloalkyl, substituted or unsubstituted C1-C16 haloalkyl, substituted or unsubstituted C3-C16 halocycloalkyl, substituted or unsubstituted C6-C16 aryl, substituted or unsubstituted 5-12 membered heteroaryl;

$R_3$, $R_4$ and $R_5$ are each independently hydrogen, halogen, $R_{17}$—O—, $R_{17}$—S—, $(R_{18}R_{19})$N—; or $R_3$ and $R_4$, or $R_4$ and $R_5$ are connected to form a substituted or unsubstituted 3-12 membered heterocycloalkane ring;

$R_6$, $R_8$, $R_{11}$, $R_{12}$, $R_{13}$, $R_{14}$ and $R_{15}$ are each independently hydrogen, substituted or unsubstituted C1-C8 alkyl, halogen;

$R_7$ is hydrogen, substituted or unsubstituted C1-C12 alkyl, substituted or unsubstituted C1-C12 haloalkyl, substituted or unsubstituted C6-C16 aryl-substituted or unsubstituted C1-C12 alkyl-, substituted or unsubstituted 5-16 membered heteroaryl-substituted or unsubstituted C1-C12 alkyl-;

$R_9$ and $R_{10}$ are connected to form a substituted or unsubstituted 3-12 membered heterocycloalkane ring;

$R_{17}$ is hydrogen, substituted or unsubstituted C1-C16 alkyl,

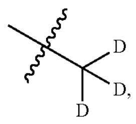

substituted or unsubstituted C3-C16 cycloalkyl, substituted or unsubstituted 3-12 membered heterocycloalkyl, substituted or unsubstituted C3-C16 cycloalkyl-substituted or unsubstituted C2-C10 acyl-, substituted or unsubstituted C3-C16 cycloalkyl-C(O)—, substituted or unsubstituted C1-C16 haloalkyl, substituted or unsubstituted C3-C16 halocycloalkyl, substituted or unsubstituted 3-12 membered heterocycloalkyl-substituted or unsubstituted C1-C12 alkyl-, substituted or unsubstituted C6-C16 aryl-substituted or unsubstituted C1-C12 alkyl-, substituted or unsubstituted C6-C16 aryl-substituted or unsubstituted C6-C16 aryl-substituted or unsubstituted C1-C12 alkyl-, substituted or unsubstituted 5-16 membered heteroaryl-substituted or unsubstituted C1-C12 alkyl-, substituted or unsubstituted C6-C16 aryl-O-substituted or unsubstituted C1-C12 alkyl-, substituted or unsubstituted C6-C16 aryl-S-substituted or unsubstituted C1-C12 alkyl-, substituted or unsubstituted 5-16 membered heteroaryl-O-substituted or unsubstituted C1-C12 alkyl-, substituted or unsubstituted 5-16 membered heteroaryl-S-substituted or unsubstituted C1-C12 alkyl-, substituted or unsubstituted C2-C8 alkenyl-substituted or unsubstituted C1-C8 alkyl-substituted or unsubstituted C2-C8 alkenyl-substituted or unsubstituted C1-C8 alkyl-, substituted or unsubstituted C2-C8 alkenyl-substituted or unsubstituted C1-C8 alkyl-, $(R_{20}R_{21})$N-substituted or unsubstituted C1-C12 alkyl-;

$R_{18}$ and $R_{19}$ are each independently hydrogen, substituted or unsubstituted C1-C12 alkyl, substituted or unsubstituted C3-C12 cycloalkyl, substituted or unsubstituted C6-C16 aryl-substituted or unsubstituted C1-C12 alkyl-; or $R_{18}$ and $R_{19}$ are connected to form a substituted or unsubstituted 3-12 membered heterocycloalkane ring;

$R_{20}$ and $R_{21}$ are each independently hydrogen, substituted or unsubstituted C1-C12 alkyl, substituted or unsubstituted C3-C12 cycloalkyl, substituted or unsubstituted C2-C10 ester group; or $R_{20}$ and $R_{21}$ are connected to form a substituted or unsubstituted 3-12 membered heterocycloalkyl.

In another preferred embodiment, the heterocyclic ring of the heterocycloalkyl, heteroaryl and heterocycloalkane ring has 1-4 (preferably 1, 2, 3 or 4) heteroatoms independently selected from the group consisting of N, O and S.

In another preferred embodiment, the heterocyclic ring of the heterocycloalkyl has 1-4 (preferably 1, 2, 3 or 4) heteroatoms independently selected from the group consisting of N, O and S.

In another preferred embodiment, the heterocyclic ring of the heteroaryl has 1-4 (preferably 1, 2, 3 or 4) heteroatoms independently selected from the group consisting of N, O and S.

In another preferred embodiment, the heterocyclic ring of the heterocycloalkane ring has 1-4 (preferably 1, 2, 3 or 4) heteroatoms independently selected from the group consisting of N, O and S.

In another preferred embodiment, the heterocycloalkyl has 0, 1, or 2 C═C ring double bonds.

In another preferred embodiment, the heterocycloalkane ring has 0, 1, or 2 C═C ring double bonds.

In another preferred embodiment, each "substituted" means that one or more (preferably 1, 2, 3, 4, 5, 6, 7, or 8) hydrogen atoms on the ring or group are independently substituted by substituent selected from the group consisting of C1-C10 alkyl, C2-C6 alkenyl, C3-C12 cycloalkyl, C1-C10 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, carbonyl (═O), hydroxyl, sulfhydryl, amino, C1-C4 carboxyl, C2-C8 ester group, C2-C4 amide group, C2-C6 acyl, C1-C10 alkoxyl, C1-C10 alkylthio, C1-C10 haloalkoxyl, C1-C10 haloalkylthio, C6-C12 aryl, C6-C12 aryl-O—, 5-10 membered heteroaryl, 5-10 membered heteroaryl-O—, 5-10 membered heterocycloalkyl, $(R_{20}R_{21})$N—.

In another preferred embodiment, each "substituted" means that one or more (preferably 1, 2, 3, 4, 5, 6, 7, or 8) hydrogen atoms on the ring or group are independently substituted by substituent selected from the group consisting of C1-C8 alkyl, C2-C6 alkenyl, C3-C12 cycloalkyl, C1-C8 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, carbonyl (═O), hydroxyl, sulfhydryl, amino, C1-C4 carboxyl, C2-C8 ester group, C2-C4 amide group, C2-C4 acyl, C1-C8 alkoxyl, C1-C8 alkylthio, C1-C8 haloalkoxyl, C1-C8 haloalkylthio, C6-C12 aryl, C6-C12 aryl-O—, 5-10 membered heteroaryl, 5-10 membered heteroaryl-O—, 5-10 membered heterocycloalkyl, $(R_{20}R_{21})$N—.

In another preferred embodiment, each "substituted" means that one or more (preferably 1, 2, 3, 4, 5, 6, 7, or 8) hydrogen atoms on the ring or group are independently substituted by substituent selected from the group consisting of C1-C6 alkyl, C2-C4 alkenyl, C3-C10 cycloalkyl, C1-C6 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, carbonyl (═O), hydroxyl, sulfhydryl, amino, C1-C4 carboxyl, C2-C6 ester group, C2-C4 amide group, C2-C4 acyl, C1-C6 alkoxyl, C1-C6 alkylthio, C1-C6 haloalkoxyl, C1-C6 haloalkylthio, C6-C12 aryl, C6-C12 aryl-O—, 5-10 membered heteroaryl, 5-10 membered heteroaryl-O—, 5-10 membered heterocycloalkyl, $(R_{20}R_{21})$N—.

In another preferred embodiment, each "substituted" means that one or more (preferably 1, 2, 3, 4, 5, 6, 7, or 8) hydrogen atoms on the ring or group are independently substituted by substituent selected from the group consisting of C1-C4 alkyl, C2-C4 alkenyl, C3-C10 cycloalkyl, C1-C4 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, carbonyl (═O), hydroxyl, sulfhydryl, amino, C1-C4 carboxyl, C2-C4 ester group, C2-C4 amide group, C2-C4 acyl, C1-C4 alkoxyl, C1-C4 alkylthio, C1-C4 haloalkoxyl, C1-C4 haloalkylthio, C6-C12 aryl, C6-C12 aryl-O—, 5-10 membered heteroaryl, 5-10 membered heteroaryl-O—, 5-10 membered heterocycloalkyl, $(R_{20}R_{21})$N—.

In another preferred embodiment, each "substituted" means that one or more (preferably 1, 2, 3, 4, 5, 6, 7 or 8) hydrogen atoms on the ring or group are each independently substituted by a substituent.

In another preferred embodiment, $R_1$ and $R_2$ are each independently hydrogen, deuterium, halogen, substituted or unsubstituted C1-C12 alkyl, substituted or unsubstituted C3-C12 cycloalkyl, substituted or unsubstituted 3-12 membered heterocycloalkyl, substituted or unsubstituted C1-C12 haloalkyl, substituted or unsubstituted C3-C12 halocycloalkyl, substituted or unsubstituted C6-C12 aryl, substituted or unsubstituted 5-12 membered heteroaryl.

In another preferred embodiment, $R_1$ and $R_2$ are each independently hydrogen, deuterium, halogen, substituted or unsubstituted C1-C10 alkyl, substituted or unsubstituted C3-C10 cycloalkyl, substituted or unsubstituted 3-10 membered heterocycloalkyl, substituted or unsubstituted C1-C10 haloalkyl, substituted or unsubstituted C3-C10 halocycloalkyl, substituted or unsubstituted C6-C10 aryl, substituted or unsubstituted 5-10 membered heteroaryl.

In another preferred embodiment, $R_1$ and $R_2$ are each independently hydrogen, deuterium, halogen, substituted or unsubstituted C1-C10 alkyl, substituted or unsubstituted C3-C8 cycloalkyl, substituted or unsubstituted 3-10 membered heterocycloalkyl, substituted or unsubstituted C1-C6 haloalkyl, substituted or unsubstituted C3-C10 halocycloalkyl, substituted or unsubstituted C6-C10 aryl, substituted or unsubstituted 5-8 membered heteroaryl.

In another preferred embodiment, $R_1$ and $R_2$ are each independently hydrogen, deuterium, halogen, substituted or unsubstituted C1-C10 alkyl, substituted or unsubstituted C3-C8 cycloalkyl, substituted or unsubstituted 3-10 membered heterocycloalkyl, substituted or unsubstituted C1-C4 haloalkyl, substituted or unsubstituted C3-C10 halocycloalkyl, substituted or unsubstituted C6-C10 aryl, substituted or unsubstituted 5-8 membered heteroaryl.

In another preferred embodiment, $R_1$ and $R_2$ are each independently hydrogen, deuterium, halogen, substituted or unsubstituted C1-C8 alkyl, substituted or unsubstituted C3-C8 cycloalkyl, substituted or unsubstituted 3-8 membered heterocycloalkyl, substituted or unsubstituted C1-C8 haloalkyl, substituted or unsubstituted C3-C8 halocycloalkyl, substituted or unsubstituted C6-C8 aryl, substituted or unsubstituted 5-8 membered heteroaryl.

In another preferred embodiment, $R_1$ and $R_2$ are each independently hydrogen, deuterium, halogen, substituted or unsubstituted C1-C6 alkyl, substituted or unsubstituted C3-C8 cycloalkyl, substituted or unsubstituted 3-8 membered heterocycloalkyl, substituted or unsubstituted C1-C6 haloalkyl, substituted or unsubstituted C3-C8 halocycloalkyl, substituted or unsubstituted C6-C8 aryl, substituted or unsubstituted 5-8 membered heteroaryl.

In another preferred embodiment, $R_1$ and $R_2$ are each independently hydrogen, deuterium, halogen, substituted or unsubstituted C1-C6 alkyl, substituted or unsubstituted C3-C8 cycloalkyl, substituted or unsubstituted 3-8 membered heterocycloalkyl, substituted or unsubstituted C1-C4 haloalkyl, substituted or unsubstituted C3-C8 halocycloalkyl, substituted or unsubstituted C6-C8 aryl, substituted or unsubstituted 5-8 membered heteroaryl.

In another preferred embodiment, $R_1$ and $R_2$ are each independently hydrogen, deuterium, halogen, substituted or unsubstituted C1-C6 alkyl, substituted or unsubstituted C3-C8 cycloalkyl, substituted or unsubstituted 3-8 membered heterocycloalkyl, substituted or unsubstituted C1-C2 haloalkyl, substituted or unsubstituted C3-C8 halocycloalkyl, substituted or unsubstituted C6-C8 aryl, substituted or unsubstituted 5-8 membered heteroaryl.

In another preferred embodiment, $R_1$ and $R_2$ are each independently hydrogen, deuterium, halogen, substituted or unsubstituted methyl, substituted or unsubstituted ethyl, substituted or unsubstituted propyl, substituted or unsubstituted butyl, substituted or unsubstituted pentyl, substituted or unsubstituted hexyl, substituted or unsubstituted heptyl, substituted or unsubstituted octyl, substituted or unsubstituted cyclopropyl, substituted or unsubstituted cyclobutyl, substituted or unsubstituted cyclopentyl, substituted or unsubstituted cyclohexyl, substituted or unsubstituted cycloheptyl, substituted or unsubstituted cyclooctyl, substituted or unsubstituted halomethyl, substituted or unsubstituted haloethyl, substituted or unsubstituted halopropyl, substituted or unsubstituted halobutyl substituted or unsubstituted halopentyl, substituted or unsubstituted halohexyl, substituted or unsubstituted phenyl, acetyl-methyl-, substituted or unsubstituted pyridinyl, substituted or unsubstituted pyrrolyl, cyclohexanone group.

In another preferred embodiment, $R_1$ and $R_2$ are each independently hydrogen, deuterium, halogen, methyl, ethyl, propyl, butyl, pentyl, hexyl, heptyl, octyl, cyclopropyl, cyclobutyl, cyclopentyl, cyclohexyl, cycloheptyl, cyclooctyl, halomethyl, haloethyl, halopropyl, halobutyl halopentyl, halohexyl, phenyl, acetyl-methyl-, pyridinyl, pyrrolyl, cyclohexanone group.

In another preferred embodiment, the pyridinyl is

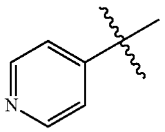 [SMILES: *c1ccncc1]

In another preferred embodiment, the acetyl-methyl- is

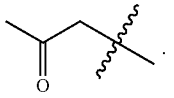 [SMILES: *CC(C)=O]

In another preferred embodiment, the pyrrolyl is

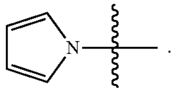 [SMILES: *n1cccc1]

In another preferred embodiment, the cyclohexanone group is

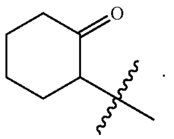 [SMILES: *C1CCCCC1=O]

In another preferred embodiment, $R_1$ and $R_2$ are hydrogen or deuterium.

In another preferred embodiment, at least one of $R_1$ and $R_2$ is not hydrogen or deuterium.

In another preferred embodiment, $R_1$ is hydrogen or deuterium, and $R_2$ is not hydrogen or deuterium.

In another preferred embodiment, $R_1$ is not hydrogen or deuterium, and $R_2$ is hydrogen or deuterium.

In another preferred embodiment, both $R_1$ and $R_2$ are not hydrogen or deuterium.

In another preferred embodiment, $R_1$ is not hydrogen or deuterium.

In another preferred embodiment, $R_2$ is not hydrogen or deuterium.

In another preferred embodiment, $R_1$ and $R_2$ are the same or different functional groups.

In another preferred embodiment, the halogen is fluorine, chlorine, bromine or iodine.

In another preferred embodiment, the halo is mono-halo, di-halo, tri-halo or full-halo.

In another preferred embodiment, halo is fluoro, chloro, bromo, iodo.

In another preferred embodiment, the halomethyl is trichloromethyl.

In another preferred embodiment, the deuterated is mono-deuterated, di-deuterated, tri-deuterated or fully-deuterated.

In another preferred embodiment, $R_1$ and $R_2$ are each independently hydrogen, deuterium, trichloromethyl, methyl, cyclobutyl, cyclopentyl, butyl, hexyl, phenyl.

In another preferred embodiment, the propyl is n-propyl.

In another preferred embodiment, the propyl is

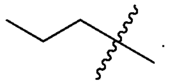 [SMILES: *CCC]

In another preferred embodiment, the butyl is n-butyl.

In another preferred embodiment, the butyl is

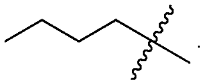 [SMILES: *CCCC]

In another preferred embodiment, the pentyl is n-pentyl.

In another preferred embodiment, the pentyl is

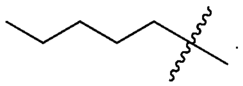 [SMILES: *CCCCC]

In another preferred embodiment, the hexyl is n-hexyl.

In another preferred embodiment, the hexyl is

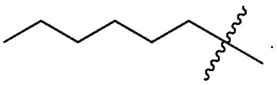 [SMILES: *CCCCCC]

In another preferred embodiment, the cyclobutyl is

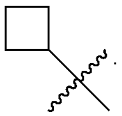 [SMILES: *C1CCC1]

In another preferred embodiment, the cyclohexyl is

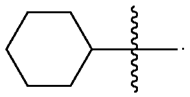 [SMILES: *C1CCCCC1]

In another preferred embodiment, $R_3$, $R_4$ and $R_5$ are each independently hydrogen, halogen, $R_{17}$—O—, $R_{17}$—S—, $(R_{18}R_{19})$N—; or $R_3$ and $R_4$, or $R_4$ and $R_5$ are connected to form a substituted or unsubstituted 3-10 membered heterocycloalkane ring.

In another preferred embodiment, $R_3$, $R_4$ and $R_5$ are each independently hydrogen, halogen, $R_{17}$—O—, $R_{17}$—S—, $(R_{18}R_{19})$N—; or $R_3$ and $R_4$, or $R_4$ and $R_5$ are connected to form a substituted or unsubstituted 3-8 membered heterocycloalkane ring.

In another preferred embodiment, $R_3$, $R_4$ and $R_5$ are each independently hydrogen, halogen, $R_{17}$—O—, $R_{17}$—S—, $(R_{18}R_{19})$N—; or $R_3$ and $R_4$, or $R_4$ and $R_5$ are connected to form a substituted or unsubstituted 3 membered heterocycloalkane ring, substituted or unsubstituted 4 membered heterocycloalkane ring, substituted or unsubstituted 5 membered heterocycloalkane ring, substituted or unsubstituted 6 membered heterocycloalkane ring, substituted or unsubstituted 7 membered heterocycloalkane ring, substituted or unsubstituted 8 membered heterocycloalkane ring, substituted or unsubstituted 9 membered heterocycloalkane ring, substituted or unsubstituted 10 membered heterocycloalkane ring.

In another preferred embodiment, $R_3$, $R_4$ and $R_5$ are each independently hydrogen, halogen (e.g, Cl, Br), $R_{17}$—O—, $R_{17}$—S—, $(R_{18}R_{19})$N—; or $R_3$ and $R_4$, or $R_4$ and $R_5$ are connected to form a substituted or unsubstituted 5 membered heterocycloalkane ring.

In another preferred embodiment, $R_3$, $R_4$ and $R_5$ are each independently hydrogen, halogen (e.g, Cl, Br), $R_{17}$—O—, $R_{17}$—S—, $(R_{18}R_{19})$N—; or $R_3$ and $R_4$, or $R_4$ and $R_5$ are connected to form a substituted or unsubstituted dioxolene ring.

In another preferred embodiment, $R_3$, $R_4$ and $R_5$ are each independently hydrogen, halogen (e.g, Cl, Br), $R_{17}$—O—, $R_{17}$—S—, $(R_{18}R_{19})$N—; or $R_3$ and $R_4$, or $R_4$ and $R_5$ are connected to form

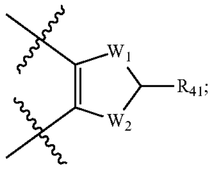

$W_1$ and $W_2$ are each independently O or S;

$R_{41}$ is hydrogen, substituted or unsubstituted C1-C8 alkyl.

In another preferred embodiment, $W_1$ is O or S.

In another preferred embodiment, $W_2$ is O or S.

In another preferred embodiment, $R_3$ is hydrogen.

In another preferred embodiment, $R_5$ is hydrogen.

In another preferred embodiment, $R_3$ and $R_4$ are connected to form

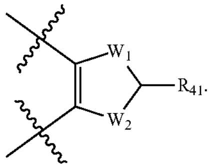

In another preferred embodiment, $R_4$ and $R_5$ are connected to form

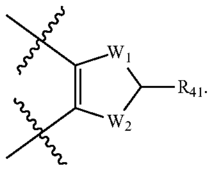

In another preferred embodiment, $R_6$, $R_8$, $R_{11}$, $R_{12}$, $R_{13}$, $R_{14}$ and $R_{15}$ are each independently hydrogen, substituted or unsubstituted C1-C8 alkyl, halogen (e.g, Br).

In another preferred embodiment, $R_6$, $R_8$, $R_{11}$, $R_{12}$, $R_{13}$, $R_{14}$ and $R_{15}$ are each independently hydrogen, substituted or unsubstituted C1-C6 alkyl, halogen (e.g, Br).

In another preferred embodiment, $R_6$, $R_8$, $R_{11}$, $R_{12}$, $R_{13}$, $R_{14}$ and $R_{15}$ are each independently hydrogen, substituted or unsubstituted C1-C4 alkyl, halogen (e.g, Br).

In another preferred embodiment, $R_6$, $R_8$, $R_{11}$, $R_{12}$, $R_{13}$, $R_{14}$ and $R_{15}$ are each independently hydrogen, halogen (e.g, Br).

In another preferred embodiment, $R_7$ is hydrogen, substituted or unsubstituted C1-C10 alkyl, substituted or unsubstituted C1-C10 haloalkyl, substituted or unsubstituted C6-C16 aryl-substituted or unsubstituted C1-C12 alkyl-, substituted or unsubstituted 5-16 membered heteroaryl-substituted or unsubstituted C1-C12 alkyl-.

In another preferred embodiment, $R_7$ is hydrogen, substituted or unsubstituted C1-C8 alkyl, substituted or unsubstituted C1-C8 haloalkyl, substituted or unsubstituted C6-C16 aryl-substituted or unsubstituted C1-C12 alkyl-, substituted or unsubstituted 5-16 membered heteroaryl-substituted or unsubstituted C1-C12 alkyl-.

In another preferred embodiment, $R_7$ is hydrogen, substituted or unsubstituted C1-C10 alkyl, substituted or unsubstituted C1-C10 haloalkyl, substituted or unsubstituted C6-C12 aryl-substituted or unsubstituted C1-C10 alkyl-, substituted or unsubstituted 5-12 membered heteroaryl-substituted or unsubstituted C1-C10 alkyl-.

In another preferred embodiment, $R_7$ is hydrogen, substituted or unsubstituted C1-C10 alkyl, substituted or unsubstituted C1-C10 haloalkyl, substituted or unsubstituted C6-C10 aryl-substituted or unsubstituted C1-C8 alkyl-, substituted or unsubstituted 5-10 membered heteroaryl-substituted or unsubstituted C1-C10 alkyl-.

In another preferred embodiment, $R_7$ is hydrogen, substituted or unsubstituted C1-C8 alkyl, substituted or unsubstituted C1-C8 haloalkyl, substituted or unsubstituted C6-C12 aryl-substituted or unsubstituted C1-C10 alkyl-, substituted or unsubstituted 5-12 membered heteroaryl-substituted or unsubstituted C1-C12 alkyl-.

In another preferred embodiment, $R_7$ is hydrogen, substituted or unsubstituted C1-C8 alkyl, substituted or unsubstituted C1-C8 haloalkyl, substituted or unsubstituted C6-C12 aryl-substituted or unsubstituted C1-C10 alkyl-, substituted or unsubstituted 5-12 membered heteroaryl-substituted or unsubstituted C1-C10 alkyl-.

In another preferred embodiment, $R_7$ is hydrogen, substituted or unsubstituted C1-C8 alkyl, substituted or unsubstituted C1-C8 haloalkyl, substituted or unsubstituted C6-C12 aryl-substituted or unsubstituted C1-C8 alkyl-, substituted or unsubstituted 5-12 membered heteroaryl-substituted or unsubstituted C1-C8 alkyl-.

In another preferred embodiment, $R_7$ is hydrogen, substituted or unsubstituted C1-C6 alkyl, substituted or unsubstituted C1-C8 haloalkyl, substituted or unsubstituted C6-C12 aryl-substituted or unsubstituted C1-C6 alkyl-, substituted or unsubstituted 5-10 membered heteroaryl-substituted or unsubstituted C1-C6 alkyl-.

In another preferred embodiment, $R_7$ is hydrogen, substituted or unsubstituted C1-C6 alkyl, substituted or unsubstituted C1-C8 haloalkyl, substituted or unsubstituted C6-C8 aryl-substituted or unsubstituted C1-C5 alkyl-, substituted or unsubstituted 5-8 membered heteroaryl-substituted or unsubstituted C1-C5 alkyl-.

In another preferred embodiment, $R_7$ is hydrogen, substituted or unsubstituted C1-C8 alkyl, substituted or unsubstituted C1-C8 haloalkyl, substituted or unsubstituted 5-8 membered heteroaryl-substituted or unsubstituted C1-C4 alkyl-,

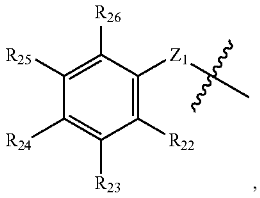

,

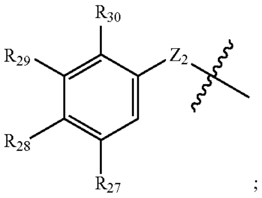

;

$Z_1$ and $Z_2$ are each independently substituted or unsubstituted C1-C8 alkylidene;

$R_{22}$, $R_{23}$, $R_{24}$, $R_{25}$, $R_{26}$, $R_{27}$, $R_{28}$, $R_{29}$ and $R_{30}$ are each independently hydrogen, C1-C8 alkyl, C3-C12 cycloalkyl, C1-C8 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, hydroxyl, sulfhydryl, amino, C1-C4 carboxyl, C2-C6 ester group, C2-C4 amide group, C1-C8 alkoxyl, C1-C8 alkylthio, C1-C8 haloalkoxyl, C1-C8 haloalkylthio, C6-C12 aryl, C6-C12 aryl-O—, 5-10 membered heteroaryl, 5-10 membered heteroaryl-O—, 5-10 membered heterocycloalkyl.

In another preferred embodiment, $R_7$ is hydrogen, substituted or unsubstituted C1-C6 alkyl, substituted or unsubstituted C1-C8 haloalkyl, pyridinyl-methyl-,

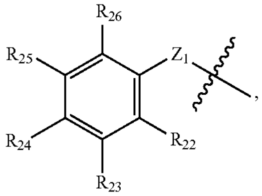

,

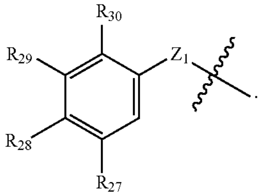

.

In another preferred embodiment, $R_7$ is hydrogen, substituted or unsubstituted methyl, substituted or unsubstituted ethyl, substituted or unsubstituted propyl, substituted or unsubstituted butyl, substituted or unsubstituted pentyl, substituted or unsubstituted hexyl, substituted or unsubstituted heptyl, substituted or unsubstituted octyl, halohexyl, pyridinyl-methyl-,

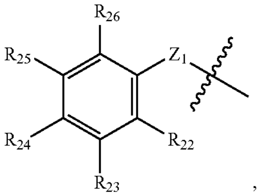

,

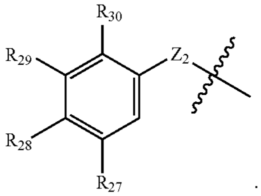

.

In another preferred embodiment, $R_7$ is hydrogen, methyl, ethyl, propyl, butyl, pentyl, hexyl, heptyl, octyl, halohexyl, pyridinyl-methyl-,

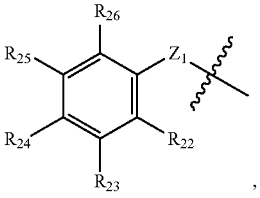

,

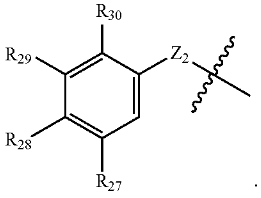

.

In another preferred embodiment, the pentyl is n-pentyl.

In another preferred embodiment, the pentyl is

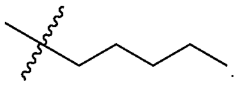 [SMILES: *CCCCC]

.

In another preferred embodiment, the octyl is

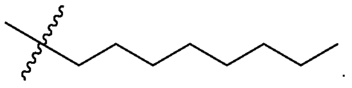 [SMILES: *CCCCCCCC]

In another preferred embodiment, the halohexyl is monohalohexyl.

In another preferred embodiment, the halohexyl is

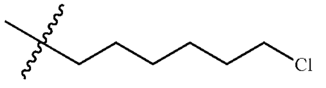

or

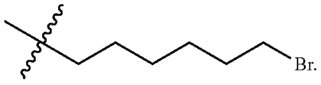

In another preferred embodiment, $R_9$ and $R_{10}$ are connected to form a substituted or unsubstituted 3-10 membered heterocycloalkane ring.

In another preferred embodiment, $R_9$ and $R_{10}$ are connected to form a substituted or unsubstituted 3-8 membered heterocycloalkane ring.

In another preferred embodiment, $R_9$ and $R_{10}$ are connected to form a substituted or unsubstituted 5-8 membered heterocycloalkane ring.

In another preferred embodiment, $R_9$ and $R_{10}$ are connected to form a substituted or unsubstituted 5-7 membered heterocycloalkane ring.

In another preferred embodiment, $R_9$ and $R_{10}$ are connected to form a substituted or unsubstituted 3 membered heterocycloalkane ring, substituted or unsubstituted 4 membered heterocycloalkane ring, substituted or unsubstituted 5 membered heterocycloalkane ring, substituted or unsubstituted 6 membered heterocycloalkane ring, substituted or unsubstituted 7 membered heterocycloalkane ring, substituted or unsubstituted 8 membered heterocycloalkane ring, substituted or unsubstituted 9 membered heterocycloalkane ring, substituted or unsubstituted 10 membered heterocycloalkane ring, substituted or unsubstituted 11 membered heterocycloalkane ring, substituted or unsubstituted 12 membered heterocycloalkane ring.

In another preferred embodiment, $R_9$ and $R_{10}$ are connected to form a substituted or unsubstituted

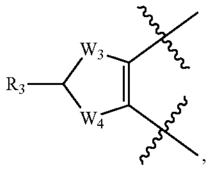

, substituted or unsubstituted

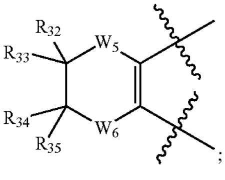

;

$W_3$, $W_4$, $W_5$ and $W_6$ are each independently O or S;

$R_{31}$, $R_{32}$, $R_{33}$, $R_{34}$ and $R_{35}$ are each independently hydrogen, C1-C8 alkyl, C3-C12 cycloalkyl, C1-C8 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, hydroxyl, sulfhydryl, amino, C1-C4 carboxyl, C2-C4 ester group, C2-C4 amide group, C1-C8 alkoxyl, C1-C8 alkylthio, C1-C8 haloalkoxyl, C1-C8 haloalkylthio, C6-C12 aryl, C6-C12 aryl-O—, 5-10 membered heteroaryl, 5-10 membered heteroaryl-O—, 5-10 membered heterocycloalkyl.

In another preferred embodiment, $R_9$ and $R_{10}$ are connected to form

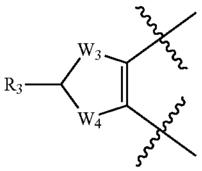

or

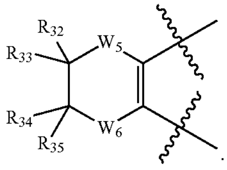

.

In another preferred embodiment, $W_3$ is O or S.

In another preferred embodiment, $W_4$ is O or S.

In another preferred embodiment, $W_5$ is O or S.

In another preferred embodiment, $W_6$ is O or S.

In another preferred embodiment, the propyl-phenyl-methy- is

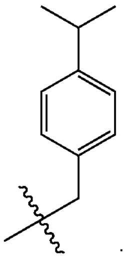 [SMILES: *Cc1ccc(C(C)C)cc1]

.

In another preferred embodiment, $R_{17}$ is hydrogen, substituted or unsubstituted C1-C12 alkyl,

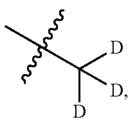

substituted or unsubstituted C3-C14 cycloalkyl, substituted or unsubstituted 3-10 membered heterocycloalkyl, substituted or unsubstituted C3-C14 cycloalkyl-substituted or unsubstituted C2-C8 acyl-, substituted or unsubstituted C3-C14 cycloalkyl-C(O)—, substituted or unsubstituted C1-C12 haloalkyl, substituted or unsubstituted C3-C12 halocycloalkyl, substituted or unsubstituted 3-10 membered heterocycloalkyl-substituted or unsubstituted C1-C10 alkyl-, substituted or unsubstituted C6-C12 aryl-substituted or unsubstituted C1-C10 alkyl-, substituted or unsubstituted C6-C12 aryl-substituted or unsubstituted C6-C12 aryl-substituted or unsubstituted C1-C10 alkyl-, substituted or unsubstituted 5-12 membered heteroaryl-substituted or unsubstituted C1-C10 alkyl-, substituted or unsubstituted C6-C12 aryl-O-substituted or unsubstituted C1-C10 alkyl-, substituted or unsubstituted C6-C12 aryl-S-substituted or unsubstituted C1-C10 alkyl-, substituted or unsubstituted 5-12 membered heteroaryl-O-substituted or unsubstituted C1-C10 alkyl-, substituted or unsubstituted 5-12 membered heteroaryl-S-substituted or unsubstituted C1-C10 alkyl-, substituted or unsubstituted C2-C6 alkenyl-substituted or unsubstituted C1-C6 alkyl-substituted or unsubstituted C2-C6 alkenyl-substituted or unsubstituted C1-C6 alkyl-, substituted or unsubstituted C2-C6 alkenyl-substituted or unsubstituted C1-C6 alkyl-, $(R_{20}R_{21})$N-substituted or unsubstituted C1-C10 alkyl-.

In another preferred embodiment, $R_{17}$ is hydrogen, substituted or unsubstituted C1-C10 alkyl,

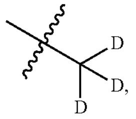

substituted or unsubstituted C3-C12 cycloalkyl, substituted or unsubstituted 3-10 membered heterocycloalkyl, substituted or unsubstituted C3-C12 cycloalkyl-substituted or unsubstituted C2-C6 acyl-, substituted or unsubstituted C3-C12 cycloalkyl-C(O)—, substituted or unsubstituted C1-C10 haloalkyl, substituted or unsubstituted C3-C10 halocycloalkyl, substituted or unsubstituted 3-10 membered heterocycloalkyl-substituted or unsubstituted C1-C8 alkyl-, substituted or unsubstituted C6-C12 aryl-substituted or unsubstituted C1-C8 alkyl-, substituted or unsubstituted C6-C12 aryl-substituted or unsubstituted C6-C12 aryl-substituted or unsubstituted C1-C8 alkyl-, substituted or unsubstituted 5-12 membered heteroaryl-substituted or unsubstituted C1-C8 alkyl-, substituted or unsubstituted C6-C12 aryl-O-substituted or unsubstituted C1-C8 alkyl-, substituted or unsubstituted C6-C12 aryl-S-substituted or unsubstituted C1-C8 alkyl-, substituted or unsubstituted 5-12 membered heteroaryl-O-substituted or unsubstituted C1-C8 alkyl-, substituted or unsubstituted 5-12 membered heteroaryl-S-substituted or unsubstituted C1-C8 alkyl-, substituted or unsubstituted C2-C4 alkenyl-substituted or unsubstituted C1-C4 alkyl-substituted or unsubstituted C2-C4 alkenyl-substituted or unsubstituted C1-C4 alkyl-, substituted or unsubstituted C2-C4 alkenyl-substituted or unsubstituted C1-C4 alkyl-, $(R_{20}R_{21})$N-substituted or unsubstituted C1-C10 alkyl-.

In another preferred embodiment, $R_{17}$ is hydrogen, substituted or unsubstituted C1-C8 alkyl,

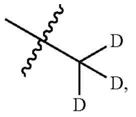

substituted or unsubstituted C3-C10 cycloalkyl, substituted or unsubstituted 3-10 membered heterocycloalkyl, substituted or unsubstituted C3-C12 cycloalkyl-substituted or unsubstituted C2-C4 acyl-, substituted or unsubstituted C3-C12 cycloalkyl-C(O)—, substituted or unsubstituted C1-C8 haloalkyl, substituted or unsubstituted C3-C8 halocycloalkyl, substituted or unsubstituted 3-10 membered heterocycloalkyl-substituted or unsubstituted C1-C6 alkyl-, substituted or unsubstituted C6-C12 aryl-substituted or unsubstituted C1-C6 alkyl-, substituted or unsubstituted C6-C12 aryl-substituted or unsubstituted C6-C12 aryl-substituted or unsubstituted C1-C6 alkyl-, substituted or unsubstituted 5-12 membered heteroaryl-substituted or unsubstituted C1-C6 alkyl-, substituted or unsubstituted C6-C12 aryl-O-substituted or unsubstituted C1-C6 alkyl-, substituted or unsubstituted C6-C12 aryl-S-substituted or unsubstituted C1-C6 alkyl-, substituted or unsubstituted 5-12 membered heteroaryl-O-substituted or unsubstituted C1-C6 alkyl-, substituted or unsubstituted 5-12 membered heteroaryl-S-substituted or unsubstituted C1-C6 alkyl-, substituted or unsubstituted C2-C4 alkenyl-substituted or unsubstituted C1-C4 alkyl-substituted or unsubstituted C2-C4 alkenyl-substituted or unsubstituted C1-C4 alkyl-, substituted or unsubstituted C2-C4 alkenyl-substituted or unsubstituted C1-C4 alkyl-, $(R_{20}R_{21})$N-substituted or unsubstituted C1-C8 alkyl-.

In another preferred embodiment, $R_{17}$ is hydrogen, substituted or unsubstituted C1-C8 alkyl,

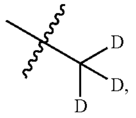

substituted or unsubstituted C3-C10 cycloalkyl, substituted or unsubstituted 3-10 membered heterocycloalkyl, substituted or unsubstituted C3-C12 cycloalkyl-substituted or unsubstituted C2-C4 acyl-, substituted or unsubstituted C3-C12 cycloalkyl-C(O)—, substituted or unsubstituted C1-C8 haloalkyl, substituted or unsubstituted C3-C8 halocycloalkyl, substituted or unsubstituted 3-10 membered heterocycloalkyl-substituted or unsubstituted C1-C6 alkyl-, substituted or unsubstituted C6-C10 aryl-substituted or unsubstituted C1-C4 alkyl-, substituted or unsubstituted C6-C10 aryl-substituted or unsubstituted C6-C10 aryl-substituted or unsubstituted C1-C4 alkyl-, substituted or unsubstituted 5-10 membered heteroaryl-substituted or unsubstituted C1-C4 alkyl-, substituted or unsubstituted C6-C10 aryl-O-substituted or unsubstituted C1-C4 alkyl-, substituted or unsubstituted C6-C10 aryl-S-substituted or unsubstituted C1-C4 alkyl-, substituted or unsubstituted 5-10 membered heteroaryl-O-substituted or unsubstituted C1-C4 alkyl-, substituted or unsubstituted 5-12 membered heteroaryl-S-substituted or unsubstituted C1-C4 alkyl-, substituted or unsubstituted C2-C4 alkenyl-substituted or unsubstituted C1-C4 alkyl-substituted or unsubstituted C2-C4 alkenyl-substituted or unsubstituted C1-C4 alkyl-, substituted or unsubstituted C2-C4 alkenyl-substituted or unsubstituted C1-C4 alkyl-, $(R_{20}R_{21})$N-substituted or unsubstituted C1-C8 alkyl-.

In another preferred embodiment, $R_{17}$ is hydrogen, substituted or unsubstituted C1-C6 alkyl,

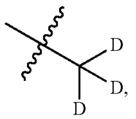

substituted or unsubstituted C3-C10 cycloalkyl, substituted or unsubstituted 3-10 membered heterocycloalkyl, substituted or unsubstituted C5-C12 cycloalkyl-substituted or unsubstituted C2-C4 acyl-, substituted or unsubstituted C5-C12 cycloalkyl-C(O)—, substituted or unsubstituted C1-C8 haloalkyl, substituted or unsubstituted C3-C8 halocycloalkyl, substituted or unsubstituted 3-10 membered heterocycloalkyl-substituted or unsubstituted C1-C6 alkyl-, substituted or unsubstituted C6-C10 aryl-substituted or unsubstituted C1-C4 alkyl-, substituted or unsubstituted C6-C10 aryl-substituted or unsubstituted C6-C10 aryl-substituted or unsubstituted C1-C4 alkyl-, substituted or unsubstituted 5-10 membered heteroaryl-substituted or unsubstituted C1-C4 alkyl-, substituted or unsubstituted C6-C10 aryl-O-substituted or unsubstituted C1-C4 alkyl-, substituted or unsubstituted C6-C10 aryl-S-substituted or unsubstituted C1-C4 alkyl-, substituted or unsubstituted 5-10 membered heteroaryl-O-substituted or unsubstituted C1-C4 alkyl-, substituted or unsubstituted 5-10 membered heteroaryl-S-substituted or unsubstituted C1-C4 alkyl-, substituted or unsubstituted C2-C4 alkenyl-substituted or unsubstituted C1-C4 alkyl-substituted or unsubstituted C2-C4 alkenyl-substituted or unsubstituted C1-C4 alkyl-, substituted or unsubstituted C2-C4 alkenyl-substituted or unsubstituted C1-C4 alkyl-, ($R_{20}R_{21}$)N-substituted or unsubstituted C1-C8 alkyl-.

In another preferred embodiment, $R_{17}$ is hydrogen, substituted or unsubstituted C1-C6 alkyl,

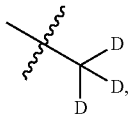

substituted or unsubstituted C3-C10 cycloalkyl, substituted or unsubstituted 3-10 membered heterocycloalkyl, substituted or unsubstituted C6-C12 cycloalkyl-substituted or unsubstituted C2 acyl-, substituted or unsubstituted C6-C12 cycloalkyl-C(O)—, substituted or unsubstituted C1-C6 haloalkyl, substituted or unsubstituted C3-C8 halocycloalkyl, substituted or unsubstituted 3-10 membered heterocycloalkyl-substituted or unsubstituted C1-C4 alkyl-, substituted or unsubstituted C6-C8 aryl-substituted or unsubstituted C1-C4 alkyl-, substituted or unsubstituted C6-C8 aryl-substituted or unsubstituted C6-C8 aryl-substituted or unsubstituted C1-C2 alkyl-, substituted or unsubstituted 5-8 membered heteroaryl-substituted or unsubstituted C1-C2 alkyl-, substituted or unsubstituted C6-C8 aryl-O-substituted or unsubstituted C1-C2 alkyl-, substituted or unsubstituted C6-C8 aryl-S-substituted or unsubstituted C1-C2 alkyl-, substituted or unsubstituted 5-8 membered heteroaryl-O-substituted or unsubstituted C1-C2 alkyl-, substituted or unsubstituted 5-8 membered heteroaryl-S-substituted or unsubstituted C1-C2 alkyl-, substituted or unsubstituted C2-C4 alkenyl-substituted or unsubstituted C1-C4 alkyl-substituted or unsubstituted C2-C4 alkenyl-substituted or unsubstituted C1-C2 alkyl-, substituted or unsubstituted C2-C4 alkenyl-substituted or unsubstituted C1-C2 alkyl-, ($R_{20}R_{21}$)N-substituted or unsubstituted C1-C8 alkyl-.

In another preferred embodiment, $R_{17}$ is hydrogen, substituted or unsubstituted C1-C6 alkyl,

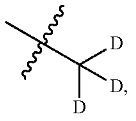

substituted or unsubstituted C6-C12 cycloalkyl-substituted or unsubstituted C2-C4 acyl-, substituted or unsubstituted C6-C12 cycloalkyl-C(O)—, substituted or unsubstituted 3-10 membered heterocycloalkyl, substituted or unsubstituted C1-C6 haloalkyl, substituted or unsubstituted 5-7 membered heterocycloalkyl-substituted or unsubstituted C1-C4 alkyl-, substituted or unsubstituted C6-C10 aryl-substituted or unsubstituted C1-C4 alkyl-, substituted or unsubstituted C6-C10 aryl-substituted or unsubstituted C6-C10 aryl-substituted or unsubstituted C1-C4 alkyl-, substituted or unsubstituted 5-10 membered heteroaryl-substituted or unsubstituted C1-C4 alkyl-, substituted or unsubstituted C6-C10 aryl-O-substituted or unsubstituted C1-C4 alkyl-, substituted or unsubstituted C6-C10 aryl-S-substituted or unsubstituted C1-C4 alkyl-, substituted or unsubstituted 5-10 membered heteroaryl-O-substituted or unsubstituted C1-C4 alkyl-, substituted or unsubstituted 5-10 membered heteroaryl-S-substituted or unsubstituted C1-C4 alkyl-, substituted or unsubstituted C2-C4 alkenyl-substituted or unsubstituted C1-C2 alkyl-substituted or unsubstituted C2-C4 alkenyl-substituted or unsubstituted C1-C2 alkyl-, substituted or unsubstituted C2-C4 alkenyl-substituted or unsubstituted C1-C2 alkyl-, ($R_{20}R_{21}$)N-substituted or unsubstituted C1-C8 alkyl-.

In another preferred embodiment, $R_{17}$ is hydrogen, substituted or unsubstituted C1-C6 alkyl,

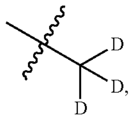

substituted or unsubstituted C8-C10 cycloalkyl-substituted or unsubstituted C2 acyl-, substituted or unsubstituted C8-C10 cycloalkyl-C(O)—, substituted or unsubstituted 5-7 membered heterocycloalkyl, substituted or unsubstituted C1-C6 haloalkyl, substituted or unsubstituted 5-7 membered heterocycloalkyl-substituted or unsubstituted C1-C2 alkyl-, substituted or unsubstituted C6-C8 aryl-O-substituted or unsubstituted C1-C2 alkyl-, substituted or unsubstituted C6-C8 aryl-S-substituted or unsubstituted C1-C2 alkyl-, substituted or unsubstituted C6-C8 aryl-substituted or unsubstituted C1-C4 alkyl-, substituted or unsubstituted C6-C8 aryl-substituted or unsubstituted C6-C8 aryl-substituted or unsubstituted C1-C2 alkyl-, substituted or unsubstituted 5-8 membered heteroaryl-substituted or unsubstituted C1-C4 alkyl-, substituted or unsubstituted 5-8 membered heteroaryl-O-substituted or unsubstituted C1-C2 alkyl-, substituted or unsubstituted 5-8 membered heteroaryl-S-substituted or unsubstituted C1-C2 alkyl-, substituted or unsubstituted C2-C4 alkenyl-substituted or unsubstituted C1-C2 alkyl-substituted or unsubstituted C2-C4 alkenyl-substituted or unsubstituted C1-C2 alkyl-, substituted or unsubstituted C2-C4 alkenyl-substituted or unsubstituted C1-C2 alkyl-, ($R_{20}R_{21}$)N-substituted or unsubstituted C1-C8 alkyl-.

In another preferred embodiment, $R_{17}$ is hydrogen, substituted or unsubstituted C1-C4 alkyl,

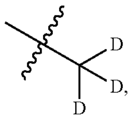

substituted or unsubstituted C3-C10 cycloalkyl, substituted or unsubstituted 3-10 membered heterocycloalkyl, substituted or unsubstituted C6-C12 cycloalkyl-substituted or unsubstituted C2 acyl-, substituted or unsubstituted C6-C12 cycloalkyl-C(O)—, substituted or unsubstituted C1-C6 haloalkyl, substituted or unsubstituted C3-C8 halocycloalkyl, substituted or unsubstituted 3-10 membered heterocycloalkyl-substituted or unsubstituted C1-C4 alkyl-, substituted or unsubstituted C6-C8 aryl-substituted or unsubstituted C1-C2 alkyl-, substituted or unsubstituted C6-C8 aryl-substituted or unsubstituted C6-C8 aryl-substituted or unsubstituted C1-C2 alkyl-, substituted or unsubstituted 5-8 membered heteroaryl-substituted or unsubstituted C1-C2 alkyl-, substituted or unsubstituted C6-C8 aryl-O-substituted or unsubstituted C1-C2 alkyl-, substituted or unsubstituted C6-C8 aryl-S-substituted or unsubstituted C1-C2 alkyl-, substituted or unsubstituted 5-8 membered heteroaryl-O-substituted or unsubstituted C1-C2 alkyl-, substituted or unsubstituted 5-8 membered heteroaryl-S-substituted or unsubstituted C1-C2 alkyl-, substituted or unsubstituted C2-C4 alkenyl-substituted or unsubstituted C1-C4 alkyl-substituted or unsubstituted C2-C4 alkenyl-substituted or unsubstituted C1-C2 alkyl-, substituted or unsubstituted C2-C4 alkenyl-substituted or unsubstituted C1-C2 alkyl-, $(R_{20}R_{21})$N-substituted or unsubstituted C1-C8 alkyl-.

In another preferred embodiment, $R_{17}$ is hydrogen, substituted or unsubstituted C1-C4 alkyl,

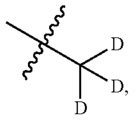

substituted or unsubstituted C6-C12 cycloalkyl-substituted or unsubstituted C2-C4 acyl-, substituted or unsubstituted C6-C12 cycloalkyl-C(O)—, substituted or unsubstituted 3-10 membered heterocycloalkyl, substituted or unsubstituted C1-C6 haloalkyl, substituted or unsubstituted 5-7 membered heterocycloalkyl-substituted or unsubstituted C1-C4 alkyl-, substituted or unsubstituted C6-C10 aryl-substituted or unsubstituted C1-C4 alkyl-, substituted or unsubstituted C6-C10 aryl-substituted or unsubstituted C6-C10 aryl-substituted or unsubstituted C1-C4 alkyl-, substituted or unsubstituted 5-10 membered heteroaryl-substituted or unsubstituted C1-C4 alkyl-, substituted or unsubstituted C6-C10 aryl-O-substituted or unsubstituted C1-C4 alkyl-, substituted or unsubstituted C6-C10 aryl-S-substituted or unsubstituted C1-C4 alkyl-, substituted or unsubstituted 5-10 membered heteroaryl-O-substituted or unsubstituted C1-C4 alkyl-, substituted or unsubstituted 5-10 membered heteroaryl-S-substituted or unsubstituted C1-C4 alkyl-, substituted or unsubstituted C2-C4 alkenyl-substituted or unsubstituted C1-C2 alkyl-substituted or unsubstituted C2-C4 alkenyl-substituted or unsubstituted C1-C2 alkyl-, substituted or unsubstituted C2-C4 alkenyl-substituted or unsubstituted C1-C2 alkyl-, $(R_{20}R_{21})$N-substituted or unsubstituted C1-C8 alkyl-.

In another preferred embodiment, $R_{17}$ is hydrogen, substituted or unsubstituted C1-C2 alkyl,

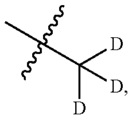

substituted or unsubstituted C8-C10 cycloalkyl-substituted or unsubstituted C2 acyl-, substituted or unsubstituted C8-C10 cycloalkyl-C(O)—, substituted or unsubstituted 5-7 membered heterocycloalkyl, substituted or unsubstituted C3-C6 haloalkyl, substituted or unsubstituted 5-7 membered heterocycloalkyl-substituted or unsubstituted C1-C2 alkyl-, substituted or unsubstituted C6-C8 aryl-O-substituted or unsubstituted C1-C2 alkyl-, substituted or unsubstituted C6-C8 aryl-S-substituted or unsubstituted C1-C2 alkyl-, substituted or unsubstituted C6-C8 aryl-substituted or unsubstituted C1-C2 alkyl-, substituted or unsubstituted C6-C8 aryl-substituted or unsubstituted C6-C8 aryl-substituted or unsubstituted C1-C2 alkyl-, substituted or unsubstituted 5-8 membered heteroaryl-substituted or unsubstituted C1-C4 alkyl-, substituted or unsubstituted 5-8 membered heteroaryl-O-substituted or unsubstituted C1-C2 alkyl-, substituted or unsubstituted 5-8 membered heteroaryl-S-substituted or unsubstituted C1-C2 alkyl-, substituted or unsubstituted C2-C4 alkenyl-substituted or unsubstituted C1-C2 alkyl-substituted or unsubstituted C2-C4 alkenyl-substituted or unsubstituted C1-C2 alkyl-, substituted or unsubstituted C2-C4 alkenyl-substituted or unsubstituted C1-C2 alkyl-, $(R_{20}R_{21})$N-substituted or unsubstituted C1-C8 alkyl-.

In another preferred embodiment, $R_{17}$ is hydrogen, substituted or unsubstituted methyl,

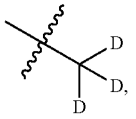

substituted or unsubstituted ethyl, substituted or unsubstituted propyl, substituted or unsubstituted pentyl, substituted or unsubstituted hexyl, substituted or unsubstituted phenyl-O-substituted or unsubstituted butyl-, haloethyl, halopropyl, halobutyl, halohexyl, substituted or unsubstituted phenyl-substituted or unsubstituted ethyl-, substituted or unsubstituted phenyl-substituted or unsubstituted propyl-, substituted or unsubstituted phenyl-substituted or unsubstituted butyl-, substituted or unsubstituted cyclodecyl-substituted or unsubstituted acetyl-, substituted or unsubstituted butenyl-substituted or unsubstituted ethyl-substituted or unsubstituted propenyl-substituted or unsubstituted methyl-, $(R_{20}R_{21})$N-substituted or unsubstituted hexyl-, $(R_{20}R_{21})$N-substituted or unsubstituted butyl-, $(R_{20}R_{21})$N-substituted or unsubstituted ethyl-, substituted or unsubstituted piperidinyl-substituted or unsubstituted ethyl-, substituted or unsubstituted butyl-substituted or unsubstituted piperazine ring-, substituted or unsubstituted methyl-substituted or unsubstituted piperidinyl-, substituted or unsubstituted phenyl-substituted or unsubstituted phenyl-substituted or unsubstituted methyl-, substituted or unsubstituted ethylenyl-substituted or unsubstituted methyl-, substituted or unsubstituted piperidinyl-substituted or unsubstituted propyl-, substituted or unsubstituted piperidinyl-substituted or unsubstituted ethyl-, dimethylamino-ethyl-.

In another preferred embodiment, $R_{17}$ is hydrogen, methyl,

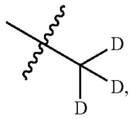

ethyl, propyl, pentyl, hexyl, phenyl-O-butyl-, haloethyl, halopropyl, halobutyl, halohexyl, phenyl-ethyl-, phenyl-propyl-, phenyl-butyl-, cyclodecyl-acetyl-, butenyl-ethyl-propenyl-methyl-, $(R_{20}R_{21})$N-hexyl-, $(R_{20}R_{21})$N-butyl-, $(R_{20}R_{21})$N-ethyl-, piperidinyl-ethyl-, butyl-piperazinyl-, methyl-piperidinyl-, phenyl-phenyl-methyl-, ethylenyl-methyl-, piperidinyl-propyl-, piperidinyl-ethyl-, dimethyl-amino-ethyl-.

In another preferred embodiment, the butyl is n-butyl.

In another preferred embodiment, the butyl is

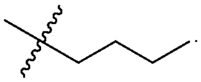 [SMILES: *CCCC]

In another preferred embodiment, the hexyl is

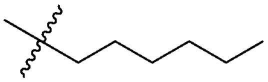,
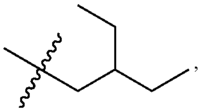,

In another preferred embodiment, the pentyl is n-pentyl.

In another preferred embodiment, the pentyl is

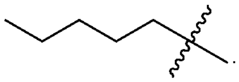 [SMILES: *CCCCC]

In another preferred embodiment, the cyclopentyl is

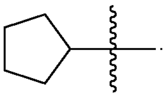 [SMILES: *C1CCCC1]

In another preferred embodiment, the phenyl-propyl- is

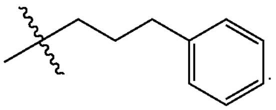 [SMILES: *CCCc1ccccc1]

In another preferred embodiment, the phenyl-butyl- is

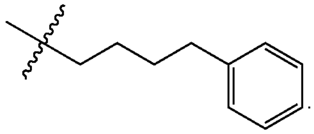 [SMILES: *CCCCc1ccccc1]

In another preferred embodiment, the phenyl-O-butyl- is

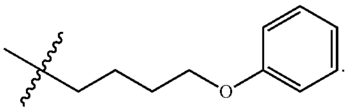 [SMILES: *CCCCOc1ccccc1]

In another preferred embodiment, haloethyl is monobromoethyl, monochloroethyl or monofluoroethyl.

In another preferred embodiment, the haloethyl is

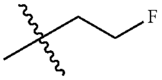 or 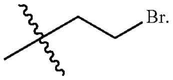

In another preferred embodiment, the propyl is n-propyl.

In another preferred embodiment, the propyl is

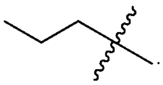

In another preferred embodiment, the halopropyl is n-halopropyl.

In another preferred embodiment, the halopropyl is monobromopropyl, monochloropropyl or monofluoropropyl.

In another preferred embodiment, the halopropyl is

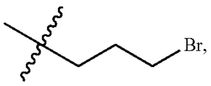
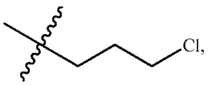
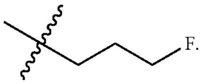

In another preferred embodiment, the butyl is n-butyl.

In another preferred embodiment, the halobutyl is n-halobutyl.

In another preferred embodiment, the halobutyl is monobromobutyl, monochlorobutyl or monofluorobutyl.

In another preferred embodiment, the halobutyl is

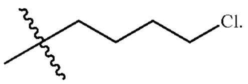 [SMILES: *CCCCCl]

In another preferred embodiment, the hexyl is n-hexyl.

In another preferred embodiment, the halohexyl is n-halohexyl.

In another preferred embodiment, the halohexyl is monochlorohexyl or monobromohexyl.

In another preferred embodiment, the halohexyl is

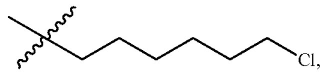

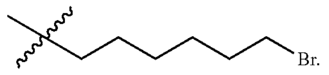

In another preferred embodiment, the cyclodecyl-acetyl- is

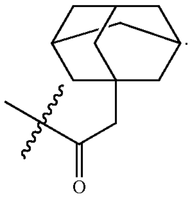 [SMILES: *C(=O)CC12CC3CC(CC(C3)C1)C2]

In another preferred embodiment, the butenyl-ethyl-propenyl-methyl- is

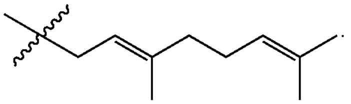 [SMILES: *C/C=C(\C)CCC=C(C)C]

In another preferred embodiment, the piperidinyl-ethyl- is

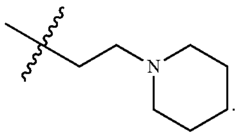 [SMILES: *CCN1CCCCC1]

In another preferred embodiment, the phenyl-phenyl-methyl- is

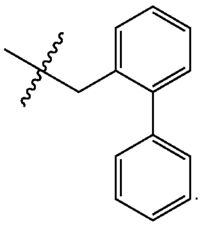 [SMILES: *Cc1ccccc1-c1ccccc1]

In another preferred embodiment, the ethylenyl-methyl- is

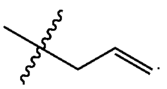 [SMILES: *CC=C]

In another preferred embodiment, the piperidinyl-propyl- is

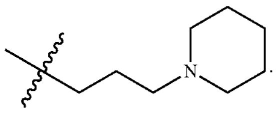 [SMILES: *CCCN1CCCCC1]

In another preferred embodiment, the piperidinyl-ethyl- is

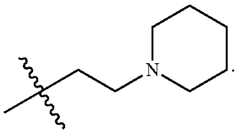 [SMILES: *CCN1CCCCC1]

In another preferred embodiment, the dimethylamino-ethyl- is

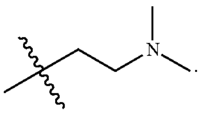 [SMILES: *CCN(C)C]

In another preferred embodiment, $R_{18}$ and $R_{19}$ are each independently hydrogen, substituted or unsubstituted C1-C8 alkyl, substituted or unsubstituted C3-C10 cycloalkyl, substituted or unsubstituted C6-C12 aryl-substituted or unsubstituted C1-C10 alkyl-; or $R_{18}$ and $R_{19}$ are connected to form a substituted or unsubstituted 3-12 membered heterocycloalkane ring.

In another preferred embodiment, $R_{18}$ and $R_{19}$ are each independently hydrogen, substituted or unsubstituted C1-C8 alkyl, substituted or unsubstituted C3-C10 cycloalkyl, substituted or unsubstituted C6-C12 aryl-substituted or unsubstituted C1-C8 alkyl-; or $R_{18}$ and $R_{19}$ are connected to form a substituted or unsubstituted 3-12 membered heterocycloalkane ring.

In another preferred embodiment, $R_{18}$ and $R_{19}$ are each independently hydrogen, substituted or unsubstituted C1-C6 alkyl, substituted or unsubstituted C3-C10 cycloalkyl, substituted or unsubstituted C6-C12 aryl-substituted or unsubstituted C1-C6 alkyl-; or $R_{18}$ and $R_{19}$ are connected to form a substituted or unsubstituted 3-10 membered heterocycloalkane ring.

In another preferred embodiment, $R_{18}$ and $R_{19}$ are each independently hydrogen, substituted or unsubstituted C1-C4 alkyl, substituted or unsubstituted C3-C10 cycloalkyl, substituted or unsubstituted C6-C12 aryl-substituted or unsubstituted C1-C4 alkyl-; or $R_{18}$ and $R_{19}$ are connected to form a substituted or unsubstituted 3-8 membered heterocycloalkane ring.

In another preferred embodiment, $R_{18}$ and $R_{19}$ are each independently hydrogen, substituted or unsubstituted C1-C4 alkyl, substituted or unsubstituted C3-C10 cycloalkyl, substituted or unsubstituted C6-C10 aryl-substituted or unsubstituted C1-C4 alkyl-; or $R_{18}$ and $R_{19}$ are connected to form a substituted or unsubstituted 3-8 membered heterocycloalkane ring.

In another preferred embodiment, $R_{18}$ and $R_{19}$ are each independently hydrogen, substituted or unsubstituted C1-C4 alkyl, substituted or unsubstituted C3-C10 cycloalkyl, substituted or unsubstituted C6-C8 aryl-substituted or unsubstituted C1-C4 alkyl-; or $R_{18}$ and $R_{19}$ are connected to form a substituted or unsubstituted 5-8 membered heterocycloalkane ring.

In another preferred embodiment, $R_{18}$ and $R_{19}$ are each independently hydrogen, substituted or unsubstituted C1-C4 alkyl, substituted or unsubstituted C3-C10 cycloalkyl, substituted or unsubstituted C6-C8 aryl-substituted or unsubstituted C1-C4 alkyl-; or $R_{18}$ and $R_{19}$ are connected to form a substituted or unsubstituted 5 membered heterocycloalkane ring, substituted or unsubstituted 6 membered heterocycloalkane ring, substituted or unsubstituted 7 membered heterocycloalkane ring, substituted or unsubstituted 8 membered heterocycloalkane ring.

In another preferred embodiment, $R_{18}$ and $R_{19}$ are each independently hydrogen, substituted or unsubstituted phenyl-substituted or unsubstituted ethyl-; or $R_{18}$ and $R_{19}$ are connected to form a substituted or unsubstituted piperazine ring, substituted or unsubstituted piperidine ring, or substituted or unsubstituted azacycloheptane ring.

In another preferred embodiment, $R_{18}$ and $R_{19}$ are each independently hydrogen, substituted or unsubstituted C1-C4 alkyl, substituted or unsubstituted C3-C10 cycloalkyl, substituted or unsubstituted C6-C8 aryl-substituted or unsubstituted C1-C4 alkyl-; or $R_{18}$ and $R_{19}$ are connected to form a substituted or unsubstituted piperazine ring, substituted or unsubstituted piperidine ring, or substituted or unsubstituted azacycloheptane ring.

In another preferred embodiment, $R_{18}$ and $R_{19}$ are each independently hydrogen, substituted or unsubstituted phenyl-substituted or unsubstituted ethyl-; or $R_{18}$ and $R_{19}$ are connected to form a substituted or unsubstituted methyl-substituted or unsubstituted piperazine ring, substituted or unsubstituted butyl-substituted or unsubstituted piperazine ring, substituted or unsubstituted methyl-substituted or unsubstituted piperidine ring, trifluoromethyl-piperidine ring, halopiperidine ring, or substituted or unsubstituted azacycloheptane ring.

In another preferred embodiment, $R_{18}$ and $R_{19}$ are each independently hydrogen, phenyl-ethyl-; or $R_{18}$ and $R_{19}$ are connected to form a methyl-piperazine ring, butyl-piperazine ring, trifluoromethyl-piperazine ring, trifluoromethoxyl-piperazine ring, halopiperazine ring, methyl-piperidine ring, trifluoromethyl-piperidine ring, trifluoromethoxyl-piperidine ring, halopiperidine ring, azacycloheptane ring, $(R_{20}R_{21})$N-piperidine ring.

In another preferred embodiment, $R_3$ is hydrogen, hydroxyl, sulfhydryl, amino, methyl-O—,

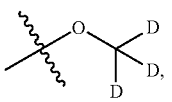

ethyl-O—, propyl-O—, pentyl-O—, hexyl-O—, phenyl-O-butyl-O—O—, haloethyl-O—, halopropyl-O—, halobutyl-O—, halohexyl-O—, phenyl-ethyl-O—, phenyl-propyl-O—, phenyl-butyl-O—, cyclodecyl-acetyl-O—, butenyl-ethyl-propenyl-methyl-O—, $(R_{20}R_{21})$N-hexyl-O—, $(R_{20}R_{21})$N-butyl-O—, $(R_{20}R_{21})$N-ethyl-O—, piperidinyl-ethyl-O—, butyl-piperazinyl-O—, methyl-piperidinyl-O—, phenyl-phenyl-methyl-O—, ethylenyl-methyl-O—, piperidinyl-propyl-O—, piperidinyl-ethyl-O—, dimethyl-amino-ethyl-O—, phenyl-ethyl-NH—, butyl-piperazinyl-, methyl-piperazinyl-, trifluoromethyl-piperazinyl-, trifluoromethoxyl-piperazinyl-, halopiperazinyl, methyl-piperidinyl-, trifluoromethyl-piperidinyl-, trifluoromethoxyl-piperidinyl-, halopiperidinyl, azacycloheptane group, $(R_{20}R_{21})$N-piperazinyl-.

In another preferred embodiment, the phenyl-ethyl- is

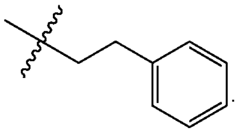 [SMILES: *CCc1ccccc1]

In another preferred embodiment, the methyl-piperazine ring is

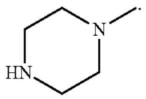

In another preferred embodiment, the methyl-piperazinyl- is

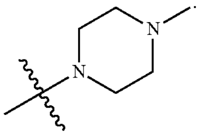 [SMILES: *N1CCN(C)CC1]

In another preferred embodiment, the butyl-piperazine ring is

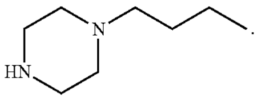

In another preferred embodiment, the butyl-piperazinyl- is

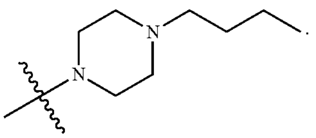 [SMILES: *N1CCN(CCCC)CC1]

In another preferred embodiment, the trifluoromethyl-piperidine ring is

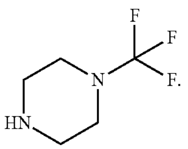

In another preferred embodiment, the trifluoromethyl-piperazinyl- is

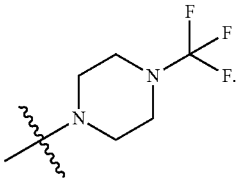 [SMILES: *N1CCN(C(F)(F)F)CC1]

In another preferred embodiment, the trifluoromethoxyl-piperazine ring is

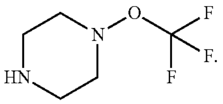

In another preferred embodiment, the trifluoromethoxyl-piperazinyl- is

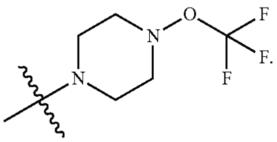 [SMILES: *N1CCN(OC(F)(F)F)CC1]

In another preferred embodiment, the halopiperazine ring is chloropiperazine ring.

In another preferred embodiment, the halopiperazine ring is

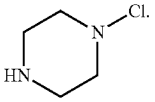

In another preferred embodiment, the halopiperazinyl is chloropiperazinyl.

In another preferred embodiment, the halopiperazinyl is

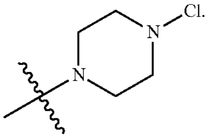 [SMILES: *N1CCN(Cl)CC1]

In another preferred embodiment, the methyl-piperidinyl-1 is

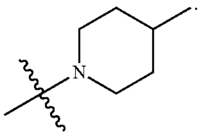 [SMILES: *N1CCC(C)CC1]

In another preferred embodiment, the methyl-piperidine ring is

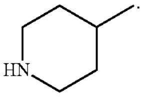

In another preferred embodiment, the trifluoromethyl-piperidinyl- is

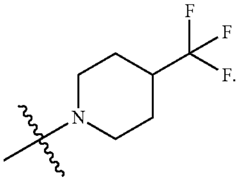 [SMILES: *N1CCC(C(F)(F)F)CC1]

In another preferred embodiment, the trifluoromethoxyl-piperidine ring is

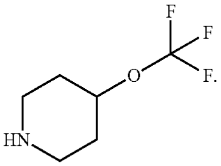 [SMILES: FC(F)(F)OC1CCNCC1]

In another preferred embodiment, the trifluoromethoxyl-piperidinyl- is

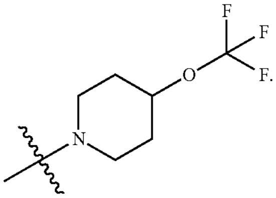 [SMILES: *N1CCC(OC(F)(F)F)CC1]

In another preferred embodiment, the trifluoromethyl-piperidine ring is

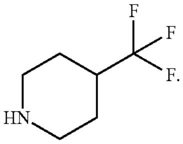

In another preferred embodiment, the halopiperidine ring is chloropiperidine ring.

In another preferred embodiment, the halopiperidine ring is

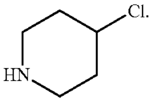

In another preferred embodiment, the halopiperidinyl is chloropiperidinyl.

In another preferred embodiment, the halopiperidinyl is

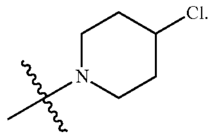 [SMILES: *N1CCC(Cl)CC1]

In another preferred embodiment, the azacycloheptane ring is

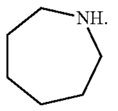

In another preferred embodiment, the azacycloheptane group is

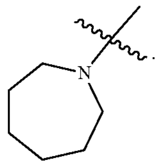 [SMILES: *N1CCCCCC1]

In another preferred embodiment, the $(R_{20}R_{21})$N-piperazinyl- is

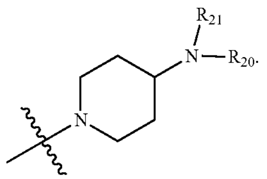

In another preferred embodiment, the $(R_{20}R_{21})$N-piperidine ring is

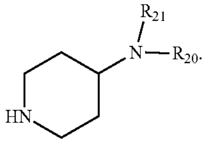

In another preferred embodiment, $R_{18}$ and $R_{19}$ are each independently hydrogen, substituted or unsubstituted C1-C4 alkyl, substituted or unsubstituted C3-C10 cycloalkyl, substituted or unsubstituted C6-C8 aryl-substituted or unsubstituted C1-C4 alkyl-; or $R_{18}$ and $R_{19}$ are connected to form

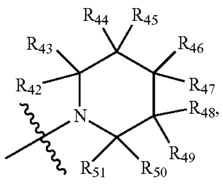

or

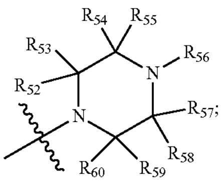

wherein, $R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, C1-C10 alkyl, C1-C10 haloalkyl, C1-C10 haloalkoxyl, C1-C10 haloalkylthio, halogen;

$R_{52}$, $R_{53}$, $R_{54}$, $R_{55}$, $R_{56}$, $R_{57}$, $R_{58}$, $R_{59}$ and $R_{60}$ are each independently hydrogen, C1-C10 alkyl, C1-C10 haloalkyl, C1-C10 haloalkoxyl, C1-C10 haloalkylthio, halogen.

In another preferred embodiment, $(R_{20}R_{21})$N— is

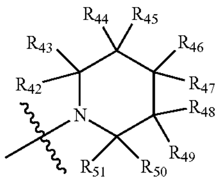

or

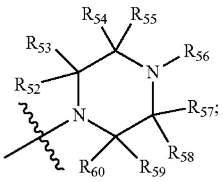

$R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, C1-C10 alkyl, C1-C10 haloalkyl, C1-C10 haloalkoxyl, C1-C10 haloalkylthio, halogen;

$R_{52}$, $R_{53}$, $R_{54}$, $R_{55}$, $R_{56}$, $R_{57}$, $R_{58}$, $R_{59}$ and $R_{60}$ are each independently hydrogen, C1-C10 alkyl, C1-C10 haloalkyl, C1-C10 haloalkoxyl, C1-C10 haloalkylthio, halogen.

In another preferred embodiment, $R_{20}$ and $R_{21}$ are each independently hydrogen, substituted or unsubstituted C1-C10 alkyl, substituted or unsubstituted C3-C10 cycloalkyl, substituted or unsubstituted C2-C8 ester group; or $R_{20}$ and $R_{21}$ are connected to form a substituted or unsubstituted 3-10 membered heterocycloalkyl.

In another preferred embodiment, $R_{20}$ and $R_{21}$ are each independently hydrogen, substituted or unsubstituted C1-C8 alkyl, substituted or unsubstituted C3-C8 cycloalkyl, substituted or unsubstituted C2-C8 ester group; or $R_{20}$ and $R_{21}$ are connected to form a substituted or unsubstituted 3-8 membered heterocycloalkyl.

In another preferred embodiment, $R_{20}$ and $R_{21}$ are each independently hydrogen, substituted or unsubstituted C1-C6 alkyl, substituted or unsubstituted C3-C8 cycloalkyl, substituted or unsubstituted C3-C7 ester group; or $R_{20}$ and $R_{21}$ are connected to form a substituted or unsubstituted 5-8 membered heterocycloalkyl.

In another preferred embodiment, $R_{20}$ and $R_{21}$ are each independently hydrogen, substituted or unsubstituted amyl ester group; or $R_{20}$ and $R_{21}$ are connected to form a substituted or unsubstituted piperidine ring.

In another preferred embodiment, $R_{20}$ and $R_{21}$ are each independently hydrogen, amyl ester group; or $R_{20}$ and $R_{21}$ are connected to form piperidine ring.

In another preferred embodiment, amyl ester group is

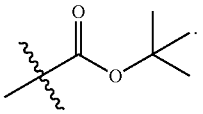 [SMILES: *C(=O)OC(C)(C)C]

In another preferred embodiment, $(R_{20}R_{21})$N-hexyl- is

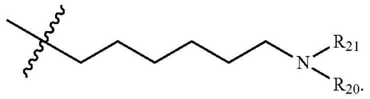

In another preferred embodiment, $(R_{20}R_{21})$N-butyl- is

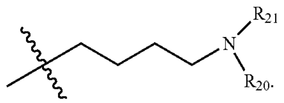

In another preferred embodiment, $(R_{20}R_{21})$N-ethyl- is

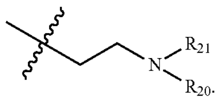

In another preferred embodiment, $R_{22}$, $R_{23}$, $R_{24}$, $R_{25}$, $R_{26}$, $R_{27}$, $R_{28}$, $R_{29}$ and $R_{30}$ are each independently hydrogen, C1-C6 alkyl, C3-C8 cycloalkyl, C1-C6 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, hydroxyl, sulfhydryl, amino, C1-C4 carboxyl, C2-C6 ester group, C2-C4 amide group, C1-C6 alkoxyl, C1-C6 alkylthio, C1-C6 haloalkoxyl, C1-C6 haloalkylthio, C6-C12 aryl, C6-C12 aryl-O—, 5-10 membered heteroaryl, 5-10 membered heteroaryl-O—, 5-10 membered heterocycloalkyl.

In another preferred embodiment, $R_{22}$, $R_{23}$, $R_{24}$, $R_{25}$, $R_{26}$, $R_{27}$, $R_{28}$, $R_{29}$ and $R_{30}$ are each independently hydrogen, C1-C6 alkyl, C1-C6 alkoxyl, C1-C6 alkylthio.

In another preferred embodiment, $R_{22}$, $R_{23}$, $R_{24}$, $R_{25}$, $R_{26}$, $R_{27}$, $R_{28}$, $R_{29}$ and $R_{30}$ are each independently hydrogen, C1-C4 alkyl, C1-C4 alkoxyl, C1-C4 alkylthio.

In another preferred embodiment, $R_{22}$, $R_{23}$, $R_{24}$, $R_{25}$, $R_{26}$, $R_{27}$, $R_{28}$, $R_{29}$ and $R_{30}$ are each independently hydrogen, C1-C3 alkyl, C1-C2 alkoxyl, C1-C2 alkylthio.

In another preferred embodiment, $R_{22}$, $R_{23}$, $R_{24}$, $R_{25}$, $R_{26}$, $R_{27}$, $R_{28}$, $R_{29}$ and $R_{30}$ are each independently hydrogen, trifluoromethoxyl, propyl.

In another preferred embodiment, propyl is isopropyl.

In another preferred embodiment, $Z_1$ and $Z_2$ are each independently substituted or unsubstituted C1-C6 alkylidene.

In another preferred embodiment, $Z_1$ and $Z_2$ are each independently substituted or unsubstituted C1-C4 alkylidene.

In another preferred embodiment, $Z_1$ and $Z_2$ are each independently substituted or unsubstituted methylidene, substituted or unsubstituted ethylidene, substituted or unsubstituted propylidene, substituted or unsubstituted butylidene, substituted or unsubstituted pentylidene, substituted or unsubstituted hexylidene.

In another preferred embodiment, $Z_1$ and $Z_2$ are each independently methylidene, ethylidene, propylidene, butylidene, pentylidene, hexylidene.

In another preferred embodiment, ethylidene is

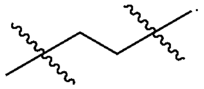 [SMILES: *CC*]

In another preferred embodiment, propyl is

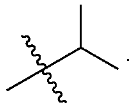 [SMILES: *C(C)C]

In another preferred embodiment, propylidene is n-propylidene.

In another preferred embodiment, propylidene is

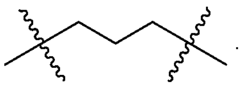 [SMILES: *CCC*]

In another preferred embodiment, butylidene is

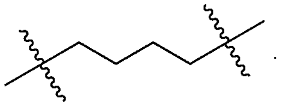 [SMILES: *CCCC*]

In another preferred embodiment, $R_{31}$, $R_{32}$, $R_{33}$, $R_{34}$ and $R_{35}$ are each independently hydrogen, C1-C6 alkyl.

In another preferred embodiment, $R_{31}$, $R_{32}$, $R_{33}$, $R_{34}$ and $R_{35}$ are each independently hydrogen, C1-C4 alkyl.

In another preferred embodiment, $R_{41}$ is hydrogen, substituted or unsubstituted C1-C6 alkyl.

In another preferred embodiment, $R_{41}$ is hydrogen, substituted or unsubstituted C1-C4 alkyl.

In another preferred embodiment, $R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, C1-C8 alkyl, C1-C8 haloalkyl, C1-C8 haloalkoxyl, C1-C8 haloalkylthio, halogen In another preferred embodiment, $R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, C1-C6 alkyl, C1-C6 haloalkyl, C1-C6 haloalkoxyl, C1-C6 haloalkylthio, halogen.

In another preferred embodiment, $R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, C1-C4 alkyl, C1-C4 haloalkyl, C1-C4 haloalkoxyl, C1-C4 haloalkylthio, halogen.

In another preferred embodiment, $R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, methyl, butyl, trifluoromethyl, trifluoromethoxyl, halogen (e.g., chlorine).

In another preferred embodiment, $R_{52}$, $R_{53}$, $R_{54}$, $R_{55}$, $R_{56}$, $R_{57}$, $R_{58}$, $R_{59}$ and $R_{60}$ are each independently hydrogen, C1-C8 alkyl, C1-C8 haloalkyl, C1-C8 haloalkoxyl, C1-C8 haloalkylthio, halogen In another preferred embodiment, $R_{52}$, $R_{53}$, $R_{54}$, $R_{55}$, $R_{56}$, $R_{57}$, $R_{58}$, $R_{59}$ and $R_{60}$ are each independently hydrogen, C1-C6 alkyl, C1-C6 haloalkyl, C1-C6 haloalkoxyl, C1-C6 haloalkylthio, halogen.

In another preferred embodiment, $R_{52}$, $R_{53}$, $R_{54}$, $R_{55}$, $R_{56}$, $R_{57}$, $R_{58}$, $R_{59}$ and $R_{60}$ are each independently hydrogen, C1-C4 alkyl, C1-C4 haloalkyl, C1-C4 haloalkoxyl, C1-C4 haloalkylthio, halogen.

In another preferred embodiment, $R_{52}$, $R_{53}$, $R_{54}$, $R_{55}$, $R_{56}$, $R_{57}$, $R_{58}$, $R_{59}$ and $R_{60}$ are each independently hydrogen, methyl, butyl, trifluoromethyl, trifluoromethoxyl, halogen (e.g., chlorine).

In another preferred embodiment, halogen is F, Cl, Br or I.

In another preferred embodiment, halo is fluoro, chloro, bromo and/or iodo.

In another preferred embodiment, the halon is mono-halo, di-halo or tri-halo.

In another preferred embodiment, the aryl is phenyl.

In another preferred embodiment, the compound of formula I has no optical activity or has optical activity.

In another preferred embodiment, the compound of formula I has no chiral carbon atom or has chiral carbon atom.

In another preferred embodiment, the compound of formula I has one chiral carbon atom.

In another preferred embodiment, the configuration of the compound of formula I is racemate, R configuration (rectus), or S configuration (sinister).

In another preferred embodiment, the compound of formula I has the following structure of formula I-1:

I-1

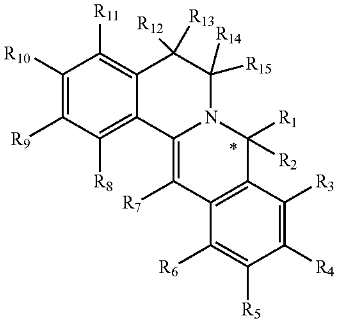

wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently defined as described above.

In another preferred embodiment, "*" represents the configuration of the compound.

In another preferred embodiment, "*" means that the configuration of the compound is racemate, R configuration (rectus), or S configuration (sinister).

In another preferred embodiment, "*" represents a chiral carbon atom.

In another preferred embodiment, the configuration of chiral carbon atom is R configuration (rectus), S configuration (sinister) or racemate.

In another preferred embodiment, the configuration of chiral carbon atom is R configuration (rectus) and/or S configuration.

In another preferred embodiment, the R configuration (rectus) and S configuration of chiral carbon atom refers to racemate.

In another preferred embodiment, the compound of formula I has the following structure of formula I-2:

I-2

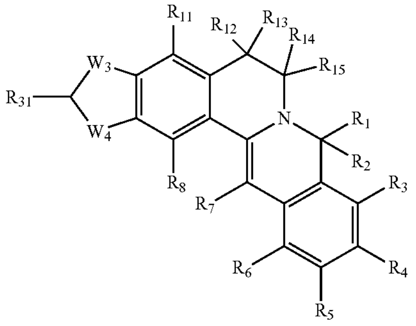

wherein, $R_1$, $R_2$, $R_3$, $R_4$, $R_5$, $R_6$, $R_7$, $R_8$, $R_{11}$, $R_{12}$, $R_{13}$, $R_{14}$, $R_{15}$, $R_{31}$, $W_3$ and $W_4$ are each independently defined as described above.

In another preferred embodiment, the compound of formula I has the following structure of formula I-3:

I-3

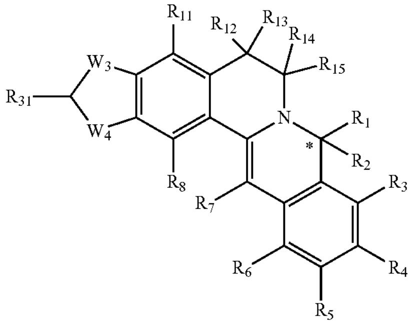

wherein, $R_1$, $R_2$, $R_3$, $R_4$, $R_5$, $R_6$, $R_7$, $R_8$, $R_{11}$, $R_{12}$, $R_{13}$, $R_{14}$, $R_{15}$, $R_{31}$, $W_3$, $W_4$ and * are each independently defined as described above.

In another preferred embodiment, the compound of formula I has the following structure of formula I-4:

I-4

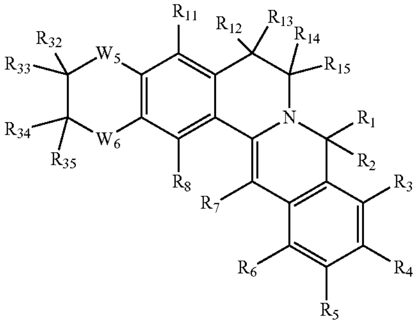

wherein, $R_1$, $R_2$, $R_3$, $R_4$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $W_5$ and $W_6$ are each independently defined as described above.

In another preferred embodiment, the compound of formula I has the following structure of formula I-5:

I-5

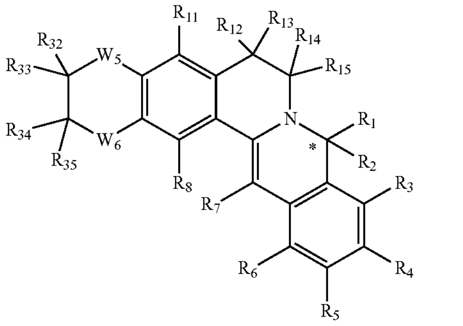

wherein, $R_1$, $R_2$, $R_3$, $R_4$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $W_5$, $W_6$ and * are each independently defined as described above.

In another preferred embodiment, the compound of formula I has the following structure of formula I-6:

I-6

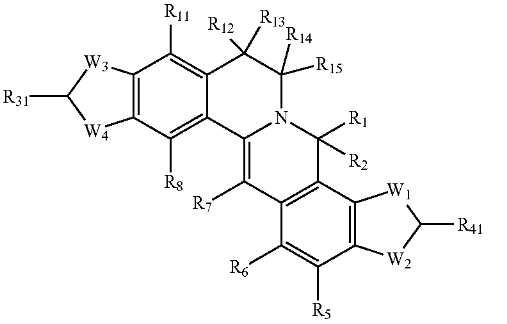

wherein, $R_1$, $R_2$, $R_5$, $R_6$, $R_7$, $R_8$, $R_{11}$, $R_{12}$, $R_{13}$, $R_{14}$, $R_{15}$, $R_{31}$, $R_{41}$, $W_1$, $W_2$, $W_3$ and $W_4$ are each independently defined as described above.

In another preferred embodiment, the compound of formula I has the following structure of formula I-7:

I-7

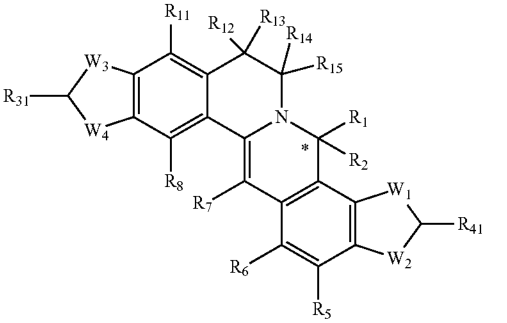

wherein, $R_1$, $R_2$, $R_5$, $R_6$, $R_7$, $R_8$, $R_{11}$, $R_{12}$, $R_{13}$, $R_{14}$, $R_{15}$, $R_{31}$, $R_{41}$, $W_1$, $W_2$, $W_3$, $W_4$ and * are each independently defined as described above.

In another preferred embodiment, the compound of formula I has the following structure of formula I-8:

I-8

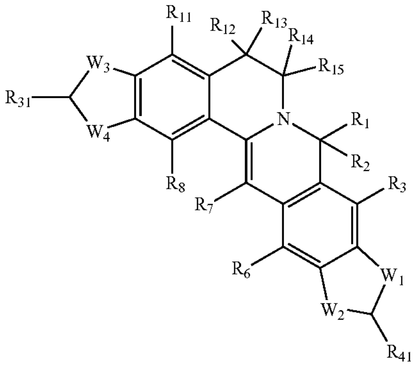

wherein, $R_1$, $R_2$, $R_3$, $R_6$, $R_7$, $R_8$, $R_{11}$, $R_{12}$, $R_{13}$, $R_{14}$, $R_{15}$, $R_{31}$, $R_{41}$, $W_1$, $W_2$, $W_3$ and $W_4$ are each independently defined as described above.

In another preferred embodiment, the compound of formula I has the following structure of formula I-9:

I-9

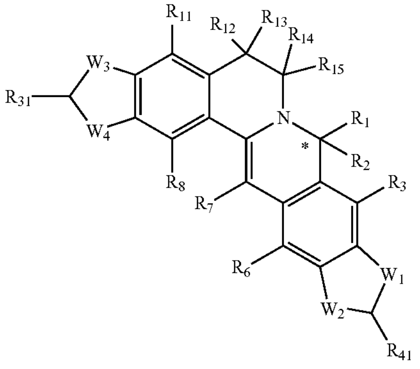

wherein, $R_1$, $R_2$, $R_3$, $R_6$, $R_7$, $R_8$, $R_{11}$, $R_{12}$, $R_{13}$, $R_{14}$, $R_{15}$, $R_{31}$, $R_{41}$, $W_1$, $W_2$, $W_3$, $W_4$ and * are each independently defined as described above.

In another preferred embodiment, the compound of formula I has the following structure of formula I-11:

I-11

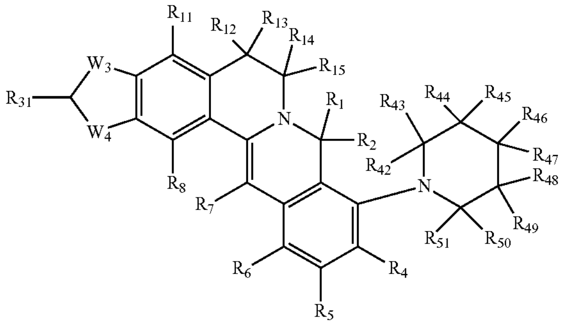

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{31}$, $R_{42}$, $R_{43}$, $R_{44}$, RAS, $R_{46}$, $R_{47}$, $R_{48}$, $R_{49}$, $R_{50}$. $R_{51}$, $W_3$ and $W_4$ are each independently defined as described above.

In another preferred embodiment, the compound of formula I has the following structure of formula I-12:

I-12

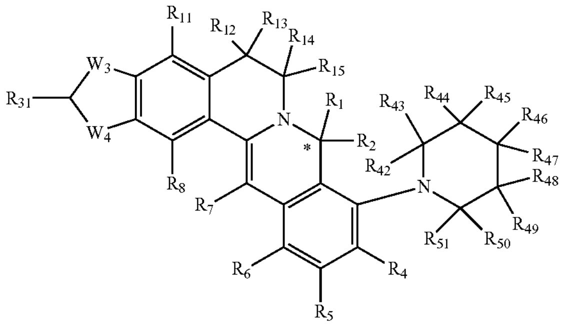

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{31}$, $R_{42}$, $R_{43}$, $R_{44}$, RAS, $R_{46}$, $R_{47}$, $R_{48}$, $R_{49}$, $R_{50}$, $R_{51}$, $W_3$, $W_4$ and * are each independently defined as described above.

In another preferred embodiment, the compound of formula I has the following structure of formula I-13:

I-13

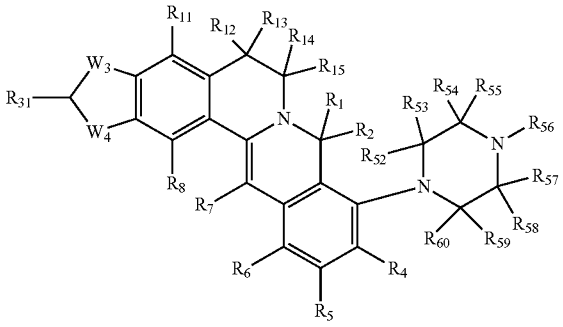

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{31}$, $R_{52}$, $R_{53}$, $R_{54}$, $R_{55}$, $R_{56}$, $R_{57}$, $R_{58}$, $R_{59}$, $R_{60}$, $W_3$ and $W_4$ are each independently defined as described above.

In another preferred embodiment, the compound of formula I has the following structure of formula I-14:

I-14

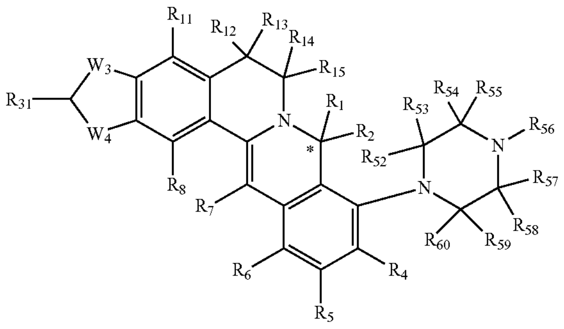

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{31}$, $R_{52}$, $R_{53}$, $R_{54}$, $R_{55}$, $R_{56}$, $R_{57}$, $R_{58}$, $R_{59}$, $R_{60}$, $W_3$, $W_4$ and * are each independently defined as described above.

In another preferred embodiment, the compound of formula I has the following structure of formula I-15:

I-15

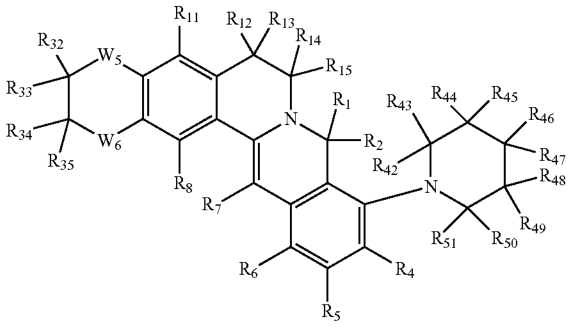

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{42}$, $R_{43}$, $R_{44}$, $R_{45}$, $R_{46}$, $R_{47}$, $R_{48}$, $R_{49}$, $R_{50}$, $R_{51}$, $W_5$ and $W_6$ are each independently defined as described above.

In another preferred embodiment, the compound of formula I has the following structure of formula I-16:

I-16

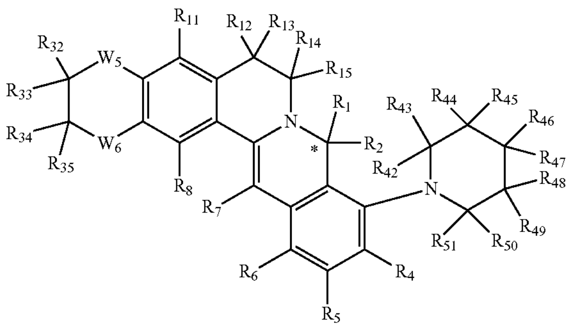

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{42}$, $R_{43}$, $R_{44}$, RAS, $R_{46}$, $R_{47}$, $R_{48}$, $R_{49}$, $R_{50}$, $R_{51}$, $W_5$, $W_6$ and * are each independently defined as described above.

In another preferred embodiment, the compound of formula I has the following structure of formula I-17:

I-17

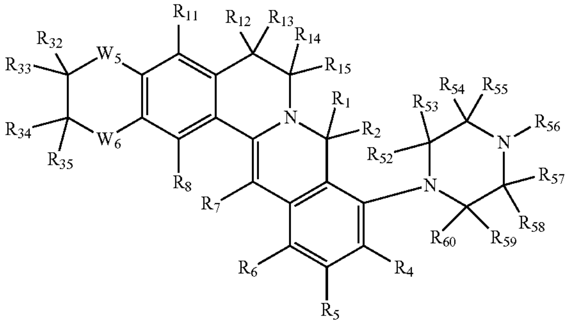

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{52}$, $R_{53}$, $R_{54}$, $R_{55}$, $R_{56}$, $R_{57}$, $R_{58}$, $R_{59}$, $R_{60}$, $W_5$ and $W_6$ are each independently defined as described above.

In another preferred embodiment, the compound of formula I has the following structure of formula I-18:

I-18

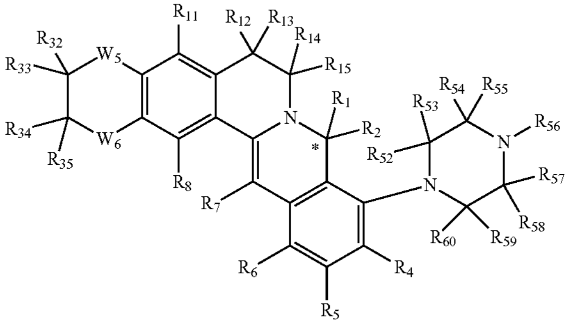

wherein, $R_1$, $R_2$, $R_4$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{52}$, $R_{53}$, $R_{54}$, $R_{55}$, $R_{56}$, $R_{57}$, $R_{58}$, $R_{59}$, $R_{60}$, $W_5$, $W_6$ and * are each independently defined as described above.

In another preferred embodiment, the compound of formula I has the following structure of formula I-19:

I-19

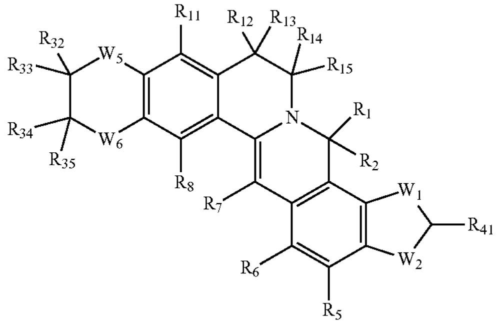

wherein, $R_1$, $R_2$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{41}$, $W_1$, $W_2$, $W_5$ $W_6$ are each independently defined as described above.

In another preferred embodiment, the compound of formula I has the following structure of formula I-20:

I-20

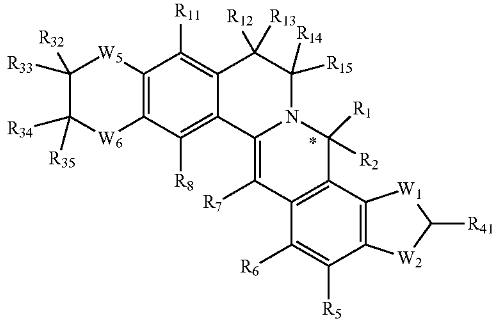

wherein, $R_1$, $R_2$, $R_5$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{41}$, $W_1$, $W_2$, $W_5$, $W_6$ and * are each independently defined as described above.

In another preferred embodiment, the compound of formula I has the following structure of formula I-21:

I-21

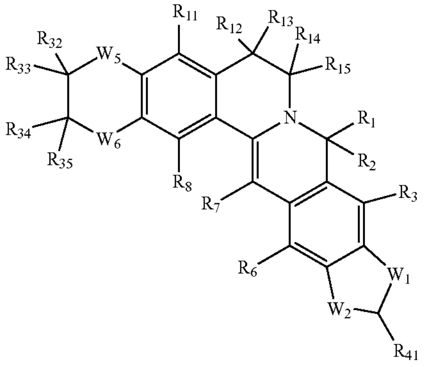

wherein, $R_1$, $R_2$, $R_3$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{41}$, $W_1$, $W_2$, $W_5$ and $W_6$ are each independently defined as described above.

In another preferred embodiment, the compound of formula I has the following structure of formula I-22:

I-22

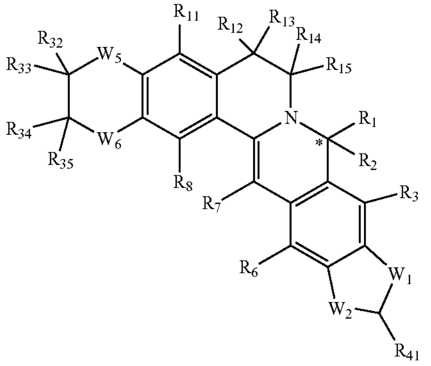

wherein, $R_1$, $R_2$, $R_3$, $R_6$, $R_7$, $R_8$, $R_{11}$, $R_{12}$, $R_{13}$, $R_{14}$, $R_{15}$, $R_{32}$, $R_{33}$, $R_{34}$, $R_{35}$, $R_{41}$, $W_1$, $W_2$, $W_5$, $W_6$ and * are each independently defined as described above.

In another preferred embodiment, the pharmaceutically acceptable salt of the compound of formula I comprises the salt formed by the compound of formula I and an acid.

In another preferred embodiment, the acid comprises one or more of hydrochloric acid, mucic acid, D-glucuronic acid, hydrobromic acid, hydrofluoric acid, hydroiodic acid, sulfuric acid, nitric acid, phosphoric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid, aspartic acid and glutamic acid.

In another preferred embodiment, the pharmaceutically acceptable salt of the compound of formula I comprises the salt formed by the compound of formula I and one or more of hydrochloric acid, mucic acid, D-glucuronic acid, hydrobromic acid, hydrofluoric acid, hydroiodic acid, sulfuric acid, nitric acid, phosphoric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid, aspartic acid and glutamic acid.

In another preferred embodiment, the pharmaceutically acceptable salt of the compound of formula I comprises the salt formed by the compound of formula I and hydrochloric acid, mucic acid, D-glucuronic acid, hydrobromic acid, hydrofluoric acid, hydroiodic acid, sulfuric acid, nitric acid, phosphoric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid, aspartic acid or glutamic acid.

In another preferred embodiment, the salt root of the pharmaceutically acceptable salt of the compound of formula I comprises the salt root formed by the loss of a $H^+$ in the acid.

In another preferred embodiment, the salt root of the pharmaceutically acceptable salt of the compound of formula I comprises the salt root formed by the loss of a $H^+$ in hydrochloric acid, mucic acid, D-glucuronic acid, hydrobromic acid, hydrofluoric acid, hydroiodic acid, sulfuric acid, nitric acid, phosphoric acid, formic acid, acetic acid, trifluoroacetic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid, aspartic acid or glutamic acid.

In another preferred embodiment, the salt root of the pharmaceutically acceptable salt of the compound of formula I comprises $F^-$, $Cl^-$, $Br^-$, $I^-$, $HCOO^-$, $CH_3COO^-$, $SO_4^{2-}$ or $NO_3^-$.

In another preferred embodiment, the compound of formula I, or an optical isomer thereof, or a racemate thereof, or a solvate thereof, or a pharmaceutically acceptable salt thereof, or a deuterated compound thereof is selected from the following group:

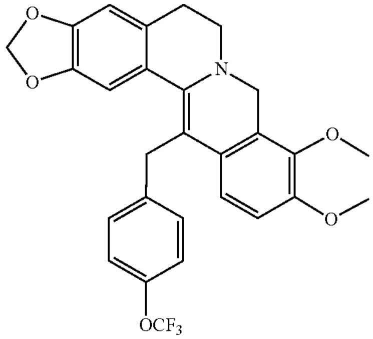

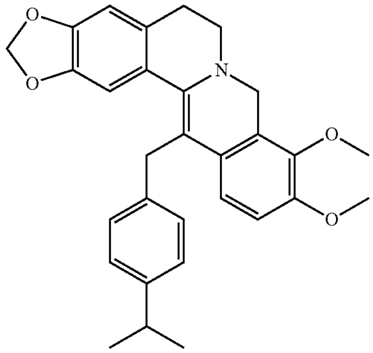

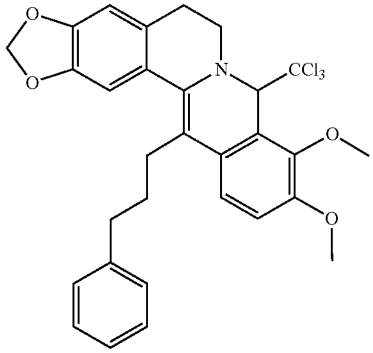

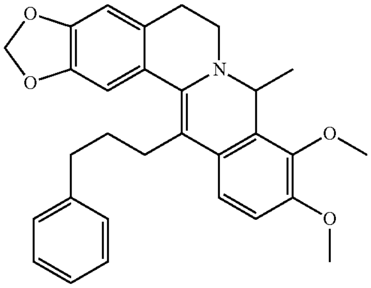

-continued
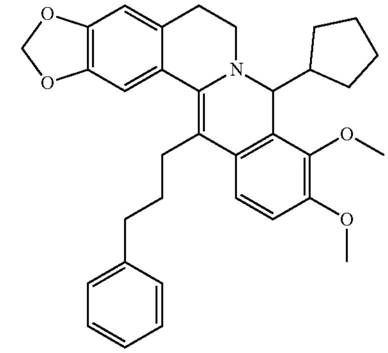
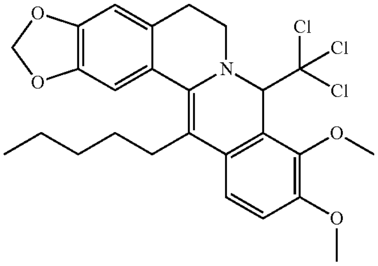
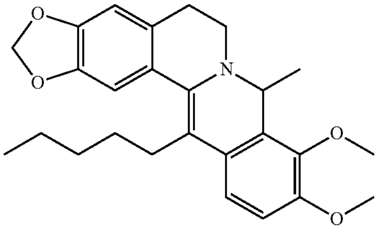
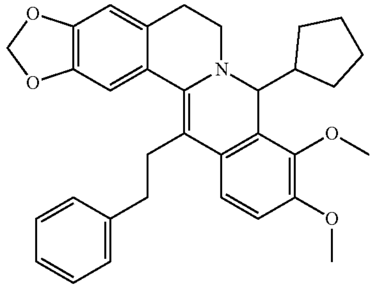
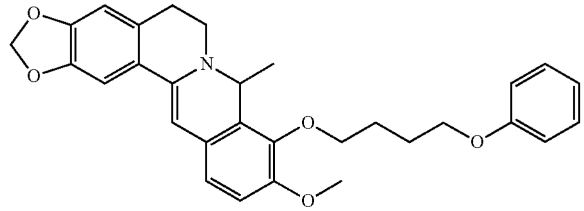
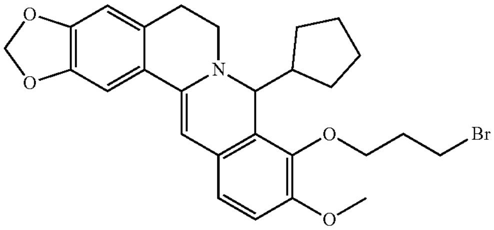
-continued
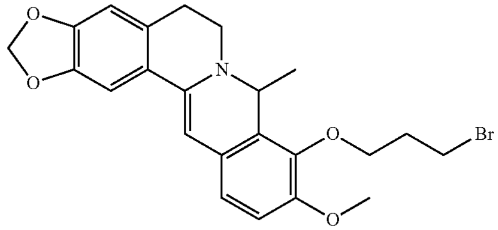
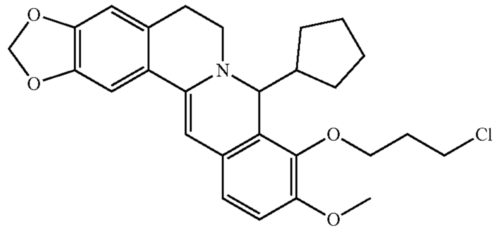
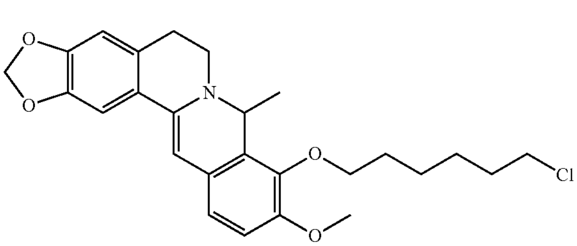
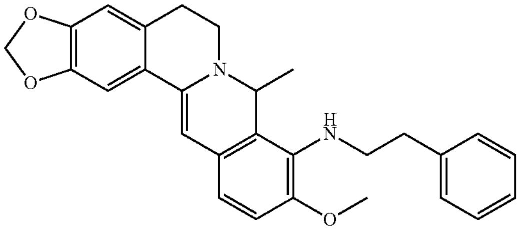
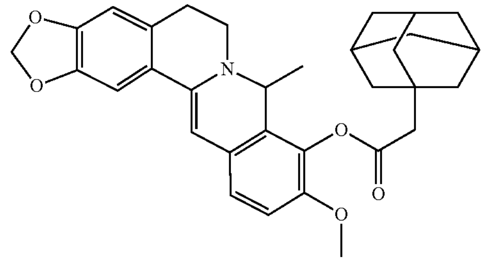
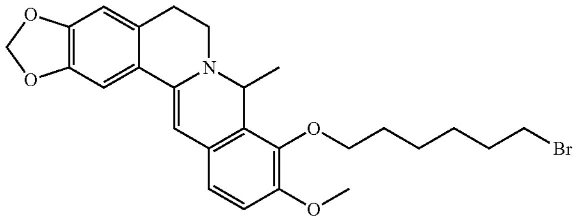
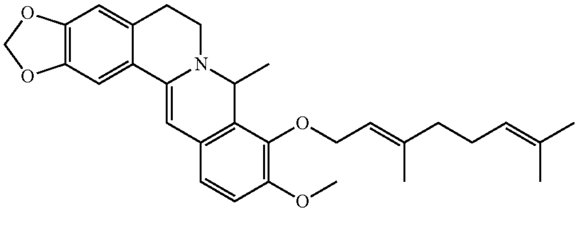

-continued
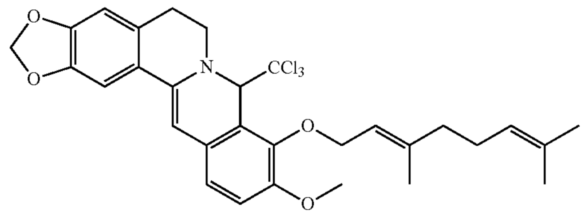
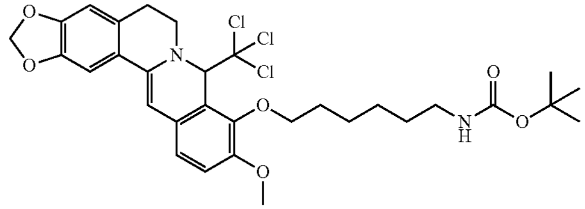
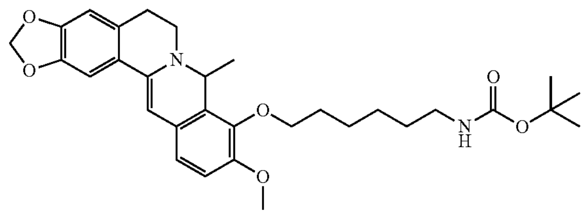
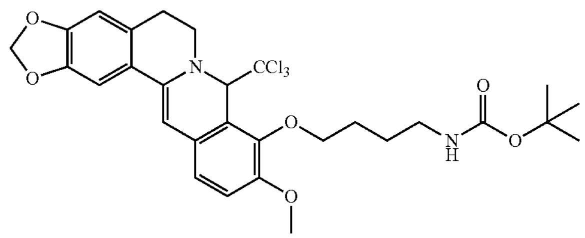
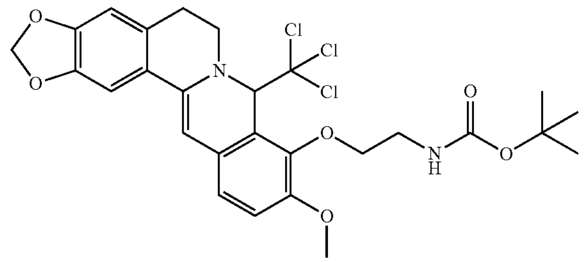
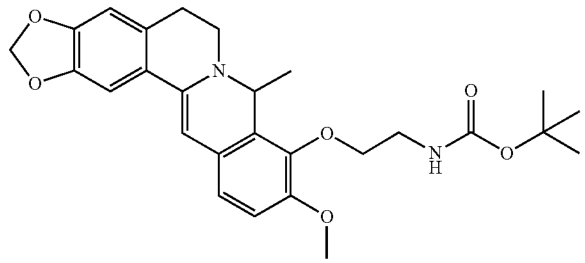
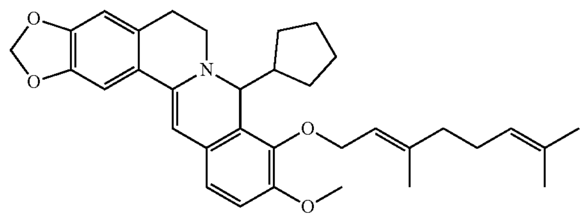
-continued
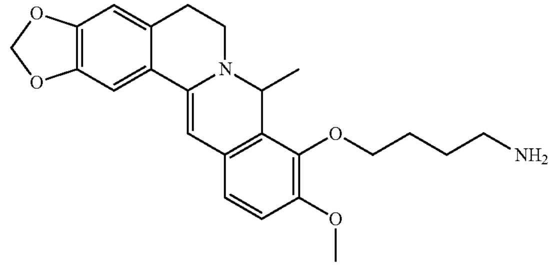
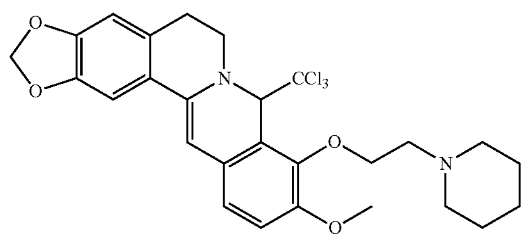
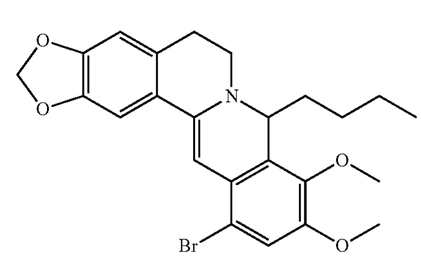
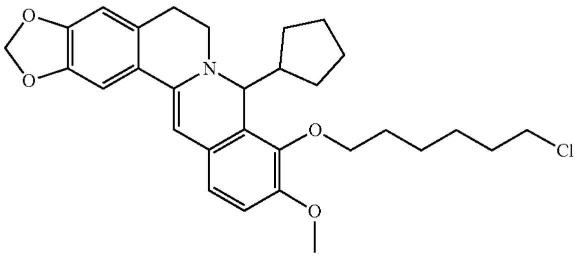
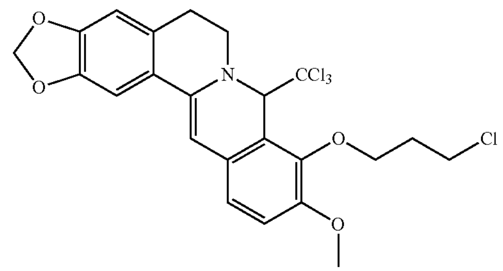
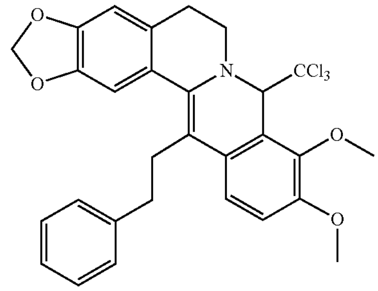

-continued
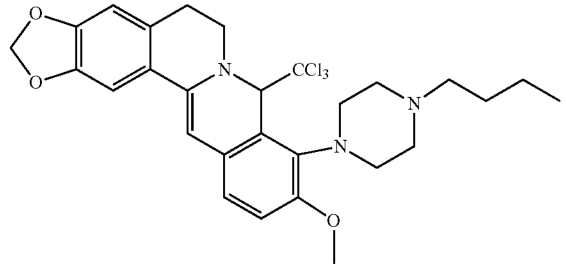
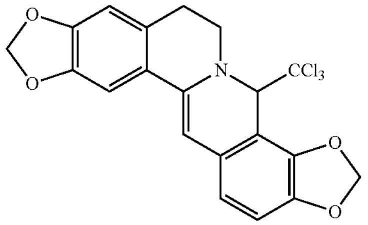
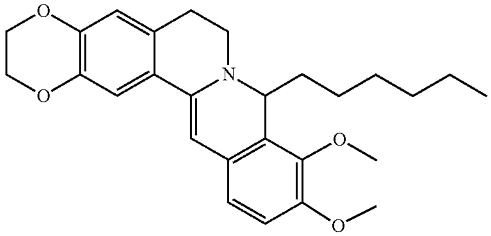
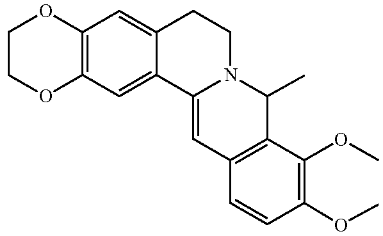
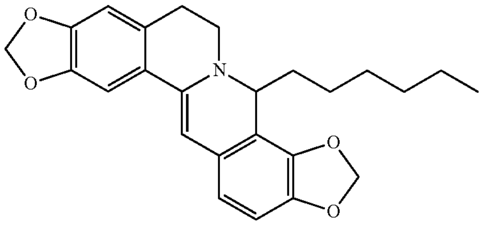
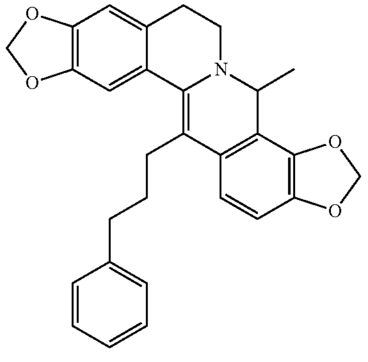
-continued
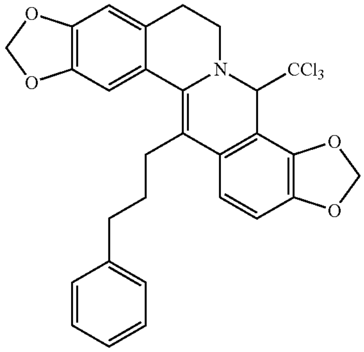
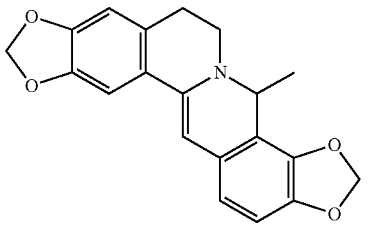
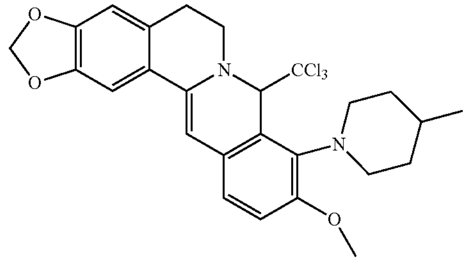
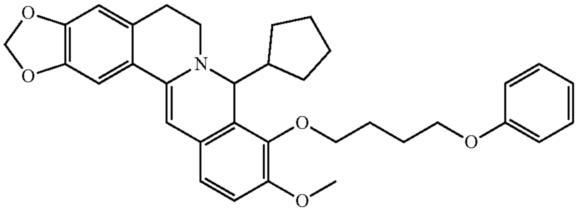
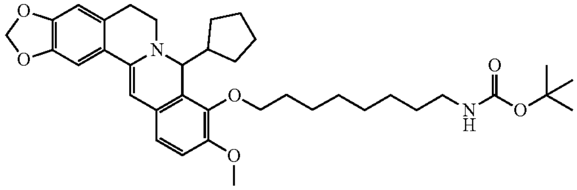
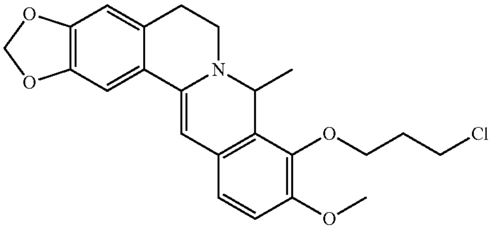
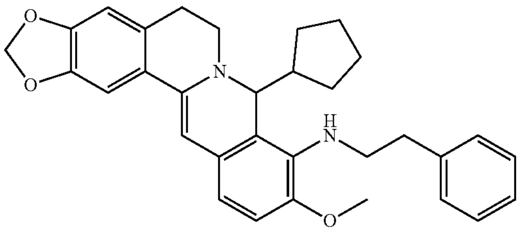

-continued
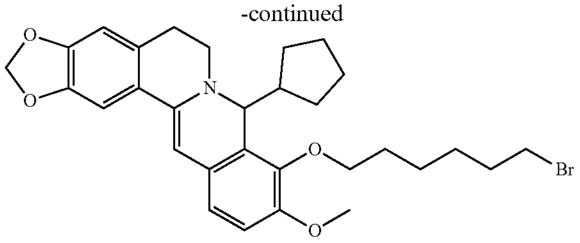
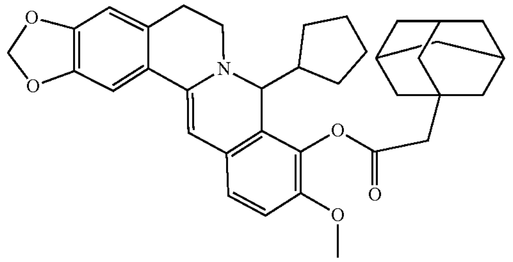
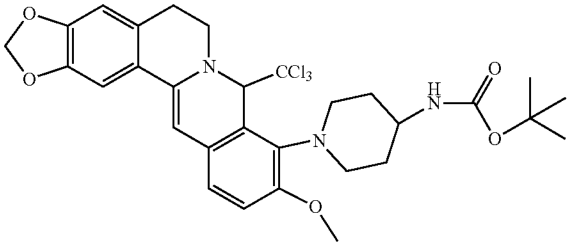
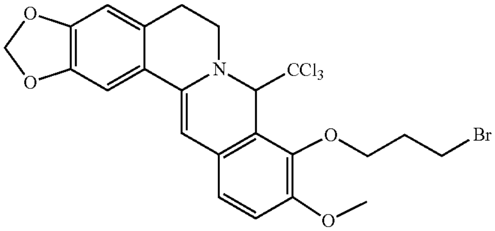
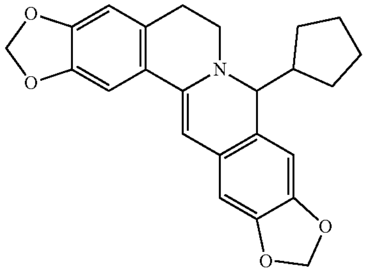
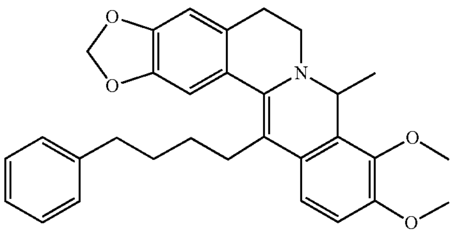
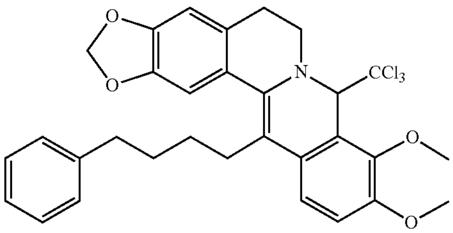
-continued
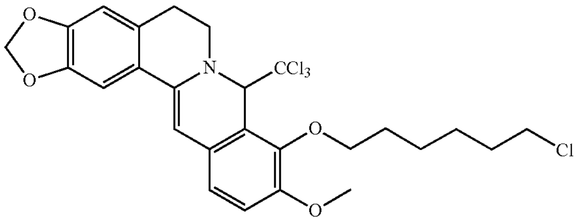
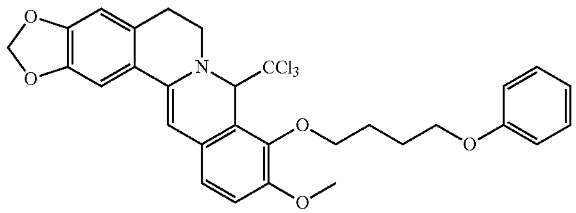
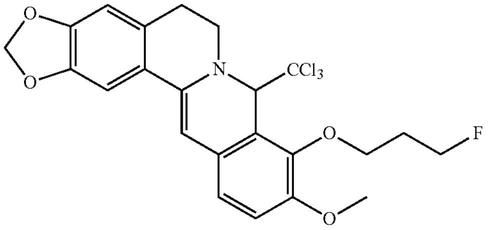
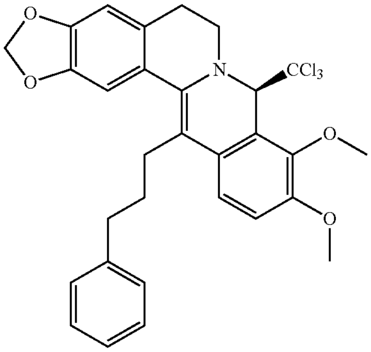
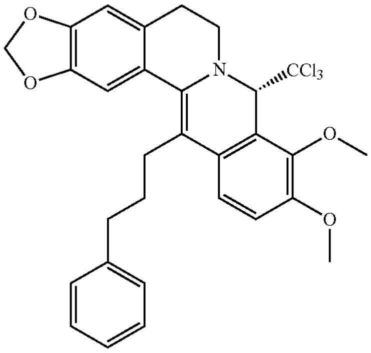
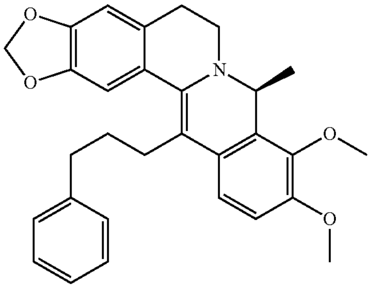

-continued
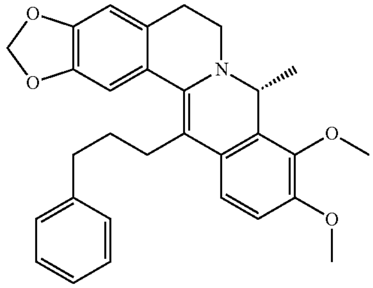
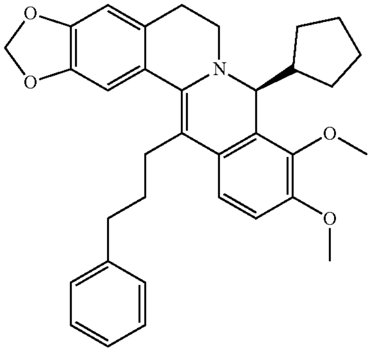
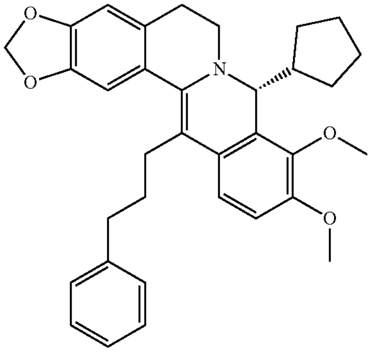
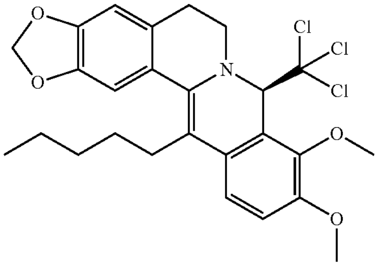
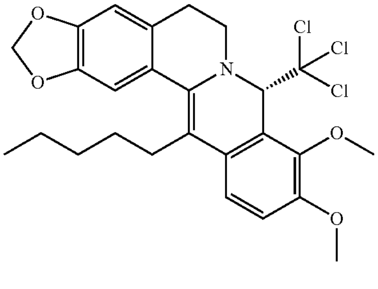
-continued
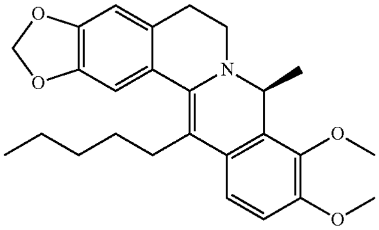
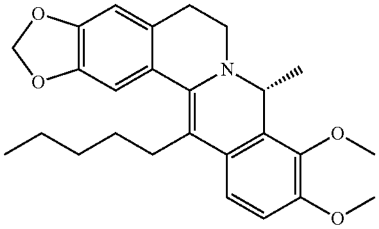
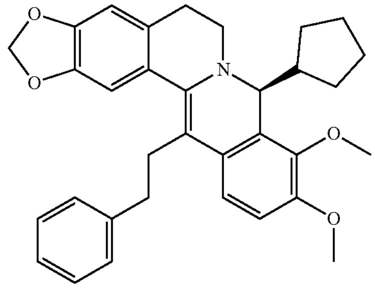
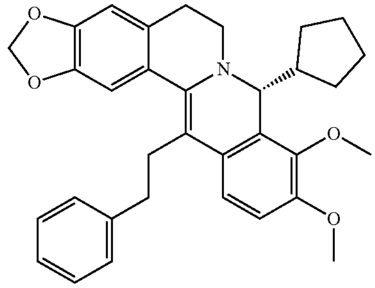
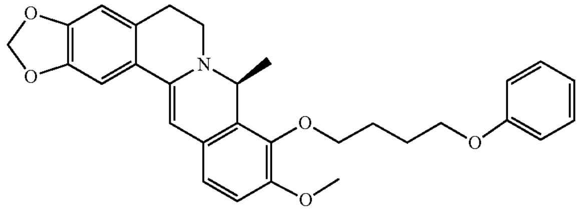
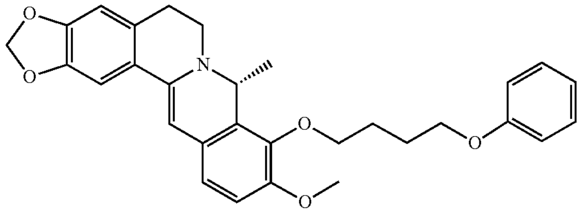
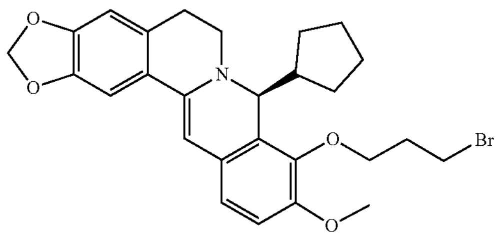

-continued
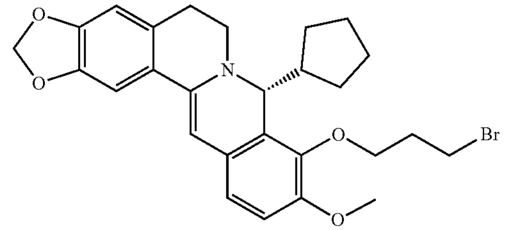
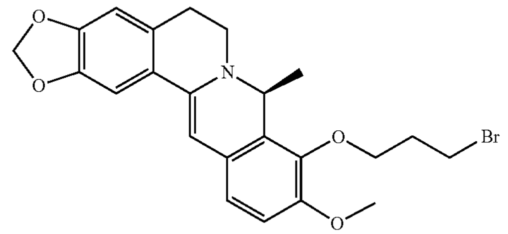
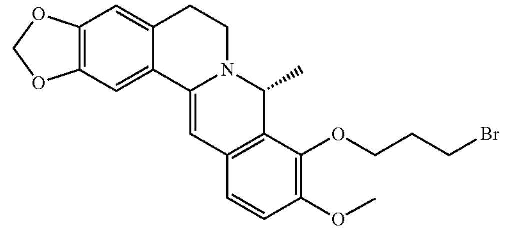
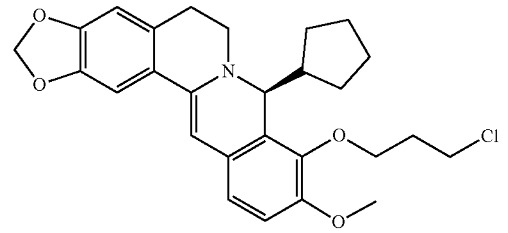
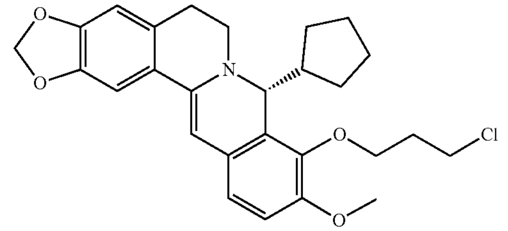
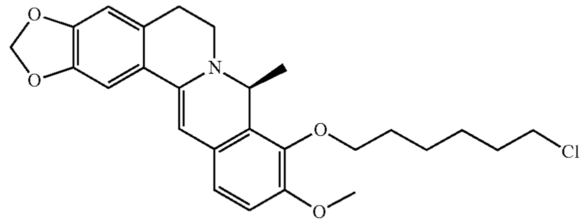
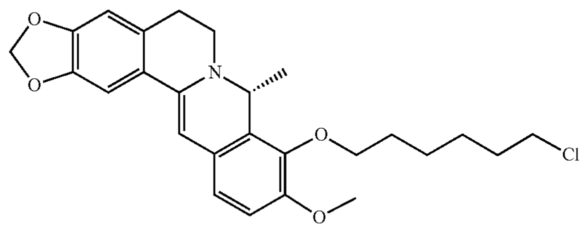
-continued
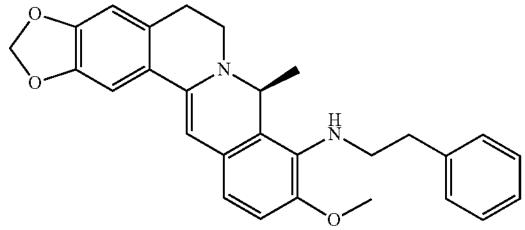
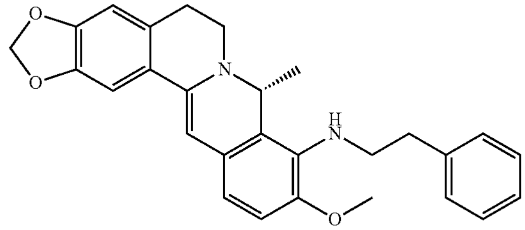
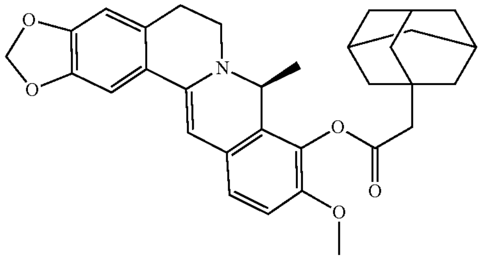
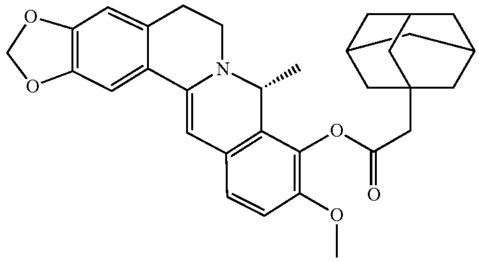
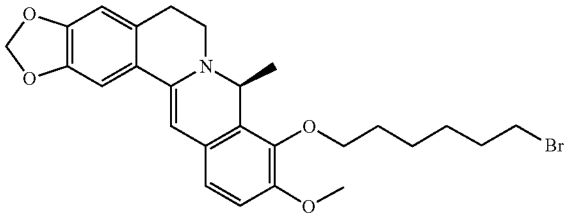
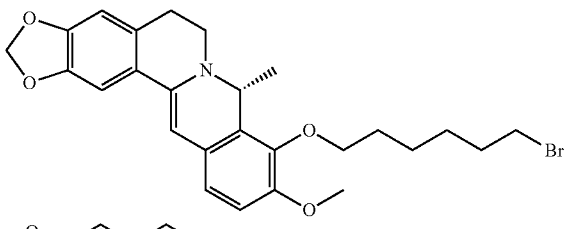
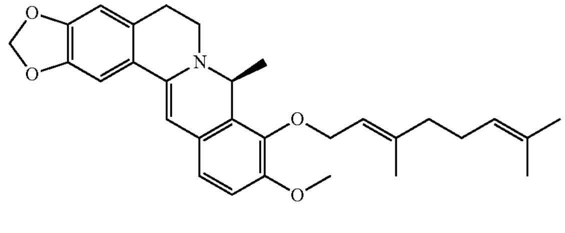

-continued
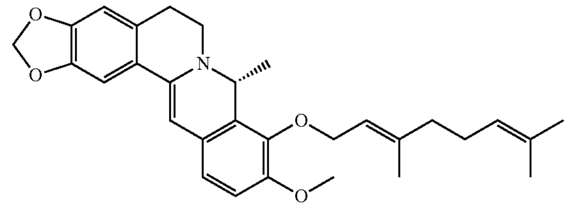
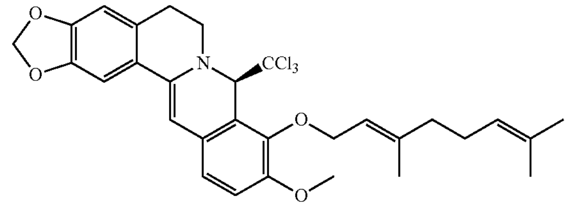
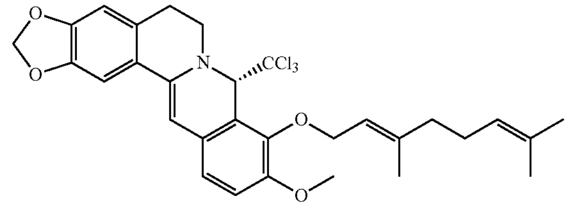
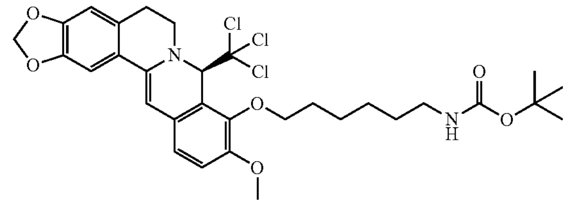
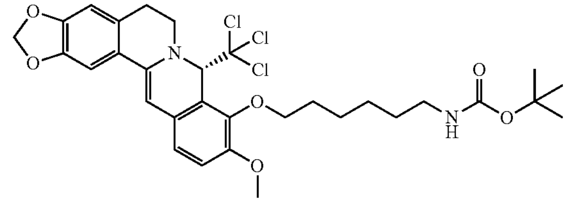
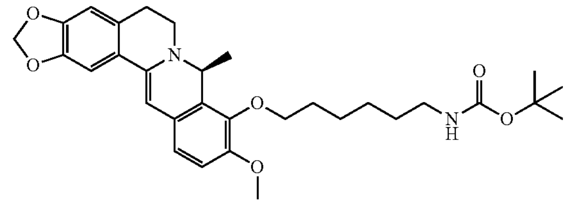
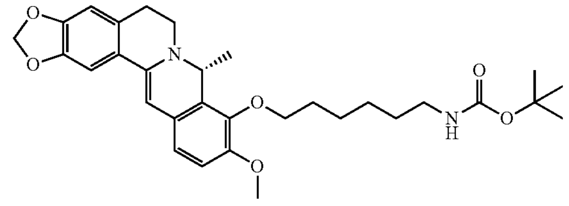
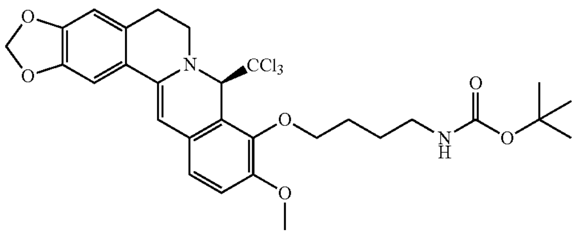
-continued
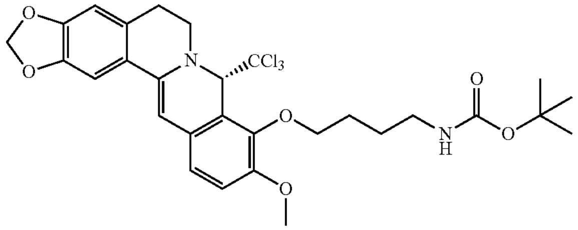
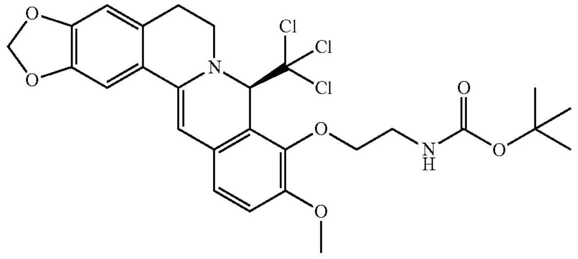
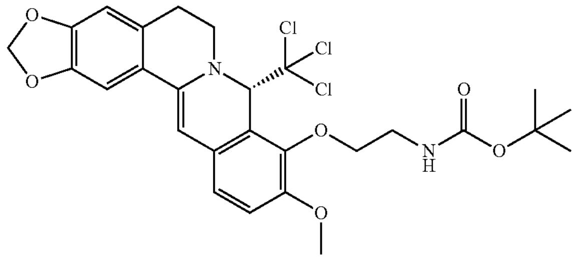
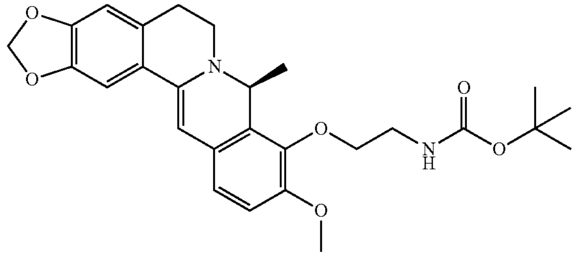
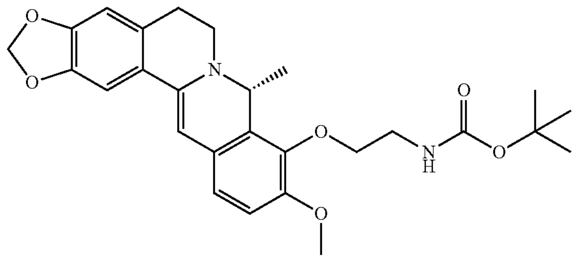
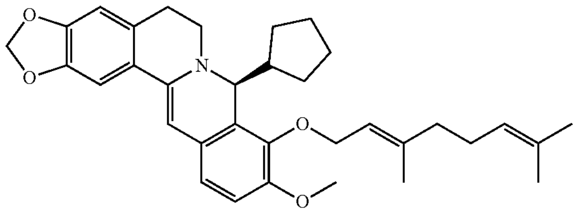
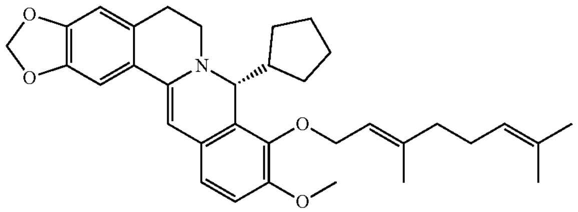

-continued
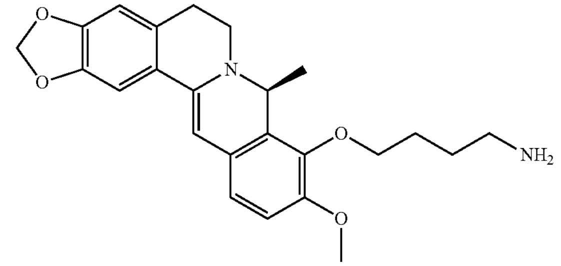
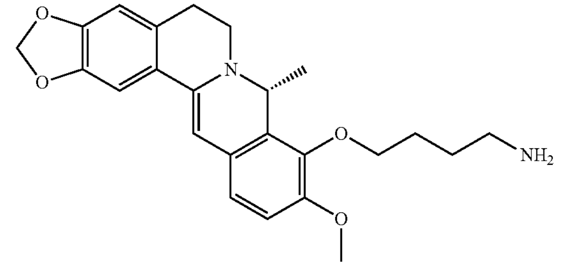
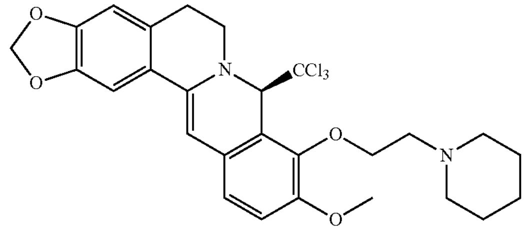
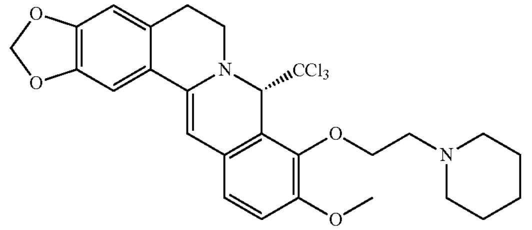
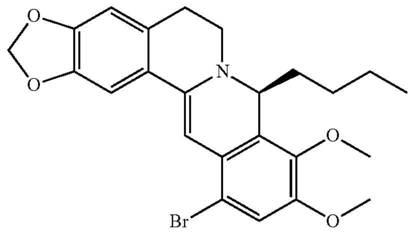
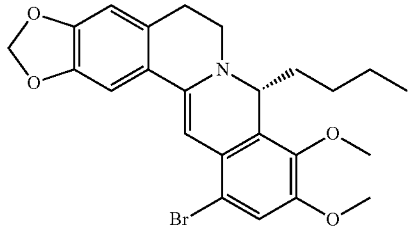
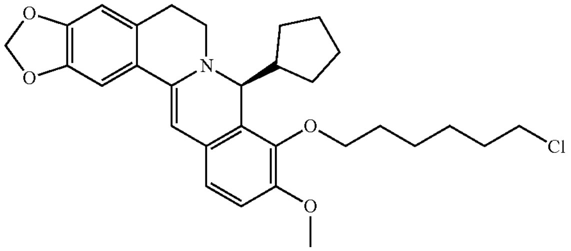
-continued
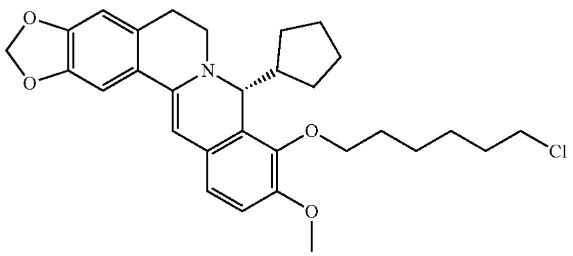
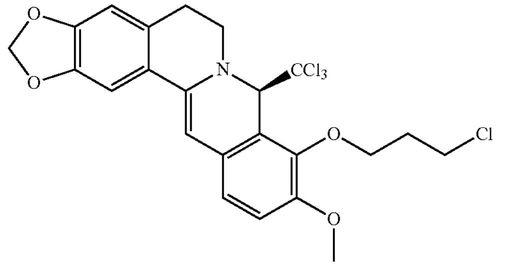
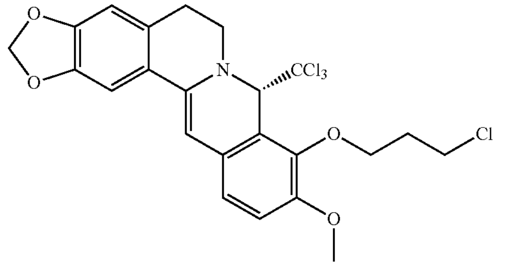
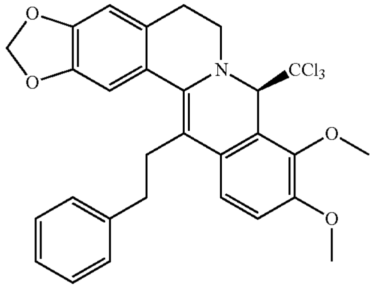
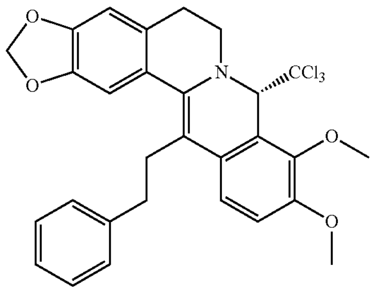
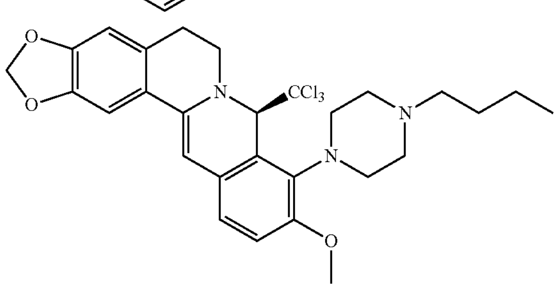

-continued
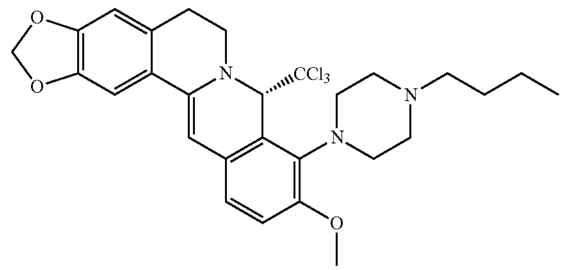
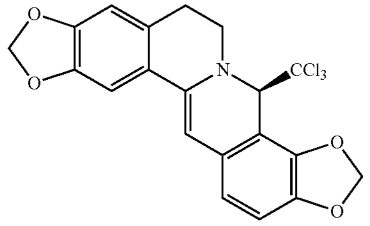
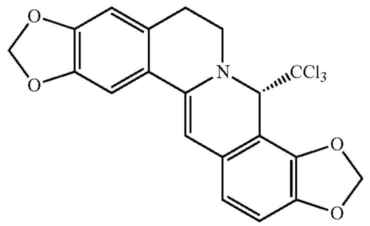
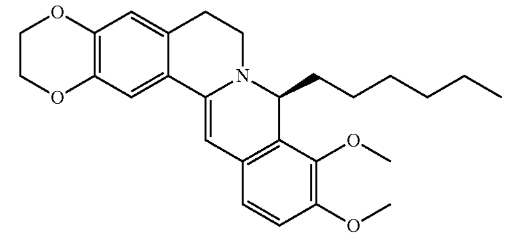
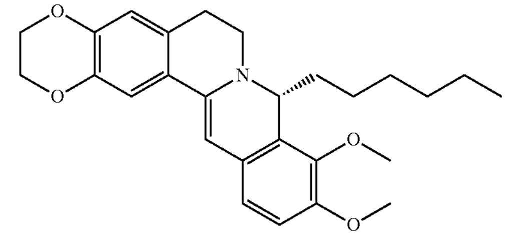
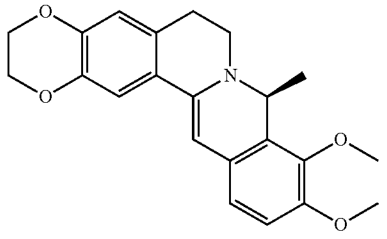
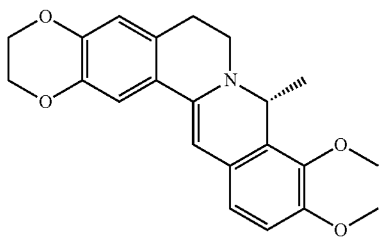
-continued
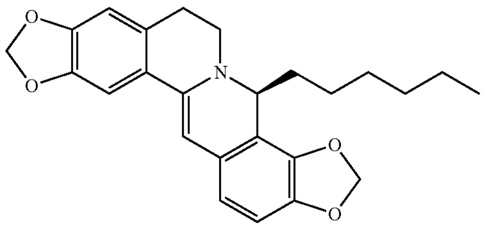
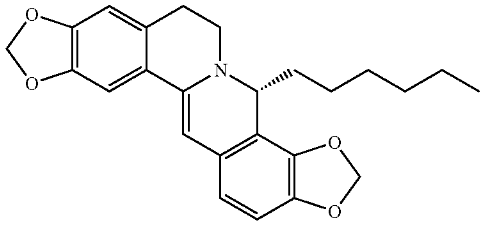
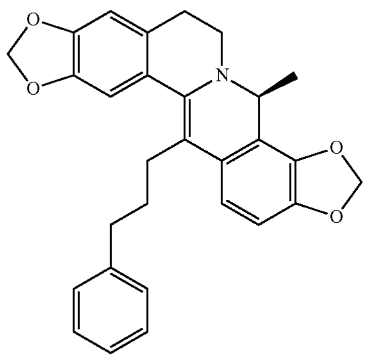
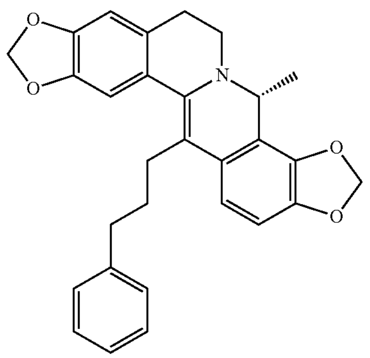
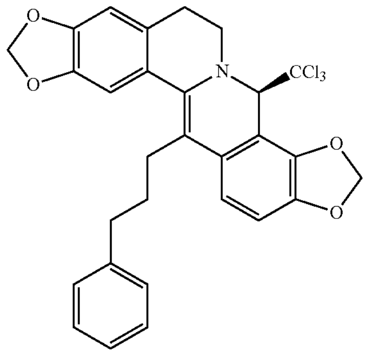

-continued
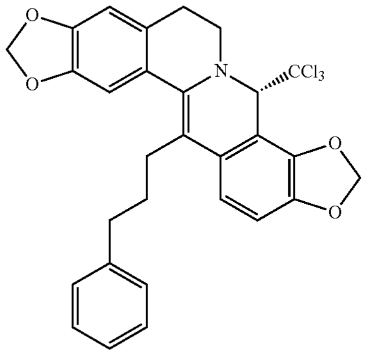
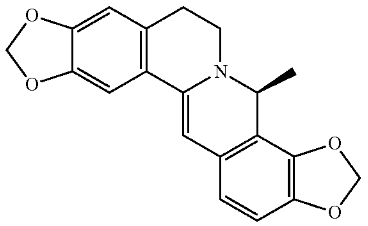
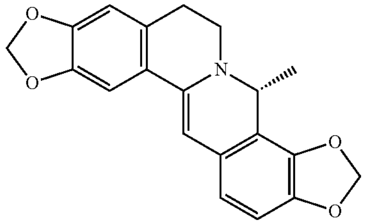
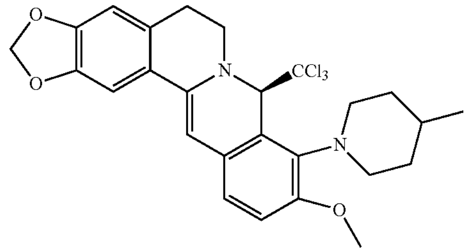
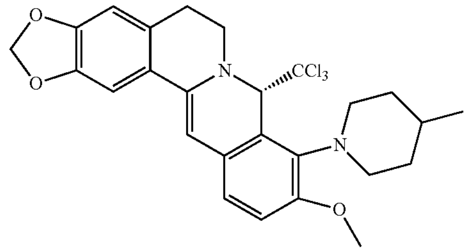
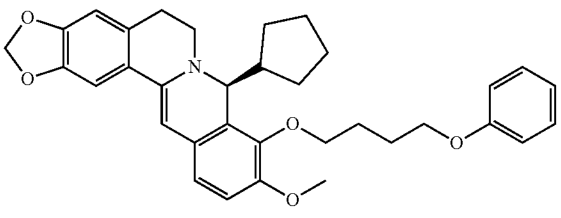
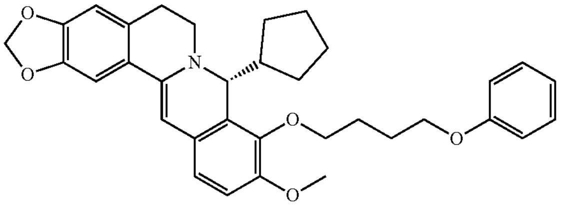
-continued
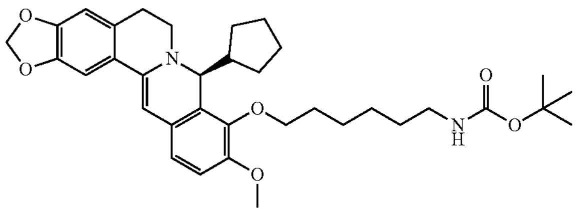
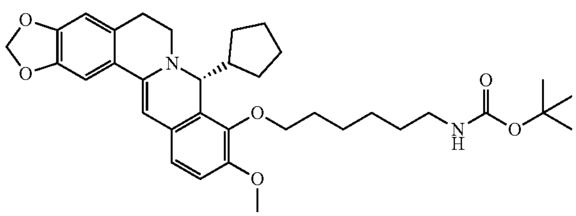
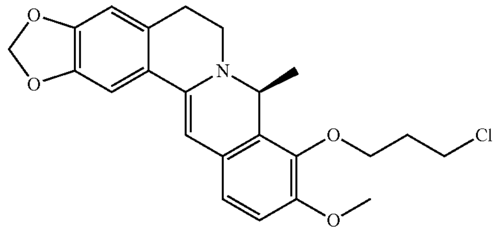
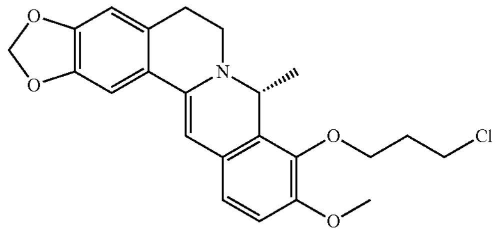
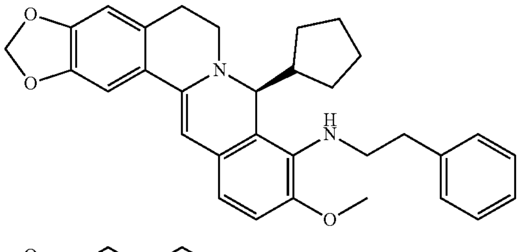
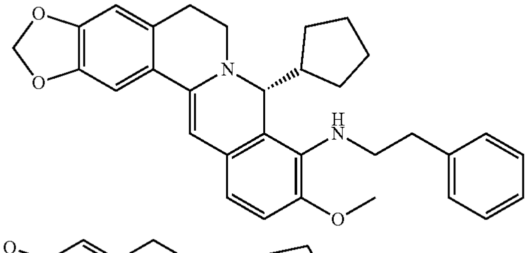
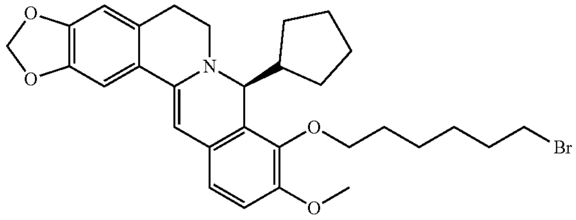

-continued
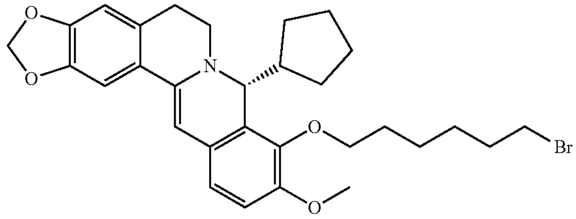
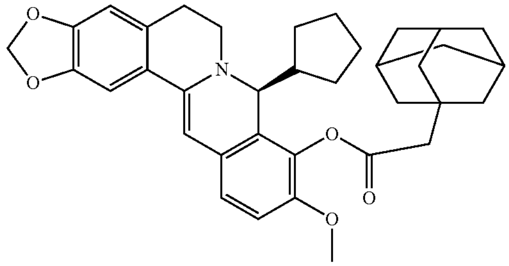
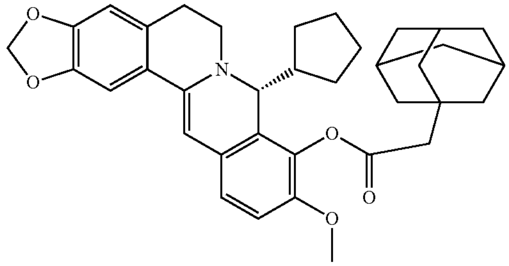
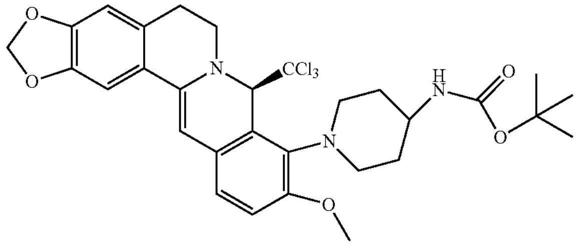
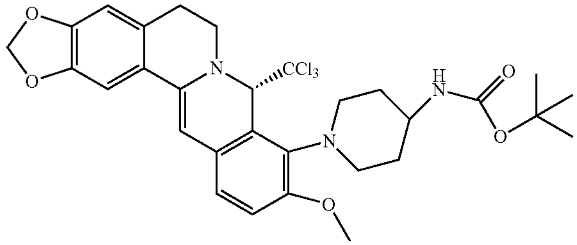
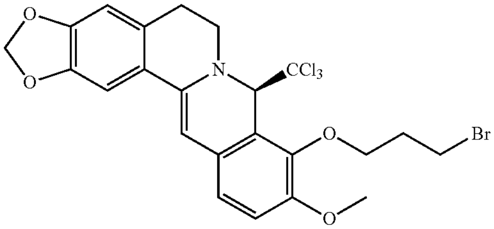
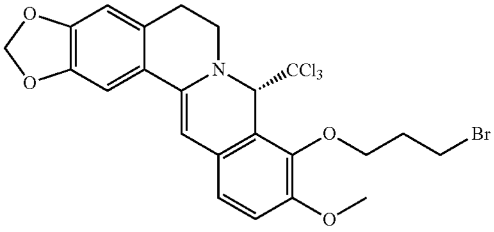
-continued
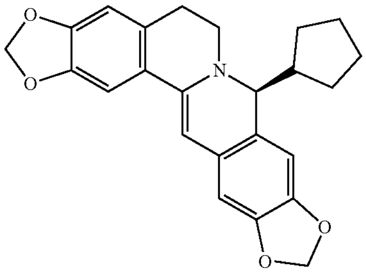
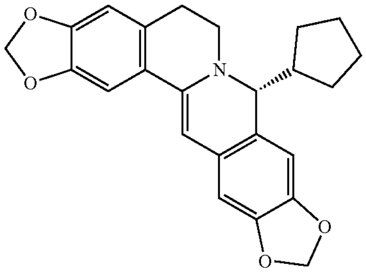
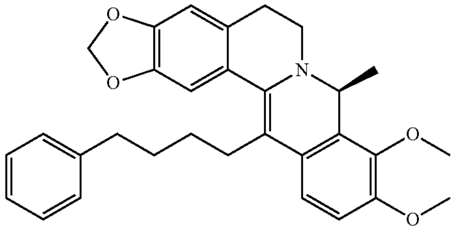
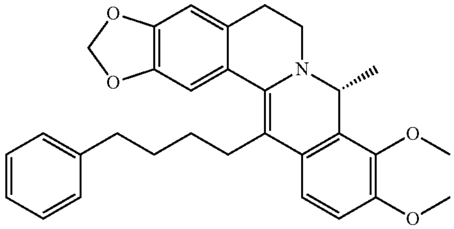
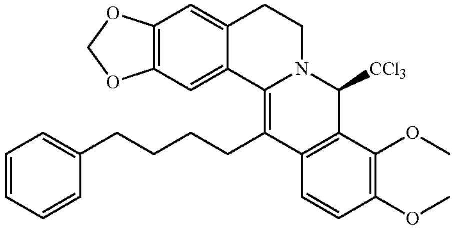
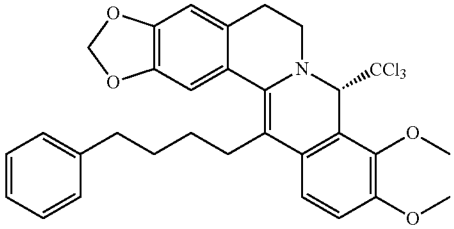
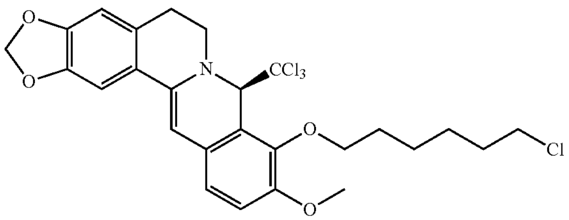

-continued
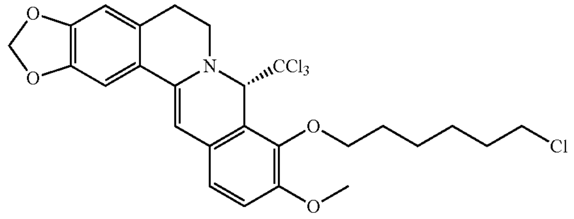
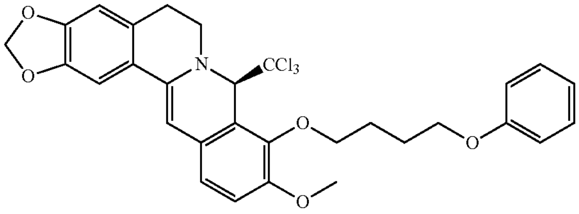
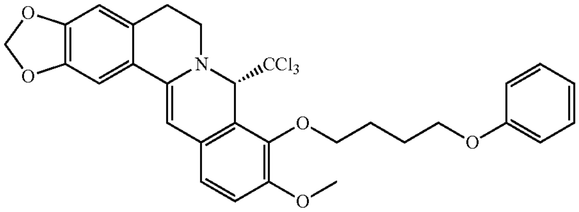
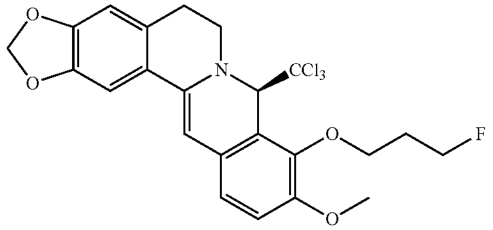
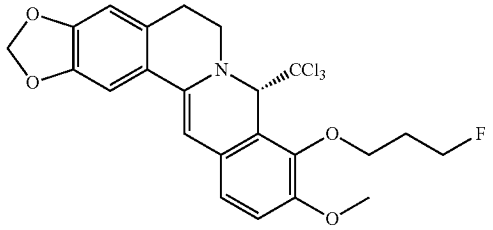
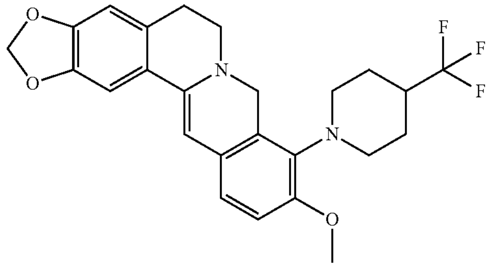
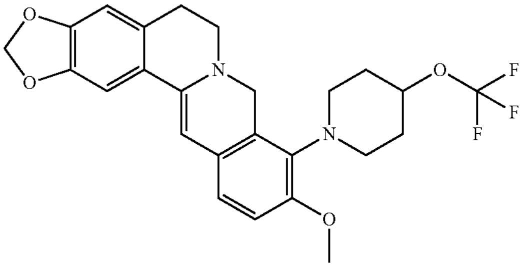
-continued
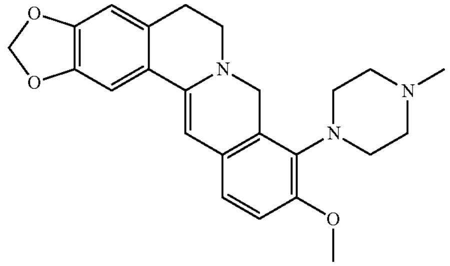
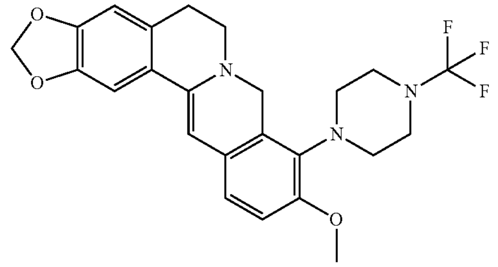
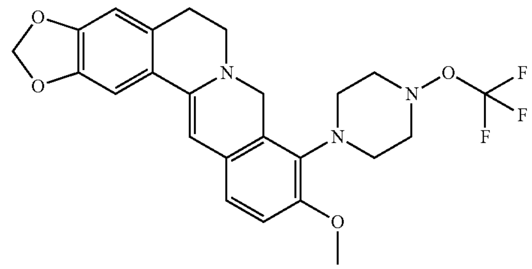
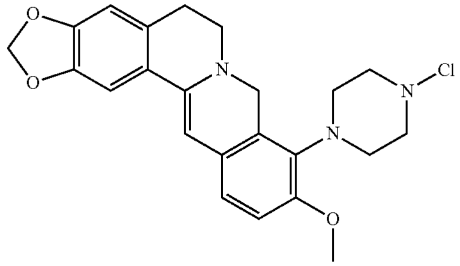
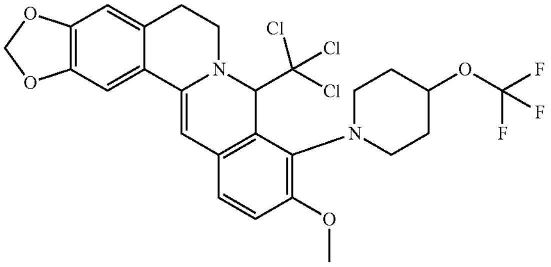
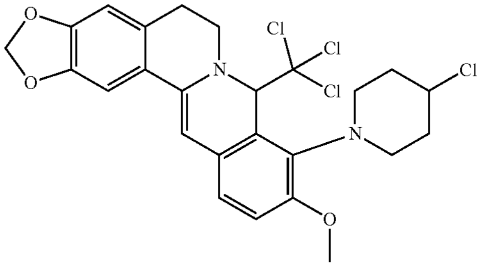

-continued
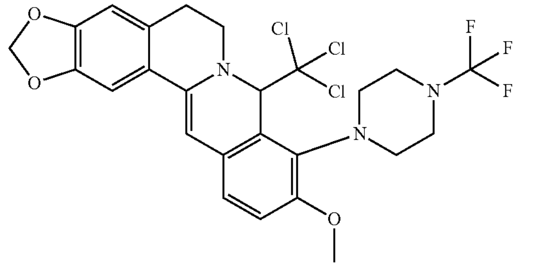
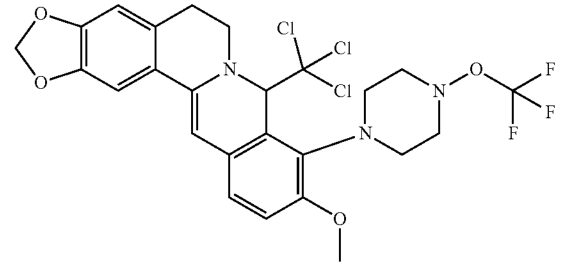
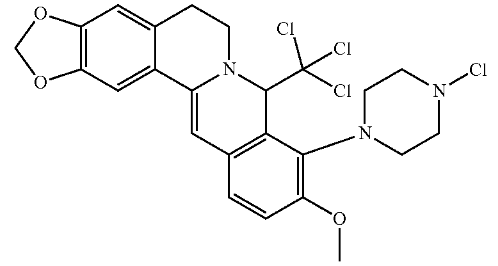
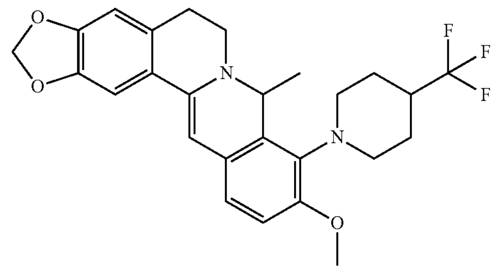
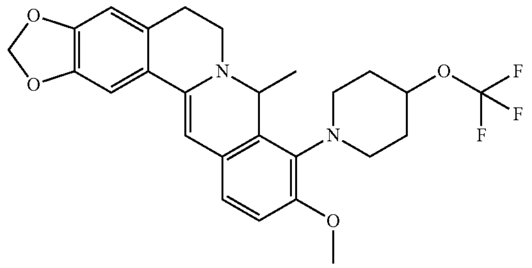
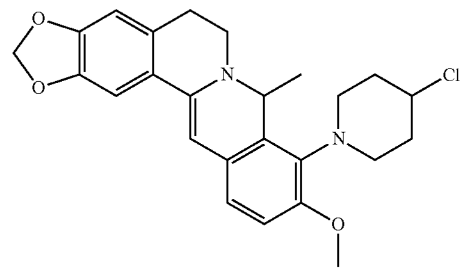
-continued
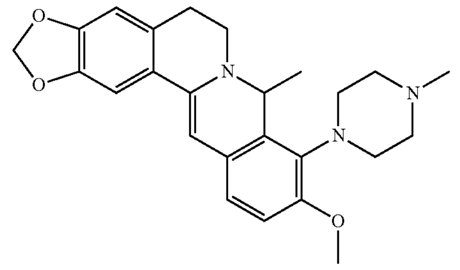
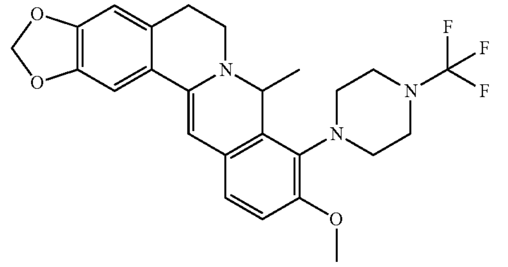
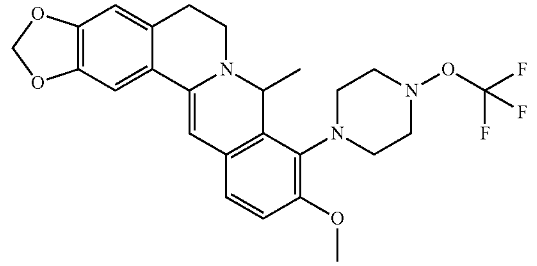
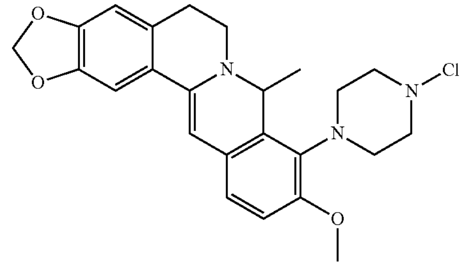
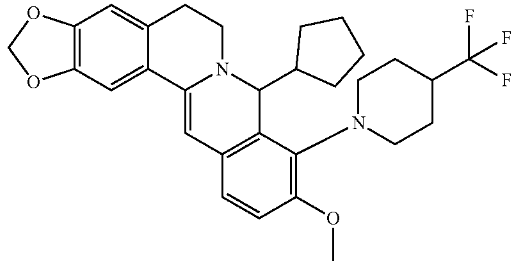
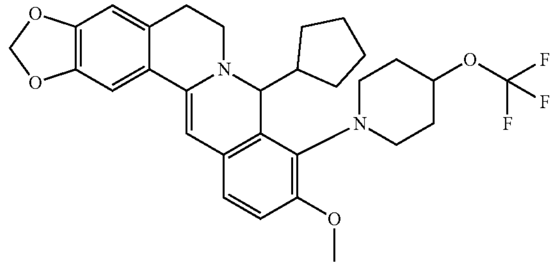

-continued
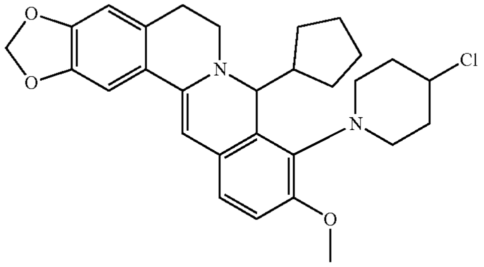
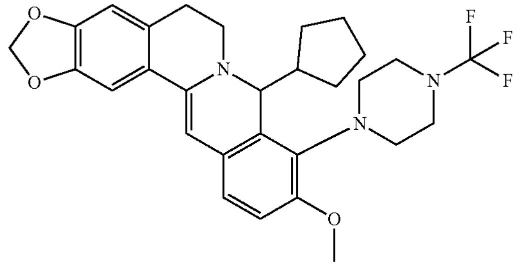
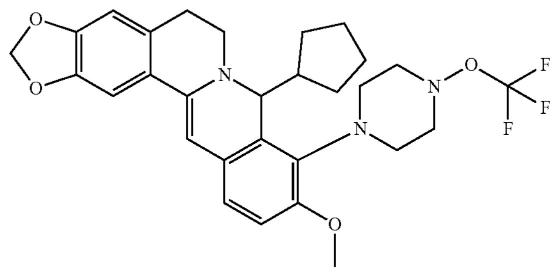
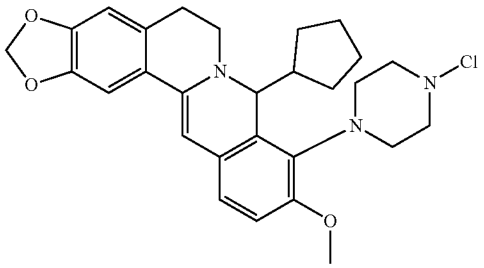
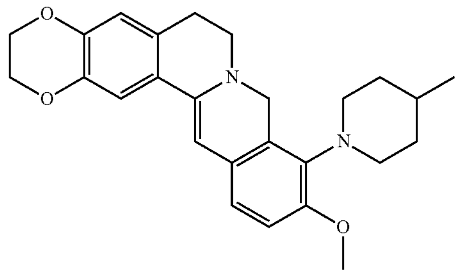
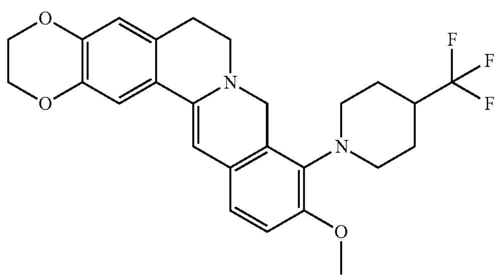
-continued
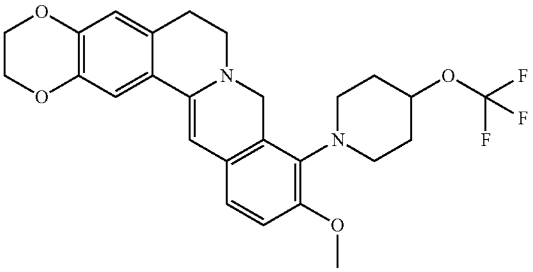
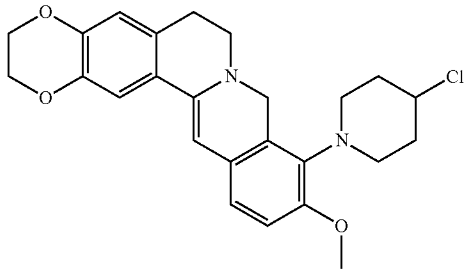
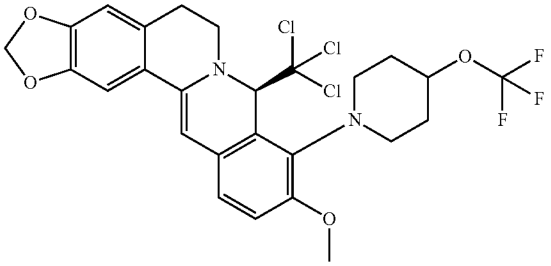
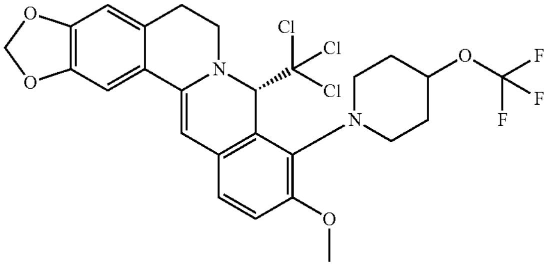
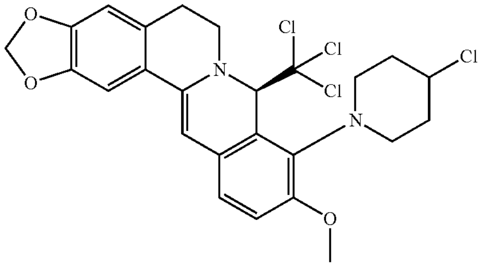
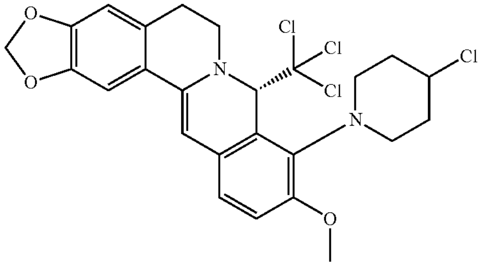

-continued
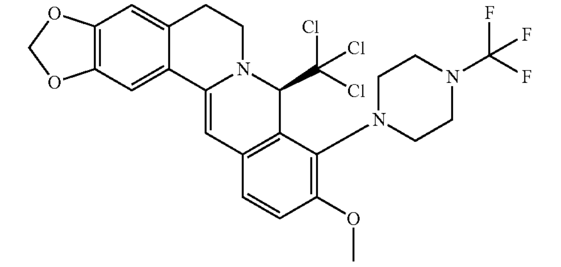
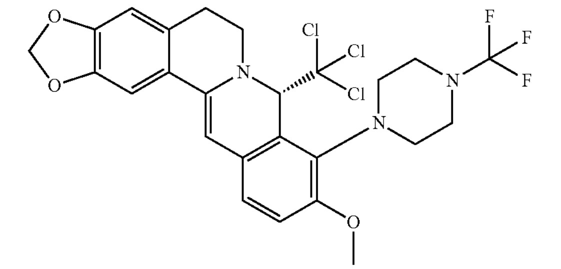
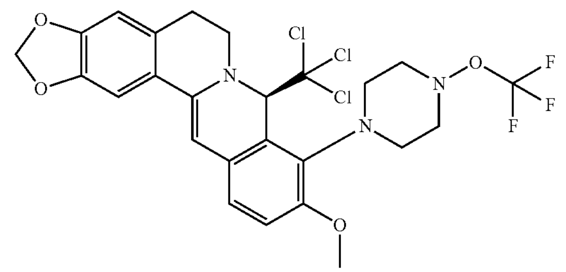
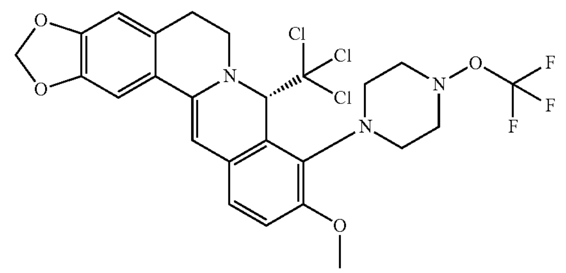
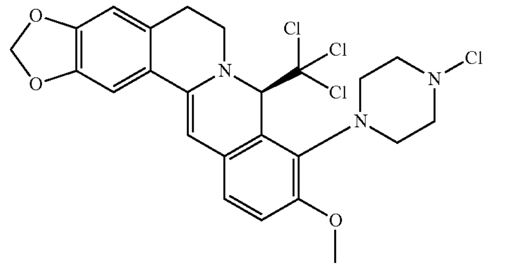
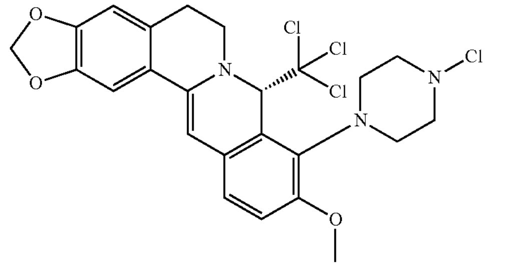
-continued
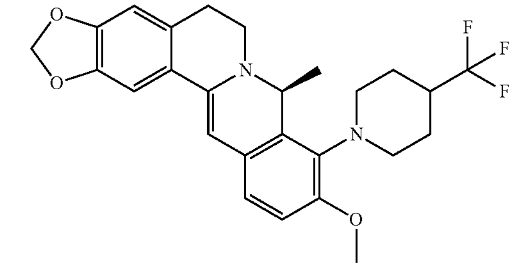
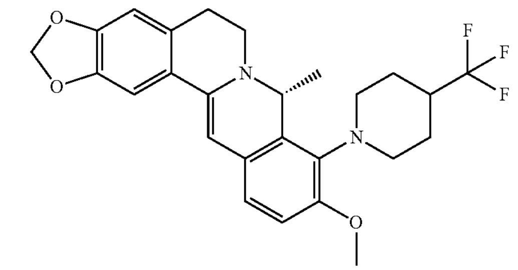
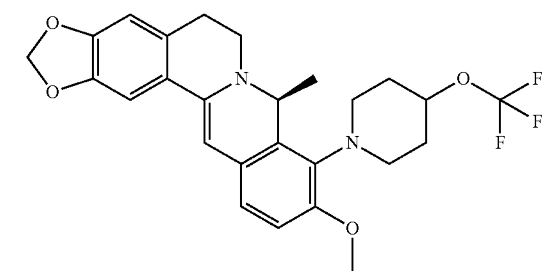
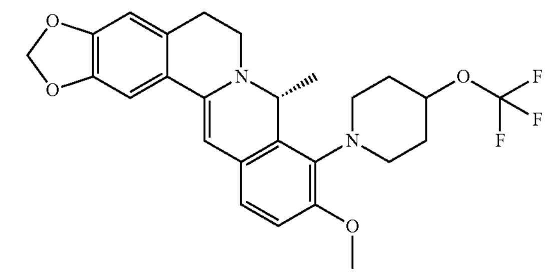
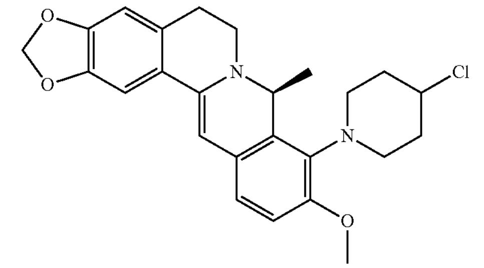
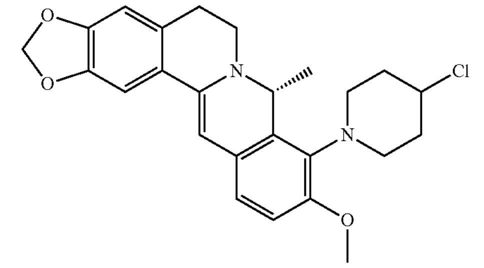

-continued
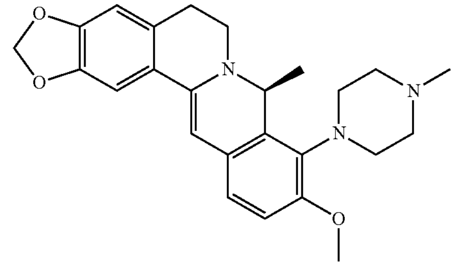
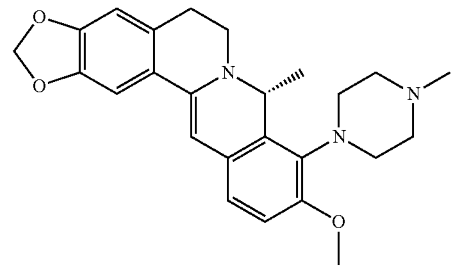
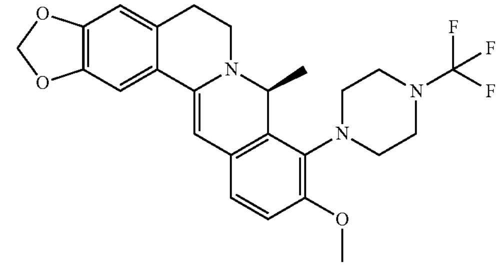
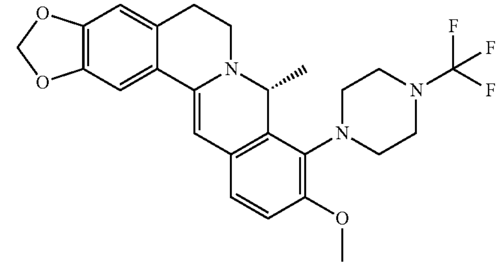
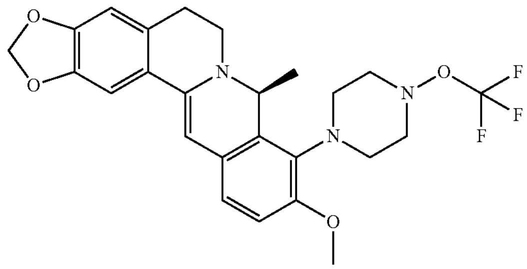
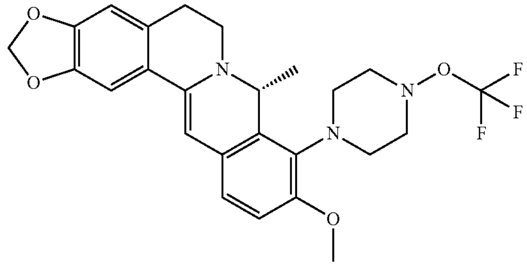
-continued
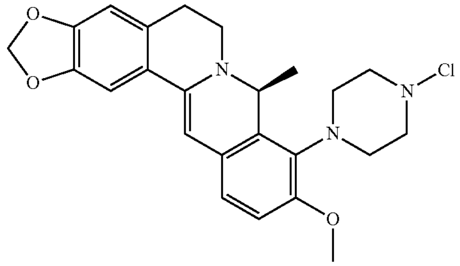
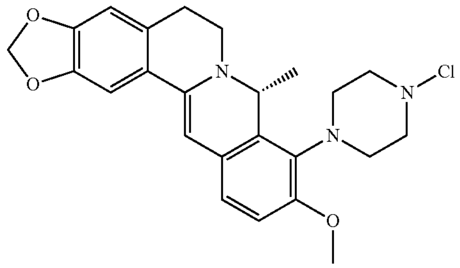
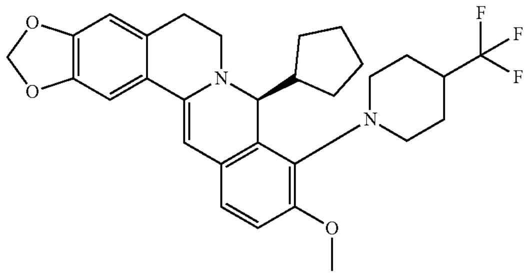
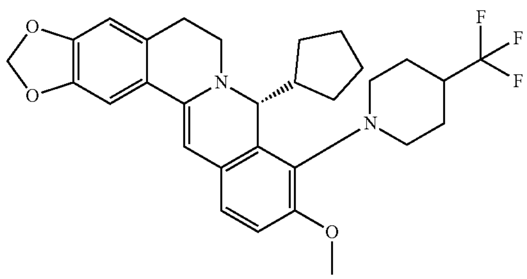
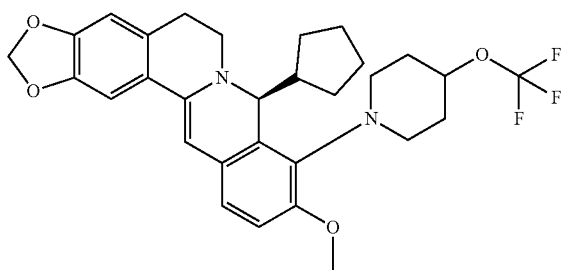
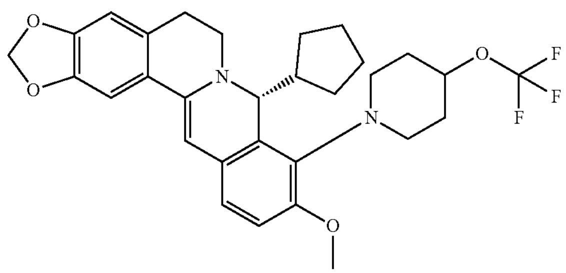

-continued
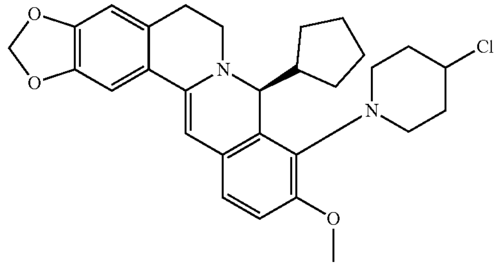
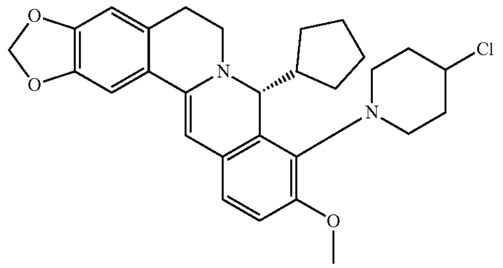
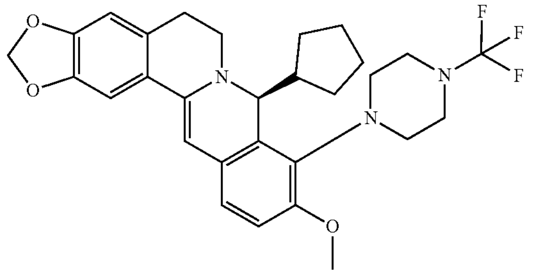
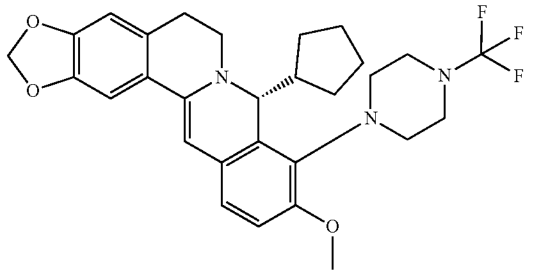
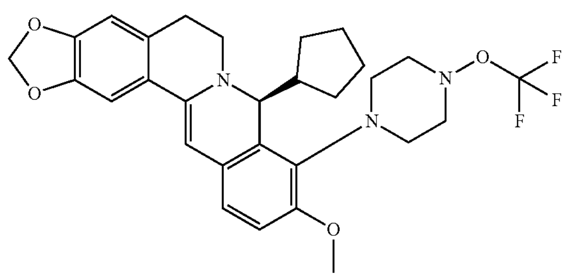
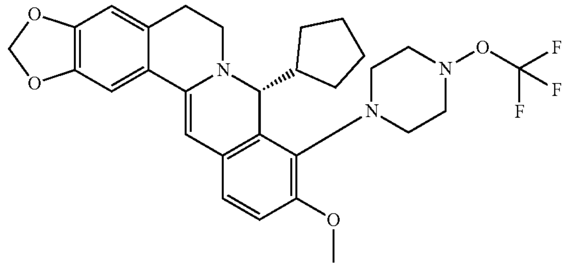
-continued
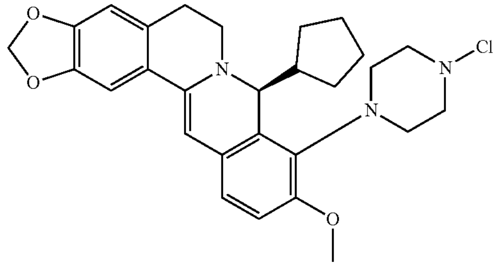
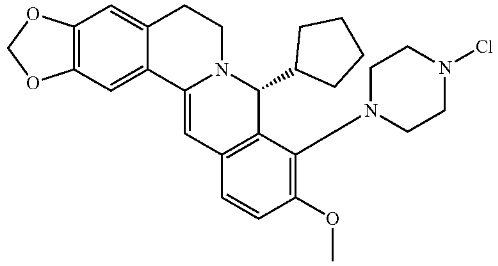
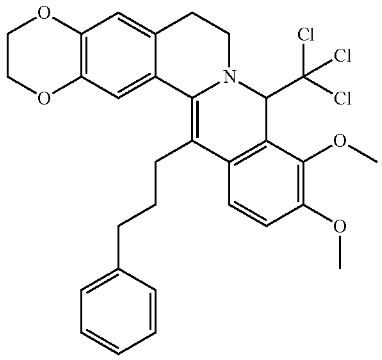
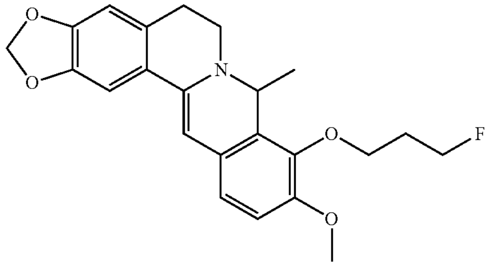
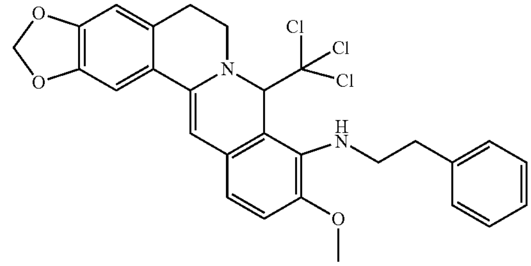
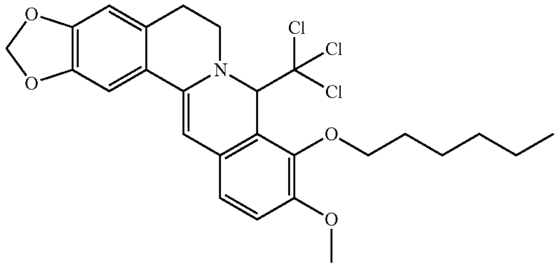

-continued
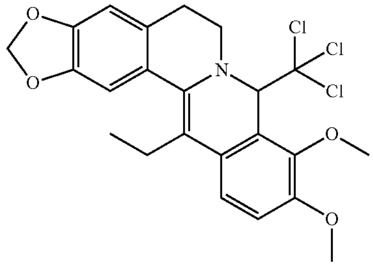
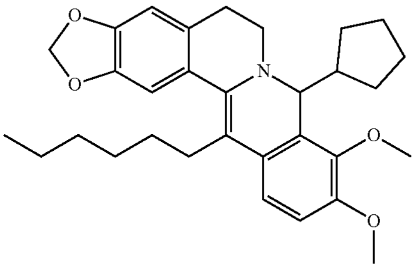
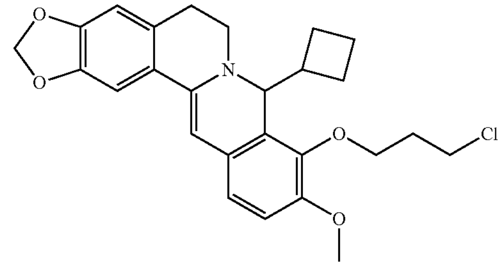
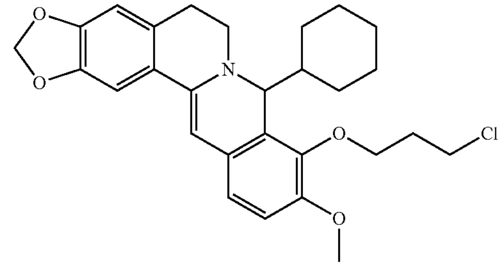
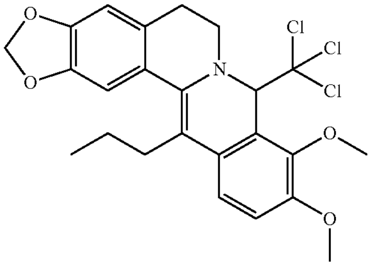
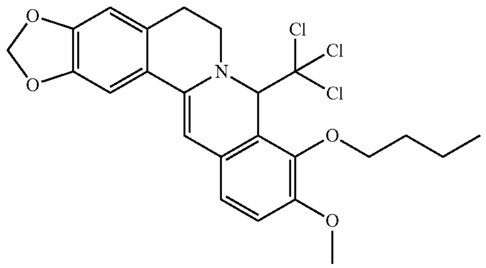
-continued
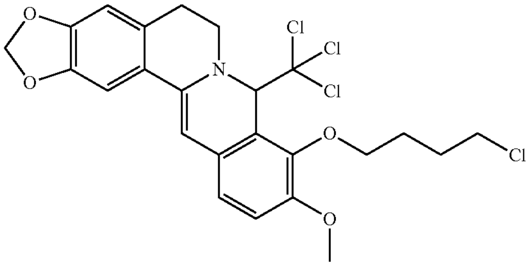
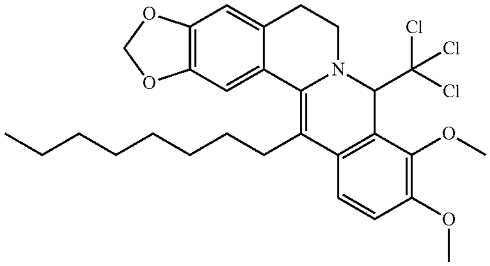
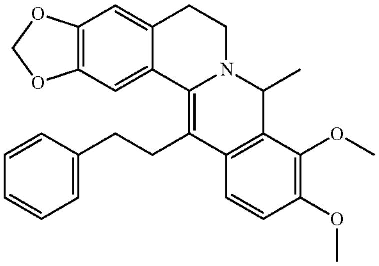
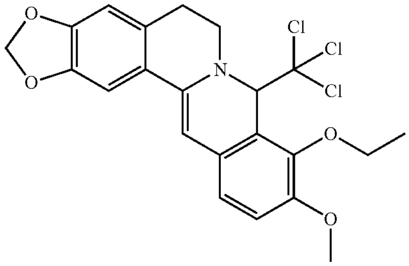
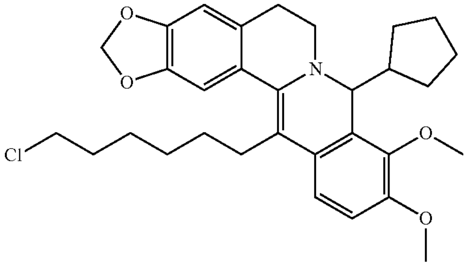
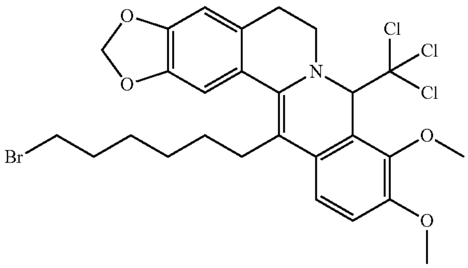

-continued
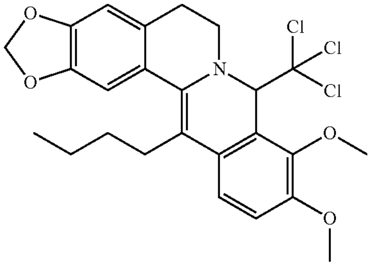
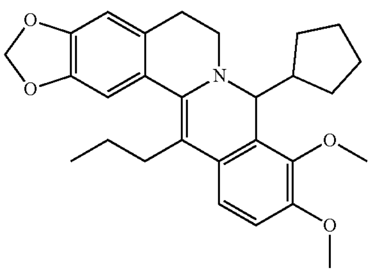
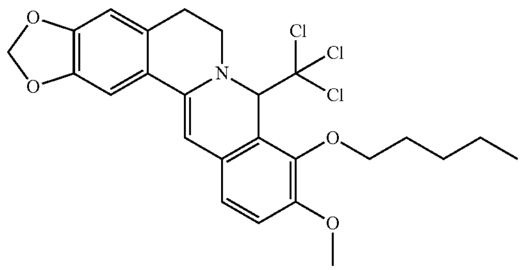
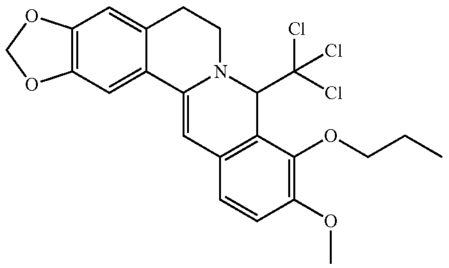
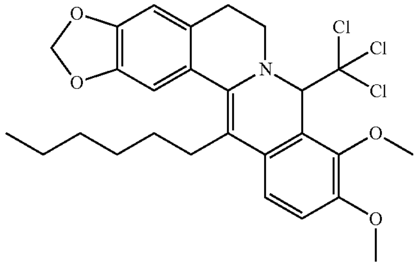
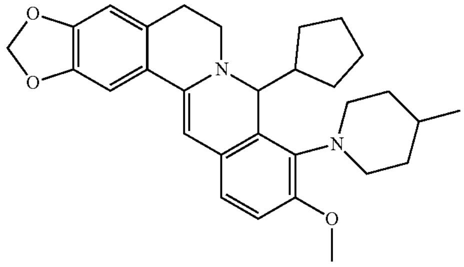
-continued
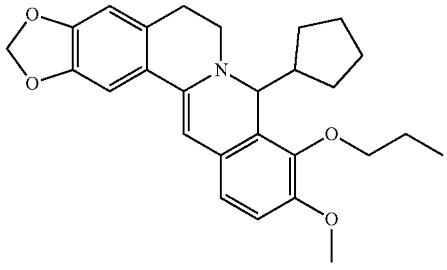
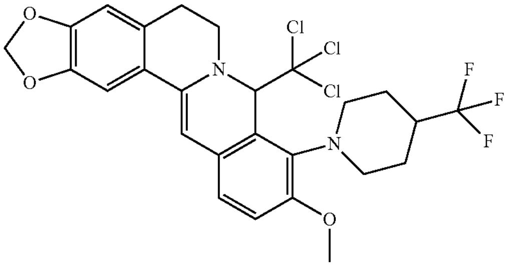 [SMILES: COc1ccc2c(c1N1CCC(C(F)(F)F)CC1)C(C(Cl)(Cl)Cl)N1CCc3cc4c(cc3C1=C2)OCO4]
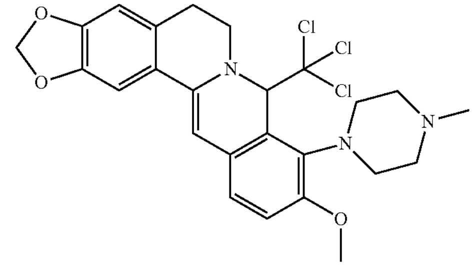
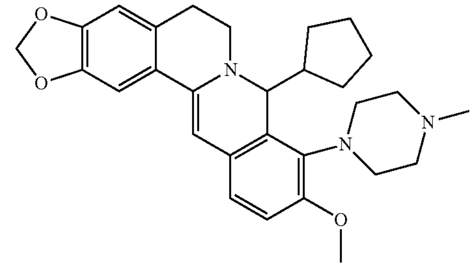
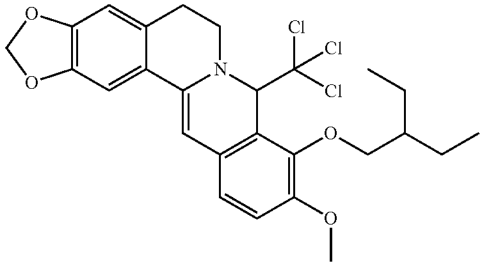
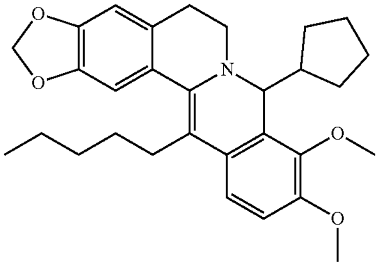

-continued
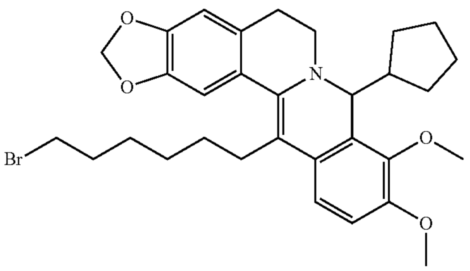
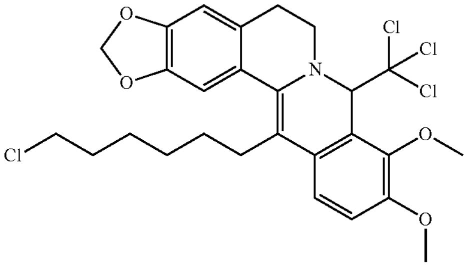
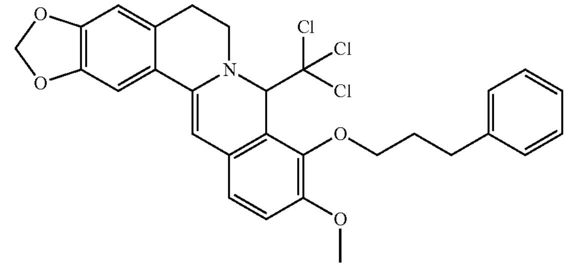
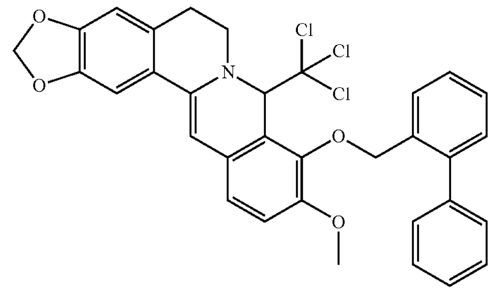
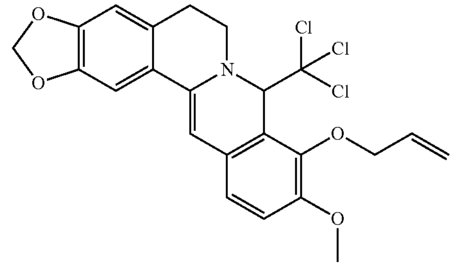
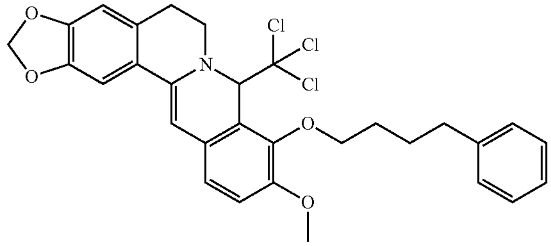
-continued
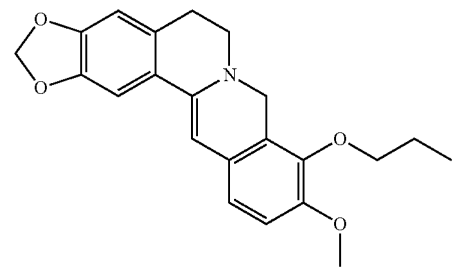
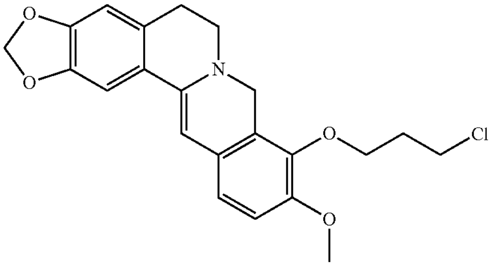
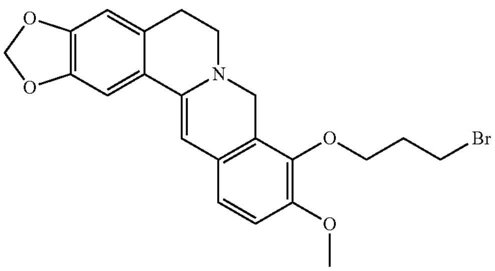
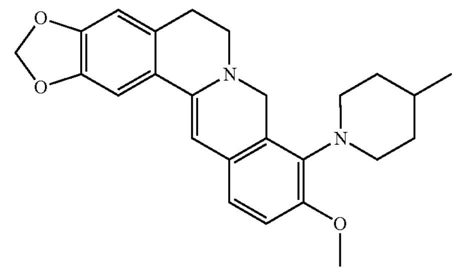
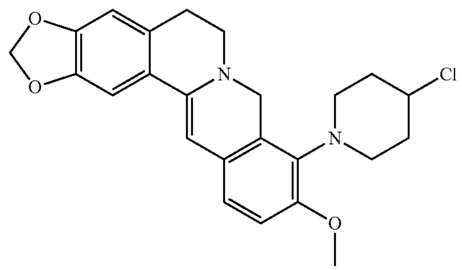
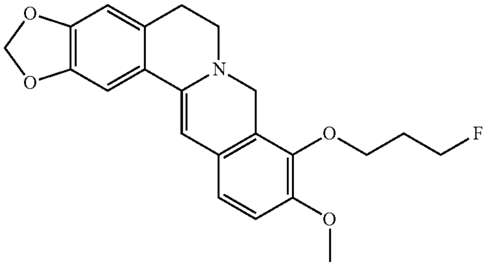

-continued
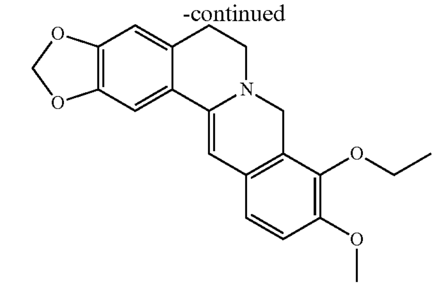
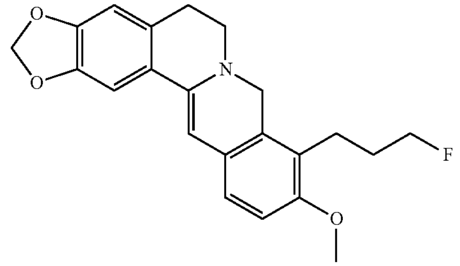
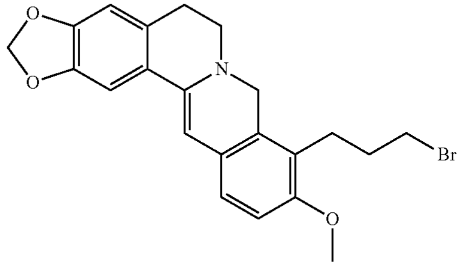
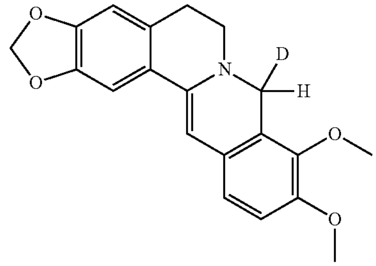
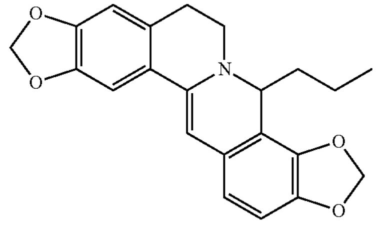
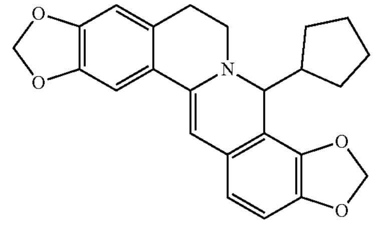
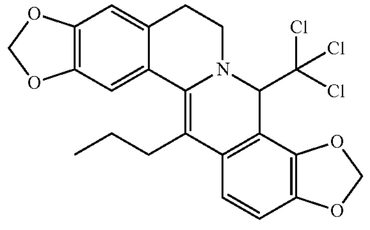
-continued
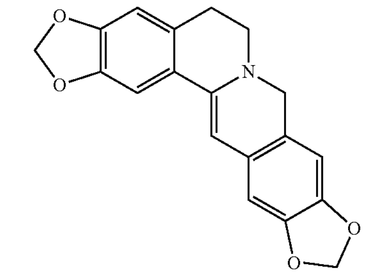
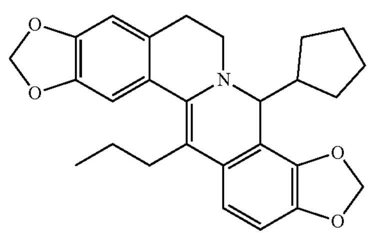
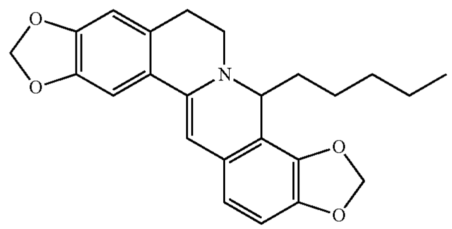
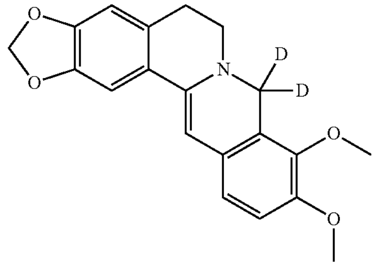
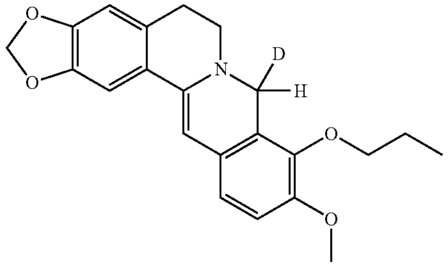
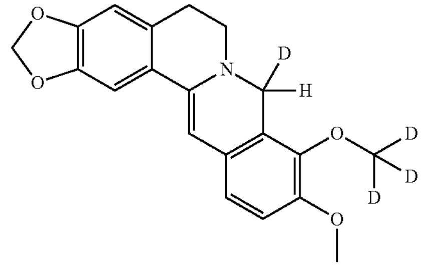

-continued
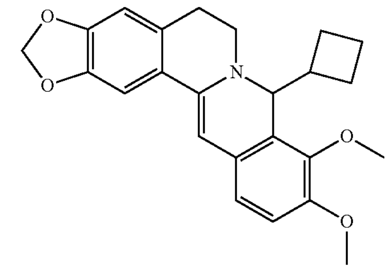
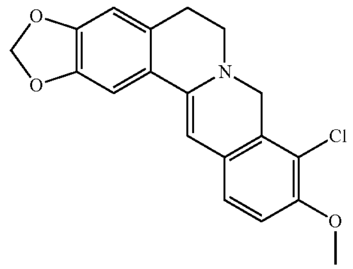
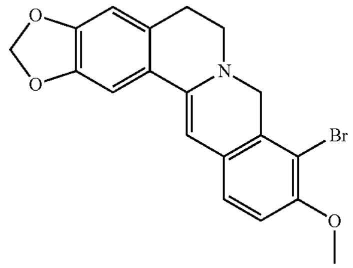
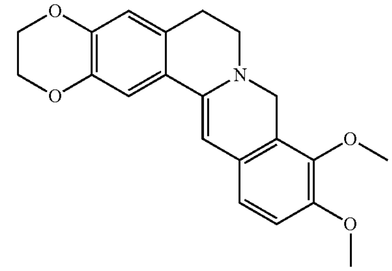
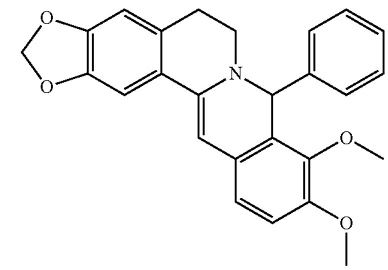
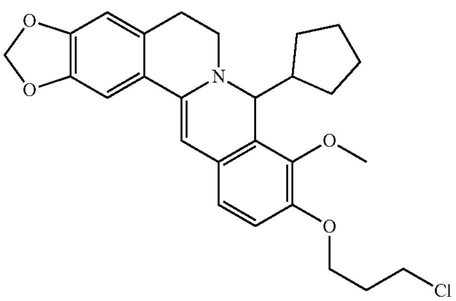
-continued
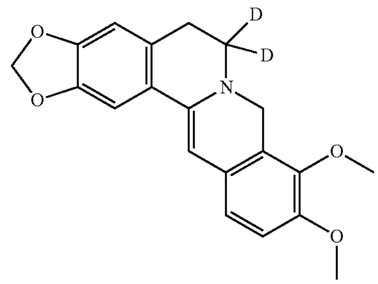
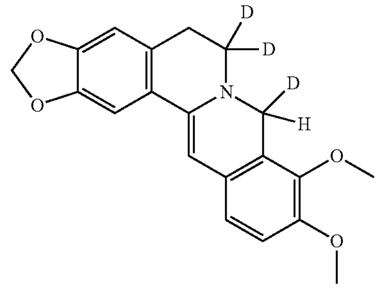
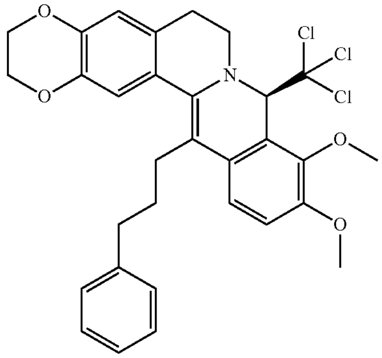
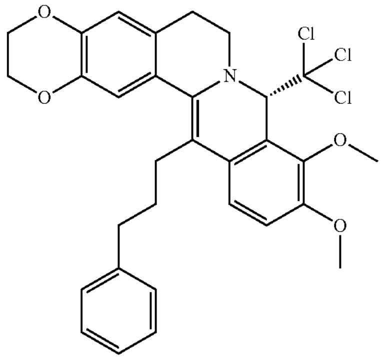
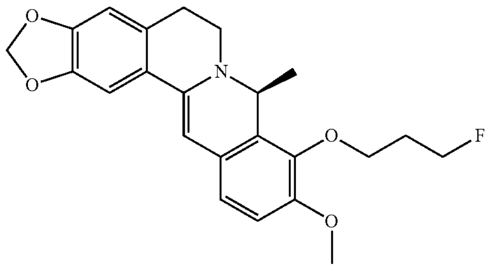

-continued
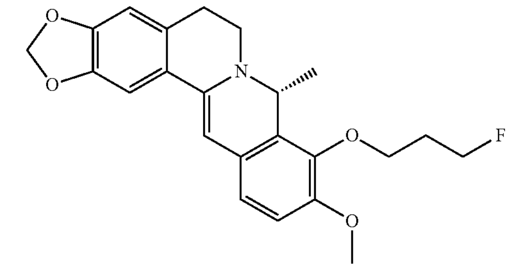
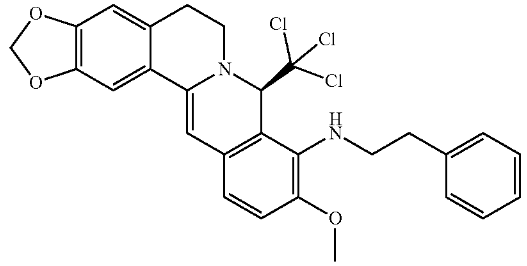
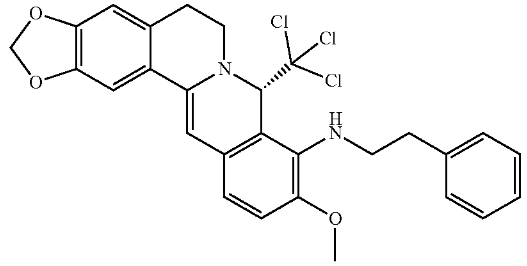
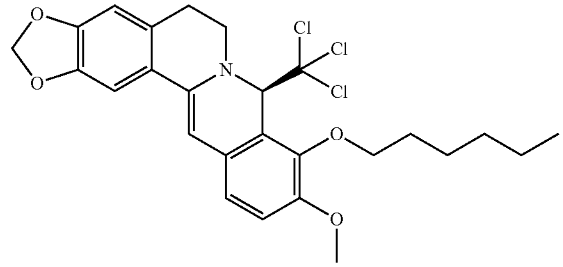
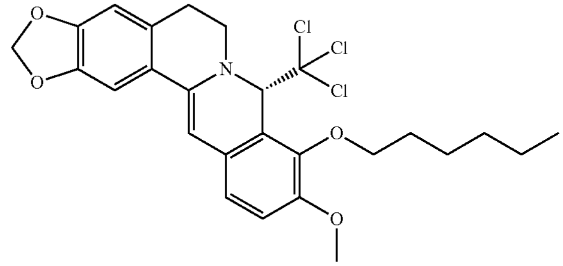
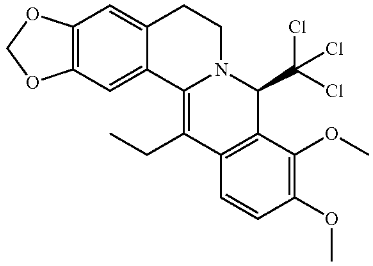
-continued
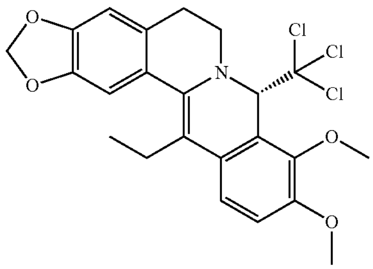
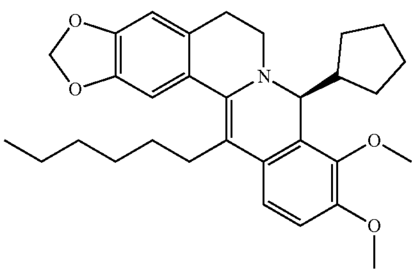
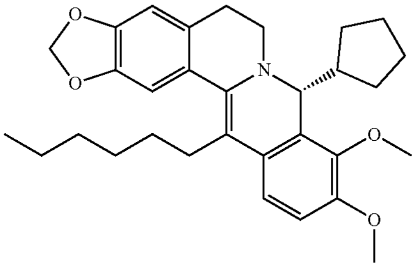
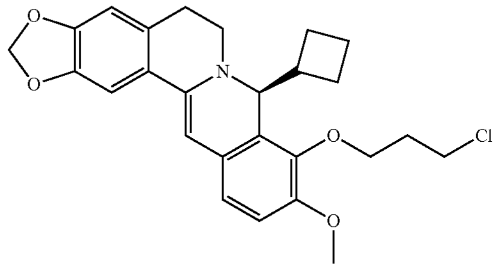
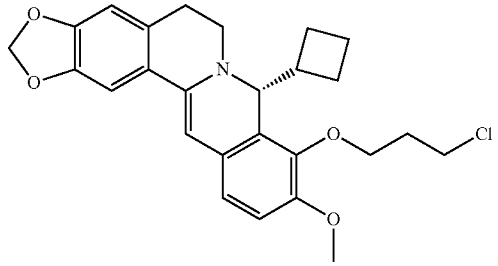
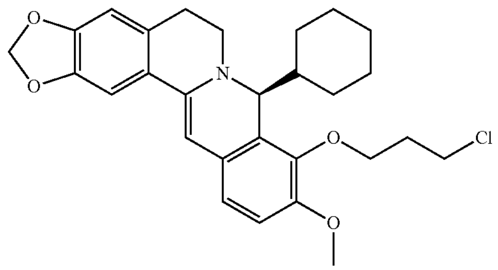

-continued
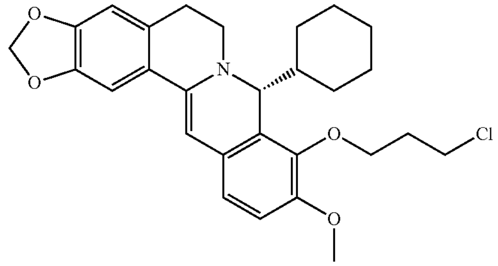
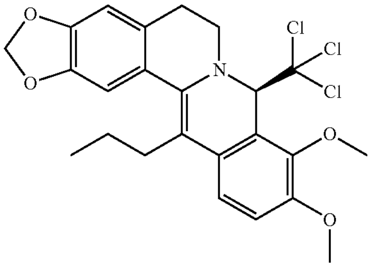
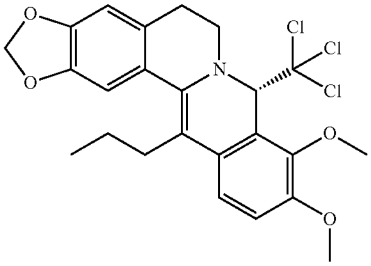
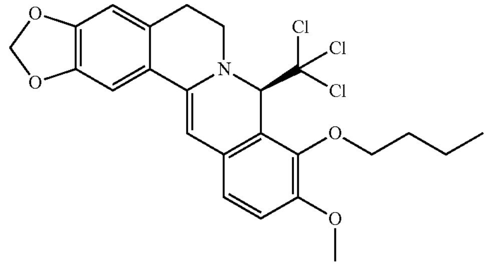
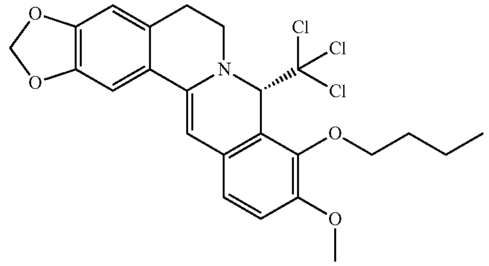
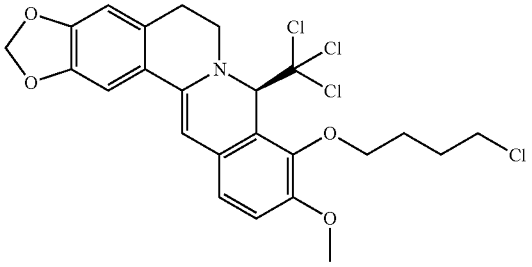
-continued
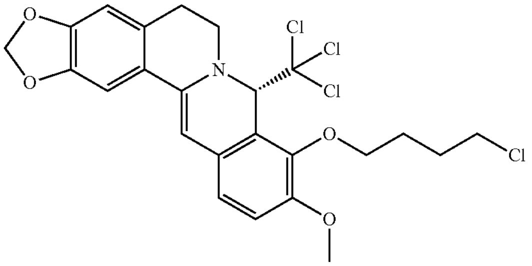
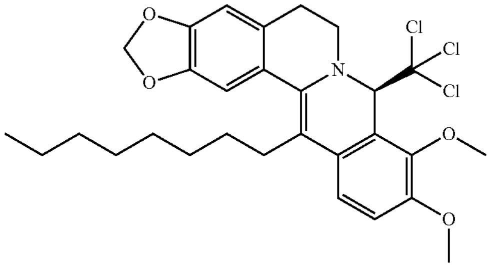
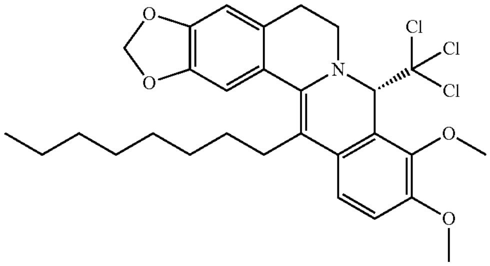
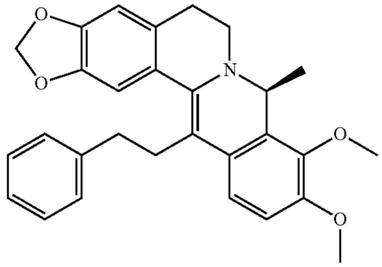
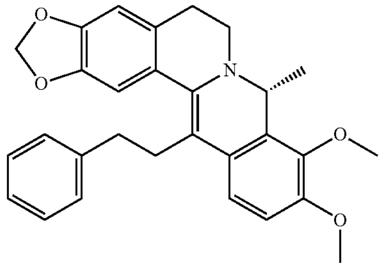
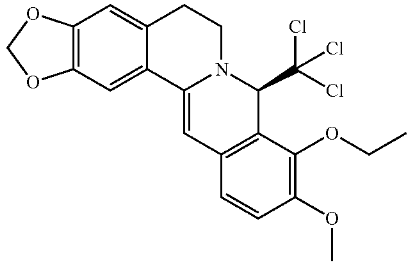

-continued
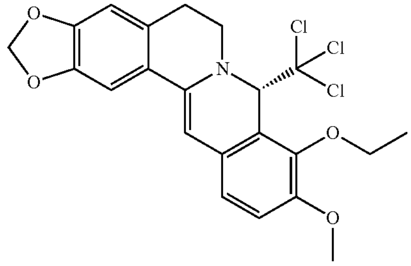
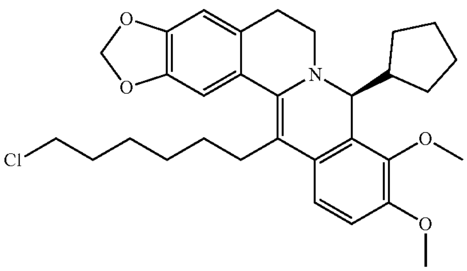
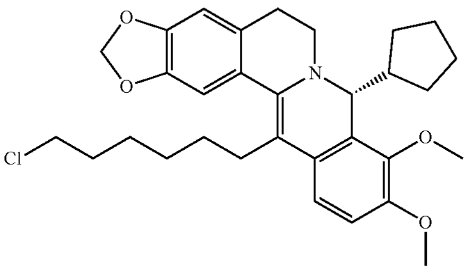
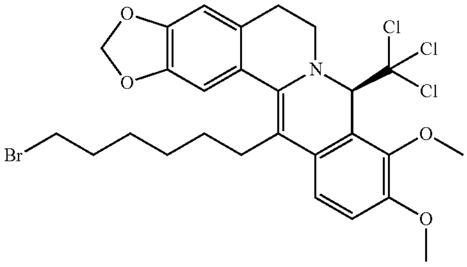
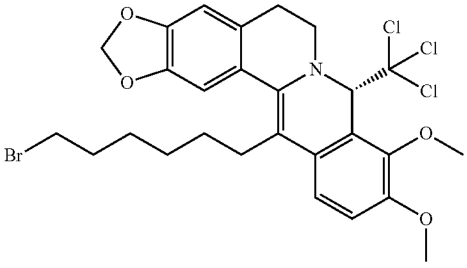
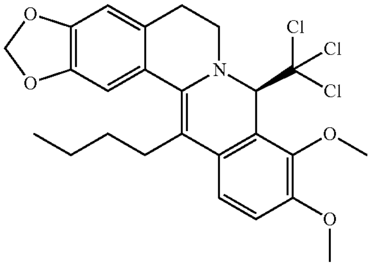
-continued
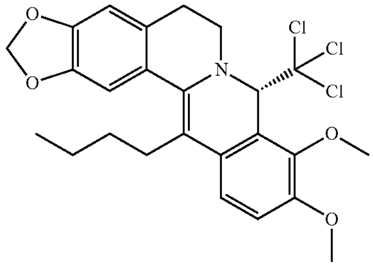
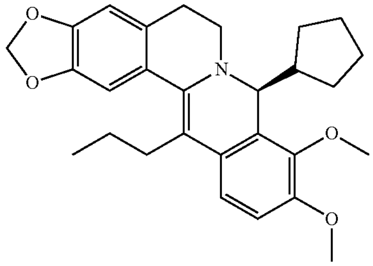
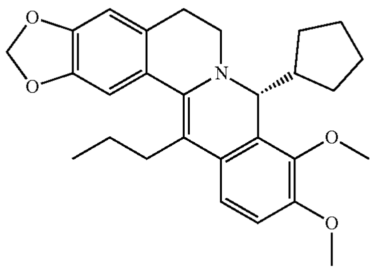
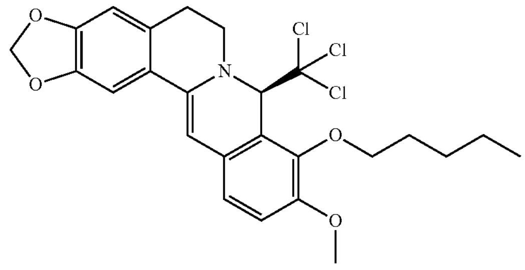
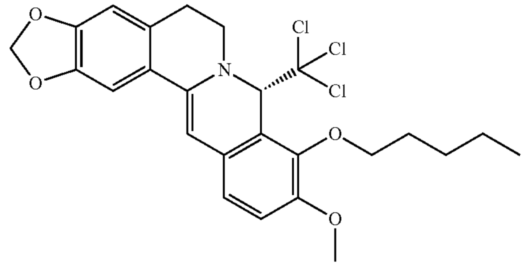
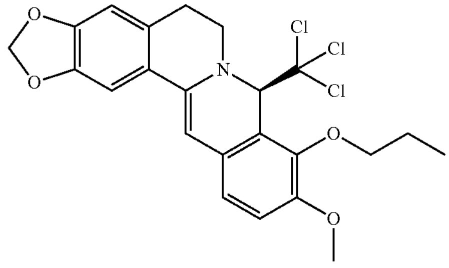

-continued
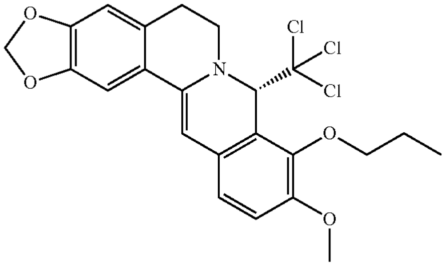
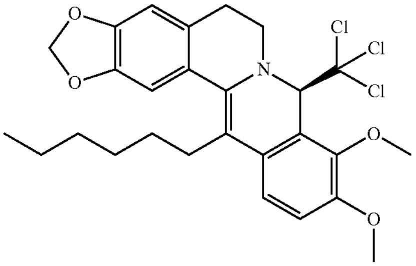
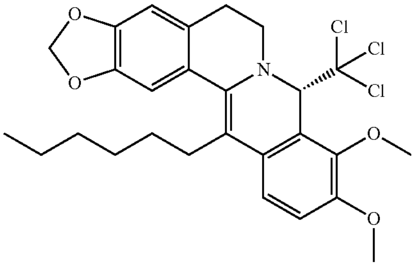
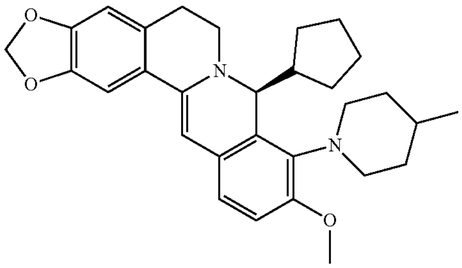
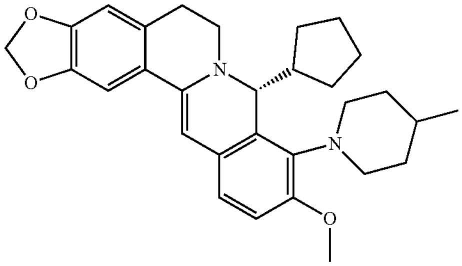
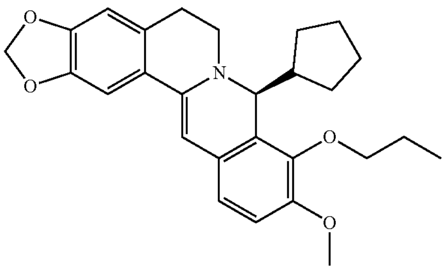
-continued
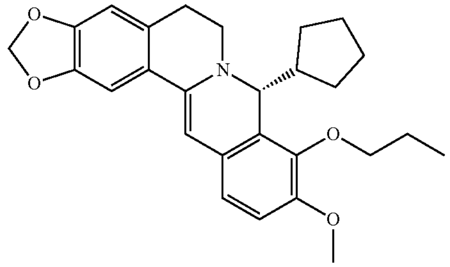
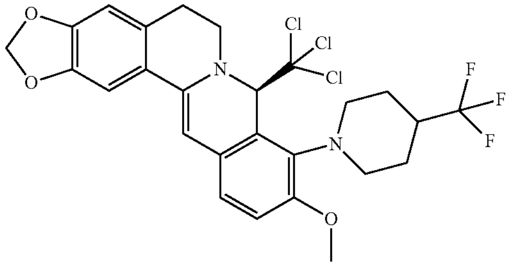
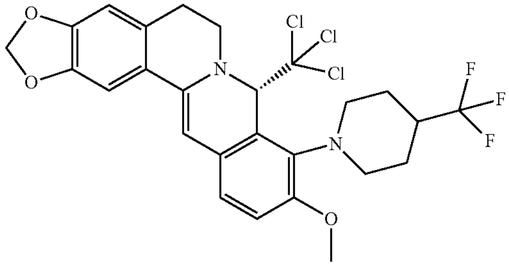
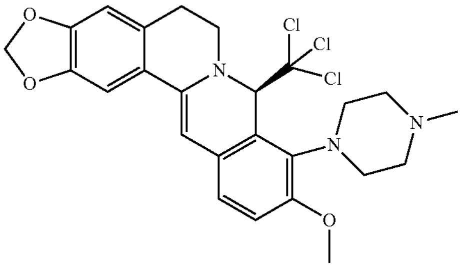
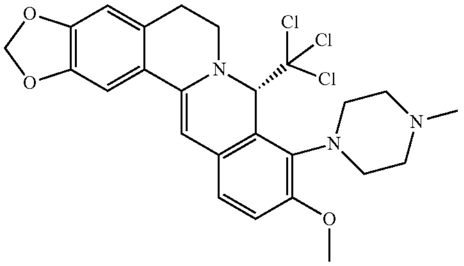
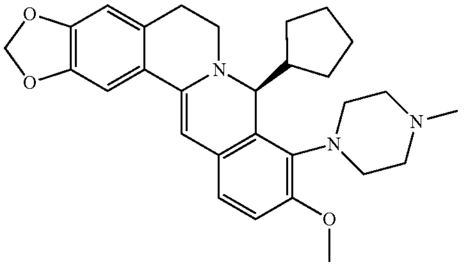

-continued
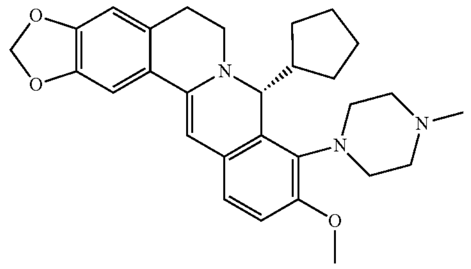
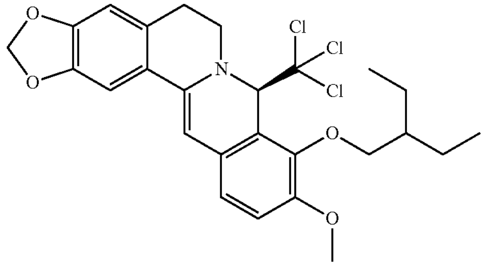
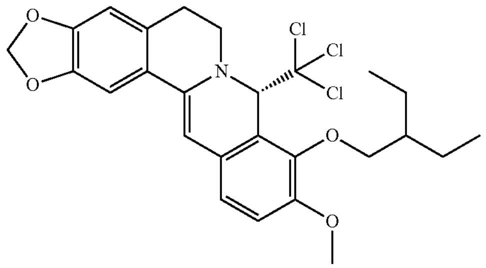
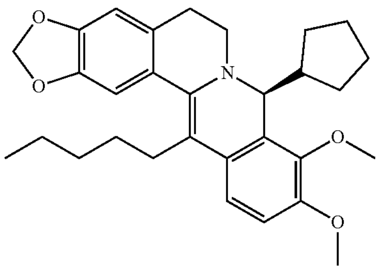
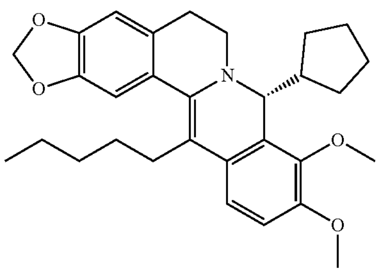
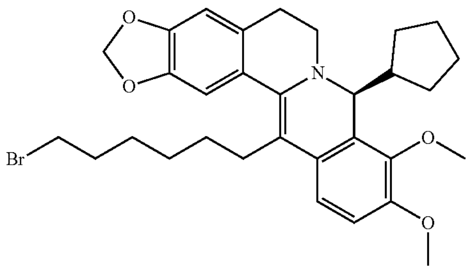
-continued
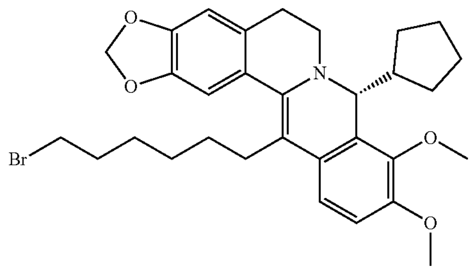
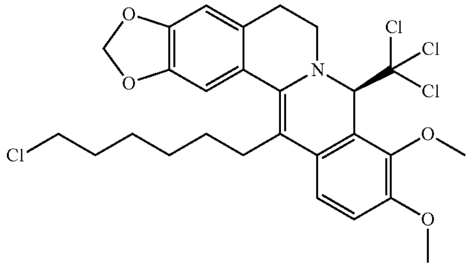
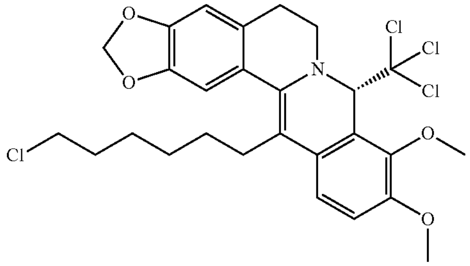
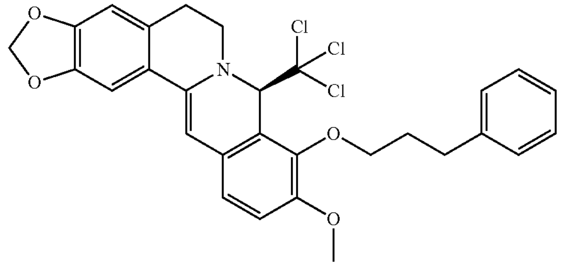
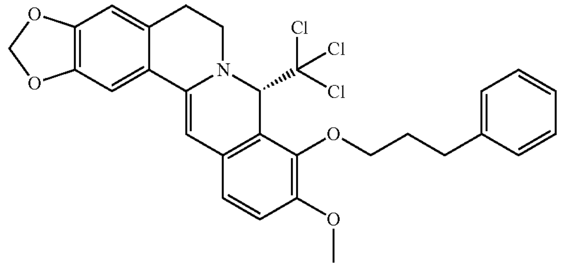
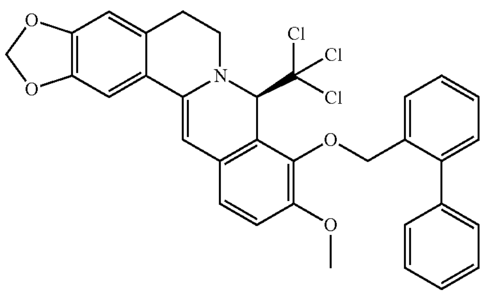

-continued
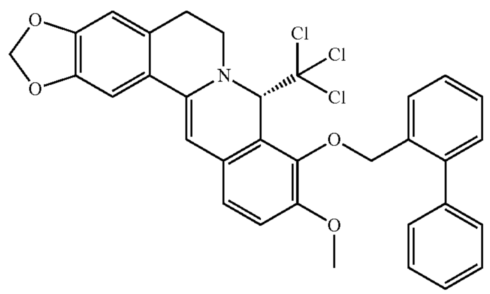
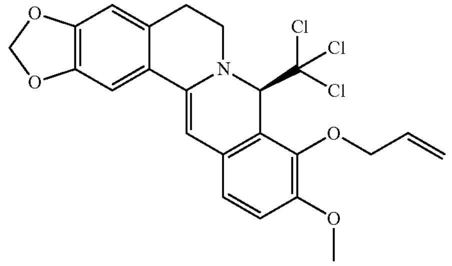
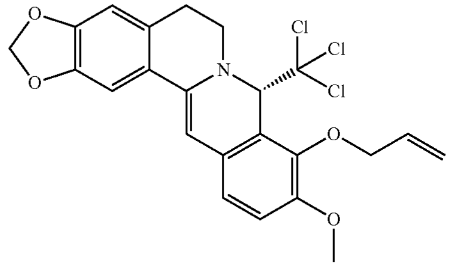
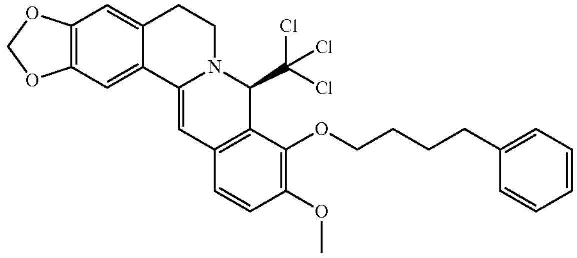
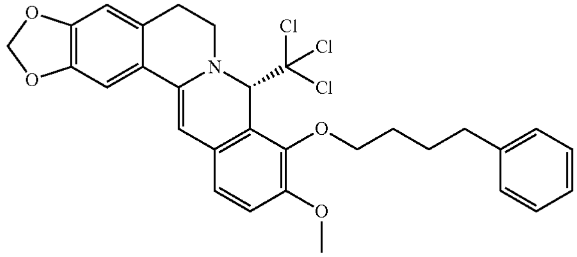
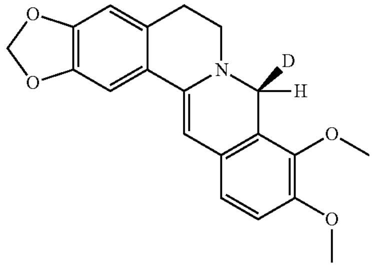
-continued
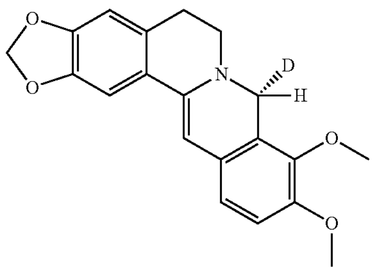
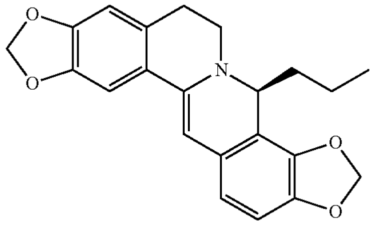
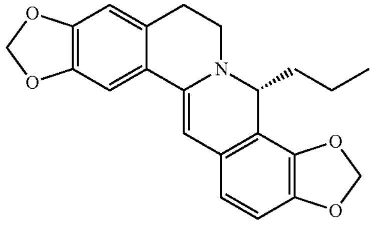
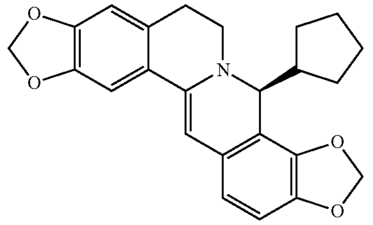
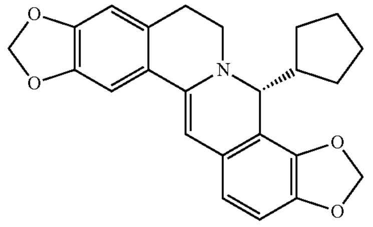
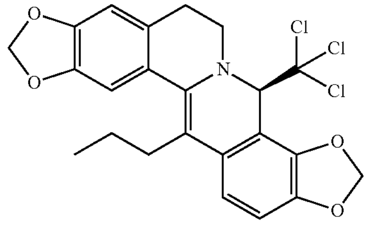
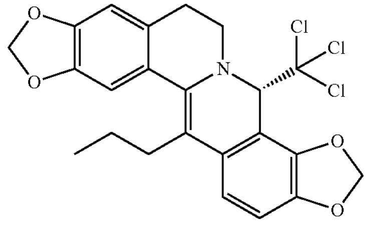

-continued
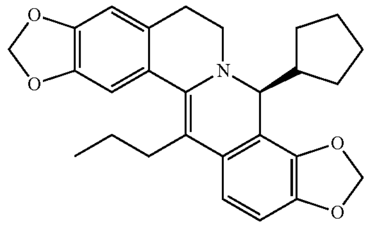
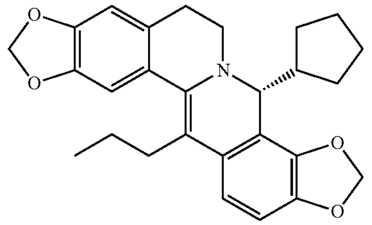
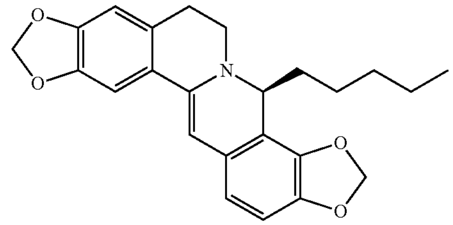
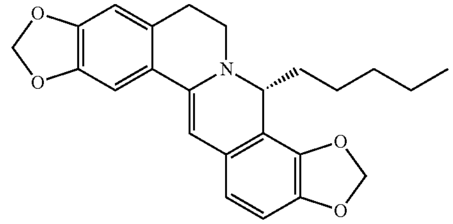
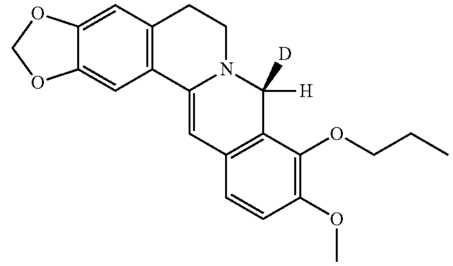
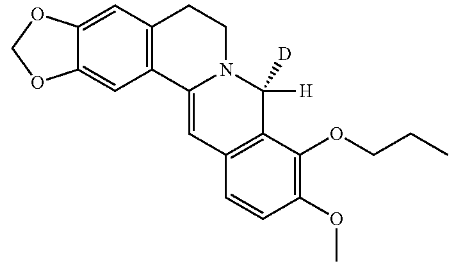
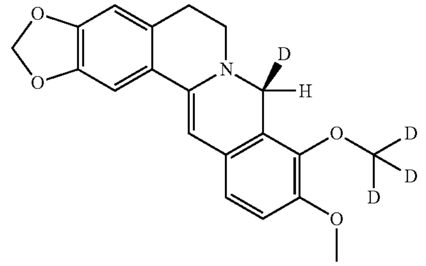
-continued
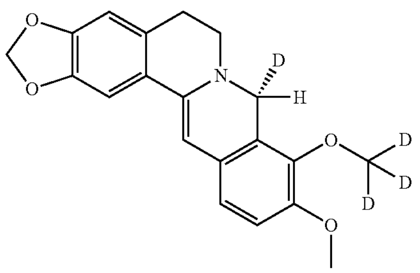
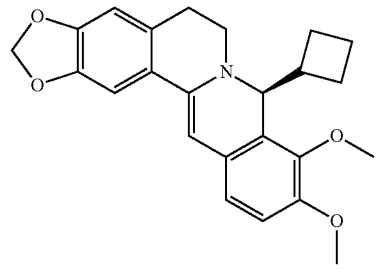
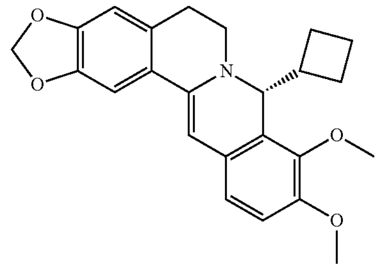
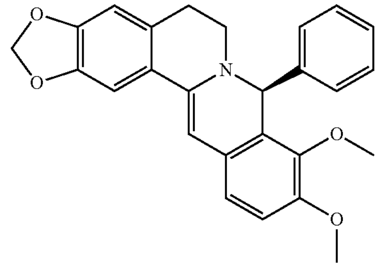
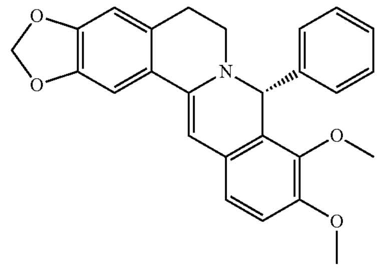
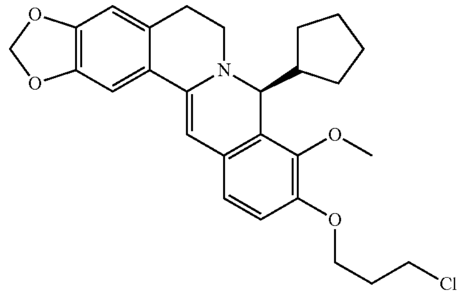

-continued
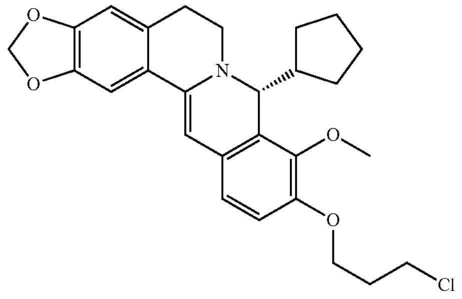
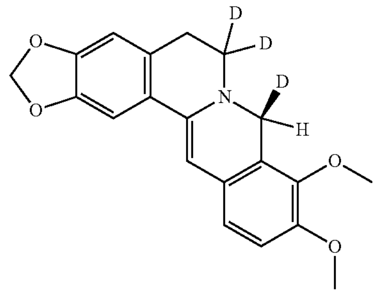
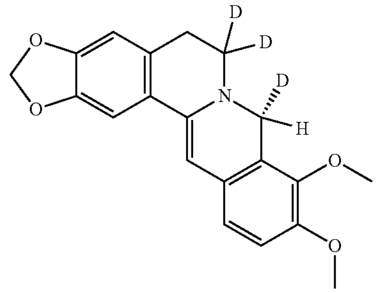
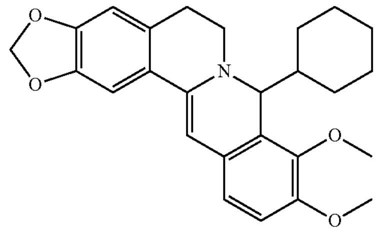
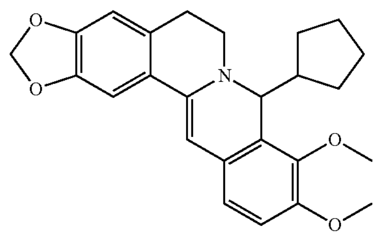
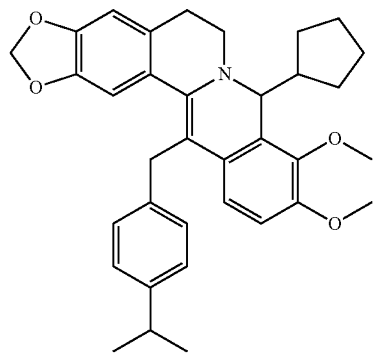
-continued
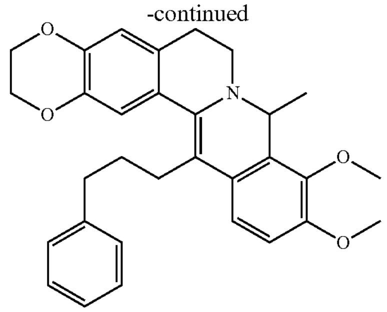
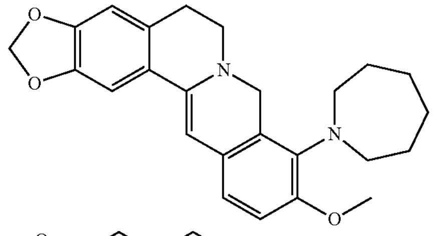
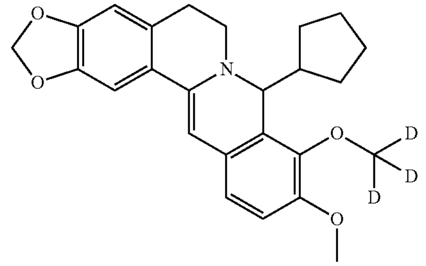
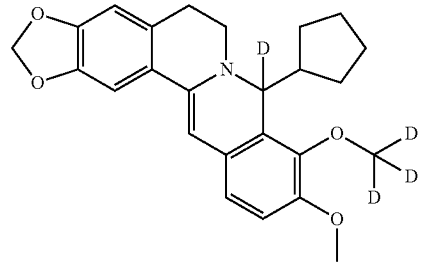
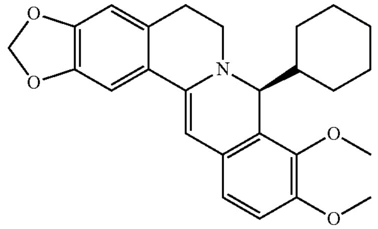
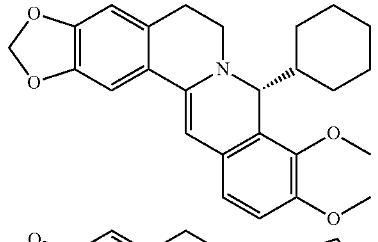
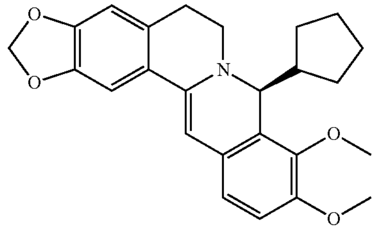

-continued

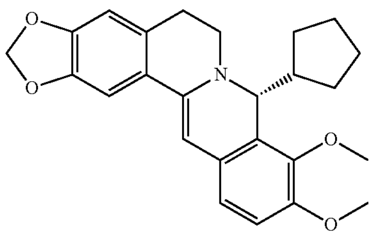

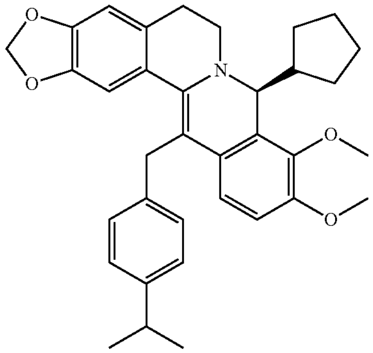

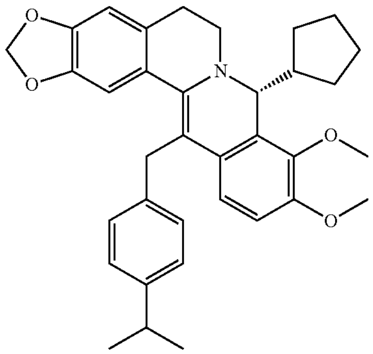

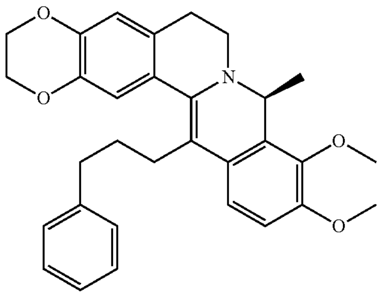

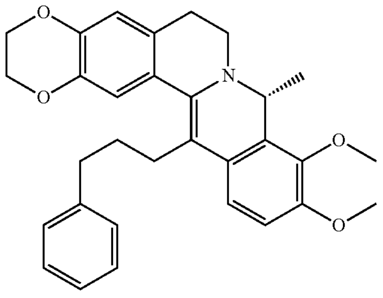

-continued

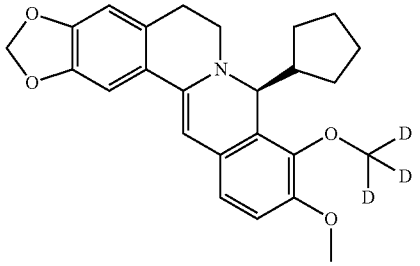

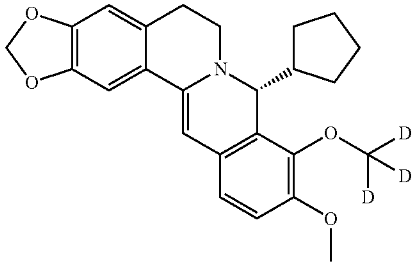

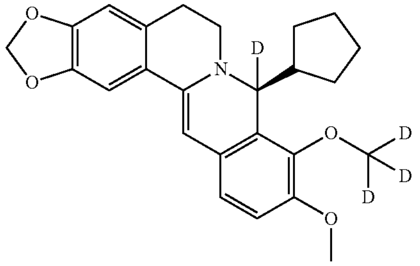

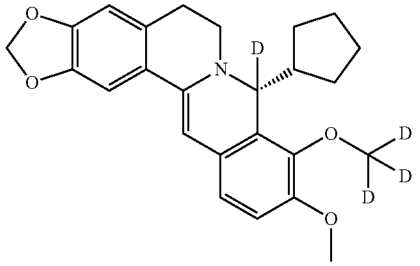

In the second aspect of the present invention, it provides a composition, the composition comprises (a) the compound of formula I, or an optical isomer thereof, or a racemate thereof, or a solvate thereof, or a pharmaceutically acceptable salt thereof, or a deuterated compound thereof according to the first aspect of the present invention; and (b) a pharmaceutically acceptable carrier.

In another preferred embodiment, the content of the (a) the compound of formula I, or an optical isomer thereof, or a racemate thereof, or a solvate thereof, or a pharmaceutically acceptable salt thereof, or a deuterated compound thereof according to the first aspect of the present invention is 0.001-99.9 wt %, based on the weight of the composition.

In another preferred embodiment, the composition is pharmaceutical composition.

In another preferred embodiment, the composition further comprises a pharmaceutically acceptable carrier.

In another preferred embodiment, the dosage form of the composition is a solid preparation, liquid preparation or semi-solid preparation.

In another preferred embodiment, the dosage form of the composition is oral preparation, external preparation or injection preparation.

In another preferred embodiment, the injection preparation is intravenous injection preparation.

In another preferred embodiment, the dosage form of the composition is tablet, injection, infusion, paste, gel, solution, microsphere or film.

In the third aspect of the present invention, it provides a use of the compound of formula I, or an optical isomer thereof, or a racemate thereof, or a solvate thereof, or a pharmaceutically acceptable salt thereof, or a deuterated compound thereof according to the first aspect of the present invention in the preparation of a composition or a preparation for preventing and/or treating tumor.

In another preferred embodiment, the tumor is human-derived tumor.

In another preferred embodiment, the tumor is human tumor.

In another preferred embodiment, the tumor comprises tumor with low or no expression of NNMT gene.

In another preferred embodiment, the tumor comprises tumor with high expression of DNA methylase.

In another preferred embodiment, the DNA methylase is selected from the group consisting of DNMT1, DNMT3a, DNMT3b, and combinations thereof.

In another preferred embodiment, the tumor comprises tumor with high expression of DNMT1.

In another preferred embodiment, the tumor comprises tumor with high expression of DNMT3a.

In another preferred embodiment, the tumor comprises tumor with high expression of DNMT3b.

In another preferred embodiment, the tumor comprises tumor with high expression of UHRF1.

In another preferred embodiment, the tumor comprises tumor with high methylation level of nucleotide site of NNMT gene and/or high methylation level of DNA CpG site of NNMT gene.

In another preferred embodiment, the tumor comprises tumor with high methylation level of nucleotide site of NNMT gene.

In another preferred embodiment, the methylation of nucleotide site of NNMT gene comprises the methylation of cytosine nucleotide site of NNMT gene.

In another preferred embodiment, the methylation of nucleotide site of NNMT gene comprises the methylation of cytosine of NNMT gene.

In another preferred embodiment, the methylation of nucleotide site of NNMT gene comprises the methylation of the 5' carbon atom on the cytosine of the NNMT gene.

In another preferred embodiment, the tumor comprises tumor with high methylation level of DNA CpG site of NNMT gene.

In another preferred embodiment, the methylation of DNA CpG site of NNMT gene comprises the methylation of cytosine nucleotide site of DNA CpG site of NNMT gene.

In another preferred embodiment, the methylation of DNA CpG site of NNMT gene comprises the methylation of cytosine of DNA CpG site of NNMT gene.

In another preferred embodiment, the methylation of DNA CpG site of NNMT gene comprises the methylation of the 5' carbon atom on the cytosine of DNA CpG site of NNMT gene.

In another preferred embodiment, the NNMT gene is human-derived NNMT gene.

In another preferred embodiment, the NNMT gene is human NNMT gene.

In another preferred embodiment, the tumor with low or no expression of NNMT gene means that no NNMT protein can be detected in 1 μg of protein extracted from tumor using NNMT antibody, preferably in 5 μg of protein extracted from tumor, more preferably in 10 μg of protein extracted from tumor, more preferably in 100 μg of protein extracted from tumor, preferably in 1000 μg of protein extracted from tumor.

In another preferred embodiment, the tumor with low or no expression of NNMT gene means the expression level of NNMT gene in tumor cell is lower than that in the same type of cell or a normal cell.

In another preferred embodiment, the tumor with low or no expression of NNMT gene means the ratio (E1/E0) of the expression level E1 of NNMT gene in the tumor cell to the expression level E0 of NNMT gene in the same type of cell or a normal cell is $<1.0$.

In another preferred embodiment, the low or no expression of NNMT gene means the ratio (E1/E0) of the expression E1 of NNMT gene in a cell (e.g., tumor cell) to the expression E0 of NNMT gene in the same type of cell or a normal cell is $<1.0$, preferably $\leq 0.7$, more preferably $\leq 0.6$, more preferably $\leq 0.5$, more preferably $\leq 0.4$, more preferably $\leq 0.3$, more preferably $\leq 0.2$, more preferably $\leq 0.1$, more preferably $\leq 0.05$, more preferably $\leq 0.01$, more preferably $\leq 0.005$, more preferably $\leq 0.001$, more preferably $\leq 0.0001$, more preferably $\leq 0.00001$, more preferably $\leq 0.000001$, more preferably $\leq 0.0000001$.

In another preferred embodiment, the cell comprises tumor cell.

In another preferred embodiment, the same type of cell comprises the same type of tumor cell.

In another preferred embodiment, the same type of cell comprises the cell (e.g., the same type of tumor cell) with normal or high expression of NNMT gene.

In another preferred embodiment, the same type of cell comprises the same type of cell (e.g., the same type of tumor cell) with normal or high expression of NNMT gene.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal expression of NNMT gene.

In another preferred embodiment, E0 refers to the expression level of NNMT gene in the cell with normal or high expression of NNMT gene.

In another preferred embodiment, the cell with normal or high expression of NNMT gene comprises the cell that is not sensitive to the compound of formula I, or an optical isomer thereof, or a racemate thereof, or a solvate thereof, or a pharmaceutically acceptable salt thereof, or a deuterated compound thereof In another preferred embodiment, the tumor with high expression of DNA methylase means that DNA methylase can be detected in 20 μg of protein extracted from tumor using DNA methylase antibody, preferably in 5 μg of protein extracted from tumor, more preferably in 1 μg of protein extracted from tumor, more preferably in 0.2 μg of protein extracted from tumor, more preferably in 0.05 μg of protein extracted from tumor, more preferably in 0.01 μg of protein extracted from tumor.

In another preferred embodiment, the tumor with high expression of DNA methylase means the expression level of DNA methylase in tumor cell is higher than that in the same type of cell or a normal cell.

In another preferred embodiment, the tumor with high expression of DNA methylase means the ratio (A1/A0) of the expression level A1 of DNA methylase in the tumor cell to the expression level A0 of DNA methylase in the same type of cell or a normal cell is $>1.0$, preferably $\geq 1.2$, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the same type of cell comprises the same type of tumor cell.

In another preferred embodiment, the same type of cell comprises the cell (e.g., the same type of tumor cell) with normal or low expression of DNA methylase.

In another preferred embodiment, the same type of cell comprises the same type of cell (e.g., the same type of tumor cell) with normal or low expression of DNA methylase.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal expression of DNA methylase.

In another preferred embodiment, A0 refers to the expression level of DNA methylase in the cell with normal or low expression of DNA methylase.

In another preferred embodiment, the cell with normal or low expression of DNA methylase comprises the cell that is not sensitive to the compound of formula I, or an optical isomer thereof, or a racemate thereof, or a solvate thereof, or a pharmaceutically acceptable salt thereof, or a deuterated compound thereof In another preferred embodiment, the tumor with high expression of DNMT1 means that DNMT1 protein can be detected in 20 μg of protein extracted from tumor using DNMT1 antibody, preferably in 5 μg of protein extracted from tumor, more preferably in 1 μg of protein extracted from tumor, more preferably in 0.2 μg of protein extracted from tumor, more preferably in 0.05 μg of protein extracted from tumor, more preferably in 0.01 μg of protein extracted from tumor.

In another preferred embodiment, the tumor with high expression of DNMT1 means the expression level of DNMT1 in tumor type of cell is higher than that in the same type of cell or a normal cell.

In another preferred embodiment, the tumor with high expression of DNMT1 means the ratio (B1/B0) of the expression level B1 of DNMT1 in the tumor cell to the expression level B0 of DNMT1 in the same type of cell or a normal cell is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the same type of cell comprises the same type of tumor cell.

In another preferred embodiment, the same type of cell comprises the cell (e.g., the same type of tumor cell) with normal or low expression of DNMT1.

In another preferred embodiment, the same type of cell comprises the same type of cell (e.g., the same type of tumor cell) with normal or low expression of DNMT1.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal expression of DNMT1.

In another preferred embodiment, B0 refers to the expression level of DNMT1 in the cell with normal or low expression of DNMT1.

In another preferred embodiment, the cell with normal or low expression of DNMT1 comprises the cell that is not sensitive to the compound of formula I, or an optical isomer thereof, or a racemate thereof, or a solvate thereof, or a pharmaceutically acceptable salt thereof, or a deuterated compound thereof In another preferred embodiment, the tumor with high expression of DNMT3a means that DNMT3a protein can be detected in 20 μg of protein extracted from tumor using DNMT3a antibody, preferably in 5 μg of protein extracted from tumor, more preferably in 1 μg of protein extracted from tumor, more preferably in 0.2 μg of protein extracted from tumor, more preferably in 0.05 μg of protein extracted from tumor, more preferably in 0.01 μg of protein extracted from tumor.

In another preferred embodiment, the tumor with high expression of DNMT3a means the expression level of DNMT3a in tumor cell is higher than that in the same type of cell or a normal cell.

In another preferred embodiment, the tumor with high expression of DNMT3a means the ratio (C1/C0) of the expression level C1 of DNMT3a in the tumor cell to the expression level C0 of DNMT3a in the same type of cell or a normal cell is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the same type of cell comprises the same type of tumor cell.

In another preferred embodiment, the same type of cell comprises the cell (e.g., the same type of tumor cell) with normal or low expression of DNMT3a.

In another preferred embodiment, the same type of cell comprises the same type of cell (e.g., the same type of tumor cell) with normal or low expression of DNMT3a.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal expression of DNMT3a.

In another preferred embodiment, C0 refers to the expression level of DNMT3a in the cell with normal or low expression of DNMT3a.

In another preferred embodiment, the cell with normal or low expression of DNMT3a comprises the cell that is not sensitive to the compound of formula I, or an optical isomer thereof, or a racemate thereof, or a solvate thereof, or a pharmaceutically acceptable salt thereof, or a deuterated compound thereof.

In another preferred embodiment, the tumor with high expression of DNMT3b means that DNMT3b protein can be detected in 20 μg of protein extracted from tumor using DNMT3b antibody, preferably in 5 μg of protein extracted from tumor, more preferably in 1 μg of protein extracted from tumor, more preferably in 0.2 μg of protein extracted from tumor, more preferably in 0.05 μg of protein extracted from tumor, more preferably in 0.01 μg of protein extracted from tumor.

In another preferred embodiment, the tumor with high expression of DNMT3b means the expression level of DNMT3b in tumor type of cell is higher than that in the same type of cell or a normal cell.

In another preferred embodiment, the tumor with high expression of DNMT3b means the ratio (D1/D0) of the expression level DI of DNMT3b in the tumor cell to the expression level DO of DNMT3b in the same type of cell or a normal cell is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the same type of cell comprises the same type of tumor cell.

In another preferred embodiment, the same type of cell comprises the cell (e.g., the same type of tumor cell) with normal or low expression of DNMT3b.

In another preferred embodiment, the same type of cell comprises the same type of cell (e.g., the same type of tumor cell) with normal or low expression of DNMT3b.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal expression of DNMT3b In another preferred embodiment, DO refers to the expression level of DNMT3b in the cell with normal or low expression of DNMT3b.

In another preferred embodiment, the cell with normal or low expression of DNMT3b comprises the cell that is not sensitive to the compound of formula I, or an optical isomer thereof, or a racemate thereof, or a solvate thereof, or a pharmaceutically acceptable salt thereof, or a deuterated compound.

In another preferred embodiment, the tumor with high expression of UHRF1 means that UHRF1 protein can be detected in 20 μg of protein extracted from tumor using UHRF1 antibody, preferably in 5 μg of protein extracted from tumor, more preferably in 1 μg of protein extracted from tumor, more preferably in 0.2 μg of protein extracted from tumor, more preferably in 0.05 μg of protein extracted from tumor, more preferably in 0.01 μg of protein extracted from tumor.

In another preferred embodiment, the tumor with high expression of UHRF1 means the expression level of UHRF1 in tumor type of cell is higher than that in the same type of cell or a normal cell.

In another preferred embodiment, the tumor with high expression of UHRF1 means the ratio (F1/F0) of the expression level F1 of UHRF1 in the tumor cell to the expression level F0 of UHRF1 in the same type of cell or a normal cell is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the same type of cell comprises the same type of tumor cell.

In another preferred embodiment, the same type of cell comprises the cell (e.g., the same type of tumor cell) with normal or low expression of UHRF1.

In another preferred embodiment, the same type of cell comprises the same type of cell (e.g., the same type of tumor cell) with normal or low expression of UHRF1.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal expression of UHRF1

In another preferred embodiment, F0 refers to the expression level of UHRF1 in the cell with normal or low expression of UHRF1.

In another preferred embodiment, the cell with normal or low expression of UHRF1 comprises the cell that is not sensitive to the compound of formula I, or an optical isomer thereof, or a racemate thereof, or a solvate thereof, or a pharmaceutically acceptable salt thereof, or a deuterated compound.

In another preferred embodiment, the high methylation level of nucleotide site of NNMT gene means the methylation level of nucleotide site of NNMT gene in a cell (e.g., tumor cell) is higher than that in the same type of cell or a normal cell.

In another preferred embodiment, the high methylation level of nucleotide site of NNMT gene means the ratio (L1/L0) of the methylation level L1 of nucleotide site of NNMT gene in a cell (e.g., tumor cell) to the methylation level L0 of nucleotide site of NNMT gene in the same type of cell or a normal cell (e.g., para-tumor tissue cell) is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the high methylation level of nucleotide site of NNMT gene means the methylation level of nucleotide site of NNMT gene in a cell (e.g., tumor cell) is ≥1%, more preferably ≥3%, more preferably ≥5%, more preferably ≥10%, more preferably ≥15%, more preferably ≥20%, more preferably ≥25%, more preferably ≥30%, more preferably ≥40%, more preferably ≥50%.

In another preferred embodiment, the cell comprises tumor cell.

In another preferred embodiment, the same type cell comprises the same type of tumor cell.

In another preferred embodiment, the same type of cell comprises the cell (e.g., the same type of tumor cell) with normal or low methylation level of nucleotide site of NNMT gene.

In another preferred embodiment, the same type of cell comprises the same type of cell (e.g., the same type of tumor cell) with normal or low methylation level of nucleotide site of NNMT gene.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal methylation level of nucleotide site of NNMT gene.

In another preferred embodiment, the cell with normal or low methylation level of nucleotide site of NNMT gene comprises the cell that is not sensitive to the compound of formula I, or an optical isomer thereof, or a racemate thereof, or a solvate thereof, or a pharmaceutically acceptable salt thereof, or a deuterated compound.

In another preferred embodiment, the high methylation level of nucleotide site of NNMT gene means the methylation level (M %) of nucleotide site of NNMT gene in a cell (e.g., tumor cell) is ≥3% and ≤M1%, wherein MI is any positive integer from 3 to 100.

In another preferred embodiment, MI is 5, 10, 15, 20, 25, 30, 35, 40, 45, 50, 55, 60, 65, 70, 80, 85, 90, 95 or 100.

In another preferred embodiment, the methylation level of nucleotide site of NNMT gene refers to the ratio of the number of methylated nucleotides to the number of all nucleotides in the NNMT gene.

In another preferred embodiment, the methylation level of nucleotide site of NNMT gene comprises the methylation level of nucleotide site in promoter region of NNMT gene.

In another preferred embodiment, the nucleotide sequence of the promoter region of NNMT gene is as shown in SEQ ID NO: 1.

In another preferred embodiment, the methylation level of nucleotide site of NNMT gene comprises the methylation level of nucleotide sites from 1050 bp before the transcription start site to 499 bp after the transcription start site in NNMT gene.

In another preferred embodiment, the sites from 1050 bp before the transcription start site to 499 bp after the transcription start site in NNMT gene is sites 951-2500 of nucleotide sequence as shown in SEQ ID NO: 1.

In another preferred embodiment, the methylation level of nucleotide site of NNMT gene comprises the methylation level of nucleotide sites from 1050 bp to 193 bp before the transcription start site in NNMT gene.

In another preferred embodiment, the sites from 1050 bp to 193 bp before the transcription start site in NNMT gene is sites 951-1808 of nucleotide sequence as shown in SEQ ID NO: 1.

In another preferred embodiment, the methylation level of nucleotide site of NNMT gene comprises the methylation level of nucleotide sites from 840 bp to 469 bp before the transcription start site in NNMT gene.

In another preferred embodiment, the sites from 840 bp to 469 bp before the transcription start site in NNMT gene is sites 1161-1532 of nucleotide sequence as shown in SEQ ID NO: 1.

In another preferred embodiment, the methylation level of nucleotide site of NNMT gene comprises the methylation level of nucleotide site between any two sites (including the two sites itself) selected from group consisting of site 114165695, site 114165730, site 114165769, site 114165804, site 114165938, site 114166050 and site 114166066 on human chromosome 11.

In another preferred embodiment, the methylation level of nucleotide site of NNMT gene comprises the methylation level of nucleotide site of one or more (e.g., 2, 3, 4, 5, 6, or 7) of site 114165695, site 114165730, site 114165769, site 114165804, site 114165938, site 114166050 and site 114166066 on human chromosome 11.

In another preferred embodiment, the methylation level of nucleotide site of NNMT gene comprises the methylation level of nucleotide sites selected from group consisting of site 114165695 on human chromosome 11, site 114165730 on human chromosome 11, site 114165769 on human chromosome 11, site 114165804 on human chromosome 11, site 114165938 on human chromosome 11, site 114166050 on human chromosome 11, site 114166066 on human chromosome 11, and combinations thereof.

In another preferred embodiment, the methylation level of nucleotide site of NNMT gene comprises the methylation level of nucleotide site between any two sites (including the two sites itself) selected from group consisting of site 1161, site 1196, site 1235, site 1270, site 1404, site 1516 and site 1532 in nucleotide sequence of SEQ ID NO: 1.

In another preferred embodiment, the methylation level of nucleotide site of NNMT gene comprises the methylation level of nucleotide site of one or more (e.g., 2, 3, 4, 5, 6, or 7) of site 1161, site 1196, site 1235, site 1270, site 1404, site 1516 and site 1532 in nucleotide sequence of SEQ ID NO: 1.

In another preferred embodiment, the methylation level of DNA CpG site of NNMT gene comprises the methylation level of nucleotide sites selected from group consisting of site 1161 in SEQ ID NO: 1, site 1196 in SEQ ID NO: 1, site 1235 in SEQ ID NO: 1, site 1270 in SEQ ID NO: 1, site 1404 in SEQ ID NO: 1, site 1516 in SEQ ID NO: 1, site 1532 in SEQ ID NO: 1, and combinations thereof.

In another preferred embodiment, the high methylation level of DNA CpG site of NNMT gene means the methylation level of DNA CpG site of NNMT gene in a cell (e.g., tumor cell) is higher than that in the same type of cell or a normal cell.

In another preferred embodiment, the high methylation level of DNA CpG site of NNMT gene means the ratio (W1/W0) of the methylation level W1 of DNA CpG site of NNMT gene in a cell (e.g., tumor cell) to the methylation level W0 of DNA CpG site of NNMT gene in the same type of cell or a normal cell (e.g., para-tumor tissue cell) is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the high methylation level of DNA CpG site of NNMT gene means the methylation level of DNA CpG site of NNMT gene in a cell (e.g., tumor cell) is ≥1%, more preferably ≥3%, more preferably ≥5%, more preferably ≥10%, more preferably ≥15%, more preferably ≥20%, more preferably ≥25%, more preferably ≥30%, more preferably ≥40%, more preferably ≥50%.

In another preferred embodiment, the cell comprises tumor cell.

In another preferred embodiment, the same type of cell comprises the same type of tumor cell.

In another preferred embodiment, the same type of cell comprises the cell (e.g., the same type of tumor cell) with normal or low methylation level of DNA CpG site of NNMT gene.

In another preferred embodiment, the same type of cell comprises the same type of cell (e.g., the same type of tumor cell) with normal or low methylation level of DNA CpG site of NNMT gene.

In another preferred embodiment, the normal cell comprises normal tissue cell (e.g., tumor origin cell, tumor-adjacent cell or para-tumor tissue cell).

In another preferred embodiment, the normal cell comprises normal tissue cell (e.g., tumor origin cell, tumor-adjacent cell or para-tumor tissue cell) with normal methylation level of DNA CpG site of NNMT gene.

In another preferred embodiment, the cell with normal or low methylation level of DNA CpG site of NNMT gene comprises the cell that is not sensitive to the compound of formula I, or an optical isomer thereof, or a racemate thereof, or a solvate thereof, or a pharmaceutically acceptable salt thereof, or a deuterated compound thereof In another preferred embodiment, the high methylation level of DNA CpG site of NNMT gene means the methylation level (M %) of DNA CpG site of NNMT gene in a cell (e.g., tumor cell) is ≥3% and ≤M2%, wherein M2 is any positive integer from 3 to 100.

In another preferred embodiment, M2 is 5, 10, 15, 20, 25, 30, 35, 40, 45, 50, 55, 60, 65, 70, 80, 85, 90, 95 or 100.

In another preferred embodiment, the methylation level of CpG site refers to the ratio of the number of methylated CpG nucleotides to the number of all nucleotides in a gene.

In another preferred embodiment, the methylation level of DNA CpG site of NNMT gene refers to the ratio of the number of methylated CpG nucleotides to the number of all nucleotides in the NNMT gene.

In another preferred embodiment, the methylation level of CpG site refers to the ratio of the number of methylated CpG nucleotides to the number of all CpG nucleotides in a gene.

In another preferred embodiment, the methylation level of DNA CpG site of NNMT gene refers to the ratio of the number of methylated DNA CpG nucleotides to the number of all CpG nucleotides in the NNMT gene.

In another preferred embodiment, the methylation level of DNA CpG site refers to the ratio of the number of methylated CpG sites to the number of all CpG sites in a DNA.

In another preferred embodiment, the methylation level of DNA CpG site refers to the ratio of the number of methylated CpG nucleotides to the number of all nucleotides in a DNA.

In another preferred embodiment, the methylation level of DNA CpG site refers to the ratio of the number of methylated CpG nucleotides to the number of all CpG nucleotides in a DNA.

In another preferred embodiment, the methylation level of DNA CpG site of NNMT gene refers to the ratio of the number of methylated DNA CpG sites to the number of all DNA CpG sites in the NNMT gene.

In another preferred embodiment, the methylation level of DNA CpG site of NNMT gene refers to the ratio of the number of methylated DNA CpG nucleotides to the number of all DNA CpG nucleotides in the NNMT gene.

In another preferred embodiment, the methylation level of DNA CpG site of NNMT gene comprises the methylation level of DNA CpG site in promoter region of NNMT gene.

In another preferred embodiment, the nucleotide sequence of the promoter region of NNMT gene is as shown in SEQ ID NO: 1.

In another preferred embodiment, the methylation level of DNA CpG site of NNMT gene comprises the methylation level of DNA CpG sites from 1050 bp before the transcription start site to 499 bp after the transcription start site in NNMT gene.

In another preferred embodiment, the sites from 1050 bp before the transcription start site to 499 bp after the transcription start site in NNMT gene is sites 951-2500 of nucleotide sequence as shown in SEQ ID NO: 1.

In another preferred embodiment, the methylation level of DNA CpG site of NNMT gene comprises the methylation level of the DNA CpG sites from 1050 bp to 193 bp before the transcription start site in NNMT gene.

In another preferred embodiment, the sites from 1050 bp to 193 bp before the transcription start site in NNMT gene is sites 951-1808 of nucleotide sequence as shown in SEQ ID NO: 1.

In another preferred embodiment, the methylation level of DNA CpG site of NNMT gene comprises the methylation level of DNA CpG sites from 840 bp to 469 bp before the transcription start site in NNMT gene.

In another preferred embodiment, the sites from 840 bp to 469 bp before the transcription start site in NNMT gene is sites 1161-1532 of nucleotide sequence as shown in SEQ ID NO: 1.

In another preferred embodiment, the methylation level of DNA CpG site of NNMT gene comprises the methylation level of DNA CpG site between any two sites (including the two sites itself) selected from group consisting of site 114165695, site 114165730, site 114165769, site 114165804, site 114165938, site 114166050 and site 114166066 on human chromosome 11.

In another preferred embodiment, the methylation level of DNA CpG site of NNMT gene comprises the methylation level of site of one or more (e.g., 2, 3, 4, 5, 6, or 7) of site 114165695, site 114165730, site 114165769, site 114165804, site 114165938, site 114166050 and site 114166066 on human chromosome 11.

In another preferred embodiment, the methylation level of DNA CpG site of NNMT gene comprises the methylation level of sites selected from group consisting of site 114165695 on human chromosome 11, site 114165730 on human chromosome 11, site 114165769 on human chromosome 11, site 114165804 on human chromosome 11, site 114165938 on human chromosome 11, site 114166050 on human chromosome 11, site 114166066 on human chromosome 11, and combinations thereof.

In another preferred embodiment, the methylation level of DNA CpG site of NNMT gene comprises the methylation level of DNA CpG site between any two sites (including the two sites itself) selected from group consisting of site 1161, site 1196, site 1235, site 1270, site 1404, site 1516 and site 1532 in nucleotide sequence of SEQ ID NO: 1.

In another preferred embodiment, the methylation level of DNA CpG site of NNMT gene comprises the methylation level of the site of one or more (e.g., 2, 3, 4, 5, 6, or 7) of site 1161, site 1196, site 1235, site 1270, site 1404, site 1516 and site 1532 in nucleotide sequence of SEQ ID NO: 1.

In another preferred embodiment, the methylation level of DNA CpG site of NNMT gene comprises the methylation level of sites selected from group consisting of site 1161 in SEQ ID NO: 1, site 1196 in SEQ ID NO: 1, site 1235 in SEQ ID NO: 1, site 1270 in SEQ ID NO: 1, site 1404 in SEQ ID NO: 1, site 1516 in SEQ ID NO: 1, site 1532 in SEQ ID NO: 1, and combinations thereof.

In another preferred embodiment, the NNMT gene inhibitor is administered to achieve low or no expression of the NNMT gene in tumor.

In another preferred embodiment, the DNA methylase promoter is administered to achieve high expression of DNA methylase in tumor.

In another preferred embodiment, the DNMT1 promoter is administered to achieve high expression of DNMT1 in tumor.

In another preferred embodiment, the DNMT3a promoter is administered to achieve high expression of DNMT3a in tumor.

In another preferred embodiment, the DNMT3b promoter is administered to achieve high expression of DNMT3b in tumor.

In another preferred embodiment, the UHRF1 promoter is administered to achieve high expression of UHRF1 in tumor.

In another preferred embodiment, the methylation promoter of nucleotide site of NNMT gene is administered to achieve high methylation level of nucleotide site of NNMT gene in tumor.

In another preferred embodiment, the methylation promoter of DNA CpG site of NNMT gene is administered to achieve high methylation level of DNA CpG site of NNMT gene in tumor.

In another preferred embodiment, the inhibitor comprises specific inhibitor.

In another preferred embodiment, the promoter comprises specific promoter.

In another preferred embodiment, the NNMT gene inhibitor comprises inhibitor that can achieve low or no expression of the NNMT gene in tumor.

In another preferred embodiment, the DNA methylase promoter comprises promoter that can achieve high expression of DNA methylase in tumor.

In another preferred embodiment, the DNMT1 promoter comprises promoter that can achieve high expression of DNMT1 in tumor.

In another preferred embodiment, the DNMT3a promoter comprises promoter that can achieve high expression of DNMT3a in tumor.

In another preferred embodiment, the DNMT3b promoter comprises promoter that can achieve high expression of DNMT3b in tumor.

In another preferred embodiment, the UHRF1 promoter comprises promoter that can achieve high expression of UHRF1 in tumor.

In another preferred embodiment, the methylation promoter of nucleotide site of NNMT gene comprises promoter that can achieve high methylation level of nucleotide site of NNMT gene in tumor.

In another preferred embodiment, the methylation promoter of DNA CpG site of NNMT gene comprises promoter that can achieve high methylation promoter of DNA CpG site of NNMT gene in tumor.

In another preferred embodiment, the tumor is selected from the group consisting of lung cancer, renal carcinoma, breast cancer, colon cancer, lymphoma, leukemia, pancreatic cancer, brain tumor, liver cancer, prostate cancer, and combinations thereof.

In another preferred embodiment, the lung cancer is selected from the group consisting of non-small cell lung cancer, small cell lung cancer, and combinations thereof.

In another preferred embodiment, the lung cancer cell comprises NCI-H82 cell.

In another preferred embodiment, the colon cancer comprises colon adenocarcinoma.

In another preferred embodiment, the colon cancer cell comprises SW48 cell.

In another preferred embodiment, the breast cancer cell comprises MDA-MB-453 cell.

In another preferred embodiment, the breast cancer comprises triple negative breast cancer.

In another preferred embodiment, the lymphoma is selected from the group consisting of B-cell lymphoma, skin T-cell lymphoma, and combinations thereof.

In another preferred embodiment, the lymphoma comprises diffuse large B-cell lymphoma.

In another preferred embodiment, the brain tumor is selected from the group consisting of brain glioblastoma, neuroglioma, brain medulloblastoma, brain neuroblastoma, and combination thereof.

In another preferred embodiment, the brain medulloblastoma comprises cerebellar medulloblastoma.

In another preferred embodiment, the brain glioblastoma comprises glioblastoma multiforme.

In another preferred embodiment, the brain tumor comprises glioblastoma.

In another preferred embodiment, the brain tumor cell comprises one or more of GB-1 cell, SF126 cell, D341 Med cell, Kelly cell and NB-1 cell.

In another preferred embodiment, the renal carcinoma is selected from the group consisting of clear cell renal cell adenocarcinoma, renal carcinoma Wilms, and combination thereof.

In another preferred embodiment, the renal carcinoma comprises clear cell renal cell adenocarcinoma.

In another preferred embodiment, the renal carcinoma comprises renal carcinoma Wilms.

In another preferred embodiment, the renal carcinoma cell comprises renal carcinoma Wilms cell.

In another preferred embodiment, the renal carcinoma cell comprises one or more of G-401 cell and 786-O cell.

In another preferred embodiment, the pancreatic cancer comprises pancreatic ductal carcinoma.

In another preferred embodiment, the pancreatic cancer cell comprises CFPAC-1 cell.

In another preferred embodiment, the leukemia is selected from the group consisting of T-lymphocyte leukemia, myeloid leukemia, and combinations thereof.

In another preferred embodiment, the T-lymphocytic leukemia comprises acute T-lymphocytic leukemia.

In another preferred embodiment, the myeloid leukemia comprises type M4 of acute myeloid leukemia.

In another preferred embodiment, the myeloid leukemia comprises FAB type M4 of acute myeloid leukemia.

In another preferred embodiment, the expression comprises protein expression and/or mRNA expression.

In another preferred embodiment, the composition or preparation is a pharmaceutical composition or pharmaceutical preparation.

In another preferred embodiment, the composition or preparation further comprises a pharmaceutically acceptable carrier.

In another preferred embodiment, the expression is mRNA expression or protein expression.

In another preferred embodiment, the dosage form of the composition or preparation is a solid preparation, liquid preparation or semi-solid preparation.

In another preferred embodiment, the dosage form of the composition or preparation is oral preparation, external preparation or injection preparation.

In another preferred embodiment, the dosage form of the composition or preparation is tablet, injection, infusion, paste, gel, solution, microsphere or film.

In the fourth aspect of the present invention, it provides a marker for determining whether the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor, the marker comprises the expression level of NNMT gene, the expression level of DNA methylase, the expression level of UHRF1, the methylation level of nucleotide site of NNMT gene, and/or the methylation level of DNA CpG site of NNMT gene.

In another preferred embodiment, the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor with low or no expression of NNMT gene, high expression of DNA methylase, high expression of UHRF1, high methylation level of nucleotide site of NNMT gene, and/or high methylation level of DNA CpG site of NNMT gene.

In another preferred embodiment, the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor with high expression of NNMT gene, low expression of DNA methylase, low expression of UHRF1, low methylation level of nucleotide site of NNMT gene, and/or low methylation level of DNA CpG site of NNMT gene.

In another preferred embodiment, "the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor" comprises "the patient tumor is sensitive to the compound of formula I, or an optical isomer thereof, or a racemate thereof, or a solvate thereof, or a pharmaceutically acceptable salt thereof, or a deuterated compound thereof according to the first aspect of the present invention".

In another preferred embodiment, "the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor" comprises "the patient tumor is not sensitive to the compound of formula I, or an optical isomer thereof, or a racemate thereof, or a solvate thereof, or a pharmaceutically acceptable salt thereof, or a deuterated compound thereof according to the first aspect of the present invention".

In another preferred embodiment, the tumor with low or no expression of NNMT gene is as described in the third aspect of the invention.

In another preferred embodiment, the DNA methylase is selected from the group consisting of DNMT1, DNMT3a, DNMT3b, and combinations thereof.

In another preferred embodiment, the tumor with high expression of DNA methylase (e.g., DNMT1) is as described in the third aspect of the invention.

In another preferred embodiment, the tumor with high expression of UHRF1 is as described in the third aspect of the invention.

In another preferred embodiment, the tumor with high methylation level of nucleotide site of NNMT gene is as described in the third aspect of the invention.

In another preferred embodiment, the tumor with high methylation level of DNA CpG site of NNMT gene is as described in the third aspect of the invention.

In another preferred embodiment, the high expression of NNMT gene means the ratio (E1/E0) of the expression E1 of NNMT gene in a cell (e.g., tumor cell) to the expression E0 of NNMT gene in the same type of cell or a normal cell is >1.0, preferably ≥1.2, more preferably ≥1.5, more preferably ≥2, more preferably ≥3, more preferably ≥5, more preferably ≥8, more preferably ≥10, more preferably ≥15, more preferably ≥20, more preferably ≥30, more preferably ≥50, such as 2-50.

In another preferred embodiment, the tumor with low expression of DNA methylase means the ratio (A1/A0) of the expression level A1 of DNA methylase in the tumor cell to the expression level A0 of DNA methylase in the same type of cell or a normal cell is ≤1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤0.000001, more preferably ≤0.0000001.

In another preferred embodiment, the tumor with low expression of DNMT1 means the ratio (B1/B0) of the expression level B1 of DNMT1 in the tumor cell to the expression level B0 of DNMT1 in the same type of cell or a normal cell is <1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤ 0.000001, more preferably ≤0.0000001.

In another preferred embodiment, the tumor with low expression of DNMT3a means the ratio (C1/C0) of the expression level C1 of DNMT3a in the tumor cell to the expression level C0 of DNA methylase in the same type of cell or a normal cell is <1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤0.000001, more preferably ≤0.0000001.

In another preferred embodiment, the tumor with low expression of DNMT3b means the ratio (D1/DO) of the expression level DI of DNMT3b in the tumor cell to the expression level DO of DNA methylase in the same type of cell or a normal cell is <1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤ 0.000001, more preferably ≤0.0000001.

In another preferred embodiment, the tumor with low expression of UHRF1 means the ratio (F1/F0) of the expression level F1 of UHRF1 in the tumor cell to the expression level F0 of UHRF1 in the same type of cell or a normal cell is <1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤ 0.000001, more preferably ≤0.0000001.

In another preferred embodiment, the low methylation level of nucleotide site of NNMT gene means the ratio (L1/L0) of the methylation level L1 of nucleotide site of NNMT gene in a cell (e.g., tumor cell) to the methylation level L0 of nucleotide site of NNMT gene in the same type of cell or a normal cell (e.g., para-tumor tissue cell) is <1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤0.000001, more preferably ≤0.0000001.

In another preferred embodiment, the low methylation level of DNA CpG site of NNMT gene means the ratio (W1/W0) of the methylation level W1 of DNA CpG site of NNMT gene in a cell (e.g., tumor cell) to the methylation level W0 of DNA CpG site of NNMT gene in the same type of cell or a normal cell (e.g., para-tumor tissue cell) is <1.0, preferably ≤0.7, more preferably ≤0.6, more preferably ≤0.5, more preferably ≤0.4, more preferably ≤0.3, more preferably ≤0.2, more preferably ≤0.1, more preferably ≤0.05, more preferably ≤0.01, more preferably ≤0.005, more preferably ≤0.001, more preferably ≤0.0001, more preferably ≤0.00001, more preferably ≤ 0.000001, more preferably ≤0.0000001.

In the fifth aspect of the present invention, it provides a detection kit, which comprises: (i) a detection reagent for detecting the expression level of NNMT gene, the expression level of DNA methylase, the expression level of UHRF1, the methylation level of nucleotide site of NNMT gene, and/or the methylation level of DNA CpG site of NNMT gene.

In another preferred embodiment, the test sample of the detection kit comprises tumor cell.

In another preferred embodiment, the level comprises protein level and/or mRNA level.

In another preferred embodiment, the expression comprises mRNA expression and/or protein expression.

In the sixth aspect of the present invention, it provides a use of the detection kit according to the fifth aspect of the present invention in the preparation of concomitant diagnose kit for determining whether the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor.

In another preferred embodiment, the concomitant diagnose kit further comprises instruction or label.

In another preferred embodiment, the instruction or label records that the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor with low or no expression of NNMT gene, high expression of DNA methylase, high expression of UHRF1, high methylation level of nucleotide site of NNMT gene, and/or high methylation level of DNA CpG site of NNMT gene.

In another preferred embodiment, the instruction or label records that the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor with high expression of NNMT gene, low expression of DNA methylase, low expression of UHRF1, low methylation level of nucleotide site of NNMT gene, and/or low methylation level of DNA CpG site of NNMT gene.

In another preferred embodiment, "the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor" is as described in the fourth aspect of the invention.

In another preferred embodiment, "the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor" is as described in the fourth aspect of the invention.

In the seventh aspect of the present invention, it provides a medicine kit, which comprises:

(i) a detection reagent for detecting the expression level of NNMT gene, the expression level of DNA methylase, the expression level of UHRF1, the methylation level of nucleotide site of NNMT gene, and/or the methylation level of DNA CpG site of NNMT gene; and (ii) the compound of formula I, or an optical isomer thereof, or a racemate thereof, or a solvate thereof, or a pharmaceutically acceptable salt thereof, or a deuterated compound thereof according to the first aspect of the present invention.

In another preferred embodiment, the expression level of NNMT gene, the expression level of DNA methylase, the expression level of UHRF1, the methylation level of nucleotide site of NNMT gene, and/or the methylation level of DNA CpG site of NNMT gene comprises the expression level of NNMT gene, the expression level of DNA methylase, the expression level of UHRF1, the methylation level of nucleotide site of NNMT gene, and/or the methylation level of DNA CpG site of NNMT gene in the tumor.

In another preferred embodiment, the detection sample comprises tumor.

In another preferred embodiment, the medicine kit further comprises instruction or label.

In another preferred embodiment, the instruction or label records that the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor with low or no expression of NNMT gene, high expression of DNA methylase, high expression of UHRF1, high methylation level of nucleotide site of NNMT gene, and/or high methylation level of DNA CpG site of NNMT gene.

In another preferred embodiment, the instruction or label records that the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor with high expression of NNMT gene, low expression of DNA methylase, low expression of UHRF1, low methylation level of nucleotide site of NNMT gene, and/or low methylation level of DNA CpG site of NNMT gene.

In the eighth aspect of the present invention, it provides a method for preventing and/or treating tumor, which comprises administering the compound of formula I, or an optical isomer thereof, or a racemate thereof, or a solvate thereof, or a pharmaceutically acceptable salt thereof, or a deuterated compound thereof according to the first aspect of the present invention to a subject in need, thereby preventing and/or treating tumor.

In another preferred embodiment, the tumor is as described in the third aspect of the invention.

In another preferred embodiment, the subject is human and non-human mammals (rodent, rabbit, monkey, livestock, dog, cat, etc.).

In another preferred embodiment, the method comprises:

firstly achieving low or no expression of NNMT gene, high expression of DNA methylase, high expression of UHRF1, high methylation level of nucleotide site of NNMT gene, and/or high methylation level of DNA CpG site of NNMT gene in the subject tumor, then administering the compound of formula I, or an optical isomer thereof, or a racemate thereof, or a solvate thereof, or a pharmaceutically acceptable salt thereof, or a deuterated compound thereof to prevent and/or treat tumor.

In another preferred embodiment, the method comprises: firstly administering NNMT gene inhibitor, DNA methylase promoter, UHRF1 promoter, methylation promoter of nucleotide site of NNMT gene, and/or methylation promoter of DNA CpG site of NNMT gene to achieve low or no expression of NNMT gene, high expression of DNA methylase, high expression of UHRF1, high methylation level of nucleotide site of NNMT gene, and/or high methylation level of DNA CpG site of NNMT gene in the subject tumor, then administering the compound of formula I, or an optical isomer thereof, or a racemate thereof, or a solvate thereof, or a pharmaceutically acceptable salt thereof, or a deuterated compound thereof to prevent and/or treat tumor.

In another preferred embodiment, the NNMT gene inhibitor, DNA methylase promoter, UHRF1 promoter, methylation promoter of nucleotide site of NNMT gene, and/or methylation promoter of DNA CpG site of NNMT gene is as described in the third aspect of the invention.

In the ninth aspect of the present invention, it provides a device or system, the device or system comprises:

(i) a detection module, the detection module is used to detect the expression level of NNMT gene, the expression level of DNA methylase, the expression level of UHRF1, the methylation level of nucleotide site of NNMT gene, and/or the methylation level of DNA CpG site of NNMT gene;

(ii) an output module, the output module comprises the information as follows:

the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor with low or no expression of NNMT gene, high expression of DNA methylase, high expression of UHRF1, high methylation level of nucleotide site of NNMT gene, and/or high methylation level of DNA CpG site of NNMT gene; and/or the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor with high expression of NNMT gene, low expression of DNA methylase, low expression of UHRF1, low methylation level of nucleotide site of NNMT gene, and/or low methylation level of DNA CpG site of NNMT gene.

In another preferred embodiment, the detection sample comprises tumor.

In another preferred embodiment, the device comprises a gene detector or protein detector.

In another preferred embodiment, the device or system further comprises sample injection module.

In another preferred embodiment, the injection module is used to inject tumor cell extract.

In another preferred embodiment, the device or system further comprises data processing module.

In another preferred embodiment, the expression level of NNMT gene, the expression level of DNA methylase, the expression level of UHRF1, the methylation level of nucleotide site of NNMT gene, and/or the methylation level of DNA CpG site of NNMT gene can be obtained by the procession of the data processing module.

In another preferred embodiment, the expression level of NNMT gene and the methylation level of DNA CpG site in promoter region of NNMT gene can be obtained by the procession of the data processing module.

In the tenth aspect of the present invention, it provides a use of NNMT gene inhibitor, DNA methylase promoter, UHRF1 promoter, methylation promoter of nucleotide site of NNMT gene, and/or methylation promoter of DNA CpG site of NNMT gene in the preparation of a composition or a preparation for enhancing the anti-tumor effect of anti-tumor drug.

In another preferred embodiment, the NNMT gene inhibitor comprises inhibitor that can achieve low or no expression of the NNMT gene in tumor.

In another preferred embodiment, the DNA methylase promoter comprises promoter that can achieve high expression of DNA methylase in tumor.

In another preferred embodiment, the DNA methylase is selected from the group consisting of DNMT1, DNMT3a, DNMT3b, and combinations thereof.

In another preferred embodiment, the DNA methylase promoter comprises DNMT1 promoter.

In another preferred embodiment, the DNMT1 promoter comprises promoter that can achieve high expression of DNMT1 in tumor.

In another preferred embodiment, the DNA methylase promoter comprises DNMT3a promoter.

In another preferred embodiment, the DNMT3a promoter comprises promoter that can achieve high expression of DNMT3a in tumor.

In another preferred embodiment, the DNA methylase promoter comprises DNMT3b promoter.

In another preferred embodiment, the DNMT3b promoter comprises promoter that can achieve high expression of DNMT3b in tumor.

In another preferred embodiment, the UHRF1 promoter comprises promoter that can achieve high expression of UHRF1 in tumor.

In another preferred embodiment, the methylation promoter of nucleotide site of NNMT gene comprises promoter that can achieve high methylation level of nucleotide site of NNMT gene in tumor.

In another preferred embodiment, the methylation promoter of DNA CpG site of NNMT gene comprises promoter that can achieve high methylation level of nucleotide site of NNMT gene in tumor.

In another preferred embodiment, the inhibitor comprises specific inhibitor.

In another preferred embodiment, the promoter comprises specific promoter.

In another preferred embodiment, the anti-tumor drug comprises the compound of formula I, or an optical isomer thereof, or a racemate thereof, or a solvate thereof, or a pharmaceutically acceptable salt thereof, or a deuterated compound thereof according to the first aspect of the present invention.

In another preferred embodiment, the tumor is as described in the third aspect of the invention.

In another preferred embodiment, the composition or preparation is a pharmaceutical composition or pharmaceutical preparation.

In another preferred embodiment, the composition or preparation further comprises a pharmaceutically acceptable carrier.

In another preferred embodiment, the dosage form of the composition or preparation is a solid preparation, liquid preparation or semi-solid preparation.

In another preferred embodiment, the dosage form of the composition or preparation is oral preparation, external preparation or injection preparation.

In another preferred embodiment, the injection preparation is intravenous injection preparation.

In another preferred embodiment, the dosage form of the composition or preparation is tablet, injection, infusion, paste, gel, solution, microsphere or film.

In the eleventh aspect of the present invention, it provides an active ingredient combination, the active ingredient combination comprises:

(1) a first active ingredient, the first active ingredient comprises anti-tumor drug; and (2) a second active ingredient, the second active ingredient comprises NNMT gene inhibitor, DNA methylase promoter, UHRF1 promoter, methylation promoter of nucleotide site of NNMT gene, and/or methylation promoter of DNA CpG site of NNMT gene.

In another preferred embodiment, the anti-tumor drug comprises the compound of formula I, or an optical isomer thereof, or a racemate thereof, or a solvate thereof, or a pharmaceutically acceptable salt thereof, or a deuterated compound thereof according to the first aspect of the present invention.

In another preferred embodiment, the NNMT gene inhibitor, DNA methylase promoter, UHRF1 promoter, methylation promoter of nucleotide site of NNMT gene, and/or methylation promoter of DNA CpG site of NNMT gene is as described in the tenth aspect of the invention.

In another preferred embodiment, the molar ratio of the first active ingredient to the second active ingredient is 0.01-600:1, preferably 0.05-500:1, more preferably 0.1-400:1, more preferably 0.2-200:1, more preferably 0.5-100:1, more preferably 0.5-80:1, most preferably 1-50:1.

In another preferred embodiment, at least one active ingredient is independent in the active ingredient combination.

In another preferred embodiment, the first active ingredient and the second active ingredient are independent of each other in the active ingredient combination.

In the twelfth aspect of the present invention, it provides a composition, the composition comprises:

(1) a first active ingredient, the first active ingredient comprises anti-tumor drug; and (2) a second active ingredient, the second active ingredient comprises NNMT gene inhibitor, DNA methylase promoter, UHRF1 promoter, methylation promoter of nucleotide site of NNMT gene, and/or methylation promoter of DNA CpG site of NNMT gene.

In another preferred embodiment, the anti-tumor drug comprises the compound of formula I, or an optical isomer thereof, or a racemate thereof, or a solvate thereof, or a pharmaceutically acceptable salt thereof, or a deuterated compound thereof according to the first aspect of the present invention.

In another preferred embodiment, the NNMT gene inhibitor, DNA methylase promoter, UHRF1 promoter, methylation promoter of nucleotide site of NNMT gene, and/or methylation promoter of DNA CpG site of NNMT gene is as described in the tenth aspect of the invention.

In another preferred embodiment, the composition is a pharmaceutical composition.

In another preferred embodiment, the pharmaceutical composition further comprises a pharmaceutically acceptable carrier.

In another preferred embodiment, the content of the first active ingredient is 0.01-99.99 wt %, preferably 0.1-99.9 wt %, more preferably 1-99 wt %, more preferably 10-99 wt %, most preferably 20-99 wt %, based on the total weight of the active ingredient in the composition.

In another preferred embodiment, the content of the second active ingredient is 0.01-99.99 wt %, preferably 0.1-99.9 wt %, more preferably 1-99 wt %, more preferably 10-99 wt %, most preferably 20-99 wt %, based on the total weight of the active ingredient in the composition.

In the thirteenth aspect of the present invention, it provides a medicine kit, the medicine kit comprises:

(A) a first preparation comprising a first active ingredient, the first active ingredient comprises anti-tumor drug; and (B) a second preparation comprising a second active ingredient, the second active ingredient comprises NNMT gene inhibitor, DNA methylase promoter, UHRF1 promoter, methylation promoter of nucleotide site of NNMT gene, and/or methylation promoter of DNA CpG site of NNMT gene.

In another preferred embodiment, the anti-tumor drug comprises the compound of formula I, or an optical isomer thereof, or a racemate thereof, or a solvate thereof, or a pharmaceutically acceptable salt thereof, or a deuterated compound thereof according to the first aspect of the present invention.

In another preferred embodiment, the NNMT gene inhibitor, DNA methylase promoter, UHRF1 promoter, methylation promoter of nucleotide site of NNMT gene, and/or methylation promoter of DNA CpG site of NNMT gene is as described in the tenth aspect of the invention.

In another preferred embodiment, the medicine kit further comprises a user manual.

In another preferred embodiment, the first preparation and the second preparation are independent preparation of each other.

In another preferred embodiment, the first preparation and the second preparation are combined preparation.

In another preferred embodiment, the user manual records that the first preparation and the second preparation are used together to enhance anti-tumor activity of anti-tumor drug.

In another preferred embodiment, the method for using together means the second preparation comprising NNMT gene inhibitor, DNA methylase promoter, UHRF1 promoter, methylation promoter of nucleotide site of NNMT gene, and/or methylation promoter of DNA CpG site of NNMT gene is administered firstly, then the anti-tumor drug is administered.

In the fourteenth aspect of the present invention, it provides a method for inhibiting tumor cell, which comprises contacting the tumor cell with the compound of formula I, or an optical isomer thereof, or a racemate thereof, or a solvate thereof, or a pharmaceutically acceptable salt thereof, or a deuterated compound thereof according to the first aspect of the present invention, thereby inhibiting tumor cell.

In another preferred embodiment, the method is vitro method.

In another preferred embodiment, the method is non-therapeutic and non-diagnostic method.

In another preferred embodiment, the contact is performed in vitro culture.

In another preferred embodiment, the tumor is as described in the third aspect of the invention.

In another preferred embodiment, the method comprises:

firstly achieving low or no expression of NNMT gene, high expression of DNA methylase, high expression of UHRF1, high methylation level of nucleotide site of NNMT gene, and/or high methylation level of DNA CpG site of NNMT gene in the tumor cell, then contacting the tumor cell with the compound of formula I, or an optical isomer thereof, or a racemate thereof, or a solvate thereof, or a pharmaceutically acceptable salt thereof, or a deuterated compound thereof according to the first aspect of the present invention, thereby inhibiting tumor cell.

In another preferred embodiment, the method comprises:

firstly administering NNMT gene inhibitor, DNA methylase promoter, UHRF1 promoter, methylation promoter of nucleotide site of NNMT gene, and/or methylation promoter of DNA CpG site of NNMT gene to achieve low or no expression of NNMT gene, high expression of DNA methylase, high expression of UHRF1, high methylation level of nucleotide site of NNMT gene, and/or high methylation level of DNA CpG site of NNMT gene in the tumor cell, then contacting the tumor cell with the compound of formula I, or an optical isomer thereof, or a racemate thereof, or a solvate thereof, or a pharmaceutically acceptable salt thereof, or a deuterated compound thereof according to the first aspect of the present invention, thereby inhibiting tumor cell.

In another preferred embodiment, the NNMT gene inhibitor, DNA methylase promoter, UHRF1 promoter, methylation promoter of nucleotide site of NNMT gene, and/or methylation promoter of DNA CpG site of NNMT gene is as described in the tenth aspect of the invention.

In the fifteenth aspect of the present invention, it provides a use of medicine kit according to the seventh aspect of the present invention in the preparation of medicine box for preventing and/or treating tumor.

In another preferred embodiment, the medicine box further comprises instruction or label.

In another preferred embodiment, the instruction or label records that the compound of formula I, or an optical isomer thereof, or a racemate thereof, or a solvate thereof, or a pharmaceutically acceptable salt thereof, or a deuterated compound thereof according to the first aspect of the present invention is suitable for use in the prevention and/or treatment of patient tumor with low or no expression of NNMT gene, high expression of DNA methylase, high expression of UHRF1, high methylation level of nucleotide site of NNMT gene, and/or high methylation level of DNA CpG site of NNMT gene.

In another preferred embodiment, the instruction or label records that the compound of formula I, or an optical isomer thereof, or a racemate thereof, or a solvate thereof, or a pharmaceutically acceptable salt thereof, or a deuterated compound thereof according to the first aspect of the present invention is not suitable for use in the prevention and/or treatment of patient tumor with high expression of NNMT gene, low expression of DNA methylase, low expression of UHRF1, low methylation level of nucleotide site of NNMT gene, and/or low methylation level of DNA CpG site of NNMT gene.

It should be understood that, in the present invention, each of the technical features specifically described above and below can be combined with each other, thereby constituting new or preferred technical solutions which need not be redundantly described one-by-one.

EMBODIMENTS FOR CARRYING OUT THE INVENTION

Figure 1:
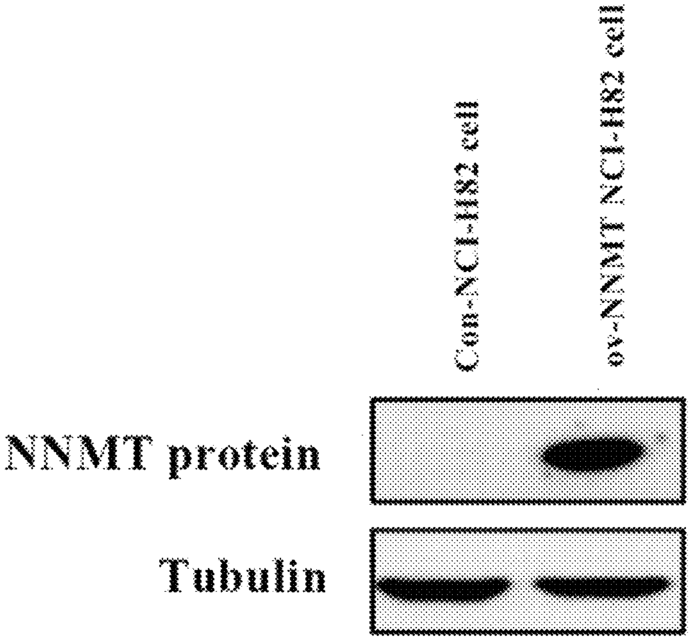
FIG. 1 shows the expression content of NNMT protein in Con-NCI-H82 cell and ov-NNMT NCI-H82 cell using Western Blot test, wherein, Con-NCI-H82 refers to the expression content of NNMT protein in NCI-H82 cell transfected with empty virus vector without carrying NNMT gene and shRNA, which is used as control; ov-NNMT NCI-H82 refers to the expression content of NNMT protein in NCI-H82 cell transfected with virus vector carrying NNMT gene.

Based on an extensive and intensive research, the inventors have unexpectedly developed a compound, the compound has excellent precision treatment effect on tumor with low or no expression of NNMT gene, high expression of DNA methylase, high expression of UHRF1, high methylation level of nucleotide site of NNMT gene, and/or high methylation level of DNA CpG site of NNMT gene. The expression level of NNMT gene, the expression level of DNA methylase, the expression level of UHRF1, the methylation level of nucleotide site of NNMT gene, and/or the methylation level of DNA CpG site of NNMT gene can be used as a marker for determining whether the compound of present invention is suitable for use in the prevention and/or treatment of patient tumor. On this basis, the inventors has completed the present invention.

Terms

Unless otherwise defined, the meanings of all technical and scientific terms used in the invention are the same as those generally understood by the skilled in the art.

As used herein, the term "comprise", "comprising", and "containing" are used interchangeably, which not only comprise open definitions, but also semi-closed and closed definitions. In other words, the term comprises "consisting of" and "essentially consisting of".

As used herein, the term "anti-tumor cancer" and "anti-tumor drug" are used interchangeably.

As used herein, the term "cancer" and "tumor" are used interchangeably.

As used herein, the term "high methylation level of DNA CpG site", "high level of DNA CpG site methylation" and "high methylation of DNA CpG site" are used interchangeably.

As used herein, the term "low methylation level of DNA CpG site", "low level of DNA CpG site methylation" and "low methylation of DNA CpG site" are used interchangeably.

As used herein, the term "high methylation level of nucleotide site", "high level of nucleotide site methylation" and "high methylation of nucleotide site" are used interchangeably.

As used herein, the term "low methylation level of nucleotide site", "low level of nucleotide site methylation" and "low methylation of nucleotide site" are used interchangeably.

As used herein, the term "IC50" and "$IC_{50}$" are used interchangeably, which refers to 50% inhibiting concentration, ie, the concentration of the inhibitor when 50% inhibitory effect is achieved.

As used herein, the term "methylation of CpG site", "methylation of CpG nucleotide" and "CpG methylation" are used interchangeably.

As used herein, the term "P/S" refers to adding penicillin and streptomycin into the culture medium.

As used herein, the term "a cell" refers to a cell (e.g., single tumor cell) or a group of cells containing multiple similar cells ((e.g., a tumor tissue).

As used herein, "the compound of present invention is suitable for use in the prevention and/or treatment of patient tumor" comprises "patient tumor is sensitive to compound of present invention".

As used herein, "the compound of present invention is not suitable for use in the prevention and/or treatment of patient tumor" comprises "patient tumor is not sensitive to compound of present invention".

As used herein, "the expression level of NNMT gene, the expression level of DNA methylase, the expression level of UHRF1, the methylation level of nucleotide site of NNMT gene, and/or the methylation level of DNA CpG site of NNMT gene" refers to one or more of the expression level of NNMT gene, the expression level of DNA methylase, the expression level of UHRF1, the methylation level of nucleotide site of NNMT gene and the methylation level of DNA CpG site of NNMT gene.

As used herein, "the low or no expression of NNMT gene, high expression of DNA methylase, high expression of UHRF1, high methylation level of nucleotide site of NNMT gene, and/or high methylation level of DNA CpG site of NNMT gene" refers to one or more of the low or no expression of NNMT gene, high expression of DNA methylase, high expression of UHRF1, high methylation level of nucleotide site of NNMT gene and high methylation level of DNA CpG site of NNMT gene.

As used herein, "the high expression of NNMT gene, low expression of DNA methylase, low expression of UHRF1, low methylation level of nucleotide site of NNMT gene, and/or low methylation level of DNA CpG site of NNMT gene" refers to one or more of the high expression of NNMT gene, low expression of DNA methylase, low expression of UHRF1, low methylation level of nucleotide site of NNMT gene and low methylation level of DNA CpG site of NNMT gene.

As used herein, the term "NNMT" refers to Nicotinamide N-Methyltransferase.

As used herein, the term "bp" refers to base pair.

As used herein, the term "SST" refers to the transcription start site.

As used herein, the term "Chr11" refers to human chromosome 11 according to human genome version GCF_000001405.25 (GRCh37. p13).

As used herein, the term "human chromosome 11" refers to human chromosome 11 according to human genome version GCF_000001405.25 (GRCh37. p13).

As used herein, the terms "before the transcription start site" and "after the transcription start site" do not comprise the transcription start site itself.

As used herein, the terms "site 114165695 on human chromosome 11" refers to nucleotide of site 114165695 on human chromosome 11; "site 114165730 on human chromosome 11" refers to nucleotide of site 114165730 on human chromosome 11; "site 114165769 on human chromosome 11" refers to nucleotide of site 114165769 on human chromosome 11; “site 114165804 on human chromosome 11” refers to nucleotide of site 114165804 on human chromosome 11; “site 114165938 on human chromosome 11” refers to nucleotide of site 114165938 on human chromosome 11; “site 114166050 on human chromosome 11” refers to nucleotide of site 114166050 on human chromosome 11; “site 114166066 on human chromosome 11” refers to nucleotide of site 114166066 on human chromosome 11.

As used herein, the gene expression comprises the protein expression of the gene and/or the mRNA expression of the gene.

As used herein, the term “DNMT3a” and “DNMT3A” are used interchangeably, which refers to DNA methyltransferase 3a.

As used herein, the term “DNMT3b” and “DNMT3B” are used interchangeably, which refers to DNA methyltransferase 3b.

As used herein, the term “DNMT1” refers to DNA methyltransferase 1.

As used herein, the term “UHRF1” refers to ubiquitin-like with PHD and ring finger domain 1.

As used herein, the term “MS-ESI” refers to Electro Spray Ionization-Mass Spectroscopy.

As used herein, the term “1H NMR” and “$^{1}$H NMR” are used interchangeably, which refers to H Nuclear Magnetic Resonance Spectra.

It should be understood that the skilled in the art can choose the substituents and substituted forms on the compound of the present invention to obtain chemically stable compounds, the compound can be synthesized by the techniques known in the art and the methods described below. If the compound is substituted by more than one substituents, it should be understood that the substituents can be on the same carbon or different carbons, as long as a stable structure is obtained.

As used herein, the term “substitute” or “substituted” means the hydrogen atom on the group is substituted by non-hydrogen atom group, but it needs to meet its valence requirements and the substituted compound is chemically stable, that is, the substituted compound does not spontaneously undergo transformations such as cyclization and elimination, etc.

As used herein, the term “deuterated” refers to one or more hydrogen atoms in a compound or group are substituted by deuterium. The deuterated can be mono-substituted, di-substituted, multi-substituted or fully-substituted.

As used herein, the term “solvate” refers to a complex formed by the coordination of a compound with a solvent molecule in a specific ratio.

As used herein, “$R_1$”, “R1” and “$R^1$” have the same meaning and can be used interchangeably, the other similar definitions have the same meaning.

As used herein, “” denotes the linking site of the group.

As used herein, the term “alkyl” refers to a saturated hydrocarbon group with linear chain (ie, unbranched chain) or branched chain, or a combination of linear and branched chains, the alkyl only have carbon and hydrogen atoms. When the number of carbon atoms is limited in front of the alkyl (e.g., C1-C6 alkyl), it refers to the number of carbon atoms (e.g., 1-6) in the alkyl, for example, C1-C4 alkyl refers to an alkyl having 1-4 carbon atoms. Representative examples comprise but are not limited to methyl, ethyl, propyl, isopropyl, butyl, isobutyl, sec-butyl, tert-butyl, or the like.

As used herein, the term “alkylidene” refers to a group formed by removing one hydrogen on the alkyl, the alkyl is as defined above. When the number of carbon atoms is limited in front of the alkylidene (e.g., C1-C6 alkylidene), it refers to the number of carbon atoms (e.g., 1-6) in the alkylidene, for example, C1-C4 alkylidene refers to an alkylidene having 1-4 carbon atoms. Representative examples comprise but are not limited to methylidene, ethylidene, propylidene, isopropylidene, butylidene, isobutylidene, sec-butylidene, tert-butylidene, or the like.

As used herein, the term “alkenyl” refers to a hydrocarbon group formed by the loss of one hydrogen atom connected to the double bond in linear or branched alkene with one or more double bonds. When the number of carbon atoms is limited in front of the alkenyl (e.g., C2-C6 alkenyl), it refers to the number of carbon atoms (e.g., 1-6) in the alkenyl, for example, C2-C4 alkenyl refers to an alkenyl having 2-4 carbon atoms in the alkenyl. Representative examples comprise but are not limited to ethylenyl (e.g., $CH_2{=}CH—$), butenyl (e.g., $C(CH_3)_2{=}CH—$), or the like.

As used herein, the term “halogen” refers to F, Cl, Br or I.

As used herein, the term “halo” means the group is substituted by halogen.

As used herein, the term “haloalkyl” means that one or more (preferably 1, 2, 3 or 4) hydrogens on the alkyl are substituted by halogen, the alkyl and halogen are as defined above. When the number of carbon atoms is limited in front of the haloalkyl (e.g., C1-C8 haloalkyl), it refers to the number of carbon atoms (e.g., 1-8) in the haloalkyl, for example, C1-C6 haloalkyl refers to an haloalkyl having 1-6 carbon atoms. Representative examples comprise but are not limited to $—CF_3$, $—CHF_2$, monofluoroisopropyl, difluorobutyl, or the like.

As used herein, the term “cycloalkyl” refers to a cyclic group having a saturated or partially saturated monocyclic ring, bicyclic ring or polycyclic ring (fused ring, bridged ring or spiro ring). When the number of carbon atoms is limited in front of the cycloalkyl (e.g., C3-C12 cycloalkyl), it refers to the number of ring carbon atoms (e.g., 3-12) in the cycloalkyl. For example, C3-C8 cycloalkyl refers to a saturated or partially saturated monocycloalkyl or dicycloalkyl having 3-8 ring carbon atoms, comprising cyclopropyl, cyclobutyl, cyclopentyl, cycloheptyl, or the like. The term “spirocycloalkyl” refers to a bicyclic or polycyclic group that shares a carbon atom (referred to spiro-atom) between single rings, the spirocycloalkyl can contain one or more double bonds, but no ring has a fully conjugated π electron system. Fused cycloalkyl refers to all carbon bicyclic or polycyclic group in which each rings in the system shares an adjacent pair of carbon atoms with other rings, one or more rings can have one or more double bonds, but no ring has a fully conjugated π electron system. Bridged cycloalkyl refers to all carbon polycyclic group in which any two rings share two non-directly connected carbon atoms, the bridged cycloalkyl can have one or more double bonds, but no ring has a fully conjugated π electron system. The representative examples of cycloalkyl comprise but are not limited to

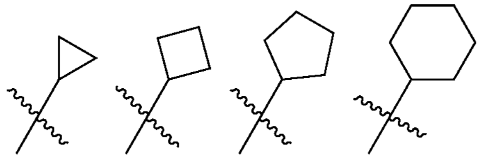

-continued

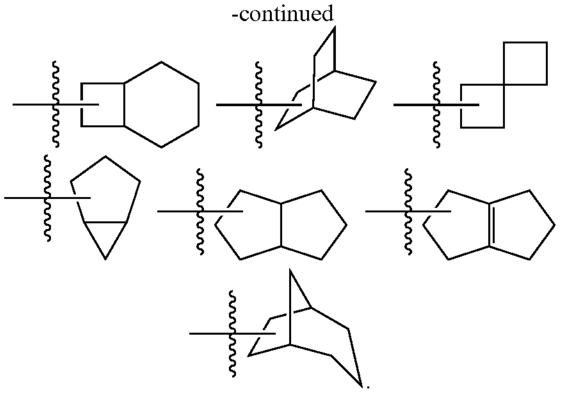

As used herein, the term “halocycloalkyl” means that one or more (preferably 1, 2, 3 or 4) hydrogens on cycloalkyl are substituted by halogen, the cycloalkyl and halogen are as defined above. When the number of carbon atoms is limited in front of the halocycloalkyl (e.g, C3-C8 halocycloalkyl), it refers to the number of ring carbon atoms (e.g., 3-8) in the halocycloalkyl, for example, C3-C8 halocycloalkyl refers to an halocycloalkyl having 3-8 ring carbon atoms. Representative examples comprises but are not limited to monofluorocyclopropyl, monochlorocyclobutyl, monofluorocyclopentyl, difluorocycloheptyl, or the like.

As used herein, the term “alkoxyl” refers to R—O— group, wherein R is alkyl, the alkyl is as defined above. When the number of carbon atoms is limited in front of the alkoxyl, for example, C1-C8 alkoxyl means that the alkyl in the alkoxyl has 1-8 carbon atoms. Representative examples of alkoxyl comprise but are not limited to methoxyl, ethoxyl, n-propoxyl, isopropoxyl, tert-butoxyl, or the like.

As used herein, the term “alkylthio” refers to R—S— group, wherein R is alkyl, the alkyl is as defined above. When the number of carbon atoms is limited in front of the alkylthio, for example, C1-C8 alkylthio means that the alkyl in the alkylthio has 1-8 carbon atoms. Representative examples of alkylthio comprise but are not limited to methylthio, ethylthio, n-propylthio, isopropylthio, tert-butylthio, or the like.

As used herein, the term “haloalkoxyl” refers to haloalkyl-O—, wherein the haloalkyl is as defined above, for example, C1-C6 haloalkoxyl refers to a haloalkoxyl having 1-6 carbon atoms. Representative examples comprise but are not limited to monofluoromethoxyl, monofluoroethoxyl, bisfluorobutoxyl, or the like.

As used herein, the term “haloalkylthio” refers to haloalkyl-S—, wherein the haloalkyl is as defined above, for example, C1-C6 haloalkylthio refers to a haloalkylthio having 1-6 carbon atoms. Representative examples of haloalkylthio comprise but are not limited to monofluoromethylthio, monofluoroethylthio, difluorobutylthio, or the like.

As used herein, the term “cycloalkoxyl” refers to R—O—, wherein R is cycloalkyl, the cycloalkyl is as defined above. When the number of carbon atoms is limited in front of the cycloalkoxyl, for example, C3-C8 cycloalkoxyl means that the cycloalkyl in the cycloalkoxyl has 3-8 ring carbon atoms. Representative examples of cycloalkoxyl comprise but are not limited to cyclopropyloxyl, cyclobutoxyl, or the like.

As used herein, the term “cycloalkylthio” refers to R—S— group, wherein R is cycloalkyl, the cycloalkyl is as defined above. When the number of carbon atoms is limited in front of the cycloalkylthio, for example, C3-C8 cycloalkylthio means that the cycloalkyl in the cycloalkylthio has 3-8 ring carbon atoms. Representative examples of cycloalkylthio comprise but are not limited to cyclopropylthio, cyclobutythio, or the like.

As used herein, the term “halocycloalkoxyl” means that one or more (preferably 1, 2, 3 or 4) hydrogens on the cycloalkoxyll are substituted by halogen, the cycloalkoxyl and halogen are as defined above. When the number of carbon atoms is limited in front of the halocycloalkoxyl (e.g., C3-C8 halocycloalkoxyl), it refers to the number of ring carbon atoms (e.g., 3-8) in the halocycloalkoxyl, for example, C3-C8 halocycloalkoxyl refers to an halocycloalkoxyl having 3-8 ring carbon atoms. Representative examples comprises but are not limited to monofluorocyclopropyl-O—, monochlorocyclobutyl-O—, monofluorocyclopentyl-O—, difluorocycloheptyl-O—, or similar functional groups, or the like.

As used herein, the term “halocycloalkylthio” means that one or more (preferably 1, 2, 3 or 4) hydrogens on the cycloalkoxyll are substituted by halogen, the cycloalkoxyl and halogen are as defined above. When the number of carbon atoms is limited in front of the halocycloalkylthio (e.g., C3-C8 halocycloalkylthio), it refers to the number of ring carbon atoms (e.g., 3-8) in the halocycloalkylthio, for example, C3-C8 halocycloalkylthio refers to an halocycloalkylthio having 3-8 ring carbon atoms. Representative examples comprises but are not limited to monofluorocyclopropyl-S—, monochlorocyclobutyl-S—, monofluorocyclopentyl-S—, difluorocycloheptyl-S—, or similar functional groups, or the like.

As used herein, the term “heterocycloalkane ring” refers to fully saturated or partially unsaturated ring (comprising but not limited to such as 3-7 membered monocyclic ring, 7-11 membered bicyclic ring, or 8-16 membered tricyclic ring), at least one heteroatom is present in a ring with at least one carbon atom. When the number of members is limited in front of the heterocycloalkane ring, it refers to the number of ring atoms in the heterocycloalkane ring, for example, 3-16 membered heterocycloalkane ring refers to a heterocycloalkane ring having 3-16 ring atoms. Each heterocyclic ring having heteroatoms can have one or more (e.g., 1, 2, 3 or 4) heteroatoms, each of heteroatoms is independently selected from the group consisting of nitrogen atom, oxygen atom or sulfur atom, wherein the nitrogen atom or sulfur atom can be oxidized, and the nitrogen atom can also be quaternized. Representative examples of monocyclic heterocycloalkane ring comprise but are not limited to azetidine ring, oxetane ring, tetrahydrofuran ring, piperidine ring, piperazine ring. Polycyclic heterocycloalkane ring comprises spiro, fused and bridged ring, the spiro, fused and bridged heterocycloalkane ring is optionally linked with other rings by single bond, or further linked with other cycloalkane ring and heterocycloalkane ring by any two or more atoms on the ring.

As used herein, the term “heterocycloalkyl” refers to fully saturated or partially unsaturated cyclic (comprising but not limited to such as 3-7 membered monocyclic ring, 7-11 membered bicyclic ring, or 8-16 membered tricyclic ring) group, at least one heteroatom is present in a ring with at least one carbon atom. When the number of members is limited in front of the heterocycloalkyl, it refers to the number of ring atoms in the heterocycloalkyl, for example, 3-16 membered heterocycloalkyl refers to a heterocycloalkyl having 3-16 ring atoms. Each heterocyclic ring having heteroatoms can have one or more (e.g., 1, 2, 3 or 4) heteroatoms, each of heteroatoms is independently selected from the group consisting of nitrogen atom, oxygen atom or sulfur atom, wherein the nitrogen atom or sulfur atom can be oxidized, and the nitrogen atom can also be quaternized. Representative examples of monocyclic heterocycloalkyl comprise but are not limited to azetidinyl, oxetanyl, tetrahydrofuranyl, piperidinyl, piperazinyl. Polycyclic heterocycloalkyl comprises spiro, fused and bridged heterocyclyl, the spiro, fused and bridged heterocycloalkyl is optionally linked with other groups by single bond, or further linked with other cycloalkane rings and heterocycloalkane ring by any two or more atoms on the ring.

As used herein, the term “aryl” refers to an full carbon monocyclic ring or fused polycyclic ring (i.e., a ring that shares adjacent carbon atom pairs) group with a conjugated $\pi$ electron system, which is aromatic cyclic hydrocarbon compound group. When the number of carbon atoms is limited in front of the aryl, for example, C6-C12 aryl means that the aryl has 6-12 ring carbon atoms, such as phenyl and naphthyl.

As used herein, the term “heteroaryl” refers to aromatic heterocyclic ring group having one to more (preferably 1, 2, 3 or 4) heteroatoms, the heteroaryl can be monocyclic ring, or polycyclic ring (bicyclic, tricyclic or polycyclic ring) fused together or covalently connected. Each of heterocyclic ring having heteroatom can have one or more (e.g., 1, 2, 3, 4) heteroatoms independently selected from the group consisting of oxygen, sulfur and nitrogen. When the number of members is limited in front of the heteroaryl, it refers to the number of ring atoms of the heteroaryl, for example, 5-12 membered heteroaryl refers to a heteroaryl having 5-12 ring atoms. Representative examples comprise but are not limited to pyrrolyl, pyrazolyl, imidazolyl, thiazolyl, furanyl, pyridyl, pyrimidinyl, etc.

As used herein, the term “carboxyl” refers to —COOH or -alkyl-COOH, the alkyl is as defined above. For example, “C2-C4 carboxyl” refers to —C1-C3 alkyl-COOH. Representative examples of carboxyl comprise but are not limited to —COOH, —$CH_2COOH$, or the like.

As used herein, the term “ester group” refers to R—C(O)—O— or —C(O)—O—R, wherein, R is alkyl, the alkyl is defined as above. For example, “$C_2$-$C_4$ ester group” refers to $C_1$-$C_3$ alkyl-C(O)—O— or —C(O)—O—$C_1$-$C_3$ alkyl. Representative examples of ester group comprise but are not limited to $CH_3C(O)O$—, $C_2HSC(O)O$—, $(CH_3)_2CHC(O)O$—, —$C(O)OCH_3$, —$C(O)OC_2H_5$, or the like.

As used herein, the term “amide group” refers to R—C(O)—N— or —C(O)—N—R, wherein, R is alkyl, the alkyl is defined as above. For example, “$C_2$-$C_4$ amide group” refers to $C_1$-$C_3$ alkyl-C(O)—N— or —C(O)—N—$C_1$-$C_3$ alkyl. Representative examples of amide group comprise but are not limited to $CH_3C(O)$—N—, $C_2HSC(O)$—N—, $(CH_3)_2$ CHC(O)—N—, —C(O)—N—$CH_3$, —C(O)—N—$C_2H_5$, or the like.

As used herein, the term “acyl” refers to

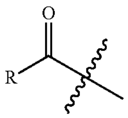, wherein R is alkyl, the alkyl is as defined above. When the number of carbon atoms is limited in front of the acyl (e.g, C2-C6 acyl), it refers to the number of carbon atoms (e.g., 2-6) in the acyl, for example, C2-C6 acyl refers to acyl having 2-6 carbon atoms. For example, the $C_2$-$C_4$ acyl refers to $C_1$-$C_3$ alkyl —C(O)—, representative examples comprises but are not limited to $CH_3C(O)$—, $C_2H_5C(O)$—, or the like.

As used herein, the term “—C(O)—” and

“ 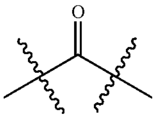 ”

are used interchangeably.

As used alone or as part of other substituent, the term “amino” refers to —$NH_2$.

As used alone or as part of other substituent, the term ‘nitro’ refers to —$NO_2$.

As used alone or as part of other substituent, the term “cyano” refers to —CN.

As used alone or as part of other substituent, the term “hydroxyl” refers to —OH.

As used alone or as part of other substituent, the term “sulfhydryl” refers to —SH.

As used herein, the term “$(R_{20}R_{21})$N—” and

“ 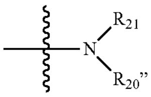 ”

are used interchangeably.

As used herein, “$R_3$ and $R_4$, or $R_4$ and $R_5$ are connected to form a substituted or unsubstituted 3-12 membered heterocycloalkane ring” means that $R_3$ and $R_4$ are connected to form a substituted or unsubstituted 3-12 membered heterocycloalkane ring, or $R_4$ and $R_5$ are connected to form a substituted or unsubstituted 3-12 membered heterocycloalkane ring, and the like.

In present invention, it should be understood that all substituents are unsubstituted, unless explicitly described herein as “substituted”. The “substituted” means that one or more hydrogen atoms on group are substituted by a substituent. The substituent is the substituent as described above or the substituent in each Example. Preferably, each “substituted” means that one or more (preferably 1, 2, 3, 4, 5, 6, 7, or 8) hydrogen atoms on the ring or group are independently substituted by substituent selected from the group consisting of C1-C10 haloalkyl, C3-C8 halocycloalkyl, C3-C8 cycloalkoxyl, C3-C8 cycloalkylthio, C3-C8 halocycloalkoxyl, C3-C8 halocycloalkylthio, halogen, nitro, —CN, carbonyl (═O), hydroxyl, sulfhydryl, amino, C1-C4 carboxyl, C2-C8 ester group, C2-C4 amide group, C2-C6 acyl, C1-C10 alkoxyl, C1-C10 alkylthio, C1-C10 haloalkoxyl, C1-C10 haloalkylthio, C6-C12 aryl, C6-C12 aryl-O—, 5-10 membered heteroaryl, 5-10 membered heteroaryl-O—, 5-10 membered heterocycloalkyl, $(R_{20}R_{21})$N—.

In the present invention, the term “prevention” refers to a method of preventing the occurrence of disease and/or its accompanying symptoms, or protecting a subject from getting disease. The term ‘prevention’ also comprises delaying the occurrence of disease and/or its accompanying symptoms and reducing the risk of getting disease for subject.

In the present invention, the term “treatment” comprises delaying and terminating the progression of the disease, or eliminating the disease, and it does not require 100% inhibition, elimination and reversal. In some embodiments, compared to the level observed in the absence of the compound of present invention, the compound of present invention alleviates, inhibits and/or reverses related disease (e.g., tumor) and its accompanying symptoms, for example, by at least about 10%, at least about 30%, at least about 50%, at least about 80%, at least about 90%, or 100%.

Compound

As used herein, the terms "compound of the present invention", "compound of formula I of the present invention" and "compound of formula I" are used interchangeably, and refer to a compound of formula I, or an optical isomer thereof, or a racemate thereof, or a solvate thereof, or a pharmaceutically acceptable salt thereof, or a deuterated compound thereof. It should be understood that the term also comprises a mixture of the above components.

I

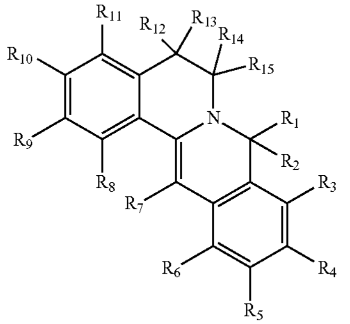

Specifically, the compound of formula I, or an optical isomer thereof, or a racemate thereof, or a solvate thereof, or a pharmaceutically acceptable salt thereof, or a deuterated compound thereof is as described above in the first aspect of the present invention.

In the present invention, the configuration of the compound of formula I can be racemate, R configuration (rectus) or S configuration (sinister). The structure and determination method of the racemate, R configuration (rectus) or S configuration (sinister) of the compound of the present invention are well known to the skilled in the art. For example, the structure of the racemate, R configuration (rectus) or S configuration (sinister) of a compound is as follows:

The racemate, R configuration (rectus) or configuration (sinister) of other compounds is the like.

Typically, the compound of formula I of the present invention is the compound (comprising salt thereof or free form without salt root) prepared in the Examples of the present invention.

The compound of formula I of the present invention can be prepared using the known organic synthesis method in the art.

The term "pharmaceutically acceptable salt" refers to a salt formed by the compound of the present invention and an acid or a base, the salt is suitable for use as a drug. Pharmaceutically acceptable salt comprises inorganic salt and organic salt. A preferred type of salt is the salt formed by the compound of the present invention and an acid. Acids suitable for salt formation comprise but are not limited to inorganic acid such as hydrochloric acid, hydrobromic acid, hydrofluoric acid, sulfuric acid, nitric acid, phosphoric acid and the like; organic acid such as formic acid, acetic acid, trifluoroacetic acid, trifluoroformic acid, propionic acid, oxalic acid, malonic acid, succinic acid, fumaric acid, maleic acid, lactic acid, malic acid, tartaric acid, citric acid, picric acid, methanesulfonic acid, benzenemethanesulfonic acid, benzenesulfonic acid and the like; and acidic amino acid such as aspartic acid and glutamic acid. A preferred type of salt is a metal salt formed by the compound of the present invention and a base. Bases suitable for salt formation comprise but are not limited to inorganic base such as sodium hydroxide, potassium hydroxide, sodium carbonate, sodium bicarbonate, sodium phosphate and the like; and organic base such as ammonia, triethylamine, diethylamine and the like.

The compound of formula I in present invention can be converted into its pharmaceutically acceptable salt using conventional methods. For example, a solution of corresponding acid can be added into the solution of above compounds, and the solvent is removed after the salt is formed, thereby forming the corresponding salt of the compound of the present invention.

The compounds of the present invention is preferably prepared as described in the Examples of the present invention.

NNMT Gene

In the present invention, the English name of NNMT is Nicotinamide N-Methyltransferase. Different databases have different identification numbers for NNMT gene as

| racemate | R configuration (rectus) or S configuration (sinister) |
| --- | --- |
| 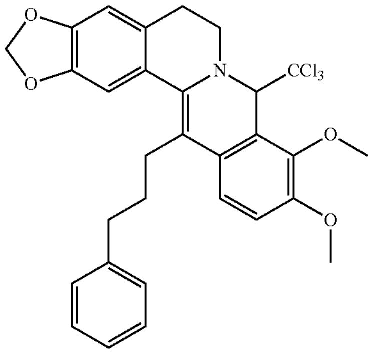 | 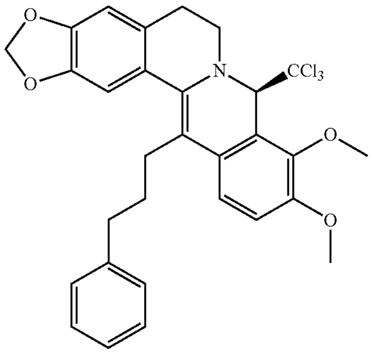 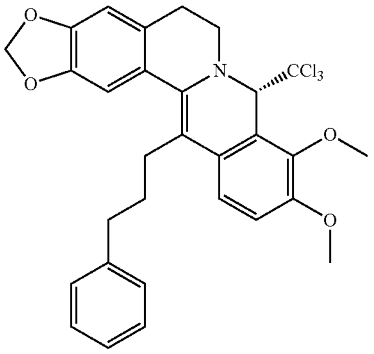 |

follows: HGNC: 7861; Entrez Gene: 4837; Ensembl: ENSG00000166741; OMIM: 600008; UniProtKB: P40261

According to version GCF_000001405.25 (GRCh37.p13) of human genome, the NNMT gene is located at 114,128,528 bp to 114,184,258 bp on human chromosome 11, the total length of DNA sequence of NNMT gene is 55,731 bp, the NNMT gene comprises promoter region, exon region and intron region, the transcription start site of NNMT gene is at site 114,166,535 bp.

The promoter region of NNMT gene is the nucleotide sequence from the 114164535 bp to 114167034 bp on human chromosome 11, i.e. the sequence from 2000 bp before the transcription start site (bold section) and 499 bp after the transcription start site (non-bold section) in NNMT gene, the total length of promoter region of NNMT gene is 2500 bp, The nucleotide sequence of the promoter region of NNMT gene is as shown in SEQ ID NO: 1 as follows:

SEQ ID NO: 1:

TATCCAAGAGCTATCAGCACTCCCATGTTTATTGTAGCACTGTTC

ACAATAGCCAAGATTTGGAAGTACTCTAAGTGTCCATTAGCAGAT

GAATGGATAAAGACAATGTGGTAATACACATAATGGAGTACTATT

CAGTCATAAAGAAGAATTAGATCCTGTCATTTGCAATAACATGGA

TGGAACTGGAGGTCATAATGTTGAGTGAAATAAACCAGGCACAGA

AAGACAAACTTTGCATGTTCTCACTTATTTATGGGAGCTAAAAAC

TAAAATAACTGAACTCACAGAGATAGAGAGTAGAAGGATGGTTAC

GAGAGGATGGGAAGGGTAGCGAGGTGGGTAGGGGGGATGTGGGGA

TCATTAATGGGTATAAAAAATAGTTAGAGGCCAGGCGCAGTGGCT

CACGCCTGTAATCCCAGCACTTTGGGAGGCCGAGGTAGGCGGAAC

ACCTGAGGAGTTCAAGACCAGCCTGGCCAATATGATGAAACCCCG

TCTCTACTAAAAATACAAAAATTAGCTGGGCGTGATGGTGTGCAC

CTGTAGTCCCAGCTGCTTGGGAGGCTGAGGCAGGAGAATCGCTGG

AACCCAAGAGGTGAAGGTTGCAGTGAGCTGAGATCGCGTCACTGC

ACTCCAGCCTGGGTGACAGAGTGAGACTCCACATCAAAAAAAAAA

AAAAAAAGTTAGAAAGATTGAATAAGACCTAATATTTGCTAGCAC

AACAGGGTGAATATAGTAAAAAATAATTTATTTGTACCTTCAAAA

ATAACTAGACAAGTATAATTGGGTTGTTTGTAACACACAAAAAAT

AAGTACTTGAAGTGGTGGATACCCCATTTACCCTGATGTGATTAT

TTTGTATTGCAGGCCTCTATCAGAATATCTCATGTAACCCATAAA

TATATACACCTACTCTGTACCCACAAAAAGTTTTTAAAAAGAAAA

ATAAATAGCAACCGAAAAAAAAAGAGAGGGAGAAAAGAAAAAAGA

AAAAAAAATCAAGTGCCTGGCTGGGTAGAATAAATTCTAAGGCCA

CAATGTTACTGACCATGGGTTTTTTGGCTCTCAGTGTATAGAAAT

TGACACAAGGCCAATAGTCTTCCCAAACATGCTTTACTGGAACTT

ACGCCCTGGCATAAGGGCCACAACAAAAGAGAGAGCGAATTCTCT

GGCTTGCTGACTCCTTGGAAAAAACCGGTAGGGATTTTTTTATTA

GGCAAAGCACAGGAATTGACGTCAGAGGCAGGATGTGCTGCTGGG

CAAAGCATACGAGAAGTGGGGTATGCAGGTCAGCATTACTTGGTT

-continued

GCAATGGTTATCTTGAGGAATGGGCCAACTGGTGGTCTGGCCAGT

GGCAACAAGGCTGTAAATCAATTATTCAGCATTCCTTCCCAAGGT

GGGACACCCGGCAACATTGTTTATCTCCTAAGGCCAGTTCCTGGA

ATTAAGTGAAAGGATGACTAATGGACATGTTGTCAGTGAGGTAGT

GGTGTGGGTTTTGTGACCAGTGGGAATGCACGAAAGAATGCTTTA

GCGGGGAGTGAGCTGAAGCCAAGCCCCATCCCTACTCTGTCTCAA

AGTGAGTTCAGAAAAGGGGATTTAAAGAATTCTTTTTTTTTTTTT

TTTTTTTTTTGAGACAGAGTCTTGCTCTGTCGCCCAGGCTGGAGT

GCAGTGGCGCCATCTTGGCTCACTGCAAGCTCCGCCCCCCGGGTT

CATGCCATTCTCCTGCCTCAGCCTCCCAAGTAGCTGGGACTGCAG

GTGCCTACCACCAAGCCCAGCTAATTTTTTGTATTTTTTTTTTAG

TAGAGACGGGGTTTCACCATGTTAGCCAGGATGGTCTCGATCTCC

TGACCTCGTGATCTGCCCGCCTTAGCCTCCCAAAGTGCTGGGATT

ACAGGCATGAGCCTCCGCCCCCGGCCTTAAATAATTCTTAAAGGA

AGTAAAGTTAACTTTGAAAGAACTATCAGGATTTGGATTGACTGA

AAGGAGTGGGGAAGCTTAGGGAGGAGGTGCTTGCCAGACACTGGG

TCATGGCAGTGGTCGGTGAAGCTGCAGTTGCCTAGGGCAGGGATG

GAGAGAGAGTCTGGGCATGAGGAGAGGGTCTCGGGATGTTTGGCT

GGACTAGATTTTACAGAAAGCCTTATCCAGGCTTTTAAAATTACT

CTTTCCAGACTTCATCTGAGACTCCTTCTTCAGCCAACATTCCTT

AGCCCTGAATACATTTCCTATCCTCATCTTTCCCTTCTTTTTTTT

CCTTTCTTTTACATGTTTAAATTTAAACCATTCTTCGTGACCCCT

TTTCTTGGGAGATTCATGGCAAGAACGAGAAGAATGATGGTGCTT

GTTAGGGGATGTCCTGTCTCTCTGAACTTTGGGGTCCTATGCATT

AAATAATTTTCCTGACGAGCTCAAGTGCTCCCTCTGGTCTACAAT

CCCTGGCGGCTGGCCTTCATCCCTTGGGCAAGCATTGCATACAGC

TCATGGCCCTCCCTCTACCATACCC.

In the present invention, the nucleotide sites from 1050 bp before the transcription start site to 499 bp after the transcription start site in NNMT gene is sites 951-2500 of nucleotide sequence as shown in SEQ ID NO: 1.

In the present invention, the nucleotide sites from 1050 bp to 193 bp before the transcription start site in NNMT gene is sites 951-1808 of nucleotide sequence as shown in SEQ ID NO: 1.

In the present invention, the nucleotide sites from 840 bp to 469 bp before the transcription start site in NNMT gene is sites 1161-1532 of nucleotide sequence as shown in SEQ ID NO: 1.

In present invention, the site 114165695, site 114165730, site 114165769, site 114165804, site 114165938, site 114166050 and site 114166066 on the human chromosome 11 correspond to the nucleotide site in SEQ ID NO: 1 as shown in Table 1:

TABLE 1

| Site on the human chromosome 11 | Corresponding to the nucleotide site in SEQ ID NO: 1 |
|---|---|
| site 114165695 | site 1161 |
| site 114165730 | site 1196 |
| site 114165769 | site 1235 |
| site 114165804 | site 1270 |
| site 114165938 | site 1404 |
| site 114166050 | site 1516 |
| site 114166066 | site 1532 |

DNA Methylation

DNA methylation is a form of chemical modification of DNA, which can change genetic performance under no change of DNA sequence. Many studies have shown that DNA methylation can cause changes in chromatin structure, DNA conformation, DNA stability and the way DNA interacts with protein, thereby regulating gene expression.

DNA methylation is one of the earliest discovered and most deeply studied epigenetic regulatory mechanisms. Broadly speaking, DNA methylation refers to the chemical modification process in which a specific base in the DNA sequence is modified with a methyl by covalent bonding with S-adenosyl methionine (SAM) as methyl donor under the catalysis of DNA methyltransferase (DNMT). This DNA methylation can occur at position C-5 of cytosine, position N-6 of adenine and position N-7 of guanine. DNA methylation in general studies mainly refers to the methylation process that occurs at the carbon atom of position C-5 on cytosine in CpG dinucleotides, the product is called 5-methylcytosine (5-mC). The 5-methylcytosine (5-mC) is the main form of DNA methylation in eukaryotic organisms such as plants and animals. DNA methylation, as a relatively stable modification state, can be passed on to new generations of DNA during DNA replication process under the action of DNA methyltransferase, which is an important epigenetic mechanism.

There are two types of DNA methylation reactions. One type is that the two unmethylated strands in the DNA are methylated, which is called denovo methylation; the other type is that the unmethylated strand of double-stranded DNA with one methylated strand and one unmethylated strand is methylated, which is called maintenance methylation.

Typically, DNA methylation is the methylation of DNA CpG site. The distribution of CpG binucleotide is very uneven in the human genome, while CpG remains or is higher than normal level in some regions of the genome. The CpG site rich region (also known as CpG island) is mainly located in the promoter region and exon regions of the gene, which is a region rich in CpG dinucleotide. About 60% of the promoters of the gene contains CpG island. The CpG is the abbreviation of cytosine (C)-phosphate (p)-guanine (G).

Gene expression is regulated by various signaling pathways, transcription factors and epigenetic modifications in the cell. DNA methylation modification is an important way in which epigenetic modifications regulate gene expression. The level of DNA methylation in a specific gene region often affects the expression level of the gene. Compared to the regulation of gene expression by signal transduction pathways and transcription factors, the effect of DNA methylation modification on gene expression is more stable in epigenetic modification, which is not easily affected by the extracellular environment. DNA methylation modification can be easily and accurately detected using existing technologies, so the DNA methylation is an ideal biomarker.

Tumor

The studies of the present invention shows the compound of present invention can be used for preventing and/or treating tumor.

As used herein, the term "tumor" and "cancer" are used interchangeably.

In a preferred embodiment of the present invention, the tumor comprises tumor with low or no expression of NNMT gene. Typically, the tumor with low or no expression of NNMT gene is as described above in the third aspect of the present invention.

In a preferred embodiment of the present invention, the tumor comprises tumor with high expression of DNA methylase. Typically, the tumor with high expression of DNA methylase is as described above in the third aspect of the present invention.

The DNA methylase of present invention comprises but is not limited to DNMT1, DNMT3a, DNMT3b, and combinations thereof. Preferably, the DNA methylase comprises DNMT1.

In a preferred embodiment of the present invention, the tumor comprises tumor with high expression of DNMT1. Typically, the tumor with high expression of DNMT1 is as described above in the third aspect of the present invention.

In a preferred embodiment of the present invention, the tumor comprises tumor with high expression of DNMT3a. Typically, the tumor with high expression of DNMT3a is as described above in the third aspect of the present invention.

In a preferred embodiment of the present invention, the tumor comprises tumor with high expression of DNMT3b. Typically, the tumor with high expression of DNMT3b is as described above in the third aspect of the present invention.

In a preferred embodiment of the present invention, the tumor comprises tumor with high expression of UHRF1 (ubiquitin-like with PHD and ring finger domain 1). Typically, the tumor with high expression of UHRF1 is as described above in the third aspect of the present invention.

In a preferred embodiment of the present invention, the tumor comprises tumor with high methylation level of nucleotide site of NNMT gene. Typically, the tumor with high methylation level of nucleotide site of NNMT gene is as described above in the third aspect of the present invention.

In a preferred embodiment of the present invention, the tumor comprises tumor with high methylation level of DNA CpG site of NNMT gene. Typically, the tumor with high methylation level of DNA CpG site of NNMT gene is as described above in the third aspect of the present invention.

Typically, the tumor of present invention is as described above in the third aspect of the present invention.

In present invention, the type of tumors corresponding to tumor cell lines are shown in Table 2

TABLE 2

| Tumor cell line | The corresponding type of tumor |
|---|---|
| NCI-H82 | Human small cell lung cancer cell |
| G-401 | Human renal carcinoma Wilms cell |
| MDA-MB-453 | Breast cancer cell |
| SW48 | Human colon adenocarcinoma cell |
| GB-1 | Human brain glioblastoma cell |
| CFPAC-1 | Human pancreatic cancer cell |
| SF126 | Human glioblastoma multiforme cell |
| 786-O | Clear cell renal cell adenocarcinoma cell |
| D341 Med | Cerebellar medulloblastoma cell |

TABLE 2-continued

| Tumor cell line | The corresponding type of tumor |
|---|---|
| Kelly | Brain neuroblastoma cell |
| NB-1 | Brain neuroblastoma cell |

Anti-Tumor Drug

The anti-tumor drug can be the compound of formula I, or an optical isomer thereof, or a racemate thereof, or a solvate thereof, or a pharmaceutically acceptable salt thereof, or a deuterated compound thereof of the present invention.

Use

A use of the compound of formula I of the present invention for preventing and/or treating tumor is provided.

Specifically, the compound of present invention has remarkable and excellent prevention and treatment effect on tumor with low or no expression of NNMT gene, high expression of DNA methylase, high expression of UHRF1, high methylation level of nucleotide site of NNMT gene, and/or high methylation level of DNA CpG site of NNMT gene. That is, the tumor with low or no expression of NNMT gene, high expression of DNA methylase, high expression of UHRF1, high methylation level of nucleotide site of NNMT gene, and/or high methylation level of DNA CpG site of NNMT gene is sensitive to the compound of the present invention. The expression level of NNMT gene, the expression level of DNA methylase, the expression level of UHRF1, the methylation level of nucleotide site of NNMT gene, and/or the methylation level of DNA CpG site of NNMT gene can be used as a marker for determining whether the compound of the present invention is suitable for use in the precision treatment on tumor, the biomarker can be used to effectively identify patient tumor sensitive to the compound of the present invention, improve treatment effects and avoid administrating the compound of the present invention to patient tumor insensitive to the compound of the present invention, thereby achieving precision treatment on tumor.

The present invention further provides a method for preventing and/or treating tumor, which comprises administering the compound of the present invention to a subject in need.

The compound of present invention has more remarkable and excellent prevention and treatment effect on tumor with low or no expression of NNMT gene, high expression of DNA methylase, high expression of UHRF1, high methylation level of nucleotide site of NNMT gene, and/or high methylation level of DNA CpG site of NNMT gene, therefore, during the prevention and/or treatment of tumor, firstly administering NNMT gene inhibitor, DNA methylase promoter, UHRF1 promoter, methylation promoter of nucleotide site of NNMT gene, and/or methylation promoter of DNA CpG site of NNMT gene to achieve low or no expression of NNMT gene, high expression of DNA methylase, high expression of UHRF1, high methylation level of nucleotide site of NNMT gene, and/or high methylation level of DNA CpG site of NNMT gene in the subject tumor, then administering the compound of the present invention to prevent and/or treat tumor. Therefore, the present invention develops a compound that can significantly enhance anti-tumor effects when combined with NNMT gene inhibitor, DNA methylase promoter, UHRF1 promoter, methylation promoter of nucleotide site of NNMT gene, and/or methylation promoter of DNA CpG site of NNMT gene. The compound of the present invention can be combined with NNMT gene inhibitor, DNA methylase promoter, UHRF1 promoter, methylation promoter of nucleotide site of NNMT gene, and/or methylation promoter of DNA CpG site of NNMT gene to significantly enhance the treatment effect of the compound on tumor.

In another preferred embodiment, the subject is human and non-human mammals (rodent, rabbit, monkey, livestock, dog, cat, etc.).

In the present invention, there are no special limitations to the method for achieving low or no expression of NNMT gene, high expression of DNA methylase, high expression of UHRF1, high methylation level of nucleotide site of NNMT gene, and/or high methylation level of DNA CpG site of NNMT gene in the tumor. For example, the low or no expression of NNMT gene, high expression of DNA methylase, high expression of UHRF1, high methylation level of nucleotide site of NNMT gene, and/or high methylation level of DNA CpG site of NNMT gene in the tumor can be specifically achieved using methods such as gene insertion, gene knockout, or gene silencing (e.g, shRNA transfection), etc.

Marker

The present invention provides a marker for determining whether the compound of present invention is suitable for use in the prevention and/or treatment of patient tumor, the marker comprises the expression level of NNMT gene, the expression level of DNA methylase, the expression level of UHRF1, the methylation level of nucleotide site of NNMT gene, and/or the methylation level of DNA CpG site of NNMT gene.

In a preferred embodiment, the expression level of NNMT gene, the expression level of DNA methylase, the expression level of UHRF1, the methylation level of nucleotide site of NNMT gene, and/or the methylation level of DNA CpG site of NNMT gene are used as a marker for determining whether the compound of present invention is suitable for use in the prevention and/or treatment of patient tumor, the method comprises as follows:

the compound of present invention is suitable for use in the prevention and/or treatment of patient tumor with low or no expression of NNMT gene, high expression of DNA methylase, high expression of UHRF1, high methylation level of nucleotide site of NNMT gene, and/or high methylation level of DNA CpG site of NNMT gene; and/or the compound of present invention is not suitable for use in the prevention and/or treatment of patient tumor with high expression of NNMT gene, low expression of DNA methylase, low expression of UHRF1, low methylation level of nucleotide site of NNMT gene, and/or low methylation level of DNA CpG site of NNMT gene.

Specifically, the tumor with low or no expression of NNMT gene, high expression of DNA methylase (e.g, NNMT1), high expression of UHRF1, high methylation level of nucleotide site of NNMT gene, and/or high methylation level of DNA CpG site of NNMT gene is as described above in the third aspect of the present invention.

In a preferred embodiment, the tumor with high expression of NNMT gene, low expression of DNA methylase (e.g, NNMT1), low expression of UHRF1, low methylation level of nucleotide site of NNMT gene, and/or low methylation level of DNA CpG site of NNMT gene is as described above in the fourth aspect of the present invention.

The present invention further provides a use of the marker (or the expression level of marker) or its detection reagent in the preparation of reagent kit for determining whether the compound of the present invention is suitable for use in the prevention and/or treatment of patient tumor.

Composition or Preparation, Active Ingredient Combination, Medical Kit and Administration Method Preferably, the composition of the present invention is pharmaceutical composition. The compositions of the present invention can comprise a pharmaceutically acceptable carrier.

The term "pharmaceutically acceptable carrier" refers to one or more compatible solid, semi-solid, liquid or gel fillers, which are suitable for use in human or animal and must have sufficient purity and sufficiently low toxicity. The "compatible" means each component and drug active ingredient in the pharmaceutical composition can be blended with each other without significantly reducing the efficacy.

It should be understood that the pharmaceutically acceptable carrier is not particularly limited in the present invention, the carrier can be selected from materials commonly used in the art, or can be obtained by a conventional method, or is commercially available. Some examples of pharmaceutically acceptable carriers are cellulose and its derivatives (e.g., methylcellulose, ethylcellulose, hydroxypropylmethylcellulose, sodium carboxymethylcellulose, etc.), gelatin, talc, solid lubricants (e.g., stearic acid, magnesium stearate), calcium sulfate, plant oil (e.g., soybean oil, sesame oil, peanut oil, olive oil, etc.), polyols (e.g., propylene glycol, glycerin, mannitol, sorbitol, etc.), emulsifier (e.g., Tween), wetting agent (e.g., sodium lauryl sulfate), buffer agent, chelating agent, thickener, pH regulator, transdermal enhancer, colorant, flavoring agent, stabilizer, antioxidant, preservative, bacteriostatic agent, pyrogen-free water, etc.

In a preferred embodiment of the present invention, the dosage form of the composition or preparation is a solid preparation, liquid preparation or semi-solid preparation.

In a preferred embodiment of the present invention, the dosage form of the composition or preparation is oral preparation, external preparation or injection preparation Typically, the dosage form of the composition or preparation is tablet, injection, infusion, paste, gel, solution, microsphere or film.

The pharmaceutical preparation should be matched with the mode of administration. The pharmaceutical preparation of the present invention can also be given together with other synergistic therapeutic drugs before, during or after the administration. When the pharmaceutical composition or preparation is administrated, a safe and effective amount of the drug is administered to a subject in need (e.g. human or non-human mammal). The safe and effective amount is usually at least about 10 μg/kg·bw, and does not exceed about 8 μg/kg·bw in most case, preferably, the dose is about 10 μg/kg·bw to 1 mg/kg·bw. Of course, the specific dose should also take into account the route of administration, the patient's health and other factors, which are within the skill range of skilled doctors.

The main advantages of the present invention comprise:

1. The present has developed a compound, the compound has excellent precision treatment effect on tumor with low or no expression of NNMT gene, high expression of DNA methylase, high expression of UHRF1, high methylation level of nucleotide site of NNMT gene, and/or high methylation level of DNA CpG site of NNMT gene. The tumor with low or no expression of NNMT gene, high expression of DNA methylase, high expression of UHRF1, high methylation level of nucleotide site of NNMT gene, and/or high methylation level of DNA CpG site of NNMT gene is highly sensitive to the compound of present invention, ie, the compound of present invention has more remarkable and excellent treatment effect on tumor with low or no expression of NNMT gene, high expression of DNA methylase, high expression of UHRF1, high methylation level of nucleotide site of NNMT gene, and/or high methylation level of DNA CpG site of NNMT gene. Therefore, the compound of present invention can realize precise treatment on tumor with low or no expression of NNMT gene, high expression of DNA methylase, high expression of UHRF1, high methylation level of nucleotide site of NNMT gene, and/or high methylation level of DNA CpG site of NNMT gene, thus improving the treatment effect of the compound of present invention on tumor and avoiding administrating the compound of present invention to patient tumor insensitive to such anti-tumor drug. Therefore, the precision treatment of the compound of the present invention on tumor with low or no expression of NNMT gene, high expression of DNA methylase, high expression of UHRF1, high methylation level of nucleotide site of NNMT gene, and/or high methylation level of DNA CpG site of NNMT gene has advantages such a more excellent prevention and treatment effect on tumors, low drug dose, and minimal side effects, which improve the precision prevention and treatment effect on tumor, reduce the side effects and improve patient compliance.

The present invention will be further illustrated below with reference to the specific examples. It should be understood that the following specific Examples are based on the technical solution and provide detailed implementation methods and specific operation processes, but the scope of protection of the present invention is not limited to the Example.

Example

DNMT3a refers to DNA methyltransferase 3a, NCBI entrez gene: 1788; Uniprotkb/Swiss-port: Q9Y6K1.

DNMT3b refers to DNA methyltransferase 3b, NCBI entrez gene: 1789; Uniprotkb/Swiss-port: Q9UBC3.

DNMT1 refers to DNA methyltransferase 1, NCBI entrez gene: 1786; Uniprotkb/Swiss-port: P26358.

UHRF1 refers to ubiquitin-like with PHD and ring finger domain 1.

NNMT refers to Nicotinamide N-Methyltransferase.

The nucleotide sequence of the promoter region of NNMT gene was as shown in SEQ ID NO: 1.

The nucleotide sites from 1050 bp before the transcription start site to 499 bp after the transcription start site in NNMT gene was sites 951-2500 of nucleotide sequence as shown in SEQ ID NO: 1.

The nucleotide sites from 1050 bp to 193 bp before the transcription start site in NNMT gene was sites 951-1808 of nucleotide sequence as shown in SEQ ID NO: 1.

The nucleotide sites from 840 bp to 469 bp before the transcription start site in NNMT gene was sites 1161-1532 of nucleotide sequence as shown in SEQ ID NO: 1.

Example 1 Synthesis of Compound AB31866

The structure of compound AB31866 was as follows:

compound AB31866

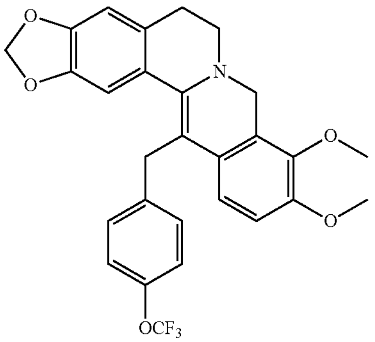

The synthesis method of compound AB31866 was as follows:

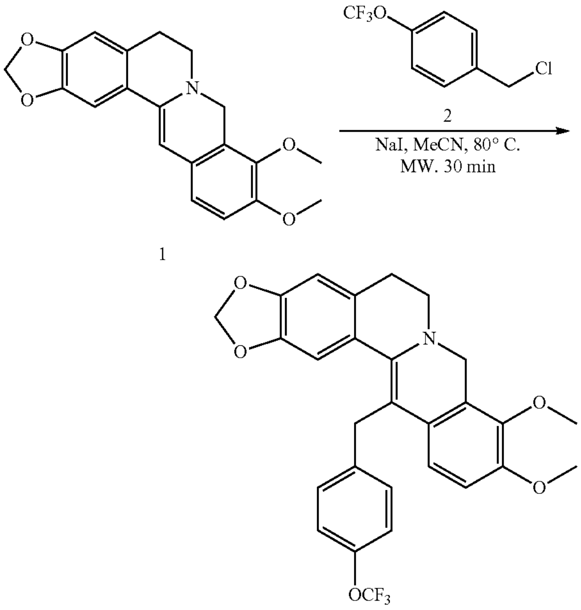

1

AB31866

Compound 1 (100 mg, 0.29 mmol, 1 eq) and compound 2 (122 mg, 0.58 mmol, 2.0 eq) were dissolved in acetonitrile (4 mL), and sodium iodide (87 mg, 0.58 mmol, 2.0 eq) was added. The mixture was reacted at 80° C. for 30 min under microwave condition, and the reaction was detected to be performed completely using LCMS. The reaction mixture was diluted with water and then extracted with ethyl acetate twice, the organic phase was dried over anhydrous sodium sulfate, filtered and rotary dried. The crude product was purified by reversed phase preparation chromatography (acetonitrile/water+0.01% formic acid) to afford compound AB31866.

Compound AB31866:

MS-ESI: calculated $[M+H]^+$: 512.16, Found: 512.10.

$^1$H NMR (400 MHz, CDCl3) δ 7.24 (s, 1H), 7.09 (d, J=8.0 Hz, 2H), 7.01-6.93 (m, 4H), 6.77 (s, 1H), 6.08 (d, J=12.0 Hz, 2H), 5.66 (d, J=20.0 Hz, 1H), 5.06 (d, J=20.0 Hz, 1H), 4.90-4.86 (m, 1H), 4.48-4.44 (m, 1H), 4.07-3.98 (m, 1H), 3.94 (s, 3H), 3.89 (m, 3H), 3.49-3.43 (m, 1H), 3.28-3.23 (m, 1H), 309-3.02 (m, 1H).

Example 2 Synthesis of Compound AB31870

The structure of compound AB31870 was as follows:

compound AB31870

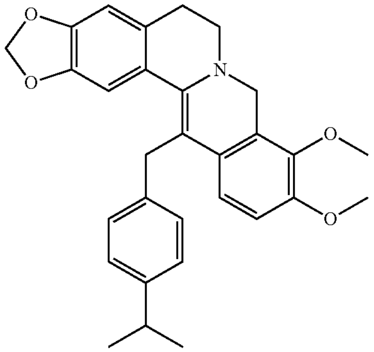

The synthesis method of compound AB31870 was as follows:

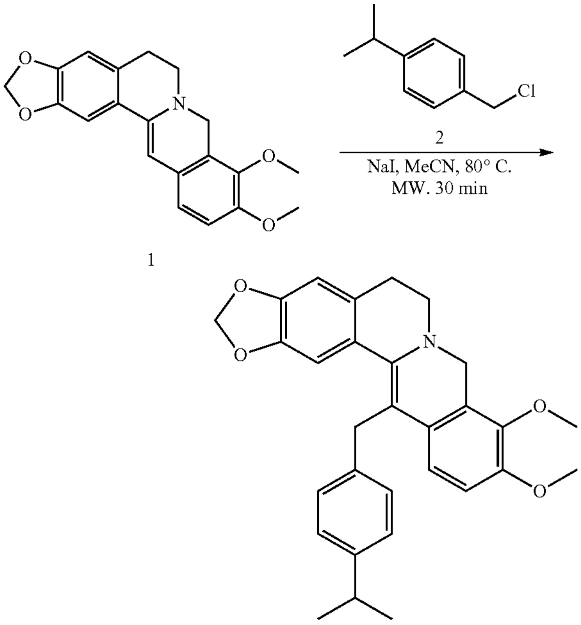

1

AB31870

Compound 1 (100 mg, 0.29 mmol, 1 eq) and compound 2 (97 mg, 0.58 mmol, 2.0 eq) were dissolved in acetonitrile (4 mL), and sodium iodide (87 mg, 0.58 mmol, 2.0 eq) was added. The mixture was reacted at 80° C. for 30 min under microwave condition, and the reaction was detected to be performed completely using LCMS. The reaction mixture was diluted with water and then extracted with ethyl acetate twice, the organic phase was dried over anhydrous sodium sulfate, filtered and rotary dried. The crude product was purified by reversed phase preparation chromatography (acetonitrile/water+0.01% formic acid) to afford compound AB31870.

Compound AB31870:

MS-ESI: Calculated $[M+H]^+$: 470.23, Found: 470.20.

$^1$H NMR (400 MHz, CDCl3) δ 7.52 (s, 1H), 7.08 (d, J=8.0 Hz, 1H), 6.98 (d, J=8.0 Hz, 3H), 6.86 (s, 1H), 6.55 (d, J=8.0 Hz, 2H), 6.13 (s, 2H), 5.04-4.92 (m, 2H), 4.17-4.13 (m, 2H), 3.89 (s, 3H), 3.85 (m, 3H), 3.36-3.17 (m, 4H), 2.86-2.79 (m, 1H), 1.17 (d, J=8.0 Hz, 6H).

Example 3 Synthesis of Compound AB31873

The structure of compound AB31873 was as follows:

compound AB31873

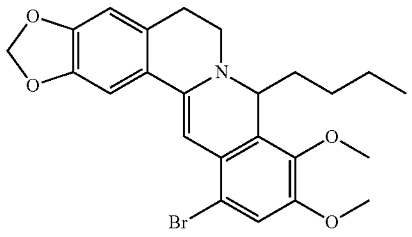

The synthesis method of compound AB31873 was as follows:

Step (1):

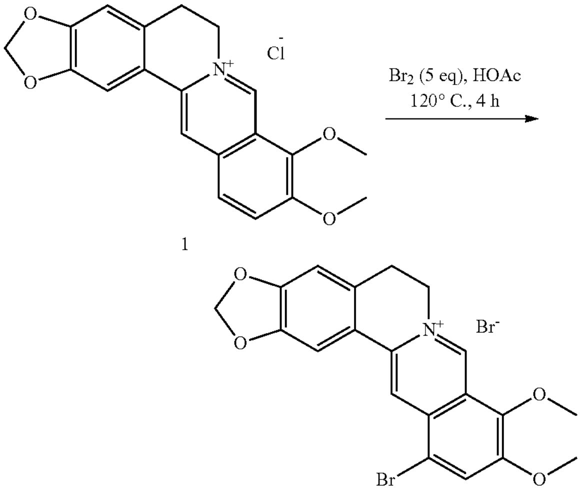

1

2

Compound 1 (1.0 g, 2.69 mmol, 1 eq) was dissolved in acetic acid (10 mL), and bromine (2.1 g, 13.45 mmol, 5 eq) was added slowly. The mixture was reacted at 120° C. for 4 h, and the reaction was detected to be performed completely using LCMS. The reaction mixture was diluted with water and then extracted with dichloromethane twice, the organic phase was washed with brine once, dried over anhydrous sodium sulfate, filtered and rotary dried. The crude product was purified by fast chromatography (100-200 mesh silica gel, DCM/MeOH=30/1) to afford compound 2.

MS-ESI: Calculated $[M]^+$ 415.04, Found: 413.95.

Step (2):

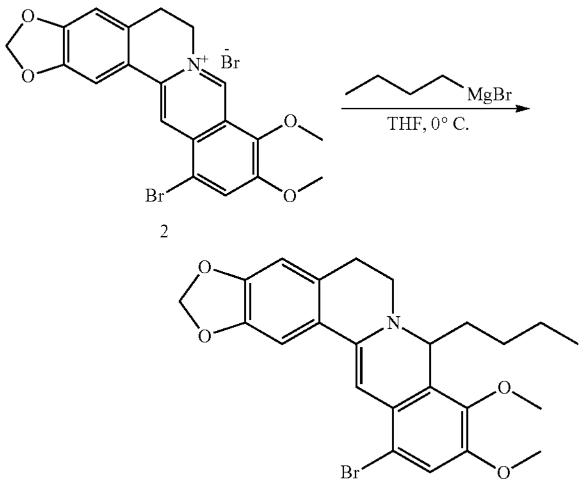

2

AB31873

Compound 2 (200 mg, 0.40 mmol, 1 eq) was dissolved in anhydrous tetrahydrofuran (10 mL), and butylmagnesium bromide (0.4 mL, 1.2 mmol, 5 eq, 3M) was added slowly at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and rotary dried. The crude product was purified by thin layer chromatography (DCM: MeOH=30:1) to afford compound AB31873.

Compound AB31873:

MS-ESI: Calculated $[M+H]^+$: 472.11, Found: 472.10.

$^1$H NMR (400 MHz, CDCl3) δ 7.23 (s, 1H), 6.97 (s, 1H), 6.60 (s, 1H), 6.02 (s, 1H), 5.95 (d, J=4.0 Hz, 2H), 4.70-4.67 (m, 1H), 3.86 (s, 3H), 3.83 (s, 3H), 3.48-3.45 (m, 1H), 3.33-3.30 (m, 1H), 2.88-2.80 (m, 2H), 1.71-1.64 (m, 2H), 1.25-1.17 (m, 4H), 0.82-078 (m, 3H).

Example 4 Synthesis of Compound AB31880

The structure of compound AB31880 was as follows:

compound AB31880

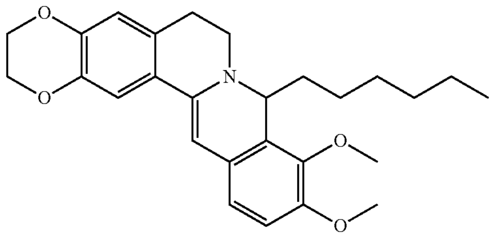

The synthesis method of compound AB31880 was as follows:

Step (1):

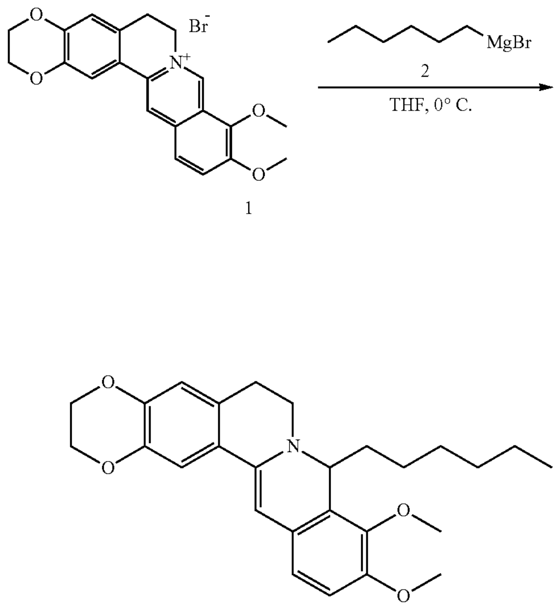

1

AB31880

Compound 2 (300 mg, 0.70 mmol, 1 eq) was dissolved in anhydrous tetrahydrofuran (10 mL), and hexylmagnesium bromide (3.5 mL, 3.50 mmol, 5 eq, 1M/L) was added slowly at 0° C. under $N_2$. The mixture was reacted at room temperature for 0.5 h, and the reaction was detected to be performed completely using TLC and LCMS. The reaction mixture was quenched with saturated aqueous ammonium chloride solution and then extracted with ethyl acetate twice, the organic phase was dried over anhydrous sodium sulfate, filtered and rotary dried. The crude product was purified by thin layer chromatography (dichloromethane:methanol=50:1) to afford compound AB31880.

Compound AB31880:

MS-ESI: Calculated $[M+H]^+$: 436.24, Found: 436.20.

$^1$H NMR (400 MHz, CDCl3) δ 7.19 (s, 1H), 6.75-6.68 (m, 2H), 6.62 (s, 1H), 5.81 (s, 1H), 4.70-4.67 (m, 1H), 4.26 (s, 4H), 3.87 (s, 3H), 3.84 (s, 3H), 3.46-3.45 (m, 1H), 3.31-3.29 (m, 1H), 2.87-2.78 (m, 2H), 1.75-1.50 (m, 4H), 1.38-1.26 (m, 6H), 0.82-0.79 (m, 3H).

Example 5 Synthesis of Compound AB31881

The structure of compound AB31881 was as follows:

compound AB31881

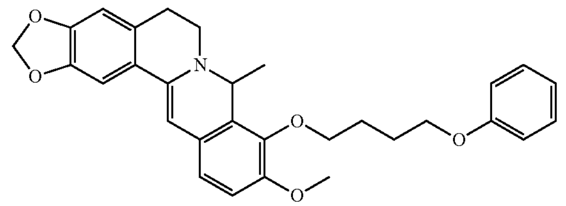

The synthesis method of compound AB31881 was as follows:

Step (1):

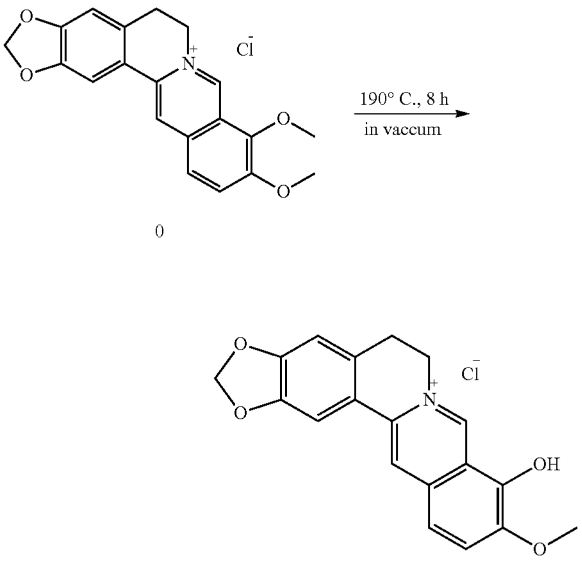

0

1

The compound 0 (10.0 g, 26.89 mmol, 1 eq) was added in a 500 mL eggplant-shaped flask, and heated at 190° C. for 8 h under vacuum, the reaction was detected to be performed completely using LCMS to afford compound 1.

MS-ESI: Calculated $[M]^+$: 322.11, Found: 322.30.

Step (2):

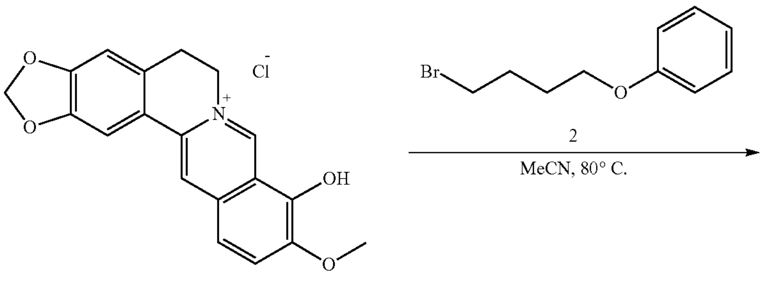

1

-continued

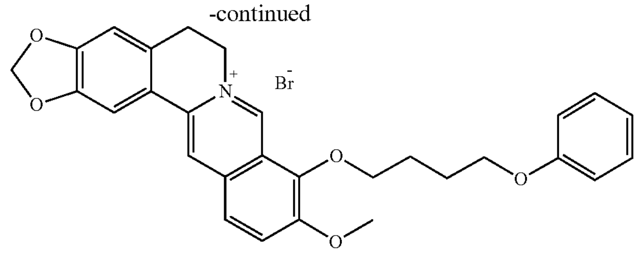

3

Compound 1 (500 mg, 1.40 mmol, 1 eq) and compound 1 (642 mg, 2.80 mmol, 2.0 eq) were dissolved in acetonitrile (10 mL). The mixture was reacted at 80° C. for overnight under $N_2$, and the reaction was detected to be performed completely using LCMS. The reaction mixture was diluted with water and then extracted with dichloromethane, the organic phase was dried over anhydrous sodium sulfate, filtered and rotary dried. The crude product was purified by fast chromatography (100-200 mesh silica gel, DCM/MeOH=50/1) to afford compound 3.

MS-ESI: Calculated $[M]^+$: 470.20, Found: 470.10.

Step (3):

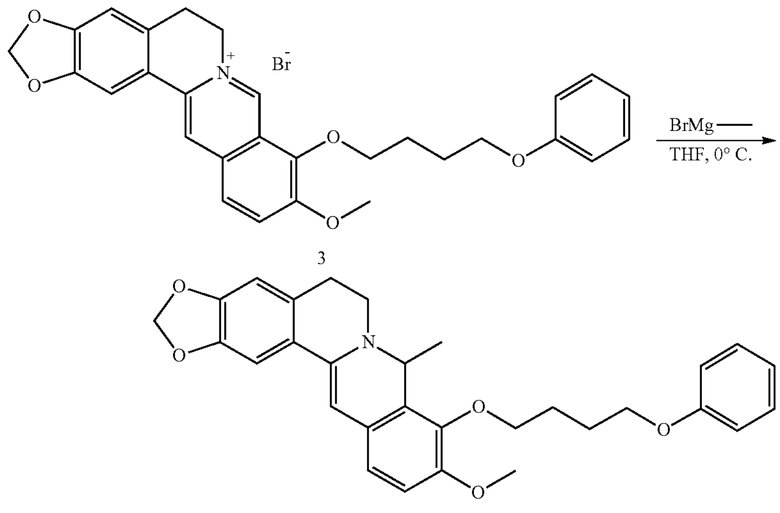

3

AB31881

Compound 3 (200 mg, 0.36 mmol, 1 eq) was dissolved in anhydrous tetrahydrofuran (10 mL), and methylmagnesium bromide (0.6 mL, 1.8 mmol, 5 eq, 3M) was added slowly at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and rotary dried. The crude product was purified by thin layer chromatography (DCM: MeOH=30:1) to afford compound AB31881.

Compound AB31881:

MS-ESI: Calculated $[M+H]^+$: 486.22, Found: 486.20.

$^1$H NMR (400 MHz, CDCl3) δ 7.31-7.27 (m, 2H), 7.16 (s, 1H), 6.96-6.92 (m, 3H), 6.73 (s, 2H), 6.59 (s, 1H), 5.94 (s, 2H), 5.86 (s, 1H), 4.87-4.82 (m, 1H), 4.20-4.14 (m, 1H), 4.10-4.07 (m, 3H), 3.82 (s, 3H), 3.42-3.36 (m, 1H), 3.21-3.18 (m, 1H), 2.95-2.88 (m, 1H), 2.78-2.74 (m, 1H), 2.06-1.98 (m, 4H), 1.18 (d, J=8.0 Hz, 3H).

Example 6 Synthesis of Compound AB31887

The structure of compound AB31887 was as follows:

compound AB31887

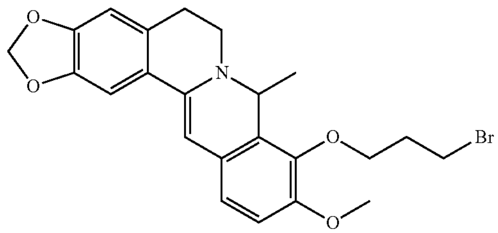

The synthesis method of compound AB31887 was as follows:

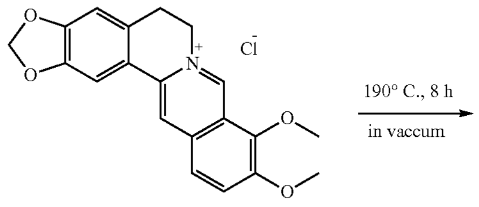

0

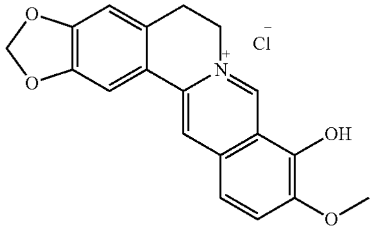

1

The compound 0 (10.0 g, 26.89 mmol, 1 eq) was added in a 500 mL eggplant-shaped flask, and heated at 190° C. for 8 h under vacuum, the reaction was detected to be performed completely using LCMS to afford compound 1.

MS-ESI: Calculated $[M]^+$: 322.11, Found: 322.30.

Step (2):

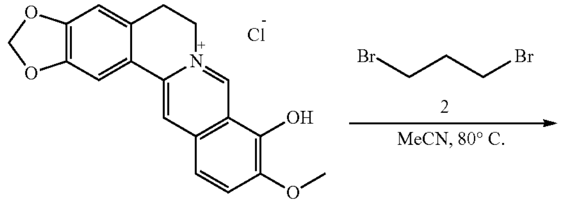

1

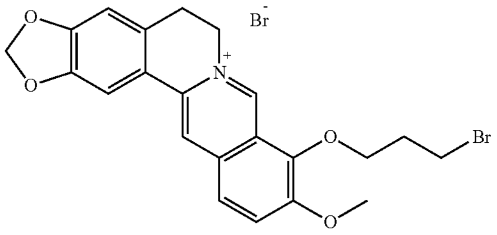

3

Compound 1 (500 mg, 1.40 mmol, 1 eq) and compound 2 (565 mg, 2.80 mmol, 2.0 eq) were dissolved in acetonitrile (10 mL). The mixture was reacted at 80° C. for overnight under $N_2$, and the reaction was detected to be performed completely using LCMS. The reaction mixture was diluted with water and then extracted with ethyl acetate, the organic phase was dried over anhydrous sodium sulfate, filtered and rotary dried. The crude product was purified by fast chromatography (100-200 mesh silica gel, DCM/MeOH=50/1) to afford compound 3.

MS-ESI: Calculated $[M]^+$: 444.06, Found: 444.00.

Step (3):

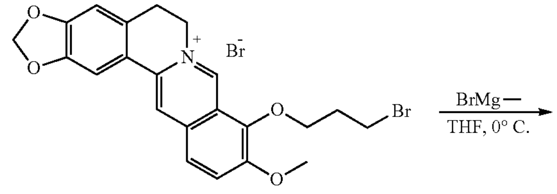

3

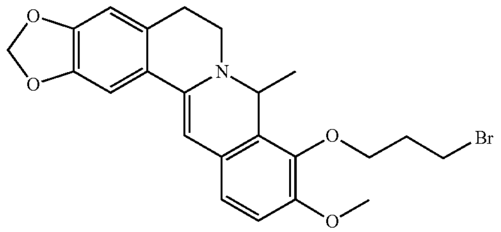

AB31887

Compound 3 (160 mg, 0.30 mmol, 1 eq) was dissolved in anhydrous tetrahydrofuran (10 mL), and methylmagnesium bromide (0.5 mL, 1.5 mmol, 5 eq, 3M) was added slowly at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and rotary dried. The crude product was purified by thin layer chromatography (DCM: MeOH=30:1) to afford compound AB31887.

Compound AB31887:

MS-ESI: Calculated $[M+H]^+$: 458.09, Found: 458.05.

$^1H$ NMR (400 MHz, CDCl3) δ 7.15 (s, 1H), 6.74 (s, 2H), 6.59 (s, 1H), 5.94 (s, 2H), 5.85 (s, 1H), 4.90-4.85 (m, 1H), 4.20-4.11 (m, 2H), 3.83 (s, 3H), 3.71-3.69 (m, 2H), 3.42-3.25 (m, 2H), 2.98-2.77 (m, 2H), 2.43-2.23 (m, 2H), 1.18 (d, J=4.0 Hz, 3H).

Example 7 Synthesis of Compound AB31888

The structure of compound AB31888 was as follows:

compound AB31888

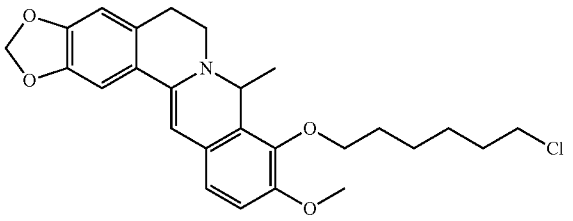

The synthesis method of compound AB31888 was as follows:

Step (1):

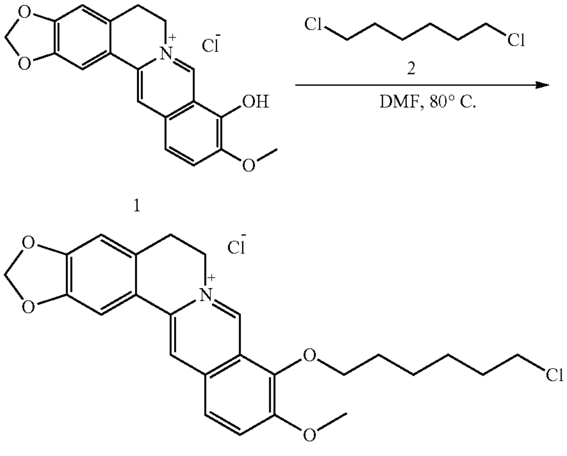

1

3

Compound 1 (300 mg, 0.84 mmol, 1 eq) and compound 2 (592 mg, 4.20 mmol, 5.0 eq) were dissolved in N, N-dimethylformamide (10 mL). The mixture was reacted at 80° C. for overnight under $N_2$, and the reaction was detected to be performed completely using LCMS. The reaction mixture was diluted with water and then extracted with ethyl acetate, the organic phase was dried over anhydrous sodium sulfate, filtered and rotary dried. The crude product was purified by fast chromatography (100-200 mesh silica gel, DCM:MeOH=50:1) to afford compound 3.

MS-ESI: Calculated $[M]^+$: 443.18, Found: 443.05.

Step (2):

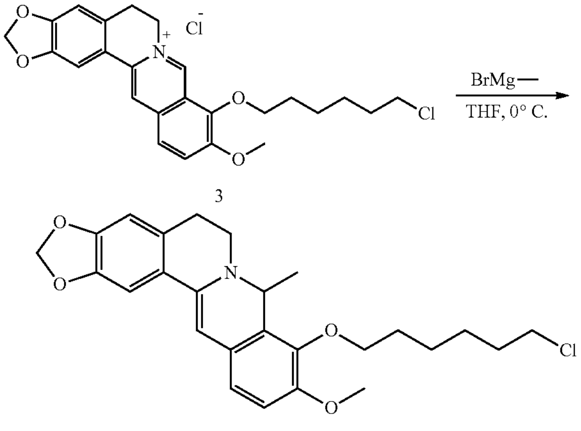

3

AB31888

Compound 3 (100 mg, 0.21 mmol, 1 eq) was dissolved in anhydrous tetrahydrofuran (10 mL), and methylmagnesium bromide (0.4 mmol, 5 eq, 3M) was added slowly at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and rotary dried. The crude product was purified by thin layer chromatography (DCM:MeOH=30:1) to afford compound AB31888.

Compound AB31888:

MS-ESI: Calculated $[M+H]^+$: 456.19, Found: 456.15.

$^1$H NMR (400 MHz, DMSO-d6) δ 7.25 (s, 1H), 6.81 (d, J=4.0 Hz, 2H), 6.77 (s, 1H), 6.66 (d, J=4.0 Hz, 1H), 6.00 (d, J=4.0 Hz, 2H), 5.93 (s, 1H), 4.77-4.73 (m, 1H), 3.97-3.94 (m, 2H), 3.75 (s, 3H), 3.68-3.64 (m, 2H), 3.27-3.21 (m, 2H), 2.84-2.74 (m, 2H), 1.78-1.70 (m, 4H), 1.49-1.45 (m, 4H), 1.05 (d, J=8.0 Hz, 3H).

Example 8 Synthesis of Compound AB31895

The structure of compound AB31895 was as follows:

compound AB31895

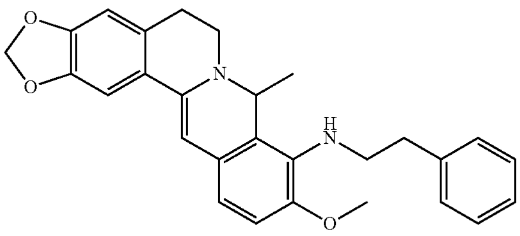

The synthesis method of compound AB31895 was as follows:

Step (1):

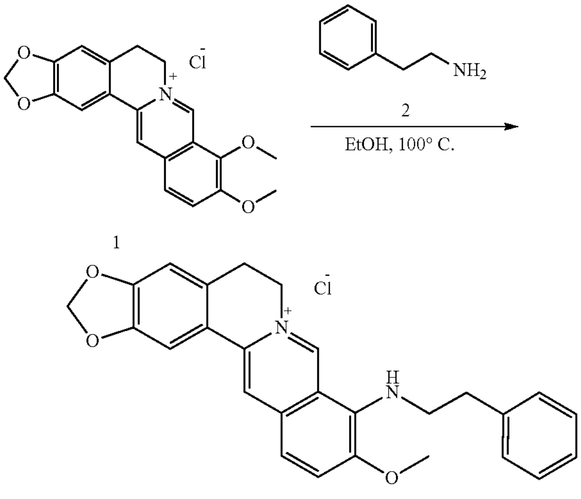

1

3

Compound 1 (1.0 g, 2.69 mmol, 1 eq) was dissolved in ethanol (20 mL) in a 50 mL sealed tube, and phenylethylamine (326 mg, 26.9 mmol, 10 eq) was added. The mixture was reacted at 100° C. for 48 h, and the reaction was detected to be performed completely using LCMS. The reaction mixture was diluted with water and then extracted with ethyl acetate twice, the organic phase was dried over anhydrous sodium sulfate, filtered and rotary dried. The crude product was purified by fast chromatography (dichloromethane:methanol=30:1) to afford compound 3.

MS-ESI: Calculated $[M]^+$: 425.19, Found: 425.15.

Step (2):

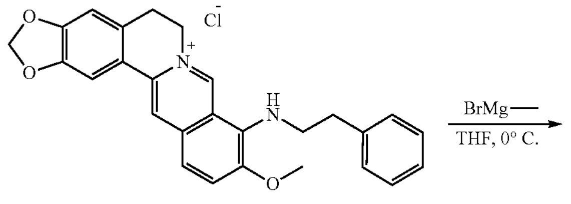

3

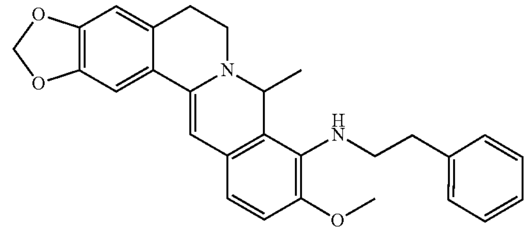

AB31895

Compound 3 (190 mg, 0.41 mmol, 1 eq) was dissolved in anhydrous tetrahydrofuran (10 mL), and methylmagnesium bromide (0.7 mL, 2.05 mmol, 5 eq, 3M) was added slowly at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate twice, the organic phase was dried over anhydrous sodium sulfate, filtered and rotary dried. The crude product was purified by thin layer chromatography (dichloromethane:methanol=50:1) to afford compound AB31895.

Compound AB31895:

MS-ESI: Calculated $[M+H]^+$: 441.21, Found: 441.20.

$^1H$ NMR (400 MHz, DMSO-d6) δ 7.28-7.18 (m, 6H), 6.72 (s, 1H), 6.68 (d, J=8.0 Hz, 1H), 6.48 (d, J=8.0 Hz, 1H), 5.96 (d, J=4.0 Hz, 2H), 5.87 (s, 1H), 4.54-4.50 (m, 1H), 3.68 (s, 3H), 3.18-3.04 (m, 5H), 2.76-2.73 (m, 4H), 0.91 (d, J=4.0 Hz, 3H).

Example 9 Synthesis of Compound AB31896

The structure of compound AB31896 was as follows:

compound AB31896

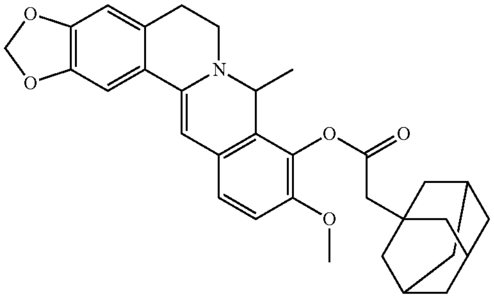

The synthesis method of compound AB31896 was as follows:

Step (1):

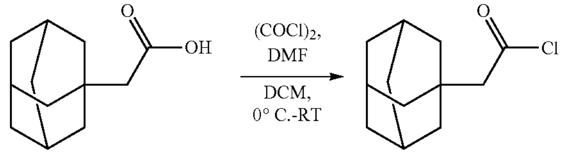

1 2

Compound 1 (500 mg, 2.57 mmol, 1 eq) was dissolved in dichloromethane (10 mL) and cooled to 0° C., oxalyl chloride (1.6 g, 12.85 mmol, 5 eq) and two drops of N, N-dimethylformamide were added. The mixture was reacted at room temperature for 2 h, and the reaction was detected to be performed completely using LCMS. The reaction mixture was distilled under reduced pressure to afford compound 2.

MS-ESI: Calculated $[M+H]^+$: 213.10, Found: not measured.

Step (2):

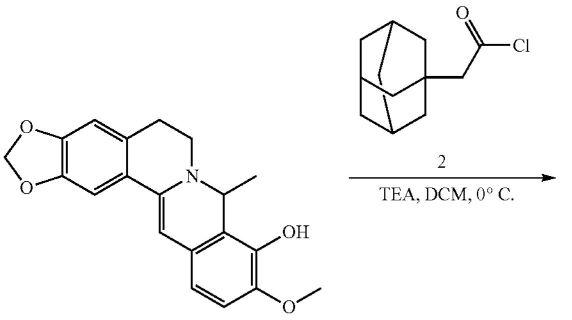

3

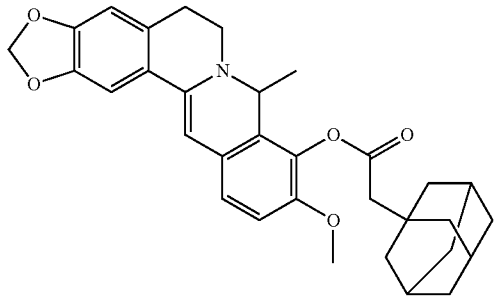

AB31896

Compound 3 (100 mg, 0.29 mmol, 1 eq) was dissolved in dichloromethane (10 mL), triethylamine (88 mg, 0.87 mmol, 3 eq) was added, the mixture was cooled to 0° C., and compound 2 (420 mg, 1.97 mmol, 6.8 eq) was added. The mixture was reacted at 0° C. for 0.5 h, and the reaction was detected to be performed completely using LCMS. The reaction mixture was diluted with water and then extracted with ethyl acetate, the organic phase was dried over sodium sulfate, filtered and spin dried. The crude product was purified by reversed phase preparation chromatography (acetonitrile/water+0.01% formic acid) to afford compound AB 31896.

MS-ESI: Calculated $[M+H]^+$: 514.25, Found: 514.25.

$^1H$ NMR (400 MHz, DMSO-d6) δ 7.27 (s, 1H), 6.91-6.83 (m, 2H), 6.77 (s, 1H), 6.01 (s, 1H), 5.99 (s, 2H), 4.61-4.55

(m, 1H), 3.71 (s, 3H), 3.28-3.14 (m, 2H), 2.79-2.74 (m, 2H), 2.34 (s, 2H), 1.72-1.63 (m, 15H), 1.02 (d, J=8.0 Hz, 3H).

Example 10 Synthesis of Compound AB31897

The structure of compound AB31897 was as follows:

compound AB31897

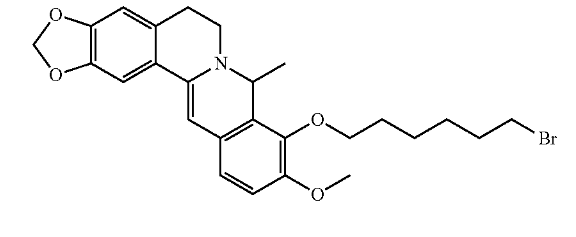

The synthesis method of compound AB31897 was as follows:

Step (1):

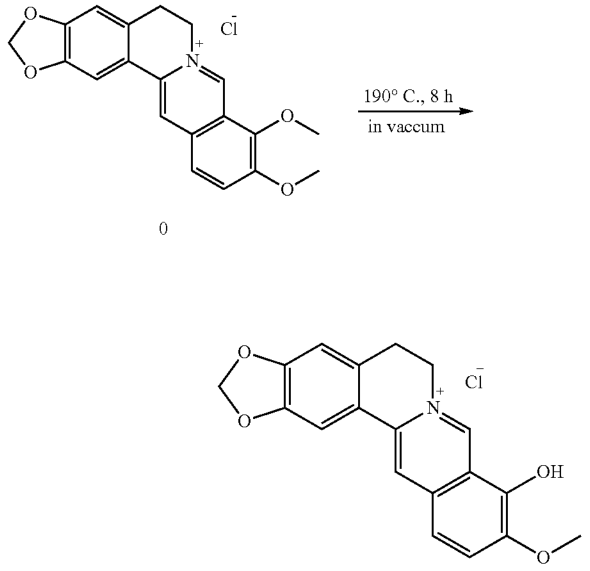

0

1

The compound 0 (10.0 g, 26.89 mmol, 1 eq) was added in a 500 mL eggplant-shaped flask, and heated at 190° C. for 8 h under vacuum, and the reaction was detected to be performed completely using LCMS to afford compound 1.

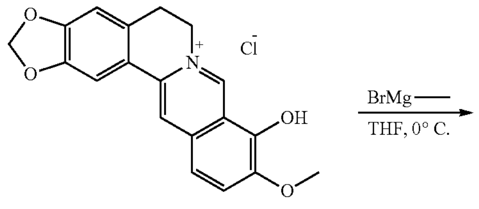

1

-continued

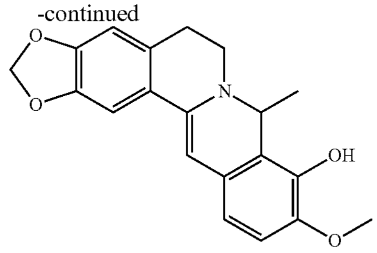

2

Compound 1 (2 g, 5.59 mmol, 1 eq) was dissolved in anhydrous tetrahydrofuran (10 mL), and methylmagnesium bromide (11.2 mL, 33.54 mmol, 6 eq, 3M) was added slowly at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate twice, the organic phase was dried over anhydrous sodium sulfate, filtered and rotary dried. The crude product was purified by thin layer chromatography (dichloromethane:methanol=100:1 to 50:1) to afford compound 2.

Step (3):

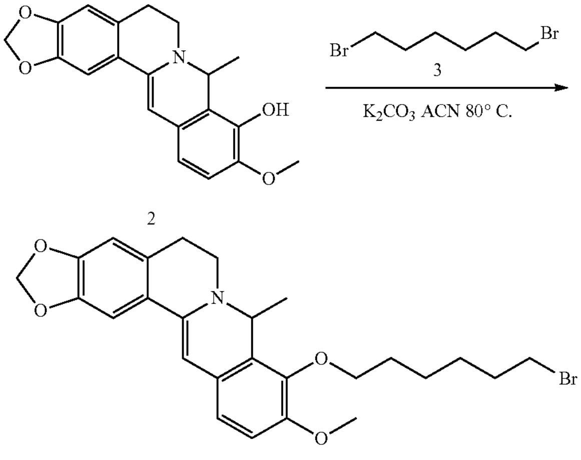

2

AB31897

Compound 2 (300 mg, 0.89 mmol, 1 eq) was dissolved in acetonitrile (10 mL), and potassium carbonate (491 mg, 3.56 mmol, 4 eq) and compound 3 (868 mg, 3.56 mmol, 4 eq) were added. The mixture was reacted at 80° C. for overnight, and the reaction was detected to be performed completely using LCMS. The reaction mixture was diluted with water and then extracted with dichloromethane twice, the organic phase was dried over anhydrous sodium sulfate, filtered and rotary dried. The crude product was purified by fast chromatography (dichloromethane:methanol=50:1) to afford compound AB31897.

Compound AB31897:

MS-ESI: Calculated $[M+H]^+$: 501.13, Found: 501.10.

$^1$H NMR (400 MHz, DMSO-d6) δ 7.22 (s, 1H), 6.79-6.74 (m, 2H), 6.64 (d, J=12.0 Hz, 1H), 5.97 (d, J=4.0 Hz, 2H), 5.89 (s, 1H), 4.74-4.69 (m, 1H), 3.94-3.91 (m, 2H), 3.72 (s, 3H), 3.55-3.51 (m, 2H), 3.25-3.15 (m, 2H), 2.79-2.68 (m, 2H), 1.85-1.79 (m, 2H), 1.72-1.65 (m, 2H), 1.44 (s, 4H), 1.03 (d, J=4.0 Hz, 3H).

Example 11 Synthesis of Compound AB31898

The structure of compound AB31898 was as follows:

AB31898

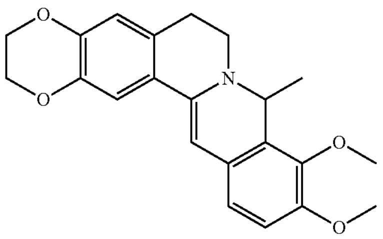

The synthesis method of compound AB31898 was as follows:

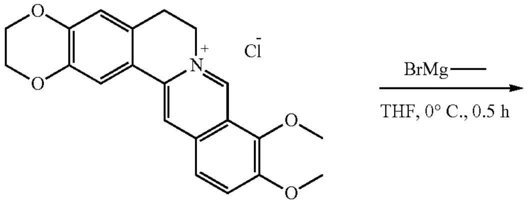

1

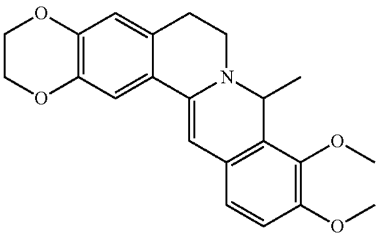

AB31898

Compound 1 (200 mg, 0.52 mmol, 1 eq) was dissolved in anhydrous tetrahydrofuran (10 mL), and methylmagnesium bromide (2.7 mL, 2.7 mmol, 5 eq, 3M) was added slowly at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and rotary dried. The crude product was purified by thin layer chromatography (DCM: MeOH=30:1) to afford compound AB31898.

Compound AB31898:

MS-ESI: Calculated $[M+H]^+$: 366.17, Found: 366.10.

$^1$H NMR (400 MHz, DMSO-d6) δ 7.11 (s, 1H), 6.81 (d, J=8.0 Hz, 1H), 6.68 (s, 1H), 6.67 (s, 1H), 5.87 (s, 1H), 4.77-4.73 (m, 1H), 4.23 (s, 4H), 3.77 (d, J=8.0 Hz, 6H), 3.28-3.20 (m, 2H), 2.79-2.66 (m, 2H), 1.05 (d, J=8.0 Hz, 3H).

Example 12 Synthesis of Compound AB35402

The structure of compound AB35402 was as follows:

compound AB35402

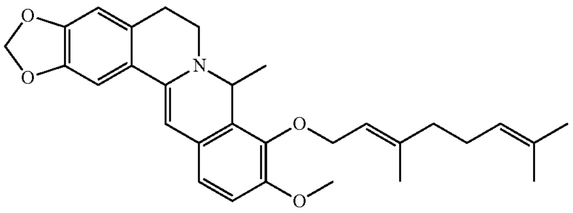

The synthesis method of compound AB35402 was as follows:

Step (1):

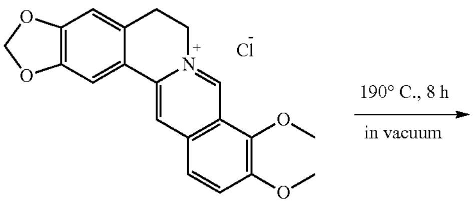

0

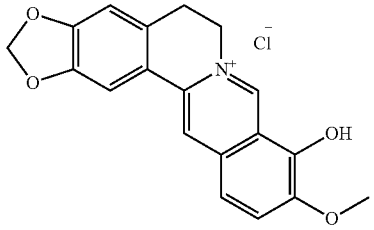

1

The compound 0 (10.0 g, 26.89 mmol, 1 eq) was added in a 500 mL eggplant-shaped flask, and heated at 190° C. for 8 h under vacuum, and the reaction was detected to be performed completely using LCMS to afford compound 1.

MS-ESI: Calculated $[M+H]^+$: 322.11, Found: 322.30.

Step (2):

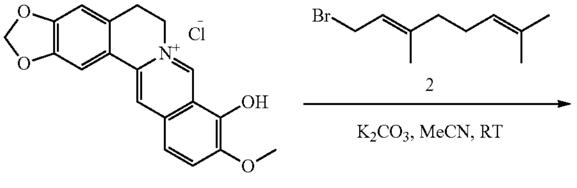

1

-continued

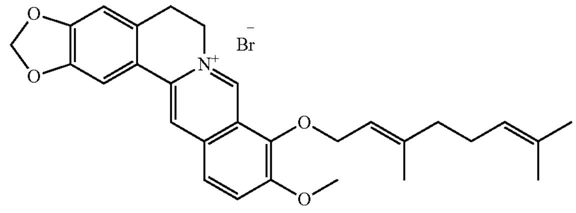

3

Compound 1 (500 mg, 1.40 mmol, 1 eq) was dissolved in acetonitrile (10 mL), and potassium carbonate (773 mg, 5.6 mmol, 4 eq) and compound 2 (912 mg, 4.20 mmol, 3 eq) were added. The mixture was reacted at room temperature for overnight, and the reaction was detected to be performed completely using LCMS. The reaction mixture was diluted with water and then extracted with ethyl acetate twice, the organic phase was dried over anhydrous sodium sulfate, filtered and spin dried. The crude product was purified by fast chromatography (dichloromethane:methanol=30:1) to afford compound 3.

MS-ESI: Calculated $[M]^+$: 458.23, Found: 458.30.

Step (3):

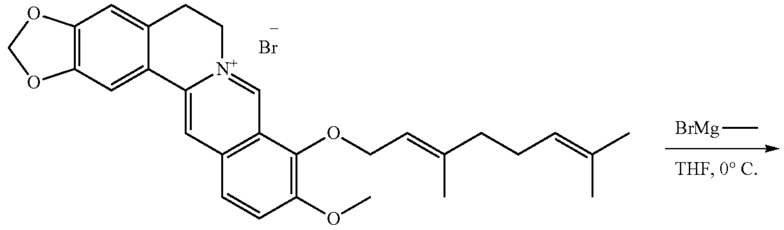

3

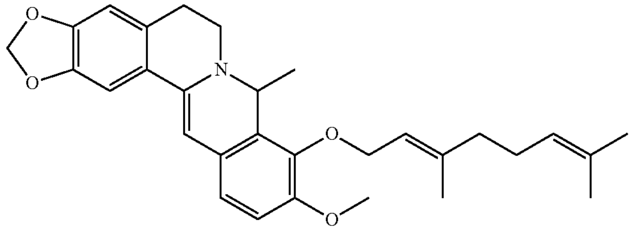

AB35402

Compound 3 (200 mg, 0.37 mmol, 1 eq) was dissolved in anhydrous tetrahydrofuran (10 mL), and methylmagnesium bromide (0.6 mL, 1.85 mmol, 5 eq, 3M) was added slowly at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate twice, the organic phase was dried over anhydrous sodium sulfate, filtered and spin dried. The crude product was purified by thin layer chromatography (dichloromethane:methanol=50:1) to afford compound AB35402.

Compound AB35402:

MS-ESI: Calculated $[M+H]^+$: 474.26, Found: 474.35.

$^1H$ NMR (400 MHz, DMSO-d6) δ 7.24 (s, 1H), 6.821 (d, J=8.0 Hz, 1H), 6.77 (s, 1H), 6.67 (d, J=12.0 Hz, 1H), 6.03 (s, 2H), 5.92 (s, 1H), 5.51-5.48 (m, 1H), 5.10-5.05 (m, 1H), 4.76-4.73 (m, 1H), 4.54-4.46 (m, 2H), 3.76 (s, 3H), 3.29-3.15 (m, 2H), 2.78-2.66 (m, 2H), 2.09-1.99 (m, 4H), 1.63 (s, 6H), 1.55 (s, 3H), 1.03 (d, J=4.0 Hz, 3H).

Example 13 Synthesis of Compound AB35405

The structure of compound AB35405 was as follows:

compound AB35405

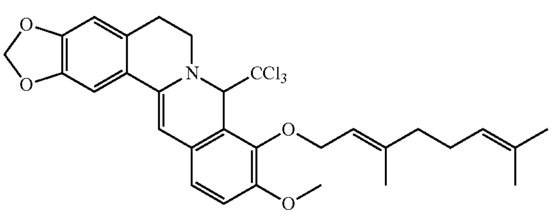

The synthesis method of compound AB35405 was as follows:

Step (1):

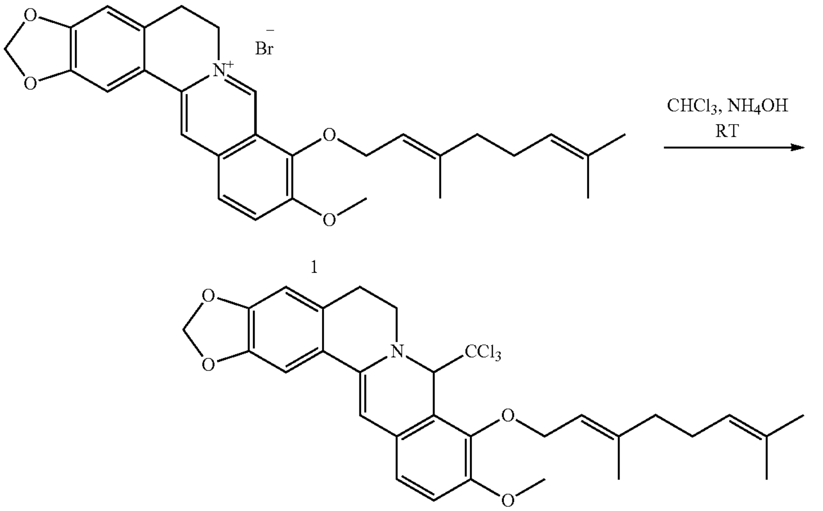

1

AB35405

Compound 1 (200 mg, 0.37 mmol, 1 eq) was dissolved in chloroform (5 mL), and aqueous ammonia (2 mL) was added. The mixture was reacted at room temperature for overnight, and the reaction was detected to be performed completely using LCMS. The reaction mixture was diluted and extracted with dichloromethane, the organic phase was dried over anhydrous sodium sulfate, filtered and spin dried. The crude product was purified by fast chromatography (PE:EA=200:1) to afford compound AB35405.

Compound AB35405:

MS-ESI: Calculated $[M+H]^+$: 576.14, Found: 576.15.

$^1H$ NMR (400 MHz, CDC13) δ 7.17 (s, 1H), 6.98-6.86 (m, 2H), 6.62 (s, 1H), 6.10 (s, 1H), 5.95 (d, J=4.0 Hz, 2H), 5.67 (s, 1H), 5.57-5.53 (m, 1H), 5.10-5.06 (m, 1H), 4.72-4.56 (m, 2H), 3.89-3.83 (m, 4H), 3.69-3.64 (m, 1H), 3.37-3.32 (m, 1H), 2.74-2.70 (m, 1H), 2.11-2.03 (m, 4H), 1.66 (d, J=8.0 Hz, 6H), 1.58 (s, 3H).

Example 14 Synthesis of Compound AB35407

The structure of compound AB35407 was as follows:

compound AB35407

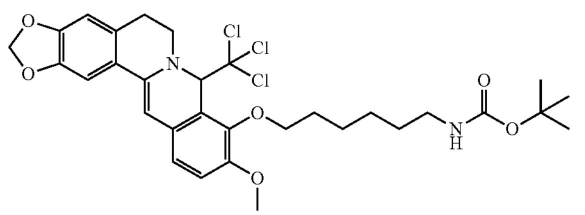

The synthesis method of compound AB35407 was as follows:

Step (1):

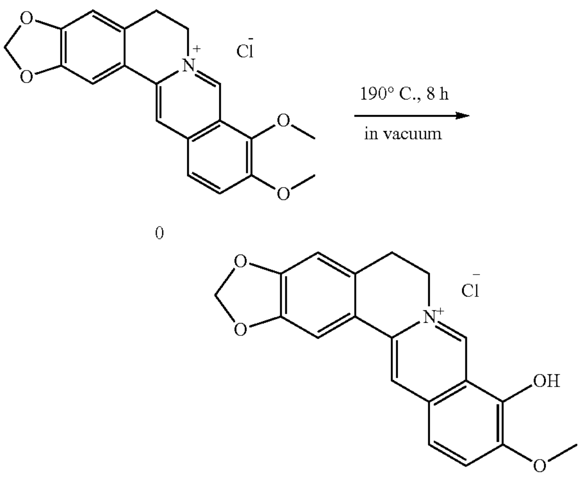

0

1

The compound 0 (10.0 g, 26.89 mmol, 1 eq) was added in a 500 mL eggplant-shaped flask, and heated at 190° C. for 8 h under vacuum, and the reaction was detected to be performed completely using LCMS to afford compound 1.

MS-ESI: Calculated $[M]^+$: 322.11, Found: 322.30.

Step (2):

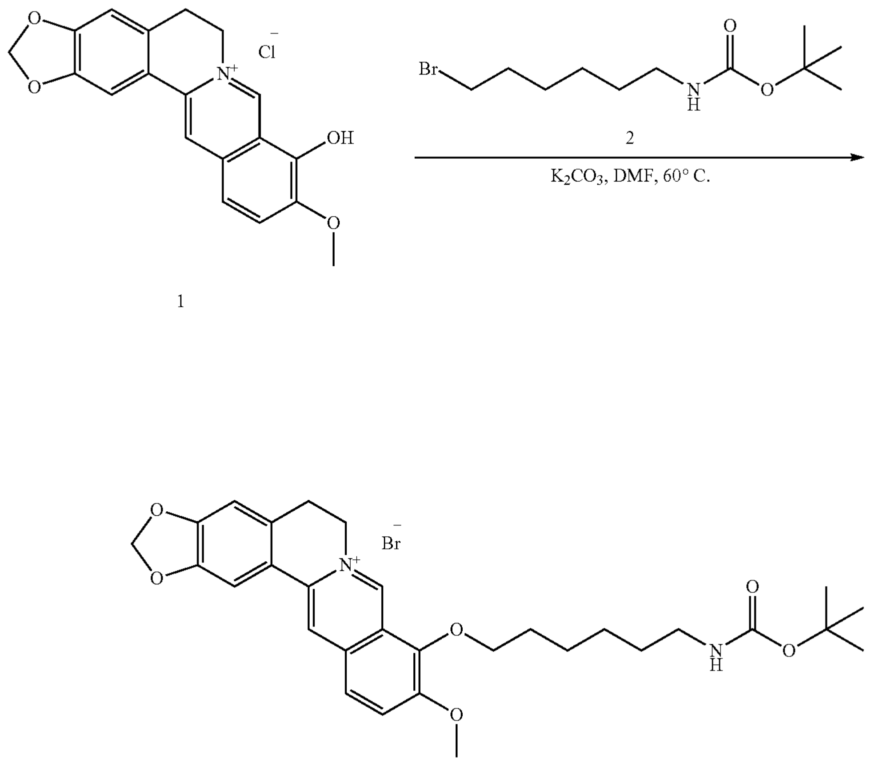

1

2

3

Compound 1 (600 mg, 1.67 mmol, 1 eq) was dissolved in N, N-dimethylformamide (10 mL), and potassium carbonate (926 mg, 6.71 mmol, 4 eq) and compound 2 (1.9 g, 6.71 mmol, 4 eq) were added. The mixture was reacted at 60° C. for overnight under $N_2$, and the reaction was detected to be performed completely using LCMS. The reaction mixture was diluted with water and then extracted with ethyl acetate twice, the phase was dried over anhydrous sodium sulfate, filtered and spin dried. The crude product was purified by fast chromatography (dichloromethane:methanol=50:1) to afford compound 3.

MS-ESI: Calculated $[M]^+$: 521.26, Found: 521.30.

Step (3):

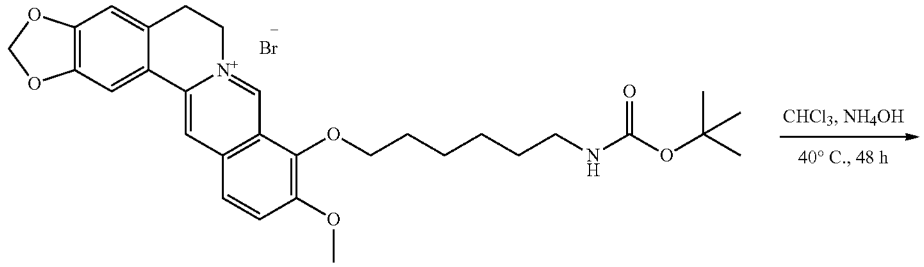

3

-continued

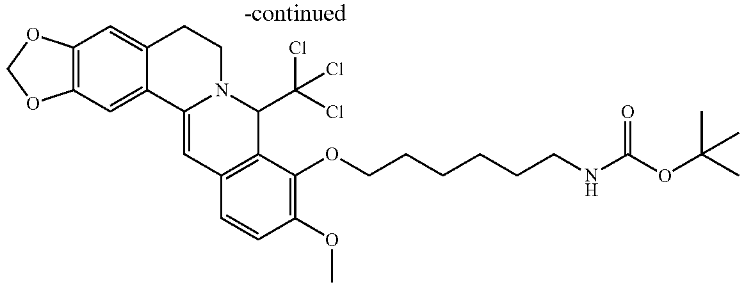

AB35407

Compound 3 (200 mg, 0.33 mmol, 1 eq) was dissolved in a mixture of chloroform (5 mL) and aqueous ammonia (2 mL). The mixture was reacted at 40° C. for 48 h, and the reaction was detected to be performed completely using LCMS. The reaction mixture was diluted with water and then extracted with dichloromethane, the organic phase was dried over anhydrous sodium sulfate, filtered and spin dried. The crude product was purified by fast chromatography (PE:EA=200:1) to afford compound AB35407.

MS-ESI: Calculated $[M+H]^+$: 639.18, Found: 639.15.

$^1$H NMR (400 MHz, CDC13) δ 7.16 (s, 1H), 6.97-6.85 (m, 2H), 6.62 (s, 1H), 6.08 (s, 1H), 5.95 (d, J=4.0 Hz, 2H), 5.62 (s, 1H), 4.52 (s, 1H), 4.28-4.23 (m, 1H), 3.89-3.82 (m, 5H), 3.69-3.67 (m, 1H), 3.36-3.31 (m, 1H), 3.16-3.09 (m, 2H), 2.76-2.72 (m, 1H), 1.83-1.69 (m, 4H), 1.58-1.51 (m, 4H), 1.44 (s, 9H).

Example 15 Synthesis of Compound AB35411

The structure of compound AB35411 was as follows:

AB35411

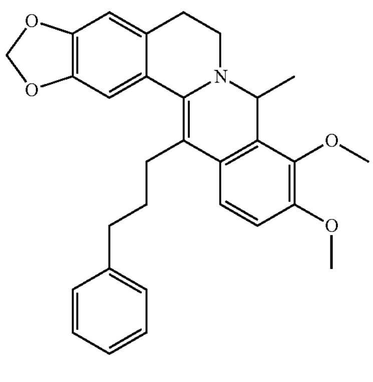

The synthesis method of compound AB35411 was as follows:

Step (1):

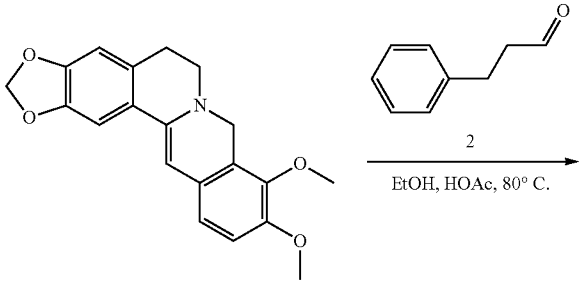

1

2

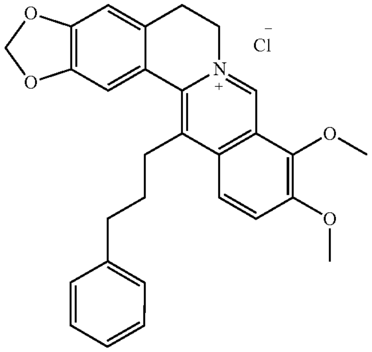

3

Compound 1 (2.0 g, 5.93 mmol, 1 eq) was dissolved in ethanol/acetic acid (10 mL/8 mL), and benzaldehyde (7.9 g, 59.3 mmol, 10 eq) was added. The mixture was reacted at 80° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 3 (1.4 g).

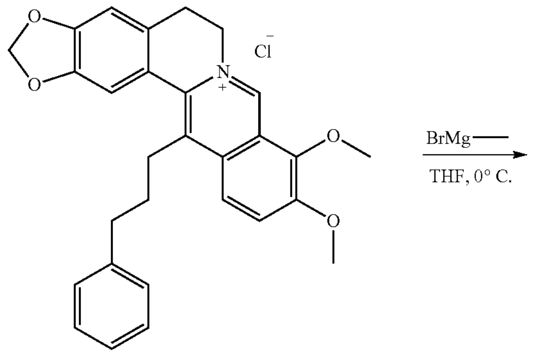

3

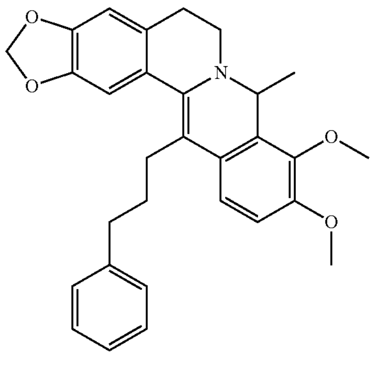

AB35411

Compound 3 (200 mg, 0.41 mmol, 1 eq) was dissolved in anhydrous tetrahydrofuran (10 mL), and methylmagnesium bromide (0.7 mL, 2.05 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was washed with brine, dried over anhydrous sodium sulfate, filtered and spin dried. The crude product was purified by thin layer chromatography (DCM/MeOH=20/1) to afford compound AB35411.

Compound AB35411:

MS-ESI: Calculated $[M+H]^+$: 470.23; Found $[M+H]^+$: 470.30.

$^1H$ NMR (400 MHz, $CDCl_3$) δ 7.34-7.28 (m, 2H), 7.24-7.16 (m, 3H), 6.97 (s, 1H), 6.90-6.76 (m, 2H), 6.65 (s, 1H), 5.97-5.96 (m, 2H), 4.77-4.73 (m, 1H), 3.89 (s, 3H), 3.86 (s, 3H), 3.24-3.22 (m, 2H), 2.84-2.65 (m, 6H), 2.14-2.08 (m, 1H), 1.90-1.81 (m, 1H), 1.07 (d, J=4.0 Hz, 3H).

Example 16 Synthesis of Compound AB35413

The structure of compound AB35413 was as follows:

AB35413

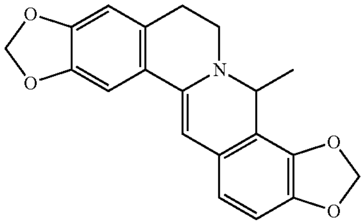

The synthesis method of compound AB35413 was as follows:

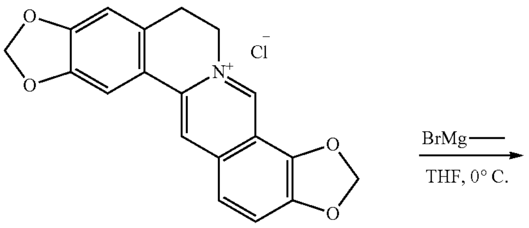

1

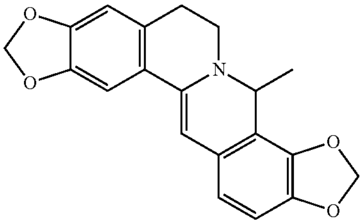

AB35413

Compound 1 (100 mg, 0.28 mmol, 1 eq) was dissolved in anhydrous tetrahydrofuran (10 mL), and methylmagnesium bromide (0.5 mL, 1.4 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was washed with brine, dried over anhydrous sodium sulfate, filtered and spin dried. The crude product was purified by thin layer chromatography (DCM/MeOH=30/1) to afford compound AB35413.

Compound AB35413:

MS-ESI: Calculated $[M+H]^+$: 336.12; Found$[M+H]^+$: 336.10.

$^1H$ NMR (400 MHz, DMSO-d6) δ 7.25 (s, 1H), 6.78 (s, 1H), 6.79 (d, J=8.0 Hz, 1H), 6.46 (d, J=8.0 Hz, 1H), 6.04 (s, 1H), 6.00 (d, J=4.0 Hz, 2H), 5.94 (s, 1H), 5.89 (s, 1H), 4.71-4.66 (m, 1H), 3.28-3.20 (m, 2H), 2.83-2.70 (m, 2H), 1.11 (d, J=8.0 Hz, 3H).

Example 17 Synthesis of Compound AB35415

The structure of compound AB35415 was as follows:

AB35415

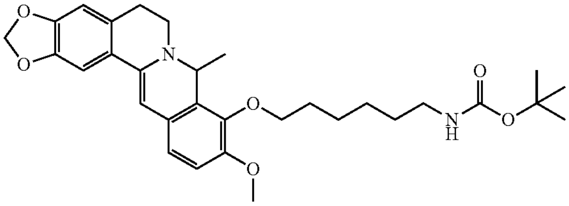

The synthesis method of compound AB35415 was as follows:

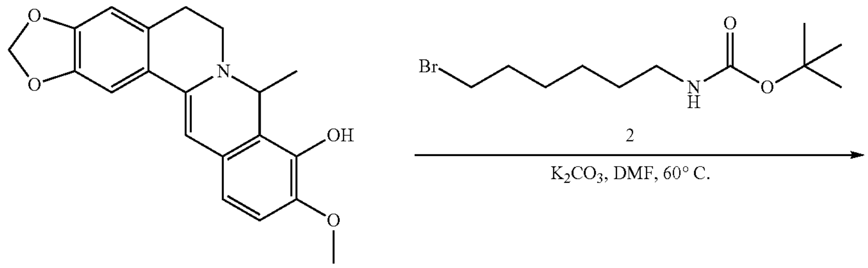

1

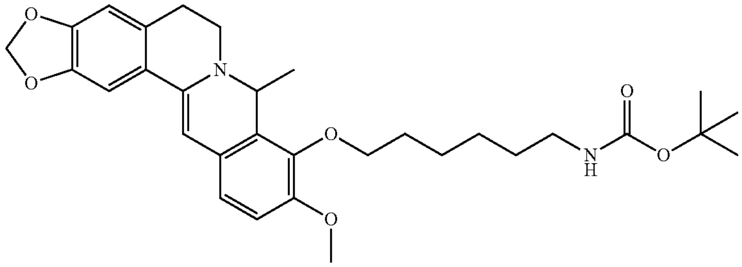

AB35415

Compound 1 (200 mg, 0.59 mmol, 1 eq) was dissolved in N, N-dimethylformamide (10 mL), and potassium carbonate (326 mg, 2.36 mmol, 4 eq) and compound 2 (661 mg, 2.36 mmol, 4 eq) were added. The mixture was reacted at 60° C. for overnight, the reaction mixture was diluted with water and then extracted with ethyl acetate twice, the organic phase was washed with brine, dried over anhydrous sodium sulfate, filtered and spin dried. The crude product was purified by reversed phase preparation chromatography (acetonitrile/water+0.01% formic acid) to afford compound AB35415.

Compound AB35415:

MS-ESI: Calculated $[M+H]^+$: 537.29; Found $[M+H]^+$: 537.35.

$^1H$ NMR (400 MHz, $CDCl_3$) δ 7.15 (s, 1H), 6.72 (s, 2H), 6.59 (s, 1H), 5.94 (s, 2H), 5.85 (s, 1H), 4.85-4.80 (m, 1H), 4.53 (s, 1H), 4.05-4.09 (m, 2H), 3.82 (s, 3H), 3.44-3.39 (m, 1H), 3.24-3.14 (m, 3H), 2.98-2.77 (m, 2H), 1.82-1.79 (m, 2H), 1.55-1.50 (m, 4H), 1.44 (s, 11H), 1.17 (d, J=8.0 Hz, 3H).

Example 18 Synthesis of Compound AB35416

The structure of compound AB35416 was as follows:

AB35416

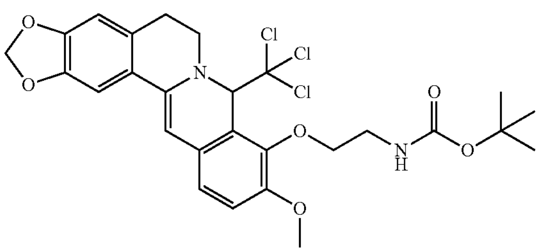

The synthesis method of compound AB35416 was as follows:

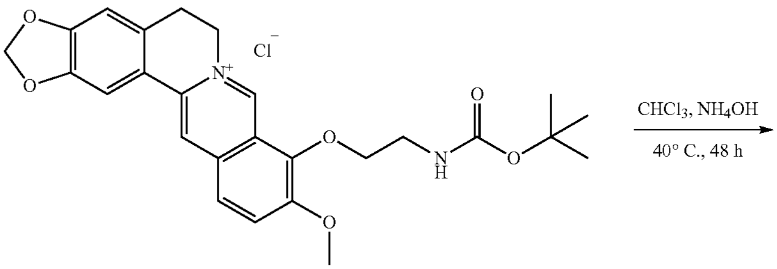

1

-continued

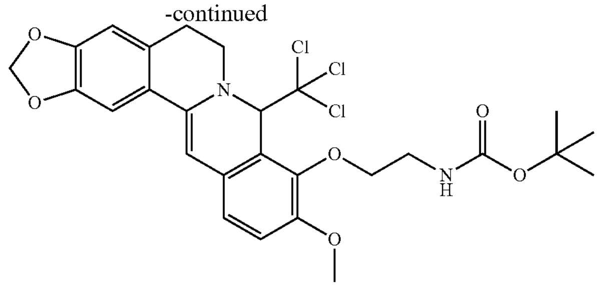

AB35416

Compound 1 (200 mg, 0.33 mmol, 1 eq) was dissolved in chloroform (5 mL), and aqueous ammonia (2 mL) was added. The mixture was reacted at 40° C. for 48 h. The reaction mixture was diluted with water and then extracted with dichloromethane, the organic phase was washed with brine, dried over anhydrous sodium sulfate, filtered and spin dried. The crude product was purified by thin layer chromatography (PE/EA=10/1) to afford compound AB35416.

Compound AB35416

MS-ESI: Calculated $[M+H]^+$: 583.11; Found $[M+H]^+$: 583.10.

$^1H$ NMR (400 MHz, $CDCl_3$) δ 7.16 (s, 1H), 6.97-6.89 (m, 2H), 6.62 (s, 1H), 6.09 (s, 1H), 5.96 (s, 2H), 5.64 (s, 1H), 4.34 (s, 1H), 4.24 (s, 1H), 3.96-3.87 (m, 5H), 3.71 (s, 1H), 3.56-3.49 (m, 2H), 3.35-3.30 (m, 1H), 2.76-2.73 (m, 1H), 1.47 (s, 9H)

Example 19 Synthesis of Compound AB35417

The structure of compound AB35417 was as follows:

AB35417

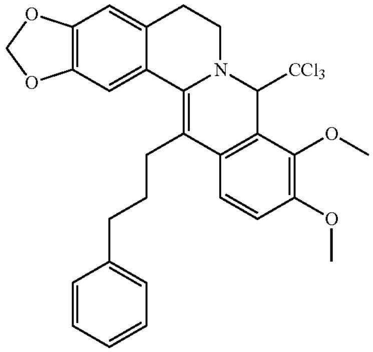

The synthesis method of compound AB35417 was as follows:

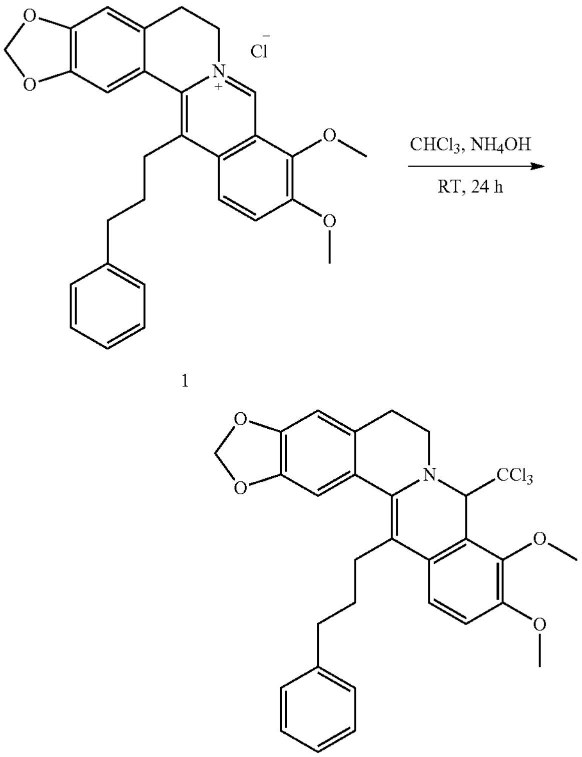

1

AB35417

Compound mg, 0.41 mmol, eq was dissolved in chloroform mL, and aqueous ammonia (2 mL) was added. The mixture was reacted at room temperature for 24 h. The reaction mixture was diluted with water and then extracted with dichloromethane, the organic phase was washed with brine, dried over anhydrous sodium sulfate, filtered and spin dried. The crude product was purified by thin layer chromatography (PE/EA=10/1) to afford compound AB35417.

Compound AB35417

MS-ESI: Calculated $[M+H]^+$: 572.11; Found $[M+H]^+$: 572.1.

$^1H$ NMR (400 MHz, $CDCl_3$) δ 7.32-7.30 (m, 2H), 7.24-7.20 (m, 3H), 6.99-6.90 (m, 2H), 6.85 (s, 1H), 6.68 (s, 1H), 5.99 (s, 2H), 5.58 (s, 1H), 4.09-4.03 (m, 1H), 3.93 (s, 3H), 3.90 (s, 3H), 3.46-3.44 (m, 1H), 2.75-2.56 (m, 6H), 2.12-2.04 (m, 1H), 1.88-1.77 (m, 1H).

Example 20 Synthesis of Compound AB35418

The structure of compound AB35418 was as follows:

AB35418

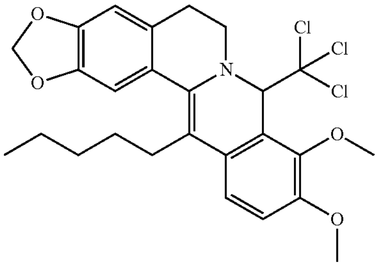

The synthesis method of compound AB35418 was as follows:

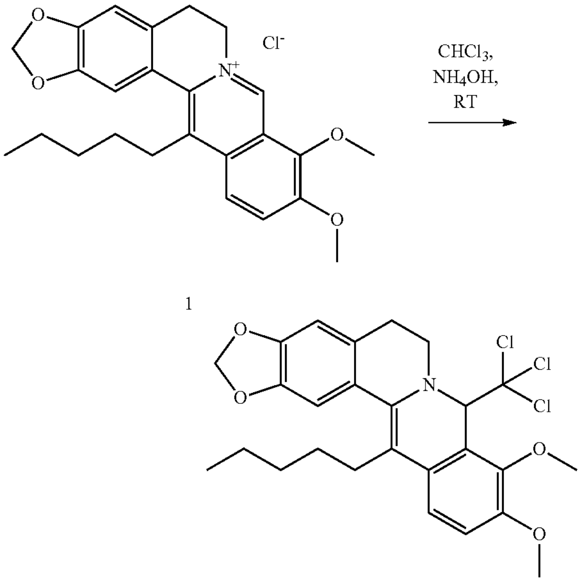

1

AB35418

Compound 1 (200 mg, 0.45 mmol, 1 eq) was dissolved in chloroform (5 mL), and aqueous ammonia (2 mL) was added. The mixture was reacted at room temperature for overnight. The reaction mixture was diluted with water and then extracted with dichloromethane, the organic phase was washed with brine, dried over anhydrous sodium sulfate, filtered and spin dried. The crude product was purified by thin layer chromatography (PE/EA=10/1) to afford compound AB35418.

Compound AB35418

MS-ESI: Calculated $[M+H]^+$: 524.11; Found $[M+H]^+$: 524.15.

$^1H$ NMR (400 MHz, DMSO-d6) δ 7.13-7.04 (m, 2H), 6.91 (s, 1H), 6.68 (s, 1H), 5.99 (s, 2H), 5.60 (s, 1H), 4.11-4.05 (m, 1H), 3.94 (s, 3H), 3.91 (s, 3H), 3.47-3.45 (m, 1H), 2.73-2.53 (m, 4H), 1.82-1.74 (m, 1H), 1.46-1.38 (m, 5H), 0.95-0.92 (m, 3H).

Example 21 Synthesis of Compound AB35420

The structure of compound AB35420 was as follows:

AB35420

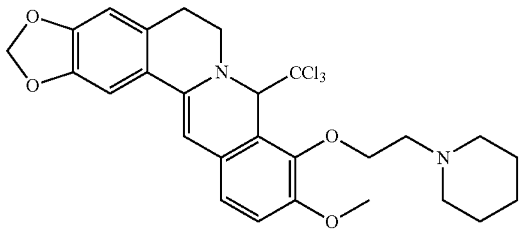

The synthesis method of compound AB35420 was as follows:

Step (1):

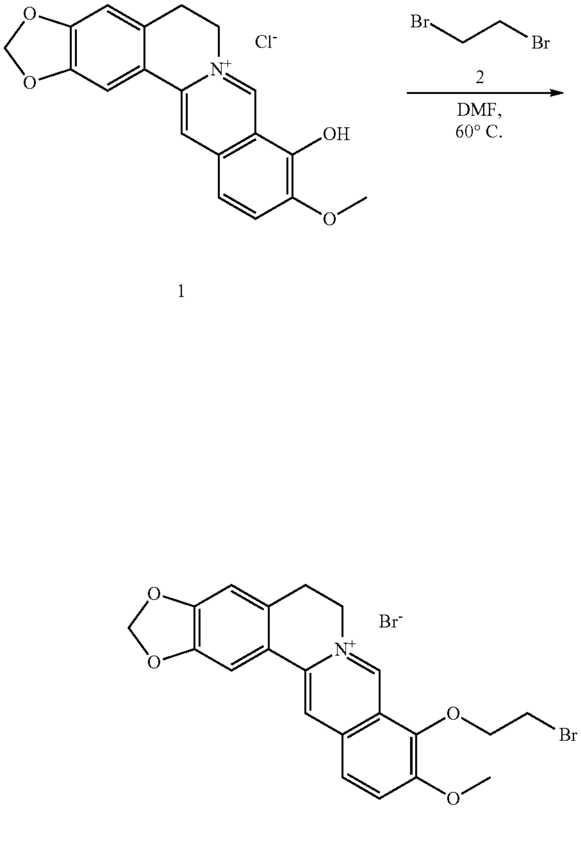

1

3

Compound 1 (5.0 g, 13.97 mmol, 1 eq) and compound 2 (21.0 g, 111.76 mmol, 8 eq) were dissolved in N, N-dimethylformamide (50 mL). The mixture was reacted at 60° C. for overnight. The reaction mixture was diluted with water and then extracted with dichloromethane twice, the organic phase was washed with brine, dried over anhydrous sodium sulfate and filtered, the filtrate was spin dried. The crude product was purified by fast chromatography (DCM/MeOH=50/1 to 20/1) to afford compound 3.

Step (2):

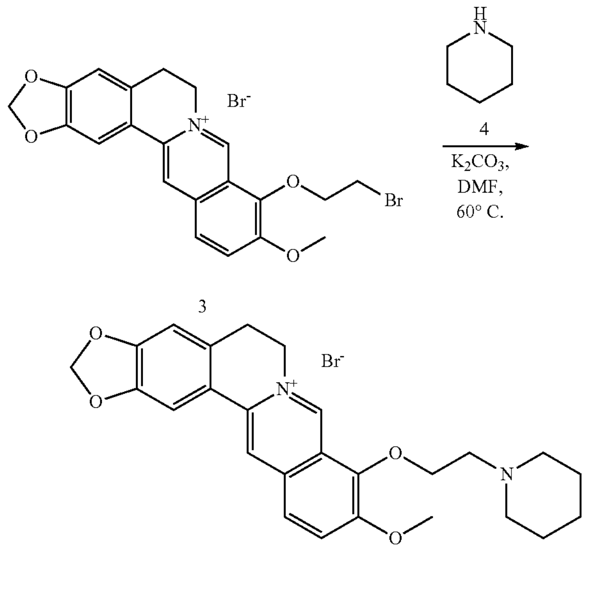

3

5

Compound 3 (250 mg, 0.49 mmol, 1 eq) and compound 4 (167 mg, 1.96 mmol, 4 eq) were dissolved in N, N-dimethylformamide (10 mL), and potassium carbonate (270 mg, 1.96 mmol, 4 eq) was added. The mixture was reacted at 60° C. for overnight, the reaction mixture was diluted with water and then extracted with dichloromethane, the organic phase was washed with brine, dried over anhydrous sodium sulfate and filtered, the filtrate was spin dried. The crude product was purified by fast chromatography (DCM/MeOH=10/1) to afford compound 5.

Step (3):

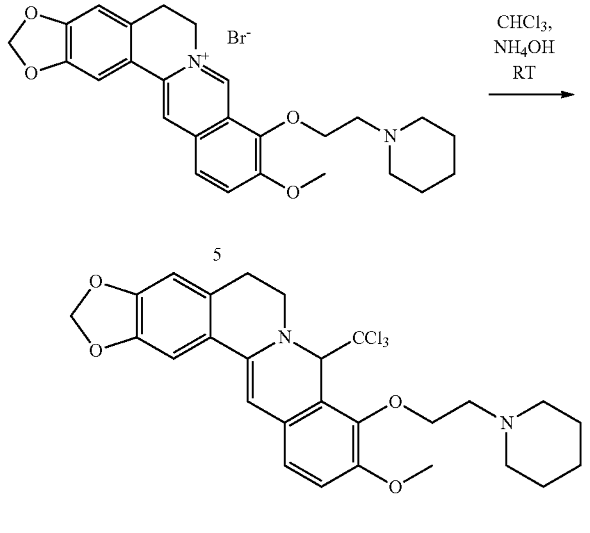

5

AB35420

Compound 5 (100 mg, 0.19 mmol, 1 eq) was dissolved in chloroform (5 mL), and aqueous ammonia (2 mL) was added. The mixture was reacted at room temperature for 48 h. The reaction mixture was diluted with water and then extracted with dichloromethane, the organic phase was washed with brine, dried over anhydrous sodium sulfate and filtered, the filtrate was spin dried. The crude product was purified by thin layer chromatography (PE/EA=10/1) to afford compound AB35420.

Compound AB35420

MS-ESI: Calculated $[M+H]^+$: 551.12; Found $[M+H]^+$: 551.10.

$^1H$ NMR (400 MHz, $CDCl_3$) δ 7.14 (s, 1H), 6.95-6.84 (m, 2H), 6.60 (s, 1H), 6.06 (s, 1H), 5.93 (s, 2H), 5.84 (s, 1H), 4.41-4.36 (m, 1H), 3.93-3.88 (m, 1H), 3.84 (s, 3H), 3.75-3.27 (m, 1H), 3.33-3.27 (m, 1H), 2.86-2.56 (m, 6H), 1.66-1.47 (m, 10).

Example 22 Synthesis of Compound AB35421

The structure of compound AB35421 was as follows:

AB35421

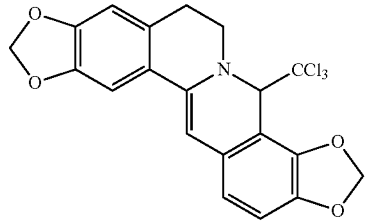

The synthesis method of compound AB35421 was as follows:

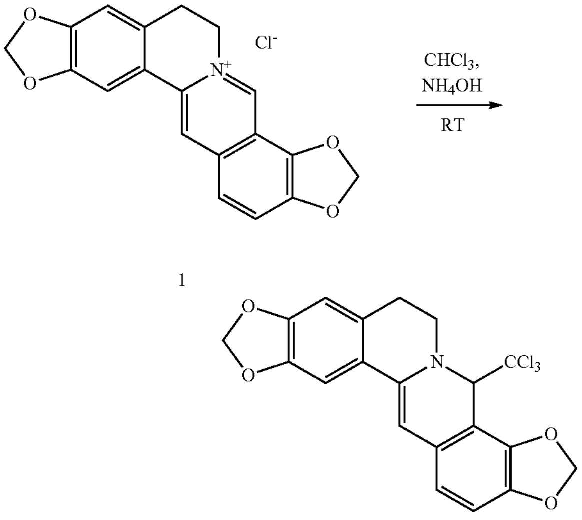

1

AB35421

Compound 1 (100 mg, 0.28 mmol, 1 eq) was dissolved in chloroform (5 mL), and aqueous ammonia (2 mL) was added. The mixture was reacted at room temperature for 48 h. The reaction mixture was diluted with water and then extracted with dichloromethane, the organic phase was washed with brine, dried over anhydrous sodium sulfate and filtered, the filtrate was spin dried. The crude product was purified by thin layer chromatography (PE/EA=10/1) to afford compound AB35421.

Compound AB35421:

MS-ESI: Calculated $[M+H]^+$: 438.00; Found$[M+H]^+$: 437.95.

$^1H$ NMR (400 MHz, $CDCl_3$) δ 7.16 (s, 1H), 6.86 (d, J=8.0 Hz, 1H), 6.87 (d, J=8.0 Hz, 1H), 6.61 (s, 1H), 6.14 (s, 1H), 6.03 (s, 1H), 5.96-5.94 (m, 2H), 5.91 (s, 1H), 5.41 (s, 1H), 3.86-3.80 (m, 1H), 3.72-3.68 (m, 1H), 3.39-3.32 (m, 1H), 2.75-2.68 (m, 1H).

Example 23 Synthesis of Compound AB35422

The structure of compound AB35422 was as follows:

AB35422

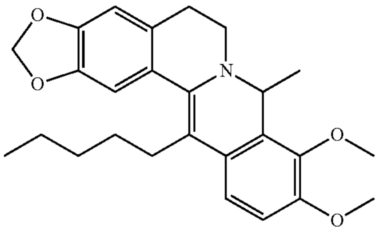

The synthesis method of compound AB35422 was as follows:

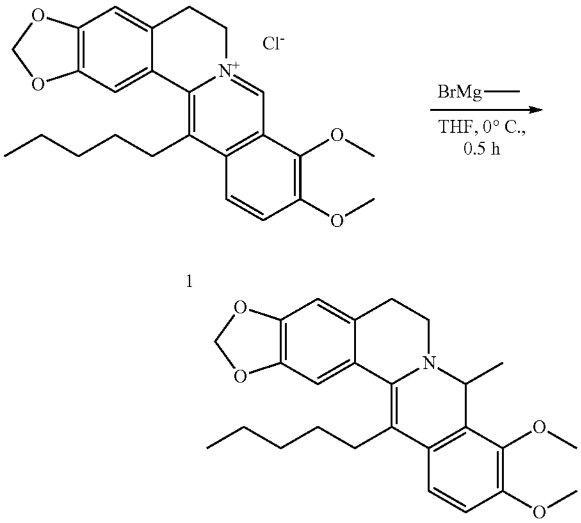

1

AB35422

Compound 1 (110 mg, 0.25 mmol, 1 eq) was dissolved in anhydrous tetrahydrofuran (10 mL), and methylmagnesium bromide (0.4 mL, 1.25 mmol, 5 eq, 3M) was added slowly at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and spin dried. The crude product was purified by thin layer chromatography (DCM: MeOH=20:1) to afford compound AB35422.

Compound AB35422:

MS-ESI: Calculated $[M+H]^+$: 422.23, Found$[M+H]^+$: 422.20.

$^1H$ NMR (400 MHz, DMSO-$d_6$) δ 6.88-6.83 (m, 4H), 6.00 (d, J=8.0 Hz, 2H), 4.65-4.61 (m, 1H), 3.76 (d, J=8.0 Hz, 6H), 3.16-3.08 (m, 3H), 2.74-2.70 (m, 3H), 1.71-1.63 (m, 1H), 1.42-1.32 (m, 5H), 0.94 (d, J=4.0 Hz, 3H), 0.89-0.86 (m, 3H).

Example 24 Synthesis of Compound AB35423

The structure of compound AB35423 was as follows:

AB35423

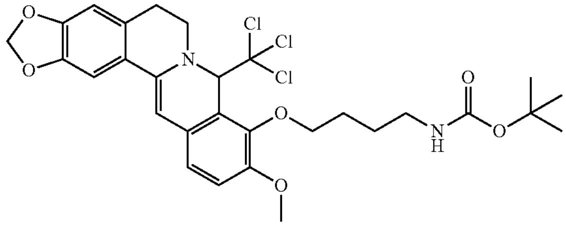

The synthesis method of compound AB35423 was as follows:

Step (1):

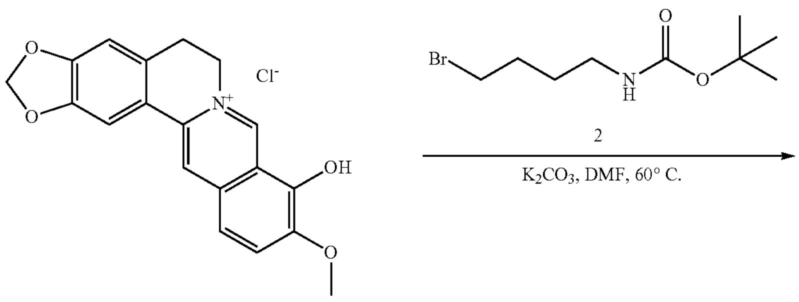

1

-continued

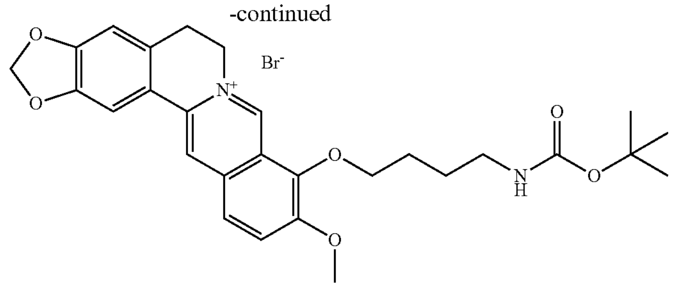

3

Compound 1 (300 mg, 0.84 mmol, 1 eq) was dissolved in N, N-dimethylformamide (10 mL), and potassium carbonate (464 mg, 3.36 mmol, 4 eq) and compound 2 (847 mg, 3.36 mmol, 4 eq) were added. The mixture was reacted at 60° C. for overnight. The reaction mixture was diluted with water and then extracted with dichloromethane twice, the phase was dried over anhydrous sodium sulfate and filtered, the filtrate was spin dried. The crude product was purified by fast chromatography (DCM/MeOH=50/1 to 20/1) to afford compound 3.

Step (2):

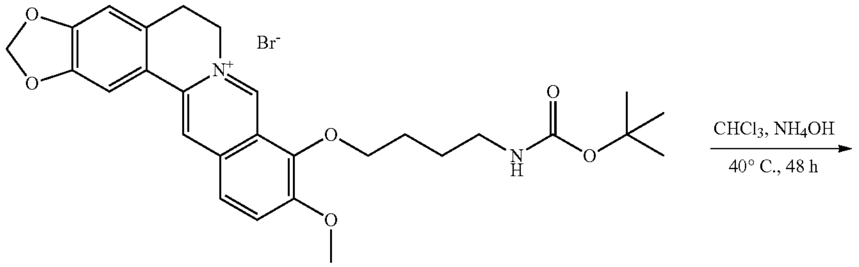

3

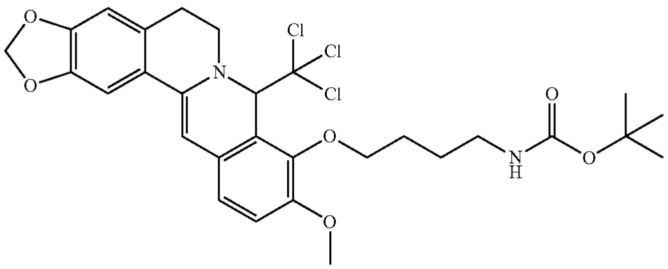

AB35423

Compound 3 (200 mg, 0.35 mmol, 1 eq) was dissolved in chloroform (5 mL), and aqueous ammonia (2 mL) was added. The mixture was reacted at 40° C. for 48 h. The reaction mixture was diluted with water and then extracted with dichloromethane, the organic phase was washed with brine, dried over anhydrous sodium sulfate and filtered, the filtrate was spin dried. The crude product was purified by thin layer chromatography (PE:EA=200:1) to afford compound AB35423.

Compound AB35423:

MS-ESI: Calculated $[M+H]^+$: 611.14; Found $[M+H]^+$: 611.05.

$^1H$ NMR (400 MHz, $CDCl_3$) δ 7.16 (s, 1H), 6.97-6.86 (m, 2H), 6.62 (s, 1H), 6.09 (s, 1H), 5.95-5.94 (m, 2H), 5.60 (s, 1H), 4.64 (s, 1H), 4.27-4.23 (m, 1H), 3.90-3.86 (m, 5H), 3.73-3.67 (m, 1H), 3.35-3.22 (m, 3H), 2.77-2.71 (m, 1H), 1.84-1.72 (m, 4H), 1.44 (s, 9H).

Example 25 Synthesis of Compound AB35424

The structure of compound AB35424 was as follows:

AB35424

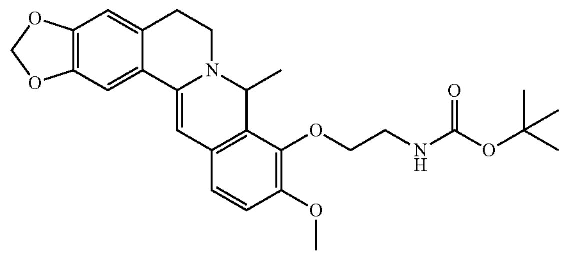

The synthesis method of compound AB35424 was as follows:

Step (1):

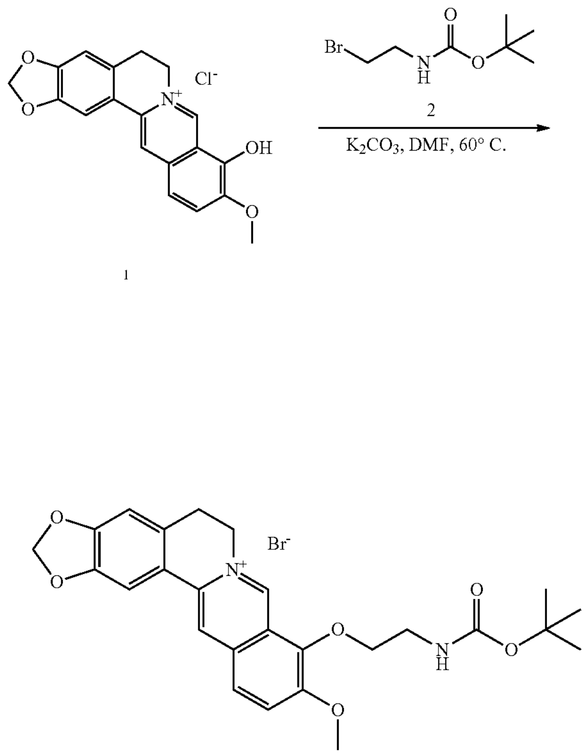

1

3

Compound 1 (300 mg, 0.84 mmol, 1 eq) was dissolved in N, N-dimethylformamide (10 mL), and potassium carbonate (464 mg, 3.36 mmol, 4 eq) and compound 2 (753 mg, 3.36 mmol, 4 eq) were added. The mixture was reacted at 60° C. for overnight. The reaction mixture was diluted with water and then extracted with dichloromethane twice, the phase was washed with brine, dried over anhydrous sodium sulfate and filtered, the filtrate was spin dried. The crude product was purified by fast chromatography (DCM/MeOH=50/1 to 20/1) to afford compound 3.

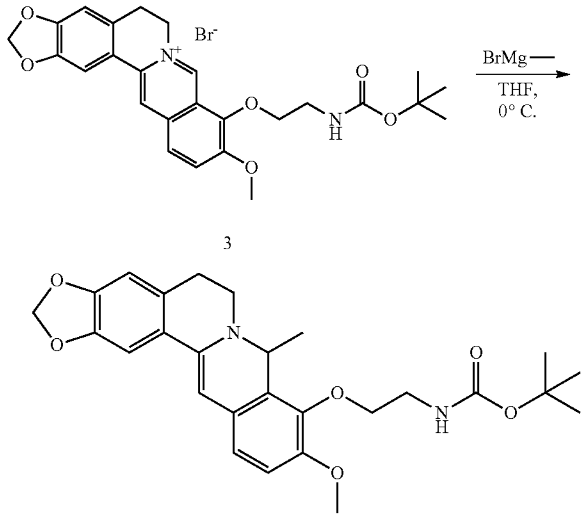

3

AB35424

Compound 3 (50 mg, 0.09 mmol, 1 eq) was dissolved in anhydrous tetrahydrofuran (10 mL), and methylmagnesium bromide (0.15 mL, 0.45 mmol, 5 eq, 3M) was added slowly at 0° C. under $N_2$. The mixture was reacted for 0.5 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by reversed phase preparation chromatography (acetonitrile/water+0.01% formic acid) to afford compound AB35424.

Compound AB35424:

MS-ESI: Calculated $[M+H]^+$: 481.23; Found $[M+H]^+$: 481.20.

$^1H$ NMR (400 MHz, DMSO-$d_6$) δ 7.25 (s, 1H), 7.04-7.02 (m, 1H), 6.82-6.66 (m, 3H), 6.00 (d, J=4.0 Hz, 2H), 5.92 (s, 1H), 4.86-4.81 (m, 1H), 3.96-3.91 (m, 2H), 3.75 (s, 3H), 3.28-3.26 (m, 4H), 2.84-2.74 (m, 2H), 1.39 (s, 9H), 1.03 (d, J=8.0 Hz, 3H).

Example 26 Synthesis of Compound AB35426

The structure of compound AB35426 was as follows:

compound AB35426

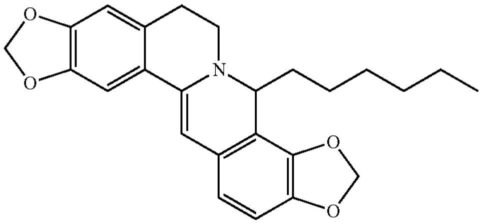

The synthesis method of compound AB35426 was as follows:

Step (1):

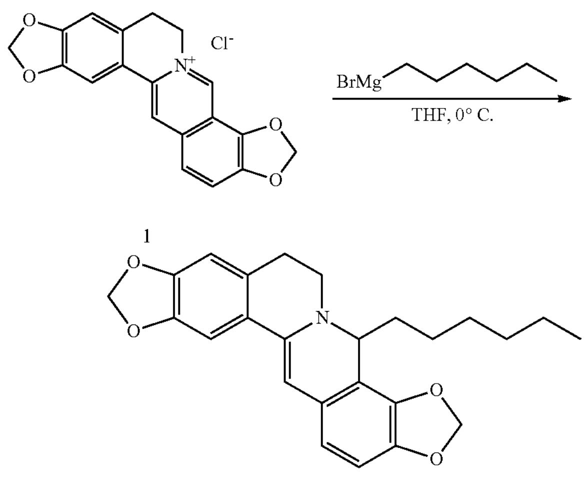

1

AB35426

Compound 3 (200 mg, 0.56 mmol, 1 eq) was dissolved in anhydrous tetrahydrofuran (10 mL), and hexylmagnesium bromide (3.4 mL, 3.36 mmol, 6 eq, 1 M) was added slowly at 0° C. under $N_2$. The mixture was reacted at room temperature for 0.5 h. The reaction mixture was quenched with saturated aqueous ammonium chloride solution and then extracted with ethyl acetate twice, the organic phase was washed with brine, dried over anhydrous sodium sulfate and filtered, the filtrate was spin dried. The crude product was purified by thin layer chromatography (dichloromethane:methanol=30:1) to afford compound AB35426.

Compound AB35426:

MS-ESI: Calculated $[M+H]^+$: 405.19; Found: 406.25.

$^1H$ NMR (400 MHz, $CDCl_3$) δ 7.13 (s, 1H), 6.66 (d, J=4.0 Hz, 1H), 6.59 (s, 1H), 6.51 (d, J=8.0 Hz, 1H), 5.95-5.94 (m, 3H), 5.83 (d, J=8.0 Hz, 2H), 4.58-4.56 (m, 1H), 3.46-3.41 (m, 1H), 3.26-3.23 (m, 1H), 2.89-2.77 (m, 2H), 1.85-1.76 (m, 1H), 1.64-1.57 (m, 1H), 1.28-1.19 (m, 8H), 0.84-0.81 (m, 3H).

Example 27 Synthesis of Compound AB35427

The structure of compound AB35427 was as follows:

AB35427

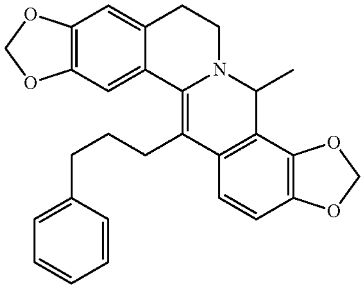

The synthesis method of compound AB35427 was as follows:

Step (1):

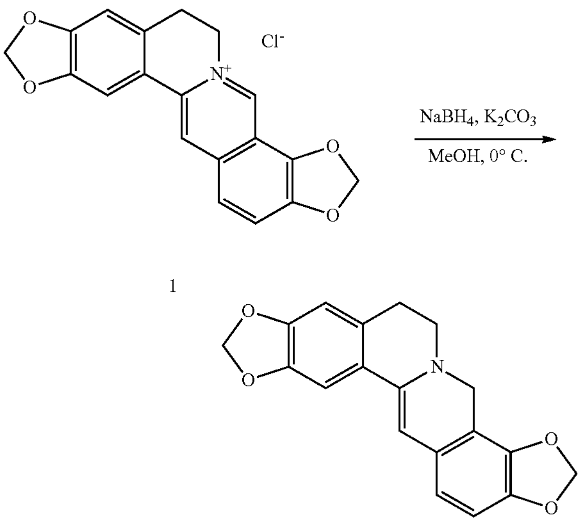

1

2

Compound 1 (500 mg, 1.41 mmol, 1 eq) was dissolved in methanol (10 mL), and potassium carbonate (583 mg, 4.22 mmol, 3.0 eq) was added, then a mixture of sodium borohydride (53 mg, 1.41 mmol, 1.0 eq) in 5% sodium hydroxide solution was slowly added dropwise at 0° C. The mixture was reacted for 2 h. The reaction mixture was filtered, the solid was washed with ethanol 2-3 times and collected to afford compound 2 (800 mg, yield: 99.9%) as a yellow solid.

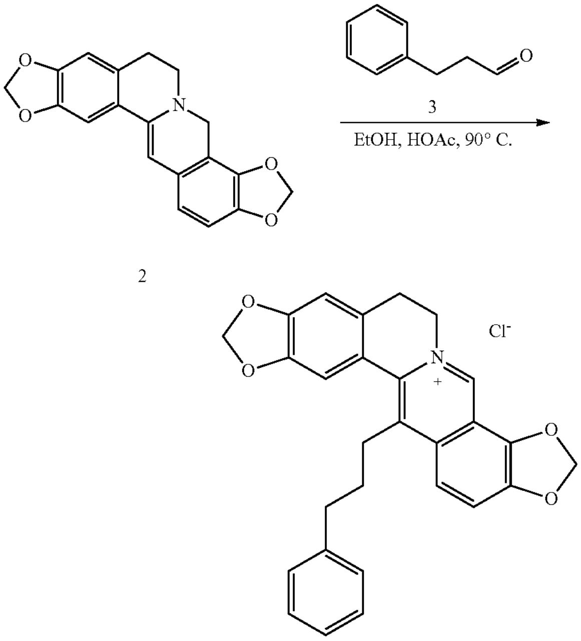

2

4

Compound 2 (400 mg, 1.26 mmol, 1 eq) was dissolved in ethanol/acetic acid (12 mL/2 mL), and phenylpropionaldehyde (1.69 g, 12.58 mmol, 10 eq) was added. The mixture was reacted at 90° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 4 (160 mg, yield: 29.0%) as a yellow solid.

Step (3):

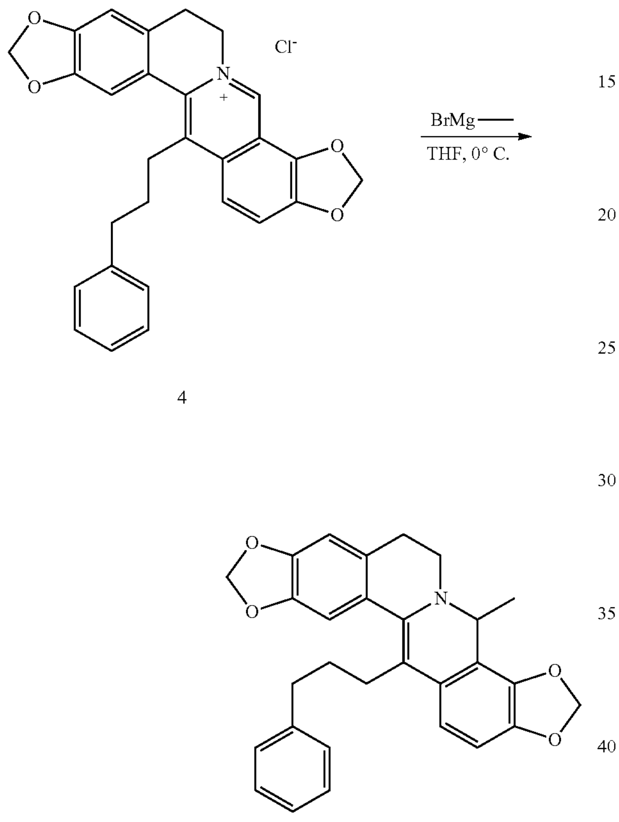

4

AB35427

Compound 4 (90 mg, 0.21 mmol, 1 eq) was dissolved in anhydrous tetrahydrofuran (10 mL), and methylmagnesium bromide (1 mL, 1.03 mmol, 5 eq, 3M) was added slowly at 0° C. under $N_2$. The mixture was reacted at room temperature for 0.5 h. The reaction mixture was quenched with saturated aqueous ammonium chloride solution and then extracted with ethyl acetate twice, the organic phase was washed with brine, dried over anhydrous sodium sulfate and filtered, the filtrate was spin dried. The crude product was purified by reversed phase preparation chromatography (acetonitrile/water+0.01% formic acid) to afford solid compound AB35427.

Compound AB35427:

MS-ESI: Calculated $[M+H]^+$: 453.20; Found: 454.20.

$^1H$ NMR (400 MHz, DMSO-d6) δ 7.23-7.21 (m, 2H), 7.17-7.15 (m, 3H), 6.81 (s, 2H), 6.69 (d, J=8.0 Hz, 1H), 6.53 (d, J=8.0 Hz, 1H), 6.00-5.99 (m, 3H), 5.90 (s, 1H), 4.55-4.51 (m, 1H), 3.16-3.04 (m, 2H), 2.73-2.46 (m, 6H), 1.95-1.69 (m, 2H), 20.99 (d, J=4.0 Hz, 3H).

Example 28 Synthesis of Compound AB35428

The structure of compound AB35428 was as follows:

AB35428

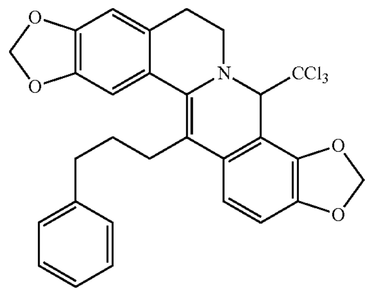

The synthesis method of compound AB35428 was as follows:

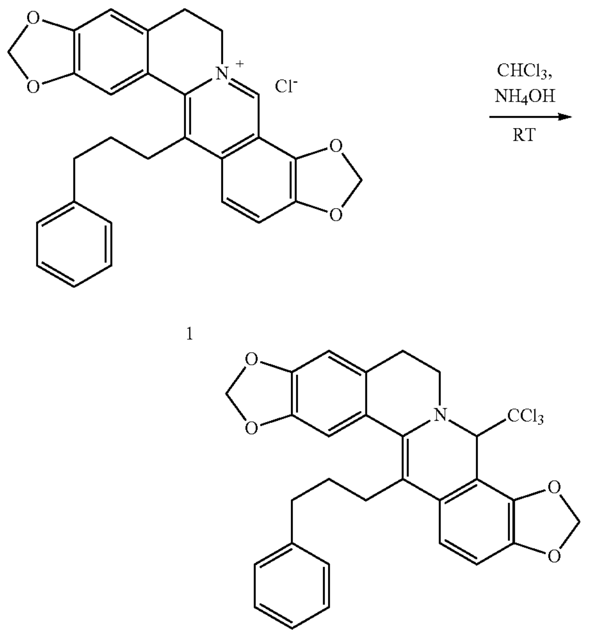

1

AB35428

Compound 1 (100 mg, 0.21 mmol, 1 eq) was dissolved in chloroform (4 mL), and aqueous ammonia (2 mL) was added. The mixture was reacted at room temperature for 48 h. The reaction mixture was washed with water and then extracted with dichloromethane, the organic phase was dried over anhydrous sodium sulfate and filtered, the filtrate was spin dried. The crude product was purified by thin layer chromatography (dichloromethane:methanol=30:1) to afford compound AB35428.

Compound AB35428:

MS-ESI: Calculated $[M+H]^+$: 556.08; Found$[M+H]^+$: 556.00.

$^1H$ NMR (400 MHz, DMSO-d6) δ 7.28-7.24 (m, 2H), 7.21-7.14 (m, 3H), 6.96 (d, J=12.0 Hz, 1H), 6.85 (s, 1H), 6.73-6.71 (m, 2H), 6.07 (s, 1H), 6.02 (d, J=4.0 Hz, 2H), 5.97 (s, 1H), 5.44 (s, 1H), 3.80-3.75 (m, 1H), 3.63-3.61 (m, 1H), 2.70-2.53 (m, 6H), 1.88-1.74 (m, 2H).

Example 29 Synthesis of Compound AB35429

The structure of compound AB35429 was as follows:

AB35429

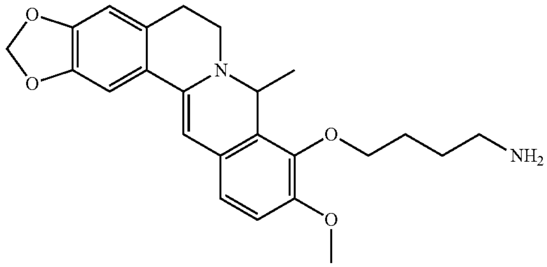

The synthesis method of compound AB35429 was as follows:

Step (1):

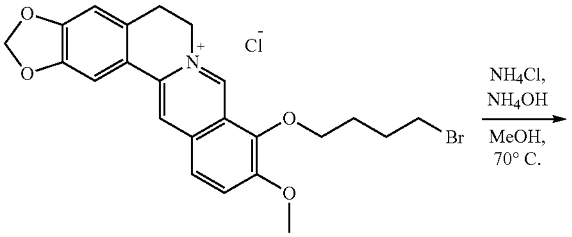

1

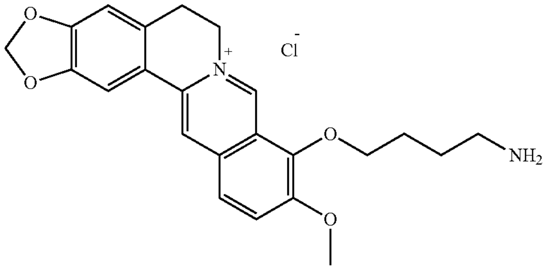

2

Compound 1 (400 mg, 0.81 mmol, 1.0 eq) was dissolved in methanol (30 mL), and aqueous ammonia (7 mL) and ammonium chloride (44 mg, 0.81 mmol, 1.0 eq) were added in sequence. The mixture was stirred at 70° C. for 16 h, and the reaction was detected to be performed completely using TLC and LCMS. The reaction mixture was diluted with water and then extracted with ethyl acetate twice, the organic phase was dried over anhydrous sodium sulfate and filtered, the filtrate was spin dried, the crude product was purified by fast chromatography (DCM/MeOH=100/1 to 50/1) to afford compound 2 (190 mg, yield: 42.2%) as a yellow solid.

Step (2):

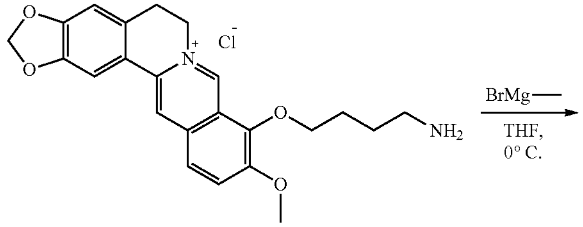

2

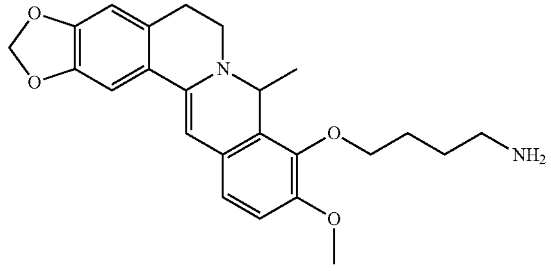

AB35429

Compound 2 (80 mg, 0.19 mmol, 1 eq) was dissolved in anhydrous tetrahydrofuran (5 mL), and methylmagnesium bromide (0.4 mL, 1.14 mmol, 6.0 eq, 3M) was added slowly at 0° C. under $N_2$. The mixture was reacted at room temperature for 0.5 h, and the reaction was detected to be performed completely using TLC and LCMS. The reaction mixture was quenched with saturated aqueous ammonium chloride solution and then extracted with ethyl acetate, the organic phase was dried over anhydrous sodium sulfate, filtered and spin dried. The crude product was purified by reversed phase preparation chromatography (acetonitrile/water+0.01% formic acid) to afford solid compound AB35429 (10 mg, yield: 12.5%) as a yellow solid Compound AB35429:

MS-ESI: Calculated $[M+H]^+$: 409.21, Found [M+H+H2O]+: 428.10.

1H NMR (400 MHz, DMSO-d6) δ 7.23 (s, 1H), 6.80-6.64 (m, 3H), 5.98 (d, J=4.0 Hz, 2H), 5.90 (s, 1H), 4.75-4.70 (m, 1H), 3.96-3.87 (m, 2H), 3.74-3.71 (m, 5H), 3.26-3.20 (m, 2H), 2.81-2.72 (m, 2H), 1.95-1.79 (m, 4H), 1.03 (d, J=8.0 Hz, 3H).

Example 30 Synthesis of Compound AB35430

The structure of compound AB35430 was as follows:

AB35430

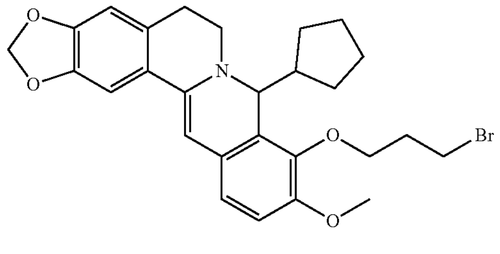

The synthesis method of compound AB35430 was as follows:

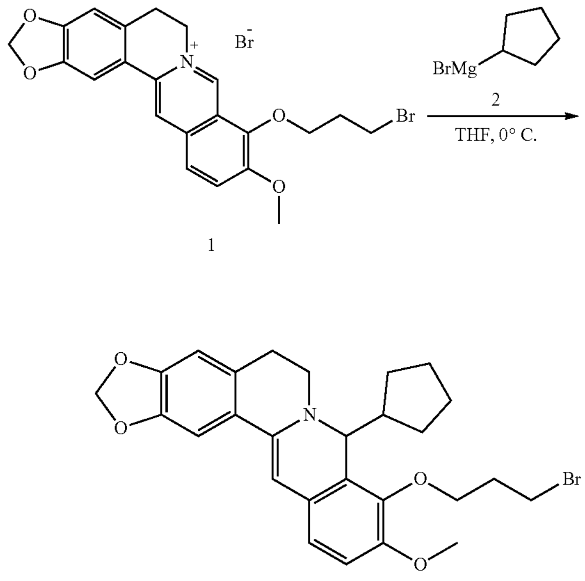

1

AB35430

Compound 1 (150 mg, 0.28 mmol, 1.0 eq) was dissolved in tetrahydrofuran (10 mL), and cyclopentylmagnesium bromide (1.4 mL, 1.4 mmol, 5 eq, 1M) was added at 0° C. The mixture was reacted at room temperature for 0.5 h, and the reaction was detected to be performed completely using TLC and LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by thin layer chromatography (dichloromethane/methanol=30/1) to afford compound AB35430.

Compound AB35430:

MS-ESI: Calculated $[M+H]^+$: 512.14, Found: 512.10.

1H NMR (400 MHz, CDCl3) δ 7.13 (s, 1H), 6.74 (s, 2H), 6.58 (s, 1H), 5.93 (s, 2H), 5.83 (s, 1H), 4.65 (d, J=4.0 Hz, 1H), 4.26-4.21 (m, 1H), 4.03-3.97 (m, 1H), 3.82 (s, 3H), 3.80-3.67 (m, 2H), 3.60-3.44 (m, 2H), 2.89-2.76 (m, 2H), 2.46-2.16 (m, 3H), 1.76-1.70 (m, 1H), 1.48-1.30 (m, 7H).

Example 31 Synthesis of Compound AB35434

The structure of compound AB35434 was as follows:

AB35434

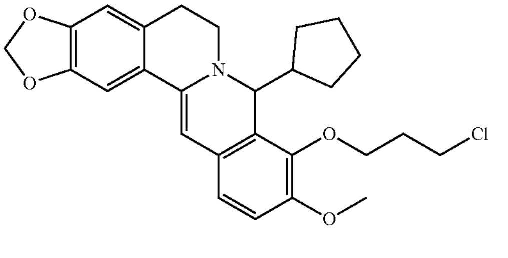

The synthesis method of compound AB35434 was as follows:

Step (1):

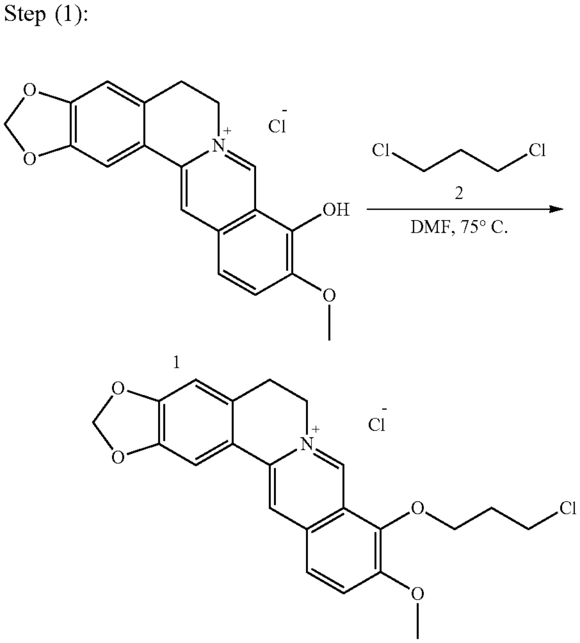

1

3

Compound 1 (500 mg, 1.4 mmol, 1.0 eq) was dissolved in DMF (10 mL), and compound 2 (949 mg, 8.4 mmol, 6 eq) was added. The mixture was reacted at 75° C. for 16 h, and the reaction was detected to be performed completely using TLC and LCMS. The organic phase was spin dried, the crude product was purified by fast chromatography (100-200 mesh silica gel, DCM/MeOH=20/1) to afford compound 3 (300 mg, yield: 49.3%) as a yellow solid.

Step (2):

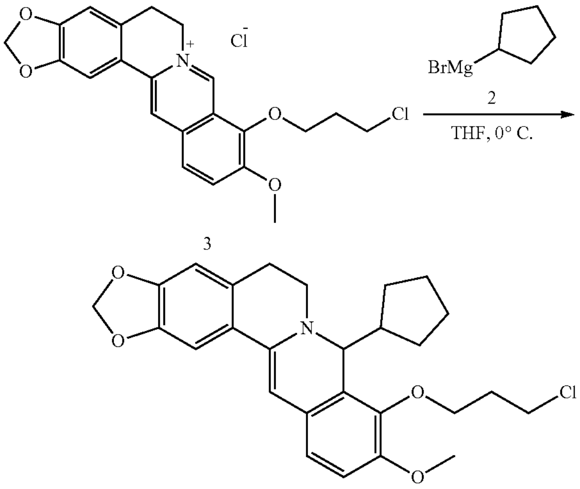

3

AB35434

Compound 3 (200 mg, 0.46 mmol, 1.0 eq) was dissolved in tetrahydrofuran (10 mL), and cyclopentylmagnesium bromide (2.8 mL, 2.76 mmol, 6.0 eq, 1M) was added at 0° C. under $N_2$. The mixture was reacted at 0° C. for 0.5 h, and the reaction was detected to be performed completely using TLC and LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.01% formic acid) to afford compound AB35434.

Compound AB35434:

MS-ESI: Calculated $[M+H]^+$: 468.19, Found: 468.45.

$^1H$ NMR (400 MHz, $CDCl_3$) δ 7.13 (s, 1H), 6.74 (s, 2H), 6.57 (s, 1H), 5.92 (s, 2H), 5.82 (s, 1H), 4.61 (d, J=8.0 Hz, 1H), 4.23-4.21 (m, 1H), 4.00-3.84 (m, 2H), 3.79 (s, 4H), 3.58-3.43 (m, 2H), 2.88-2.81 (m, 2H), 2.36-2.28 (m, 2H), 2.16-2.06 (m, 1H), 1.74-1.37 (m, 8H).

Example 32 Synthesis of Compound AB35436

The structure of compound AB35436 was as follows:

AB35436

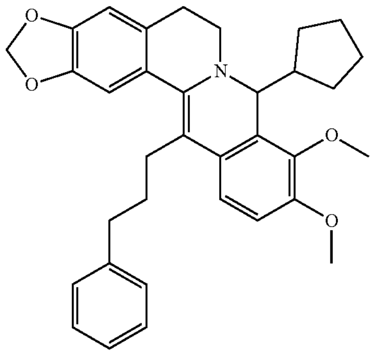

The synthesis method of compound AB35436 was as follows:

Step (1):

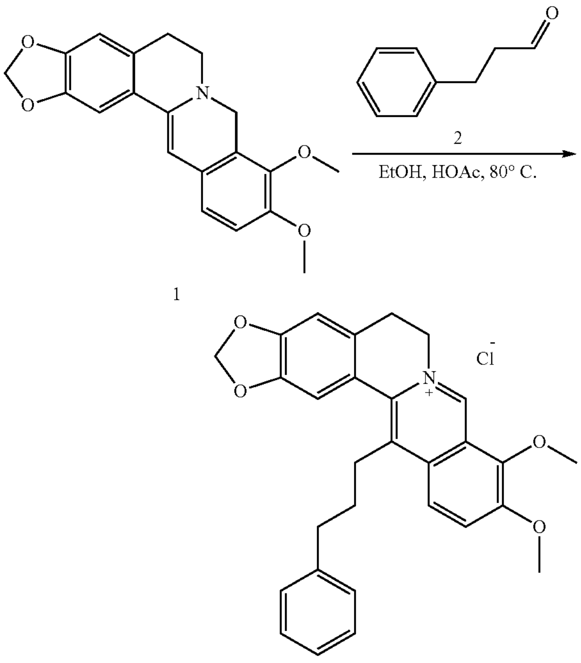

1

3

Compound 1 (2.0 g, 5.93 mmol, 1 eq) was dissolved in ethanol/acetic acid (10 mL/8 mL), and phenylpropionaldehyde (7.9 g, 59.3 mmol, 10 eq) was added. The mixture was reacted at 80° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 3 (1.4 g, yield: 48.2%) as a yellow solid.

Step (2):

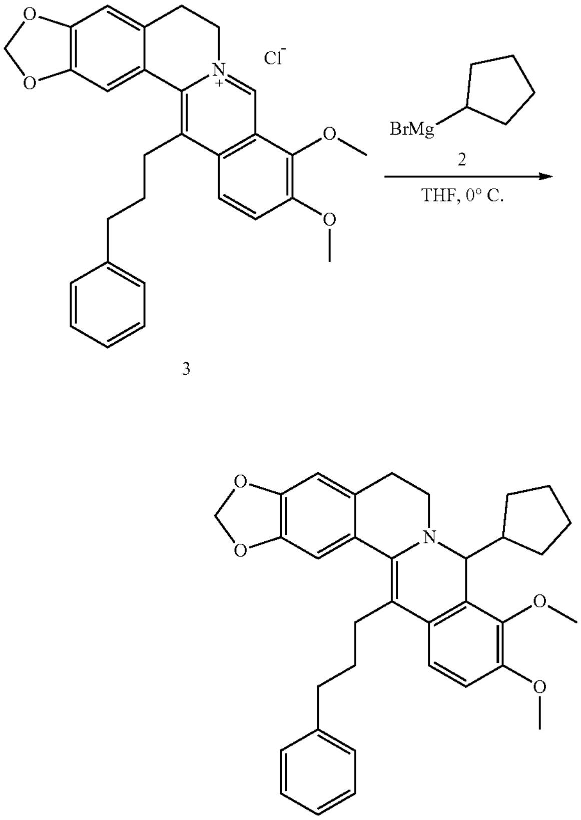

3

AB35436

Compound 3 (200 mg, 0.41 mmol, 1 eq) was dissolved in anhydrous tetrahydrofuran (10 mL), and cyclopentylmagnesium bromide (0.7 mL, 2.05 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was washed with brine, dried over anhydrous sodium sulfate and filtered, the filtrate was spin dried. The crude product was purified by reversed phase preparation chromatography (acetonitrile/water+0.01% formic acid) to afford compound AB35436.

Compound AB35436:

MS-ESI: Calculated $[M+H]^+$: 524.28; Found: 524.30.

$^1H$ NMR (400 MHz, $CDCl_3$) δ 7.26-7.16 (m, 5H), 6.83-6.74 (m, 4H), 6.01 (d, J=4.0 Hz, 2H), 4.40 (d, J=8.0 Hz, 1H), 3.76 (s, 3H), 3.72 (s, 3H), 2.69-2.65 (m, 2H), 2.12-2.05 (m, 1H), 1.98-1.85 (m, 2H), 1.76-1.68 (m, 1H), 1.47-1.43 (m, 4H), 1.34-1.16 (m, 9H).

Example 33 Synthesis of Compound AB35438

The structure of compound AB35438 was as follows:

AB35438

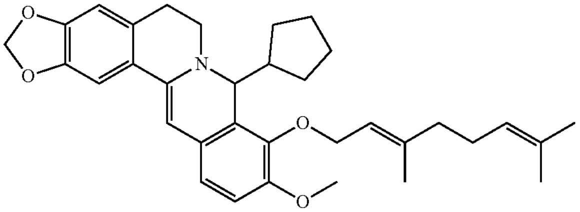

The synthesis method of compound AB35438 was as follows:

Step (1):

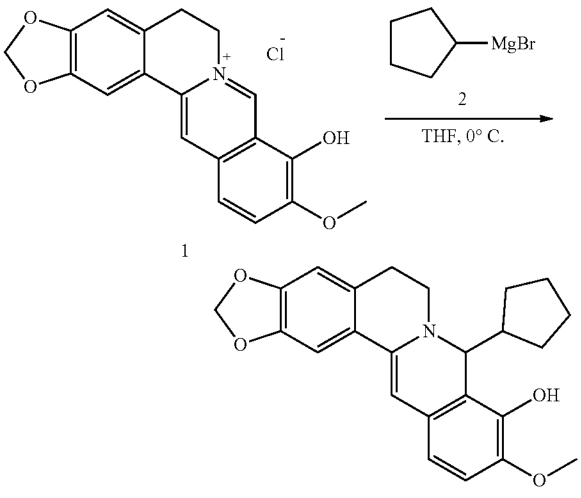

1

3

Compound 1 (2 g, 5.59 mmol, 1 eq) was dissolved in anhydrous tetrahydrofuran (20 mL), and cyclopentylmagnesium bromide (28 mL, 27.95 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by fast chromatography (DCM/MeOH=100/1 to 50/1) to afford compound 3 (1.2 g, yield: 54.5%) as a yellow solid.

Step (2):

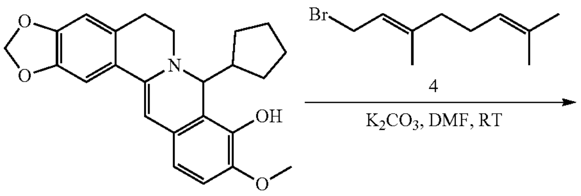

3

-continued

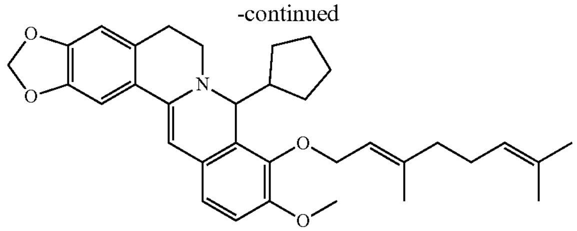

AB35438

Compound 3 (200 mg, 0.51 mmol, 1 eq) was dissolved in dimethylformamide (10 mL), and compound 4 (222 mg, 1.02 mmol, 2 eq) and potassium carbonate (211 mg, 1.53 mmol, 3 eq) were added. The mixture was reacted at room temperature for 12 h. The reaction mixture was diluted with water and then extracted with ethyl acetate twice, the organic phase was washed with brine, dried over anhydrous sodium sulfate and filtered, the filtrate was spin dried. The crude product was purified by reversed phase preparation chromatography (acetonitrile/water+0.01% formic acid) to afford compound AB35438.

Compound AB35438:

MS-ESI: Calculated $[M+H]^+$: 528.31; Found: 528.45.

$^1H$ NMR (400 MHz, DMSO-d6) δ 6.81 (s, 2H), 6.77 (d, J=8.0 Hz, 1H), 6.55 (d, J=8.0 Hz, 1H), 5.98 (d, J=12.0 Hz, 2H), 5.09-5.00 (m, 2H), 4.58 (d, J=8.0 Hz, 1H), 3.75 (s, 3H), 3.30-3.10 (s, 5H), 2.70-2.51 (m, 2H), 2.10-1.98 (m, 5H), 1.66 (s, 3H), 1.53 (s, 3H), 1.50 (s, 3H), 1.41-1.37 (m, 4H), 1.30-1.21 (m, 4H).

Example 34 Synthesis of Compound AB35440

The structure of compound AB35440 was as follows:

AB35440

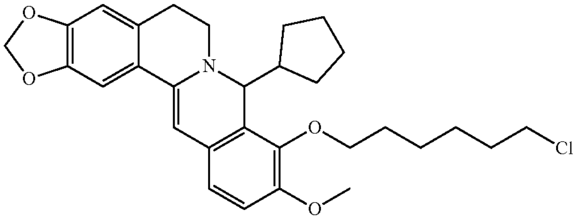

The synthesis method of compound AB35440 was as follows:

Step (1):

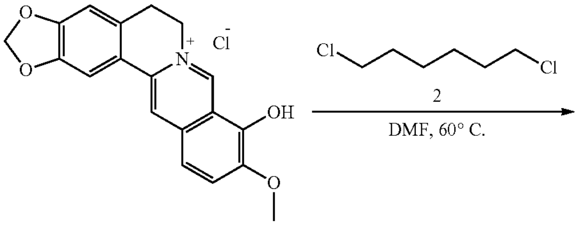

1

-continued

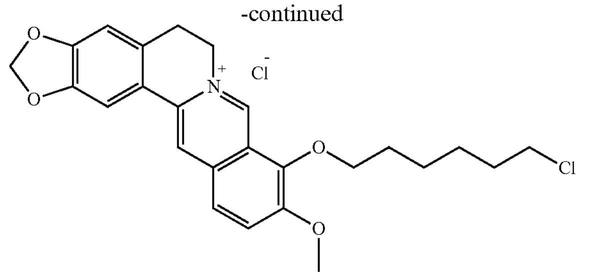

3

Compound 1 (500 mg, 1.40 mmol, 1 eq) was dissolved in N, N-dimethylformamide (5 mL), and compound 2 (862 mg, 5.6 mmol, 4 eq) was added. The mixture was reacted at 60° C. for 16 h, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (DCM/MeOH=50/1 to 20/1) to afford compound 3 (100 mg, yield: 15%) as a yellow solid.

Step (2):

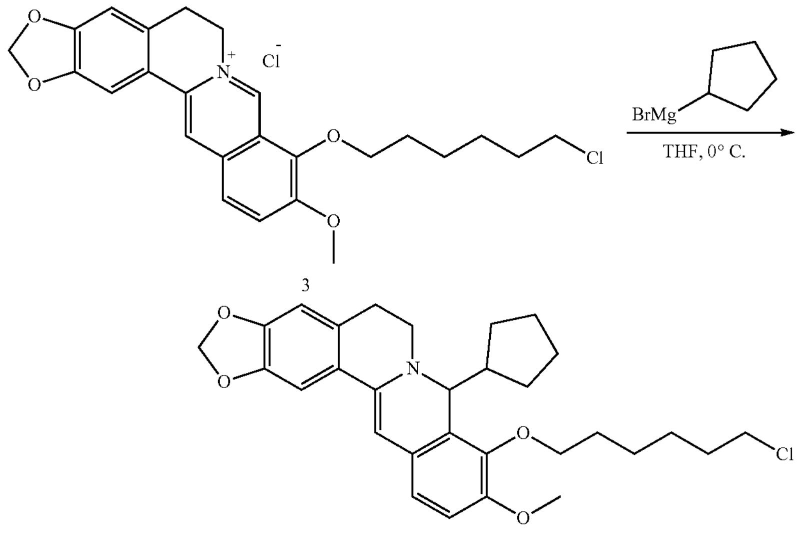

3

AB35440

Compound 3 (100 g mg, 0.21 mmol, 1 eq) was dissolved in anhydrous tetrahydrofuran (5 mL), and cyclopentylmagnesium bromide (0.4 mL, 1.05 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.01% formic acid) to afford compound AB35440.

Compound AB35440:

MS-ESI: Calculated $[M+H]^+$ 510.24; Found: 510.25.

$^1H$ NMR (400 MHz, DMSO-d6) δ 7.21 (s, 1H), 6.79 (d, J=8.0 Hz, 1H), 6.74 (s, 1H), 6.64 (d, J=8.0 Hz, 1H), 5.97 (s, 2H), 5.89 (s, 1H), 4.50 (d, J=8.0 Hz, 1H), 4.03-4.00 (m, 1H), 3.77-3.72 (m, 4H), 3.65-3.61 (m, 2H), 3.42-3.36 (m, 2H), 2.90-2.84 (m, 1H), 2.66-2.64 (m, 1H), 2.20-2.13 (m, 1H), 1.73-1.57 (m, 6H), 1.47-1.41 (m, 6H), 1.28-1.15 (m, 4H).

Example 35 Synthesis of Compound AB35441

The structure of compound AB35441 was as follows:

AB35441

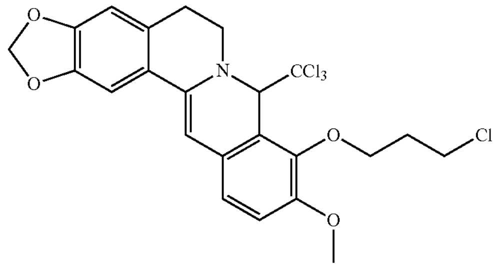

The synthesis method of compound AB35441 was as follows:

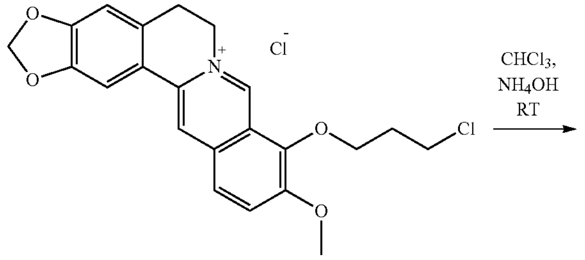

1

-continued

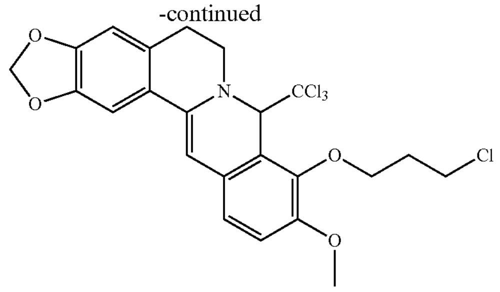

AB35441

Compound 1 (100 mg, 0.23 mmol, 1 eq) was dissolved in a mixture of aqueous ammonia (3 ml) and chloroform (6 ml). The mixture was reacted at room temperature for 48 h. The reaction mixture was diluted with water and then extracted with dichloromethane, the organic phase was dried over anhydrous sodium sulfate and filtered, the filtrate was spin dried. The crude product was purified by thin layer chromatography (dichloromethane/methanol=50/1) to afford compound AB35441.

Compound AB35441:

MS-ESI: Calculated $[M+H]^+$: 516.02; Found: 516.25.

$^1$H NMR (400 MHz, DMSO-d6) δ 7.31 (s, 1H), 7.09 (d, J=12.0 Hz, 1H), 6.89 (d, J=4.0 Hz, 1H), 6.77 (s, 1H), 6.32 (s, 1H), 5.99 (d, J=4.0 Hz, 2H), 5.63 (s, 1H), 4.23-4.19 (m, 1H), 3.90-3.88 (m, 3H), 3.79-3.74 (m, 4H), 3.65-3.60 (m, 1H), 3.27-3.21 (m, 1H), 2.73-2.67 (m, 1H), 2.21-2.20 (m, 1H), 2.09-2.02 (m, 1H).

Example 36 Synthesis of Compound AB35444

The structure of compound AB35444 was as follows:

AB35444

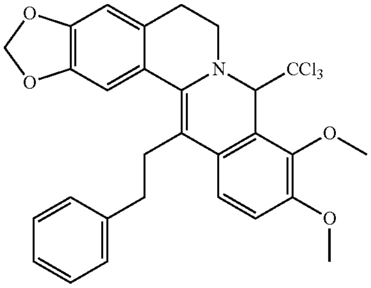

The synthesis method of compound AB35444 was as follows:

Step (1):

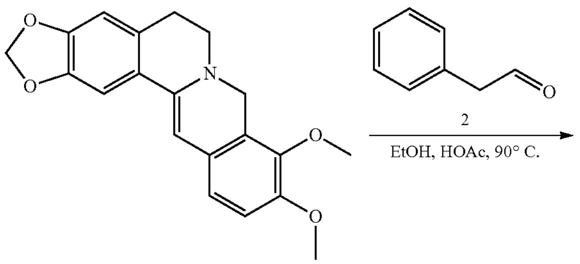

1

-continued

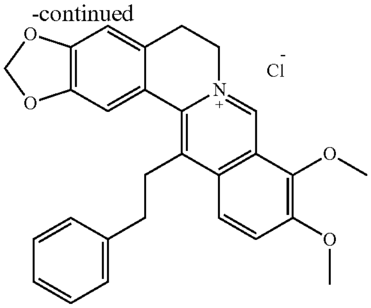

3

Compound 1 (3.0 g, 8.89 mmol, 1 eq) was dissolved in ethanol/acetic acid (30 mL/5 mL), and phenylacetaldehyde (10.7 g, 88.9 mmol, 10 eq) was added. The mixture was reacted at 90° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 3 (1.8 g, yield: 42.8%) as a yellow solid.

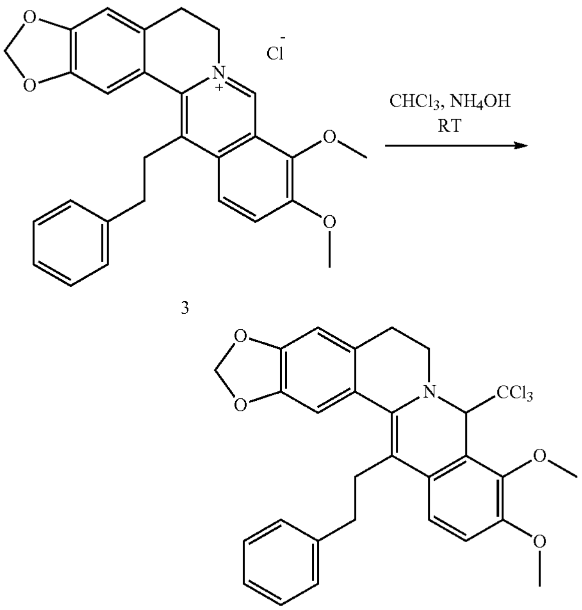

3

AB35444

Compound 1 (300 mg, 0.63 mmol, 1 eq) was dissolved in aqueous ammonia (4 ml), and chloroform (8 ml) was added. The mixture was reacted at room temperature for 48 h under $N_2$. The reaction mixture was diluted with water and then extracted with dichloromethane, the organic phase was dried over anhydrous sodium sulfate and filtered, the filtrate was spin dried. The crude product was purified by fast chromatography (DCM/MeOH=100/1 to 50/1) to afford compound AB 35444.

Compound AB35444:

MS-ESI: Calculated $[M+H]^+$: 558.10; Found: 558.05.

$^1$H NMR (400 MHz, DMSO-d6) δ 7.30 (d, J=4.0 Hz, 4H), 7.21-7.18 (m, 3H), 6.97 (s, 1H), 6.87 (s, 1H), 6.03 (s, 1H), 6.00 (s, 1H), 5.58 (s, 1H), 3.85-3.79 (m, 7H), 3.62-3.59 (m, 1H), 2.90-2.70 (m, 5H), 2.58-2.51 (m, 1H).

Example 37 Synthesis of Compound AB35445

The structure of compound AB35445 was as follows:

AB35445

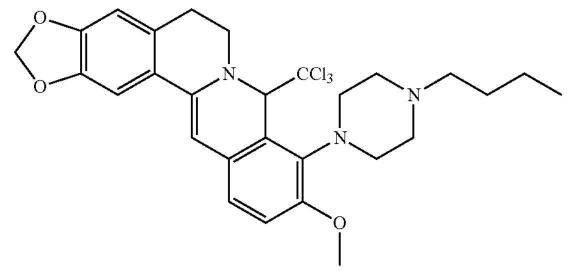

The synthesis method of compound AB35445 was as follows:

Step (1):

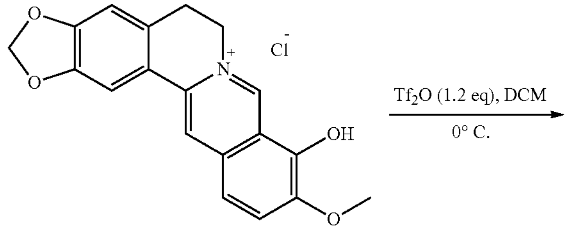

1

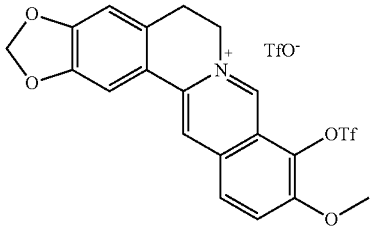

2

Compound 1 (5.0 g, 13.97 mmol, 1.0 eq) was dissolved in dichloromethane (300 mL), and trifluoromethanesulfonic anhydride (4.3 g, 15.37 mmol, 1.1 eq) was slowly added dropwise at 0° C. The mixture was reacted at room temperature for 1 h, and the reaction was detected to be performed completely using TLC and LCMS. The reaction mixture was quenched with water and then extracted with dichloromethane twice, the organic phase was dried over anhydrous sodium sulfate and filtered, the filtrate was spin dried. The crude product was purified by fast chromatography (dichloromethane/methanol=100/1 to 50/1) to afford compound 2 (3.4 g, yield: 40.5%) as a yellow solid.

Step (2):

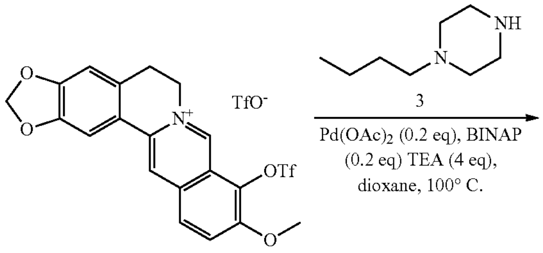

2

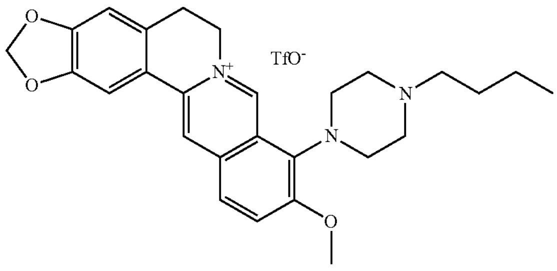

4

Compound 2 (300 mg, 0.49 mmol, 1.0 eq) was dissolved in dioxane (10 mL), and compound 3 (330 mg, 2.32 mmol, 4.6 eq), triethylamine (201 mg, 1.99 mmol, 4.0 eq), palladium acetate (22 mg, 0.099 mmol, 0.2 eq), and 1,1'-binaphthalene-2,2'-biphenylphosphine (62 mg, 0.099 mmol, 0.2 eq) were added. The mixture was reacted at 100° C. for 16 h under $N_2$, and the reaction was detected to be performed completely using TLC and LCMS. The reaction mixture was diluted with water and then extracted with ethyl acetate twice, the organic phase was dried over anhydrous sodium sulfate and filtered, the filtrate was spin dried. The crude product was purified by fast chromatography (dichloromethane/methanol=50/1) to afford compound 4 (150 mg, yield: 51.4%) as a yellow solid.

Step (3):

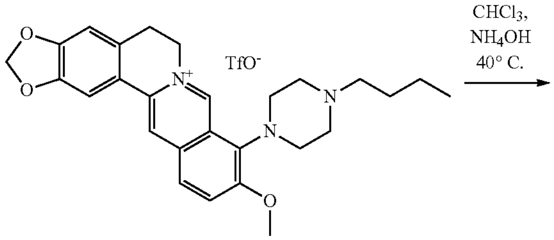

4

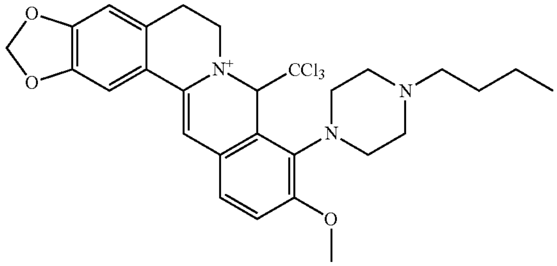

AB35445

Compound 4 (150 mg, 0.25 mmol, 1 eq) was dissolved in a mixture of chloroform (8 ml) and aqueous ammonia (4 ml). The mixture was reacted at 40° C. for overnight, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (dichloromethane/methanol=100/1 to 50/1) to afford compound AB35445.

Compound AB35445:

MS-ESI: Calculated [M+H]$^+$: 564.15, Found: 564.40.

$^1$H NMR (400 MHz, DMSO-d6) δ 7.27 (s, 1H), 7.03-6.98 (m, 2H), 6.77 (s, 1H), 6.25 (s, 1H), 5.98 (d, J=8.0 Hz, 2H), 5.93 (s, 1H), 3.76 (s, 3H), 3.72-3.59 (m, 3H), 3.17-3.03 (m, 2H), 2.81-2.68 (m, 4H), 2.59-2.48 (m, 1H), 2.29-2.25 (m, 2H), 2.18-2.03 (m, 2H), 1.42-1.39 (m, 2H), 1.29-1.26 (m, 2H), 0.89-0.85 (m, 3H).

Example 38 Synthesis of Compound AB35448

The structure of compound AB35448 was as follows:

AB35448

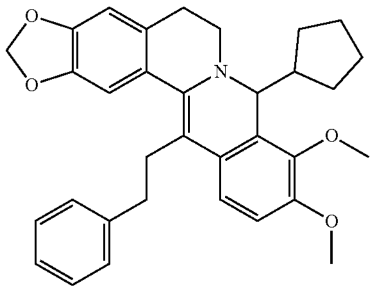

The synthesis method of compound AB35448 was as follows:

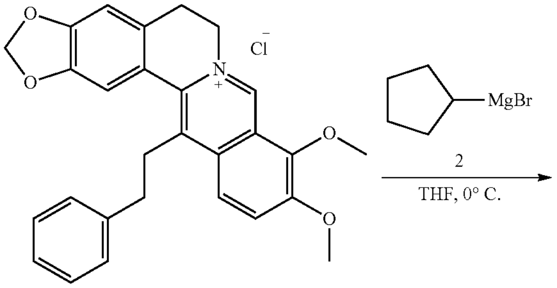

1

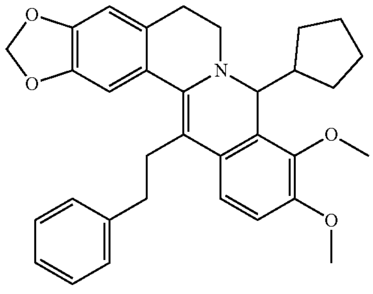

AB35448

Compound 1 (300 mg, 0.63 mmol, 1 eq) was dissolved in anhydrous tetrahydrofuran (10 mL), and cyclopentylmagnesium bromide (3.2 mL, 3.15 mmol, 5.0 eq, 1M) was added at 0° C. under $N_2$. The mixture was reacted at room temperature for 0.5. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.01% formic acid) to afford compound AB35448.

MS-ESI: Calculated [M+H]$^+$: 510.26; Found: 510.20.

$^1$H NMR (400 MHz, DMSO-d6) δ 7.30-7.25 (m, 4H), 7.20-7.16 (m, 1H), 7.05-6.93 (m, 2H), 6.81 (d, J=4.0 Hz, 2H), 6.00 (s, 2H), 4.43 (d, J=8.0 Hz, 1H), 3.79 (s, 3H), 3.75 (s, 3H), 3.35-3.32 (m, 2H), 2.91-2.65 (m, 5H), 2.51-2.48 (m, 1H), 2.21-2.13 (m, 1H), 1.50-1.24 (m, 9H).

Example 39 Synthesis of Compound AB35453

The structure of compound AB35453 was as follows:

AB35453

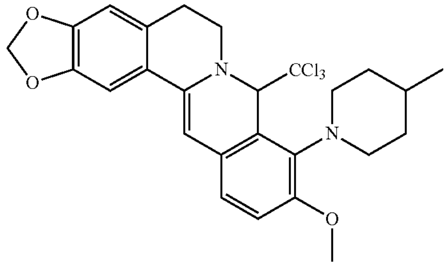

The synthesis method of compound AB35453 was as follows:

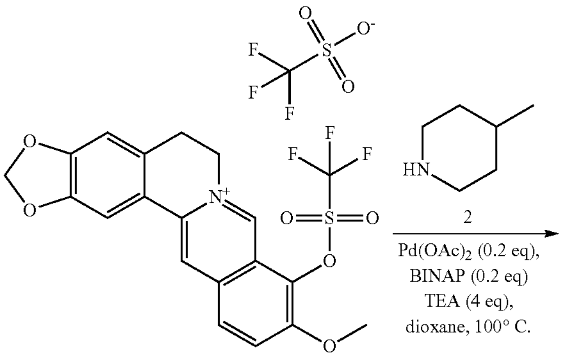

1

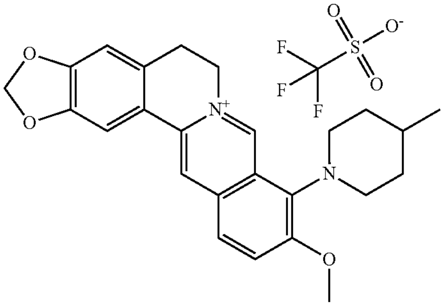

3

Compound 1 (700 mg, 1.16 mmol, 1.0 eq) was dissolved in dioxane (20 mL), and compound 2 (460 mg, 4.64 mmol, 4.0 eq), triethylamine (469 mg, 4.64 mmol, 4.0 eq), palladium acetate (52 mg, 0.232 mmol, 0.2 eq) and 1,1'-binaphthalene-2,2'-biphenylphosphine (144 mg, 0.232 mmol, 0.2 eq) were added. The mixture was reacted at 100° C. for 16 h under $N_2$, and the reaction was detected to be performed completely using TLC and LCMS. The reaction mixture was diluted with water and then extracted with ethyl acetate twice, the organic phase was dried over anhydrous sodium sulfate and filtered, the filtrate was spin dried. The crude product was purified by fast chromatography (dichloromethane/methanol=50/1) to afford compound 3 (280 mg).

Step (2):

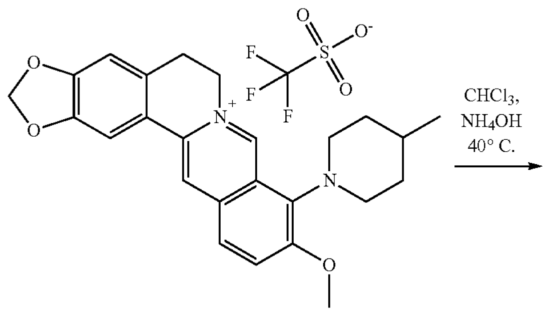

3

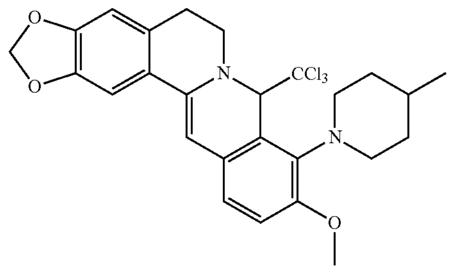

AB35453

Compound 3 (150 mg, 0.27 mmol, 1 eq) was dissolved in a mixture of chloroform (8 ml) and aqueous ammonia (4 ml). The mixture was reacted at 40° C. for overnight, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (dichloromethane/methanol=100/1 to 50/1) to afford compound AB35453.

Compound AB35453:

MS-ESI: Calculated $[M+H]^+$: 521.11, Found: 521.15.

$^1$H NMR (400 MHz, $CDCl_3$) δ 7.15 (s, 1H), 6.98-6.90 (m, 2H), 6.61 (s, 1H), 6.07 (s, 1H), 6.03 (s, 1H), 5.95 (d, J=4.0 Hz, 2H), 3.91-3.86 (m, 1H), 3.81 (s, 3H), 3.68-3.64 (m, 1H), 3.55-3.49 (m, 1H), 3.31-3.26 (m, 1H), 3.06-2.99 (m, 2H), 2.78-2.72 (m, 2H), 1.68-1.61 (m, 1H), 1.49-1.45 (m, 1H), 1.36-1.26 (m, 3H), 0.99 (d, J=4.0 Hz, 3H).

Example 40 Synthesis of Compound AB35454

The structure of compound AB35454 was as follows:

AB35454

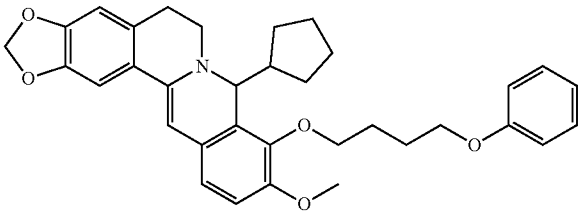

The synthesis method of compound AB35454 was as follows:

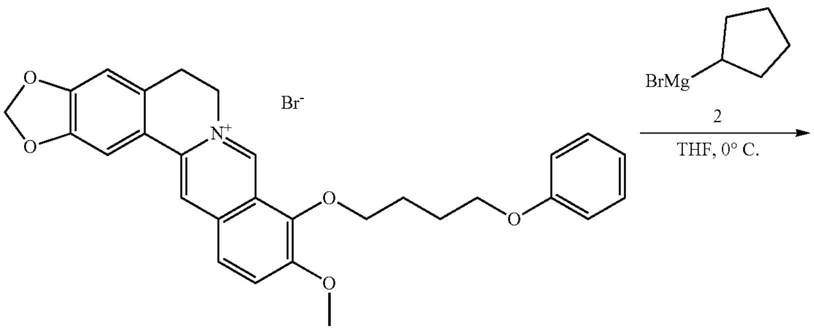

1

-continued

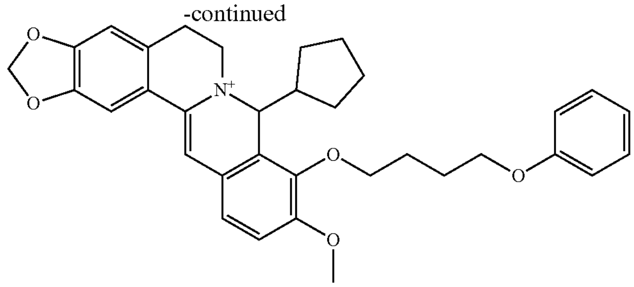

AB35454

Compound 1 (200 mg, 0.36 mmol, 1 eq) was dissolved in tetrahydrofuran (10 mL), and cyclopentylmagnesium bromide (2.2 mL, 2.16 mmol, 6.0 eq, 1M) was added at 0° C. under $N_2$. The mixture was reacted at room temperature for 0.5 h, and the reaction was detected to be performed completely using TLC and LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.01% formic acid) to afford compound AB35454.

MS-ESI: Calculated $[M+H]^+$: 540.27, Found: 540.40.

$^1$H NMR (400 MHz, DMSO-d6): δ 7.27-7.23 (m, 2H), 7.20 (s, 1H), 6.92-6.89 (m, 3H), 6.79 (d, J=8.0 Hz, 1H), 6.72 (s, 1H), 6.65 (d, J=8.0 Hz, 1H), 5.96 (s, 2H), 5.88 (s, 1H), 4.51 (d, J=8.0 Hz, 1H), 4.11-4.02 (m, 3H), 3.81-3.79 (m, 1H), 3.71 (s, 3H), 3.35-3.28 (m, 2H), 2.89-2.79 (m, 1H), 2.61-2.56 (m, 1H), 2.18-2.12 (m, 1H), 1.91-1.82 (m, 4H), 1.54-1.15 (m, 8H).

Example 41 Synthesis of Compound AB35455

The structure of compound AB35455 was as follows:

AB35455

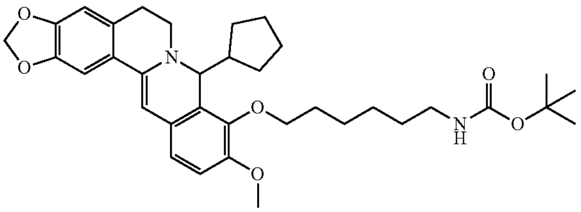

The synthesis method of compound AB35455 was as follows:

Step (1):

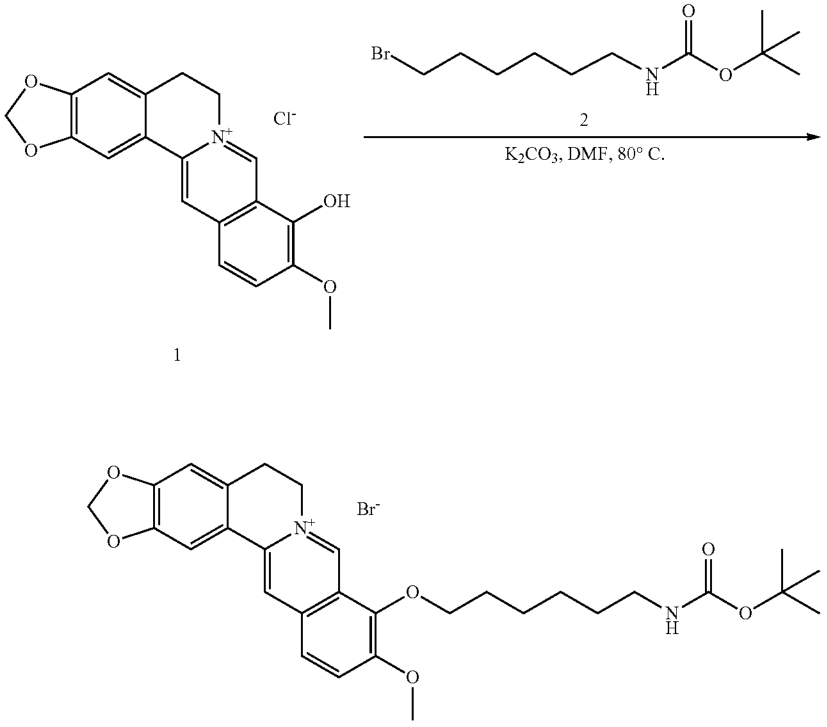

1

2

3

Compound 1 (500 mg, 1.40 mmol, 1.0 eq) was dissolved in DMF (30 mL), and compound 2 (784 mg, 2.8 mmol, 2 eq) and potassium carbonate (386 mg, 2.8 mmol, 2 eq) were added. The mixture was reacted at 60° C. for 16 h under $N_2$, and the reaction was detected to be performed completely using TLC and LCMS. The reaction mixture was diluted with water and then extracted with ethyl acetate twice, the phase was dried over anhydrous sodium sulfate and filtered, the filtrate was spin dried. The crude product was purified by fast chromatography (dichloromethane/methanol=50/1) to afford compound 3 (580 mg, yield: 68.9%) as a yellow solid.

Step (2):

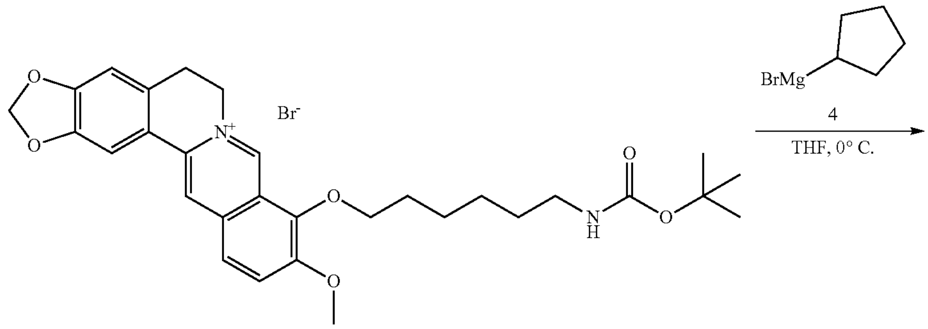

3

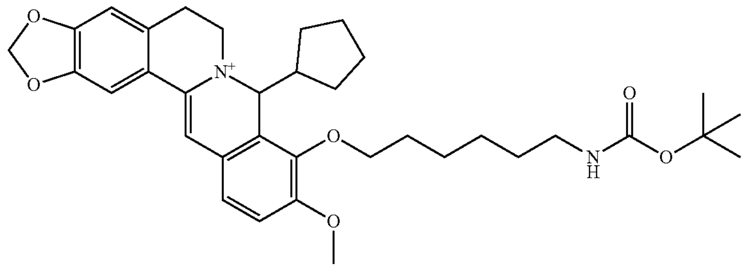

AB35455

Compound 3 (580 mg, 0.96 mmol, 1 eq) was dissolved in tetrahydrofuran (20 mL), and cyclopentylmagnesium bromide (6 mL, 5.8 mmol, 6.0 eq, 1M) was slowly added dropwise at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.1% formic acid) to afford compound AB35455.

Compound AB35455:

MS-ESI: Calculated $[M+H]^+$: 591.34, Found: 591.45.

$^1$H NMR (400 MHz, DMSO-d6) δ 7.20 (s, 1H), 6.79-6.63 (m, 4H), 5.97 (s, 2H), 5.88 (s, 1H), 4.50 (d, J=8.0 Hz, 1H), 4.04-4.00 (m, 1H), 3.71 (s, 4H), 3.35-3.33 (m, 2H), 2.90-2.85 (m, 3H), 2.66-2.61 (m, 1H), 2.19-2.12 (m, 1H), 1.65-1.57 (m, 3H), 1.38-1.15 (m, 22H).

Example 42 Synthesis of Compound AB35456

The structure of compound AB35456 was as follows:

AB35456

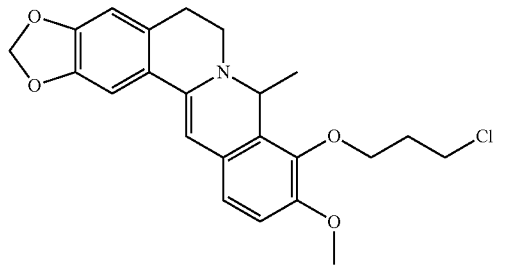

The synthesis method of compound AB35456 was as follows:

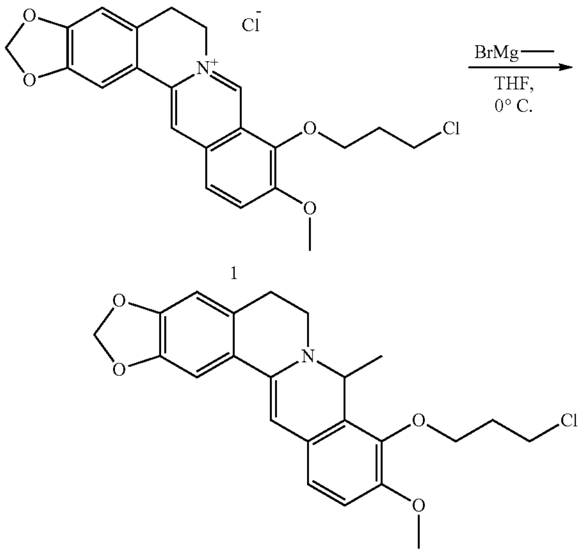

1

AB35456

Compound 1 (100 mg, 0.23 mmol, 1 eq) was dissolved in tetrahydrofuran (10 mL), and methylmagnesium bromide (0.4 mL, 1.15 mmol, 5.0 eq, 3M) was added at 0° C. The mixture was reacted at room temperature for 0.5 h, and the reaction was detected to be performed completely using TLC and LCMS. The reaction mixture was quenched with saturated aqueous ammonium chloride solution and then extracted with dichloromethane twice, the organic phase was dried over anhydrous sodium sulfate and filtered, the filtrate was spin dried. The crude product was purified by reversed phase preparation chromatography (acetonitrile/water+0.1% formic acid) to afford compound AB35456.

MS-ESI: Calculated $[M+H]^+$: 413.14, Found: 413.90.

$^1H$ NMR (400 MHz, DMSO-d6) δ 7.23 (s, 1H), 6.80 (d, J=8.0 Hz, 1H), 6.75 (s, 1H), 6.65 (d, J=8.0 Hz, 1H), 5.98 (d, J=4.0 Hz, 2H), 5.91 (s, 1H), 4.78-4.73 (m, 1H), 4.06-4.03 (m, 2H), 3.86-3.83 (m, 2H), 3.73 (s, 3H), 3.32-3.18 (m, 2H), 2.81-2.72 (m, 2H), 2.17-2.11 (m, 2H), 1.04 (d, J=4.0 Hz, 3H).

Example 43 Synthesis of Compound AB35457

The structure of compound AB35457 was as follows:

AB35457

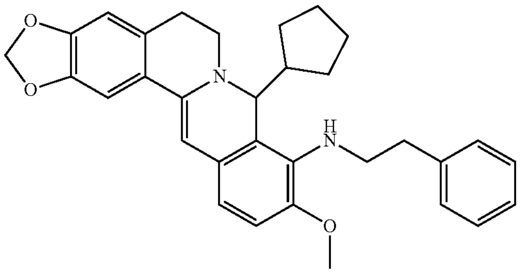

The synthesis method of compound AB35457 was as follows:

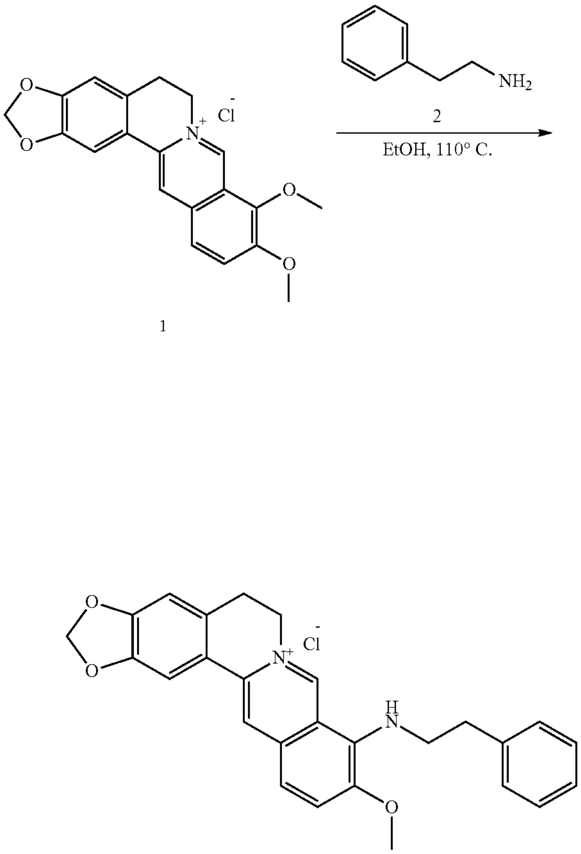

1

3

Compound 1 (500 mg, 1.34 mmol, 1.0 eq) was dissolved in ethanol (5 mL) in a sealed tube, and compound 2 (815 mg, 6.72 mmol, 5 eq) was added. The mixture was reacted at 110° C. for 16 h under $N_2$, and the reaction was detected to be performed completely using TLC and LCMS. The reaction mixture was spin dried. The crude product was purified by fast chromatography (dichloromethane:methanol=20:1) to afford compound 3 (150 mg, yield: 24.3%).

Step (2):

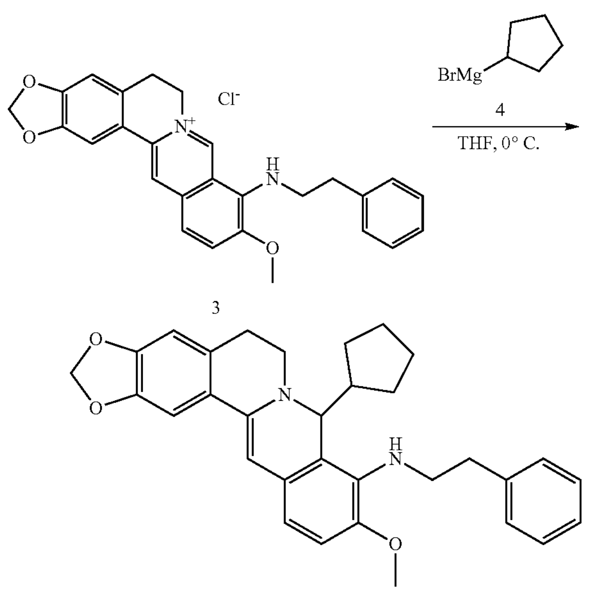

3

AB35457

Compound 3 (150 mg, 0.32 mmol, 1.0 eq) was dissolved in tetrahydrofuran (10 mL), and cyclopentylmagnesium bromide (3 mL) was added at 0° C. The mixture was reacted at room temperature for 0.5 h, and the reaction was detected to be performed completely using TLC and LCMS. The reaction mixture was quenched with saturated aqueous ammonium chloride solution and then extracted with dichloromethane twice, the organic phase was dried over anhydrous sodium sulfate and filtered, the filtrate was spin dried. The crude product was purified by reversed phase preparation chromatography (acetonitrile/water+0.1% formic acid) to afford compound AB35457.

Compound AB35457:

MS-ESI: Calculated $[M+H]^+$: 495.26, Found: 495.40.

$^1H$ NMR (400 MHz, DMSO-d6) δ 7.29-7.19 (m, 6H), 6.72-6.67 (m, 2H), 6.49 (d, J=8.0 Hz, 1H), 5.96 (s, 2H), 5.84 (s, 1H), 4.23 (d, J=8.0 Hz, 1H), 3.71-3.68 (m, 4H), 3.34-3.24 (m, 4H), 2.87-2.77 (m, 3H), 2.62-2.59 (m, 1H), 2.12-2.06 (m, 1H), 1.44-1.33 (m, 4H), 1.15-0.96 (m, 4H).

Example 44 Synthesis of Compound AB35458

The structure of compound AB35458 was as follows:

AB35458

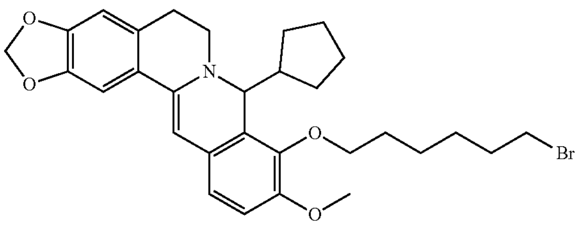

The synthesis method of compound AB35458 was as follows:

Step (1):

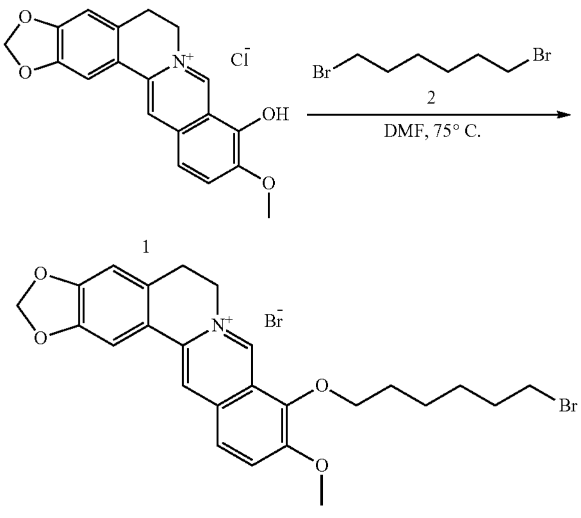

1

3

Compound 1 (500 mg, 1.4 mmol, 1.0 eq) was dissolved in DMF (10 mL), and compound 2 (1.7 g, 7 mmol, 5 eq) was added. The mixture was reacted at 75° C. for 16 h under $N_2$, and the reaction was detected to be performed completely using TLC and LCMS. The reaction mixture was spin dried. The crude product was purified by fast chromatography (dichloromethane/methanol=30/1) to afford compound 3 (500 mg, yield: 63.2%).

Step (2):

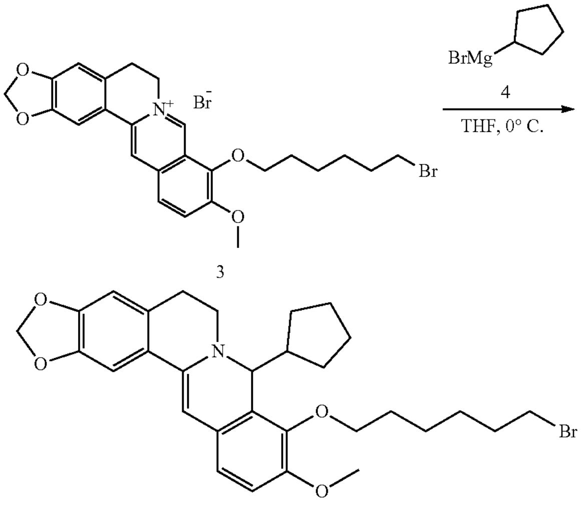

3

AB35458

Compound 3 (150 mg, 0.26 mmol, 1 eq) was dissolved in anhydrous tetrahydrofuran (10 mL), and cyclopentylmagnesium bromide (1.3 mL, 1.3 mmol, 5.0 eq, 1M) was added at 0° C. The mixture was reacted at room temperature for 0.5 h, and the reaction was detected to be performed completely using TLC and LCMS. The reaction mixture was quenched with saturated aqueous ammonium chloride solution and then extracted with dichloromethane twice, the organic phase was dried over anhydrous sodium sulfate and filtered, the filtrate was spin dried. The crude product was purified by reversed phase preparation chromatography (acetonitrile/water+0.1% formic acid) to afford compound AB35458.

Compound AB35458:

MS-ESI: Calculated $[M+H]^+$: 554.19, Found: 554.15.

$^1H$ NMR (400 MHz, DMSO-d6) δ 7.23 (s, 1H), 6.81 (d, J=8.0 Hz, 1H), 6.76 (s, 1H), 6.66 (d, J=8.0 Hz, 1H), 5.99 (s, 2H), 5.91 (s, 1H), 4.52 (d, J=8.0 Hz, 1H), 4.08-4.02 (m, 1H), 3.78-3.74 (m, 4H), 23.55-3.53 (m, 2H), 3.42-3.35 (m, 2H), 2.92-2.86 (m, 1H), 2.69-2.63 (m, 1H), 2.22-2.15 (m, 1H), 1.85-1.82 (m, 2H), 1.70-1.66 (m, 2H), 1.60-1.48 (m, 8H), 1.31-1.17 (m, 4H).

Example 45 Synthesis of Compound AB35459

The structure of compound AB35459 was as follows:

AB35459

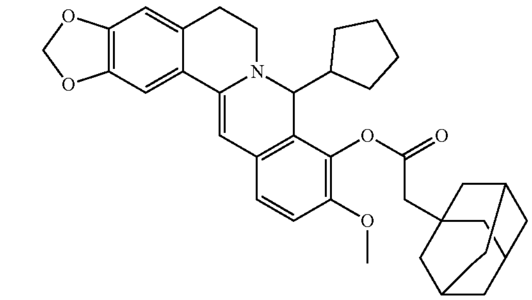

The synthesis method of compound AB35459 was as follows:

Step (1):

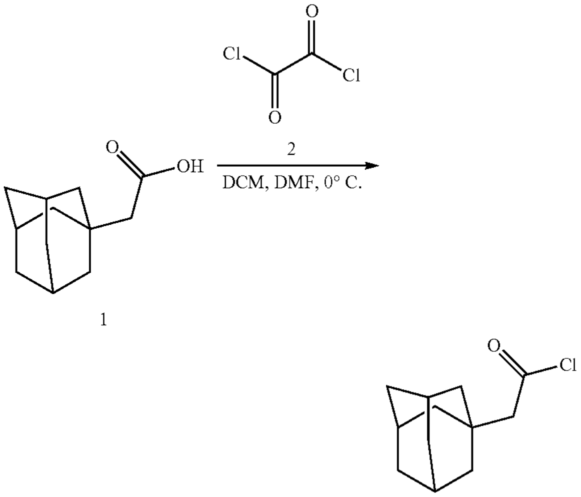

2

1

3

Compound 1 (1 g, 5.15 mmol, 1 eq) was dissolved in dichloromethane (10 mL), and compound 2 (2.0 g, 15.45 mmol, 3 eq) and a small amount of dimethylformamide (2 drops) were added at 0° C. The mixture was reacted at room temperature for 2 h, and the reaction was detected to be performed completely using TLC and LCMS. The organic phase was spin dried to afford compound 3 (1.0 g, yield: 90.9%).

Step (2):

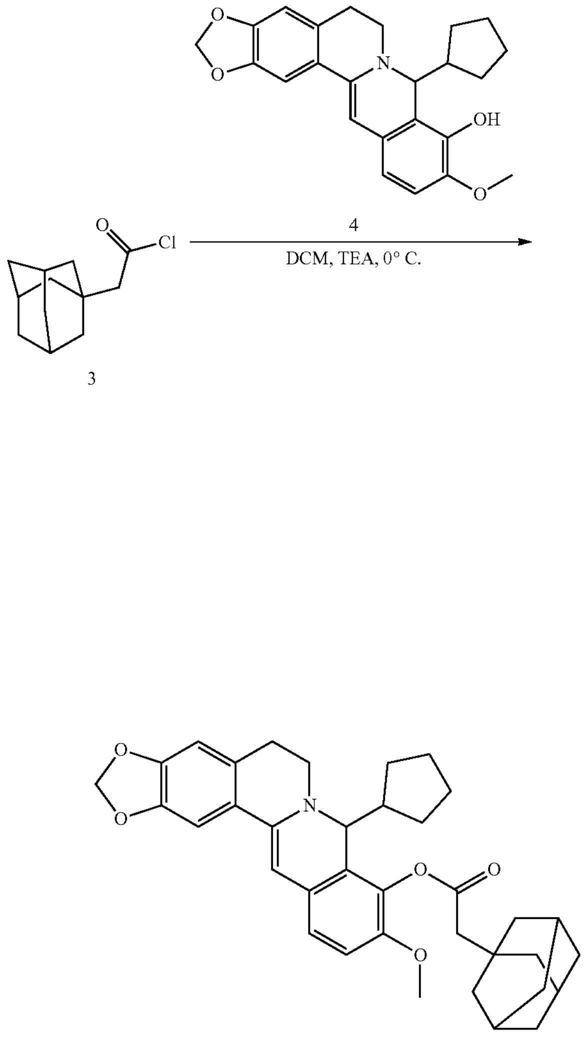

4

3

AB35459

Compound 4 (434 mg, 1.11 mmol, 1 eq) was dissolved in dichloromethane, trimethylamine (560 mg, 5.55 mmol, 5 eq) was added, then compound 3 (708 mg, 3.33 mmol, 3 eq) was added at 0° C. The mixture was reacted at room temperature for 16 h, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by reversed phase preparation chromatography (acetonitrile/water+0.1% formic acid) to afford compound AB35459.

Compound AB35459:

MS-ESI: Calculated $[M+H]^+$: 568.30, Found: 568.30.

$^1H$ NMR (400 MHz, DMSO-d6) δ 7.22 (s, 1H), 6.89-6.80 (m, 2H), 6.74 (s, 1H), 5.97 (s, 2H), 5.94 (s, 1H), 4.33 (d, J=4.0 Hz, 1H), 3.68 (s, 3H), 3.30-3.26 (m, 2H), 2.88-2.80 (m, 1H), 2.68-2.60 (m, 1H), 2.30 (s, 2H), 2.19-2.11 (m, 1H), 1.70-1.60 (m, 16H), 1.45-1.35 (m, 3H), 1.27-1.20 (m, 4H).

Example 46 Synthesis of Compound AB35465

The structure of compound AB35465 was as follows:

AB35465

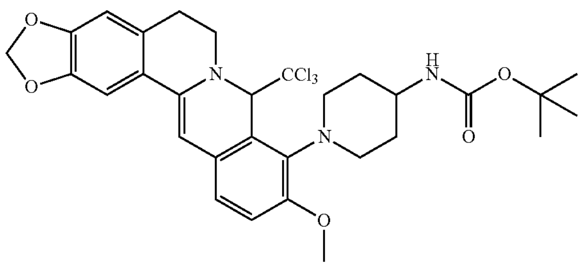

The synthesis method of compound AB35465 was as follows:

Step (1):

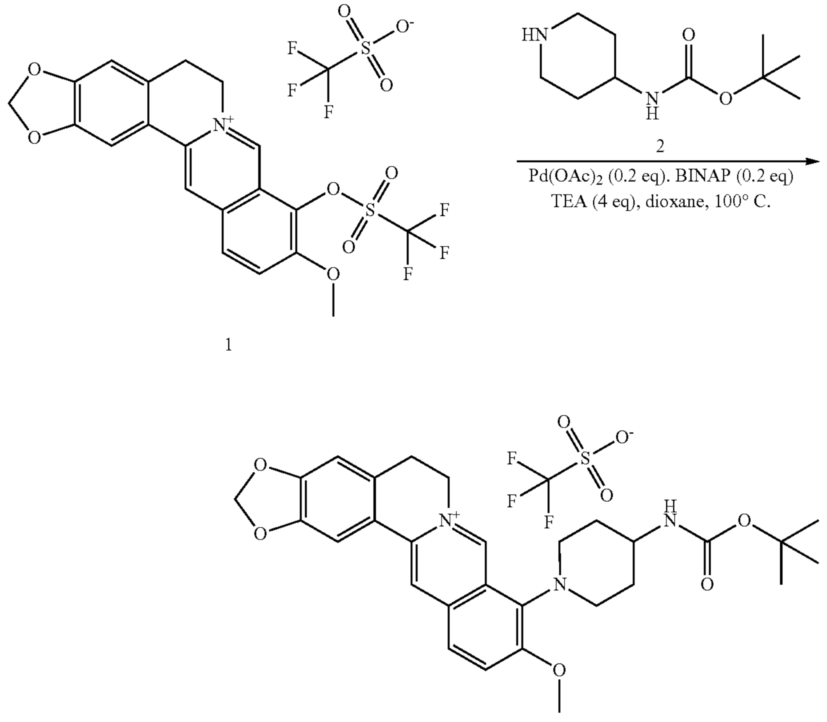

1

2

3

Compound 1 (1.0 g, 1.66 mmol, 1.0 eq) was dissolved in dioxane (30 mL), and compound 2 (1.3 g, 6.64 mmol, 4.0 eq), triethylamine (671 mg, 6.64 mmol, 4.0 eq), palladium acetate (74 mg, 0.332 mmol, 0.2 eq), and 1,1'-binaphthalene-2,2'-biphenylphosphine (207 mg, 0.332 mmol, 0.2 eq) were added. The mixture was reacted at 100° C. for 16 h under $N_2$, and the reaction was detected to be performed completely using TLC and LCMS. The reaction mixture was diluted with water and then extracted with ethyl acetate twice, the organic phase was dried over anhydrous sodium sulfate and filtered, the filtrate was spin dried. The crude product was purified by fast chromatography (dichloromethane/methanol=50/1) to afford compound 3 (1.0 g, yield: 92.6%) as a yellow solid.

Step (2):

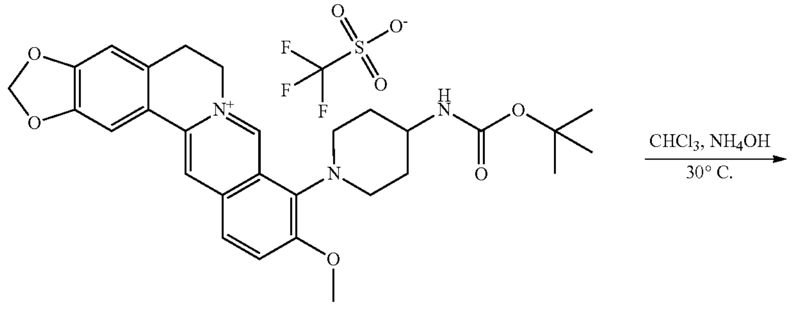

3

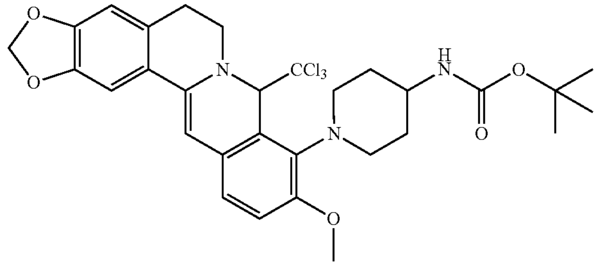

AB35465

Compound 3 (300 mg, 0.46 mmol, 1 eq) was dissolved in a mixture of chloroform (8 ml) and aqueous ammonia (4 ml). The mixture was reacted at 30° C. for overnight, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (dichloromethane/methanol=100/1 to 50/1) to afford compound AB35465.

Compound AB35465:

MS-ESI: Calculated $[M+H]^+$: 622.16, Found: 622.30.

$^1H$ NMR (400 MHz, $CDCl_3$) δ 7.12 (s, 1H), 6.97-6.87 (m, 2H), 6.60 (s, 1H), 6.04 (s, 1H), 5.96-5.93 (m, 3H), 4.48 (s, 1H), 3.88-3.84 (s, 1H), 3.79 (s, 3H), 3.62-3.53 (m, 3H), 3.24-3.20 (m, 1H), 3.14-3.02 (m, 2H), 2.76-2.71 (m, 2H), 2.02-1.82 (m, 2H), 1.52-1.44 (m, 11H).

Example 47 Synthesis of Compound AB35466

The structure of compound AB35466 was as follows:

AB35466

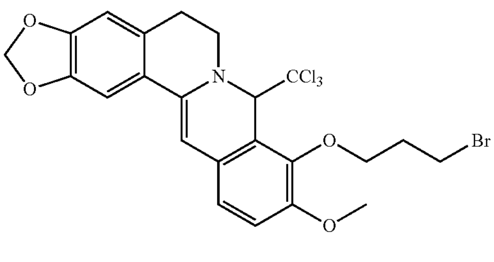

The synthesis method of compound AB35466 was as follows:

Step (1):

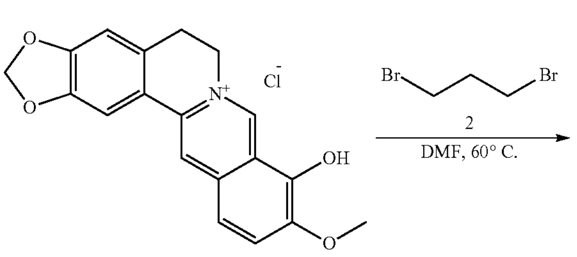

1

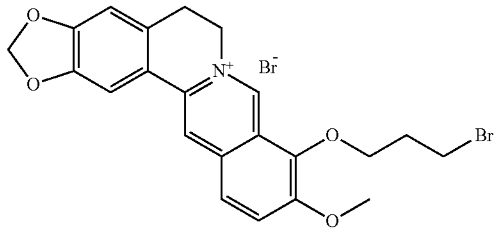

3

Compound 1 (500 mg, 1.40 mmol, 1 eq) was dissolved in N, N-dimethylformamide (10 mL), and compound 2 (1.1 g, 5.6 mmol, 4 eq) was added. The mixture was reacted at 60° C. for 16 h, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (DCM/MeOH=50/1 to 20/1) to afford compound 3 (420 mg, yield: 57.4%) as a yellow solid.

Step (2):

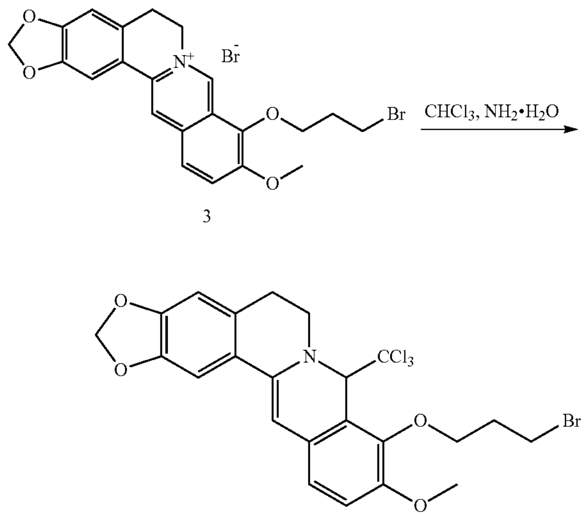

3

AB35466

Compound 3 (200 mg, 0.38 mmol, 1.0 eq) was dissolved in a mixture of chloroform (8 ml) and aqueous ammonia (4 ml). The mixture was reacted at 30° C. for overnight, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (dichloromethane/methanol=100/1 to 50/1) to afford compound AB35466.

Compound AB35466:

MS-ESI: Calculated $[M+H]^+$: 559.95, Found: 559.95.

$^1H$ NMR (400 MHz, DMSO-d6) δ 7.31 (s, 1H), 7.08 (d, J=8.0 Hz, 1H), 6.89 (d, J=8.0 Hz, 1H), 6.77 (s, 1H), 6.32 (s, 1H), 5.99 (d, J=4.0 Hz, 2H), 5.65 (s, 1H), 4.22-4.20 (m, 1H), 3.88-3.85 (m, 1H), 3.79-3.74 (m, 6H), 3.67-3.60 (m, 1H), 3.28-3.20 (m, 1H), 2.73-2.66 (m, 1H), 2.33-2.26 (m, 1H), 2.15-2.08 (m, 1H).

Example 48 Synthesis of Compound AB35433

The structure of compound AB35433 was as follows:

AB35433

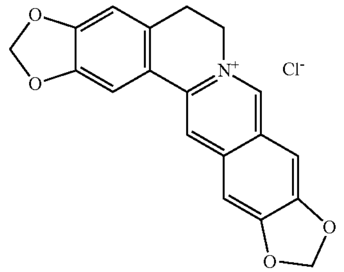

The synthesis method of compound AB35433 was as follows:

Step (1):

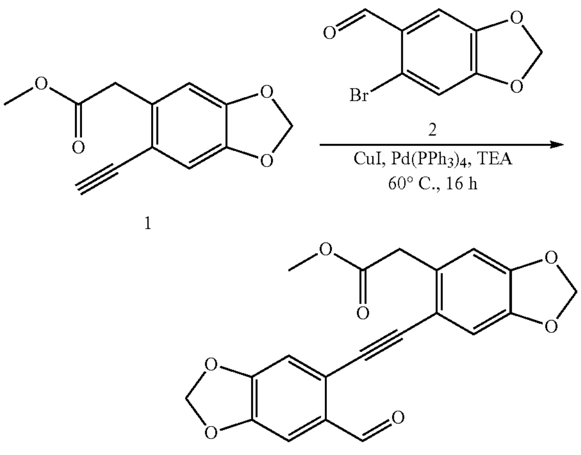

1

3

Compound 1 (6.2 g, 28.29 mmol, 1.2 eq) and compound 2 (5.4 g, 23.58 mmol, 1.0 eq) were dissolved in tetrahydrofuran (100 mL), and copper iodide (135 mg, 0.71 mmol, 0.03 eq), bis (triphenylphosphine) palladium dichloride (492 mg, 0.70 mmol, 0.03 eq) and triethylamine (7.2 g, 70.74 mmol, 3 eq) were added. The mixture was reacted at 60° C. for 16 h under $N_2$, and the reaction was detected to be performed completely using TLC and LCMS. The reaction mixture was diluted with water and then extracted with dichloromethane twice, the organic phase was washed with brine once, dried over anhydrous sodium sulfate and filtered, the filtrate was spin dried. The crude product was purified by fast chromatography (100-200 mesh silica gel, PE/EA=3/1) to afford compound 3 (6.5 g, yield: 75.6%) as a yellow solid.

Step (2):

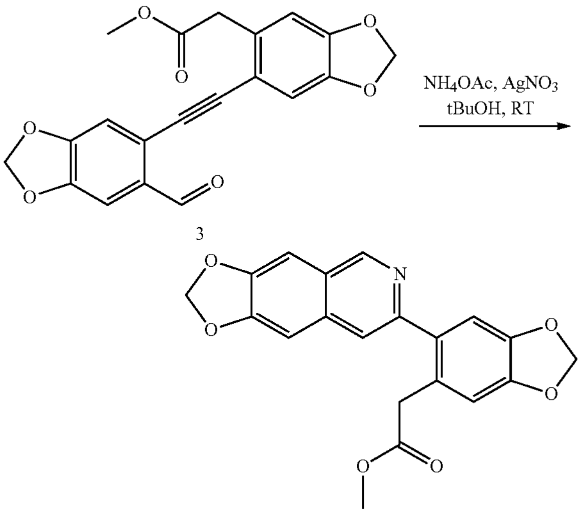

3

4

Compound 3 (2.0 g, 5.46 mmol, 1.0 eq) was dissolved in tert-butanol (50 mL), and ammonium acetate (2.1 g, 27.32 mmol, 5.0 eq) and silver nitrate (1.85 g, 10.93 mmol, 0.2 eq) were added. The mixture was reacted at room temperature for 16 h, and the reaction was detected to be performed completely using TLC and LCMS. The reaction mixture was diluted with water and then extracted with dichloromethane twice, the organic phase was washed with brine once, dried over anhydrous sodium sulfate and filtered, the filtrate was spin dried. The crude product was purified by fast chromatography (100-200 mesh silica gel, PE/EA=3/1) to afford compound 4 (1.5 g, yield: 75.3%) as a yellow solid.

Step (3):

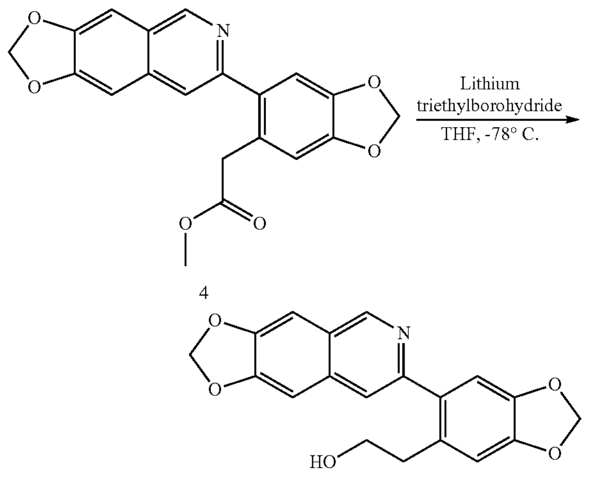

4

5

Compound 4 (1.5 g, 4.11 mmol, 1.0 eq) was dissolved in tetrahydrofuran (20 mL), and lithium triethylborohydride (16.4 mL, 16.44 mmol, 4 eq) was slowly added dropwise at −78° C. The mixture was reacted at room temperature for 3 h, and the reaction was detected to be performed completely using TLC and LCMS. The reaction mixture was diluted with saturated sodium chloride aqueous solution and then extracted with ethyl acetate twice, the organic phase was washed with brine once, dried over anhydrous sodium sulfate and filtered, the filtrate was spin dried to afford compound 5 (630 mg, yield: 47.1%) as a yellow solid.

Step (4):

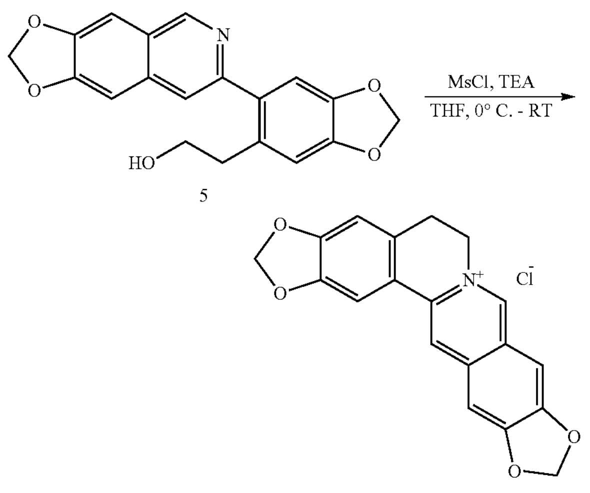

5

AB35433

Compound 5 (100 mg, 0.29 mmol, 1.0 eq) was dissolved in THE (5 mL), and methanesulfonyl chloride (68 mg, 0.58 mmol, 2.0 eq) and triethylamine (117 mg, 1.16 mmol, 4.0 eq) were added at 0° C. The mixture was reacted at room temperature for 2 h, and the reaction was detected to be performed completely using TLC and LCMS. The reaction mixture was filtered, the solid was purified by reversed phase preparation chromatography (acetonitrile/water+0.01% formic acid) to afford solid compound AB35433.

Compound AB35433:

MS-ESI: Calculated [M]+: 320.09, Found: 320.06.

$^1$H NMR (400 MHz, DMSO-d6) δ 9.48 (s, 1H), 8.72 (s, 1H), 7.73 (s, 1H), 7.69 (s, 1H), 7.50 (s, 1H), 7.08 (s, 1H), 6.40 (s, 2H), 6.15 (s, 2H), 4.74-4.41 (m, 2H), 3.18-3.14 (m, 2H).

Example 49 Synthesis of Compound AB35467

The structure of compound AB35467 was as follows:

AB35467

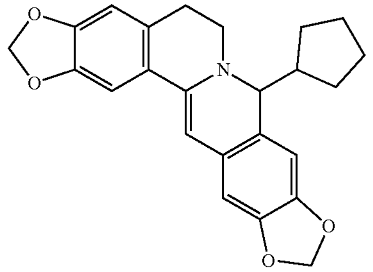

The synthesis method of compound AB35467 was as follows:

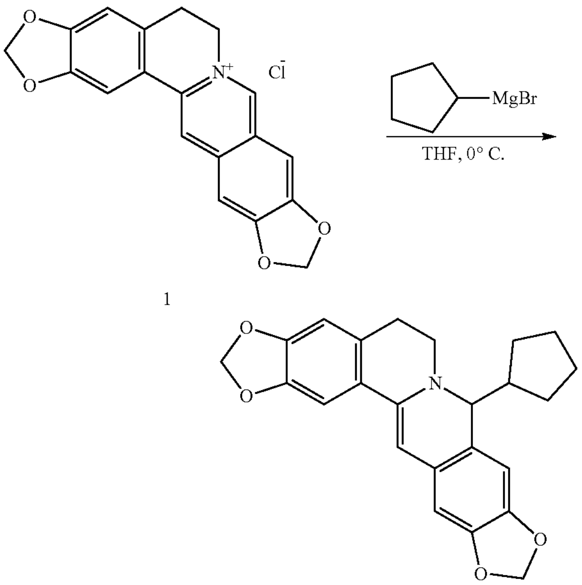

1

AB35467

Compound 1 (200 mg, 0.56 mmol, 1.0 eq) was dissolved in anhydrous tetrahydrofuran (10 mL), and cyclopentylmagnesium bromide (3.4 mL, 3.36 mmol, 6.0 eq, 1M) was added at 0° C. The mixture was reacted at room temperature for 0.5 h, and the reaction was detected to be performed completely using TLC and LCMS. The reaction mixture was quenched with saturated aqueous ammonium chloride solution and then extracted with dichloromethane twice, the organic phase was dried over anhydrous sodium sulfate and filtered, the filtrate was spin dried. The crude product was purified by reversed phase preparation chromatography (acetonitrile/water+0.1% formic acid) to afford compound AB35467.

Compound AB35467:

MS-ESI: Calculated $[M+H]^+$: 390.17, Found: 390.15.

$^1H$ NMR (400 MHz, DMSO-d6) δ 7.17 (s, 1H), 6.75 (s, 1H), 6.58 (s, 1H), 6.52 (s, 1H), 5.97 (s, 2H), 5.88 (s, 2H), 5.79 (s, 1H), 4.15 (d, J=8.0 Hz, 1H), 3.42-3.37 (m, 1H), 2.87-2.82 (m, 1H), 2.65-2.60 (m, 1H), 2.21-2.15 (m, 1H), 1.60-1.56 (m, 1H), 1.45-1.10 (m, 8H).

Example 50 Synthesis of Compound AB35468

The structure of compound AB35468 was as follows:

AB35468

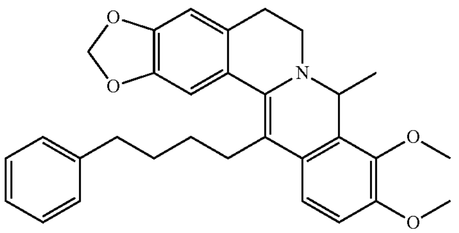

The synthesis method of compound AB35468 was as follows:

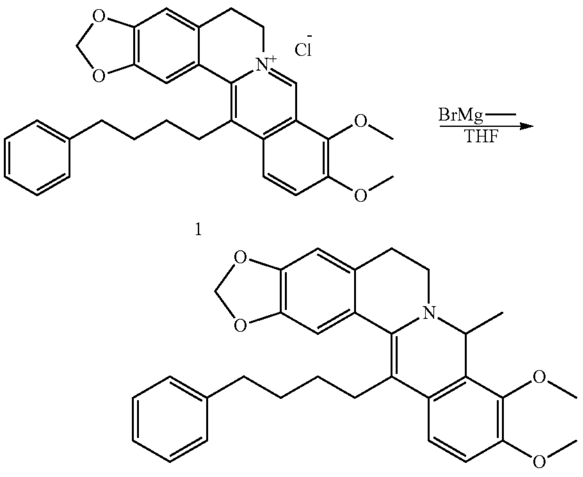

1

AB35468

Compound 1 (200 mg, 0.39 mmol, 1.0 eq) was dissolved in anhydrous tetrahydrofuran (10 mL), and methylmagnesium bromide (0.6 mL, 1.95 mmol, 5.0 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.1% formic acid, 30%-40% acetonitrile, reverse phase column Green ODS, 21.2*250 mm, 10 μm, 120 Å) to afford compound AB35468.

MS-ESI: Calculated $[M+H]^+$: 484.24; Found $[M+H]^+$: 484.25.

$^1H$ NMR (400 MHz, DMSO-d6): δ 7.27-7.23 (m, 2H), 7.18-7.12 (m, 3H), 6.85-6.82 (m, 4H), 6.01 (d, J=4.0 Hz, 2H), 4.65-4.60 (m, 1H), 3.76 (s, 3H), 3.74 (s, 3H), 3.18-3.08 (m, 2H), 2.74-2.59 (m, 6H), 1.72-1.63 (m, 3H), 1.45-1.40 (m, 1H), 0.93 (d, J=4.0 Hz, 3H).

Example 51 Synthesis of Compound AB35469

The structure of compound AB35469 was as follows:

AB35469

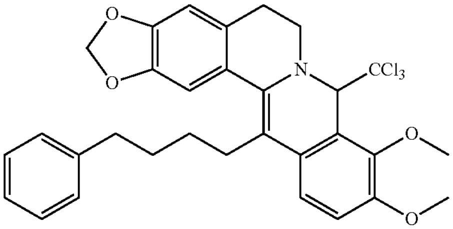

The synthesis method of compound AB35469 was as follows:

Step (1):

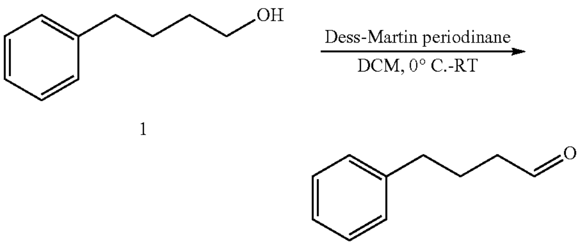

1

2

Compound 1 (10 g, 66.57 mmol, 1 eq) was dissolved in dichloromethane (200 mL), and Dess-Martin Periodinane (3.4 g, 79.88 mmol, 1.2 eq) was added in batches at 0° C. The mixture was reacted at room temperature for 2 h, and the reaction was detected to be performed completely using TLC. The reaction mixture was filtered, the filtrate was concentrated. The crude product was purified by fast chromatography (PE/EA=100/1) to afford compound 2 (7.8 g, yield: 79.6%) as a yellow liquid.

Step (2):

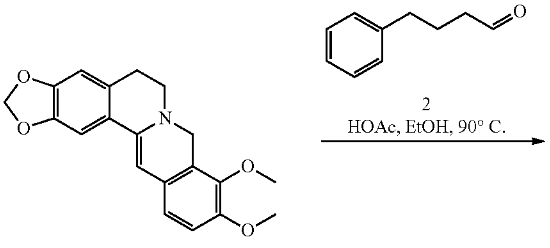

3

-continued

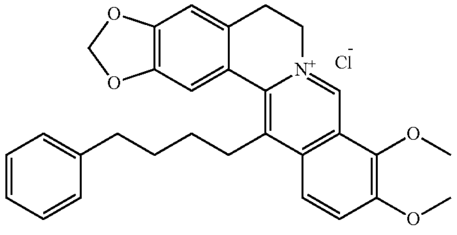

4

Compound 3 (2 g, 5.9 mmol, 1 eq) was dissolved in ethanol/acetic acid (30 mL/5 mL), and compound 2 (7.8 g, 52.6 mmol, 9 eq) was added. The mixture was reacted at 90° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 4 (1.2 g, yield: 40.4%) as a yellow solid.

Step (3):

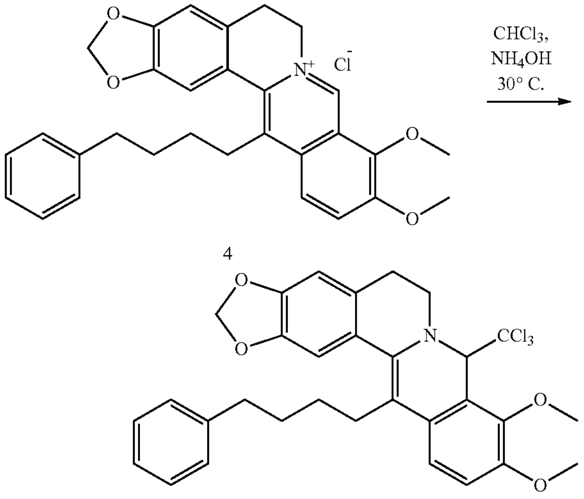

4

AB35469

Compound 4 (200 mg, 0.39 mmol, 1 eq) was dissolved in chloroform (8 mL), and aqueous ammonia (4 mL) was added. The mixture was reacted at 30° C. for 48 h under $N_2$. The reaction mixture was diluted with water and then extracted with dichloromethane, the organic phase was dried over anhydrous sodium sulfate and filtered, the filtrate was spin dried. The crude product was purified by fast chromatography (DCM/MeOH=100/1 to 50/1) to afford compound AB35469.

Compound AB35469:

MS-ESI: Calculated $[M+H]^+$: 586.13; Found $[M+H]^+$: 586.10.

$^1H$ NMR (400 MHz, $CDCl_3$) δ 7.30-7.26 (m, 2H), 7.21-7.17 (m, 3H), 7.07-7.00 (m, 2H), 6.86 (s, 1H), 6.67 (s, 1H), 5.97 (s, 2H), 5.58 (s, 1H), 4.09-4.02 (m, 1H), 3.93 (s, 3H), 3.89 (s, 3H), 3.46-3.42 (m, 1H), 2.80-2.53 (m, 6H), 1.83-1.75 (m, 3H), 1.54-1.47 (m, 1H).

Example 52 Synthesis of Compound AB35475

The structure of compound AB35475 was as follows:

AB35475

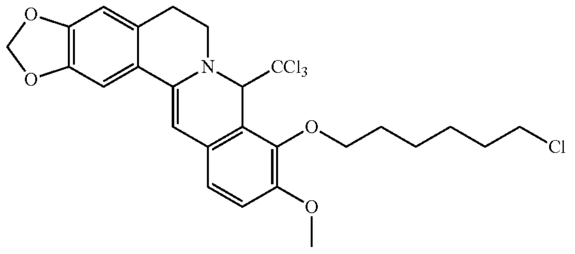

The synthesis method of compound AB35475 was as follows:

Step (1):

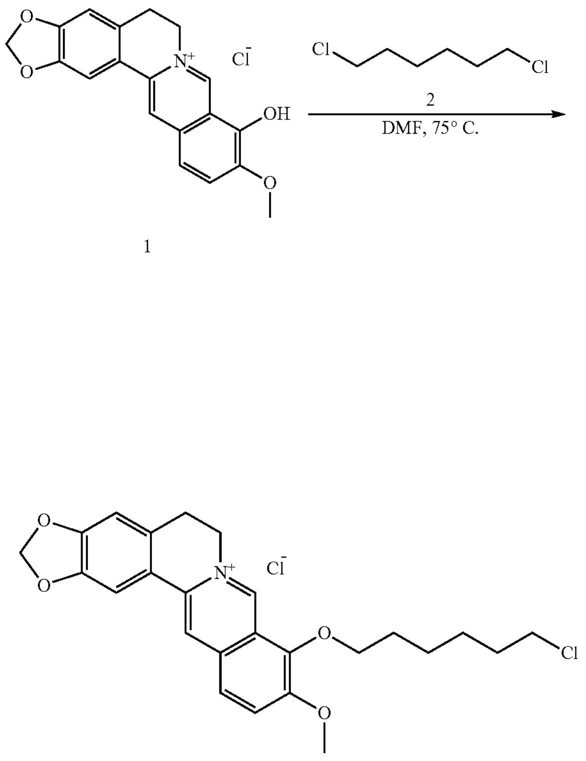

1

3

Compound 1 (1.0 g, 2.79 mmol, 1 eq) was dissolved in N, N-dimethylformamide (20 mL), and compound 2 (1.7 g, 11.16 mmol, 4 eq) was added. The mixture was reacted at 75° C. for 16 h, and the reaction was detected to be performed completely using TLC and LCMS. The solvent was spin dried, and water was added, the mixture was extracted with dichloromethane twice, the organic phase was dried over anhydrous sodium sulfate and filtered, the filtrate was spin dried. The crude product was purified by fast chromatography (DCM/MeOH=50/1 to 20/1) to afford compound 3 (400 mg, yield: 25.6%).

Step (2):

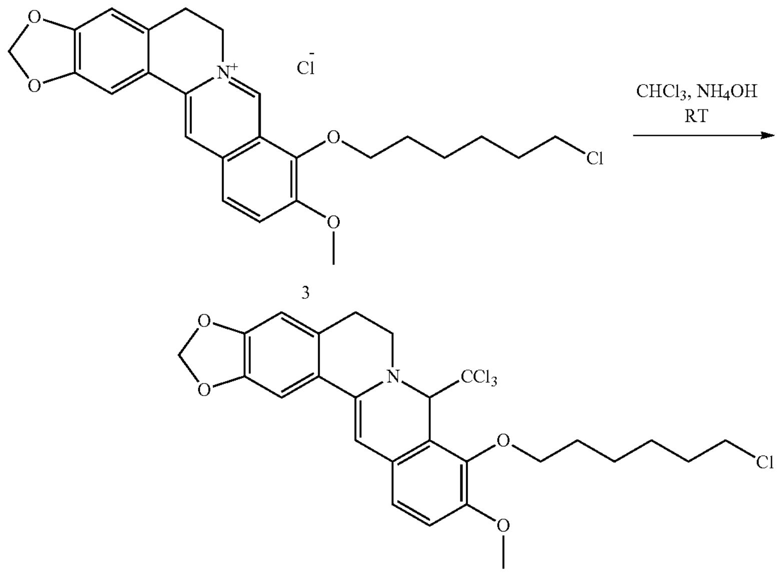

3

AB35475

Compound 3 (200 mg, 0.42 mmol, 1 eq) was dissolved in a mixture of chloroform (8 ml) and aqueous ammonia (4 ml). The mixture was reacted at room temperature for overnight, and the reaction was detected to be performed completely using TLC and LCMS. The reaction mixture was diluted with water and then extracted with dichloromethane twice, the organic phase was dried over anhydrous sodium sulfate, filtered and spin dried. The crude product was purified fast chromatography (dichloromethane/methanol=100/1 to 50/1) to afford compound AB35475.

Compound AB35475:

MS-ESI: Calculated $[M+H]^+$: 558.07, Found: 558.05.

$^1H$ NMR (400 MHz, DMSO-d6) δ 7.29 (s, 1H), 7.05 (d, J=8.0 Hz, 1H), 6.85 (d, J=8.0 Hz, 1H), 6.77 (s, 1H), 6.29 (s, 1H), 5.98 (d, J=4.0 Hz, 2H), 5.55 (s, 1H), 4.12-4.08 (m, 1H), 3.81-3.78 (m, 1H), 3.77 (s, 3H), 3.74-3.71 (m, 1H), 3.63-3.60 (m, 3H), 3.25-3.19 (m, 1H), 2.72-2.66 (m, 1H), 1.73-1.64 (m, 4H), 1.47-1.41 (m, 4H).

Example 53 Synthesis of Compound AB35476

The structure of compound AB35476 was as follows:

AB35476

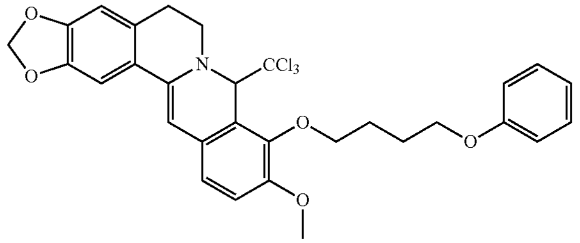

The synthesis method of compound AB35476 was as follows:

Step (1):

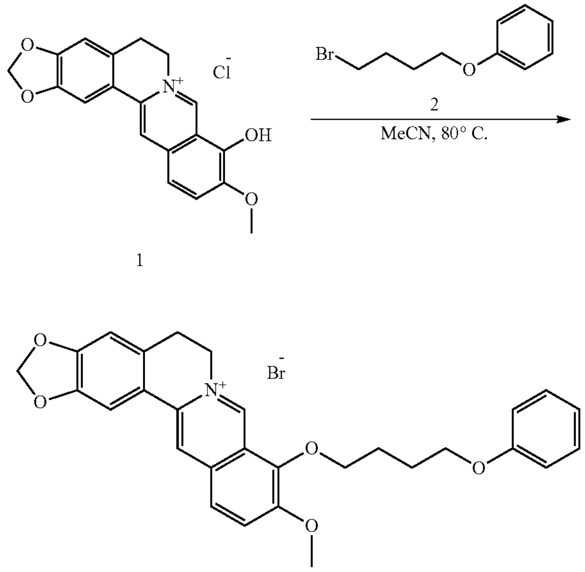

1

3

Compound 1 (2.0 g, 5.59 mmol, leq) was dissolved in acetonitrile (40 mL), and compound 2 (5.1 g, 22.36 mmol, 4 eq) was added. The mixture was reacted at 80° C. for 16 h, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (DCM/MeOH=50/1 to 20/1) to afford compound 3 (1.48 g, yield: 48.2%) as a yellow solid.

Step (2):

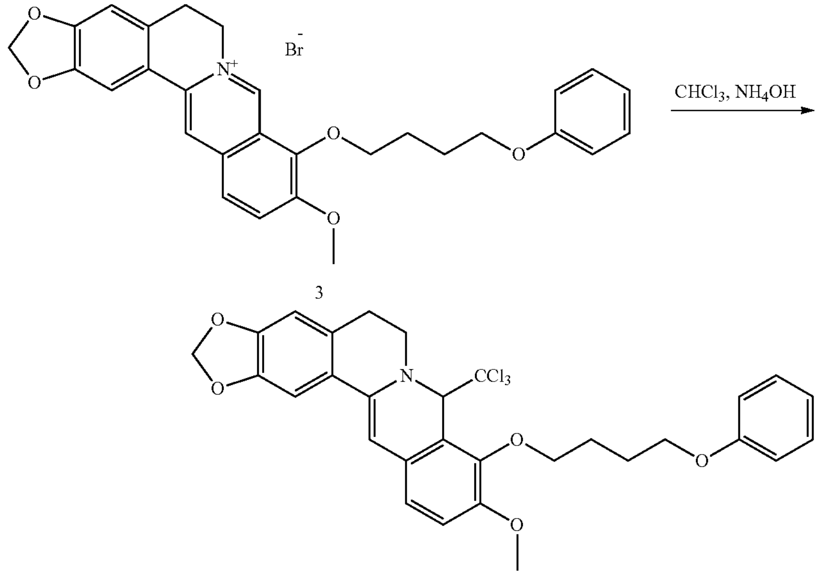

3

AB35476

Compound 3 (1.3 g, 2.36 mmol, 1.0 eq) was dissolved in a mixture of chloroform (40 ml) and aqueous ammonia (20 ml). The mixture was reacted at 30° C. for overnight, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified fast chromatography (dichloromethane/methanol=100/1 to 50/1) to afford compound AB35476.

Compound AB35476:

MS-ESI: Calculated $[M+H]^+$: 588.11, Found: 588.10.

$^1$H NMR (400 MHz, DMSO-d6) δ 7.30 (s, 1H), 7.27-7.23 (m, 2H), 7.07 (d, J=12.0 Hz, 1H), 6.91-6.85 (m, 4H), 6.76 (s, 1H), 6.29 (s, 1H), 5.98 (d, J=8.0 Hz, 2H), 5.58 (s, 1H), 4.21-4.16 (m, 1H), 4.04-4.01 (m, 2H), 3.91-3.86 (m, 1H), 3.77 (s, 3H), 3.69-3.65 (m, 1H), 3.59-3.53 (m, 1H), 3.22-3.14 (m, 1H), 2.66-2.62 (m, 1H), 1.90-1.82 (m, 2H), 1.21-1.10 (m, 1H), 0.83-0.71 (m, 1H).

Example 54 Synthesis of Compound AB35478

The structure of compound AB35478 was as follows:

AB35478

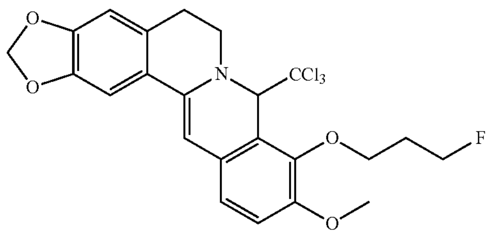

The synthesis method of compound AB35478 was as follows:

Step (1):

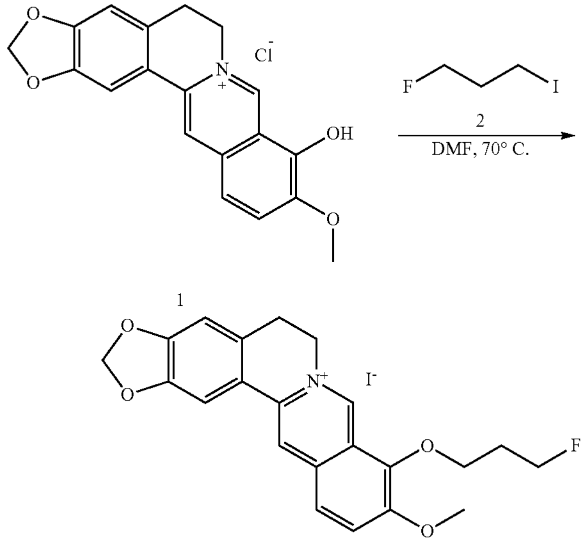

1

3

Compound 1 (1.5 g, 4.19 mmol, 1 eq) was dissolved in N, N-dimethylformamide (30 mL), and compound 2 (3.1 g, 16.76 mmol, 4 eq) was added. The mixture was reacted at 70° C. for 16 h, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified by fast chromatography (DCM:MeOH=50:1) to afford compound 3 (560 mg, yield: 26.2%) as a yellow solid.

Step (2):

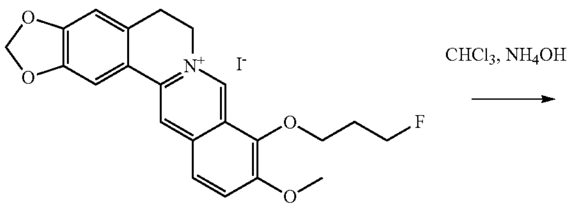

3

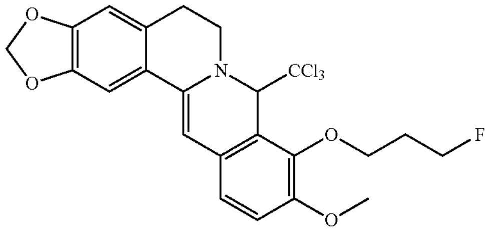

AB35478

Compound 3 (160 mg, 0.31 mmol, 1.0 eq) was dissolved in a mixture of chloroform (8 ml) and aqueous ammonia (4 ml). The mixture was reacted at 30° C. for overnight, and the reaction was detected to be performed completely using TLC and LCMS. The reaction mixture was diluted with water and then extracted with dichloromethane twice, the organic phase was dried over anhydrous sodium sulfate and filtered, the filtrate was spin dried. The crude product was purified fast chromatography (dichloromethane/methanol=100/1 to 50/1) to afford compound AB35478.

MS-ESI and $^{1}$H NMR of compound AB35478 were as follows:

MS-ESI: Calculated $[M+H]^+$: 500.05, Found: 500.25.

$^{1}$H NMR (400 MHz, $CDCl_3$) δ 7.15 (s, 1H), 6.97-6.87 (m, 2H), 6.60 (s, 1H), 6.09 (s, 1H), 5.94 (d, J=4.0 Hz, 2H), 5.61 (s, 1H), 4.98-4.80 (m, 1H), 4.78-4.62 (m, 1H), 4.37-4.33 (m, 1H), 3.96-3.82 (m, 5H), 3.71-3.64 (m, 1H), 3.35-3.28 (m, 1H), 2.74-2.68 (m, 1H), 2.24-2.10 (m, 2H).

Example 55

Compound SJ0002 was prepared by conventional method, the structure of compound SJ0002 was as follows:

compound SJ0002

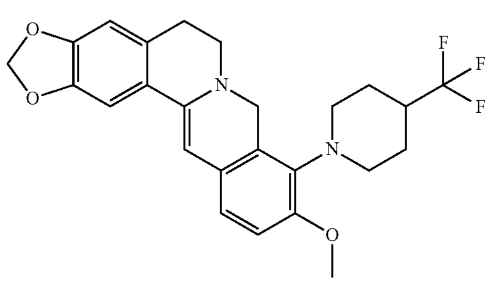

Example 56

Compound SJ0003 was prepared by conventional method, the structure of compound SJ0003 was as follows:

compound SJ0003

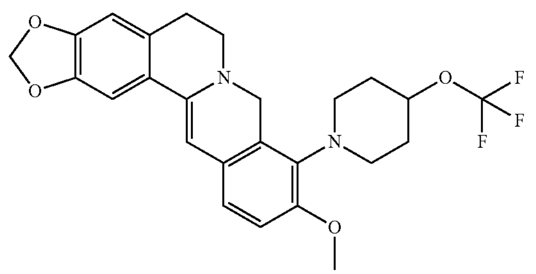

Example 57

Compound SJ0005 was prepared by conventional method, the structure of compound SJ0005 was as follows:

compound SJ0005

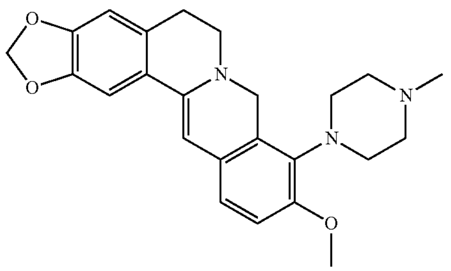

Example 58

Compound SJ0006 was prepared by conventional method, the structure of compound SJ0006 was as follows:

compound SJ0006

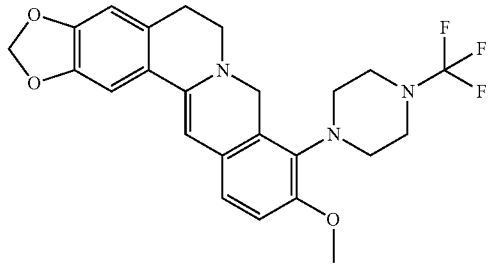

Example 59

Compound SJ0007 was prepared by conventional method, the structure of compound SJ0007 was as follows:

compound SJ0007

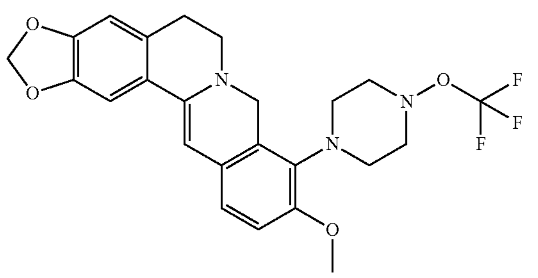

Example 60

Compound SJ0008 was prepared by conventional method, the structure of compound SJ0008 was as follows:

compound SJ0008

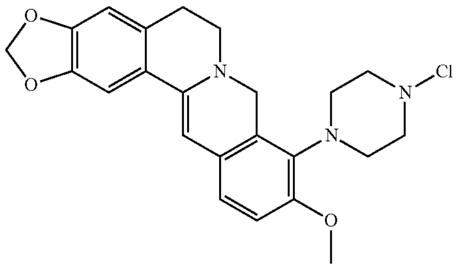

Example 61

Compound SJ0010 was prepared by conventional method, the structure of compound SJ0010 was as follows:

compound SJ0010

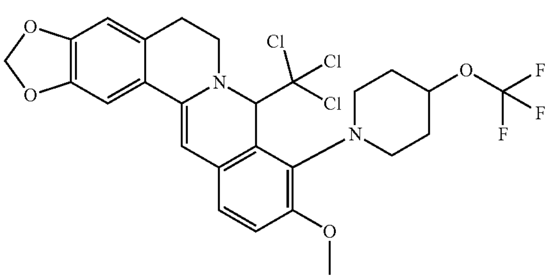

Example 62

Compound SJ0011 was prepared by conventional method, the structure of compound SJ0011 was as follows:

compound SJ0011

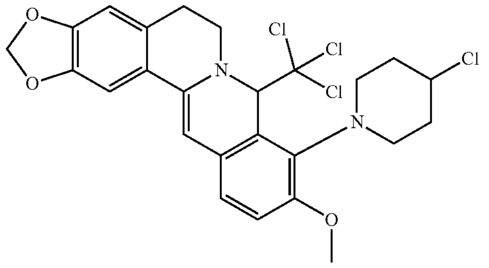

Example 63

Compound SJ0013 was prepared by conventional method, the structure of compound SJ0013 was as follows:

compound SJ0013

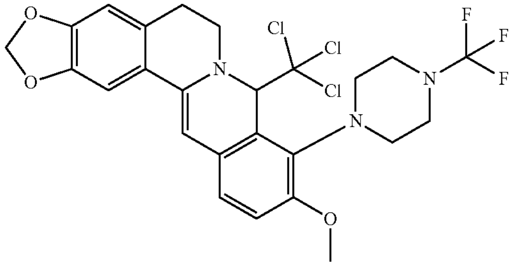

Example 64

Compound SJ0014 was prepared by conventional method, the structure of compound SJ0014 was as follows:

compound SJ0014

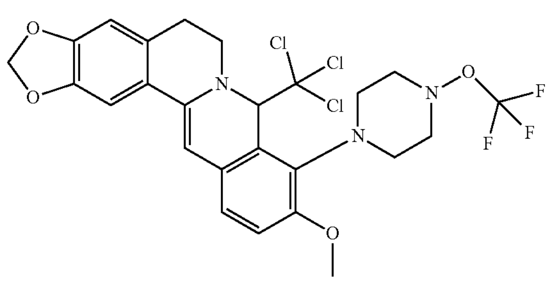

Example 65

Compound SJ0015 was prepared by conventional method, the structure of compound SJ0015 was as follows:

compound SJ0015

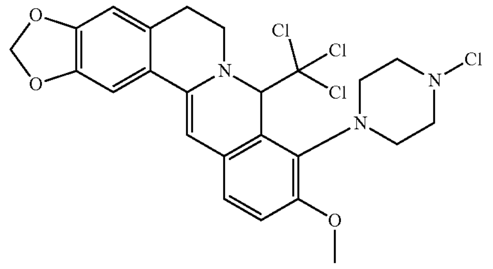

Example 66

Compound SJ0017 was prepared by conventional method, the structure of compound SJ0017 was as follows:

compound SJ0017

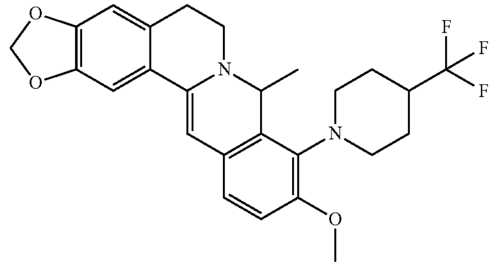

Example 67

Compound SJ0018 was prepared by conventional method, the structure of compound SJ0018 was as follows:

compound SJ0018

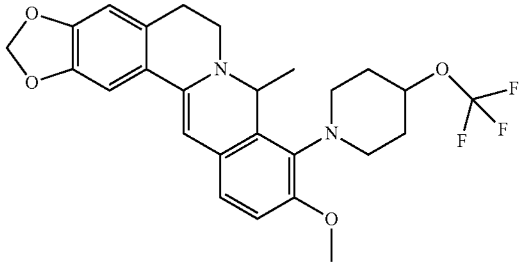

Example 68

Compound SJ0019 was prepared by conventional method, the structure of compound SJ0019 was as follows:

compound SJ0019

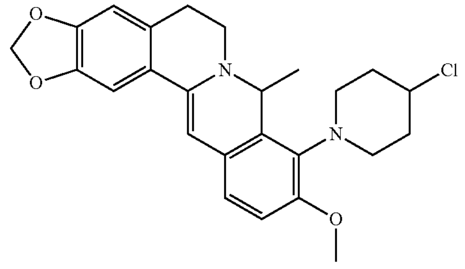

Example 69

Compound SJ0020 was prepared by conventional method, the structure of compound SJ0020 was as follows:

compound SJ0020

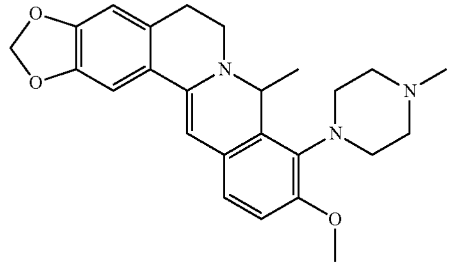

Example 70

Compound SJ0021 was prepared by conventional method, the structure of compound SJ0021 was as follows:

compound SJ0021

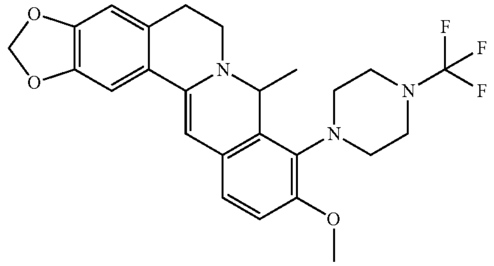

Example 71

Compound SJ0022 was prepared by conventional method, the structure of compound SJ0022 was as follows:

compound SJ0022

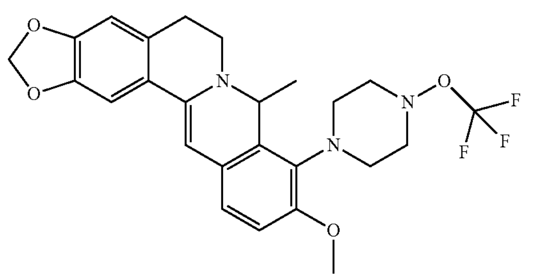

Example 72

Compound SJ0023 was prepared by conventional method, the structure of compound SJ0023 was as follows:

compound SJ0023

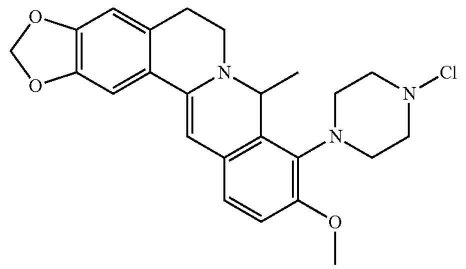

Example 73

Compound SJ0025 was prepared by conventional method, the structure of compound SJ0025 was as follows:

compound SJ0025

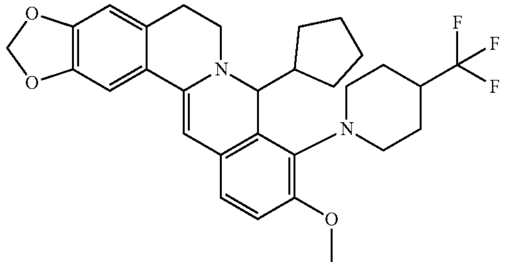

Example 74

Compound SJ0026 was prepared by conventional method, the structure of compound SJ0026 was as follows:

compound SJ0026

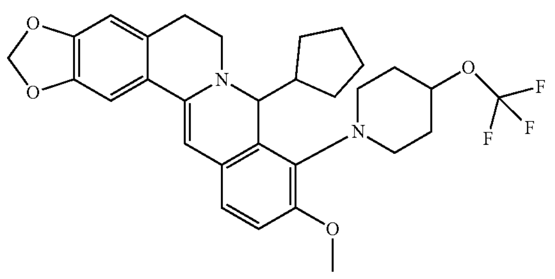

Example 75

Compound SJ0027 was prepared by conventional method, the structure of compound SJ0027 was as follows:

compound SJ0027

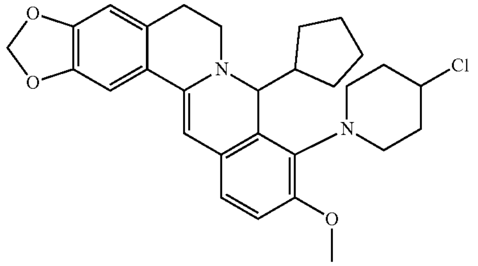

Example 76

Compound SJ0029 was prepared by conventional method, the structure of compound SJ0029 was as follows:

compound SJ0029

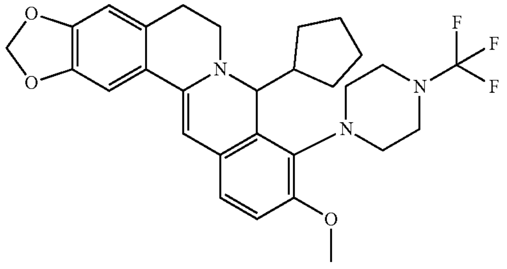

Example 77

Compound SJ0030 was prepared by conventional method, the structure of compound SJ0030 was as follows:

compound SJ0030

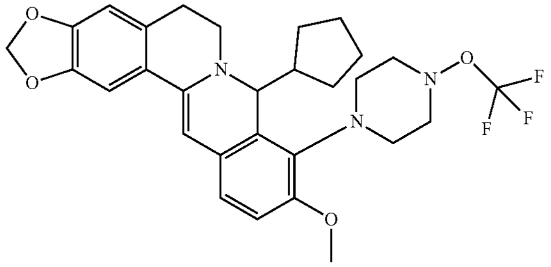

Example 78

Compound SJ0031 was prepared by conventional method, the structure of compound SJ0031 was as follows:

compound SJ0031

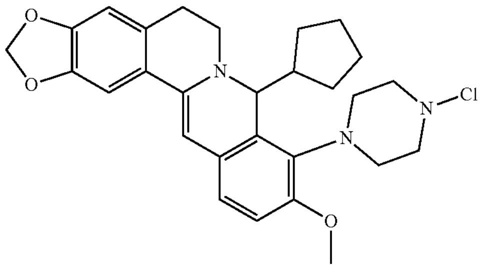

Example 79

Compound SJ0032 was prepared by conventional method, the structure of compound SJ0032 was as follows:

compound SJ0032

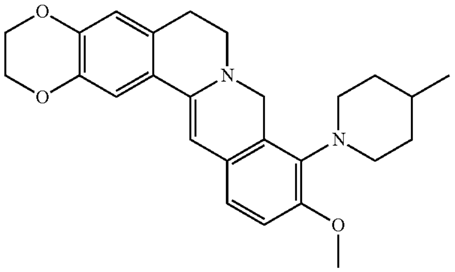

Example 80

Compound SJ0033 was prepared by conventional method, the structure of compound SJ0033 was as follows:

compound SJ0033

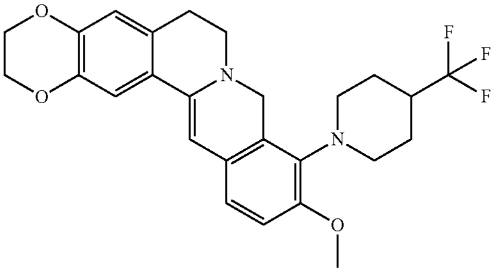

Example 81

Compound SJ0034 was prepared by conventional method, the structure of compound SJ0034 was as follows:

compound SJ0034

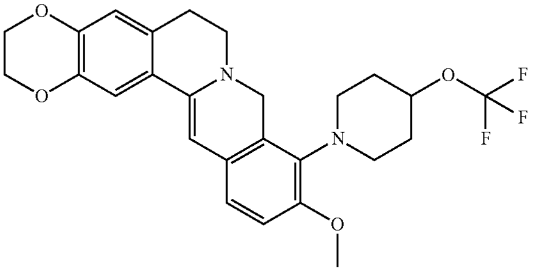

Example 82

Compound SJ0035 was prepared by conventional method, the structure of compound SJ0035 was as follows:

compound SJ0035

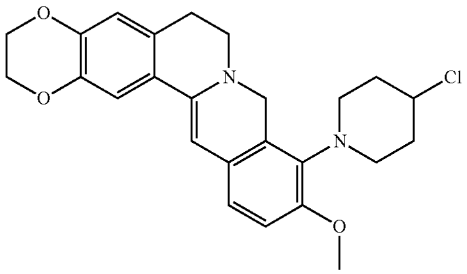

Example 83 Synthesis of Compound AB35484

The structure of compound AB35484 was as follows:

compound AB35484

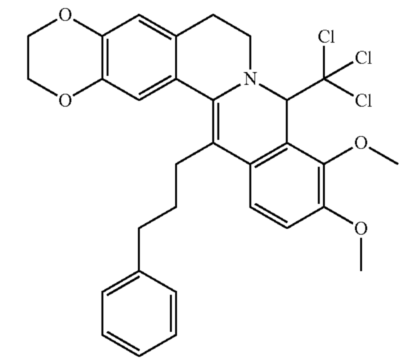

The synthesis method of compound AB35484 was as follows:

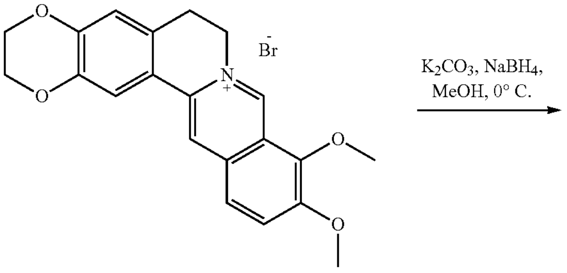

1

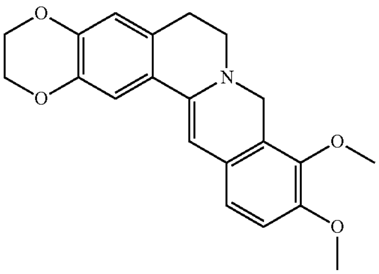

2

Compound 1 (7.1 g, 16.5 mmol, 1 eq) was dissolved in methanol (50 mL), and potassium carbonate (6.8 g, 49.5 mmol, 3.0 eq) and sodium borohydride (499 mg, 13.2 mmol, 0.8 eq) were added at 0° C. The mixture was reacted at 0° C. for 1 h. and the reaction was detected to be performed completely using LCMS. The reaction mixture was quenched with saturated aqueous ammonium chloride solution and filtered, the solid was filtered and washed with a small amount of water and methanol to obtain compound 2.

Step (2):

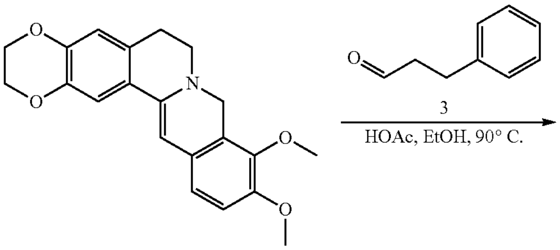

2

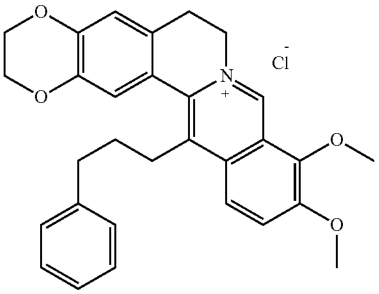

4

Compound 2 (1.0 g, 2.84 mmol, 1 eq) was dissolved in ethanol/acetic acid (10 mL/8 mL), and phenylpropionaldehyde (3.8 g, 28.4 mmol, 10 eq) was added. The mixture was reacted at 90° C. for 4 h, an appropriate amount of hydrochloric acid was added, the mixture was concentrated and spin dried, a small amount of dichloromethane and an appropriate amount of ethyl acetate were added, the mixture was stewed for 0.5 h and then filtered to remove impurity solid. The filtrate was stewed for overnight and filtered to afford compound 4.

Step (3):

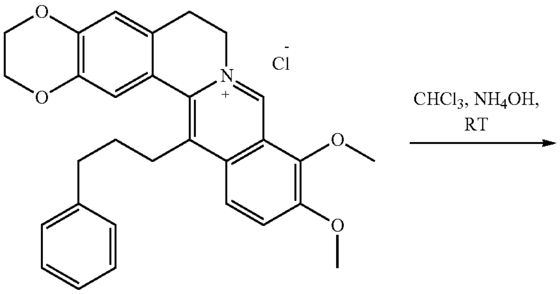

4

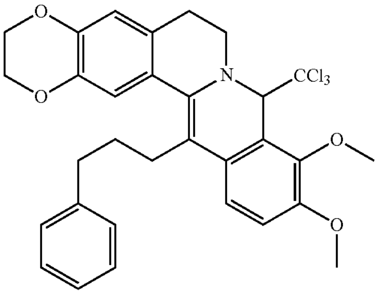

AB35484

Compound 4 (200 mg, 0.39 mmol, 1 eq) was dissolved in a mixture of aqueous ammonia (5 mL) and chloroform (10 mL). The mixture was reacted at room temperature for overnight, and the reaction was detected to be performed completely using LCMS. The reaction mixture was diluted with water and then extracted with dichloromethane, the organic phase was dried over anhydrous sodium sulfate, filtered, and spin dried. The crude product was purified by fast chromatography (dichloromethane/methanol=100/1 to 50/1) to afford compound AB35484.

The MS-ESI and $^1$H NMR spectra of compound AB35484 were as follows:

MS-ESI: Calculated $[M+H]^+$: 586.13, Found: 586.10.

$^1$H NMR (400 MHz, DMSO-d6) δ 7.29-7.25 (m, 2H), 7.21-7.17 (m, 3H), 7.06 (d, J=8.0 Hz, 1H), 6.88 (d, J=8.0 Hz, 1H), 6.75 (s, 2H), 5.53 (s, 1H), 4.28-4.21 (m, 4H), 3.84-3.79 (m, 7H), 3.56-3.54 (m, 1H), 2.68-2.51 (m, 6H), 1.90-1.70 (m, 2H).

Example 84 Synthesis of Compound AB35485

The structure of compound AB35485 was as follows:

AB35485

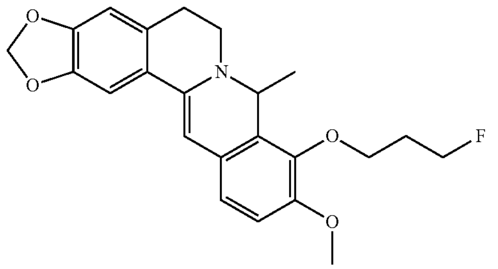

The synthesis method of compound AB35485 was as follows:

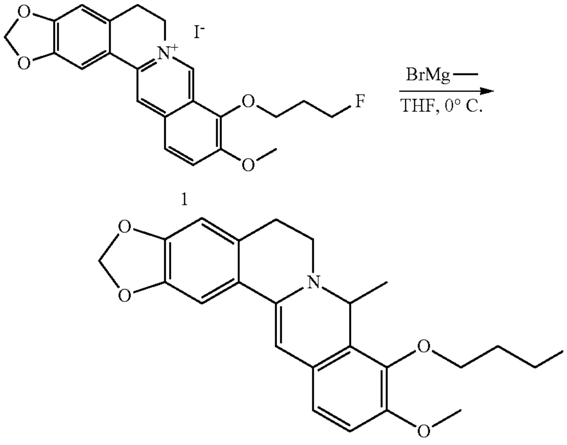

1

AB35485

Compound 1 (200 mg, 0.39 mmol, 1 eq) was dissolved in anhydrous tetrahydrofuran (10 mL), and methylmagnesium bromide (0.7 mL, 1.95 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.1% formic acid) to afford compound AB35485.

The MS-ESI and $^1$H NMR spectra of compound AB35485 were as follows:

MS-ESI: Calculated $[M+H]^+$: 398.17; Found$[M+H]^+$: 398.15.

$^1$H NMR (400 MHz, DMSO-d6) δ 7.21 (s, 1H), 6.79 (d, J=8.0 Hz, 1H), 6.74 (s, 1H), 6.65 (d, J=8.0 Hz, 1H), 5.97 (d, J=4.0 Hz, 2H), 5.90 (s, 1H), 4.73-4.68 (m, 2H), 4.59-4.56 (m, 1H), 4.03-4.00 (m, 2H), 3.72 (s, 3H), 3.24-3.16 (m, 2H), 2.76-2.71 (m, 2H), 2.11-2.01 (m, 2H), 1.02 (d, J=8.0 Hz, 3H).

Example 85 Synthesis of Compound AB35486

The structure of compound AB35486 was as follows:

AB35486

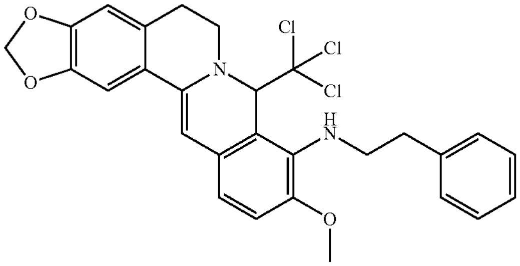

The synthesis method was as follows:

Step (1):

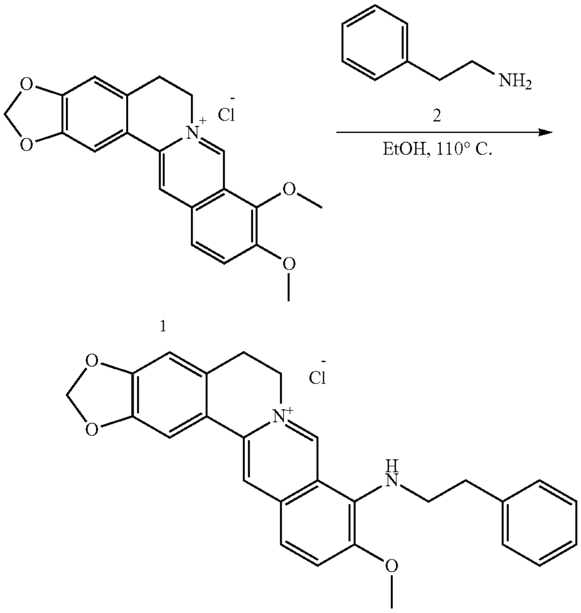

1

3

Compound 1 (3.0 g, 5.38 mmol, 1 eq) was dissolved in ethanol (50 mL), and phenylethylamine (652 mg, 53.8 mmol, 10 eq) was added. The mixture was reacted at 110°

C. for 48 h under $N_2$, the reaction was completed. The reaction mixture was concentrated, the crude product was purified by fast chromatography (DCM/MeOH=100/1 to 50/1) to afford compound 3.

Step (2):

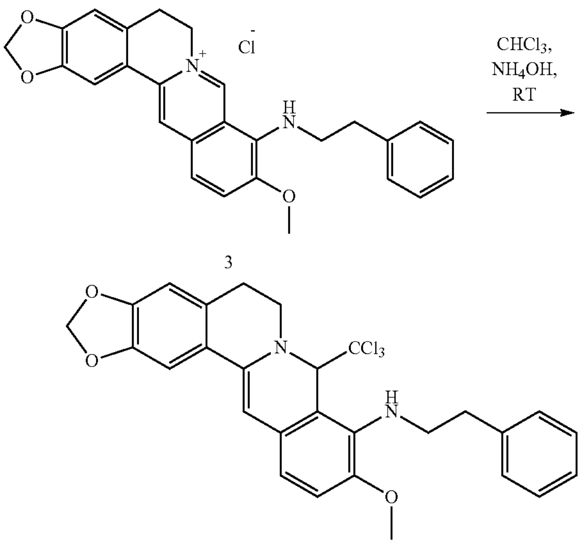

3

AB35486

Compound 3 (1.5 g, 3.25 mmol, 1 eq) was dissolved in chloroform (20 ml), and aqueous ammonia (10 ml) was added. The mixture was reacted at room temperature for overnight under $N_2$, and the reaction was detected to be performed completely using LCMS. The reaction mixture was diluted with water and then extracted with dichloromethane, the organic phase was dried over anhydrous sodium sulfate, filtered and spin dried. The crude product was purified by fast chromatography (DCM/MeOH=100/1 to 50/1) to afford compound AB35486.

The MS-ESI and $^1$H NMR spectra of compound AB35486 were as follows:

MS-ESI: Calculated $[M+H]^+$: 543.09, Found: 543.10.

$^1$H NMR (400 MHz, DMSO-d6) δ 7.30-7.25 (m, 3H), 7.21-7.17 (m, 3H), 6.92 (d, J=8.0 Hz, 1H), 6.74 (s, 1H), 6.67 (d, J=12.0 Hz, 1H), 6.24 (s, 1H), 5.97 (d, J=8.0 Hz, 2H), 5.68 (s, 1H), 4.38-4.35 (m, 1H), 3.74 (s, 3H), 3.70-3.44 (m, 2H), 3.28-3.24 (m, 2H), 2.77-2.65 (m, 4H).

Example 86 Synthesis of Compound AB35487

The structure of compound AB35487 was as follows:

AB35487

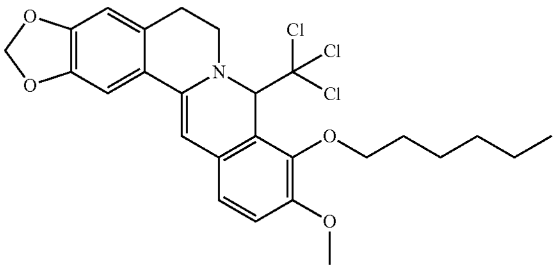

The synthesis method of compound AB35487 was as follows:

Step (1):

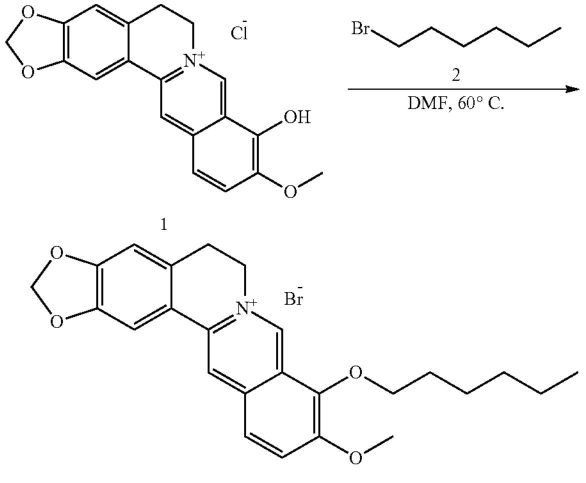

1

3

Compound 1 (2.0 g, 5.59 mmol, 1 eq) was dissolved in N, N-dimethylformamide (30 mL), and compound 2 (4.6 g, 27.95 mmol, 5 eq) was added. The mixture was reacted at 60° C. for overnight. The reaction mixture was diluted with water and then extracted with dichloromethane twice, the organic phase was washed with brine, dried over anhydrous sodium sulfate and filtered, the filtrate was spin dried. The crude product was purified by fast chromatography (DCM/MeOH=500/1 to 30/1) to afford compound 3.

Step (2):

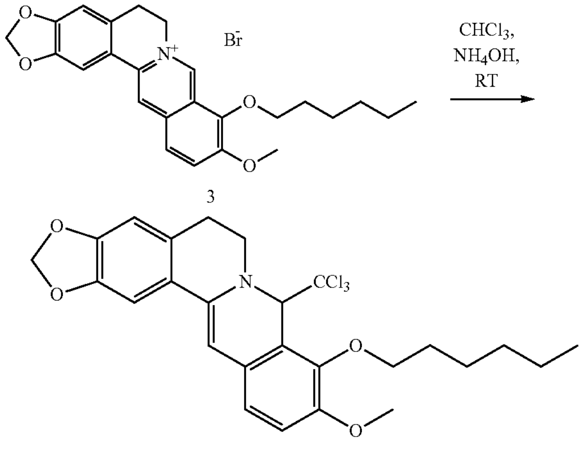

3

AB35487

Compound 3 (200 mg, 0.41 mmol, 1 eq) was dissolved in chloroform (10 mL), and aqueous ammonia (5 mL) was added. The mixture was reacted at room temperature for overnight. The reaction mixture was diluted with water and then extracted with dichloromethane, the organic phase was washed with brine, dried over anhydrous sodium sulfate and filtered, the filtrate was spin dried. The crude product was purified by fast chromatography (DCM/MeOH=100/1) to afford compound AB35487.

The MS-ESI and 1H NMR spectra of compound AB35487 were as follows:

MS-ESI: Calculated $[M+H]^+$: 524.10; Found $[M+H]^+$: 524.10.

$^1H$ NMR (400 MHz, DMSO-d6) δ 7.33 (s, 1H), 7.09 (d, J=8.0 Hz, 1H), 6.89 (d, J=8.0 Hz, 1H), 6.80 (s, 1H), 6.32 (s, 1H), 6.01 (d, J=8.0 Hz, 2H), 5.59 (s, 1H), 4.18-4.13 (m, 1H), 3.80 (s, 3H), 3.73-3.62 (m, 2H), 3.26-3.24 (m, 1H), 2.76-2.70 (m, 1H), 2.01-1.97 (m, 1H), 1.75-1.70 (m, 2H), 1.50-1.48 (m, 2H), 1.35-1.32 (m, 4H), 0.91-0.87 (m, 3H).

Example 87 Synthesis of Compound AB35488

The structure of compound AB35488 was as follows:

AB35488

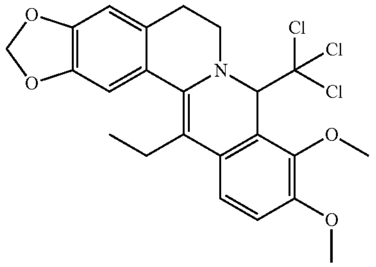

The synthesis method of compound AB35488 was as follows:

Step (1):

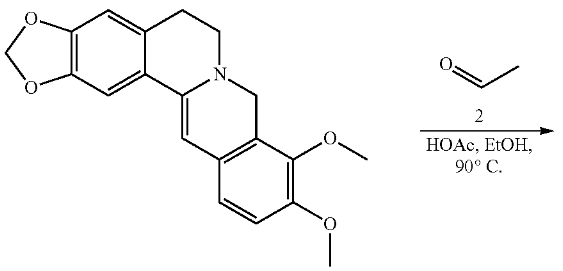

1

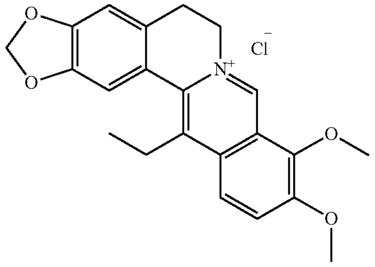

3

Compound 1 (2.0 g, 5.93 mmol, 1 eq) was dissolved in ethanol/acetic acid (10 mL/8 mL), and acetaldehyde (12 mL, 59.3 mmol, 10 eq, 5M in THF) was added. The mixture was reacted at 90° C. for 4 h under $N_2$, the reaction was completed, an appropriate amount of hydrochloric acid was added, and the mixture was concentrated and spin dried, a small amount of dichloromethane and an appropriate amount of ethyl acetate were added, the mixture was stewed for 0.5 h and then filtered to remove impurity solid. The filtrate was stewed for overnight and filtered to afford compound 3.

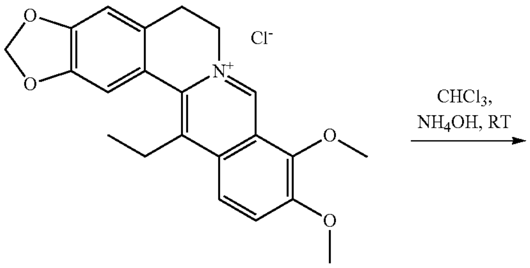

3

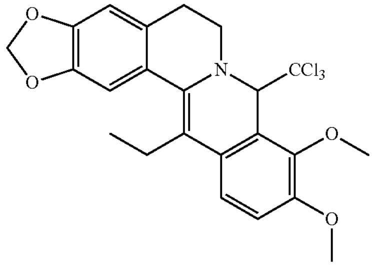

AB35488

Compound 3 (200 mg, 0.50 mmol, 1 eq) was dissolved in a mixture of chloroform (10 mL) and aqueous ammonia (5 mL). The mixture was reacted at room temperature for overnight under $N_2$, and the reaction was detected to be performed completely using LCMS. The reaction mixture was diluted with water and then extracted with dichloromethane, the organic phase was dried over anhydrous sodium sulfate and filtered, the filtrate was spin dried. The crude product was purified by fast chromatography (DCM/MeOH=100/1) to afford compound AB35488.

The MS-ESI and 1H NMR spectra of compound AB35488 were as follows:

MS-ESI: Calculated $[M+H]^+$: 482.06, Found: 482.05.

$^1H$ NMR (400 MHz, DMSO-d6) δ 7.15-7.08 (m, 2H), 6.88 (s, 1H), 6.82 (s, 1H), 6.02 (s, 2H), 5.55 (s, 1H), 3.87-3.80 (s, 7H), 3.58-3.56 (m, 1H), 2.70-2.58 (m, 4H), 1.15-1.11 (m, 3H).

Example 88 Synthesis of Compound AB35489

The structure of compound AB35489 was as follows:

AB35489

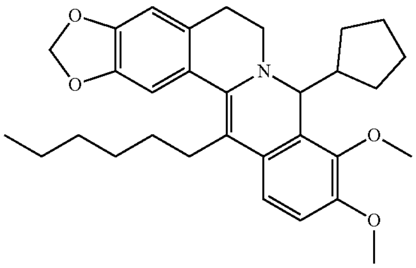

The synthesis method of compound AB35489 was as follows:

Step (1):

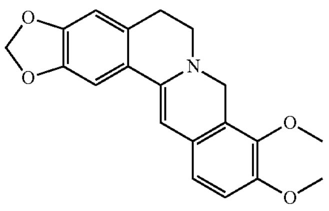

1

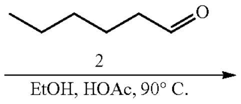

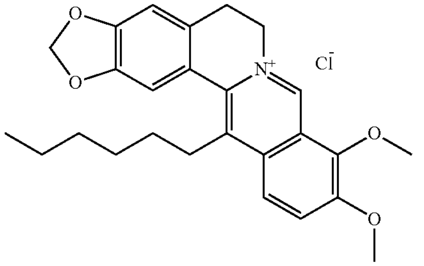

3

Compound 1 (2.0 g, 5.93 mmol, 1 eq) was dissolved in ethanol/acetic acid (20 mL/10 mL), and hexanal (5.9 g, 59.3 mmol, 10 eq) was added was added. The mixture was reacted at 90° C. for 4 h under $N_2$, the reaction was completed, an appropriate amount of hydrochloric acid was added, and the mixture was concentrated and spin dried, a small amount of dichloromethane and an appropriate amount of ethyl acetate were added, the mixture was stewed for 0.5 h and then filtered to remove impurity solid. The filtrate was stewed for overnight, the solid was filtered and dried to afford compound 3.

Step (2):

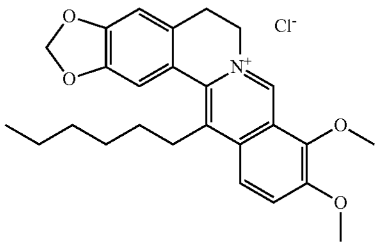

3

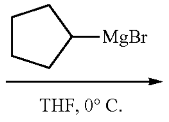

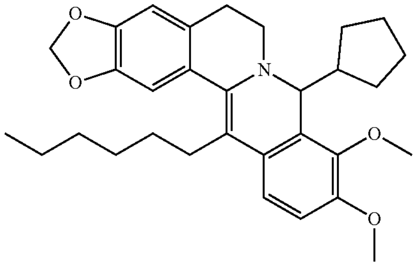

AB35489

Compound 3 (200 mg, 0.44 mmol, 1 eq) was dissolved in anhydrous tetrahydrofuran (10 mL), and cyclopentylmagnesium bromide (2.2 mL, 0.50 mmol, 5 eq, 1M) was added at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate twice, the organic phase was dried over anhydrous sodium sulfate, filtered and spin dried. The crude product was purified by fast chromatography (DCM/MeOH=100/1) to afford compound AB35489.

The MS-ESI and $^1$H NMR spectra of compound AB35489 were as follows:

MS-ESI: Calculated $[M+H]^+$: 490.29, Found: 490.30.

$^1$H NMR (400 MHz, DMSO-d6) δ 6.88 (s, 2H), 6.84 (d, J=4.0 Hz, 2H), 6.01 (d, J=4.0 Hz, 2H), 4.41 (d, J=8.0 Hz, 1H), 3.76 (s, 3H), 3.73 (s, 3H), 2.66-2.60 (m, 2H), 2.12-2.05 (m, 1H), 1.63-1.61 (m, 1H), 1.38-1.21 (m, 19H), 0.87-0.83 (m, 3H).

Example 89 Synthesis of Compound AB35490

The structure of compound AB35490 was as follows:

AB35490

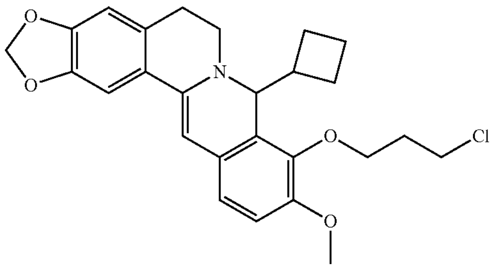

The synthesis method of compound AB35490 was as follows:

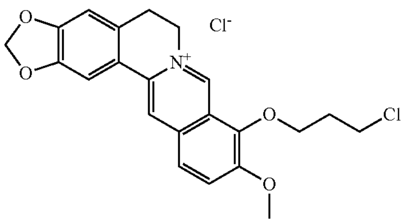

1

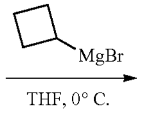

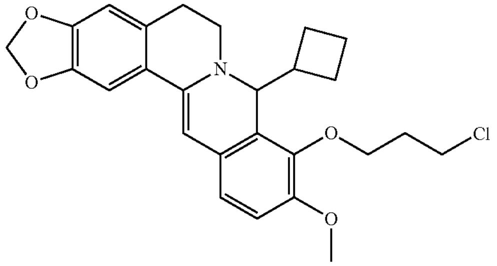

AB35490

Compound 1 (150 mg, 0.34 mmol, 1 eq) was dissolved in anhydrous tetrahydrofuran (10 mL), and cyclobutylmagnesium bromide (0.6 mL, 1.7 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.1% formic acid) to afford compound AB35490.

The MS-ESI and $^1$H NMR spectra of compound AB35490 were as follows:

MS-ESI: Calculated $[M+H]^+$: 454.17; Found$[M+H]^+$: 454.25.

$^1$H NMR (400 MHz, DMSO-d6) δ 7.21 (s, 1H), 6.80-6.65 (m, 3H), 5.97 (s, 2H), 5.88 (s, 1H), 4.53 (d, J=8.0 Hz, 1H), 4.13-4.11 (m, 1H), 3.89-3.86 (m, 3H), 3.73 (s, 3H), 3.32-3.31 (m, 2H), 2.80-2.75 (m, 2H), 2.65-2.62 (m, 1H), 2.20-2.07 (m, 2H), 1.83-1.75 (m, 3H), 1.57-1.55 (m, 2H), 1.38-1.32 (m, 1H).

Example 90 Synthesis of Compound AB35491

The structure of compound AB35491 was as follows:

AB35491

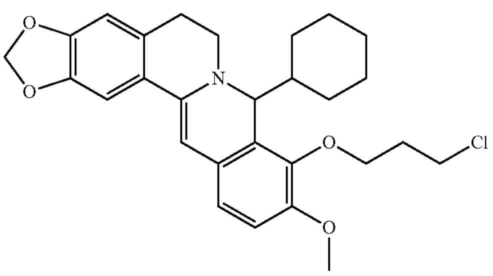

The synthesis method of compound AB35491 was as follows:

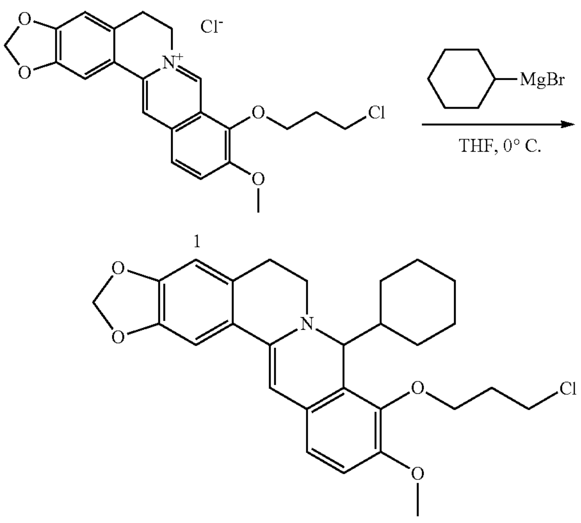

1

AB35491

Compound 1 (150 mg, 0.34 mmol, 1 eq) was dissolved in anhydrous tetrahydrofuran (10 mL), and cyclohexylmagnesium bromide (1.7 mL, 1.7 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by reversed phase preparation chromatography (acetonitrile/water+0.1% formic acid) to afford compound AB35491.

The MS-ESI and #H NMR spectra of compound AB35491 were as follows:

MS-ESI: Calculated $[M+H]^+$: 482.21; Found$[M+H]^+$: 482.20.

$^1$H NMR (400 MHz, DMSO-d6) δ 7.20 (s, 1H), 6.81-6.63 (m, 3H), 5.96 (s, 2H), 5.83 (s, 1H), 4.45 (d, J=4.0 Hz, 1H), 4.09-4.07 (m, 1H), 3.90-3.86 (m, 3H), 3.72 (s, 3H), 3.38-3.35 (m, 2H), 2.89-2.87 (m, 1H), 2.63-2.61 (m, 1H), 2.14-2.02 (m, 2H), 1.64-1.46 (m, 6H), 1.04-0.95 (m, 5H).

Example 91 Synthesis of Compound AB35492

The structure of compound AB35492 was as follows:

AB35492

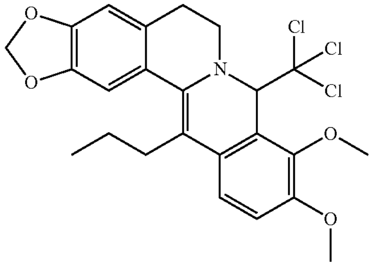

The synthesis method of compound AB35492 was as follows:

Step (1):

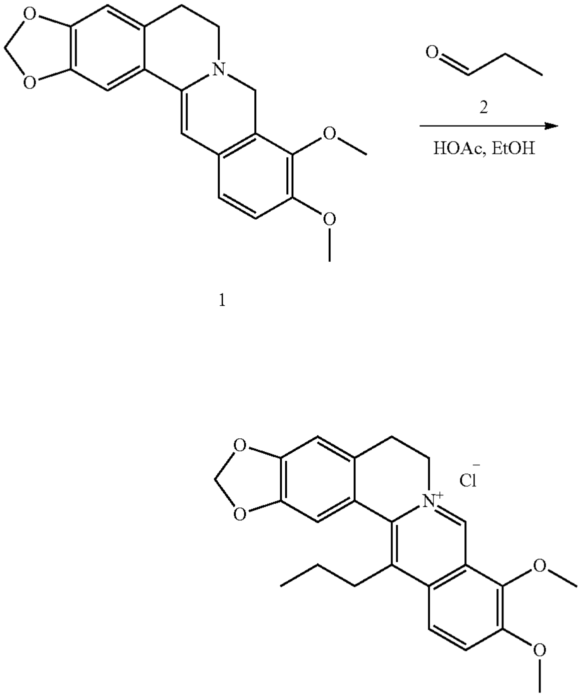

1

3

Compound 1 (2.0 g, 5.93 mmol, 1 eq) was dissolved in ethanol/acetic acid (20 mL/10 mL), and propionaldehyde (3.4 g, 59.3 mmol, 10 eq) was added. The mixture was reacted at 90° C. for 4 h under $N_2$, the reaction was completed, an appropriate amount of hydrochloric acid was added, the mixture was concentrated and spin dried, a small amount of dichloromethane and an appropriate amount of ethyl acetate were added, the mixture was stewed for 0.5 h and then filtered to remove impurity solid. The filtrate was stewed for overnight and filtered to afford compound 3.

Step (2):

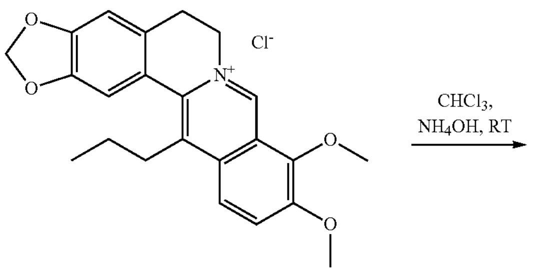

3

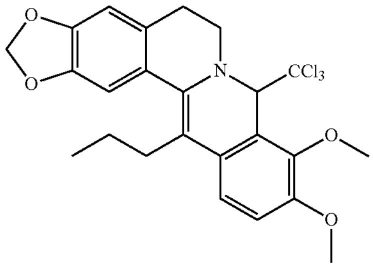

AB35492

Compound 3 (200 mg, 0.48 mmol, 1 eq) was dissolved in chloroform (10 mL), and aqueous ammonia (5 mL) was added. The mixture was reacted at room temperature for overnight under $N_2$. The reaction mixture was diluted with water and extracted with dichloromethane, the organic phase was dried over anhydrous sodium sulfate, filtered and spin dried. The crude product was purified by fast chromatography (DCM/MeOH=100/1) to afford compound AB35492.

The MS-ESI and $^1H$ NMR spectra of compound AB35492 were as follows:

MS-ESI: Calculated $[M+H]^+$: 496.07, Found: 496. 50.

$^1H$ NMR (400 MHz, DMSO-d6) δ 7.14-7.06 (m, 2H), 6.87 (s, 1H), 6.77 (s, 1H), 6.02 (d, J=8.0 Hz, 2H), 5.54 (s, 1H), 3.86-3.79 (m, 7H), 3.59-3.56 (m, 1H), 2.73-2.70 (m, 1H), 2.56-2.49 (m, 3H), 1.66-1.59 (m, 1H), 1.42-1.38 (m, 1H), 0.97-0.94 (m, 3H).

Example 92 Synthesis of Compound AB35494

The structure of compound AB35494 was as follows:

AB35494

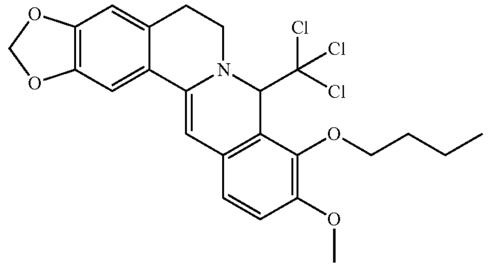

The synthesis method of compound AB35494 was as follows:

Step (1):

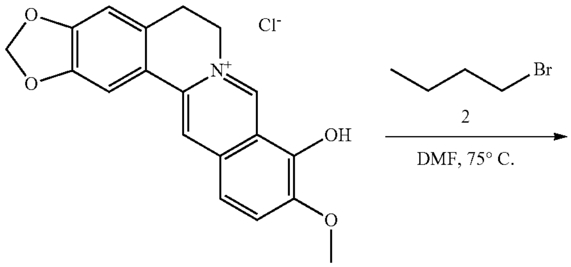

1

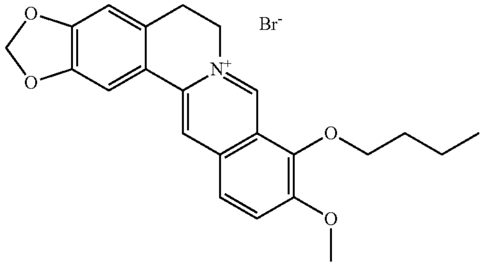

3

Compound 1 (500 mg, 1.40 mmol, 1 eq) was dissolved in N, N-dimethylformamide (10 mL), and bromobutane (959 mg, 7.0 mmol, 5 eq) was added. The mixture was reacted at 75° C. for 16 h under $N_2$, the reaction was completed. The reaction mixture was concentrated, the crude product was purified by fast chromatography (DCM/MeOH=50/1) to afford compound 3.

Step (2):

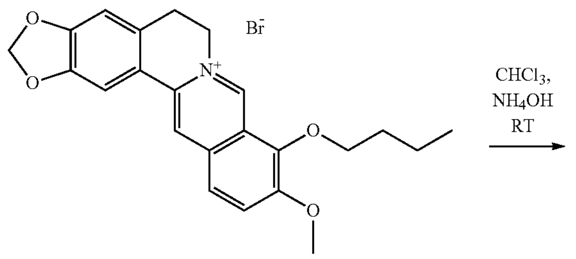

3

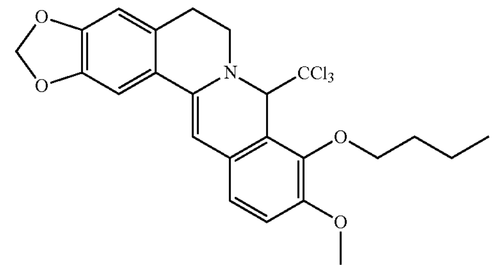

AB35494

Compound 3 (200 mg, 0.44 mmol, 1 eq) was dissolved in chloroform (10 mL), and aqueous ammonia (5 mL) was added. The mixture was reacted at room temperature for overnight under $N_2$, the reaction was completed. The reaction mixture was diluted with water and then extracted with dichloromethane, the organic phase was dried over anhydrous sodium sulfate, filtered, and spin dried. The crude product was purified by fast chromatography (DCM/MeOH=100/1) to afford compound AB35494.

The MS-ESI and $^1H$ NMR spectra of compound AB35494 were as follows:

MS-ESI: Calculated $[M+H]^+$: 496.07, Found: 496.30.

$^1H$ NMR (400 MHz, DMSO-d6) δ 7.30 (s, 1H), 7.06 (d, J=8.0 Hz, 1H), 6.86 (d, J=8.0 Hz, 1H), 6.77 (s, 1H), 6.30 (s, 1H), 5.99 (d, J=4.0 Hz, 2H), 5.56 (s, 1H), 4.15-4.10 (m, 1H), 3.77-3.73 (m, 4H), 3.61-3.59 (m, 2H), 3.26-3.19 (m, 1H), 2.72-2.66 (m, 1H), 1.64-1.55 (m, 2H), 1.50-1.45 (m, 2H), 0.94-0.91 (m, 3H).

Example 93 Synthesis of Compound AB35496

The structure of compound AB35496 was as follows:

AB35496

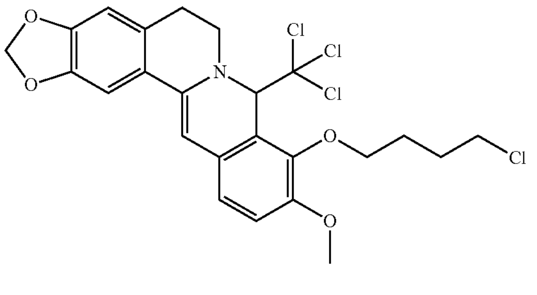

The synthesis method of compound AB35496 was as follows:

Step (1):

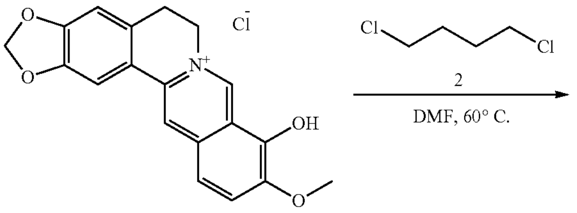

1

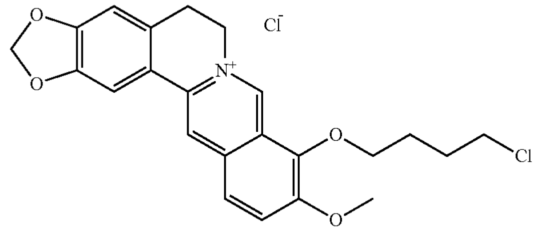

3

Compound 1 (1.0 g, 2.79 mmol, 1 eq) was dissolved in N, N-dimethylformamide (20 mL), and compound 2 (1.8 g, 13.95 mmol, 5 eq) was added. The mixture was reacted at 60° C. for 16 h under $N_2$, the reaction was completed. The reaction mixture was concentrated, the crude product was purified by fast chromatography (DCM/MeOH=50/1) to afford compound 3.

Step (2):

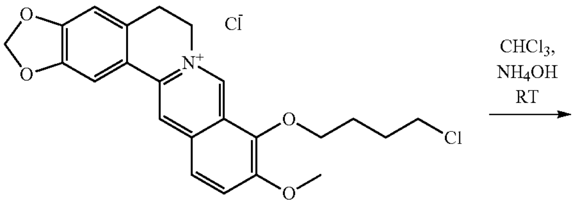

3

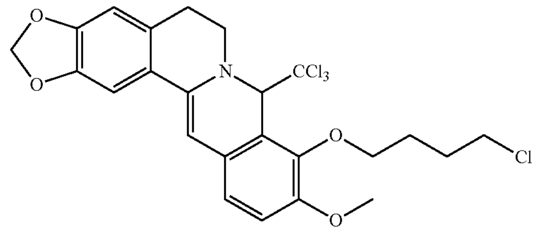

AB35496

Compound 3 (200 mg, 0.45 mmol, 1 eq) was dissolved in chloroform (10 mL), and aqueous ammonia (5 mL) was added. The mixture was reacted at room temperature for overnight under $N_2$, the reaction was completed. The reaction mixture was diluted with water and then extracted with dichloromethane, the organic phase was dried over anhydrous sodium sulfate, filtered, and spin dried. The crude product was purified by fast chromatography (DCM/MeOH=100/1) to afford compound AB35496.

The MS-ESI and $^1H$ NMR spectra of compound AB35496 were as follows:

MS-ESI: Calculated $[M+H]^+$: 530.03, Found: 530.25.

$^1H$ NMR (400 MHz, DMSO-d6) δ 7.30 (s, 1H), 7.07 (d, J=8.0 Hz, 1H), 6.87 (d, J=8.0 Hz, 1H), 6.77 (s, 1H), 6.29 (s, 1H), 5.99 (d, J=4.0 Hz, 2H), 5.56 (s, 1H), 4.16-4.11 (m, 1H), 3.80-3.78 (m, 1H), 3.72 (s, 3H), 3.61-3.59 (m, 3H), 3.56-3.54 (m, 1H), 3.26-3.19 (m, 1H), 2.72-2.67 (m, 1H), 1.95-1.90 (m, 2H), 1.82-1.78 (m, 2H).

Example 94 Synthesis of Compound AB35497

The structure of compound AB35497 was as follows:

AB35497

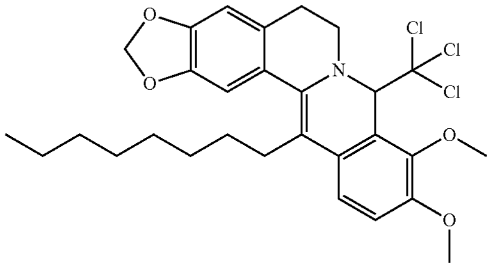

The synthesis method of compound AB35497 was as follows:

Step (1):

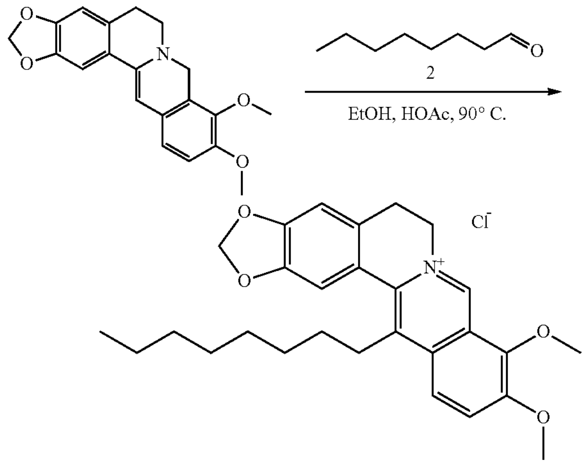

3

Compound 1 (2.0 g, 5.93 mmol, 1 eq) was dissolved in ethanol/acetic acid (20 mL/10 mL), and octanal (7.6 g, 59.3 mmol, 10 eq) was added. The mixture was reacted at 90° C. for 4 h under $N_2$, the reaction was completed, an appropriate amount of hydrochloric acid was added, the mixture was concentrated and spin dried, a small amount of dichloromethane and an appropriate amount of ethyl acetate were added, the mixture was stewed for 0.5 h and then filtered to remove impurity solid. The filtrate was stewed for overnight and filtered to afford compound 3.

Step (2):

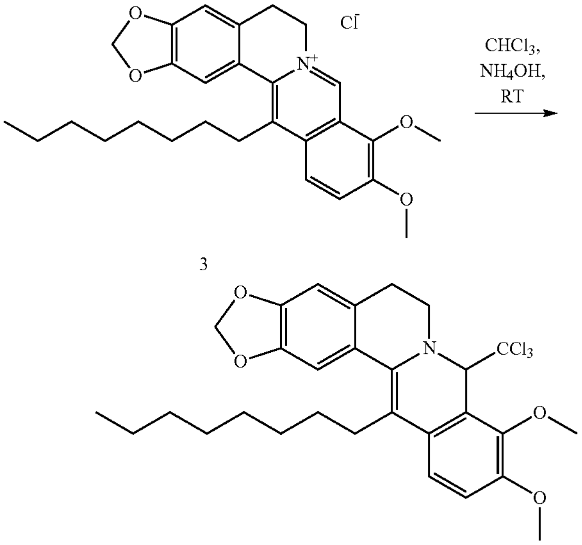

3

AB35497

Compound 3 (200 mg, 0.41 mmol, 1 eq) was dissolved in chloroform (10 mL), and aqueous ammonia (5 mL) was added. The mixture was reacted at room temperature for overnight under $N_2$, the reaction was completed. The reaction mixture was diluted with water and then extracted with dichloromethane, the organic phase was dried over anhydrous sodium sulfate, filtered, and spin dried. The crude product was purified by fast chromatography (DCM/MeOH=100/1) to afford compound AB35497.

The MS-ESI and $^1H$ NMR spectra of compound AB35497 were as follows:

MS-ESI: Calculated $[M+H]^+$: 566.16, Found: 566.15.

$^1H$ NMR (400 MHz, DMSO-d6) δ 7.15-7.04 (m, 2H), 6.88 (s, 1H), 6.79 (s, 1H), 6.02 (d, J=4.0 Hz, 2H), 5.55 (s, 1H), 3.87-3.80 (m, 7H), 3.57-3.54 (m, 1H), 2.70-2.65 (m, 1H), 2.57-2.51 (m, 3H), 1.66-1.58 (m, 1H), 1.37-1.24 (m, 11H), 0.85-0.82 (m, 3H).

Example 95 Synthesis of Compound AB35498

The structure of compound AB35498 was as follows:

AB35498

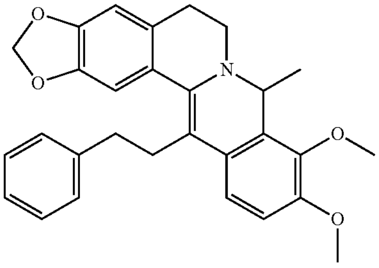

The synthesis method of compound AB35498 was as follows:

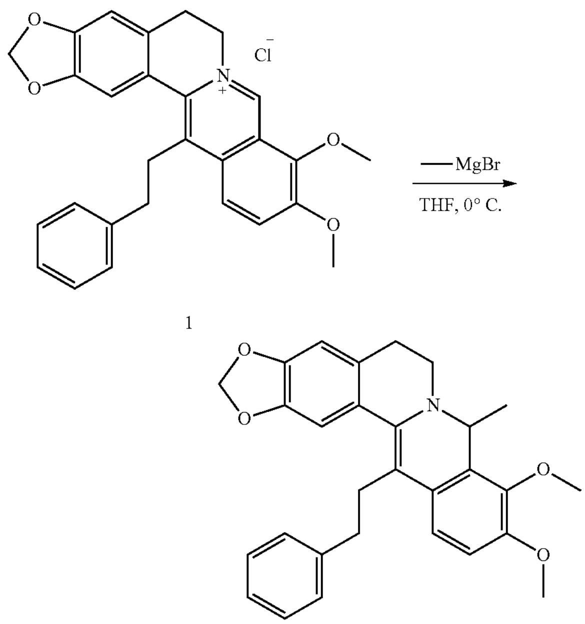

1

AB35498

Compound 1 (240 mg, 0.50 mmol, 1 eq) was dissolved in anhydrous tetrahydrofuran (10 mL), and methylmagnesium bromide (0.8 mL, 2.5 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by thin layer chromatography (DCM/MeOH=30/1) to afford compound AB35498.

The MS-ESI and $^1$H NMR spectra of compound AB35498 were as follows:

MS-ESI: Calculated $[M+H]^+$: 456.21; Found$[M+H]^+$: 456.40.

$^1$H NMR (400 MHz, DMSO-d6) δ 7.29-7.24 (m, 4H), 7.19-7.16 (m, 1H), 7.05-6.94 (m, 2H), 6.89 (s, 1H), 6.81 (s, 1H), 5.99 (s, 2H), 4.69-4.65 (m, 1H), 3.78 (d, J=8.0 Hz, 6H), 3.25-3.10 (m, 2H), 2.90-2.60 (m, 6H), 0.98 (d, J=4.0 Hz, 3H).

Example 96 Synthesis of Compound AB35499

The structure of compound AB35499 was as follows:

AB35499

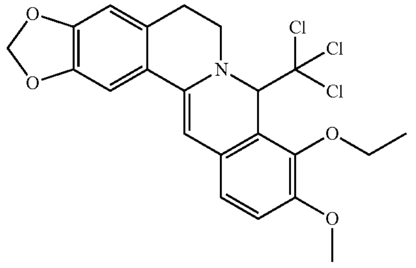

The synthesis method of compound AB35499 was as follows:

Step (1):

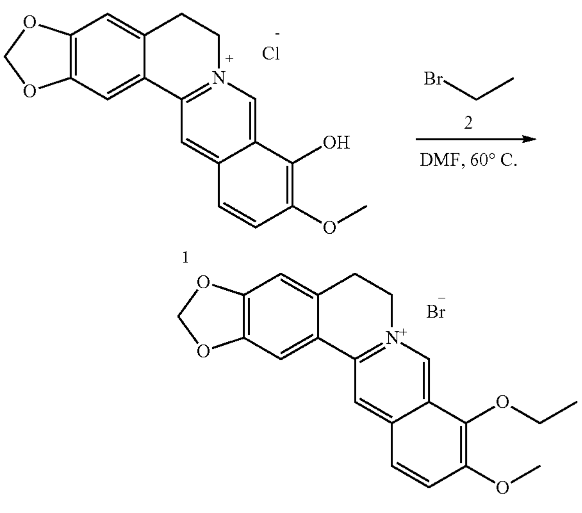

1

3

Compound 1 (2.0 g, 5.59 mmol, 1 eq) was dissolved in N, N-dimethylformamide (50 mL), and bromoethane (53.0 g, 27.95 mmol, 10 eq) was added. The mixture was reacted at 60° C. for 16 h under $N_2$, the reaction was completed. The reaction mixture was concentrated, the crude product was purified by fast chromatography (DCM/MeOH=50/1) to afford compound 3.

Step (2):

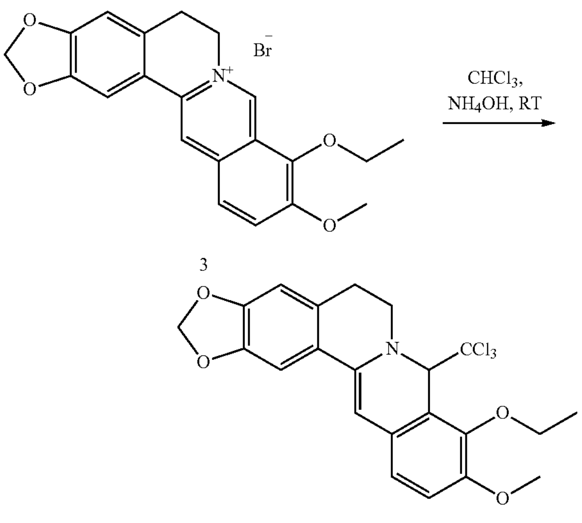

3

AB35499

Compound 3 (200 mg, 0.46 mmol, 1 eq) was dissolved in chloroform (10 mL), and aqueous ammonia (5 mL) was added. The mixture was reacted at room temperature for overnight under N2, the reaction was completed. The reaction mixture was diluted with water and then extracted with dichloromethane, the organic phase was dried over anhydrous sodium sulfate, filtered and spin dried. The crude product was purified by fast chromatography (DCM/MeOH=100/1) to afford compound AB35499.

The MS-ESI and $^1$H NMR spectra of compound AB35499 were as follows:

MS-ESI: Calculated [M+H]$^+$: 468.04; Found[M+H]$^+$: 468.05.

$^1$H NMR (400 MHz, DMSO-d6) δ 7.30 (s, 1H), 7.06 (d, J=8.0 Hz, 1H), 6.86 (d, J=8.0 Hz, 1H), 6.77 (s, 1H), 6.29 (s, 1H), 5.98 (d, J=8.0 Hz, 2H), 5.60 (s, 1H), 4.09-3.96 (m, 2H), 3.78-3.75 (m, 4H), 3.60-3.58 (m, 1H), 3.22-3.19 (m, 1H), 2.67-2.65 (m, 1H), 1.28-1.24 (m, 3H).

Example 97 Synthesis of Compound AB35500

The structure of compound AB35500 was as follows:

AB35500

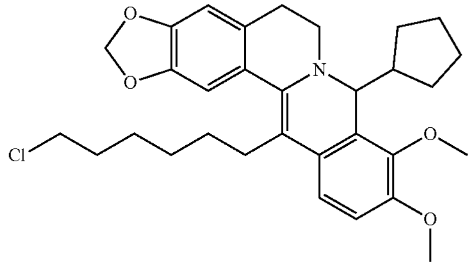

The synthesis method of compound AB35500 was as follows:

Step (1):

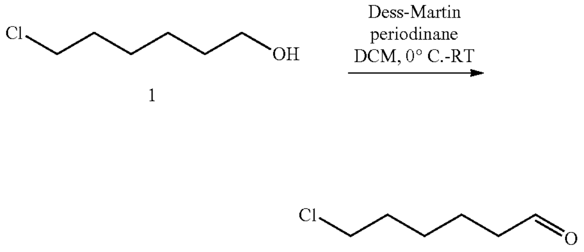

1

2

Compound 1 (30 g, 219.59 mmol, 1 eq) was dissolved in dichloromethane (300 mL), and Dess-Martin Periodinane (111.7 g, 263.51 mmol, 1.2 eq) was added in batches at 0° C. The mixture was reacted at room temperature for 2 h, the reaction was completed. The solid was filtered, the filtrate was concentrated. The crude product was purified by fast chromatography (PE/EA=100/1) to afford compound 2.

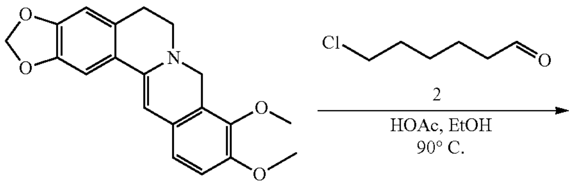

3

-continued

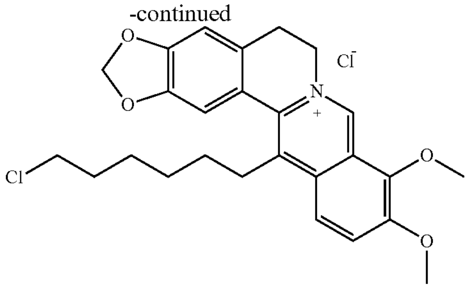

4

Compound 3 (2 g, 5.93 mmol, 1 eq) was dissolved in ethanol/acetic acid (30 mL/5 mL), and compound 2 (8.0 g, 59.3 mmol, 10 eq) was added. The mixture was reacted at 90° C. for 4 h, the reaction was completed, an appropriate amount of hydrochloric acid was added, and the mixture was concentrated and spin dried, a small amount of dichloromethane and an appropriate amount of ethyl acetate were added, the mixture was stewed for 0.5 h and then filtered to remove solid. The filtrate was stewed for overnight, the solid was filtered and dried to afford compound 4.

Step (3):

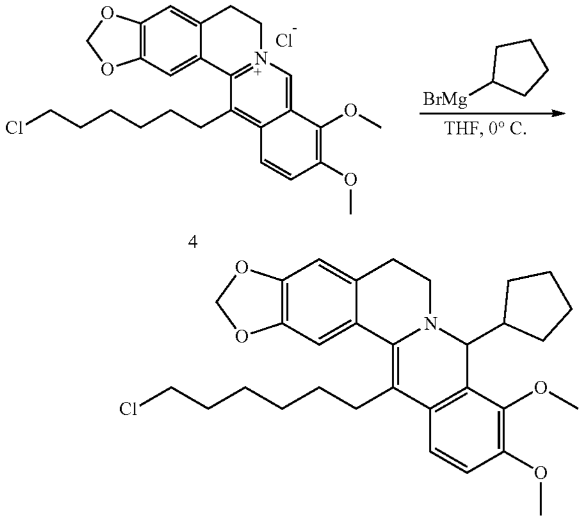

AB35500

Compound 4 (300 mg, 0.61 mmol, 1 eq) was dissolved in anhydrous tetrahydrofuran (10 mL), and cyclopentylmagnesium bromide (3 mL, 3.05 mmol, 5 eq, 1M) was added at 0° C. under $N_2$. The mixture was reacted at room temperature for 0.5 h, the reaction was completed. The reaction mixture was quenched with saturated aqueous ammonium chloride solution and then extracted with ethyl acetate, the organic phase was dried over anhydrous sodium sulfate, filtered and spin dried. The crude product was purified by fast chromatography (DCM/MeOH=100/1 to 50/1) to afford compound AB35500.

The MS-ESI and $^1$H NMR spectra of compound AB35500 were as follows:

MS-ESI: Calculated [M+H]$^+$: 524.25; Found [M+H]$^+$: 524.25.

$^1$H NMR (400 MHz, DMSO-d6) δ 6.88 (s, 2H), 6.84 (d, J=4.0 Hz, 2H), 6.01 (s, 2H), 4.41 (d, J=8.0 Hz, 1H), 3.76 (s,

3H), 3.73 (s, 3H), 3.62-3.59 (m, 2H), 3.34 (s, 1H), 2.66-2.53 (m, 4H), 2.12-2.05 (m, 1H), 1.71-1.58 (m, 3H), 1.40-1.19 (m, 14H).

Example 98 Synthesis of Compound AB35501

The structure of compound AB35501 was as follows:

AB35501

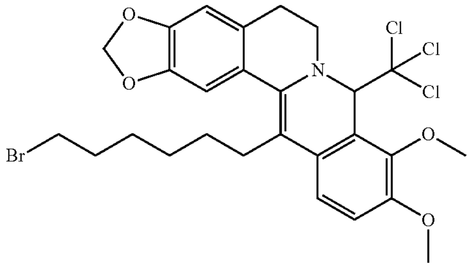

The synthesis method of compound AB35501 was as follows:

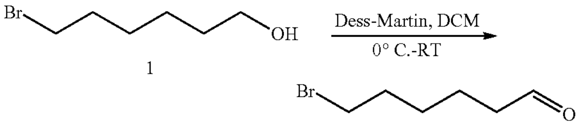

1

2

Compound 1 (25 g, 138.07 mmol, 1 eq) was dissolved in dichloromethane (300 mL), and Dess-Martin Periodinane (70.2 g, 165.68 mmol, 1.2 eq) was added in batches at 0° C. The mixture was reacted at room temperature for 2 h, and the reaction was completed. The solid was filtered, the filtrate was concentrated. The crude product was purified by fast chromatography (PE/EA=100/1) to afford compound 2.

Step (2):

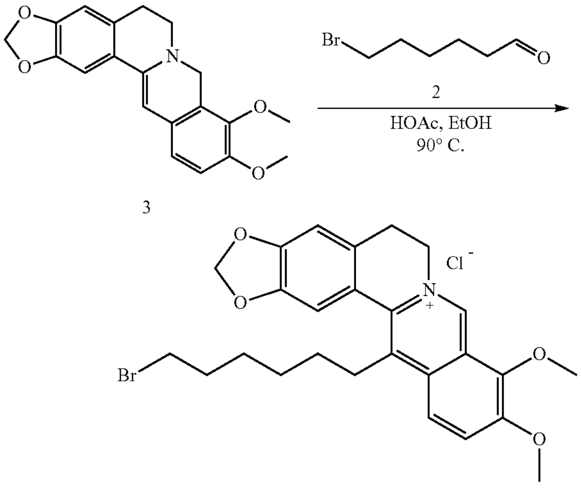

3

2

4

Compound 3 (2 g, 5.93 mmol, 1 eq) was dissolved in ethanol/acetic acid (30 mL/5 mL), and compound 2 (10.6 g, 59.3 mmol, 10 eq) was added. The mixture was reacted at 90° C. for 4 h, the reaction was completed, an appropriate amount of hydrochloric acid was added, and the mixture was concentrated and spin dried, a small amount of dichloromethane and an appropriate amount of ethyl acetate were added, the mixture was stewed for 0.5 h and then filtered to remove solid. The filtrate was stewed for overnight, the solid was filtered and dried to afford compound 4.

Step (3):

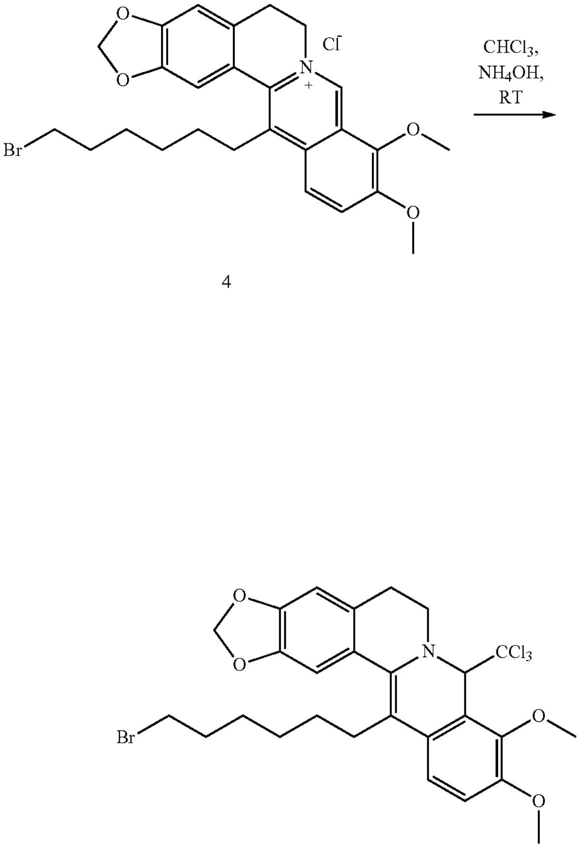

4

AB35501

Compound 4 (200 mg, 0.39 mmol, 1 eq) was dissolved in chloroform (10 mL), and aqueous ammonia (4 mL) was added. The mixture was reacted at room temperature for overnight, the reaction was completed. The reaction mixture was diluted with water and then extracted with dichloromethane, the organic phase was dried over anhydrous sodium sulfate, filtered and spin dried. The crude product was purified by fast chromatography (DCM/MeOH=100/1) to afford compound AB35501.

The MS-ESI and $^1H$ NMR spectra of compound AB35501 were as follows:

MS-ESI: Calculated $[M+H]^+$: 616.03; Found $[M+H]^+$: 616.00.

$^1H$ NMR (400 MHz, DMSO-d6) δ 7.15-7.05 (m, 2H), 6.88 (s, 1H), 6.79 (s, 1H), 6.03 (d, J=4.0 Hz, 2H), 5.73 (s, 1H), 5.55 (s, 1H), 3.87-3.80 (m, 7H), 3.54-3.52 (m, 1H), 3.51-3.49 (m, 2H), 2.70-2.68 (m, 1H), 2.58-2.53 (m, 2H), 1.81-1.78 (m, 2H), 1.63-1.58 (m, 1H), 1.45-1.37 (m, 5H).

Example 99 Synthesis of Compound AB35502

The structure of compound AB35502 was as follows:

AB35502

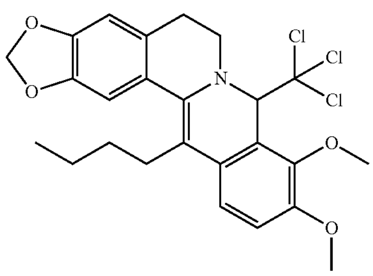

Step (1):

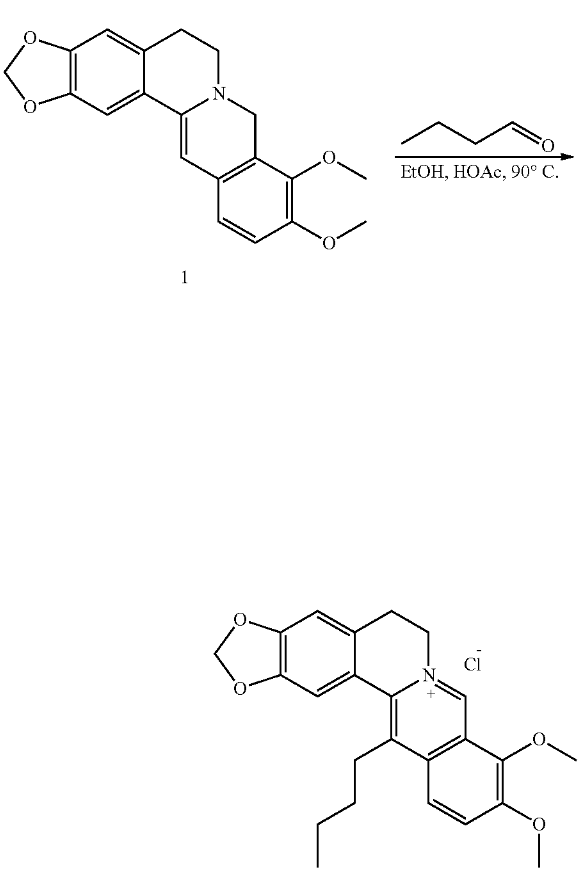

1

2

Compound 1 (2 g, 5.93 mmol, 1 eq) was dissolved in ethanol/acetic acid (30 mL/5 mL), and butyraldehyde (4.3 g, 59.3 mmol, 10 eq) was added. The mixture was reacted at 90° C. for 4 h, the reaction was completed, an appropriate amount of hydrochloric acid was added, the mixture was concentrated and spin dried, a small amount of dichloromethane and an appropriate amount of ethyl acetate were added, the mixture was stewed for 0.5 h and then filtered to remove solid. The filtrate was stewed for overnight, the solid was filtered and dried to afford compound 2.

Step (2):

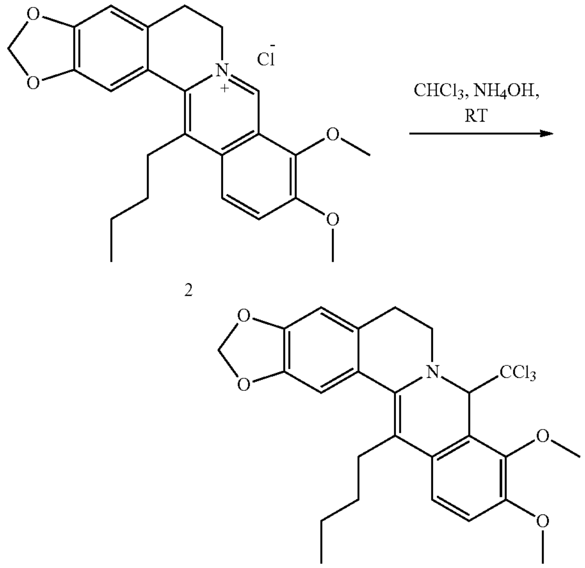

2

AB35502

Compound 2 (200 mg, 0.47 mmol, 1 eq) was dissolved in chloroform (10 mL), and aqueous ammonia (4 mL) was added. The mixture was reacted at room temperature for overnight, the reaction was completed. The reaction mixture was diluted with water and then extracted with dichloromethane, the organic phase was dried over anhydrous sodium sulfate, filtered and spin dried. The crude product was purified by fast chromatography (DCM/MeOH=100/1) to afford compound AB35502.

The MS-ESI and $^1$H NMR spectra of compound AB35502 were as follows:

MS-ESI: Calculated $[M+H]^+$: 510.09; Found $[M+H]^+$: 510.05.

$^1$H NMR (400 MHz, DMSO-d6) δ 7.16-7.06 (m, 2H), 6.88 (s, 1H), 6.80 (s, 1H), 6.02 (d, J=8.0 Hz, 2H), 5.55 (s, 1H), 3.87-3.80 (m, 7H), 3.57-3.54 (m, 1H), 2.70-2.64 (m, 1H), 2.60-2.53 (m, 3H), 1.65-1.59 (m, 1H), 1.40-1.36 (m, 3H), 0.94-0.91 (m, 3H).

Example 100 Synthesis of Compound AB35504

The structure of compound AB35504 was as follows:

AB35504

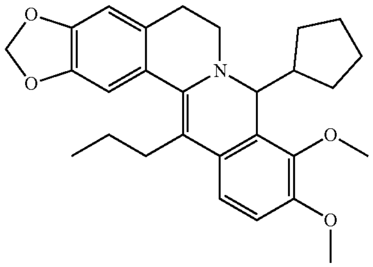

The synthesis method of compound AB35504 was as follows:

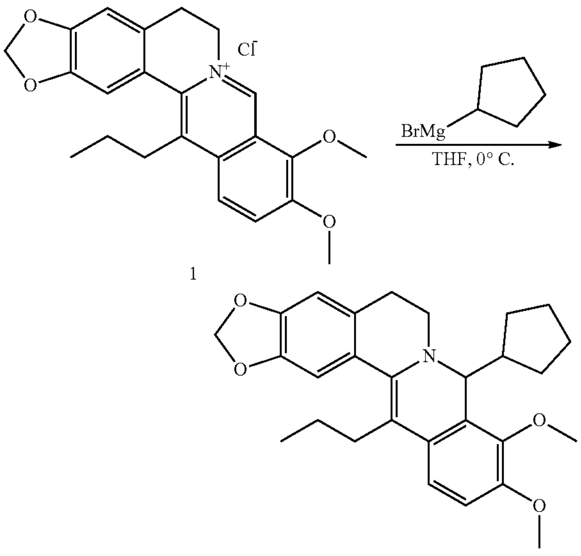

1

AB35504

Compound 1 (200 mg, 0.48 mmol, 1 eq) was dissolved in anhydrous tetrahydrofuran (10 mL), and cyclopentylmagnesium bromide (2.4 mL, 2.4 mmol, 5 eq, 1M) was slowly added dropwise at 0° C. under $N_2$. The mixture was reacted for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate and filtered, the filtrate was spin dried. The crude product was purified by thin layer chromatography (dichloromethane:methanol=50:1) to afford compound AB35504.

The MS-ESI and $^1$H NMR spectra of compound AB35504 were as follows:

MS-ESI: Calculated $[M+H]^+$: 448.24, Found: 448.45.

$^1$H NMR (400 MHz, DMSO-d6) δ 6.88-6.83 (m, 4H), 6.01 (s, 2H), 4.41 (d, J=8.0 Hz, 1H), 3.74 (d, J=12.0 Hz, 6H), 3.32 (s, 1H), 2.70-2.66 (m, 1H), 2.56-2.49 (m, 3H), 2.15-2.10 (m, 1H), 1.73-1.62 (m, 1H), 1.42-1.20 (m, 10H), 0.97-0.95 (m, 3H).

Example 101 Synthesis of Compound AB35505

The structure of compound AB35505 was as follows:

AB35505

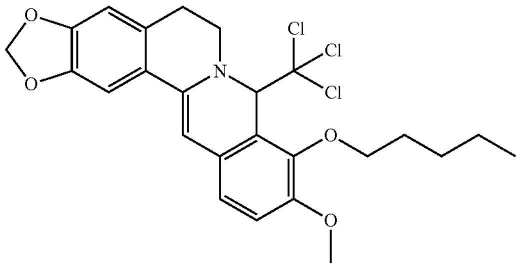

The synthesis method of compound AB35505 was as follows:

Step (1):

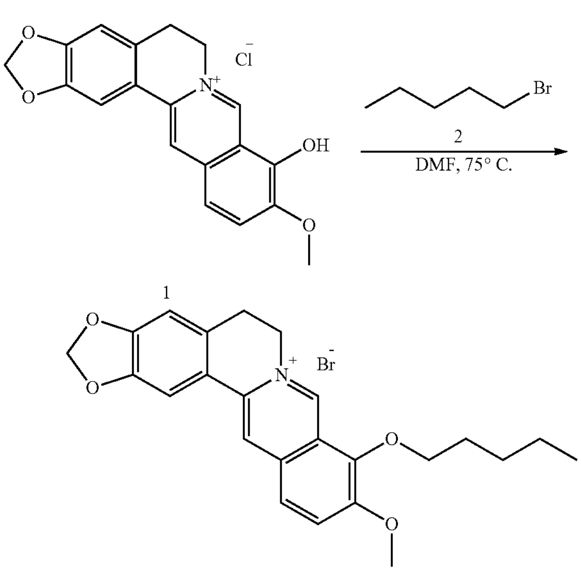

1

3

Compound 1 (500 mg, 1.40 mmol, 1 eq) was dissolved in N, N-dimethylformamide (20 mL), and bromopentane (1.0 g, 7.0 mmol, 5 eq) was added. The mixture was reacted at 75° C. for overnight, the reaction was completed. The reaction mixture was concentrated, the crude product was purified by fast chromatography (DCM/MeOH=50/1 to 30/1) to afford compound 3.

Step (2):

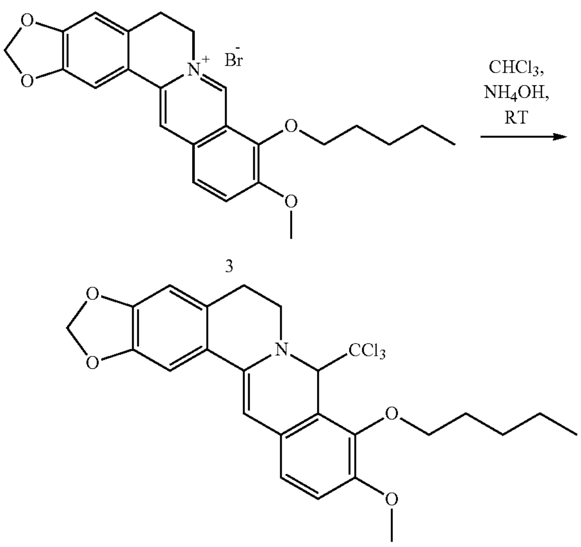

3

AB35505

Compound 3 (200 mg, 0.42 mmol, 1 eq) was dissolved in chloroform (10 mL), and aqueous ammonia (5 mL) was added. The mixture was reacted at room temperature for overnight, the reaction was completed. The reaction mixture was diluted with water and then extracted with dichloromethane, the organic phase was dried over anhydrous sodium sulfate, filtered and spin dried. The crude product was purified by fast chromatography (PE/EA=50/1) to afford compound AB35505.

The MS-ESI and $^1H$ NMR spectra of compound AB35505 were as follows:

MS-ESI: Calculated $[M+H]^+$: 510.09; Found $[M+H]^+$: 510.30.

$^1H$ NMR (400 MHz, DMSO-d6) δ 7.30 (s, 1H), 7.06 (d, J=8.0 Hz, 1H), 6.86 (d, J=8.0 Hz, 1H), 6.77 (s, 1H), 6.30 (s, 1H), 5.99 (d, J=4.0 Hz, 2H), 5.56 (s, 1H), 4.15-4.09 (m, 1H), 3.83-3.79 (m, 4H), 3.70-3.59 (m, 2H), 3.27-3.20 (m, 1H), 2.72-2.67 (m, 1H), 1.69-1.62 (m, 2H), 1.49-1.36 (m, 4H), 0.90-0.86 (m, 3H).

Example 102 Synthesis of Compound AB35506

The structure of compound AB35506 was as follows:

AB35506

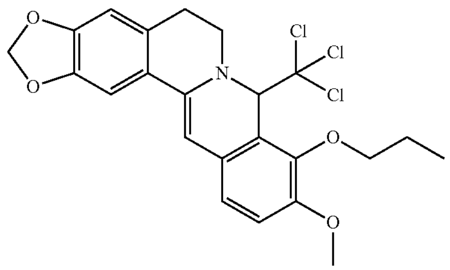

The synthesis method of compound AB35506 was as follows:

Step (1):

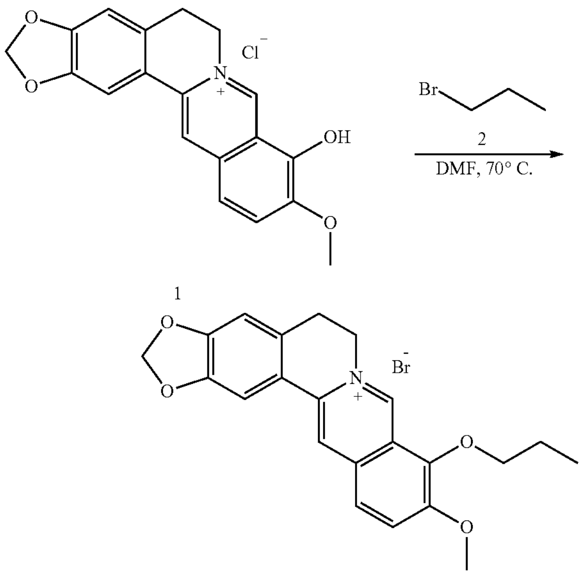

1

3

Compound 1 (1 g, 2.79 mmol, 1 eq) was dissolved in N, N-dimethylformamide (20 mL), and compound 2 (1.7 g, 13.95 mmol, 5 eq) was added. The mixture was reacted at 70° C. for overnight. The reaction mixture was diluted with water and then extracted with dichloromethane twice, the organic phase was washed with brine, dried over anhydrous sodium sulfate and filtered, the filtrate was spin dried, the crude product was purified by fast chromatography (DCM/MeOH=50/1 to 30/1) to afford compound 3.

Step (2):

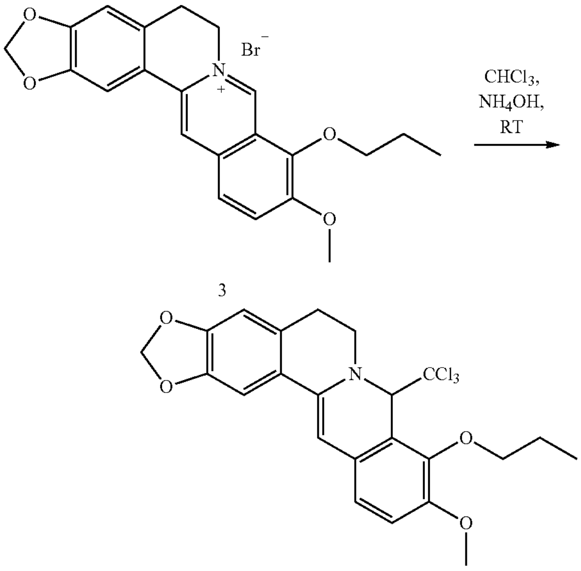

3

AB35506

Compound 3 (350 mg, 0.79 mmol, 1 eq) was dissolved in chloroform (10 mL), and ammonia water (5 mL) was added. The mixture was reacted at room temperature for overnight. The reaction mixture was diluted with water and then extracted with dichloromethane, the organic phase was washed with brine, dried over anhydrous sodium sulfate and filtered, the filtrate was spin dried. The crude product was purified by fast chromatography (petroleum ether/ethyl acetate=50/1) to afford compound AB35506.

The MS-ESI and $^1H$ NMR spectra of compound AB35506 were as follows:

MS-ESI: Calculated $[M+H]^+$: 482.06; Found $[M+H]^+$: 482.25.

$^1H$ NMR (400 MHz, $CDCl_3$) δ 7.30 (s, 1H), 7.06 (d, J=8.0 Hz, 1H), 6.86 (d, J=8.0 Hz, 1H), 6.77 (s, 1H), 6.30 (s, 1H), 5.99 (d, J=4.0 Hz, 2H), 5.57 (s, 1H), 4.12-4.07 (m, 1H), 3.74-3.70 (m, 5H), 3.61-3.59 (m, 1H), 3.25-3.20 (m, 1H), 2.72-2.66 (m, 1H), 1.69-1.65 (m, 2H), 1.02-0.98 (m, 3H).

Example 103 Synthesis of Compound AB35508

The structure of compound AB35508 was as follows:

AB35508

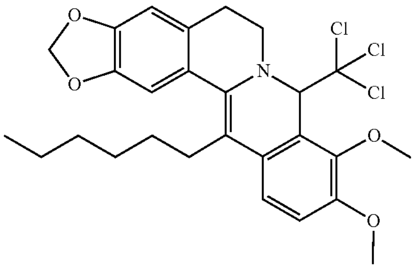

The synthesis method of compound AB35508 was as follows:

Step (1):

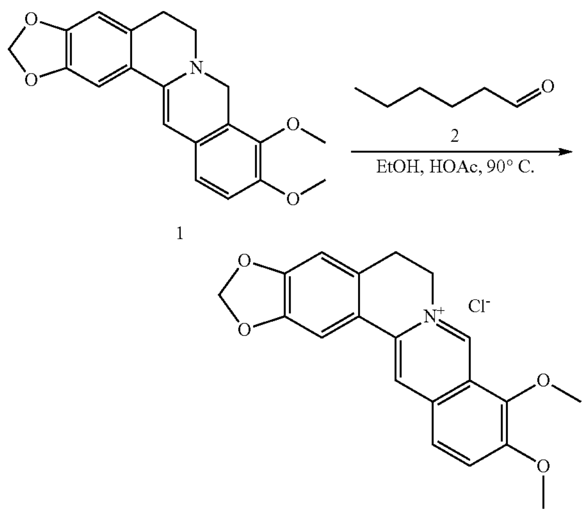

1

2

3

Compound 1 (2 g, 5.93 mmol, 1 eq) was dissolved in ethanol/acetic acid (30 mL/5 mL), and hexanal (5.9 g, 59.3 mmol, 10 eq) was added. The mixture was stirred at 90° C. for 4 h, the reaction was completed, an appropriate amount of hydrochloric acid was added, the mixture was concentrated and spin dried, a small amount of dichloromethane and an appropriate amount of ethyl acetate were added, the mixture was stewed for 0.5 h and then filtered to remove solid. The filtrate was stewed for overnight, the solid was filtered and dried to afford compound 3.

Step (2):

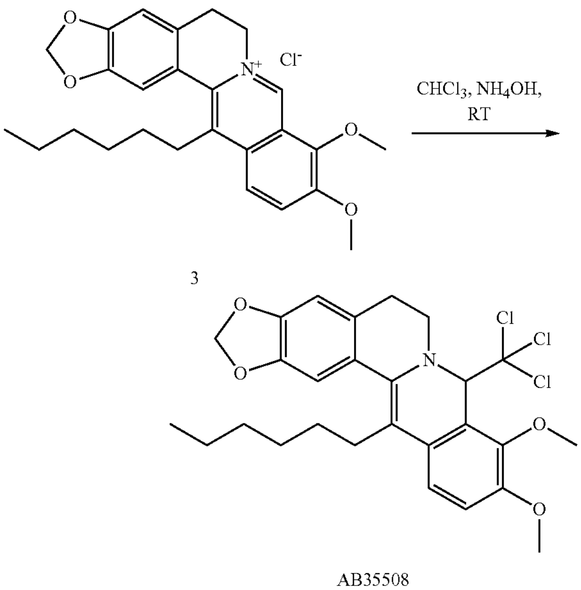

3

AB35508

Compound 3 (400 mg, 0.88 mmol, 1 eq) was dissolved in chloroform (20 mL), and aqueous ammonia (10 mL) was added. The mixture was reacted at room temperature for overnight, the reaction was completed. The reaction mixture was diluted with water and then extracted with dichloromethane, the organic phase was dried over anhydrous sodium sulfate, filtered and spin dried. The crude product was purified by fast chromatography (DCM/MeOH=100/1) to afford compound AB35508.

The MS-ESI and $^1$H NMR spectra of compound AB35508 were as follows:

MS-ESI: Calculated $[M+H]^+$: 5.38.12; Found $[M+H]^+$: 538.40.

$^1$H NMR (400 MHz, DMSO-d6) δ 7.16-7.05 (m, 2H), 6.88 (s, 1H), 6.79 (s, 1H), 6.02 (d, J=8.0 Hz, 2H), 5.55 (s, 1H), 4.07 (s, 1H), 3.81 (d, J=8.0 Hz, 6H), 3.60-3.57 (m, 1H), 2.74-2.54 (m, 2H), 1.38-1.21 (m, 10H), 0.87-0.84 (m, 3H).

Example 104 Synthesis of Compound AB35510

The structure of compound AB35510 was as follows:

AB35510

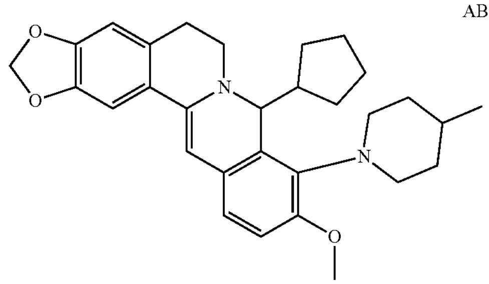

The synthesis method of compound AB35510 was as follows:

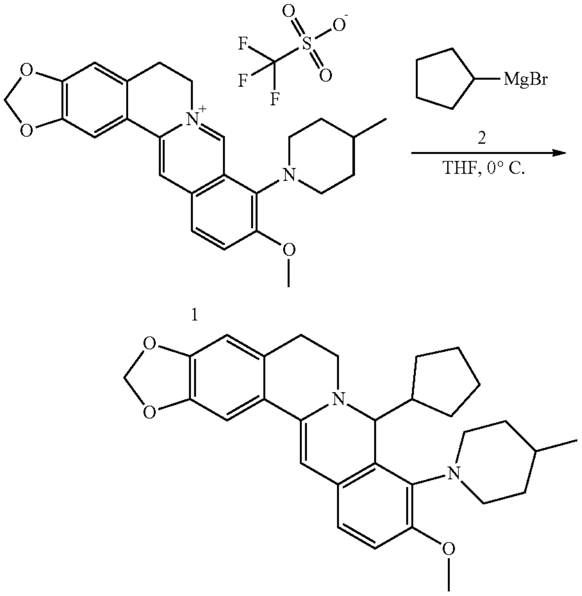

1

2

AB35510

Compound 1 (300 mg, 0.54 mmol, 1.0 eq) was dissolved in tetrahydrofuran (10 mL), and compound 2 (2.7 mL, 2.7 mmol, 5.0 eq, 1M in THF) was added at 0° C. The mixture was reacted at 0° C. for 0.5 h, and the reaction was detected to be performed completely using LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by fast chromatography (dichloromethane: methanol=100:1 to 50/1) to afford compound AB35510.

The MS-ESI and $^{1}H$ NMR spectra of compound AB35510 were as follows:

MS-ESI: Calculated $[M+H]^+$: 473.28, Found: 473.50.

$^{1}H$ NMR (400 MHz, DMSO-d6) δ 7.22 (s, 1H), 6.75 (s, 3H), 5.99 (s, 2H), 5.91 (s, 1H), 4.70 (d, J=8.0 Hz, 1H), 3.72 (s, 3H), 3.46-3.44 (m, 2H), 2.98-2.72 (m, 2H), 2.65-2.50 (m, 3H), 2.16-2.07 (m, 1H), 1.61-1.11 (m, 14H), 0.96 (d, J=4.0 Hz, 3H).

Example 105 Synthesis of Compound AB35512

The structure of compound AB35512 was as follows:

AB35512

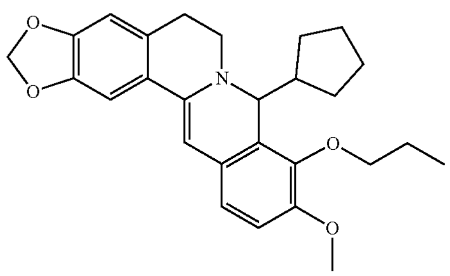

The synthesis method of compound AB35512 was as follows:

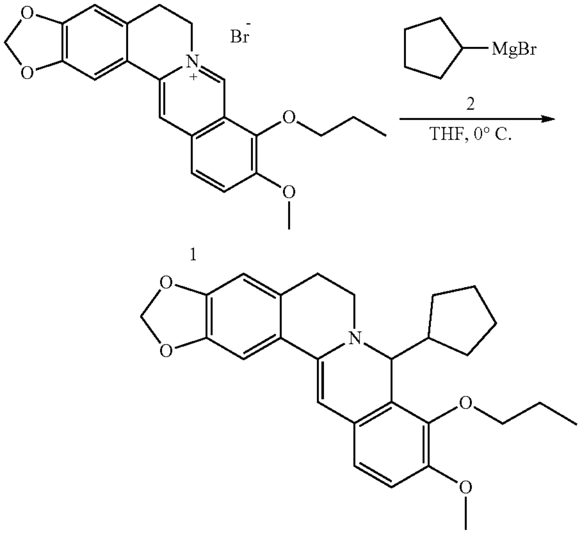

1

AB35512

Compound 1 (300 mg, 0.67 mmol, 1.0 eq) was dissolved in tetrahydrofuran (10 mL), and compound 2 (3.4 mL, 3.35 mmol, 5.0 eq, 1M in THF) was added at 0° C. The mixture was reacted at 0° C. for 0.5 h under $N_2$, and the reaction was detected to be performed completely using LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by fast chromatography (dichloromethane:methanol=100:1 to 50/1) to afford compound AB35512.

The MS-ESI and $^{1}H$ NMR spectra of compound AB35512 were as follows:

MS-ESI: Calculated $[M+H]^+$: 434.23, Found: 434.45.

$^{1}H$ NMR (400 MHz, DMSO-d6) δ 7.19 (s, 1H), 6.79-6.62 (m, 3H), 5.96 (s, 2H), 5.88 (s, 1H), 4.51 (d, J=8.0 Hz, 1H), 4.00-3.96 (m, 1H), 3.71-3.65 (m, 4H), 3.40-3.35 (m, 2H), 2.87-2.83 (m, 1H), 2.46-2.43 (m, 1H), 2.16-2.14 (m, 1H), 1.67-1.15 (m, 10H), 1.00-0.97 (m, 3H).

Example 106 Synthesis of Compound AB35514

The structure of compound AB35514 was as follows:

AB35514

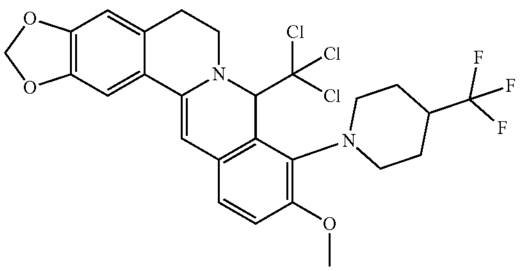

The synthesis method of compound AB35514 was as follows:

Step (1):

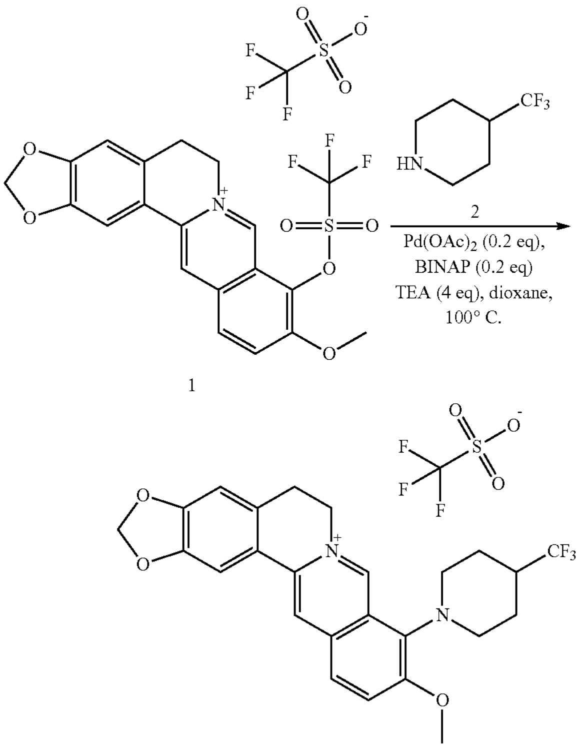

1

AB35513

Compound 1 (480 mg, 0.79 mmol, 1.0 eq) and compound 2 (484 mg, 3.16 mmol, 4.0 eq) were dissolved in dioxane (10 mL), and triethylamine (319 mg, 3.16 mmol, 4.0 eq), palladium acetate (35 mg, 0.16 mmol, 0.2 eq) and 1,1'-binaphthalene-2,2'-biphenylphosphine (100 mg, 0.16 mmol, 0.2 eq) were added. The mixture was reacted at 100° C. for 16 h under $N_2$, and the reaction was detected to be performed completely using LCMS. The reaction mixture was spin dried, the crude product was purified by fast chromatography (dichloromethane/methanol=100:1 to 50/1) to afford compound AB35513.

Step (2):

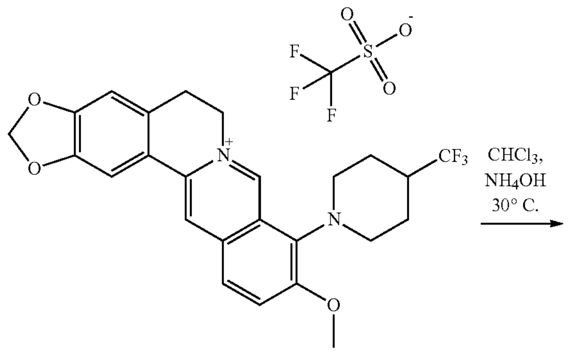

AB35513

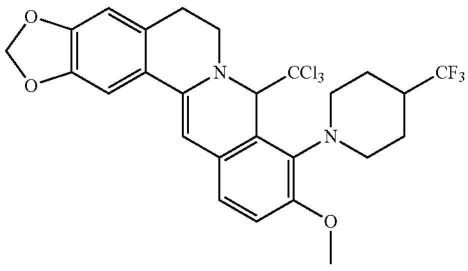

AB35514

Compound AB35513 (220 mg, 0.36 mmol, 1.0 eq) was dissolved in a mixture of chloroform (10 ml) and aqueous ammonia (2 ml). The mixture was reacted at 30° C. for 16 h, and the reaction was detected to be performed completely using LCMS. The reaction mixture was washed with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35514.

The MS-ESI and $^1$H NMR spectra of compound AB35514 were as follows:

MS-ESI: Calculated $[M]^+$: 403.20, Found: 403.20.

$^1$H NMR (400 MHz, DMSO-d6) δ 7.26 (s, 1H), 6.98-6.95 (m, 2H), 6.77 (s, 1H), 6.23 (s, 1H), 5.98-5.97 (m, 2H), 5.86 (s, 1H), 3.77-3.73 (m, 4H), 3.71-3.47 (m, 2H), 3.20-3.16 (m, 1H), 3.05-2.93 (m, 2H), 2.71-2.47 (m, 2H), 2.38-2.30 (m, 1H), 1.76-1.51 (m, 4H).

Example 107 Synthesis of Compound AB35518

The structure of compound AB35518 was as follows:

AB35518

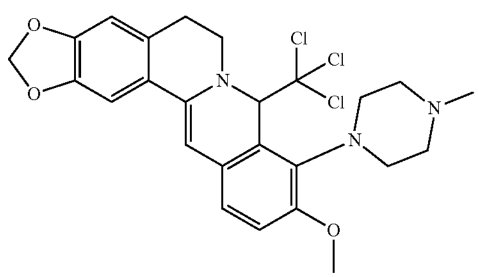

The synthesis method of compound AB35518 was as follows:

Step (1):

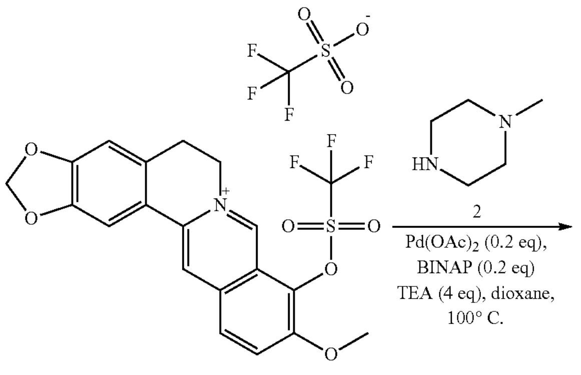

1

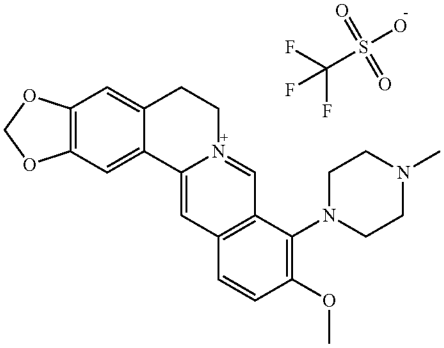

AB35517

Compound 1 (800 mg, 1.32 mmol, 1.0 eq) and compound 2 (529 mg, 5.28 mmol, 4.0 eq) were dissolved in dioxane (10 mL), and triethylamine (533 mg, 5.28 mmol, 4.0 eq), palladium acetate (64 mg, 0.26 mmol, 0.2 eq), and 1,1'-binaphthalene-2,2'-biphenylphosphine (162 mg, 0.26 mmol, 0.2 eq) were added. The mixture was reacted at 100° C. for 16 h under $N_2$, and the reaction was detected to be performed completely using LCMS. The reaction mixture was spin dried, the crude product was purified by fast chromatography (dichloromethane/methanol=100:1 to 50/1) to afford compound AB35517.

Step (2):

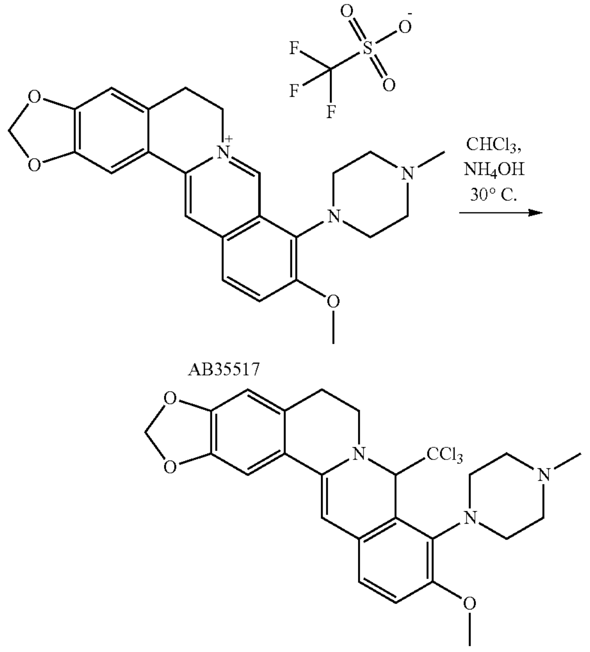

AB35517

AB35518

Compound AB35517 (355 mg, 0.64 mmol, 1.0 eq) was dissolved in a mixture of chloroform (10 ml) and aqueous ammonia (2 ml). The mixture was reacted at 30° C. for 16 h, and the reaction was detected to be performed completely using LCMS. The reaction mixture was washed with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35518.

The MS-ESI and $^1$H NMR spectra of compound AB35518 were as follows:

MS-ESI: Calculated $[M]^+$: 522.10, Found: 522.10.

$^1$H NMR (400 MHz, DMSO-d6) δ 7.30 (s, 1H), 7.01-6.98 (m, 2H), 6.80 (s, 1H), 6.28 (s, 1H), 6.01 (d, J=8.0 Hz, 2H), 5.96 (s, 1H), 3.79 (s, 3H), 3.76-3.64 (m, 3H), 3.33-3.09 (m, 2H), 2.70-2.50 (m, 5H), 2.22-2.09 (m, 5H).

Example 108 Synthesis of Compound AB35519

The structure of compound AB35519 was as follows:

AB35519

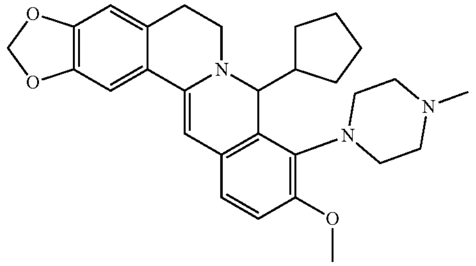

The synthesis method of compound AB35519 was as follows:

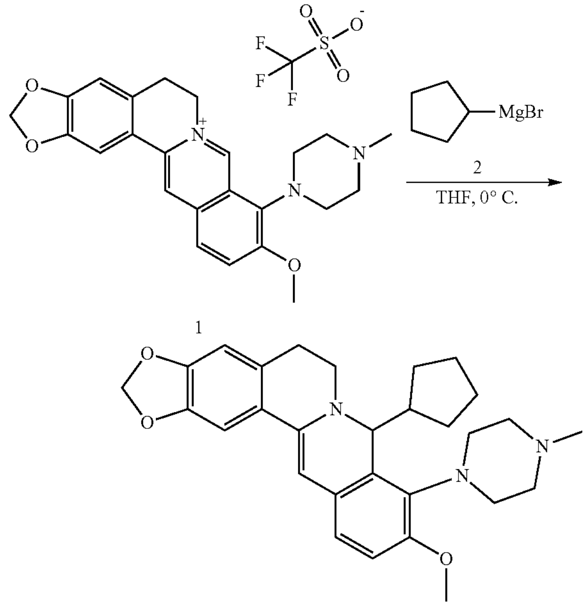

1

AB35519

Compound 1 (475 mg, 0.86 mmol, 1.0 eq) was dissolved in tetrahydrofuran (10 mL), and compound 2 (4.3 mL, 4.3 mmol, 5.0 eq, 1M in THF) was added at 0° C. The mixture was reacted at 0° C. for 0.5 h under $N_2$, and the reaction was detected to be performed completely using LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by fast chromatography (dichloromethane:methanol=100:1 to 50/1) to afford compound AB35519.

The MS-ESI and $^1$H NMR spectra of compound AB35519 were as follows:

MS-ESI: Calculated $[M+H]^+$: 474.27, Found: 474.25.

$^1$H NMR (400 MHz, $CDCl_3$) δ 7.13 (s, 1H), 6.82-6.67 (m, 2H), 6.56 (s, 1H), 5.92 (s, 2H), 5.82 (s, 1H), 4.82 (d, J=8.0 Hz, 1H), 3.76-3.74 (m, 1H), 3.55 (s, 3H), 3.54-3.51 (m, 1H), 3.41-3.33 (m, 2H), 2.79-2.73 (m, 6H), 2.35 (s, 3H), 2.18-2.16 (m, 3H), 1.58-1.49 (m, 2H), 1.39-1.24 (m, 6H).

Example 109 Synthesis of Compound AB35521

The structure of compound AB35521 was as follows:

AB35521

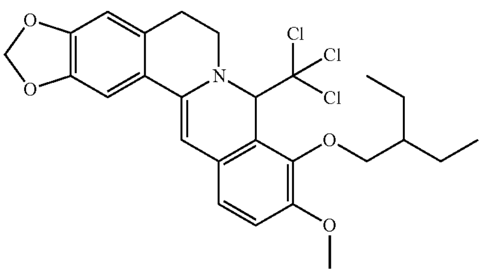

The synthesis method of compound AB35521 was as follows:

Step (1):

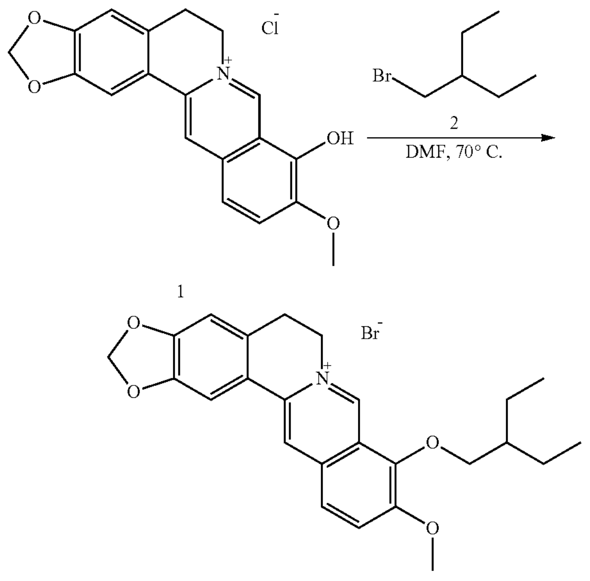

1

AB35520

Compound 1 (1 g, 2.79 mmol, 1 eq) was dissolved in N, N-dimethylformamide (20 mL), and compound 2 (460 mg, 13.95 mmol, 5 eq) was added. The mixture was reacted at 70° C. for overnight. The reaction mixture was washed with water and then extracted with dichloromethane twice, the organic phase was washed with brine, dried over anhydrous sodium sulfate and filtered, the filtrate was spin dried. The crude product was purified by fast chromatography (DCM/MeOH=50/1 to 30/1) to afford compound AB35520.

Step (2):

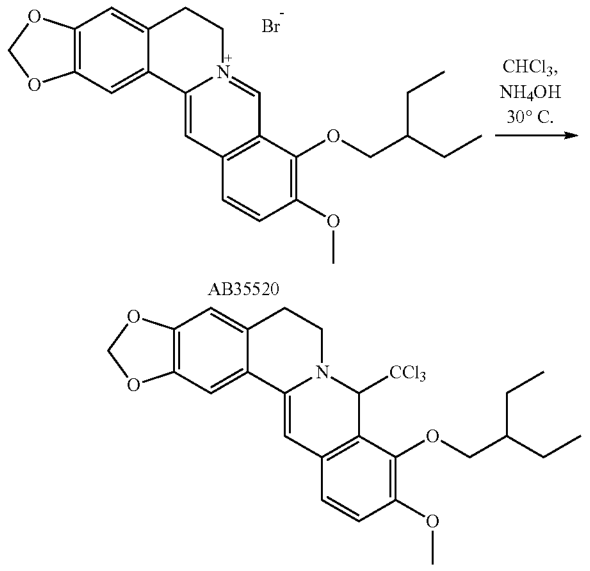

AB35520

AB35521

Compound AB35520 (300 mg, 0.62 mmol, 1.0 eq) was dissolved in a mixture of chloroform (10 ml) and aqueous ammonia (2 ml). The mixture was reacted at 30° C. for 16 h, and the reaction was detected to be performed completely using LCMS. The reaction mixture was washed with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35521.

The MS-ESI and $^1$H NMR spectra of compound AB35521 were as follows:

MS-ESI: Calculated $[M]^+$: 524.10, Found: 524.10.

$^1$H NMR (400 MHz, DMSO-d6) δ 7.30 (s, 1H), 7.04-6.86 (m, 2H), 6.76 (s, 1H), 6.30 (s, 1H), 5.98-5.96 (m, 2H), 5.52 (s, 1H), 4.17-4.14 (m, 1H), 3.66 (s, 3H), 3.65-3.56 (m, 3H), 3.24-3.19 (m, 1H), 2.48-2.46 (m, 1H), 1.51-1.39 (m, 5H), 0.93-0.90 (m, 6H).

Example 110 Synthesis of Compound AB35522

The structure of compound AB35522 was as follows:

AB35522

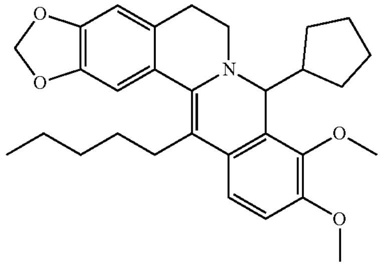

The synthesis method of compound AB35522 was as follows:

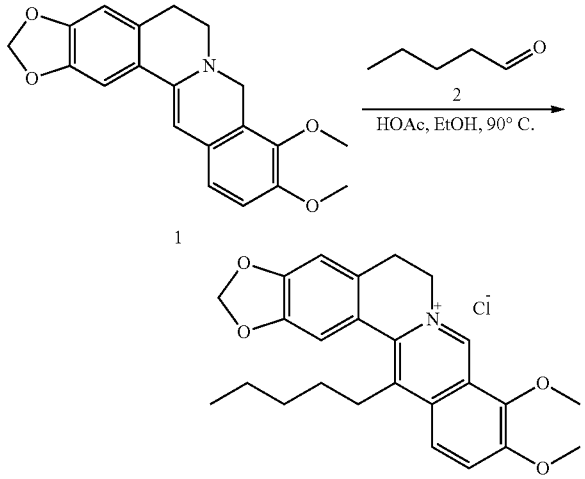

1

3

Compound 1 (1.0 g, 2.96 mmol, 1 eq) was dissolved in ethanol/acetic acid (20 mL/10 mL), and pentanal (2.5 g, 29.6 mmol, 10 eq) was added. The mixture was stirred at 90° C. for 4 h under $N_2$, the reaction was completed, an appropriate amount of hydrochloric acid was added, the mixture was concentrated and spin dried, a small amount of dichloromethane and an appropriate amount of ethyl acetate were added, the mixture was stewed for 0.5 h and then filtered to remove impurity solid. The filtrate was stewed for overnight and then filtered to afford compound 3.

Step (2):

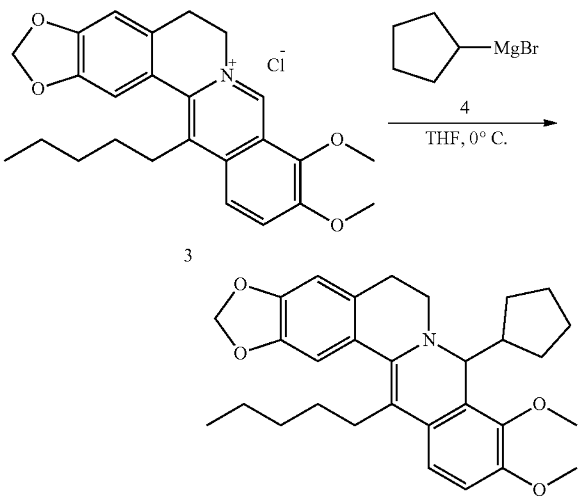

3

AB35522

Compound 3 (300 mg, 0.68 mmol, 1 eq) was dissolved in tetrahydrofuran (10 mL), and cyclopentylmagnesium bromide (3.4 mL, 3.4 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate, the organic phase was dried over anhydrous sodium sulfate, filtered and spin dried. The crude product was purified by fast chromatography (DCM/MeOH=100/1) to afford compound AB35522.

The MS-ESI and $^1$H NMR spectra of compound AB35522 were as follows:

MS-ESI: Calculated $[M+H]^+$: 476.28, Found: 476. 25.

$^1$H NMR (400 MHz, DMSO-d6) δ 6.91 (s, 2H), 6.87 (d, J=8.0 Hz, 2H), 6.04 (d, J=8.0 Hz, 2H), 6.45 (d, J=4.0 Hz, 1H), 3.80 (s, 3H), 3.76 (s, 3H), 3.37-3.33 (m, 2H), 2.69-2.51 (m, 4H), 2.15-2.09 (m, 1H), 1.69-1.62 (m, 1H), 1.38-1.22 (m, 13H), 0.92-0.89 (m, 3H).

Example 111 Synthesis of Compound AB35523

The structure of compound AB35523 was as follows:

AB35523

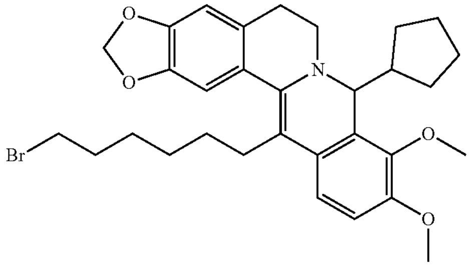

The synthesis method of compound AB35523 was as follows:

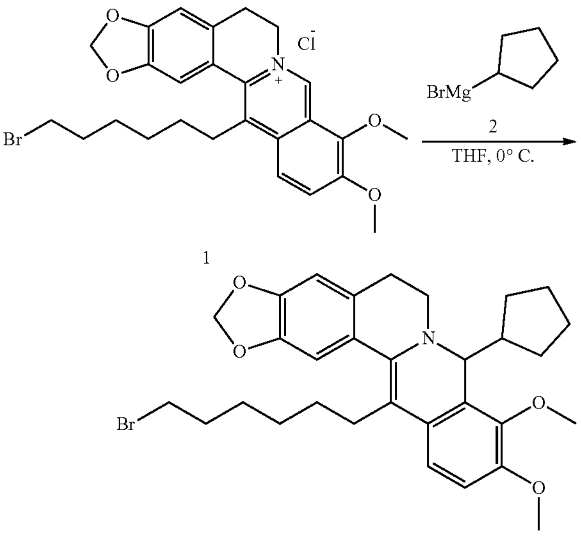

1

AB35523

Compound 1 (300 mg, 0.56 mmol, 1.0 eq) was dissolved in tetrahydrofuran (10 mL), and compound 2 (2.8 mL, 2.8 mmol, 5.0 eq, 1M in THF) was added at 0° C. The mixture was reacted at 0° C. for 0.5 h under $N_2$, and the reaction was detected to be performed completely using LCMS. The reaction mixture was quenched with saturated aqueous ammonium chloride solution and then extracted with ethyl acetate twice, the organic phase was dried over anhydrous sodium sulfate and filtered, the filtrate was spin dried. The crude product was purified by fast chromatography (dichloromethane/methanol=100/1 to 50/1) to afford compound AB35523.

The MS-ESI and $^1$H NMR spectra of compound AB35523 were as follows:

MS-ESI: Calculated $[M+H]^+$: 568.20, Found: 568.20.

$^1$H NMR (400 MHz, DMSO-d6) δ 6.88 (s, 2H), 6.84 (d, J=4.0 Hz, 2H), 6.01 (s, 2H), 4.01 (d, J=8.0 Hz, 1H), 3.77 (s, 3H), 3.73 (s, 3H), 3.50-3.48 (m, 2H), 3.31 (s, 1H), 2.66-2.48 (m, 4H), 2.09-2.06 (m, 1H), 1.78-1.76 (m, 2H), 1.45-1.42 (m, 1H), 1.29-1.19 (m, 14H).

Example 112 Synthesis of Compound AB35524

The structure of compound AB35524 was as follows:

AB35524

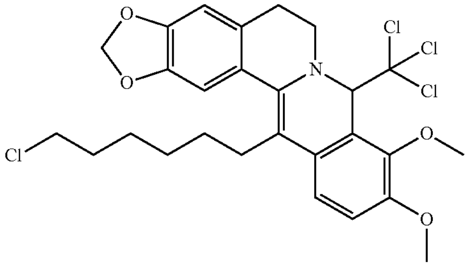

The synthesis method of compound AB35524 was as follows:

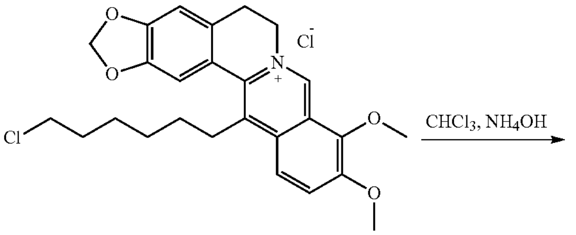

1

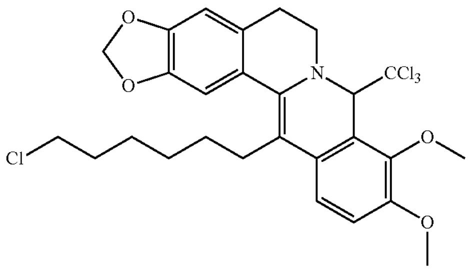

AB35524

Compound 1 (300 mg, 0.61 mmol, 1.0 eq) was dissolved in a mixture of chloroform (10 ml) and aqueous ammonia (2 ml). The mixture was reacted at 30° C. for 16 h, and the reaction was detected to be performed completely using LCMS. The reaction mixture was washed with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35524.

The MS-ESI and $^{1}$H NMR spectra of compound AB35524 were as follows:

MS-ESI: Calculated $[M+H]^+$: 572.08, Found: 572.10.

$^{1}$H NMR (400 MHz, DMSO-d6) δ 7.14-7.04 (m, 2H), 6.87 (s, 1H), 6.78 (s, 1H), 6.01 (d, J=8.0 Hz, 2H), 5.54 (m, 1H), 3.85-3.79 (m, 7H), 3.60-3.56 (m, 3H), 2.73-2.53 (m, 4H), 1.72-1.59 (m, 3H), 1.45-1.35 (m, 5H).

Example 113 Synthesis of Compound AB35525

The structure of compound AB35525 was as follows:

AB35525

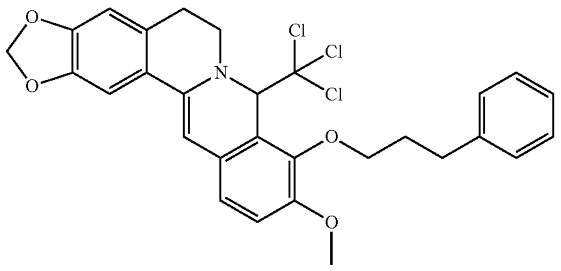

The synthesis method of compound AB35525 was as follows:

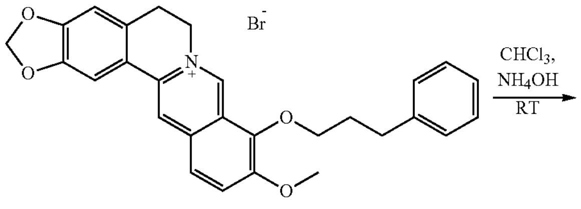

1

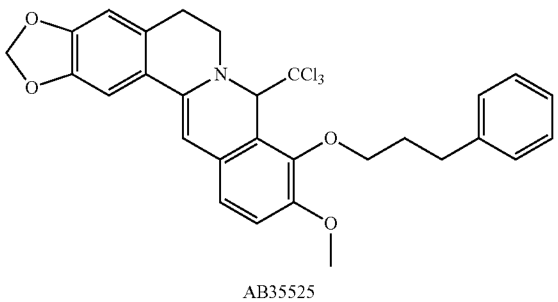

AB35525

Compound 1 (300 mg, 0.58 mmol, 1.0 eq) was dissolved in a mixture of chloroform (10 ml) and aqueous ammonia (2 ml). The mixture was reacted at room temperature for 16 h, and the reaction was detected to be performed completely using LCMS. The reaction mixture was washed with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35525.

The MS-ESI and $^{1}$H NMR spectra of compound AB35525 were as follows:

MS-ESI: Calculated $[M+H]^+$: 558.10, Found: 558.10.

$^{1}$H NMR (400 MHz, DMSO-d6) δ 7.30-7.15 (m, 6H), 7.06 (d, J=8.0 Hz, 1H), 6.87 (d, J=8.0 Hz, 1H), 6.77 (s, 1H), 6.30 (s, 1H), 5.98 (d, J=8.0 Hz, 2H), 5.55 (m, 1H), 4.15-4.09 (m, 1H), 3.78-3.67 (m, 4H), 3.57-3.50 (m, 2H), 3.20-3.17 (m, 1H), 3.11-2.62 (m, 3H), 2.02-1.95 (m, 2H).

Example 114 Synthesis of Compound AB35531

The structure of compound AB35531 was as follows:

AB35531

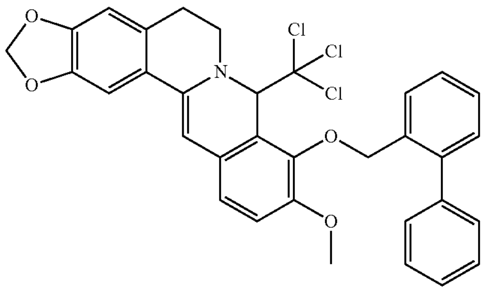

The synthesis method of compound AB35531 was as follows:

Step (1):

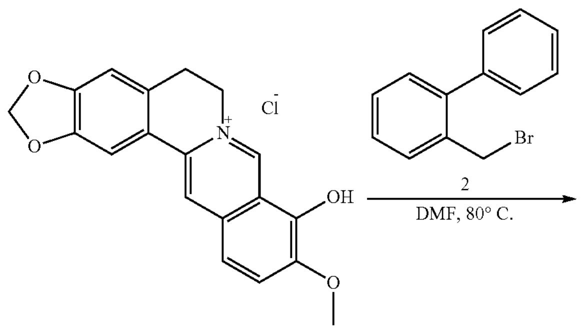

1

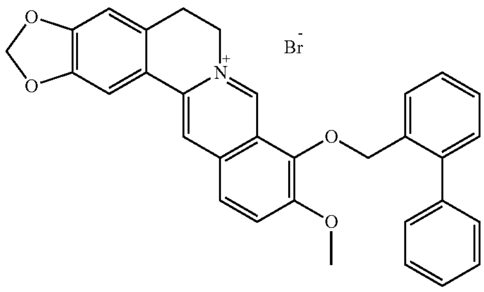

3

Compound 1 (500 mg, 1.4 mmol, 1 eq) was dissolved in N, N-dimethylformamide (20 mL), and compound 2 (1.7 g, 7 mmol, 5 eq) was added. The mixture was reacted at 80° C. for overnight. The reaction mixture was diluted with water and then extracted with dichloromethane twice, the organic phase was washed with brine, dried over anhydrous sodium sulfate and filtered, the filtrate was spin dried. The crude product was purified by fast chromatography (DCM/MeOH=50/1 to 30/1) to afford compound 3.

Step (2):

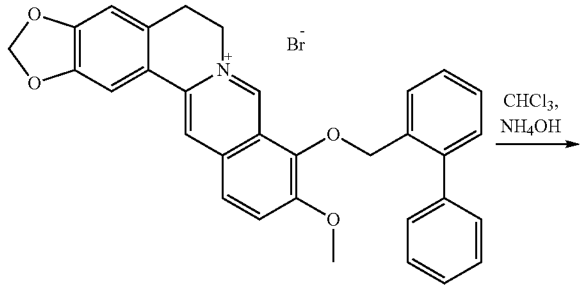

3

-continued

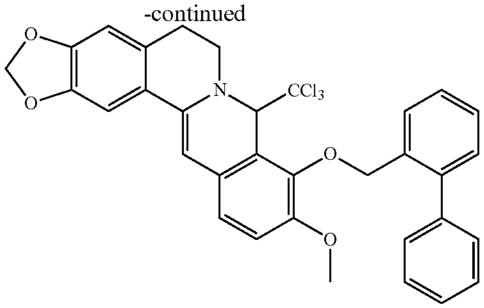

AB35531

Compound 3 (300 mg, 0.53 mmol, 1.0 eq) was dissolved in a mixture of chloroform (10 ml) and aqueous ammonia (2 ml). The mixture was reacted at 30° C. for 16 h, and the reaction was detected to be performed completely using LCMS. The reaction mixture was diluted with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35531.

The MS-ESI and $^1$H NMR spectra of compound AB35531 were as follows:

MS-ESI: Calculated $[M+H]^+$: 606.10, Found: 606.10.

$^1$H NMR (400 MHz, DMSO-d6) δ 7.43-7.36 (m, 9H), 7.29 (s, 1H), 7.04-6.77 (m, 2H), 6.77 (s, 1H), 6.26 (s, 1H), 6.01 (d, J=4.0 Hz, 2H), 5.10 (s, 1H), 5.02 (d, J=8.0 Hz, 1H), 4.85 (d, J=8.0 Hz, 1H), 3.73 (s, 3H), 3.22-3.25 (m, 1H), 3.11-3.04 (m, 2H), 2.59-2.55 (m, 1H).

Example 115 Synthesis of Compound AB35534

The structure of compound AB35534 was as follows:

AB35534

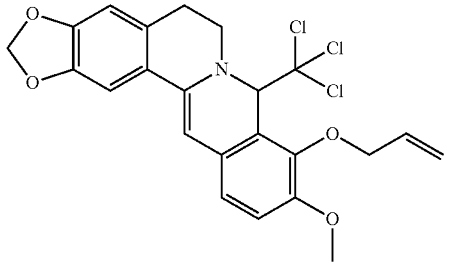

The synthesis method of compound AB35534 was as follows:

Step (1):

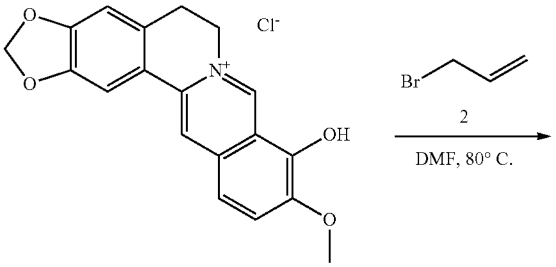

1

-continued

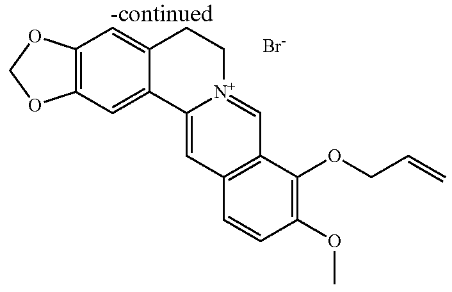

3

Compound 1 (1 g, 2.79 mmol, 1 eq) was dissolved in N, N-dimethylformamide (20 mL), and compound 2 (1.7 g, 13.95 mmol, 5 eq) was added. The mixture was reacted at 80° C. for overnight. The reaction mixture was washed with water and then extracted with dichloromethane twice, the organic phase was washed with brine, dried over anhydrous sodium sulfate and filtered, the filtrate was spin dried. The crude product was purified by fast chromatography (DCM/MeOH=50/1 to 30/1) to afford compound 3.

Step (2):

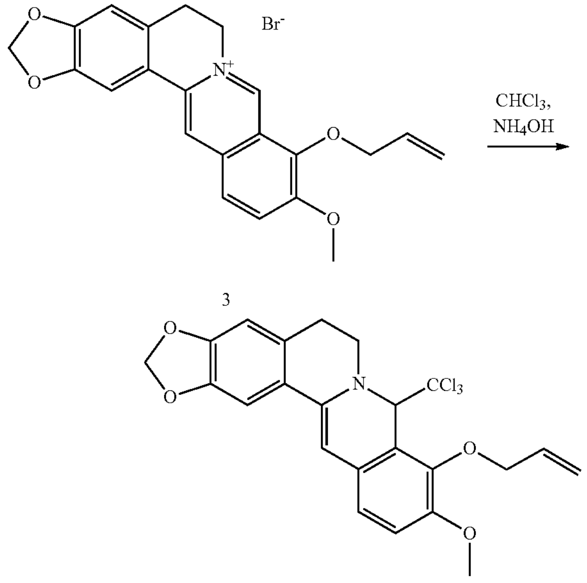

3

AB35534

Compound 3 (500 mg, 1.13 mmol, 1.0 eq) was dissolved in a mixture of chloroform (10 ml) and aqueous ammonia (2 ml). The mixture was reacted at 30° C. for 16 h, and the reaction was detected to be performed completely using LCMS. The reaction mixture was washed with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35534.

The MS-ESI and $^1$H NMR spectra of compound AB35534 were as follows:

MS-ESI: Calculated $[M+H]^+$: 480.05, Found: 480.05.

$^1$H NMR (400 MHz, DMSO-d6) δ 7.30 (s, 1H), 7.07-6.87 (m, 2H), 6.77 (s, 1H), 6.30 (s, 1H), 6.07-5.97 (m, 3H), 5.58 (s, 1H), 3.32-5.18 (m, 2H), 4.65-4.61 (m, 1H), 4.40-4.38 (m, 1H), 3.79 (s, 3H), 3.70-3.57 (m, 2H), 3.22-3.20 (m, 1H), 2.70-2.65 (m, 1H).

Example 116 Synthesis of Compound AB35535

The structure of compound AB35535 was as follows:

AB35535

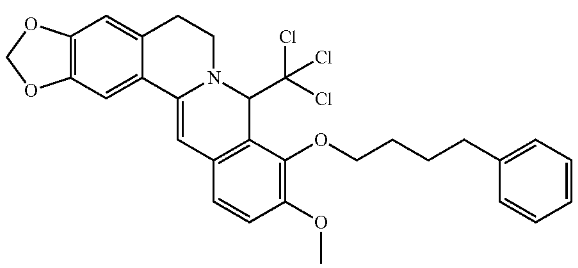

The synthesis method of compound AB35535 was as follows:

Step (1):

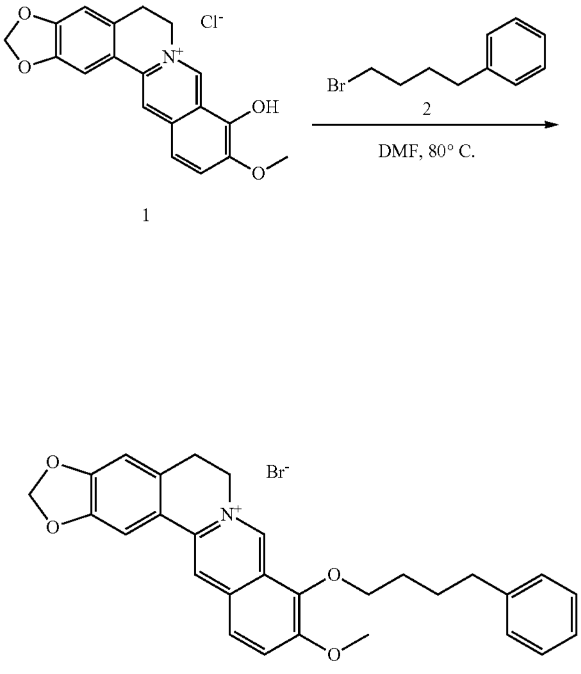

1

2

3

Compound 1 (500 mg, 1.4 mmol, 1 eq) was dissolved in N, N-dimethylformamide (20 mL), and compound 2 (1.5 g, 7 mmol, 5 eq) was added. The mixture was reacted at 80° C. for overnight. The reaction mixture was diluted with water and then extracted with dichloromethane twice, the organic phase was washed with brine, dried over anhydrous sodium sulfate and filtered, the filtrate was spin dried. The crude product was purified by fast chromatography (DCM/MeOH=50/1 to 30/1) to afford compound 3.

Step (2):

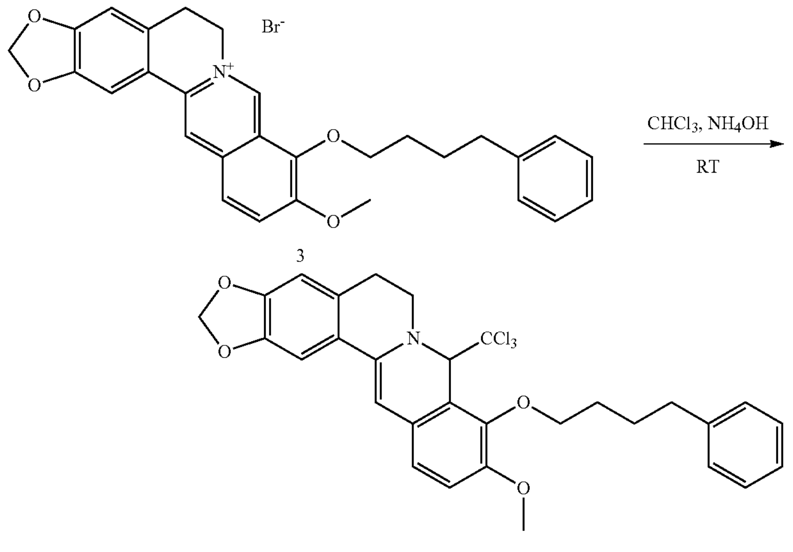

3

AB35535

Compound 3 (300 mg, 0.56 mmol, 1.0 eq) was dissolved in a mixture of chloroform (10 ml) and aqueous ammonia (2 ml). The mixture was reacted at room temperature for 16 h, and the reaction was detected to be performed completely using LCMS. The reaction mixture was diluted with water and then extracted with dichloromethane, the organic phase was dried over anhydrous sodium sulfate and filtered, the filtrate was spin dried. The crude product was purified by fast chromatography (dichloromethane/methanol=100/1 to 50/1) to afford compound AB35535.

The MS-ESI and $^1$H NMR spectra of compound AB35535 were as follows:

MS-ESI: Calculated $[M+H]^+$: 572.11, Found: 572.11.

$^1$H NMR (400 MHz, DMSO-d6) δ 7.30 (s, 1H), 7.23-7.12 (m, 5H), 7.05 (d, J=8.0 Hz, 1H), 6.85 (d, J=8.0 Hz, 1H), 6.76 (s, 1H), 6.29 (s, 1H), 5.98 (d, J=8.0 Hz, 2H), 5.53 (s, 1H), 4.17-4.13 (m, 1H), 3.78-3.77 (m, 1H), 3.76 (s, 3H), 3.62-3.50 (m, 2H), 3.19-3.17 (m, 1H), 2.63-2.61 (m, 3H), 1.76-1.66 (m, 4H).

Example 117 Synthesis of Compound AB35536

The structure of compound AB35536 was as follows:

AB35536

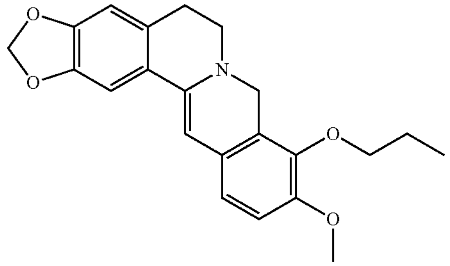

The synthesis method of compound AB35536 was as follows:

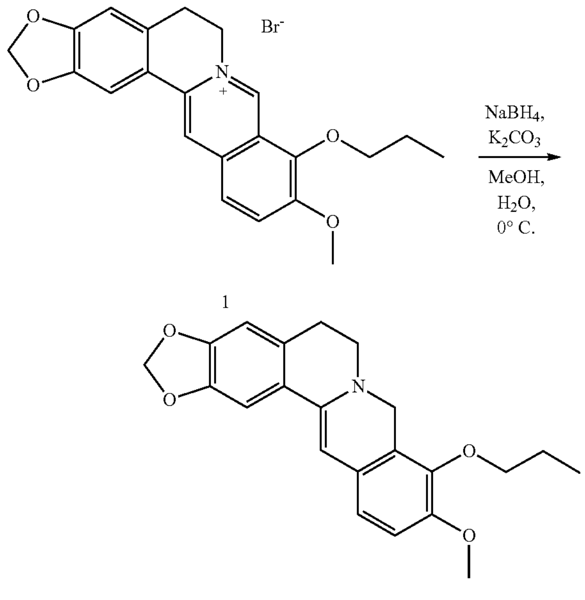

1

AB35536

Compound 1 (500 mg, 1.12 mmol, 1.0 eq) was dissolved in methanol (10 mL), and aqueous potassium carbonate solution (464 mg, 3.36 mmol, 3.0 eq, 3 mL) and aqueous sodium borohydride solution (13 mg, 0.336 mmol, 0.3 eq, 0.3 mL) were added at 0° C. The mixture was reacted at 0° C. for 3 min, and the reaction was detected to be performed completely using LCMS, the solid was filtered and then washed with water, the crude product was purified by fast chromatography (dichloromethane/methanol=0-2%) to afford compound AB35536.

The MS-ESI and $^1$H NMR spectra of compound AB35536 were as follows:

MS-ESI: Calculated $[M+H]^+$: 366.17, Found: 366.30.

$^1$H NMR (400 MHz, DMSO-d6) δ 7.26 (s, 1H), 6.79-6.64 (m, 3H), 6.02 (s, 1H), 5.97 (s, 2H), 4.17 (s, 2H), 3.82-3.79 (m, 2H), 3.72 (s, 3H), 3.02-3.00 (m, 2H), 2.77-2.76 (m, 2H), 1.68-1.63 (m, 2H), 0.97-0.93 (m, 3H).

Example 118 Synthesis of Compound AB35543

The structure of compound AB35543 was as follows:

AB35543

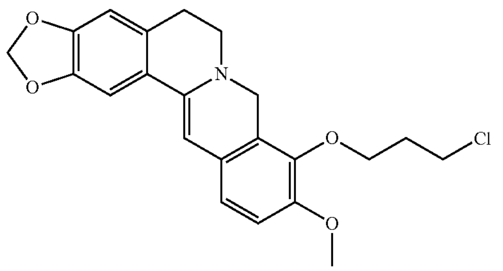

The synthesis method of compound AB35543 was as follows:

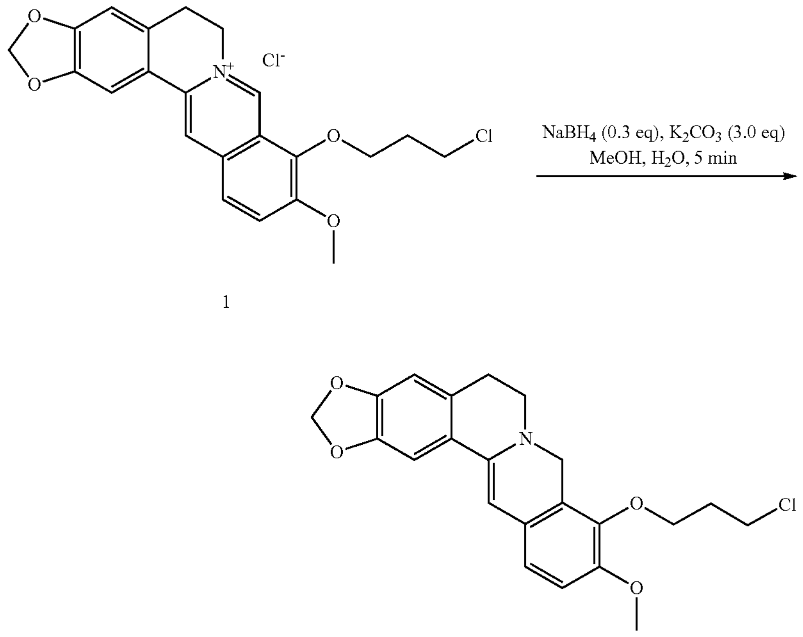

1

AB35543

Compound 1 (830 mg, 1.91 mmol, 1.0 eq) was dissolved in methanol (10 mL), and aqueous potassium carbonate solution (791 mg, 5.73 mmol, 3.0 eq, 3 mL) and aqueous sodium borohydride solution (22 mg, 0.573 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-2%) to afford compound AB35543.

The MS-ESI and 1H NMR spectra of Compound AB35543 were as follows:

MS-ESI: Calculated $[M+H]^+$: 400.13, Found: 400.15.

$^1$H NMR (400 MHz, DMSO-d6) δ 7.29 (s, 1H), 6.84-6.69 (m, 3H), 6.05 (s, 1H), 6.00 (s, 2H), 4.21 (s, 2H), 4.01-3.98 (m, 2H), 3.87-3.84 (m, 2H), 3.76 (s, 3H), 3.07-3.04 (m, 2H), 2.81-2.78 (m, 2H), 2.15-2.09 (m, 2H).

Example 119 Synthesis of Compound AB35544

The structure of compound AB35544 was as follows:

AB35544

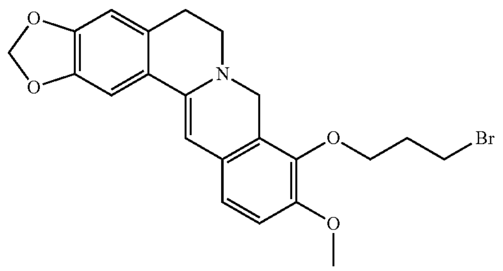

The synthesis method of compound AB35544 was as follows:

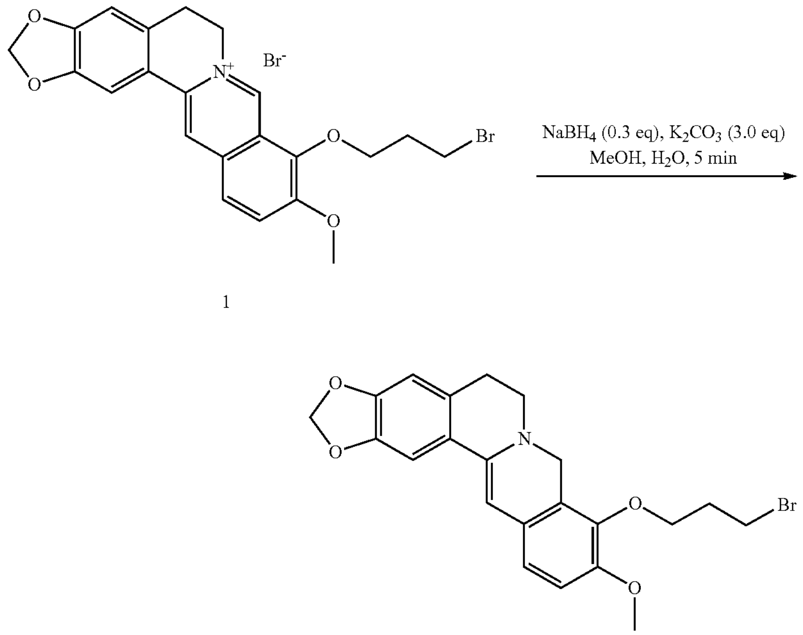

1

AB35544

Compound 1 (125 mg, 0.24 mmol, 1.0 eq) was dissolved in methanol (10 mL), and aqueous potassium carbonate solution (99 mg, 0.72 mmol, 3.0 eq, 3 mL) and aqueous sodium borohydride solution (3 mg, 0.072 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-2%) to afford compound AB35544.

The MS-ESI and $^1H$ NMR spectra of compound AB35544 were as follows:

MS-ESI: Calculated $[M+H]^+$: 444.08, Found: 444.05.

$^1H$ NMR (400 MHz, DMSO-d6) δ 7.29 (s, 1H), 6.84-6.69 (m, 3H), 6.05 (s, 1H), 6.00 (s, 2H), 4.22 (s, 2H), 4.00-3.97 (m, 2H), 3.76-3.71 (m, 5H), 3.07-3.04 (m, 2H), 2.81-2.78 (m, 2H), 2.23-2.18 (m, 2H).

Example 120 Synthesis of Compound AB35545

The structure of compound AB35545 was as follows:

AB35545

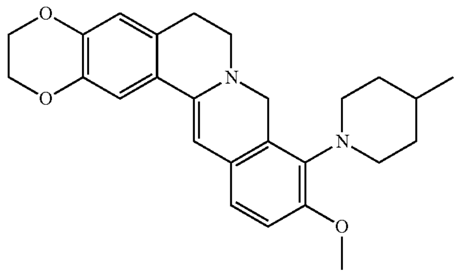

The synthesis method of compound AB35545 was as follows:

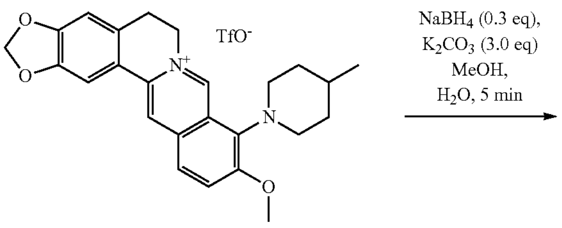

1

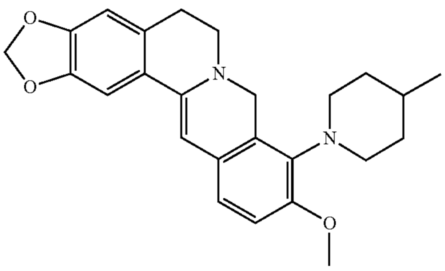

AB35545

Compound 1 (145 mg, 0.26 mmol, 1.0 eq) was dissolved in methanol (10 mL), and aqueous potassium carbonate solution (108 mg, 0.78 mmol, 3.0 eq, 3 mL) and aqueous sodium borohydride solution (3 mg, 0.078 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB35545.

The MS-ESI and $^1$H NMR spectra of compound AB35545 were as follows:

MS-ESI: Calculated [M+H]$^+$: 405.21, Found: 405.25.

$^1$H NMR (400 MHz, DMSO-d6) δ 7.28 (s, 1H), 6.75-6.74 (m, 3H), 6.03 (s, 1H), 6.00 (s, 2H), 4.25 (s, 2H), 3.73 (s, 3H), 3.21-3.16 (m, 2H), 3.05-3.02 (m, 2H), 2.81-2.78 (m, 2H), 2.72 (d, J=12.0 Hz, 2H), 1.62 (d, J=12.0 Hz, 2H), 1.39 (s, 1H), 1.30-1.23 (m, 2H), 0.96 (d, J=4.0 Hz, 3H).

Example 121 Synthesis of Compound AB35550

The structure of compound AB35550 was as follows:

AB35550

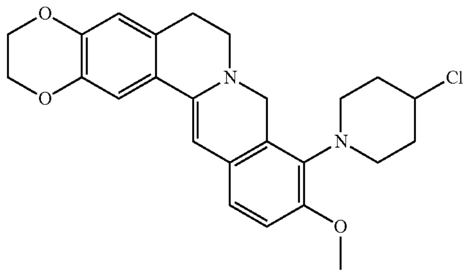

The synthesis method of compound AB35550 was as follows:

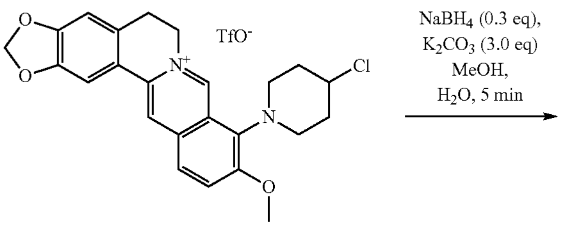

1

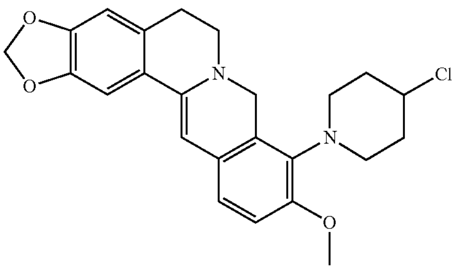

AB35550

Compound 1 (530 mg, 0.92 mmol, 1.0 eq) was dissolved in methanol (10 mL), and aqueous potassium carbonate solution (381 mg, 2.76 mmol, 3.0 eq, 3 mL) and aqueous sodium borohydride solution (10 mg, 0.078 mmol, 0.27 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB35550.

The MS-ESI and $^1$H NMR spectra of compound AB35550 were as follows:

MS-ESI: Calculated [M+H]$^+$: 425.16, Found: 425.15.

$^1$H NMR (400 MHz, DMSO-d6) δ 7.29 (s, 1H), 6.75 (s, 3H), 6.03 (s, 1H), 6.00 (s, 2H), 4.28 (s, 2H), 4.14-4.08 (m, 1H), 3.76-3.73 (m, 3H), 3.60-3.53 (m, 1H), 3.29-3.23 (m, 2H), 3.08-3.02 (m, 2H), 2.80-2.76 (m, 3H), 2.62-2.57 (m, 1H), 2.13-2.10 (m, 2H), 1.91-1.85 (m, 2H).

Example 122 Synthesis of Compound AB35590

The structure of compound AB35590 was as follows:

AB35590

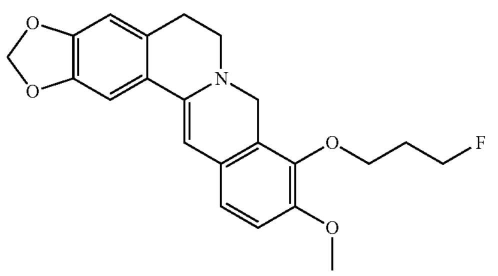

The synthesis method of compound AB35590 was as follows:

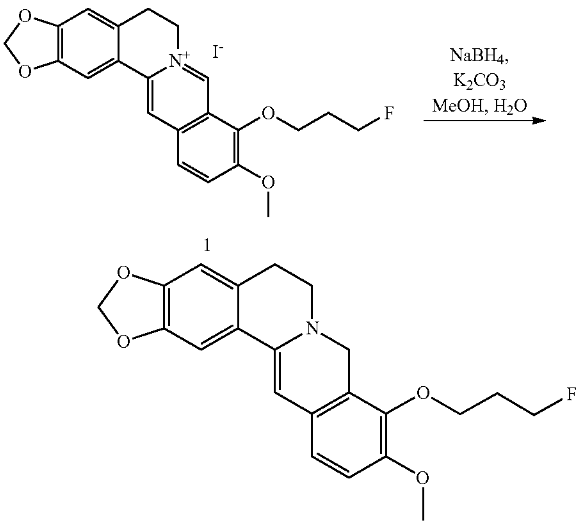

1

AB35590

Compound 1 (100 mg, 0.19 mmol, 1.0 eq) was dissolved in methanol (5 mL), and aqueous potassium carbonate solution (81 mg, 0.59 mmol, 3.0 eq, 2 mL) and aqueous sodium borohydride solution (2 mg, 0.057 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB35590.

The MS-ESI and $^1$H NMR spectra of compound AB35590 were as follows:

MS-ESI: Calculated $[M+H]^+$: 384.16, Found: 384.20.

$^1$H NMR (400 MHz, DMSO-d6) δ 7.30 (s, 1H), 6.84-6.69 (m, 3H), 6.06 (s, 1H), 6.00 (s, 2H), 4.73-4.70 (m, 1H), 4.61-4.58 (m, 1H), 4.20 (s, 2H), 3.99-3.96 (m, 2H), 3.76 (s, 3H), 3.07-3.04 (m, 2H), 2.81-2.78 (m, 2H), 2.11-2.01 (m, 2H).

Example 123 Synthesis of Compound AB35594

The structure of compound AB35594 was as follows:

AB35594

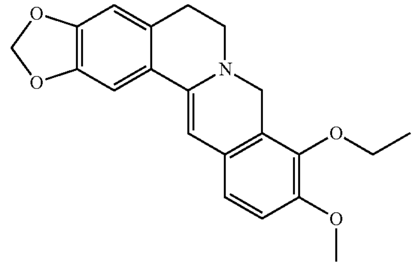

The synthesis method of compound AB35594 was as follows:

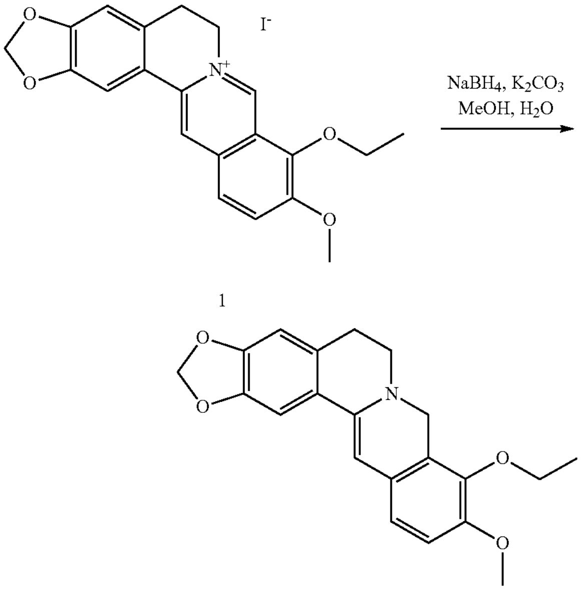

1

AB35594

Compound 1 (390 mg, 0.82 mmol, 1.0 eq) was dissolved in methanol (10 mL), and aqueous potassium carbonate solution (339 mg, 2.46 mmol, 3.0 eq, 2 mL) and aqueous sodium borohydride solution (9 mg, 0.057 mmol, 0.24 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB35594.

The MS-ESI and $^1$H NMR spectra of compound AB35594 were as follows:

MS-ESI: Calculated $[M+H]^+$: 352.15, Found: 352.20.

$^1$H NMR (400 MHz, DMSO-d6) δ 7.29 (s, 1H), 6.82-6.67 (m, 3H), 6.05 (s, 1H), 6.00 (s, 2H), 4.20 (s, 2H), 3.97-3.92 (m, 2H), 3.75 (s, 3H), 3.07-3.04 (m, 2H), 2.81-2.50 (m, 2H), 1.29-1.25 (m, 3H).

Example 124 Synthesis of Compound AB35599

The structure of compound AB35599 was as follows:

AB35599

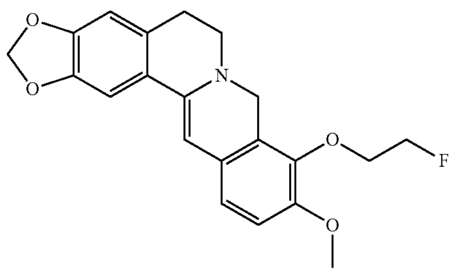

The synthesis method of compound AB35599 was as follows:

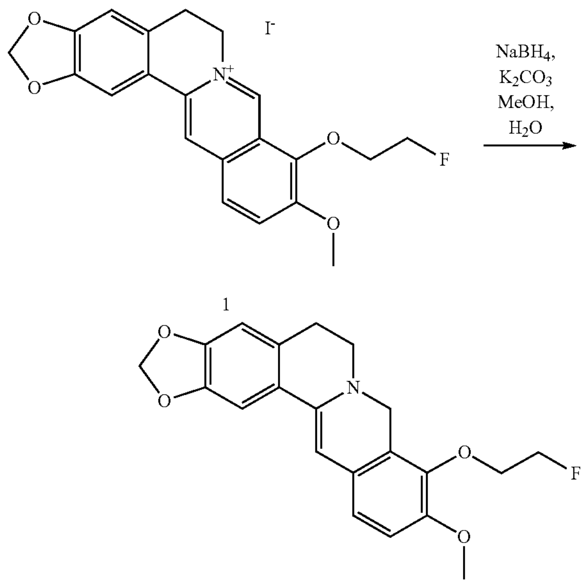

1

AB35599

Compound 1 (500 mg, 1.0 mmol, 1.0 eq) was dissolved in methanol (10 mL), and aqueous potassium carbonate solution (414 mg, 3.0 mmol, 3.0 eq, 2 mL) and aqueous sodium borohydride solution (11 mg, 0.3 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB35599.

The MS-ESI and $^1$H NMR spectra of compound AB35599 were as follows:

MS-ESI: Calculated $[M+H]^+$: 370.14, Found: 370.00.

$^1$H NMR (400 MHz, DMSO-d6) δ 7.30 (s, 1H), 6.85-6.70 (m, 3H), 6.06 (s, 1H), 6.00 (s, 2H), 4.72-4.71 (m, 1H), 4.60-4.59 (m, 1H), 4.22 (s, 3H), 4.14-4.12 (m, 1H), 3.76 (s, 3H), 3.05-3.02 (m, 2H), 2.81-2.78 (m, 2H).

Example 125 Synthesis of Compound AB36403

The structure of compound AB36403 was as follows:

AB36403

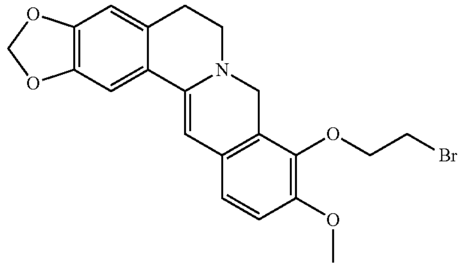

The synthesis method of compound AB36403 was as follows:

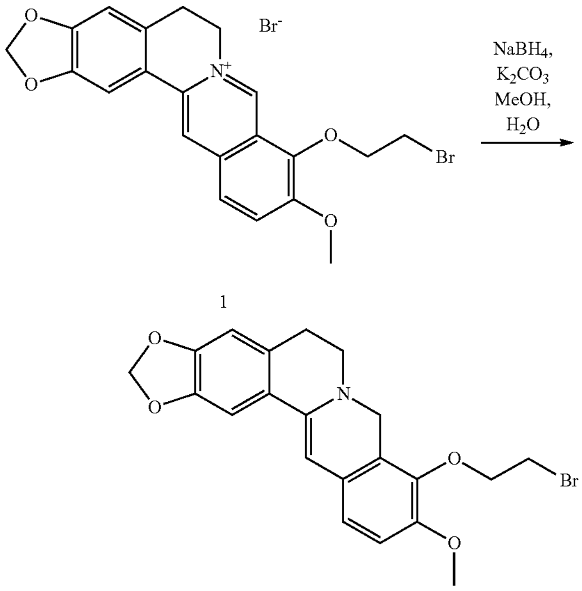

1

AB36403

Compound 1 (500 mg, 0.98 mmol, 1.0 eq) was dissolved in methanol (10 mL), and aqueous potassium carbonate solution (406 mg, 2.94 mmol, 3.0 eq, 2 mL) and aqueous sodium borohydride solution (11 mg, 0.057 mmol, 0.29 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36403.

The MS-ESI and $^1$H NMR spectra of compound AB36403 were as follows:

MS-ESI: Calculated $[M+H]^+$: 430.06, Found: 430.25.

$^1$H NMR (400 MHz, DMSO-d6) δ 7.30 (s, 1H), 6.84-6.70 (m, 3H), 6.06 (s, 1H), 6.00 (s, 2H), 4.29-4.24 (m, 4H), 3.80-3.74 (m, 5H), 3.07-3.04 (m, 2H), 2.81-2.78 (m, 2H).

Example 126 Synthesis of Compound AB36415

The structure of compound AB36415 was as follows:

AB36415

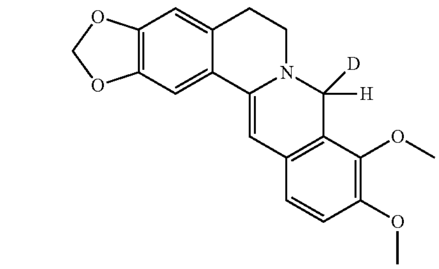

The synthesis method of compound AB36415 was as follows:

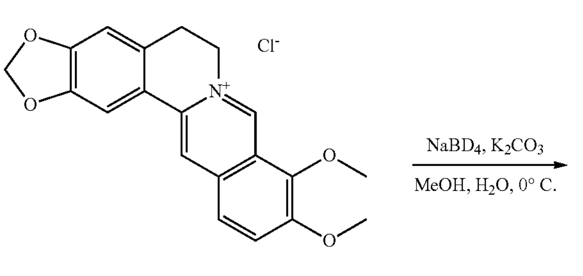

1

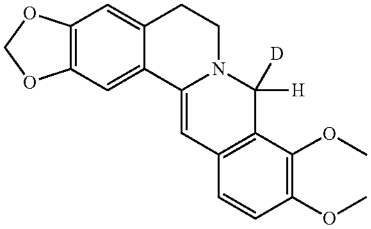

AB36415

Compound 1 (500 mg, 1.34 mmol, 1.0 eq) was dissolved in methanol (10 mL), and aqueous potassium carbonate solution (555 mg, 4.02 mmol, 3.0 eq, 2 mL) and aqueous deuterated sodium borohydride solution (15 mg, 0.057 mmol, 0.40 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36415.

The MS-ESI and 1H NMR spectra of Compound AB36415 were as follows:

MS-ESI: Calculated $[M+H]^+$: 339.14, Found: 339.05.

$^1$H NMR (400 MHz, DMSO-d6) δ 7.29 (s, 1H), 6.83-6.68 (m, 3H), 6.05 (s, 1H), 6.00 (s, 2H), 4.16 (s, 1H), 3.76 (s, 3H), 3.71 (s, 3H), 3.07-3.03 (m, 2H), 2.81-2.78 (m, 2H).

Example 127 Synthesis of Compound AB36416

The structure of compound AB36416 was as follows:

AB36416

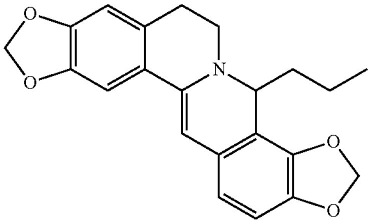

The synthesis method of compound AB36416 was as follows:

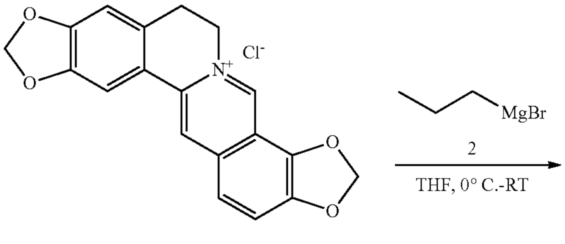

1

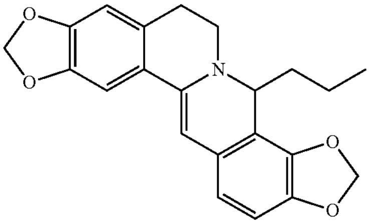

AB36416

Compound 1 (300 mg, 0.84 mmol, 1.0 eq) was dissolved in tetrahydrofuran (20 mL), and compound 2 (4.2 mL, 4.2 mmol, 5.0 eq, 1 mol/L) was added at 0° C. The mixture was reacted at room temperature for 30 min. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane:methanol=0-5%) to afford compound AB36416.

The MS-ESI and $^1$H NMR spectra of compound AB36416 were as follows:

MS-ESI: Calculated $[M+H]^+$: 364.15, Found: 364.15.

$^1$H NMR (400 MHz, DMSO-d6) δ 7.19 (s, 1H), 6.74 (s, 1H), 6.66 (d, J=8.0 Hz, 1H), 6.43 (d, J=8.0 Hz, 1H), 5.99 (s, 1H), 5.97 (d, J=4.0 Hz, 2H), 5.86 (s, 1H), 5.82 (s, 1H), 4.53-4.50 (m, 1H), 3.25-3.19 (m, 2H), 2.82-2.64 (m, 2H), 169-1.45 (m, 2H), 1.20-1.08 (m, 2H), 0.77-0.74 (m, 3H).

Example 128 Synthesis of Compound AB36423

The structure of compound AB36423 was as follows:

AB36423

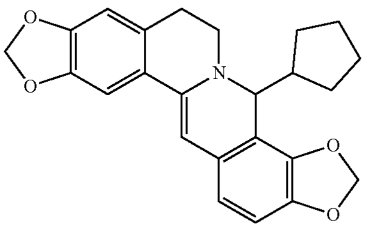

The synthesis method of compound AB36423 was as follows:

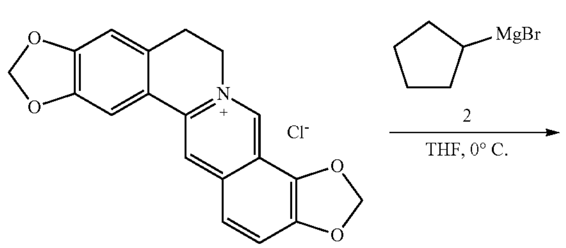

1

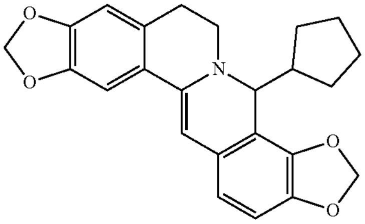

AB36423

Compound 1 (300 mg, 0.84 mmol, 1.0 eq) was dissolved in tetrahydrofuran (20 mL), and compound 2 (4.2 mL, 4.2 mmol, 5.0 eq, 1 mol/L) was added at 0° C. The mixture was reacted at room temperature for 30 min. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane:methanol=0-5%) to afford compound AB36423.

The MS-ESI and $^1$H NMR spectra of compound AB36423 were as follows:

MS-ESI: Calculated [M+H]$^+$: 390.17, Found: 390.30.

$^1$H NMR (400 MHz, DMSO-d6) δ 7.18 (s, 1H), 6.73 (s, 1H), 6.67 (d, J=4.0 Hz, 1H), 6.44 (d, J=4.0 Hz, 1H), 5.97 (s, 1H), 5.96 (s, 2H), 5.88 (s, 1H), 5.80 (s, 1H), 4.42 (d, J=8.0 Hz, 1H), 3.43-3.38 (m, 2H), 2.86-2.80 (m, 1H), 2.66-2.58 (m, 1H), 2.28-2.20 (m, 1H), 1.59-1.40 (m, 4H), 1.34-1.19 (m, 4H).

Example 129 Synthesis of Compound AB36427

The structure of compound AB36427 was as follows:

AB36427

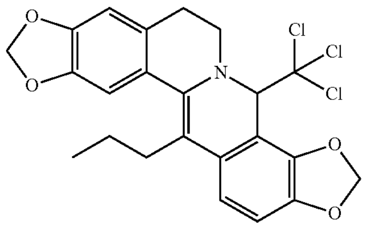

The synthesis method of compound AB36427 was as follows:

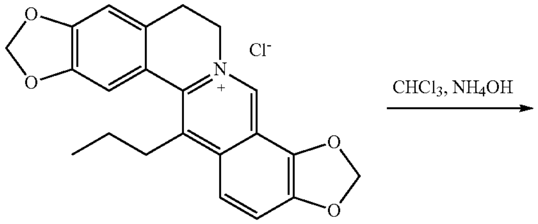

1

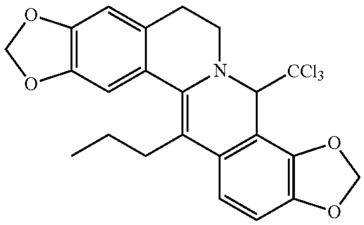

AB36427

Compound 1 (200 mg, 5.5 mmol, 1.0 eq) was dissolved in a mixture of chloroform (10 ml) and aqueous ammonia (5 ml). The mixture was reacted at room temperature for overnight. The reaction mixture diluted with water and then extracted with dichloromethane, the organic phase was washed with brine, dried over anhydrous sodium sulfate and filtered, the filtrate was spin dried. The crude product was purified by fast chromatography (DCM/MeOH=50/1) to afford compound AB36427.

The MS-ESI and $^1$H NMR spectra of compound AB36427 were as follows:

MS-ESI: Calculated [M+H]$^+$: 480.04; Found [M+H]$^+$: 479.95.

$^1$H NMR (400 MHz, $CDCl_3$) δ 7.92 (s, 2H), 6.89 (m, 1H), 6.68 (s, 1H), 6.04-5.94 (m, 4H), 5.34 (s, 1H), 4.09-4.02 (m, 1H), 3.47-3.43 (m, 1H), 2.80-2.63 (m, 3H), 2.56-2.48 (s, 1H), 1.82-1.76 (m, 1H), 1.50-1.43 (m, 1H), 1.06-1.02 (m, 3H).

Example 130 Synthesis of Compound AB36428

The structure of compound AB36428 was as follows:

AB36428

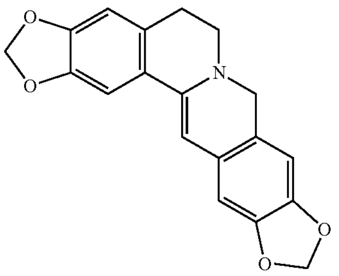

The synthesis method of compound AB36428 was as follows:

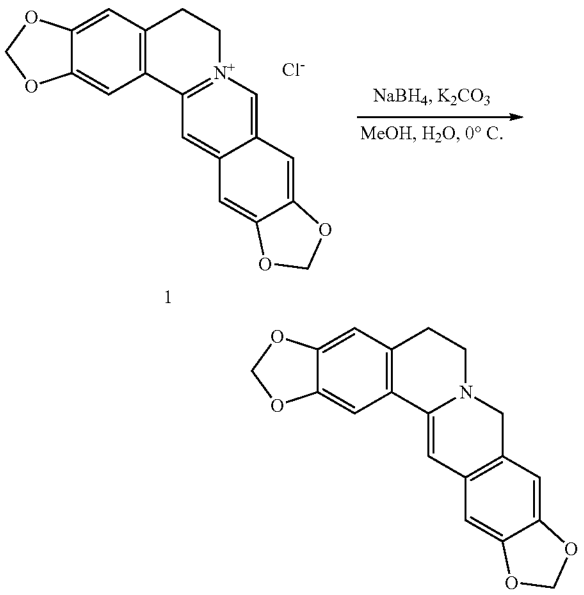

1

AB36428

Compound 1 (300 mg, 0.84 mmol, 1.0 eq) was dissolved in methanol (10 mL), and aqueous potassium carbonate solution (348 mg, 2.52 mmol, 3.0 eq, 2 mL) and aqueous sodium borohydride solution (9 mg, 0.25 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36428.

The MS-ESI and $^1$H NMR spectra of compound AB36428 were as follows:

MS-ESI: Calculated $[M+H]^+$: 322.10, Found: 322.35.

$^1$H NMR (400 MHz, DMSO-d6) δ 7.27 (s, 1H), 6.76 (s, 1H), 6.71 (s, 1H), 6.58 (s, 1H), 6.06 (s, 1H), 6.00 (s, 2H), 5.92 (s, 2H), 4.07 (s, 2H), 3.02-3.00 (m, 2H), 2.80-2.77 (m, 2H).

Example 131 Synthesis of Compound AB36432

The structure of compound AB36432 was as follows:

AB36432

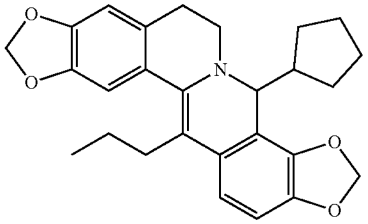

The synthesis method of compound AB36432 was as follows:

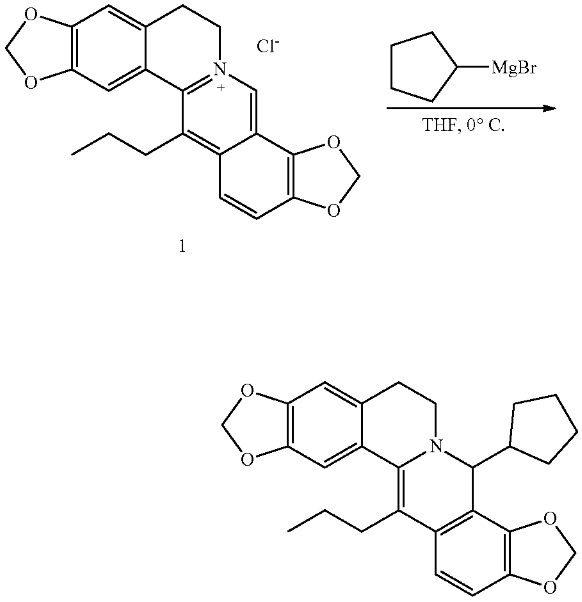

1

AB36432

Compound 1 (300 mg, 0.75 mmol, 1 eq) was dissolved in tetrahydrofuran (10 mL), and cyclopentylmagnesium bromide (3.7 mL, 3.75 mmol, 5 eq, 1M) was added at 0° C. under $N_2$. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (DCM/MeOH=50/1) to afford compound AB36432.

The MS-ESI and $^1$H NMR spectra of compound AB36432 were as follows:

MS-ESI: Calculated $[M+H]^+$: 432.21; Found $[M+H]^+$: 432.25.

$^1$H NMR (400 MHz, DMSO-d6) δ 6.85 (s, 2H), 6.77-6.71 (m, 2H), 6.04 (s, 1H), 6.03 (s, 2H), 5.90 (s, 1H), 4.34-4.32 (d, J=8.0 Hz, 1H), 3.32-3.26 (m, 2H), 2.72-2.62 (m, 1H), 2.60-2.50 (m, 2H), 2.22-2.16 (m, 1H), 1.71-1.62 (m, 1H), 1.50-1.23 (m, 10H), 0.99-0.96 (m, 3H).

Example 132 Synthesis of Compound AB36433

The structure of compound AB36433 was as follows:

AB36433

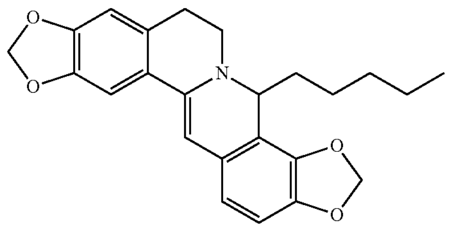

The synthesis method of compound AB36432 was as follows:

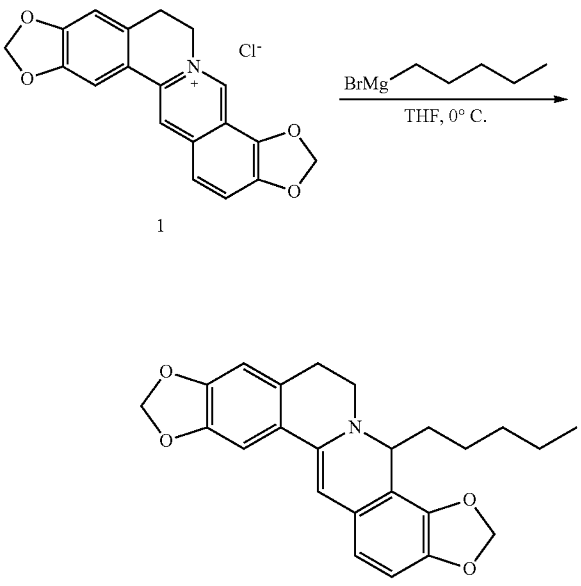

1

AB36433

Compound 1 (300 mg, 0.84 mmol, 1 eq) was dissolved in tetrahydrofuran (10 mL), and pentylmagnesium bromide (4.2 mL, 4.21 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (DCM/MeOH=50/1) to afford compound AB36433.

The MS-ESI and $^1$H NMR spectra of compound AB36433 were as follows:

MS-ESI: Calculated $[M+H]^+$: 392.18; Found $[M+H]^+$: 392.25.

$^1$H NMR (400 MHz, DMSO-d6) δ 7.22 (s, 1H), 6.76 (s, 1H), 6.69 (d, J=8.0 Hz, 1H), 6.46 (d, J=8.0 Hz, 1H), 6.00-5.86 (m, 5H), 4.55-4.52 (m, 1H), 3.32-3.23 (m, 2H), 2.83-2.67 (m, 2H), 1.70-1.51 (m, 2H), 1.22-1.11 (m, 6H), 0.78-0.75 (m, 3H).

Example 133 Synthesis of Compound AB36434

The structure of compound AB36434 was as follows:

AB36434

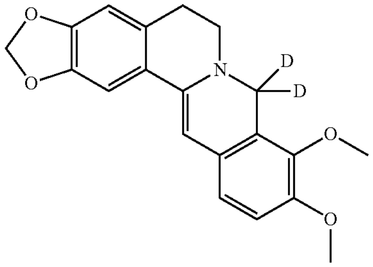

The synthesis method of compound AB36434 was as follows:

Step (1):

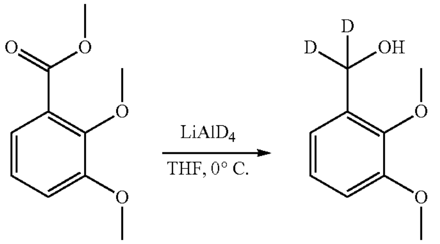

1 2

Compound 1 (4.5 g, 22.93 mmol, 1 eq) was dissolved in tetrahydrofuran (40 mL), and deuterated lithium aluminum hydride (1.9 g, 45.86 mmol, 2 eq) was added at 0 at 0° C. under $N_2$. The mixture was reacted for 0.5 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane:methanol=50:1) to afford compound 2.

Step (2):

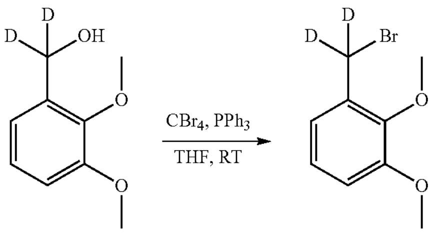

2 3

Compound 2 (2.8 g, 16.45 mmol, 1 eq) was dissolved in tetrahydrofuran (30 mL), and triphenylphosphine (4.3 g, 16.45 mmol, 1 eq) and carbon tetrabromide (5.4 g, 16.45 mmol, 1 eq) were added. The mixture was reacted at room temperature for 16 h under $N_2$. The reaction mixture diluted with water and then extracted with dichloromethane, the organic phase was dried over anhydrous sodium sulfate and filtered, the filtrate was spin dried. The crude product was purified by fast chromatography (petroleum ether:ethyl acetate=50:1) to afford compound 3.

Step (3):

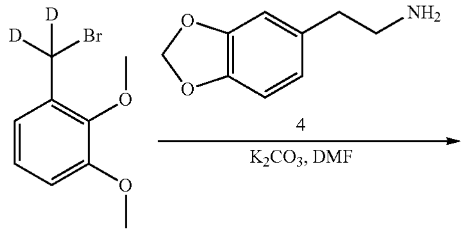

3

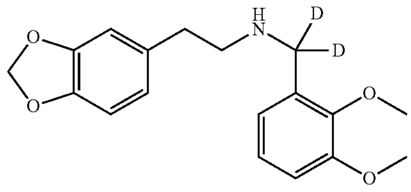

5

Compound 3 (2.1 g, 9.01 mmol, 1 eq) was dissolved in N, N-dimethylformamide (30 mL), and potassium carbonate (2.5 g, 18.02 mmol, 2 eq) and compound 4 (1.5 g, 9.01 mmol, 1 eq) were added. The mixture was reacted at room temperature for 16 h. The reaction mixture was diluted with water and then extracted with ethyl acetate, the organic phase was dried over anhydrous sodium sulfate and filtered, the filtrate was spin dried. The crude product was purified by fast chromatography (dichloromethane:methanol=20:1) to afford compound 5.

Step (4):

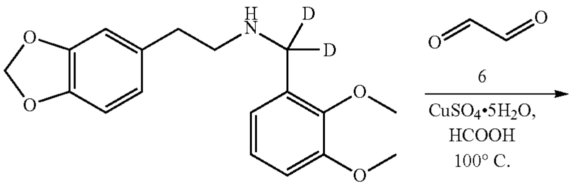

5

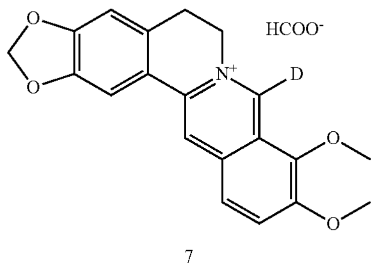

+

7

-continued

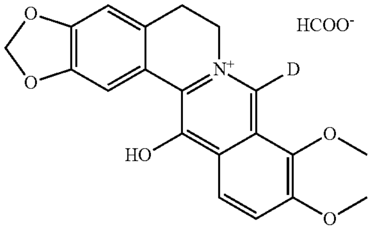

8 (AB36443)

Compound 5 (647 mg, 2.04 mmol, 1 eq) was dissolved in formic acid (5 mL), and copper sulfate pentahydrate (1.3 g, 6.53 mmol, 2.6 eq) and aqueous glyoxal solution (947 mg, 6.49 mmol, 3.2 eq, 40%) were added. The mixture was reacted at 100° C. for 16 h. The reaction mixture was cooled, the solid was filtered and then washed with methanol, the filtrate was spin dried. The crude product was purified by fast chromatography ((dichloromethane:methanol=10:1) to afford compound 7 (100 mg, yield: 12.8%) and compound 8 (AB36443).

Step (5):

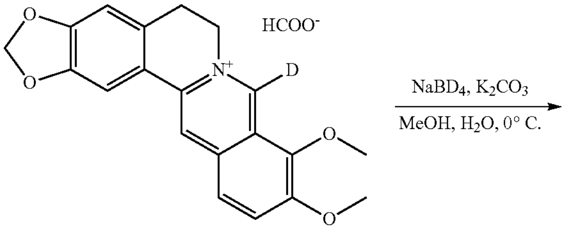

7

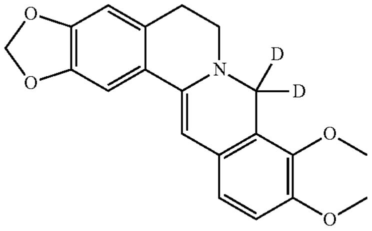

AB36434

Compound 7 (100 mg, 0.26 mmol, 1.0 eq) was dissolved in methanol (5 mL), and aqueous potassium carbonate solution (108 mg, 0.78 mmol, 3.0 eq, 1 mL) and aqueous deuterated sodium borohydride solution (3 mg, 0.078 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36434.

The MS-ESI and $^1H$ NMR spectra of compound AB36434 were as follows:

MS-ESI: Calculated $[M+H]^+$: 340.15, Found: 340.05.

$^1H$ NMR (400 MHz, DMSO-d6) δ 7.29 (s, 1H), 6.83-6.68 (m, 3H), 6.04 (s, 1H), 6.00 (s, 2H), 3.76 (s, 3H), 3.71 (s, 3H), 3.07-3.04 (m, 2H), 2.81-2.78 (m, 2H).

Example 134 Synthesis of Compound AB36437

The structure of compound AB36437 was as follows:

AB36437

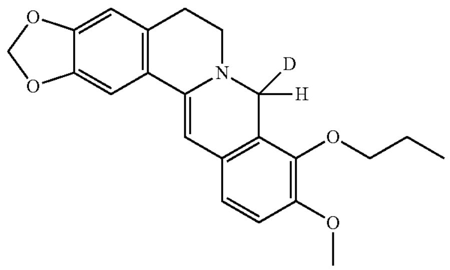

The synthesis method of compound AB36437 was as follows:

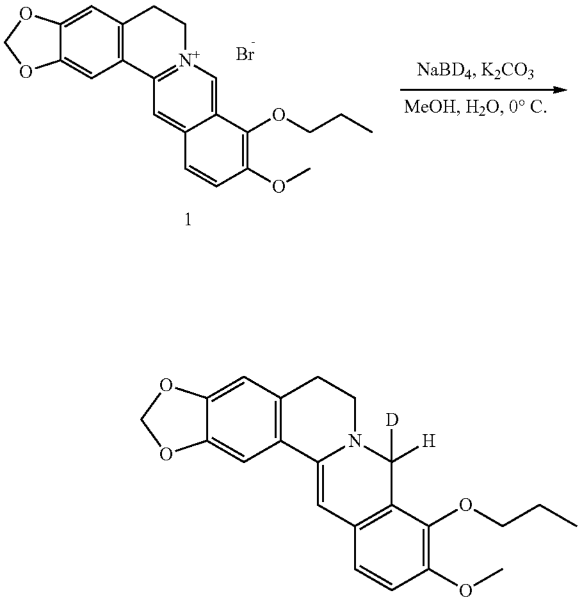

1

AB36437

Compound 1 (400 mg, 0.90 mmol, 1.0 eq) was dissolved in methanol (5 mL), and aqueous potassium carbonate solution (377 mg, 2.7 mmol, 3.0 eq, 1 mL) and aqueous deuterated sodium borohydride solution (11 mg, 0.288 mmol, 0.27 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36437.

The MS-ESI and $^{1}$H NMR spectra of compound AB36437 were as follows:

MS-ESI: Calculated $[M+H]^+$: 367.17, Found: 367.20.

$^{1}$H NMR (400 MHz, DMSO-d6) δ 7.29 (s, 1H), 6.82-6.67 (m, 3H), 6.05 (s, 1H), 6.00 (s, 2H), 4.15 (s, 1H), 3.86-3.82 (m, 2H), 3.75 (s, 3H), 3.08-3.03 (m, 2H), 2.81-2.78 (m, 2H), 1.71-1.66 (m, 2H), 1.00-0.96 (m, 3H).

Example 135 Synthesis of Compound AB36446

The structure of compound AB36446 was as follows:

AB36446

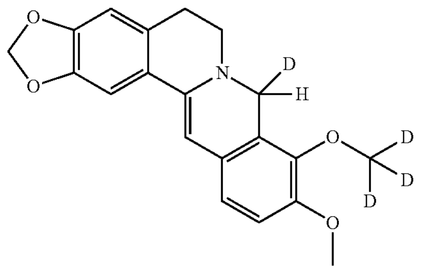

The synthesis method of compound AB36446 was as follows:

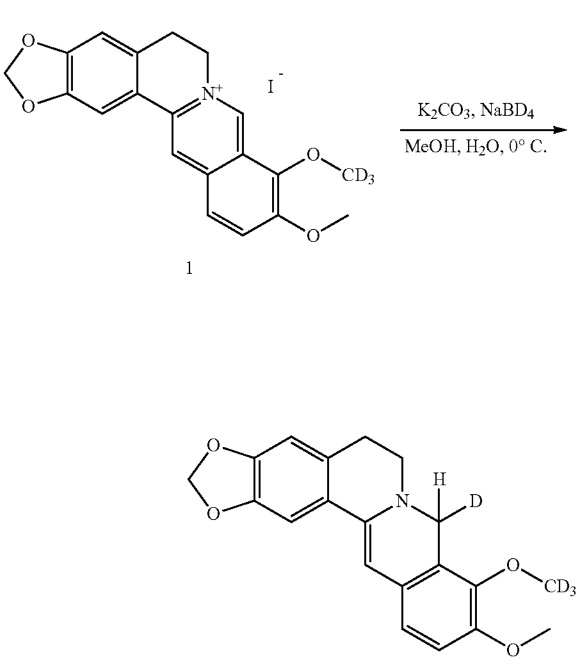

1

AB36446

Compound 1 (200 mg, 0.43 mmol, 1.0 eq) was dissolved in methanol (5 mL), and aqueous potassium carbonate solution (178 mg, 1.29 mmol, 3.0 eq, 1 mL) and aqueous deuterated sodium borohydride solution (5 mg, 0.129 mmol, 0.27 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36446.

The MS-ESI and $^{1}$H NMR spectra of compound AB36446 were as follows:

MS-ESI: Calculated $[M+H]^+$: 342.16, Found: 342.05.

$^{1}$H NMR (400 MHz, DMSO-d6) δ 7.29 (s, 1H), 6.83-6.68 (m, 3H), 6.05 (s, 1H), 6.00 (s, 2H), 4.16 (s, 1H), 3.76 (s, 3H), 3.07-3.03 (m, 2H), 2.81-2.78 (m, 2H).

Example 136 Synthesis of Compound AB36447

The structure of compound AB36447 was as follows:

AB36447

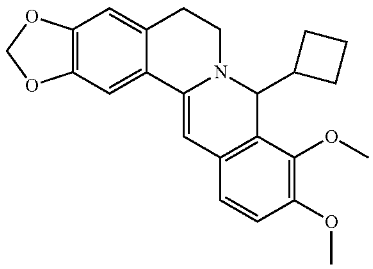

The synthesis method of compound AB36447 was as follows:

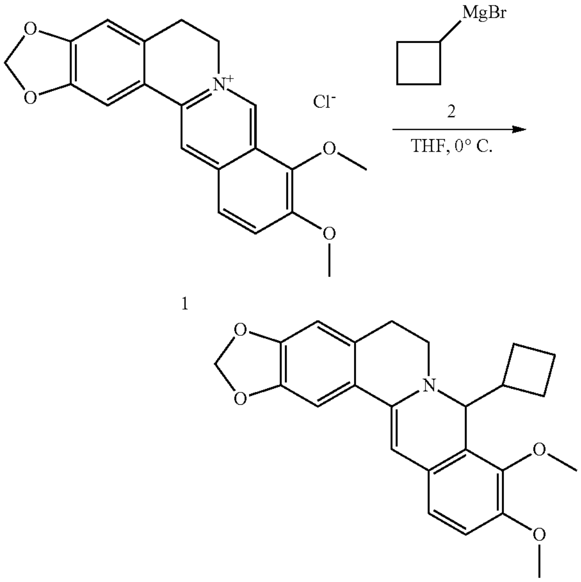

1

AB36447

Compound 1 (500 mg, 1.34 mmol, 1 eq) was dissolved in tetrahydrofuran (10 mL), and compound 2 (6.7 mL, 6.7 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (DCM/MeOH=50/1) to afford compound AB36447.

The MS-ESI and $^1$H NMR spectra of compound AB36447 were as follows:

MS-ESI: Calculated $[M+H]^+$: 392.18; Found $[M+H]^+$: 392.15.

$^1$H NMR (400 MHz, $CDCl_3$) δ 7.22 (s, 1H), 6.82-6.66 (m, 3H), 5.99 (d, J=4.0 Hz, 2H), 5.88 (s, 1H), 4.51 (d, J=8.0 Hz, 1H), 3.76 (d, J=4.0 Hz, 6H), 3.33-3.32 (m, 2H), 2.82-2.75 (m, 2H), 2.68-2.61 (m, 1H), 1.93-1.80 (m, 3H), 1.63-1.54 (m, 2H), 1.40-1.35 (m, 1H).

Example 137 Synthesis of Compound AB36450

The structure of compound AB36450 was as follows:

AB36450

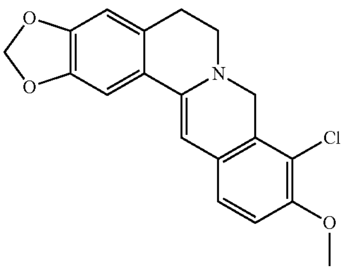

The synthesis method of compound AB36450 was as follows:

Step (1):

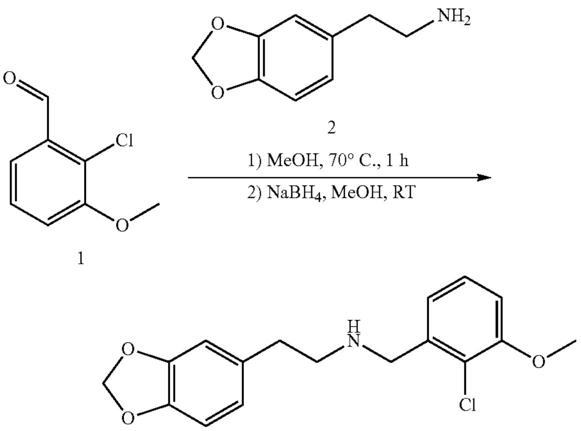

1

3

Compound 1 (3 g, 17.58 mmol, 1 eq) was dissolved in methanol (50 mL), and compound 2 (2.9 g, 17.58 mmol, 1 eq) was added. The mixture was reacted at 70° C. for 1 h, then cooled to 0° C., sodium borohydride (1.3 g, 35.16 mmol, 2 eq) was slowly added. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane:methanol=20:1) to afford compound 3.

Step (2):

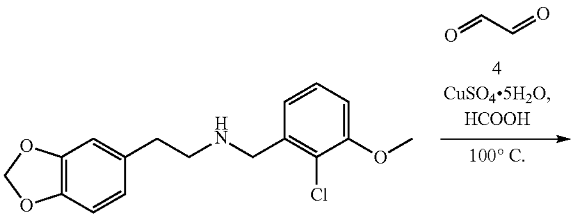

3

-continued

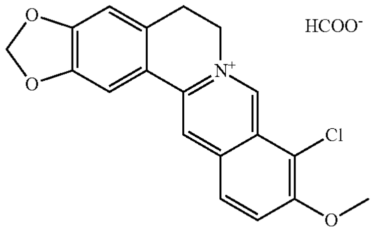

5

Compound 3 (2 g, 6.25 mmol, 1 eq) was dissolved in formic acid (10 mL), and copper sulfate pentahydrate (4.0 g, 16.25 mmol, 2.6 eq) and aqueous glyoxal solution (2.9 g, 20 mmol, 3.2 eq, 40%) were added. The mixture was reacted at 100° C. for 16 h under $N_2$. The reaction mixture was cooled, the solid was filtered and then washed with methanol, the filtrate was spin dried. The crude product was purified by fast chromatography ((dichloromethane:methanol=10:1) to afford compound 5.

Step (3):

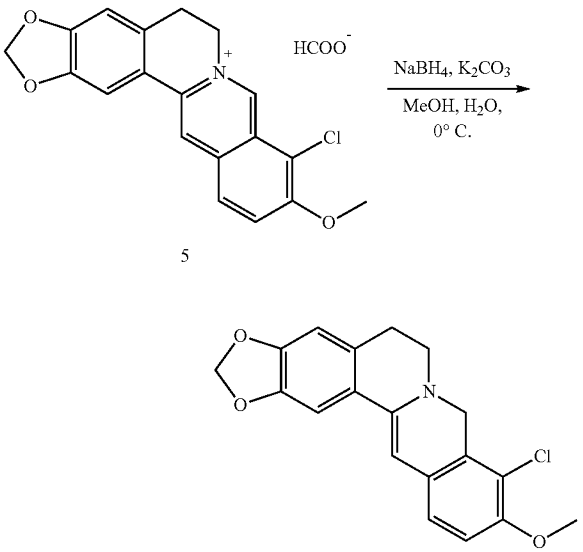

5

AB36450

Compound 5 (250 mg, 0.65 mmol, 1.0 eq) was dissolved in methanol (5 mL), and aqueous potassium carbonate solution (260 mg, 1.95 mmol, 3.0 eq, 1 mL) and aqueous sodium borohydride solution (7 mg, 0.195 mmol, 0.3 eq, 0.3 mL) was added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36450.

The MS-ESI and $^1H$ NMR spectra of compound AB36450 were as follows:

MS-ESI: Calculated $[M+H]^+$: 342.09, Found: 342.00.

$^1H$ NMR (400 MHz, DMSO-d6) δ 7.30 (s, 1H), 6.95-6.90 (m, 2H), 6.77 (s, 1H), 6.07 (s, 1H), 6.01 (s, 2H), 4.31 (s, 2H), 3.81 (s, 3H), 3.09-3.06 (m, 2H), 2.82-2.79 (m, 2H).

Example 138 Synthesis of Compound AB36460

The structure of compound AB36460 was as follows:

AB36460

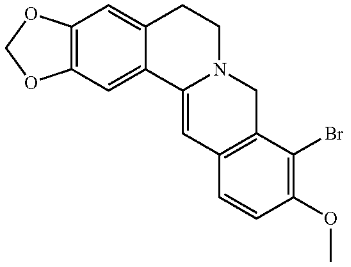

The synthesis method of compound AB36460 was as follows:

Step (1):

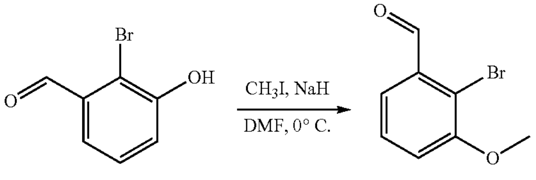

1

2

Compound 1 (2.5 g, 12.44 mmol, 1 eq) was dissolved in N, N-dimethylformamide (50 mL), and sodium hydride (597 mg, 14.93 mmol, 1.2 eq, 60% in mineral oil) was added at 0° C. The mixture was reacted for 5 h, iodine methane (1.7 g, 12.44 mmol, 1 eq) was added, then the mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane/methanol=100:1) to afford compound 2.

Step (2):

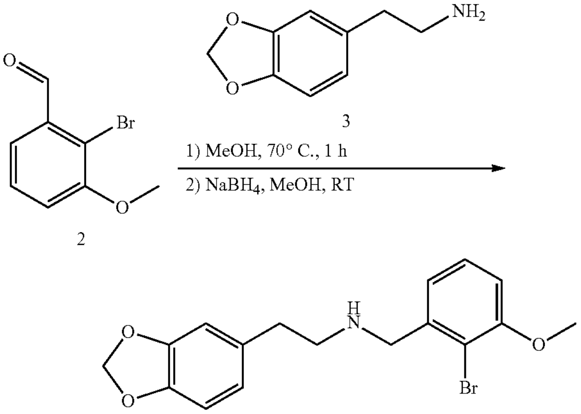

3

2

4

Compound 2 (2.5 g, 11.63 mmol, 1 eq) was dissolved in methanol (50 mL), and compound 3 (1.9 g, 11.63 mmol, 1 eq) was added. The mixture was reacted at 70° C. for 1 h, then cooled to 0° C., sodium borohydride (879 mg, 23.26 mmol, 2 eq) was slowly added. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane:methanol=20:1) to afford compound 4.

Step (3):

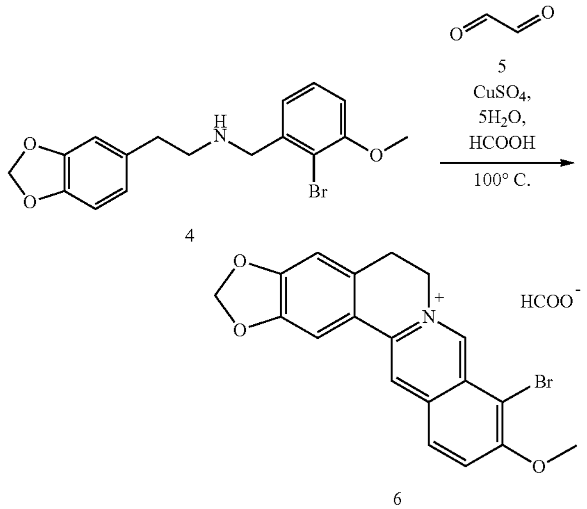

4

5

6

Compound 4 (2.5 g, 6.86 mmol, 1 eq) was dissolved in formic acid (20 mL), and copper sulfate pentahydrate (4.4 g, 17.84 mmol, 2.6 eq) and aqueous glyoxal solution (3.2 g, 21.95 mmol, 3.2 eq, 40%) were added. The mixture was reacted at 100° C. for 16 h under $N_2$. The reaction mixture was cooled, the solid was filtered and then washed with methanol, the filtrate was spin dried. The crude product was purified by fast chromatography ((dichloromethane:methanol=10:1) to afford compound 6.

Step (4):

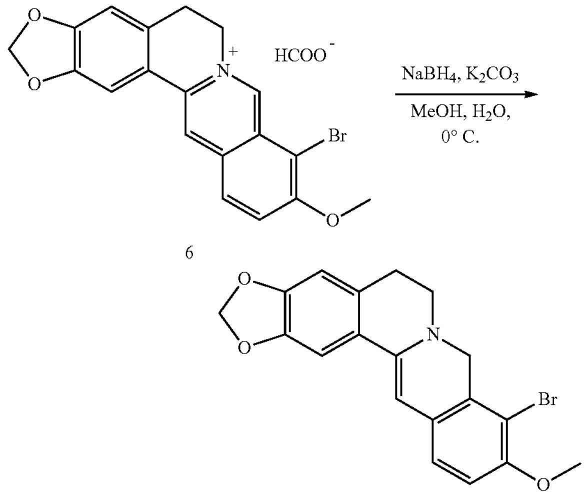

6

AB36460

Compound 6 (400 mg, 0.93 mmol, 1.0 eq) was dissolved in methanol (10 mL), and aqueous potassium carbonate solution (385 mg, 2.79 mmol, 3.0 eq, 2 mL) and aqueous sodium borohydride solution (10 mg, 0.279 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36460.

The MS-ESI and $^1$H NMR spectra of compound AB36460 were as follows:

MS-ESI: Calculated $[M+H]^+$: 386.03, Found: 386.00.

$^1$H NMR (400 MHz, DMSO-d6) δ 7.31 (s, 1H), 6.94-6.89 (m, 2H), 6.67 (s, 1H), 6.07 (s, 1H), 6.01 (s, 2H), 4.30 (s, 2H), 3.80 (s, 3H), 3.07-3.05 (m, 2H), 2.82-2.79 (s, 2H).

Example 139 Synthesis of Compound AB36463

The structure of compound AB36463 was as follows:

AB36463

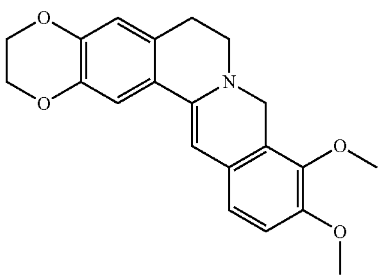

The synthesis method of compound AB36463 was as follows:

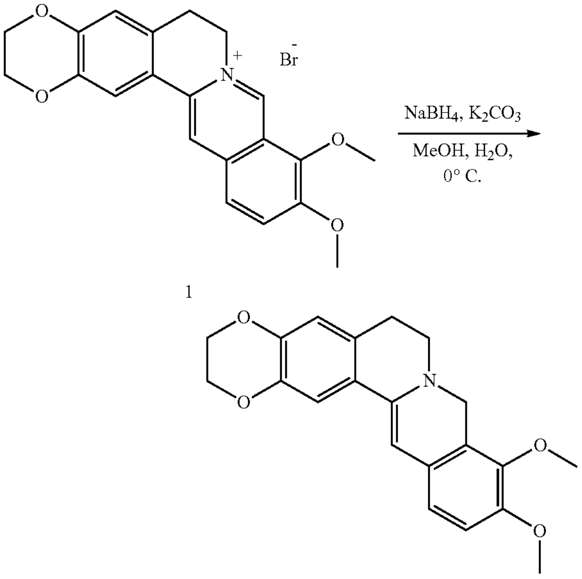

1

AB36463

Compound 1 (500 mg, 1.16 mmol, 1.0 eq) was dissolved in methanol (10 mL), and aqueous potassium carbonate solution (480 mg, 3.48 mmol, 3.0 eq, 2 mL) and aqueous sodium borohydride solution (13 mg, 0.348 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36463.

The MS-ESI and $^{1}H$ NMR spectra of compound AB36463 were as follows:

MS-ESI: Calculated $[M+H]^+$: 352.15, Found: 352.15.

$^{1}H$ NMR (400 MHz, $CDCl_3$) δ 7.22 (s, 1H), 6.72 (s, 2H), 6.61 (s, 1H), 5.96 (s, 1H), 4.32 (s, 2H), 4.26 (s, 4H), 3.84 (s, 6H), 3.14-3.11 (m, 2H), 2.87-2.84 (m, 2H).

Example 140 Synthesis of Compound AB36467

The structure of compound AB36467 was as follows:

AB36467

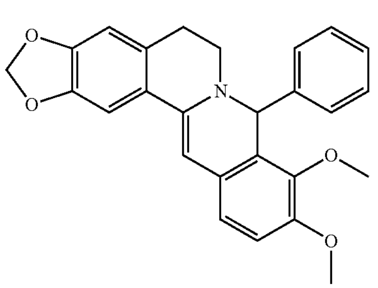

The synthesis method of compound AB36467 was as follows:

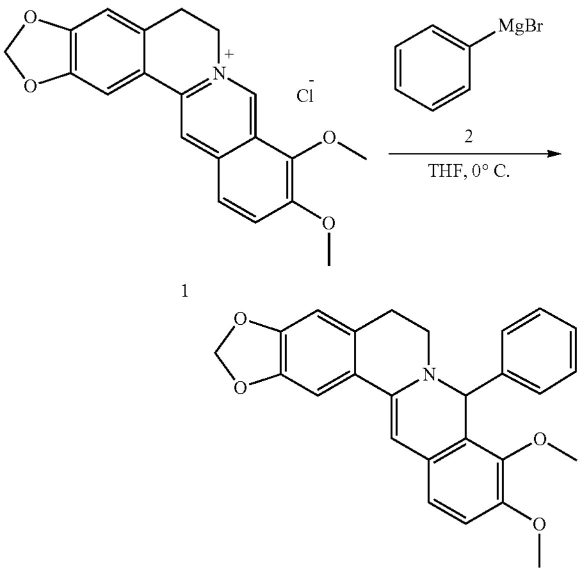

AB36467

Compound 1 (300 mg, 0.81 mmol, 1 eq) was dissolved in tetrahydrofuran (10 mL), and compound 2 (4 mL, 4.03 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (DCM/MeOH=50/1) to afford compound AB36467.

The MS-ESI and $^{1}H$ NMR spectra of compound AB36467 were as follows:

MS-ESI: Calculated $[M+H]^+$: 414.17; Found $[M+H]^+$: 414.20.

$^{1}H$ NMR (400 MHz, $CDCl_3$) δ 7.65 (d, J=8.0 Hz, 2H), 7.49-7.38 (m, 4H), 7.05-6.96 (m, 2H), 6.76 (s, 1H), 6.15 (s, 2H), 6.09 (s, 1H), 5.99 (s, 1H), 4.03 (s, 3H), 3.78 (s, 3H), 3.52-3.47 (m, 1H), 3.34-3.28 (m, 1H), 3.20-3.141 (m, 1H), 2.93-2.87 (m, 1H).

Example 141 Synthesis of Compound AB36474

The structure of compound AB36474 was as follows:

AB36474

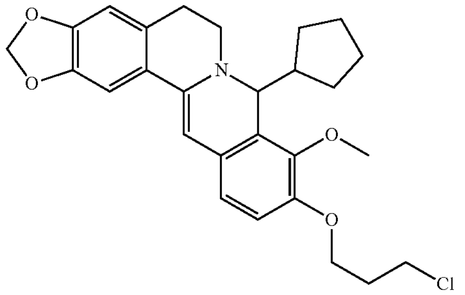

The synthesis method of compound AB36474 was as follows:

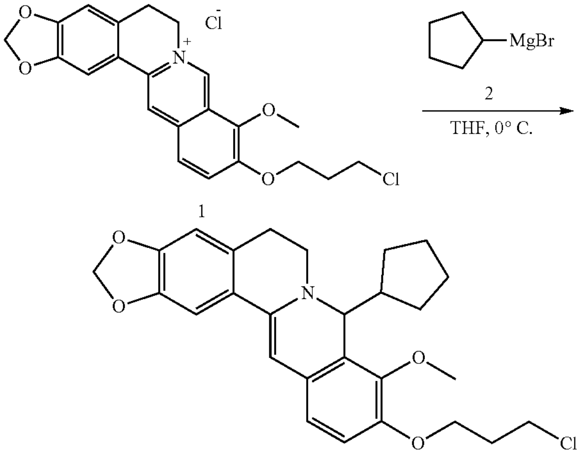

AB36474

Compound 1 (300 mg, 0.69 mmol, 1.0 eq) was dissolved in tetrahydrofuran (10 mL), and compound 2 (3.5 mL, 3.45 mmol, 5 eq, 1M) was added at 0° C. The mixture was reacted for 30 min, the reaction was completed. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane/methanol=0-5%) to afford compound AB36474.

The MS-ESI and $^{1}H$ NMR spectra of compound AB36474 were as follows:

MS-ESI: Calculated $[M+H]^+$: 468.19, Found: 468.15.

$^1H$ NMR (400 MHz, DMSO-d6) δ 7.19 (s, 1H), 6.82-6.62 (m, 3H), 5.96 (s, 2H), 5.87 (s, 1H), 4.51 (d, J=8.0 Hz, 1H), 4.06-4.00 (m, 2H), 3.81-3.77 (m, 2H), 3.74 (s, 3H), 3.41-3.36 (m, 2H), 2.87-2.82 (m, 1H), 2.67-2.59 (m, 1H), 2.19-2.11 (m, 3H), 1.56-1.16 (m, 8H).

Example 142 Synthesis of Compound AB36476

The structure of compound AB36476 was as follows:

AB36476

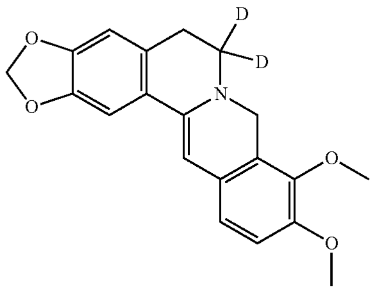

The synthesis method of compound AB36476 was as follows:

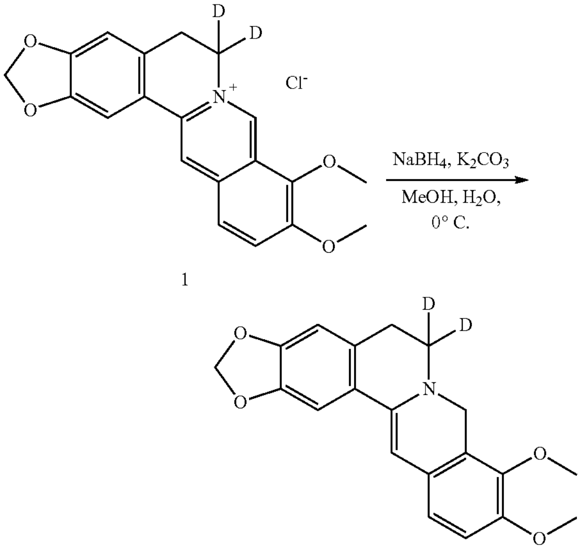

1

AB36476

Compound 1 (200 mg, 0.53 mmol, 1.0 eq) was dissolved in methanol (5 mL), and aqueous potassium carbonate solution (219 mg, 1.59 mmol, 3.0 eq, 1 mL) and aqueous sodium borohydride solution (6 mg, 0.159 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36476.

The MS-ESI and $^1H$ NMR spectra of compound AB36476 were as follows:

MS-ESI: Calculated $[M+H]^+$: 340.15, Found: 340.10.

$^1H$ NMR (400 MHz, DMSO-d6) δ 7.29 (s, 1H), 6.83-6.68 (m, 3H), 6.04 (s, 1H), 6.00 (s, 2H), 4.20 (s, 2H), 3.76 (s, 3H), 3.71 (s, 3H), 2.78 (s, 2H).

Example 143 Synthesis of Compound AB36477

The structure of compound AB36477 was as follows:

AB36477

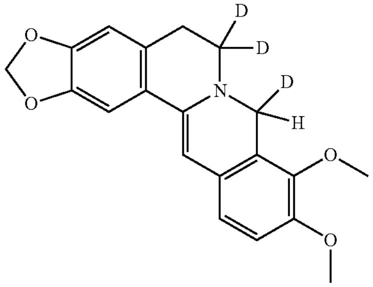

The synthesis method of compound AB36477 was as follows:

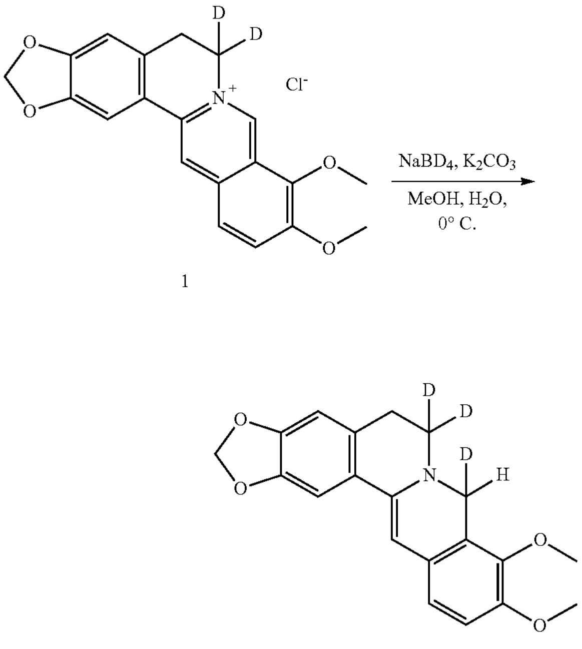

1

AB36477

Compound 1 (200 mg, 0.53 mmol, 1.0 eq) was dissolved in methanol (5 mL), and aqueous potassium carbonate solution (219 mg, 1.59 mmol, 3.0 eq, 1 mL) and aqueous deuterated sodium borohydride solution (7 mg, 0.159 mmol, 0.3 eq, 0.3 mL) were added at 0° C. The mixture was reacted at 0° C. for 5 min, and the reaction was detected to be performed completely using LCMS, the solid was filtered and then washed with water, the crude product was purified by fast chromatography (dichloromethane/methanol=0-5%) to afford compound AB36477.

The MS-ESI and $^1H$ NMR spectra of compound AB36477 were as follows:

MS-ESI: Calculated $[M+H]^+$: 341.15, Found: 341.10.

$^1H$ NMR (400 MHz, DMSO-d6) δ 7.29 (s, 1H), 6.83-6.68 (m, 3H), 6.04 (s, 1H), 6.00 (s, 2H), 4.16 (s, 1H), 3.76 (s, 3H), 3.71 (s, 3H), 2.78 (s, 2H).

Example 144 Synthesis of Compound AB31893

The structure of compound AB31893 was as follows:

AB31893

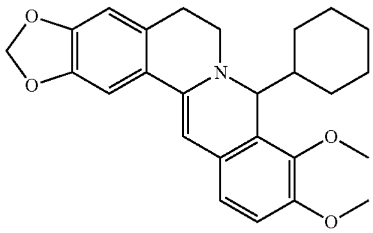

The synthesis method of compound AB31893 was as follows:

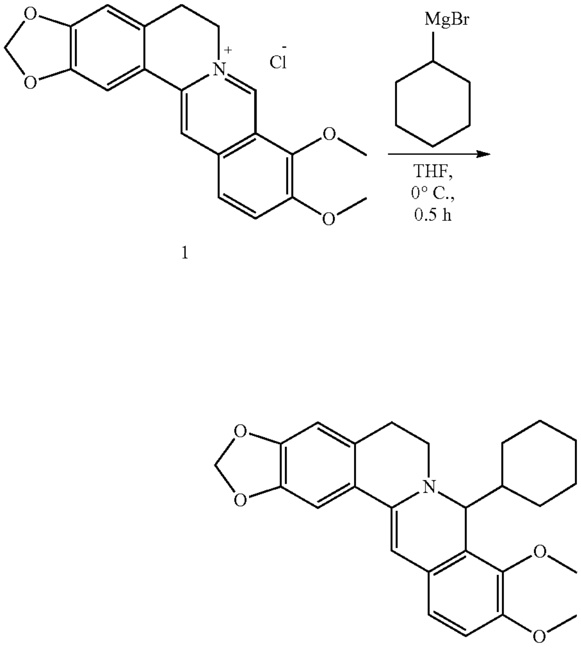

1

AB31893

Compound 1 (200 mg, 0.54 mmol, 1 eq) was dissolved in anhydrous tetrahydrofuran (10 mL), and cyclohexylmagnesium bromide (2.7 mL, 2.7 mmol, 5 eq, 1M) was slowly added dropwise at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and pin dried. The crude product was purified by thin layer chromatography (DCM/MeOH=50/1) to afford compound AB 31893.

MS-ESI: Calculated $[M+H]^+$: 420.21, Found: 420.20.

$^1H$ NMR (400 MHz, DMSO-d6) δ 7.23 (s, 1H), 6.82 (d, J=8.0 Hz, 1H), 6.76 (s, 1H), 6.66 (d, J=8.0 Hz, 1H), 5.99 (s, 2H), 5.85 (s, 1H), 4.46-4.45 (m, 1H), 3.75 (d, J=8.0 Hz, 6H), 3.41-3.38 (m, 2H), 2.96-2.89 (m, 1H), 2.68-2.64 (m, 1H), 1.65-1.50 (m, 7H), 1.11-1.03 (m, 4H).

Example 145 Synthesis of Compound AB31900

The structure of compound AB31900 was as follows:

AB31900

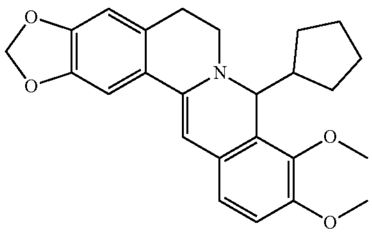

The synthesis method of compound AB31900 was as follows:

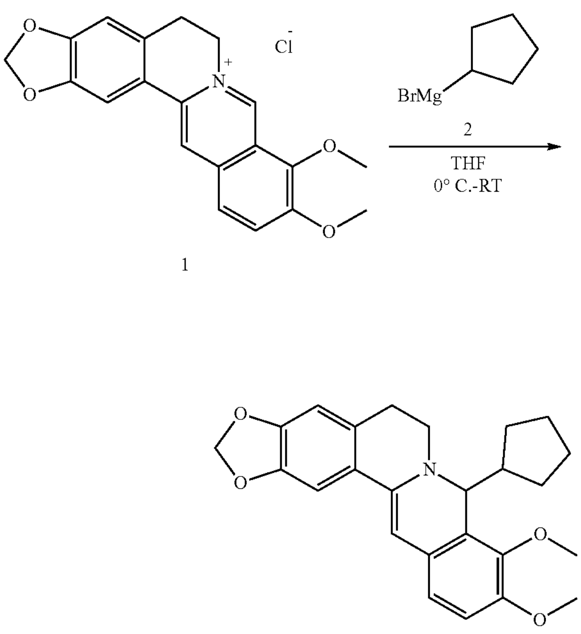

1

AB31900

Compound 1 (200 mg, 0.54 mmol, 1 eq) was dissolved in anhydrous tetrahydrofuran (10 mL), and cyclopentylmagnesium bromide (2.7 mL, 2.7 mmol, 5 eq, 1M) was slowly added dropwise at 0° C. under $N_2$. The mixture was reacted at room temperature for 0.5 h, and the reaction was detected to be performed completely using LCMS. The reaction mixture was quenched with saturated aqueous ammonium chloride solution and then extracted with ethyl acetate, the organic phase was dried over anhydrous sodium sulfate, filtered and spin dried. The crude product was purified by thin layer chromatography (DCM:MeOH=30:1) to afford compound AB31900.

MS-ESI: Calculated $[M+H]^+$: 406.20, Found: 406.20.

$^1H$ NMR (400 MHz, DMSO-d6) δ 7.20 (s, 1H), 6.79 (d, J=8.0 Hz, 1H), 6.73 (s, 1H), 6.64 (d, J=8.0 Hz, 1H), 5.96 (s, 2H), 5.87 (s, 1H), 4.51 (d, J=8.0 Hz, 1H), 3.72 (s, 6H), 3.41-3.35 (m, 2H), 2.86-2.63 (m, 2H), 2.17-2.15 (m, 1H), 1.55-1.15 (m, 8H).

Example 146 Synthesis of Compound AB35460

The structure of compound AB35460 was as follows:

AB35460

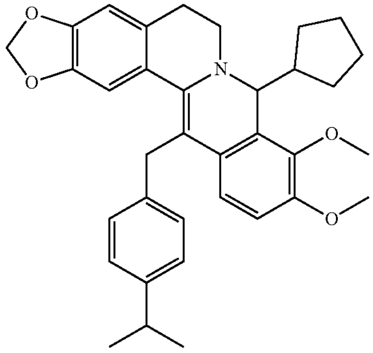

The synthesis method of compound AB35460 was as follows:

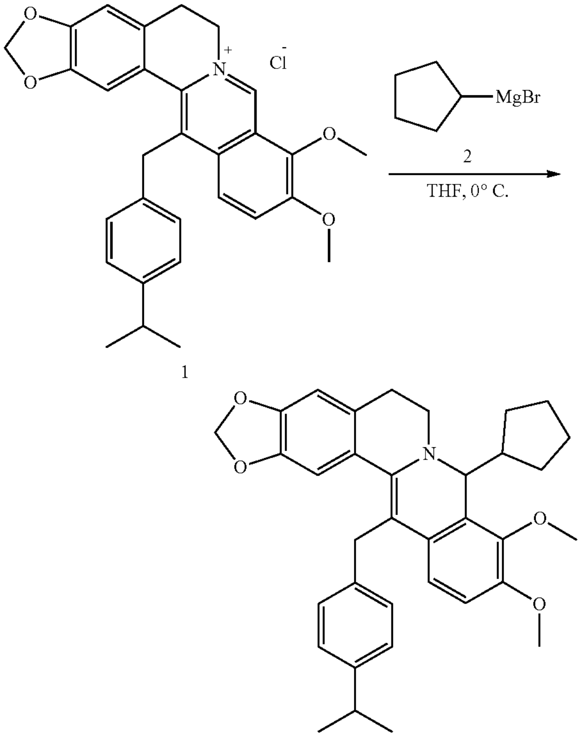

1

AB35460

Compound 1 (200 mg, 0.4 mmol, 1 eq) was dissolved in anhydrous tetrahydrofuran (10 mL), and cyclopentylmagnesium bromide (2.0 mL, 2.0 mmol, 5 eq, 1M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate, filtered and spin dried. The crude product was purified by reversed phase preparation chromatography (acetonitrile/water+0.1% formic acid) to afford compound AB35460.

MS-ESI: Calculated $[M+H]^+$: 538.29, Found$[M+H]^+$: 538.35.

$^1$H NMR (400 MHz, DMSO-d6) δ 7.15 (s, 4H), 6.85 (s, 1H), 6.77-6.69 (m, 3H), 5.93 (s, 2H), 4.51 (d, J=8.0 Hz, 1H), 3.94 (s, 2H), 3.73 (d, J=12.0 Hz, 6H), 3.41-3.36 (m, 2H), 2.79-2.60 (m, 3H), 2.27-2.23 (m, 1H), 1.55-1.30 (m, 8H), 1.15 (d, J=8.0 Hz, 6H).

Example 147 Synthesis of Compound AB35493

The structure of compound AB35493 was as follows:

AB35493

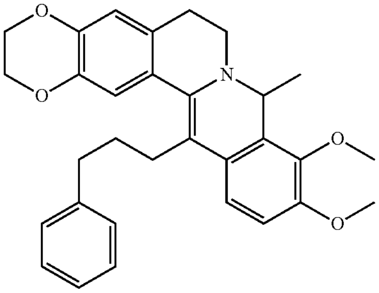

The synthesis method of compound AB35493 was as follows:

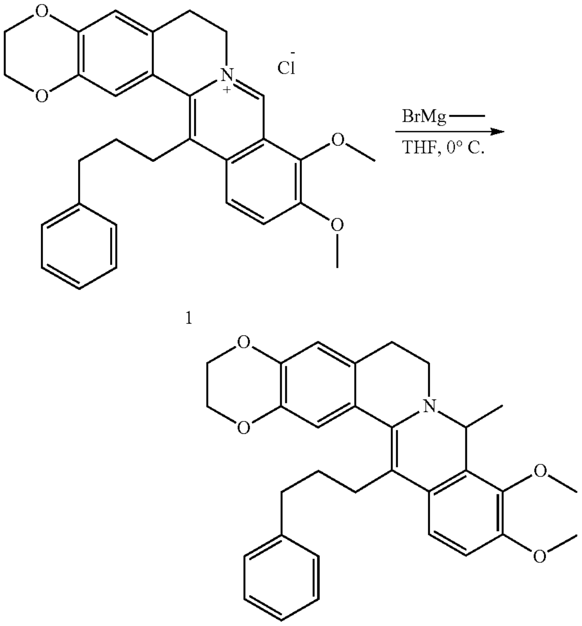

1

AB35493

Compound 1 (100 mg, 0.4 mmol, 1 eq) was dissolved in anhydrous tetrahydrofuran (10 mL), and methylmagnesium bromide (0.7 mL, 2.0 mmol, 5 eq, 3M) was added at 0° C. under $N_2$. The mixture was reacted at room temperature for 0.5 h. The reaction mixture was quenched with saturated aqueous ammonium chloride solution and then extracted with ethyl acetate twice, the organic phase was dried over anhydrous sodium sulfate, filtered and spin dried. The crude product was purified by reversed phase preparation chromatography (acetonitrile/water+0.1% formic acid) to afford compound AB35493.

MS-ESI: Calculated $[M+H]^+$: 484.24; Found$[M+H]^+$: 484.45.

$^1$H NMR (400 MHz, DMSO-d6) δ 7.27-7.23 (m, 2H), 7.19-7.13 (m, 3H), 6.86-6.71 (m, 4H), 4.64-4.60 (m, 1H), 4.27-4.18 (m, 4H), 3.75 (d, J=8.0 Hz, 6H), 3.15-3.07 (m, 2H), 2.67-2.54 (m, 6H), 1.95-1.89 (m, 1H), 1.76-1.69 (m, 1H), 0.93 (d, J=8.0 Hz, 3H).

Example 148 Synthesis of Compound AB36493

The structure of compound AB36493 was as follows:

AB36493

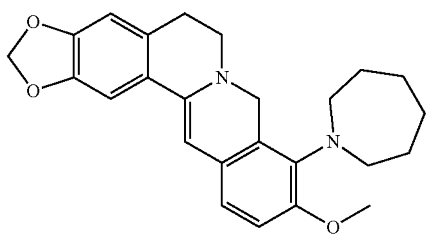

The synthesis method of compound AB36493 was as follows:

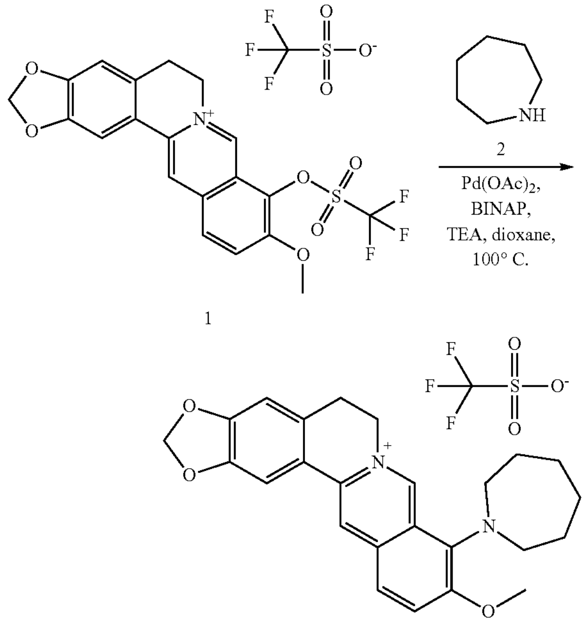

1

3

Compound 1 (500 mg, 0.83 mmol, 1.0 eq) and compound 2 (329 mg, 3.32 mmol, 4.0 eq) were dissolved in dioxane (10 mL), and triethylamine (335 mg, 3.32 mmol, 4.0 eq), palladium acetate (37 mg, 0.166 mmol, 0.2 eq), and 1,1'-binaphthalene-2,2'-biphenylphosphine (103 mg, 0.166 mmol, 0.2 eq) were added. The mixture was reacted at 100° C. for 16 h under $N_2$, and the reaction was detected to be performed completely using LCMS. The reaction mixture was spin dried, the crude product was purified by fast chromatography (dichloromethane/methanol=100:1 to 50/1) to afford compound 3.

Step (2):

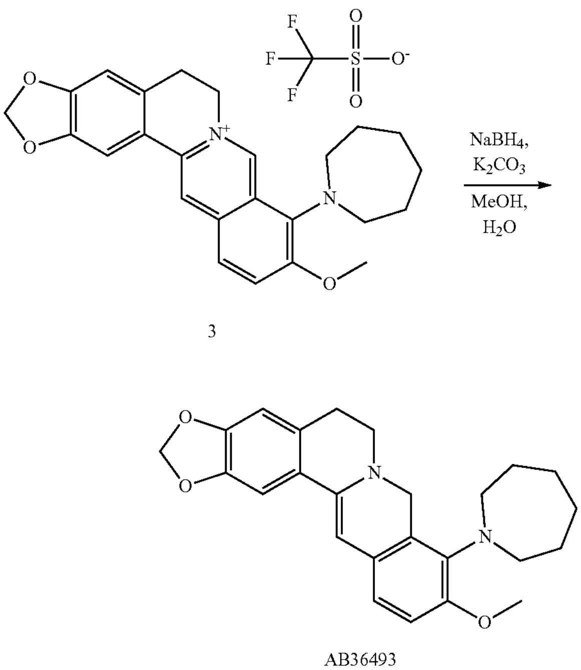

3

AB36493

Compound 3 (91 mg, 0.16 mmol, 1.0 eq) was dissolved in methanol (5 mL), and aqueous potassium carbonate solution (66 mg, 0.48 mmol, 3.0 eq, 1 mL) and aqueous sodium borohydride solution (2 mg, 0.048 mmol, 0.3 eq, 0.3 mL) were added at 0° C. The mixture was reacted at room temperature for 5 min, the solid was filtered and purified by fast chromatography (dichloromethane/methanol=100/1 to 50/1) to afford compound AB36493.

The MS-ESI and 1H NMR spectra of Compound AB36493 were as follows:

MS-ESI: Calculated $[M+H]^+$: 405.21, Found: 405.50.

$^1$H NMR (400 MHz, DMSO-d6) δ 7.28 (s, 1H), 6.78-6.72 (m, 3H), 6.04 (s, 1H), 5.99 (s, 2H), 4.32 (s, 2H), 3.74 (s, 3H), 3.22-3.13 (m, 2H), 3.05-3.03 (m, 2H), 2.81-2.74 (m, 4H), 1.80-1.53 (m, 8H).

Example 149 Synthesis of Compound AB36501

AB36501

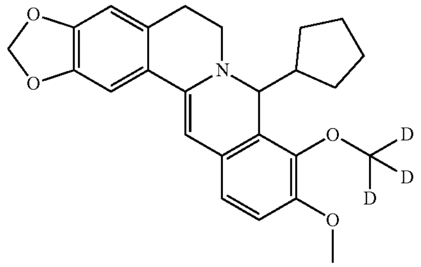

The synthesis method of compound AB36501 was as follows:

Step (1):

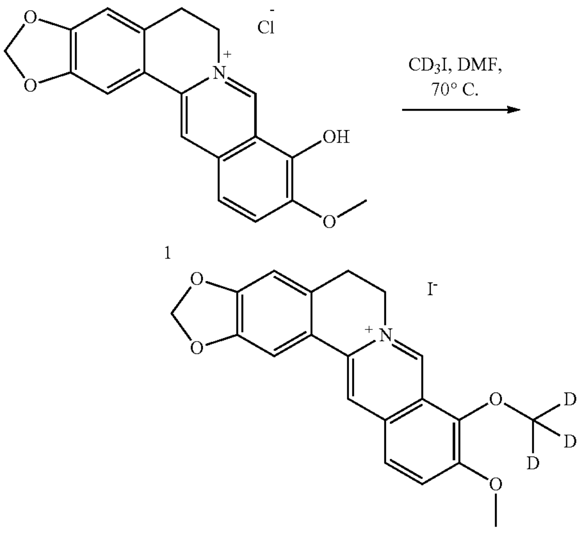

1

2

Compound 1 (3 g, 8.38 mmol, 1.0 eq) was dissolved in N, N-dimethylformamide (50 mL) and deuterated iodomethane (6.1 g, 41.9 mmol, 5.0 eq) was added. The mixture was reacted at 70° C. for 16 h. The reaction mixture was diluted with water and then extracted with ethyl acetate, the organic phase was dried over anhydrous sodium sulfate and filtered, the filtrate was spin dried. The crude product was purified by fast chromatography (dichloromethane/methanol=0-10%) to afford compound 2.

Step (2):

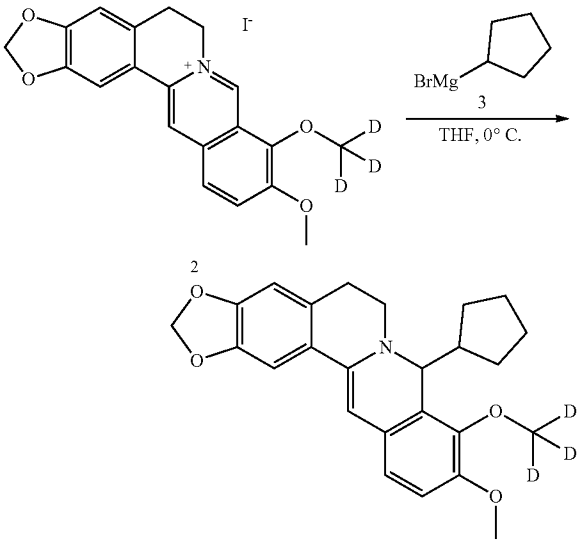

2

AB36501

Compound 2 (300 mg, 0.64 mmol, 1.0 eq) was dissolved in tetrahydrofuran (10 mL), and cyclopentylmagnesium bromide (3.2 mL, 3.2 mmol, 5.0 eq, 1M in THF) was added at 0° C. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane/methanol=0-5%) to afford compound AB36501.

The MS-ESI and $^1$H NMR spectra of compound AB36501 were as follows:

MS-ESI: Calculated $[M+H]^+$: 409.22; Found: 409.15.

$^1$H NMR (400 MHz, DMSO-d6) δ 7.22 (s, 1H), 6.83-6.66 (m, 3H), 5.99 (s, 2H), 5.90 (s, 1H), 4.54 (d, J=8.0 Hz, 1H), 3.76 (s, 3H), 3.46-3.40 (m, 2H), 2.90-2.86 (m, 1H), 2.68-2.62 (m, 1H), 2.22-2.16 (m, 1H), 1.59-1.19 (m, 8H).

Example 150 Synthesis of Compound AB36509

AB36509

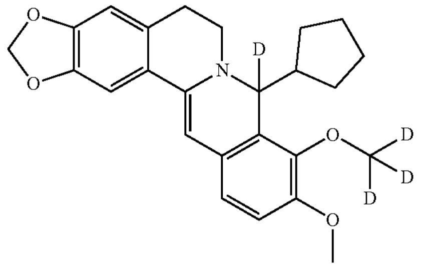

The synthesis method of compound AB36509 was as follows:

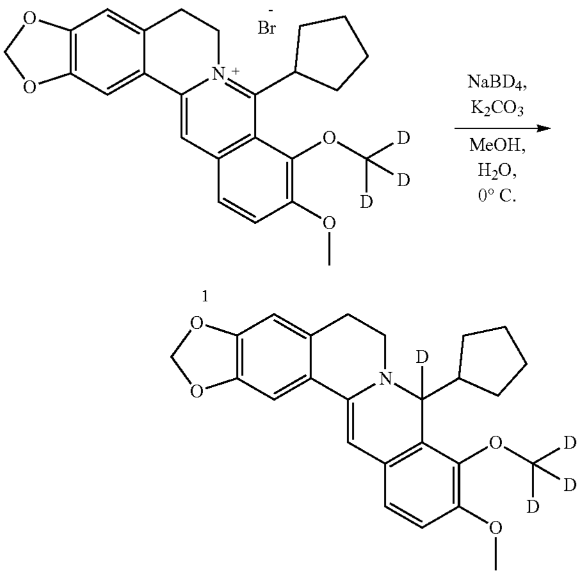

1

AB36509

Compound 1 (200 mg, 0.41 mmol, 1.0 eq) was dissolved in methanol (10 mL), and aqueous potassium carbonate solution (3 mL, 1.23 mmol, 3.0 eq) and aqueous deuterated sodium borohydride solution (0.3 mL, 2.46 mmol, 0.3 eq) were added at 0° C. The mixture was reacted at 0° C. for 5 min, and the reaction mixture was filtered, and filter cake was collected. The crude product was purified by fast chromatography (dichloromethane/methanol=0-5%) to afford compound AB36509.

The MS-ESI and $^1$H NMR spectra of compound AB36509 were as follows:

MS-ESI: Calculated $[M+H]^+$: 410.22; Found: 410.15.

$^1$H NMR (400 MHz, DMSO-d6) δ 7.23 (s, 1H), 6.82 (d, J=8.0 Hz, 1H), 6.76 (s, 1H), 6.67 (d, J=8.0 Hz, 1H), 5.99 (s, 2H), 5.90 (s, 1H), 3.76 (s, 3H), 3.44-3.37 (m, 2H), 2.91-2.85 (m, 1H), 2.70-2.63 (m, 1H), 2.23-2.15 (m, 1H), 1.60-1.17 (m, 8H).

Example 151 Synthesis of Compound AB35442

The structure of compound AB35442 was as follows:

AB35442

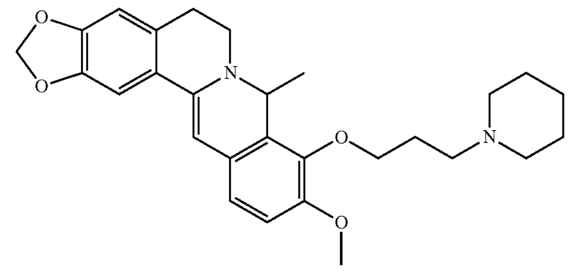

The synthesis method of compound AB35442 was as follows:

Step (1):

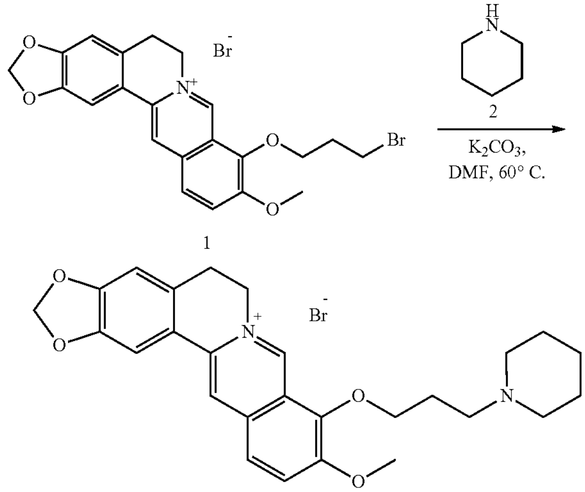

Compound 1 (200 mg, 0.38 mmol, 1.0 eq) was dissolved in DMF (10 mL), and compound 2 (200 mg, 2.28 mmol, 6 eq) and potassium carbonate (156 mg, 1.14 mmol, 3.0 eq) were added. The mixture was reacted at 60° C. for 16 h under $N_2$, and the reaction was detected to be performed completely using TLC and LCMS, the organic solvent was spin dried. The crude product was purified by thin layer chromatography (DCM/MeOH=10/1) to afford compound 3.

Step (2):

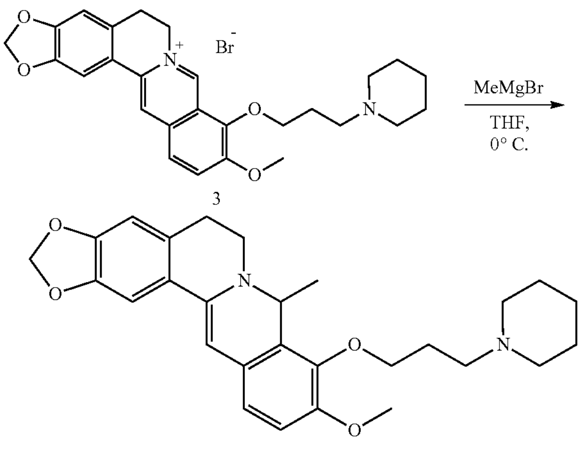

AB35442

Compound 3 (150 mg, 0.28 mmol, 1.0 eq) was dissolved in tetrahydrofuran (10 mL), and methylmagnesium bromide (0.6 mL, 1.68 mmol, 6 eq, 3M) was added at 0° C. The mixture was reacted at room temperature for 0.5 h, and the reaction was detected to be performed completely using TLC and LCMS. The reaction mixture was quenched with saturated aqueous ammonium chloride solution and then extracted with dichloromethane twice, the organic phase was dried over anhydrous sodium sulfate and filtered, the filtrate was spin dried. The crude product was purified by reversed phase preparation chromatography (acetonitrile/water+0.01% formic acid) to afford compound AB35442.

The MS-ESI and $^1$H NMR spectra of compound AB35442 were as follows:

MS-ESI: Calculated $[M+H]^+$: 463.26, Found: 463.35.

$^1$H NMR (400 MHz, DMSO-d6) δ 8.24 (s, 1H), 7.23 (s, 1H), 6.78 (d, J=8.0 Hz, 1H), 6.75 (s, 1H), 6.64 (d, J=8.0 Hz, 1H), 5.98 (d, J=4.0 Hz, 2H), 5.90 (s, 1H), 4.76-4.71 (m, 1H), 3.96-3.93 (m, 2H), 3.72 (s, 3H), 3.31-3.24 (m, 1H), 3.21-3.16 (m, 1H), 2.81-2.72 (m, 2H), 2.44-2.38 (m, 5H), 1.87-1.80 (m, 2H), 1.52-1.46 (m, 4H), 1.41-1.35 (m, 2H), 1.03 (d, J=8.0 Hz, 3H).

Example 152 Synthesis of Compound AB35443

The structure of compound AB35443 was as follows:

AB35443

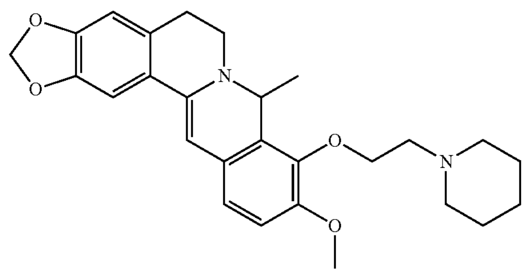

The synthesis method of compound AB35443 was as follows:

Step (1):

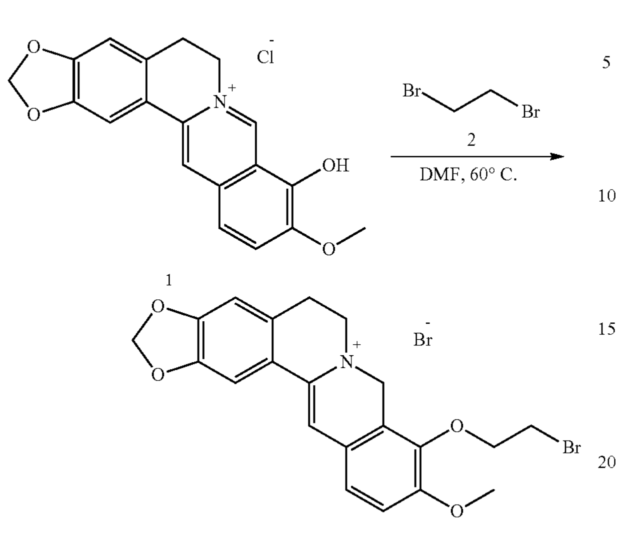

1

3

Compound 1 (5.0 g, 13.97 mmol, 1.0 eq) was dissolved in DMF (50 mL), and compound 2 (26.2 g, 139.7 mmol, 10 eq) was added. The mixture was reacted at 60° C. for 16 h under $N_2$, and the reaction was detected to be performed completely using TLC and LCMS, the organic solvent was spin dried. The crude product was purified by fast chromatography (DCM/MeOH=100/1 to 50/1) to afford compound 3.

Step (2):

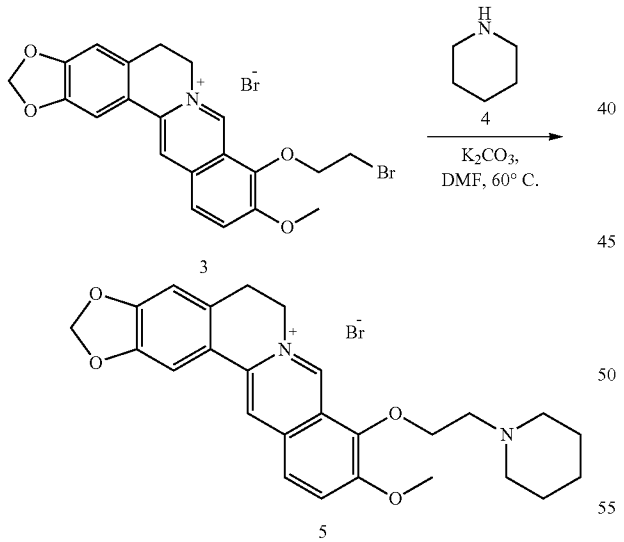

3

5

Compound 3 (200 mg, 0.39 mmol, 1.0 eq) was dissolved in DMF (10 mL), and compound 4 (200 mg, 2.34 mmol, 6 eq) and potassium carbonate (162 mg, 1.17 mmol, 3.0 eq) were added. The mixture was reacted at 60° C. for 16 h under $N_2$, and the reaction was detected to be performed completely using TLC and LCMS, the organic solvent was spin dried. The crude product was purified by thin layer chromatography (DCM/MeOH=10/1) to afford compound 5.

Step (3):

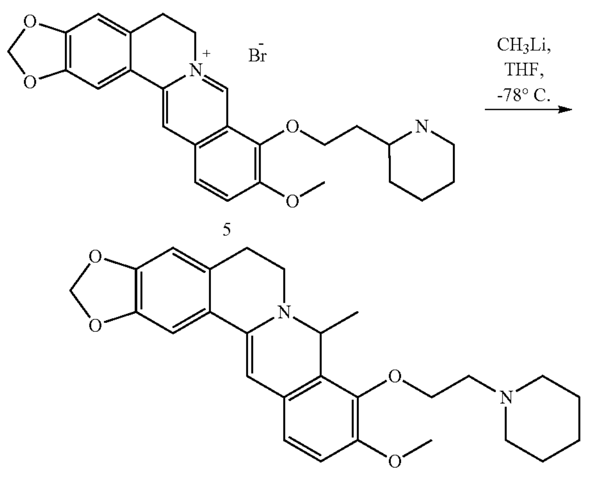

5

AB35443

Compound 5 (150 mg, 0.29 mmol, 1.0 eq) was dissolved in tetrahydrofuran (10 mL), and methyllithium (0.9 mL, 0.87 mmol, 3 eq, 1M) was added at −78° C. The mixture was reacted for 0.5 h, and the reaction was detected to be performed completely using TLC and LCMS. The mixture was quenched with saturated ammonium chloride solution and then extracted with dichloromethane twice, the organic phase was dried over anhydrous sodium sulfate and filtered, the filtrate was spin dried, the crude product was purified by reversed phase preparation chromatography (acetonitrile/water+0.01% formic acid) to afford compound AB35443.

The MS-ESI and $^1$H NMR spectra of compound AB35543 were as follows:

MS-ESI: Calculated $[M+H]^+$: 449.24, Found: 449.40.

$^1$H NMR (400 MHz, DMSO-d6) δ 8.23 (s, 1H), 7.23 (s, 1H), 6.78 (d, J=8.0 Hz, 1H), 6.75 (s, 1H), 6.64 (d, J=8.0 Hz, 1H), 5.98 (d, J=4.0 Hz, 2H), 5.89 (s, 1H), 4.86-4.85 (m, 1H), 4.04-4.00 (m, 2H), 3.72 (s, 3H), 3.3-3.24 (m, 1H), 3.19-3.15 (m, 1H), 2.82-2.71 (m, 2H), 2.59-2.56 (m, 2H), 2.42-2.39 (m, 3H), 1.50-1.48 (m, 4H), 1.38-1.34 (m, 2H), 1.02 (d, J=8.0 Hz, 3H).

Example 153 Synthesis of Compound AB35446

The structure of compound AB35446 was as follows:

AB35446

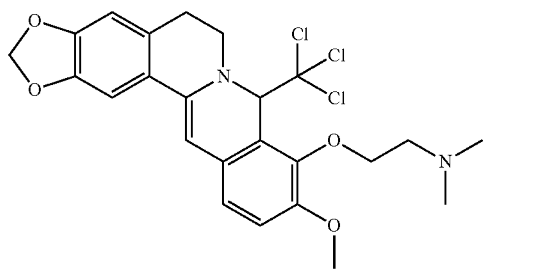

The synthesis method of compound AB35446 was as follows:

Step (1):

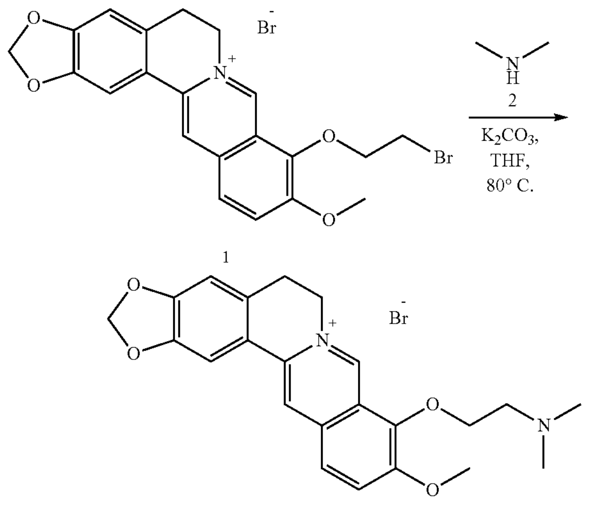

1

3

Compound 1 (500 mg, 0.98 mmol, 1.0 eq) was dissolved in tetrahydrofuran (5 mL) in a sealed tube, compound 2 (3 mL, 5.88 mmol, 6 eq, 2M) and potassium carbonate (402 mg, 2.94 mmol, 3.0 eq) were added. The mixture was reacted at 80° C. for 16 h under $N_2$, and the reaction was detected to be performed completely using TLC and LCMS, the organic phase was spin dried. The crude product was purified by thin layer chromatography (DCM:MeOH=10/1) to afford compound 3.

Step (2):

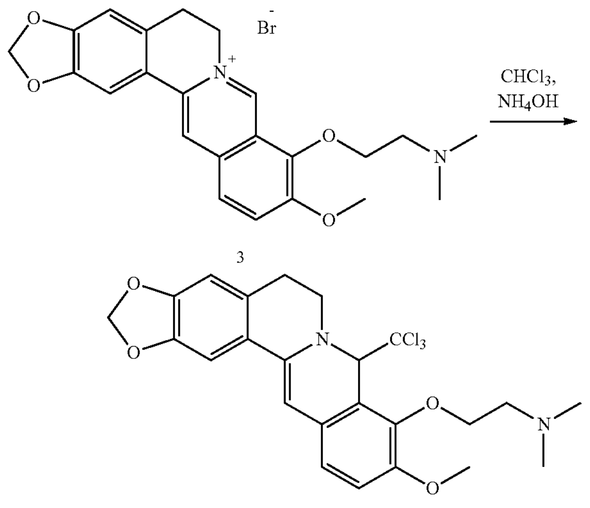

3

AB35446

Compound 3 (120 mg, 0.25 mmol, 1 eq) was dissolved in a mixture of aqueous ammonia (3 ml) and chloroform (6 ml). The mixture was reacted at room temperature for 48 h. The reaction mixture was diluted with water and then extracted with dichloromethane, the organic phase was dried over anhydrous sodium sulfate and filtered, the filtrate was spin dried. The crude product was purified by thin layer chromatography (DCM/MeOH=20/1) to afford compound AB 5446.

The MS-ESI and $^1$H NMR spectra of compound AB35546 were as follows:

MS-ESI: Calculated $[M+H]^+$: 511.09, Found: 511.05.

$^1$H NMR (400 MHz, DMSO-d6) δ 7.31 (s, 1H), 7.05 (d, J=8.0 Hz, 1H), 6.85 (d, J=8.0 Hz, 1H), 6.77 (s, 1H), 6.28 (s, 1H), 6.22 (s, 1H), 5.99 (d, J=4.0 Hz, 2H), 4.26-4.22 (m, 1H), 3.87-3.83 (m, 1H), 3.78 (s, 3H), 3.72-3.69 (m, 1H), 3.62-3.58 (m, 1H), 3.28-3.21 (m, 2H), 2.72-2.67 (m, 1H), 2.61-2.55 (m, 1H), 2.24 (s, 6H).

Example 154 Synthesis of Compound AB35447

The structure of compound AB35447 was as follows:

AB35447

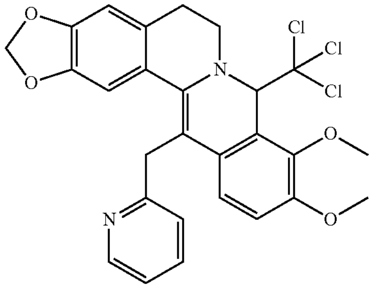

The synthesis method of compound AB35447 was as follows:

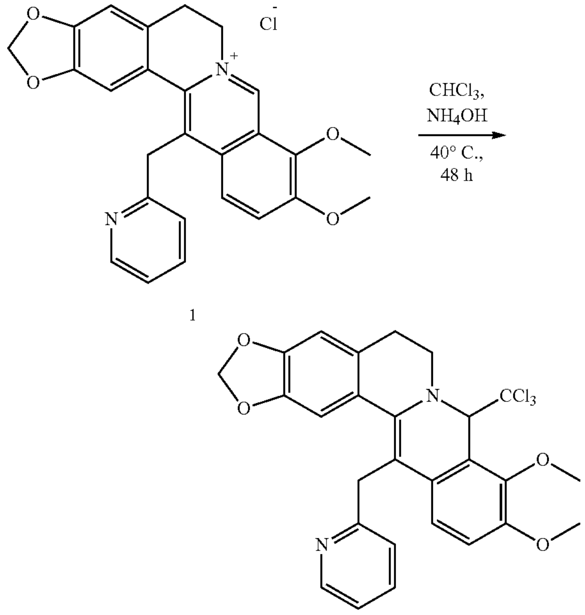

1

AB35447

Compound 1 (280 mg, 0.60 mmol, 1 eq) was dissolved in a mixture of chloroform (12 ml) and aqueous ammonia (6 ml). The mixture was reacted at 40° C. for 48 h under $N_2$. The reaction mixture was extracted with dichloromethane twice, the organic phase was dried over anhydrous sodium sulfate and filtered, the filtrate was spin dried. The crude product was purified by thin layer chromatography (PE/PA=2/1) to afford compound AB 35447.

The MS-ESI and $^1$H NMR spectra of compound AB35447 were as follows:

MS-ESI: Calculated $[M+H]^+$: 545.07, Found: 545.10.

$^1$H NMR (400 MHz, DMSO-d6) δ 8.48 (d, J=4.0 Hz, 1H), 7.67-7.63 (m, 1H), 7.31-7.28 (m, 2H), 7.18-7.15 (m, 1H), 7.06-6.98 (m, 2H), 6.90 (s, 1H), 5.97 (d, J=4.0 Hz, 2H), 5.68 (s, 1H), 4.15-4.03 (m, 2H), 3.92-3.85 (m, 1H), 3.80 (s, 3H), 3.77 (s, 3H), 3.70-3.65 (m, 1H), 2.80-2.60 (m, 2H).

Example 155 Synthesis of Compound AB36426

The structure of compound AB36426 was as follows:

AB36426

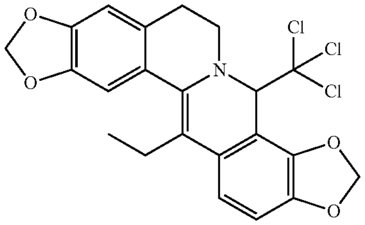

The synthesis method of compound AB36426 was as follows:

Step (1):

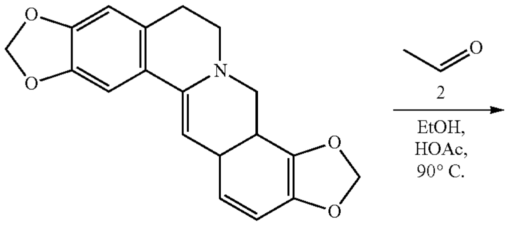

1

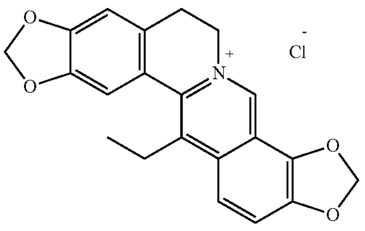

3

Compound 1 (1 g, 3.1 mmol, 1 eq) was dissolved in ethanol/acetic acid (10 mL/8 mL), and compound 2 (1.4 g, 30.9 mmol, 10 eq) was added. The mixture was reacted at 90° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 3.

Step (2):

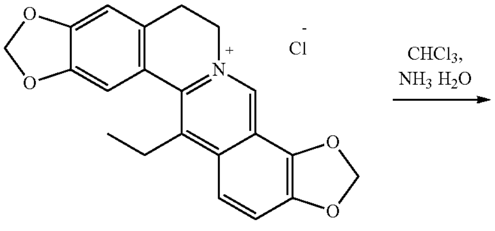

3

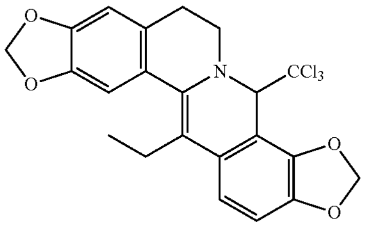

AB36426

Compound 3 (200 mg, 0.5 mmol, 1 eq) was dissolved in a mixture of chloroform (10 ml) and aqueous ammonia (5 ml). The mixture was reacted at room temperature for overnight. The reaction mixture was diluted with water and then extracted with dichloromethane twice, the organic phase was washed with brine, dried over anhydrous sodium sulfate, filtered and spin dried. The crude product was purified by fast chromatography (DCM/MeOH=50/1) to afford compound AB36426.

The MS-ESI and $^1$H NMR spectra of compound AB36426 were as follows:

MS-ESI: Calculated $[M+H]^+$: 466.03; Found $[M+H]^+$: 466.15.

$^1$H NMR (400 MHz, DMSO-d6) δ 7.02-6.88 (m, 4H), 6.10 (s, 1H), 6.03 (s, 2H), 6.00 (s, 1H), 5.50 (s, 1H), 3.86-3.80 (m, 1H), 3.66-3.63 (m, 1H), 3.37-3.36 (m, 2H), 2.79-2.76 (m, 1H), 2.61-2.50 (m, 1H), 2.13 (s, 3H).

Example 156 Synthesis of Compound AB36442

The structure of compound AB36442 was as follows:

AB36442

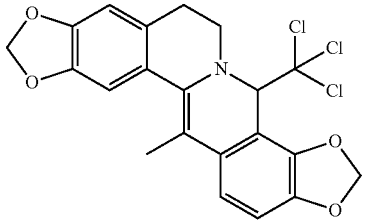

The synthesis method of compound AB356442 was as follows:

Step (1):

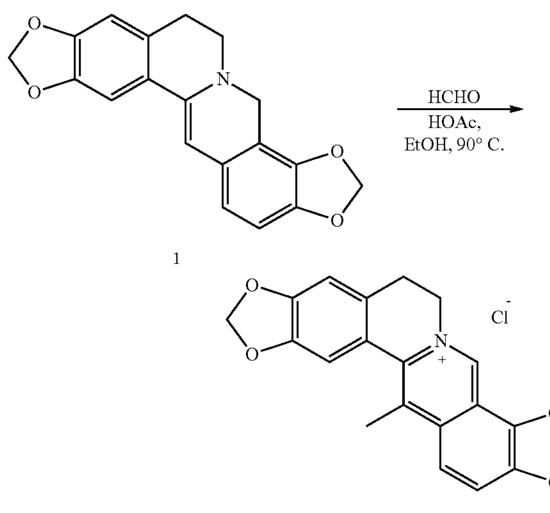

1

2

Compound 1 (1 g, 3.1 mmol, 1 eq) was dissolved in ethanol/acetic acid (10 mL/8 mL), and formaldehyde tetrahydrofuran solution (31 mL, 30.9 mmol, 10 eq, 1M) was added. The mixture was reacted at 90° C. for 4 h, an appropriate amount of hydrochloric acid was added, and the mixture was concentrated. To crude product was added a small amount of dichloromethane and an appropriate amount of ethyl acetate, the mixture was stewed for 0.5 h and then filtered to remove solid. The filtrate was stewed for overnight to precipitate a solid, the solid was filtered and collected to afford compound 2.

Step (2):

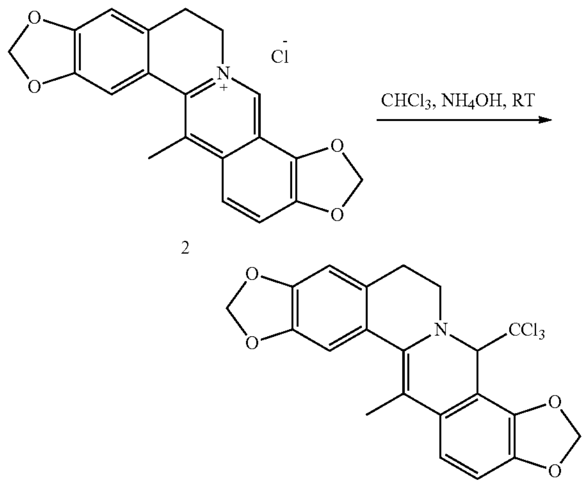

2

AB36442

Compound 2 (200 mg, 0.54 mmol, 1 eq) was dissolved in a mixture of chloroform (10 ml) and aqueous ammonia (5 ml). The mixture was reacted at room temperature for overnight. The reaction mixture was diluted with water and then extracted with dichloromethane twice, the organic phase was dried over anhydrous sodium sulfate and filtered, the filtrate was spin dried. The crude product was purified by fast chromatography (DCM/MeOH=50/1) to afford compound AB36442.

The MS-ESI and $^1H$ NMR spectra of compound AB36442 were as follows:

MS-ESI: Calculated $[M+H]^+$: 452.01; Found $[M+H]^+$: 452.20.

$^1H$ NMR (400 MHz, $CDCl_3$) δ 7.00-6.88 (m, 4H), 76.10 (s, 1H), 6.03 (s, 2H), 6.00 (s, 1H), 5.50 (s, 1H), 3.86-3.80 (m, 1H), 3.66-3.63 (m, 1H), 2.79-2.76 (m, 1H), 2.58-2.50 (m, 1H), 2.13 (s, 3H).

Example 157 Synthesis of Compound AB36472

The structure of compound AB35472 was as follows:

AB36472

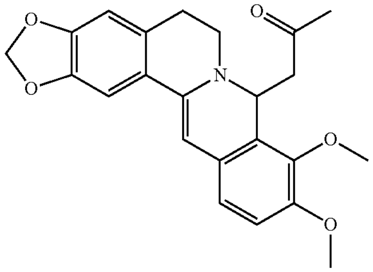

The synthesis method of compound AB356472 was as follows:

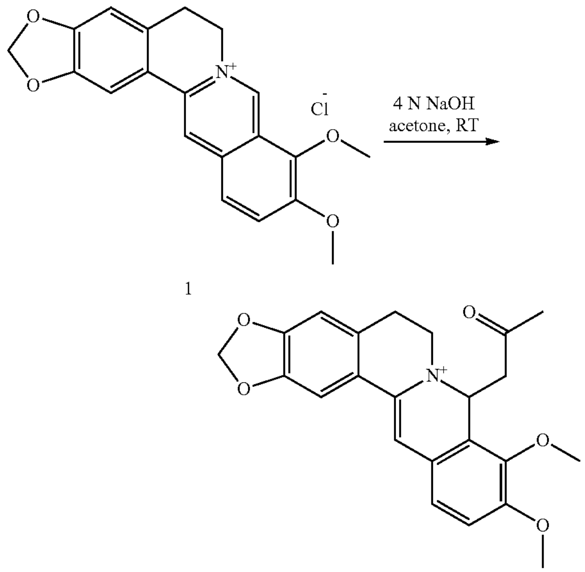

1

AB36472

Compound 1 (372 mg, 1 mmol, 1 eq) was dissolved in acetone (5 mL) in a sealed tube, and 4N sodium hydroxide solution (2 mL) was added. The mixture was reacted at room temperature for 1 h. The solid was filtered and washed with water. The crude product was purified by fast chromatography (dichloromethane:methanol=50:1) to afford compound AB36472.

MS-ESI: Calculated $[M+H]^+$: 394.16; Found: 394.10.

$^1H$ NMR (400 MHz, $CDCl_3$) δ 7.25 (s, 1H), 6.87-6.70 (m, 3H), 6.00 (d, J=4.0 Hz, 3H), 6.22-6.19 (m, 1H), 3.76 (d, J=4.0 Hz, 6H), 3.27-3.18 (m, 2H), 2.96-2.90 (m, 1H), 2.80-2.69 (m, 2H), 2.32-2.27 (m, 1H), 2.03 (s, 3H).

Example 158 Synthesis of Compound AB36488

The structure of compound AB36488 was as follows:

AB36488

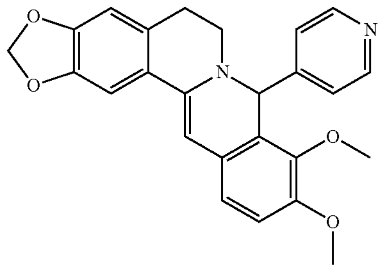

The synthesis method of compound AB36488 was as follows:

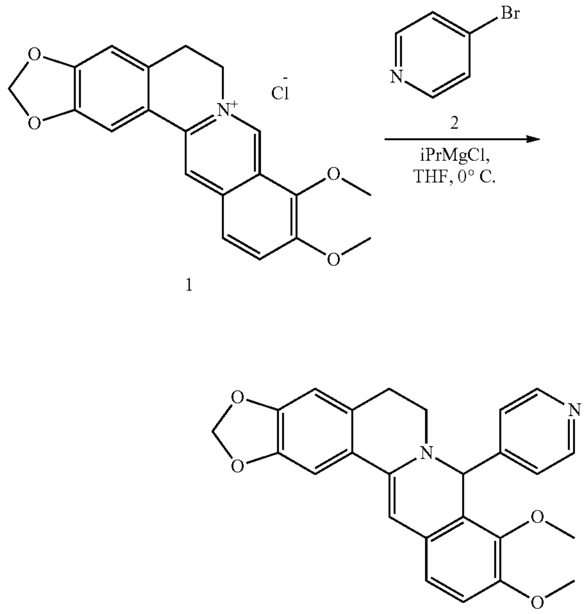

1

AB36488

Compound 2 (1.3 g, 8.23 mmol, 4.0 eq) was dissolved in tetrahydrofuran (10 mL) and isopropylmagnesium chloride solution (5 mL, 10.3 mmol, 5.0 eq, 2M in THF) was added at 0° C. The mixture was reacted for 30 min, compound 1 (766 mg, 2.06 mmol, 1.0 eq) was added, and then the mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by normal phase preparation chromatography (dichloromethane/methanol=0%-2%) to afford compound AB36488.

MS-ESI: Calculated $[M]^+$: 415.16; Found: 415.10.

$^1$H NMR (400 MHz, DMSO-d6) δ 8.44-8.42 (m, 2H), 7.31-7.28 (m, 3H), 6.91-6.79 (m, 2H), 6.74 (s, 1H), 6.00 (s, 3H), 5.75 (s, 1H), 3.75 (s, 3H), 3.61 (s, 3H), 3.41-3.36 (m, 1H), 2.94-2.87 (m, 1H), 2.79-2.71 (m, 2H).

Example 159 Synthesis of Compound AB36496

The structure of compound AB36496 was as follows:

AB36496

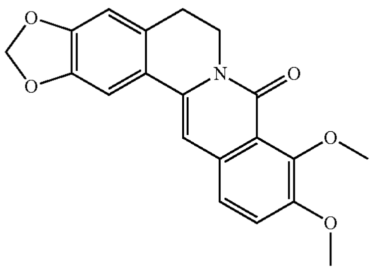

The synthesis method of compound AB36496 was as follows:

Step (1):

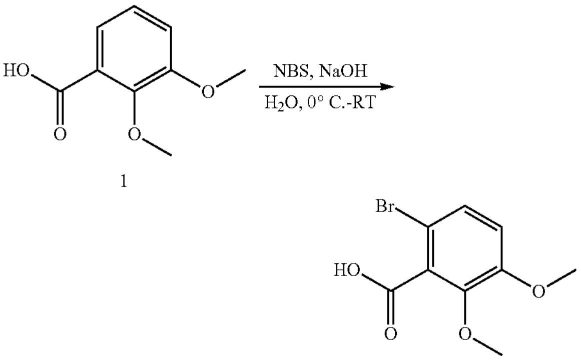

1

2

Compound 1 (5 g, 27.44 mmol, 1.0 eq) was dissolved in aqueous sodium hydroxide solution (60 mL, 60.37 mmol, 2.2 eq), and N-bromosuccinimide (5.9 g, 32.93 mmol, 1.2 eq) was added at 0° C. The mixture was reacted at room temperature for 16 h. The reaction mixture was quenched with 5% aqueous sodium bisulfite solution, adjusted to pH=1 with 12M hydrochloric acid, and extracted with ethyl acetate. The organic phase was dried over anhydrous sodium sulfate, filtered and spin dried to afford compound 2.

Step (2):

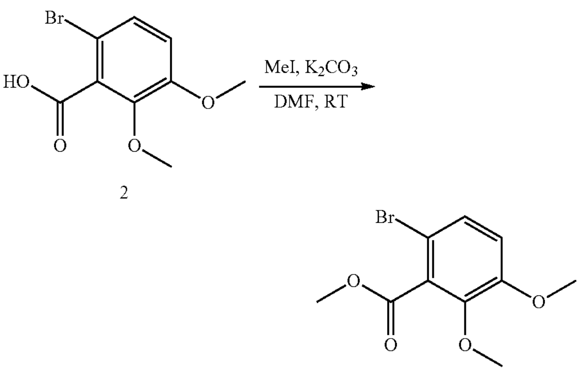

2

3

Compound 2 (7.9 g, 30.26 mmol, 1.0 eq) was dissolved in N, N-dimethylformamide (100 mL), and potassium carbonate (8.3 g, 60.52 mmol, 2.0 eq) and iodomethane (5.1 g, 36.31 mmol, 1.2 eq) were added. The mixture was reacted at room temperature for 16 h. The reaction mixture was spin dried, the crude product was purified by normal phase preparation chromatography (petroleum ether/ethyl acetate=0%-10%) to afford compound 3.

Step (3):

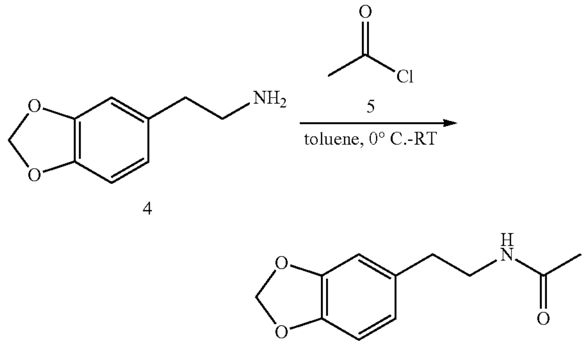

4
5
6

Compound 4 (10 g, 60.18 mmol, 1.0 eq) was dissolved in toluene (100 mL), and compound 5 (4.7 g, 60.18 mmol, 1.0 eq) was added at 0° C. The mixture was reacted at room temperature for 16 h. The reaction mixture was spin dried, the crude product was purified by normal phase preparation chromatography (dichloromethane/methanol=0%-10%) to afford compound 6.

Step (4):

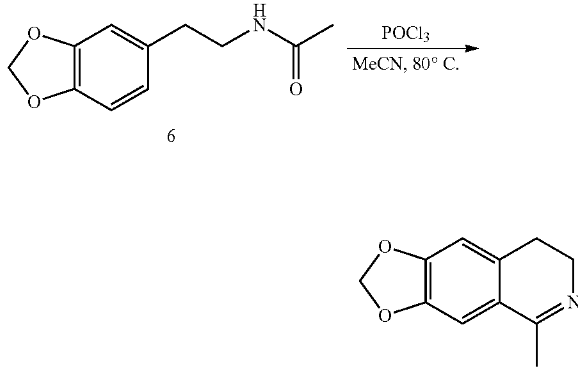

6
7

Compound 6 (11.5 g, 55.49 mmol, 1.0 eq) was dissolved in acetonitrile (50 mL), and phosphorus oxychloride (8.5 g, 55.49 mmol, 1.0 eq) was added. The reaction was reacted at 80° C. for 16 h, and then cooled to room temperature. The reaction mixture was quenched with water, adjusted to pH=7-8 with 2N aqueous sodium hydroxide solution, and extracted with dichloromethane. The organic phase was dried over anhydrous sodium sulfate and filtered, the filtrate was spin dried, the crude product was purified by normal phase preparation chromatography (dichloromethane/methanol=0%-10%) to afford compound 7.

Step (5):

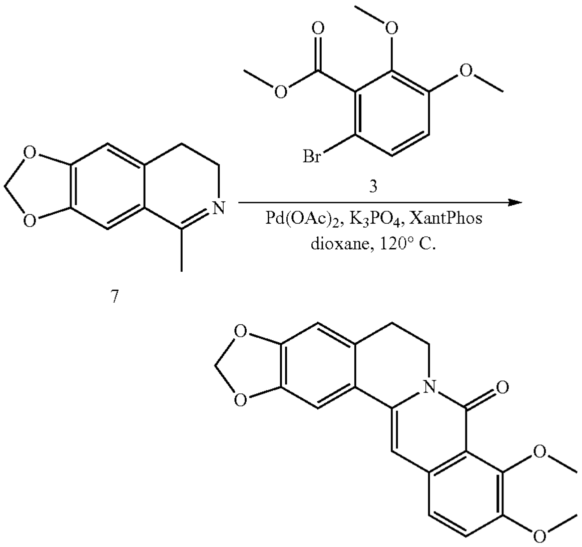

3
7
AB36496

Compound 7 (250 mg, 1.32 mmol, 1.0 eq) was dissolved in 1,4-dioxane (5 mL), and compound 3 (436 mg, 1.58 mmol, 1.2 eq), potassium phosphate (839 mg, 3.96 mmol, 3 eq), palladium acetate (30 mg, 0.132 mmol, 0.1 eq), and 4,5-diphenylphosphine-9,9-dimethyloxanthracene (153 mg, 0.264 mmol, 0.2 eq) were added. The mixture was reacted at 120° C. for 16 h, the reaction mixture was spin dried, the crude product was purified by reversed phase preparation chromatography (acetonitrile/water+0.1% formic acid) to afford compound AB36496.

The MS-ESI and $^1H$ NMR spectra of compound AB36496 were as follows:

MS-ESI: Calculated $[M+H]^+$: 352.11; Found: 352.05.

$^1H$ NMR (400 MHz, DMSO-d6) δ 7.54-7.40 (m, 3H), 7.10 (s, 1H), 6.93 (s, 1H), 6.07 (s, 2H), 4.13-4.10 (m, 2H), 3.87 (s, 3H), 3.77 (s, 3H), 2.89-2.87 (m, 2H).

Example 160 Synthesis of Compound AB36497

The structure of compound AB36497 was as follows:

AB36497

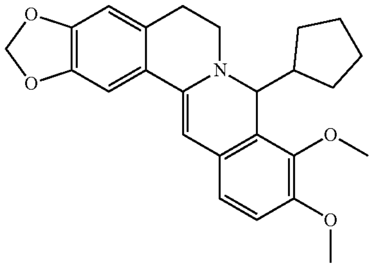

The synthesis method of compound AB356497 was as follows:

Step (1):

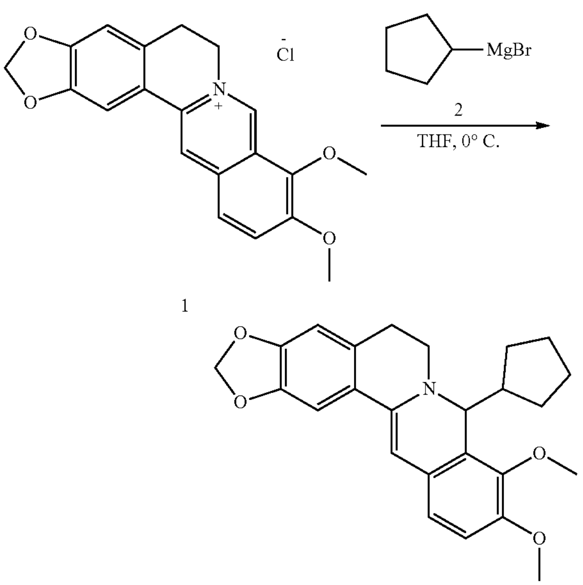

1

3

Compound 1 (1 g, 2.69 mmol, 1.0 eq) was dissolved in tetrahydrofuran (20 mL), and cyclopentylmagnesium bromide (13.5 mL, 13.45 mmol, 5.0 eq, 1M in THF) at 0° C. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by fast chromatography (dichloromethane/methanol=0-5%) to afford compound 3.

Step (2):

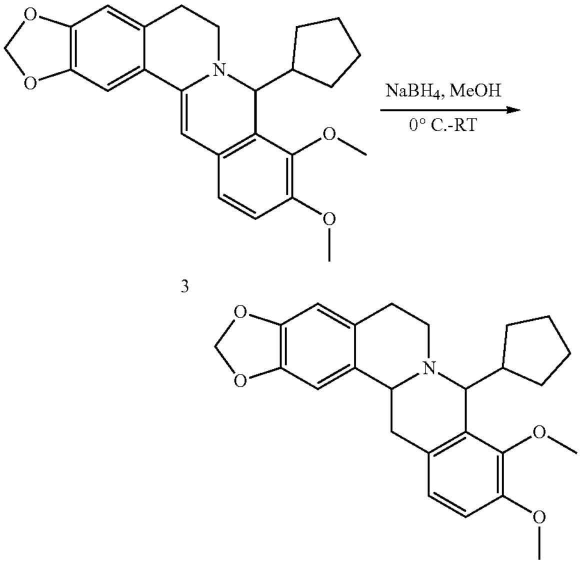

3

AB36497

Compound 2 (500 mg, 1.23 mmol, 1.0 eq) was dissolved in methanol (50 mL), and sodium borohydride (93 mg, 2.46 mmol, 2.0 eq) was added at 0° C. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by reversed phase preparation chromatography (acetonitrile/water+0.1% formic acid) to afford compound AB36497.

The MS-ESI and $^1H$ NMR spectra of compound AB36497 were as follows:

MS-ESI: Calculated $[M+H]^+$: 408.21; Found: 408.00.

$^1H$ NMR (400 MHz, DMSO-d6) δ 6.93 (s, 1H), 6.90-6.82 (m, 2H), 6.63 (s, 1H), 5.91 (s, 2H), 4.00 (d, J=4.0 Hz, 1H), 3.75 (s, 3H), 3.70 (s, 3H), 3.28-3.25 (m, 2H), 3.07-2.94 (m, 2H), 2.74-2.71 (m, 1H), 2.70-2.68 (m, 1H), 2.52-2.47 (m, 1H), 2.44-2.40 (m, 1H), 1.99-1.94 (m, 2H), 1.57-1.27 (m, 5H), 0.95 (s, 1H).

Example 161 Synthesis of Compound AB36512

The structure of compound AB36512 was as follows:

AB36512

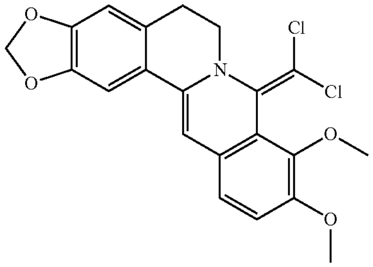

The synthesis method of compound AB36512 was as follows:

Step (1):

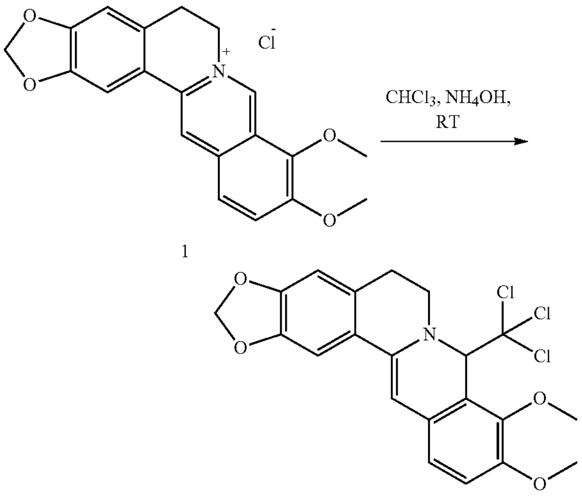

1

2

Compound 1 (1.5 g, 4.0 mmol, 1 eq) was dissolved in chloroform (20 mL), and aqueous ammonia (10 mL) was added. The mixture was reacted at room temperature for overnight. The reaction mixture was diluted with water and then extracted with dichloromethane, the organic phase was washed with brine, dried over anhydrous sodium sulfate and filtered, the filtrate was spin dried. The crude product was purified by fast chromatography (petroleum ether/ethyl acetate=10/1) to afford compound 2.

Step (2):

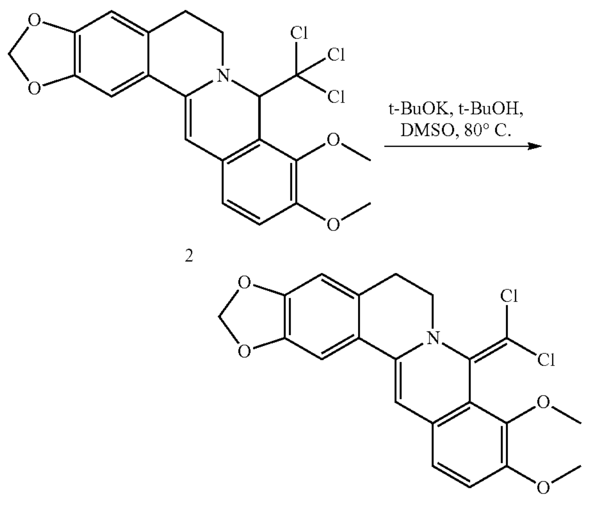

2

AB36512

Compound 2 (500 mg, 1.1 mmol, 1.0 eq) was dissolved in a mixture of tertbutanol (5 mL) and dimethyl sulfoxide (5 mL), and potassium t-butoxide (617 mg, 5.5 mmol, 5.0 eq) was added. The mixture was reacted at 80° C. for 2 h. The reaction mixture was diluted with water and then extracted with ethyl acetate, the organic phase was washed with brine, dried over anhydrous sodium sulfate and filtered, the filtrate was spin dried. The crude product was purified by fast chromatography (petroleum ether/ethyl acetate=10/1) to afford compound AB36512.

The MS-ESI and $^1$H NMR spectra of compound AB36512 were as follows:

MS-ESI: Calculated [M+H]$^+$: 418.06; Found: 418.00.

$^1$H NMR (400 MHz, DMSO-d6) δ 7.43 (s, 1H), 7.10 (d, J=8.0 Hz, 1H), 6.92 (d, J=8.0 Hz, 1H), 6.82 (s, 1H), 6.57 (s, 1H), 6.03 (s, 2H), 3.79 (s, 3H), 3.72 (s, 4H), 3.46-3.41 (m, 1H), 3.28-3.24 (m, 1H), 2.79-2.70 (m, 1H).

Example 162 Synthesis of Compound AB31878

The structure of compound AB31878 was as follows:

AB31878

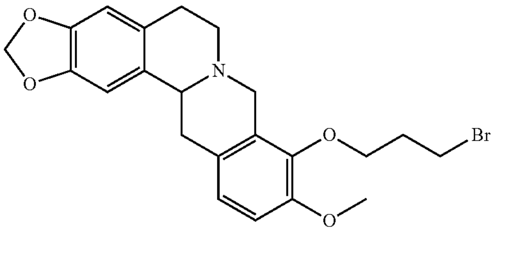

The synthesis method of compound AB3188 was as follows:

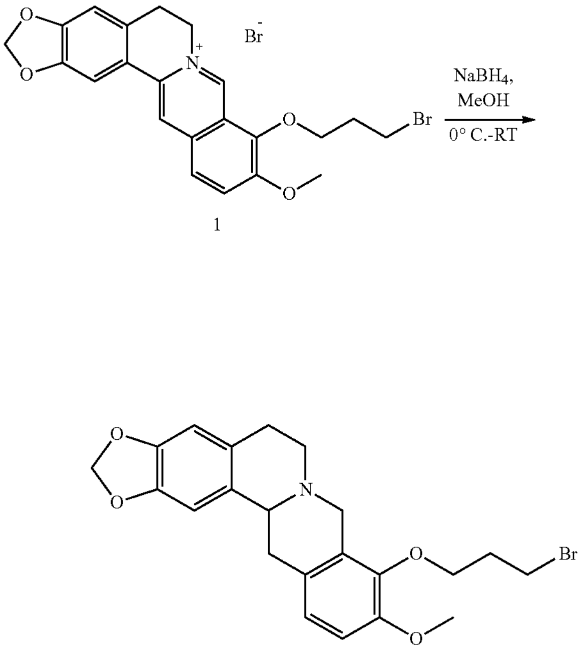

1

AB31878

Compound 1 (200 mg, 0.38 mmol, 1.0 eq) was dissolved in methanol (5 mL), and sodium borohydride (29 mg, 0.76 mmol, 2.0 eq) was added at 0° C. The mixture was reacted at room temperature for 1 h. The reaction mixture was quenched with saturated aqueous ammonium chloride solution and then extracted with ethyl acetate, the organic phase was dried over anhydrous sodium sulfate and filtered, the filtrate was spin dried. The crude product was purified by reversed preparation column chromatography (acetonitrile/water+0.1% formic acid) to afford compound AB31878.

MS-ESI: Calculated [M+H]$^+$: 446.09; Found: 446.30.

$^1$H NMR (400 MHz, DMSO-d6) δ 6.88 (s, 1H), 6.84 (d, J=8.0 Hz, 2H), 6.63 (s, 1H), 5.91 (s, 2H), 4.06 (d, J=16.0 Hz, 1H), 3.99-3.95 (m, 2H), 3.73 (s, 3H), 3.71-3.68 (m, 2H), 3.37-3.34 (m, 2H), 3.29-3.27 (m, 2H), 3.05-3.03 (m, 1H), 2.89-2.86 (m, 1H), 2.59-2.54 (m, 1H), 2.45-2.42 (m, 1H), 2.19-2.16 (m, 2H).

Example 163 Synthesis of Compound AB36520

The structure of compound AB36520 was as follows:

AB36520

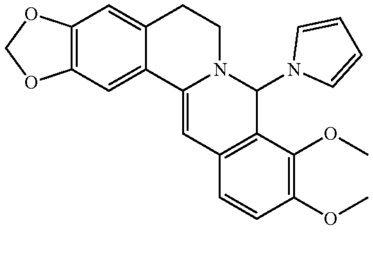

The synthesis method of compound AB36520 was as follows:

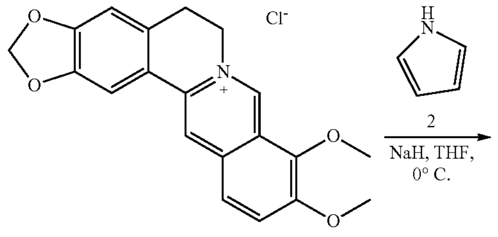

1

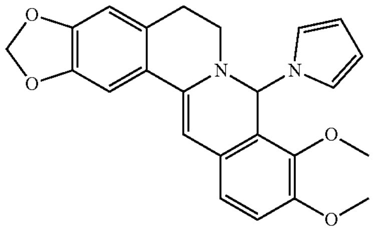

AB36520

Compound 2 (180 mg, 2.68 mmol, 2.0 eq) was dissolved in anhydrous tetrahydrofuran (10 mL), and sodium hydride (107 mg, 2.68 mmol, 2.0 eq, 60% in mineral oil) was added at 0° C. The mixture was reacted for 5 h, compound 1 (500 mg, 1.34 mmol, 1.0 eq) was added, then the mixture was reacted at room temperature for 1 h. The reaction mixture was quenched with saturated aqueous ammonium chloride solution and then extracted with ethyl acetate, the organic phase was dried over anhydrous sodium sulfate, filtered and spin dried. The crude product was purified by normal preparation chromatography (dichloromethane/methanol=0%-5%) to afford compound AB36520.

MS-ESI: Calculated $[M+H]^+$: 403.16; Found: 403.05.

$^1$H NMR (400 MHz, DMSO-d6) δ 7.31 (s, 1H), 7.06-6.98 (m, 2H), 6.75 (d, J=12.0 Hz, 2H), 6.65-6.63 (m, 2H), 6.29 (s, 1H), 5.99 (s, 2H), 5.87-5.84 (m, 2H), 3.78 (s, 3H), 3.56-3.54 (m, 1H), 3.38 (s, 3H), 2.81-2.65 (m, 3H).

Example 164 Synthesis of Compound AB36525

The structure of compound AB36525 was as follows:

AB36525

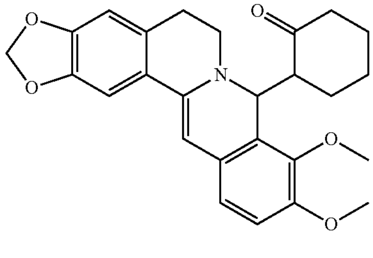

The synthesis method of compound AB36525 was as follows:

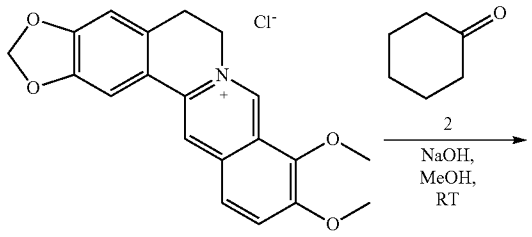

1

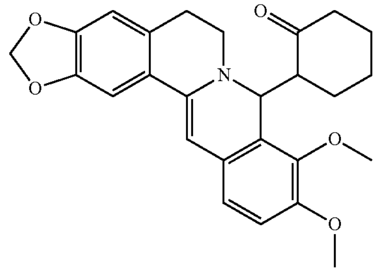

AB36525

Compound 1 (400 mg, 1.07 mmol, 2.0 eq) was dissolved in methanol (10 mL), and 1N sodium hydroxide solution (1 mL) was added. The mixture was reacted for 0.5 h, and filtered to remove the solid, cyclohexanone (1 mL) was added to the filtrate, then the mixture was reacted at room temperature for 1 h, the solid was filtered, washed with methanol and dried to afford compound AB36525.

MS-ESI: Calculated $[M+H]^+$: 434.19; Found: 434.15.

$^1$H NMR (400 MHz, DMSO-d6) δ 7.15 (s, 1H), 6.81 (d, J=8.0 Hz, 1H), 6.70 (s, 1H), 6.62 (d, J=8.0 Hz, 1H), 5.95 (s, 2H), 5.73 (s, 1H), 5.57 (s, 1H), 3.72 (s, 3H), 3.69 (s, 3H), 3.23-3.18 (m, 1H), 3.05-3.03 (m, 1H), 2.66-2.59 (m, 2H), 2.26-2.15 (m, 3H), 1.95-1.93 (m, 1H), 1.78-1.76 (m, 1H), 1.61-1.59 (m, 1H), 1.48-1.35 (m, 3H).

Example 165

Figure 2:
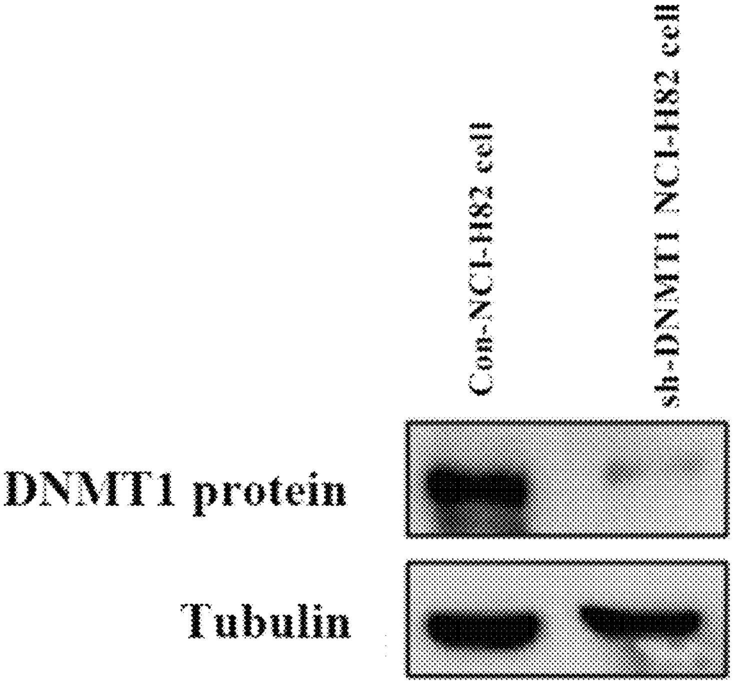
FIG. 2 shows the expression content of DNMT1 protein in Con-NCI-H82 cell and sh-DNMT1 NCI-H82 cell using Western Blot test, wherein, Con-NCI-H82 refers to the expression content of DNMT1 protein in NCI-H82 cell transfected with empty virus vector without carrying NNMT gene and shRNA, which is used as control; sh-DNMT1 NCI-H82 refers to the expression content of DNMT1 protein in NCI-H82 cell transfected with virus vector carrying shRNA.

The role of expression level of NNMT and DNMT1 in the sensitivity of NCI-H82 cell to the compounds prepared in the Examples of the present invention was determined Experiment Method and Result:

The expression of NNMT protein in NCI-H82 cell was overexpressed by inserting the NNMT gene into NCI-H82 cell using a viral vector, and the NNMT protein-overexpressing NCI-H82 cell (ov-NNMT NCI-H82 cell) was obtained. The expression of DNMT1 in NCI-H82 cell was knocked down by transfecting shRNA (the nucleotide sequence of shRNA was GATCCGGGATGAGTCCATCAAGGAAGATTCAAGAGATCTTCCTTGATGGACTCATCCT TTTTTG (SEQ ID No: 2)) using a viral vector, and the NCI-H82 cell with low expression of DNMT1 protein (sh-DNMT1 NCI-H82 cell) was obtained. The control NCI-H82 cell (Con-NCI-H82 cell) was obtained by transfecting NCI-H82 cell with empty virus vector without carrying NNMT gene and shRNA. The expressing content of NNMT protein and DNMT1 protein in the Con-NCI-182 cell, the expressing content of NNMT protein in the ov-NNMT NCI-H82 cell, and the expressing content of DNMT1 protein in the sh-DNMT1 NCI-1H82 cell were detected using Western Blot assay (as shown in FIG. 1 and FIG. 2), it could be seen from FIG. 1 and FIG. 2 that the NNMT protein was overexpressed in the ov-NNMT NCI-1H82 cell and the expression of DNMT1 protein was knocked down (i.e, low expression) in the sh-DNMT1 NCI-1H82 cell compared with the expression level of NNMT protein and DNMT protein in the Con-NCI-1H82 cell.

Figure 3:
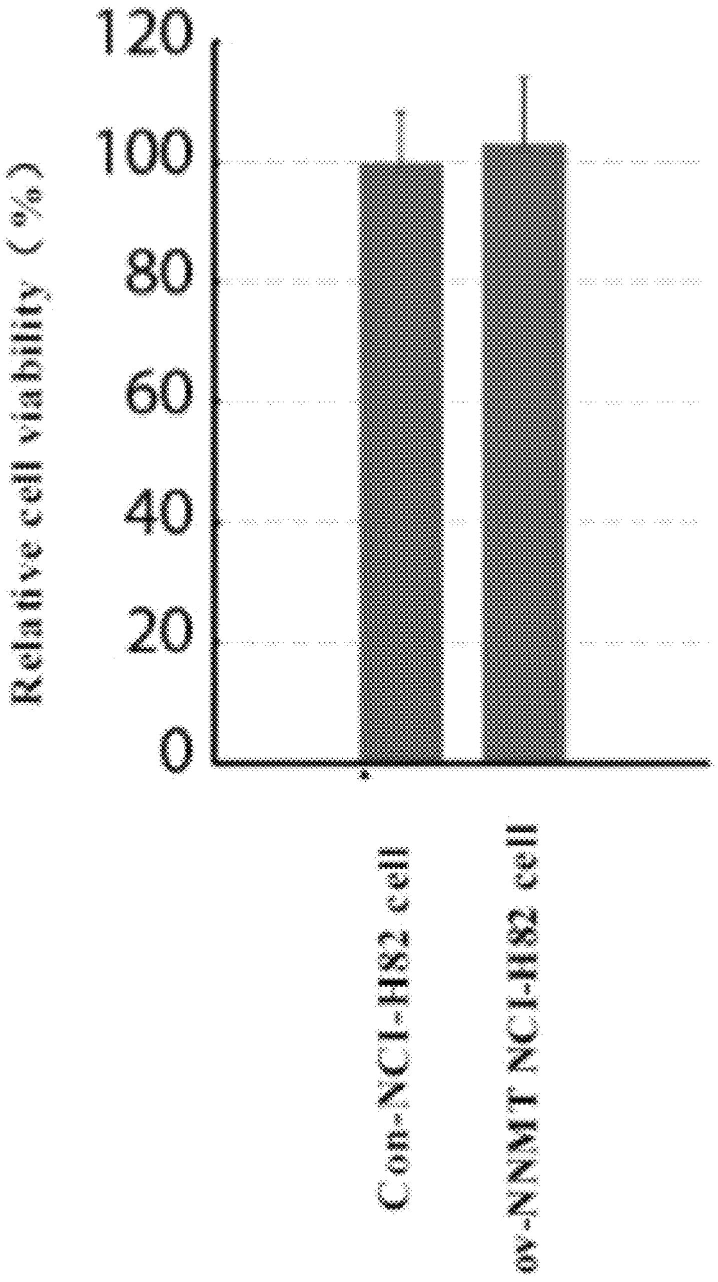
FIG. 3 shows the relative cell viability of Con-NCI-H82 cell and ov-NNMT NCI-H82 cell, wherein, Con-NCI-H82 refers to the cell viability of NCI-H82 cell transfected with empty virus vector without carrying NNMT gene and shRNA, which is used as control; ov-NNMT NCI-H82 refers to the cell viability of NCI-H82 cell transfected with virus vector carrying NNMT gene.
Figure 4:
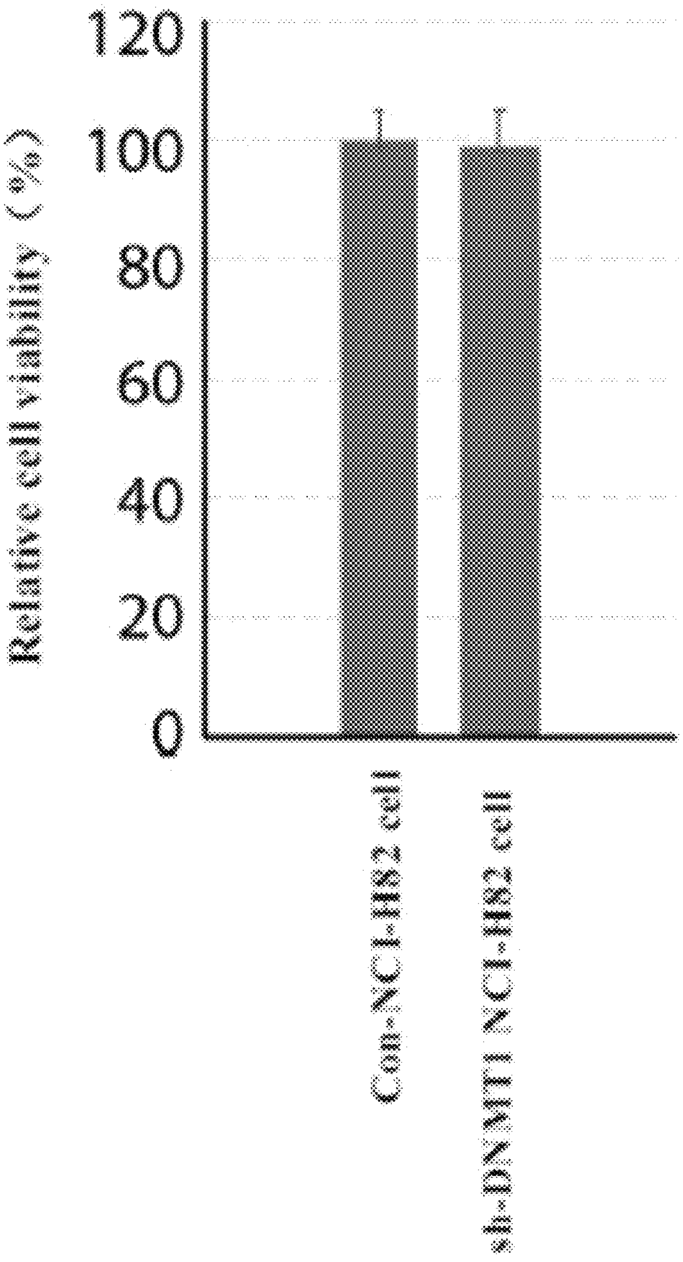
FIG. 4 shows the relative cell viability of Con-NCI-H82 cell and sh-DNMT1 NCI-H82 cell, wherein, Con-NCI-H82 refers to the cell viability of NCI-H82 cell transfected with empty virus vector without carrying NNMT gene and shRNA, which is used as control; sh-DNMT1 NCI-H82 refers to the cell viability of NCI-H82 cell transfected with virus vector carrying shRNA.

The cell viability of Con-NCI-1H82 cell, ov-NNMT NCI-1H82 cell and sh-DNMT1 NCI-1H82 cell was detected using the Promega CellTiter-Glo kit which reflected cell viability by measuring intracellular ATP content (as shown in FIG. 3 and FIG. 4), it could be seen from FIG. 3 and FIG. 4 that the cell viability of Con-NCI-1H82 cell, ov-NNMT NCI-1H82 cell and sh-DNMT1 NCI-1H82 cell was almost the same, and the difference in cell viability was not statistically significant.

The inhibitory effect ($IC_{50}$ value) of the compounds (dissolved in DMSO) prepared in the Examples of the present invention on Con-NCI-H82 cell, ov-NNMT NC-82 cell and sh-DNMT1 NCI-1H82 cell was detected using Promega CellTiter-Glo kit which directly measured intracellular ATP content, the result was shown in Table 3 below:

TABLE 3 the inhibitory effect of the compounds prepared in the Examples of the present invention on Con-NCI-H82 cell, ov-NNMT NCI-H82 cell and sh-DNMT1 NCI-H82 cell ($IC_{50}$, μM)

| Compound | Con-NCI-H82 (μM) | OV-NNMT NCI-H82 (μM) | sh-DNMT1 NCI-H82 (μM) |
|---|---|---|---|
| compound AB31866 | 0.82 | 1.86 | 3.48 |
| compound AB31870 | 0.53 | 1.32 | 2.54 |
| compound AB35417 | 0.57 | 1.78 | 3.12 |
| compound AB35411 | 1.24 | 2.51 | 4.34 |
| compound AB35436 | 1.27 | 3.28 | 5.32 |
| compound AB35418 | 0.53 | 1.26 | 2.25 |
| compound AB35422 | 2.32 | 5.48 | 4.94 |
| compound AB35448 | 1.34 | 2.98 | 2.88 |
| compound AB31881 | 2.01 | 4.04 | 3.98 |
| compound AB35430 | 0.85 | 3.18 | 6.32 |
| compound AB31887 | 2.83 | 5.78 | 5.69 |
| compound AB35434 | 1.68 | 5.12 | 4.98 |
| compound AB31888 | 2.26 | 4.64 | 6.12 |
| compound AB31895 | 1.14 | 3.24 | 4.68 |
| compound AB31896 | 1.31 | 4.53 | 3.98 |
| compound AB31897 | 1.43 | 5.32 | 4.96 |
| compound AB35402 | 0.88 | 2.43 | 3.45 |
| compound AB35405 | 0.92 | 2.13 | 3.86 |
| compound AB35407 | 0.74 | 2.73 | 3.44 |
| compound AB35415 | 1.14 | 3.42 | 5.48 |
| compound AB35423 | 2.16 | 4.96 | 4.36 |
| compound AB35416 | 2.31 | 5.23 | 6.35 |
| compound AB35424 | 5.02 | 11.21 | 10.82 |
| compound AB35438 | 0.72 | 2.12 | 3.22 |
| compound AB35429 | 1.89 | 5.32 | 5.04 |
| compound AB35420 | 4.99 | 12.48 | 18.21 |
| compound AB31873 | 2.88 | 6.32 | 6.08 |
| compound AB35440 | 0.98 | 2.56 | 4.12 |
| compound AB35441 | 1.01 | 3.21 | 2.98 |
| compound AB35444 | 1.15 | 4.21 | 5.28 |
| compound AB35445 | 5.55 | 13.42 | 16.35 |
| compound AB31880 | 0.99 | 3.32 | 3.86 |
| compound AB31898 | 3.69 | 8.64 | 12.12 |
| compound AB35426 | 0.46 | 1.56 | 2.12 |
| compound AB35427 | 0.56 | 1.82 | 3.24 |
| compound AB35428 | 4.23 | 10.25 | 15.36 |
| compound AB35413 | 5.48 | 14.23 | 20.34 |
| compound AB35421 | 5.77 | 12.36 | 21.22 |
| compound AB35453 | 0.23 | 1.32 | 2.08 |
| compound AB35454 | 1.02 | 3.25 | 4.98 |
| compound AB35455 | 1.11 | 3.33 | 3.12 |
| compound AB35456 | 2.36 | 6.72 | 8.42 |
| compound AB35457 | 0.96 | 2.56 | 2.33 |
| compound AB35458 | 1.56 | 4.12 | 5.32 |
| compound AB35459 | 4.97 | 12.32 | 16.48 |
| compound AB35465 | 2.69 | 9.32 | 8.84 |
| compound AB35466 | 1.01 | 3.56 | 4.48 |
| compound AB35467 | 5.64 | 13.32 | 15.42 |
| compound AB35468 | 0.82 | 3.12 | 4.32 |
| compound AB35469 | 0.79 | 3.52 | 5.32 |
| compound AB35475 | 1.29 | 4.12 | 4.02 |
| compound AB35476 | 0.99 | 3.69 | 4.56 |
| compound AB35478 | 1.23 | 4.32 | 4.02 |
| compound AB35484 | 0.77 | 3.56 | 3.32 |
| compound AB35485 | 4.55 | 12.32 | 16.76 |
| compound AB35486 | 0.25 | 1.34 | 2.56 |
| compound AB35487 | 0.49 | 1.98 | 3.23 |
| compound AB35488 | 1.98 | 7.56 | 9.32 |
| compound AB35489 | 0.82 | 3.78 | 3.56 |
| compound AB35490 | 2.68 | 7.52 | 8.46 |
| compound AB35491 | 2.22 | 6.86 | 6.54 |
| compound AB35492 | 1.46 | 4.56 | 4.44 |
| compound AB35494 | 0.43 | 2.12 | 1.96 |
| compound AB35496 | 2.92 | 6.32 | 8.24 |
| compound AB35497 | 1.25 | 3.56 | 5.68 |
| compound AB35498 | 1.28 | 4.12 | 4.38 |
| compound AB35499 | 2.16 | 6.96 | 6.52 |
| compound AB35500 | 1.11 | 2.98 | 2.88 |
| compound AB35501 | 0.87 | 2.12 | 2.56 |
| compound AB35502 | 2.93 | 7.18 | 7.02 |
| compound AB35504 | 2.22 | 4.96 | 6.76 |
| compound AB35505 | 0.52 | 2.14 | 3.36 |
| compound AB35506 | 0.83 | 2.66 | 2.52 |
| compound AB35508 | 0.74 | 3.12 | 2.98 |
| compound AB35510 | 0.31 | 1.56 | 1.86 |
| compound AB35512 | 0.62 | 2.42 | 2.32 |
| compound AB35514 | 0.37 | 1.36 | 1.98 |
| compound AB35518 | 3.52 | 10.12 | 13.26 |
| compound AB35519 | 2.19 | 5.68 | 4.68 |
| compound AB35521 | 0.61 | 2.32 | 3.14 |
| compound AB35522 | 1.36 | 3.68 | 5.64 |
| compound AB35523 | 1.02 | 2.99 | 2.86 |
| compound AB35524 | 1.34 | 4.32 | 4.02 |
| compound AB35525 | 0.51 | 2.02 | 3.15 |
| compound AB35531 | 0.92 | 3.55 | 3.98 |
| compound AB35534 | 1.32 | 3.96 | 3.84 |
| compound AB35535 | 0.22 | 1.21 | 1.32 |
| compound AB35536 | 0.52 | 2.24 | 2.56 |
| compound AB35543 | 0.55 | 2.68 | 3.12 |
| compound AB35544 | 0.28 | 1.02 | 2.04 |
| compound AB35545 | 0.14 | 1.33 | 1.56 |
| compound AB35550 | 2.12 | 4.69 | 4.58 |
| compound AB35590 | 1.52 | 4.68 | 4.04 |
| compound AB35594 | 1.26 | 4.12 | 3.98 |
| compound AB35599 | 1.38 | 3.43 | 6.42 |
| compound AB36403 | 0.38 | 1.54 | 1.46 |
| compound AB36415 | 0.88 | 2.56 | 3.64 |
| compound AB36416 | 1.08 | 3.44 | 4.51 |
| compound AB36423 | 1.85 | 5.11 | 4.98 |
| compound AB36427 | 3.28 | 7.56 | 6.98 |
| compound AB36428 | 0.45 | 1.44 | 2.29 |
| compound AB36432 | 1.26 | 3.68 | 4.46 |
| compound AB36433 | 0.54 | 1.95 | 3.01 |
| compound AB36434 | 1.02 | 2.56 | 3.68 |
| compound AB36437 | 0.65 | 2.73 | 3.12 |
| compound AB36447 | 2.02 | 4.98 | 7.12 |
| compound AB36450 | 2.08 | 5.32 | 8.34 |
| compound AB36460 | 1.06 | 3.33 | 4.58 |
| compound AB36463 | 0.92 | 3.44 | 3.24 |
| compound AB36467 | 3.92 | 9.32 | 13.12 |
| compound AB36474 | 1.33 | 4.12 | 6.08 |
| compound AB36476 | 1.24 | 4.86 | 7.34 |
| compound AB36477 | 1.22 | 5.68 | 8.82 |
| compound AB31893 | 1.12 | 4.12 | 5.68 |
| compound AB31900 | 1.08 | 4.88 | 6.58 |
| compound AB35460 | 0.66 | 2.02 | 2.56 |
| compound AB35493 | 0.68 | 1.53 | 2.07 |
| compound AB36493 | 0.29 | 1.58 | 1.98 |
| compound AB36501 | 0.97 | 4.33 | 5.12 |
| compound AB36509 | 0.51 | 1.68 | 2.58 |
| compound AB35442 | 9.22 | 8.38 | 9.32 |

TABLE 3-continued

| the inhibitory effect of the compounds prepared in the Examples of the present invention on Con-NCI-H82 cell, ov-NNMT NCI-H82 cell and sh-DNMT1 NCI-H82 cell ($IC_{50}$, μM) | | | |
|---|---|---|---|
| Compound | Con-NCI-H82 (μM) | OV-NNMT NCI-H82 (μM) | sh-DNMT1 NCI-H82 (μM) |
| compound AB35443 | 20.64 | 18.06 | 20.85 |
| compound AB35446 | 18.35 | 16.32 | 17.88 |
| compound AB35447 | 26.25 | 25.66 | 24.32 |
| compound AB36426 | 18.63 | 18.08 | 18.8 |
| compound AB36442 | 14.96 | 13.35 | 14.08 |
| compound AB36472 | 4.28 | 4.32 | 4.11 |
| compound AB36488 | 8.23 | 8.06 | 7.83 |
| compound AB36496 | 12.88 | 10.12 | 12.6 |
| compound AB36497 | 19.87 | 18.32 | 16.98 |
| compound AB36512 | 4.36 | 4.08 | 3.96 |
| compound AB31878 | 8.23 | 7.98 | 8.46 |
| compound AB36520 | 2.56 | 2.42 | 2.62 |
| compound AB36525 | 3.86 | 3.53 | 3.96 |

Note:

$IC_{50}$ refered to 50% inhibiting concentration, ie, the concentration of the compound when 50% inhibitory effect was achieved. Con-NCI-H82 refered to the NCI-H82 cell transfected with empty virus vector without carrying NNMT gene and shRNA, which was used as control; ov-NNMT NCI-H82 refered to the NCI-H82 cell transfected with virus vector carrying NNMT gene, the NNMT protein was overexpressed in the ov-NNMT NCI-H82 cell; sh-DNMT1 NCI-H82 refered to the NCI-H82 cell transfected with virus vector carrying shRNA; the expression of DNMT1 was knocked down (i.e, low expression) in the sh-DNMT1 NCI-H82 cell.

As was shown in Table 3, the NNMT protein in NCI-1H82 cell was overexpressed and the expression of DNMT1 in NCI-1H82 cell was knocked down in the Example, the results further confirmed that the compounds prepared in the Examples of the present invention had significant inhibitory effect on tumor cell with low or no expression of NNMT gene and high expression of DNMT1 while the compounds prepared in the Examples of the present invention had weak inhibitory effect on tumor cells with high expression of NNMT gene and low expression of DNMT1. Decreasing the expression of NNMT gene and increasing the expression of DNMT1 in tumor could significantly improve the inhibitory effect of the compounds prepared in the Examples of the present invention on tumor on tumor, the expression level of NNMT gene in tumor cell was significantly negative correlation with the sensitivity of tumor cell to the compounds prepared in the Examples of the present invention, while the expression level of DNMT1 in tumor cell was significantly positive correlation with the sensitivity of tumor cell to the compounds prepared in the Examples of the present invention. Therefore, the compounds prepared in the Examples of the present invention had more significant inhibitory effect on tumor cell with low or no expression of NNMT gene and high expression of DNMT1, the tumor cell with low or no expression of NNMT gene and high expression of DNMT1 were highly sensitive to the compounds prepared in the Examples of the present invention. Therefore, the compounds prepared in the Examples of the present invention has excellent precision treatment on the tumor cell with low or no expression of NNMT gene and high expression of DNMT1.

Example 166

The inhibitory effect of the compounds prepared in the Examples of the present invention on various tumor cell lines was detected using cell viability assay reagent.

Experimental Background:

Cell viability was detected using the Promega CellTiter-Glo kit, cell viability was determined by directly measuring intracellular ATP content. In the experiment, the $IC_{50}$ value of the compounds prepared in the Examples of the present invention on various tumor cell lines was detected.

Experimental Method and Result:

Each tumor cell was cultured in relevant medium. After cell passage, the gradient diluted compounds prepared in the Examples of the present invention was added. After 3 days of culture, the relevant $IC_{50}$ (50% inhibiting concentration) was measured. The name, source and culture conditions of each tumor cell line were as follows:

Cell line NCI-H82 (ATCC, No. HTB-175) was cultured in 10% fetal bovine serum-containing RPMI1640 medium (+P/S).

Cell line G-401 (ATCC, No. CRL-1441) was cultured in 10% fetal bovine serum-containing McCoy's 5a medium (+P/S).

Cell line MDA-MB-453 (ATCC, No. HTB-131) was cultured in 10% fetal bovine serum-containing Leibovitz's L-15 medium (+P/S).

Cell line SW48 (ATCC, No. CCL-231) was cultured in 10% fetal bovine serum-containing Leibovitz's L-15 medium (+P/S).

Cell line CFPAC-1 (ATCC, No. CRL-1918) was cultured in 10% fetal bovine serum-containing IMDM medium (+P/S).

Cell line 786-0 (ATCC, No. CRL-1932) was cultured in 10% fetal bovine serum-containing RPMI164B medium (+P/S).

Cell line GB-1 (JCRB, No. IFO50489) was cultured in 10% fetal bovine serum-containing DMEM medium (+P/S).

Cell line SF126 (JCRB, No. IFO50286) was cultured in 10% fetal bovine serum-containing EMEM medium (+P/S).

The experiment result was shown in Table 4, Table 5, Table 6 and Table 7 below:

TABLE 4

| inhibitory effect of the compounds prepared in the Examples of the present invention on different cell lines ($IC_{50}$, μM) | | | | | | |
|---|---|---|---|---|---|---|
| Cell | compound AB35441 | compound AB35434 | compound AB36447 | compound AB31900 | compound AB31893 | compound AB36501 |
| NCI-H82 | 1.01 | 1.68 | 2.02 | 1.08 | 1.12 | 0.97 |
| G-401 | 1.56 | 2.64 | 2.68 | 1.32 | 1.44 | 0.88 |
| MDA-MB-453 | 0.98 | 2.32 | 2.12 | 1.46 | 1.68 | 1.32 |
| SW48 | 1.22 | 3.05 | 1.96 | 1.28 | 1.85 | 1.16 |
| CFPAC-1 | 12.32 | >30 | 20.14 | 18.32 | 10.91 | 9.88 |
| 786-O | 16.48 | 22.18 | >30 | 15.68 | 9.72 | 13.12 |
| GB-1 | 24.36 | 25.66 | 24.56 | >30 | 15.46 | 13.34 |
| SF-126 | >30 | >30 | >30 | 20.12 | 12.35 | 15.45 |

Note:

$IC_{50}$ refered to 50% inhibiting concentration, ie, the concentration of the compound when 50% inhibitory effect was achieved.

TABLE 5 inhibitory effect of the compounds prepared in the Examples of the present invention on different cell lines ($IC_{50}$, μM)

| Cell | compound AB35476 | compound AB35429 | compound AB35417 | compound AB35436 | compound AB31866 | compound AB35405 |
|---|---|---|---|---|---|---|
| NCI-H82 | 0.99 | 1.89 | 0.57 | 1.27 | 0.82 | 0.92 |
| G-401 | 1.32 | 2.02 | 1.11 | 1.89 | 1.08 | 0.88 |
| MDA-MB-453 | 0.85 | 2.43 | 1.32 | 1.01 | 2.32 | 1.76 |
| SW48 | 1.11 | 1.46 | 0.98 | 1.56 | 1.96 | 2.34 |
| CFPAC-1 | 14.24 | 13.38 | 9.88 | 11.38 | 12.39 | 18.32 |
| 786-O | 12.32 | 12.54 | 10.23 | 15.36 | 15.64 | 13.12 |
| GB-1 | 15.78 | 18.36 | 14.12 | >30 | 10.46 | 15.98 |
| SF-126 | 18.34 | 15.35 | 12.34 | 22.12 | 20.13 | 20.32 |

Note:
$IC_{50}$ refered to 50% inhibiting concentration, ie, the concentration of the compound when 50% inhibitory effect was achieved.

TABLE 6 inhibitory effect of the compounds prepared in the Examples of the present invention on different cell lines ($IC_{50}$, μM)

| Cell | compound AB35536 | compound AB35506 | compound AB35512 | compound AB35534 | compound AB35590 | compound AB35543 |
|---|---|---|---|---|---|---|
| NCI-H82 | 0.52 | 0.83 | 0.62 | 1.32 | 1.52 | 0.55 |
| G-401 | 1.39 | 1.27 | 1.33 | 2.03 | 2.66 | 1.06 |
| MDA-MB-453 | 0.94 | 1.56 | 1.56 | 1.88 | 1.98 | 0.88 |
| SW48 | 1.27 | 2.13 | 2.02 | 2.45 | 2.15 | 1.56 |
| CFPAC-1 | 9.96 | 14.13 | 17.28 | 16.88 | 15.32 | 10.22 |
| 786-O | 15.46 | 10.32 | 15.35 | 14.32 | 13.88 | 9.88 |
| GB-1 | 16.49 | 25.46 | 23.48 | 20.19 | 22.46 | 13.44 |
| SF-126 | 23.38 | 19.89 | 18.11 | 19.03 | 17.67 | 15.88 |

Note
$IC_{50}$ refered to 50% inhibiting concentration, ie, the concentration of the compound when 50% inhibitory effect was achieved.

TABLE 7 inhibitory effect of the compounds prepared in the Examples of the present invention on different cell lines ($IC_{50}$, μM)

| Cell | compound AB35430 | compound AB35525 | compound AB36423 | compound AB35510 | compound AB35504 | compound AB36437 |
|---|---|---|---|---|---|---|
| NCI-H82 | 0.85 | 0.51 | 1.85 | 0.31 | 2.22 | 0.65 |
| G-401 | 1.32 | 0.98 | 2.32 | 1.21 | 3.12 | 0.98 |
| MDA-MB-453 | 0.96 | 1.68 | 1.66 | 0.56 | 1.96 | 1.34 |
| SW48 | 1.56 | 2.34 | 2.54 | 1.99 | 3.56 | 2.55 |
| CFPAC-1 | 12.12 | 16.18 | 14.32 | 13.09 | 25.55 | 14.43 |
| 786-O | 16.09 | 14.01 | 22.33 | 24.66 | 20.38 | 20.17 |
| GB-1 | 16.86 | >30 | 16.13 | 14.56 | >30 | 19.86 |
| SF-126 | 23.45 | 19.84 | >30 | 24.32 | >30 | 16.78 |

Note:
$IC_{50}$ refered to 50% inhibiting concentration, ie, the concentration of the compound when 50% inhibitory effect was achieved.

The Table 4, Table 5, Table 6 and Table 7 showed the sensitivity of different tumor cells to the compounds prepared in the Examples of the present invention, NCI-H82 (human small cell lung cancer cell), G-401 (human renal carcinoma Wilms cell), MDA-MB-453 (breast cancer cell) and SW48 (human colon adenocarcinoma cell) were sensitive to the compounds prepared in the Examples of the present invention with low $IC_{50}$ value, while 786-0 (clear cell renal cell adenocarcinoma cell), CFPAC-1 (human pancreatic cancer cell), GB-1 (human brain glioblastoma cell) and SF126 (human glioblastoma multiforme cell) were not sensitive to the compounds prepared in the Examples of the present invention with high $IC_{50}$ value.

Example 167

The mRNA transcription level of NNMT gene in four tumor cell lines sensitive to the compounds prepared in the Examples of the present invention and four tumor cell lines insensitive to the compounds prepared in the Examples of the present invention was measured using RT-qPCR gene expression analysis test, and the expression of NNMT gene in the tumor cell lines was measured respectively. The results were shown in FIG. 5.

Figure 5:
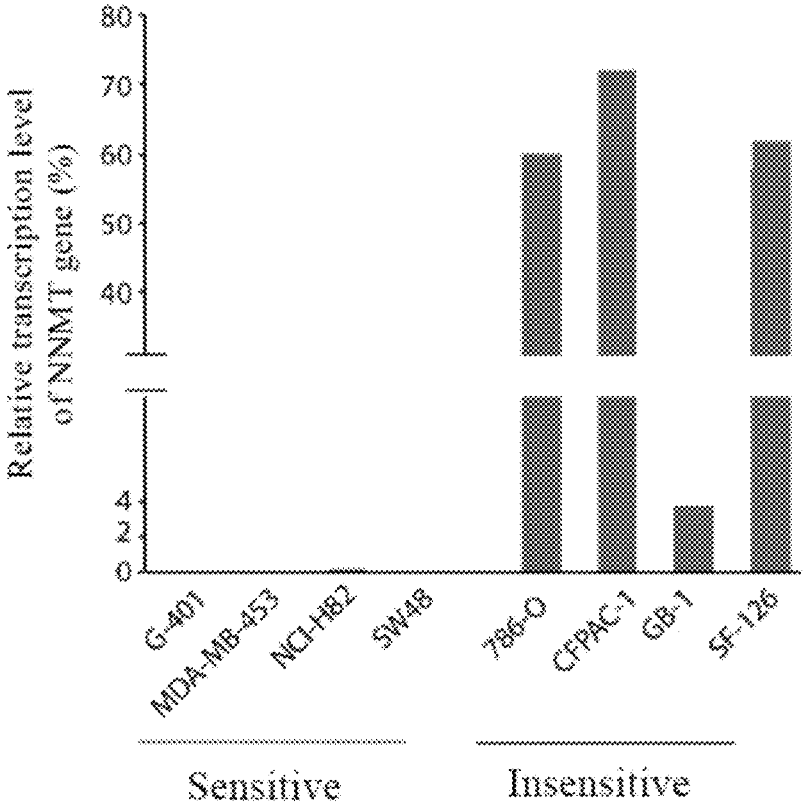
FIG. 5 shows the expression of NNMT gene in tumor cells sensitive and insensitive to the compounds prepared in the example.

As shown in FIG. 5, the mRNA transcription level of NNMT gene in four tumor cell lines (NCI-H82, G-401, MDA-MB-453 and SW48) sensitive to the compounds prepared in the Examples of the present invention and four tumor cell lines (786-0, CFPAC-1, GB-1, and SF126) insensitive to the compounds prepared in the Examples of the present invention was measured using RT-qPCR gene expression analysis test, the results showed the expression of NNMT gene was low in sensitive cell lines (NCI-H82, G-401, MDA-MB-453 and SW48), and the expression of NNMT gene was high in insensitive cell lines (786-0, CFPAC-1, GB-1 and SF126).

Therefore, the FIG. 5 showed that compared with tumor cell lines with high expression of NNMT gene, the inhibitory effect of the compounds prepared in the Examples of the present invention on tumor cell lines with low expression of NNMT gene was significantly enhanced, i.e, the expression of NNMT gene in tumor cell was negatively correlated with the sensitivity of tumor cell to the compounds prepared in the Examples of the present invention. Therefor, the tumor with low expression of NNMT gene was highly sensitive to the compounds prepared in the Examples of the present invention, the compounds prepared in the Examples of the present invention has excellent precision treatment on the tumor with low expression of NNMT gene.

Example 168

The promoter region of NNMT gene, the region from 1050 bp before the transcription start site to 499 bp after the transcription start site in NNMT gene and the region from 1050 bp to 193 bp before the transcription start site in NNMT gene were subjected to bisulfite sequencing to measure methylation level of DNA CpG site in four tumor cell lines (NCI-H82, G-401, MDA-MB-453 and SW48) sensitive to the compounds prepared in the Examples of the present invention and four tumor cell lines (786-0, CFPAC-1, GB-1 and SF126) insensitive to the compounds prepared in the Examples of the present invention. Firstly, genomic DNA was subjected to bisulfite, unmethylated cytosine was deamined to form uracil, and methylated cytosine could not be deamined, so the methylation sites could be determined by comparing the sequencing samples treated with bisulfite to the sequencing samples treated without bisulfite, and the result was shown in FIG. 6, FIG. 7, and FIG. 8.

Figure 6:
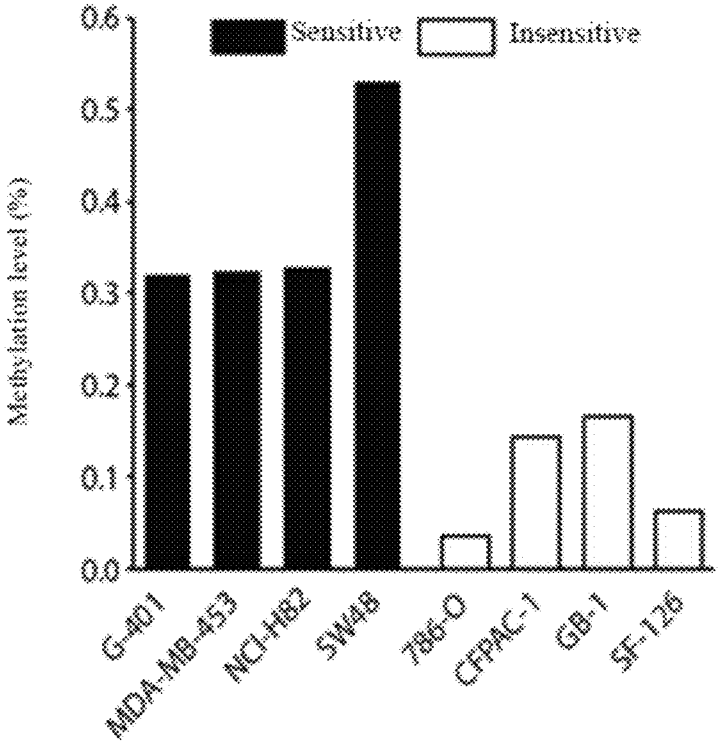
FIG. 6 shows the methylation level of DNA CpG site of promoter region of NNMT gene in tumor cells sensitive and insensitive to the compounds prepared in the example.
Figure 7:
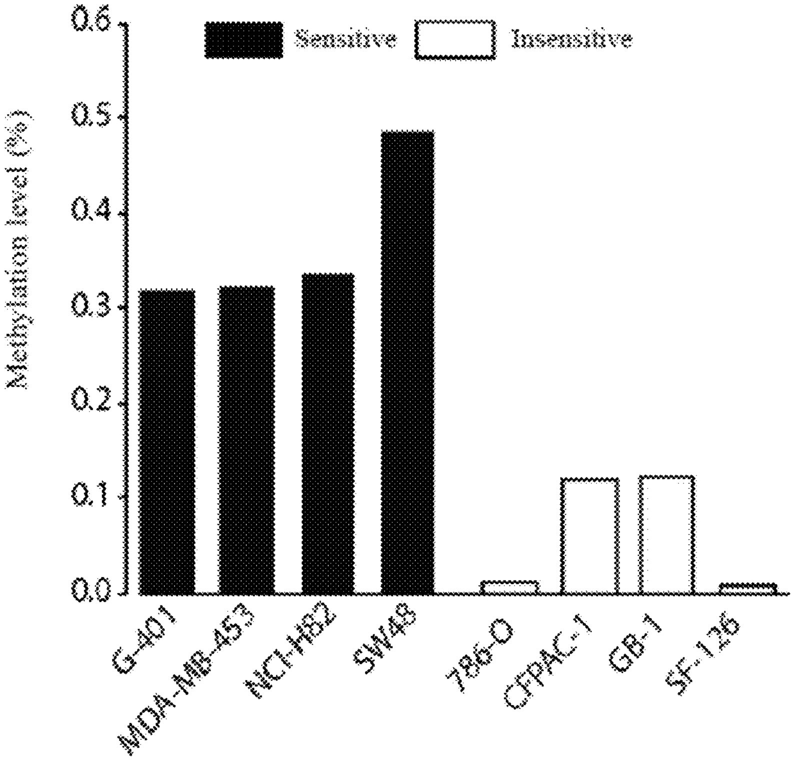
FIG. 7 shows the methylation level of DNA CpG sites from 1050 bp before the transcription start site to 499 bp after the transcription start site in NNMT gene in tumor cells sensitive and insensitive to the compounds prepared in the example.
Figure 8:
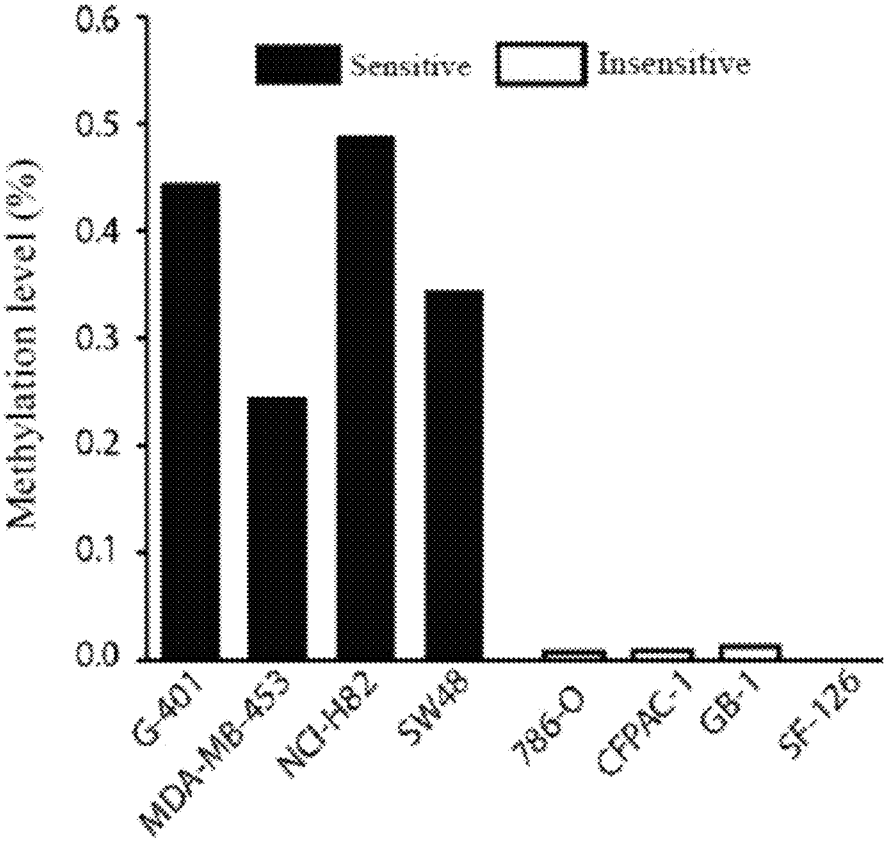
FIG. 8 shows the methylation level of DNA CpG sites from 1050 bp to 193 bp before the transcription start site in NNMT gene in tumor cells sensitive and insensitive to the compounds prepared in the example.

As shown in FIG. 6 (the promoter region of NNMT gene), FIG. 7 (the region from 1050 bp before the transcription start site to 499 bp after the transcription start site in NNMT gene) and FIG. 8 (the region from 1050 bp to 193 bp before the transcription start site in NNMT gene), the compounds prepared in the Examples of the present invention had significantly stronger inhibitory effect on tumor cells with high methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene, while the compounds prepared in the Examples of the present invention had significantly weaker inhibitory effect on tumor cells with low methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene, indicating the methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene was positively correlated with the sensitivity of tumor cell to the compounds prepared in the Examples of the present invention. Therefore, the tumor cells with high methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene were highly sensitive to the compounds prepared in the Examples of the present invention, the compounds prepared in the Examples of the present invention has excellent precision treatment on the tumor with high methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene.

Example 169

The methylation of specific DNA CpG sites from 840 bp (i.e., site 114165695 on human chromosome 11) to 469 bp (i.e., site 114166066 on human chromosome 11) before the transcription start site in NNMT gene in three tumor cell lines (NCI-H82, G-401 and SW48) sensitive to the compounds prepared in the Examples of the present invention and three tumor cell lines (786-0, CFPAC-1 and SF126) insensitive to the compounds prepared in the Examples of the present invention was studied.

Firstly, genomic DNA was subjected to bisulfite, unmethylated cytosine was deamined to form uracil, and methylated cytosine could not be deamined, so the methylation sites could be determined by comparing the sequencing samples treated with bisulfite to the sequencing samples treated without bisulfite, then PCR amplification and sequencing analysis were performed on the region using corresponding primers to measure the methylation level of CpG site in the DNA region.

Figure 9:
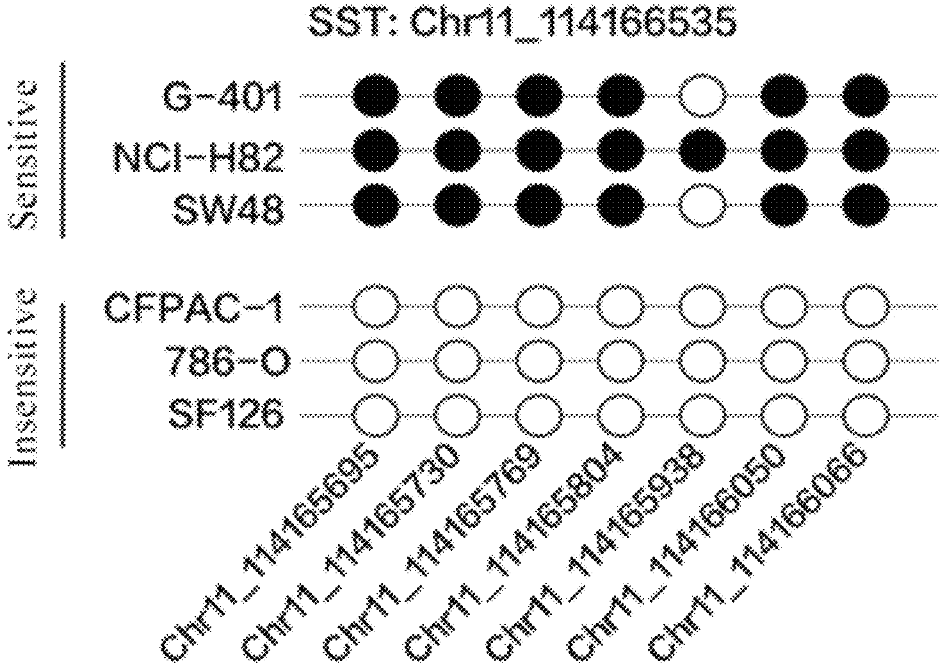
FIG. 9 shows the methylation level of DNA CpG sites of specific NNMT gene (ie, site 114165695, site 114165730, site 114165769, site 114165804, site 114165938, site 114166050, site 114166066 on human chromosome 11) in tumor cells sensitive and insensitive to the compounds prepared in the example, black dot indicates that the relevant site is methylated, white dot indicates that the relevant site is not methylated, SST refers to the transcription starting site, and Chr11 refers to human chromosome 11 according to human genome version GCF_00000 1405.25 (GRCh37.p13).

The study showed that almost all of the seven CpG sites (site 114165695, site 114165730, site 114165769, site 114165804, site 114165938, site 114166050 and site 114166066 on the human chromosome 11) were methylated in cell lines (NCI-H82, G-401 and SW48) sensitive to the compounds prepared in the Examples of the present invention, while none of the above seven CpG sites were methylated in cell lines ((786-0, CFPAC-1 and SF126) insensitive to the compounds prepared in the Examples of the present invention, the methylation of related sites was shown in FIG. 9.

The sites of the nucleotide sequence in SEQ ID NO: 1 corresponding to the site 114165695, site 114165730, site 114165769, site 114165804, site 114165938, site 114166050 and site 114166066 on the human chromosome 11 were as follows:

| The site on the human chromosome 11 | Corresponding to the sites of the nucleotide sequence in SEQ ID NO: 1 |
|---|---|
| site 114165695 | site 1161 |
| site 114165730 | site 1196 |
| site 114165769 | site 1235 |
| site 114165804 | site 1270 |
| site 114165938 | site 1404 |
| site 114166050 | site 1516 |
| site 114166066 | site 1532 |

Example 170

The inhibitory effect of the compounds prepared in the Examples of the present invention on various brain tumor cell lines was detected using cell viability assay reagent.

Experimental Background:

Cell viability was detected using the Promega CellTiter-Glo kit, cell viability was determined by directly measuring intracellular ATP content. In the experiment, the $IC_{50}$ value of the compounds prepared in the Examples of the present invention on various brain tumor cell lines was detected.

Experimental Method and Result:

Each tumor cell was cultured in relevant medium. After cell passage, the gradient diluted compounds prepared in the Examples of the present invention was added. After 3 days of culture, the relevant $IC_{50}$ (50% inhibiting concentration) was measured. The name, source and culture conditions of each tumor cell line were as follows:

Cell line D341 Med (ATCC, No. HTB-187) was cultured in 20% fetal bovine serum-containing EMEM medium (+P/S).

Cell line Kelly (ECACC, No. 92110411) was cultured in 10% fetal bovine serum and 2 mM glutamine-containing RPMI1640 medium.

Cell line NB-1 (ATCC, No. HTB-131) was cultured in 10% fetal bovine serum-containing Leibovitz's L-15 medium (+P/S).

The experiment result was shown in Table 8, Table 9, Table 10 and Table 11 below:

TABLE 8 inhibitory effect of the compounds prepared in the Examples of the present invention on different brain cell lines ($IC_{50}$, μM)

| Cell | compound AB35441 | compound AB35434 | compound AB36447 | compound AB31900 | compound AB31893 | compound AB36501 |
|---|---|---|---|---|---|---|
| D341 Med | 2.32 | 3.15 | 2.75 | 0.98 | 1.46 | 0.76 |
| Kelly | 3.16 | 2.46 | 1.98 | 1.12 | 2.09 | 1.38 |
| NB-1 | 1.98 | 2.98 | 2.04 | 0.88 | 1.88 | 2.06 |
| GB-1 | 24.36 | 25.66 | 24.56 | >30 | 15.46 | 13.34 |
| SF-126 | >30 | >30 | >30 | 20.12 | 12.35 | 15.45 |

Note:

$IC_{50}$ refered to 50% inhibiting concentration, ie, the concentration of the compound when 50% inhibitory effect was achieved.

TABLE 9 inhibitory effect of the compounds prepared in the Examples of the present invention on different brain cell lines ($IC_{50}$, μM)

| Cell | compound AB35476 | compound AB35429 | compound AB35417 | compound AB35436 | compound AB31866 | compound AB35405 |
|---|---|---|---|---|---|---|
| D341 Med | 0.89 | 2.02 | 0.88 | 1.54 | 1.54 | 0.76 |
| Kelly | 1.32 | 3.16 | 1.24 | 3.12 | 1.32 | 3.12 |
| NB-1 | 2.46 | 3.45 | 2.39 | 2.98 | 2.19 | 2.46 |
| GB-1 | 15.78 | 18.36 | 14.12 | >30 | 10.46 | 15.98 |
| SF-126 | 18.34 | 15.35 | 12.34 | 22.12 | 20.13 | 20.32 |

Note:

$IC_{50}$ refered to 50% inhibiting concentration, ie, the concentration of the compound when 50% inhibitory effect was achieved.

TABLE 10 inhibitory effect of the compounds prepared in the Examples of the present invention on different brain cell lines ($IC_{50}$, μM)

| Cell | compound AB35536 | compound AB35506 | compound AB35512 | compound AB35534 | compound AB35590 | compound AB35543 |
|---|---|---|---|---|---|---|
| D341 Med | 1.06 | 1.66 | 2.01 | 3.12 | 2.78 | 1.68 |
| Kelly | 2.56 | 3.59 | 4.23 | 2.09 | 3.16 | 1.54 |
| NB-1 | 3.11 | 3.88 | 1.56 | 1.58 | 1.99 | 2.36 |
| GB-1 | 16.49 | 25.46 | 23.48 | 20.19 | 22.46 | 13.44 |
| SF-126 | 23.38 | 19.89 | 18.11 | 19.03 | 17.67 | 15.88 |

Note:

$IC_{50}$ refered to 50% inhibiting concentration, ie, the concentration of the compound when 50% inhibitory effect was achieved.

TABLE 11

| inhibitory effect of the compounds prepared in the Examples of the present invention on different brain cell lines ($IC_{50}$, μM) | | | | | | |
|---|---|---|---|---|---|---|
| Cell | compound AB35430 | compound AB35525 | compound AB36423 | compound AB35510 | compound AB35504 | compound AB36437 |
| D341 Med | 1.32 | 0.96 | 1.55 | 0.76 | 1.58 | 2.12 |
| Kelly | 2.01 | 3.12 | 3.12 | 2.02 | 3.03 | 1.89 |
| NB-1 | 2.55 | 1.88 | 2.98 | 1.68 | 3.58 | 2.58 |
| GB-1 | 16.86 | >30 | 16.13 | 14.56 | >30 | 19.86 |
| SF-126 | 23.45 | 19.84 | >30 | 24.32 | >30 | 16.78 |

Note:

$IC_{50}$ refered to 50% inhibiting concentration, ie, the concentration of the compound when 50% inhibitory effect was achieved.

The Table 4 showed the sensitivity of different brain tumor cells to the compounds prepared in the Examples of the present invention, D341 Med (cerebellar medulloblastoma cell), Kelly (brain neuroblastoma cell) and NB-1 (brain neuroblastoma cell) were sensitive to the compounds prepared in the Examples of the present invention with low $IC_{50}$ value, while GB-1 (human brain glioblastoma cell) and SF-126 (human glioblastoma multiforme cell) were not sensitive to the compounds prepared in the Examples of the present invention with high $IC_{50}$ value.

Example 171

The mRNA transcription level of NNMT gene in three brain tumor cell lines (D341 Med, Kelly and NB-1) sensitive to the compounds prepared in the Examples of the present invention and two brain tumor cell lines (GB-1 and SF126) insensitive to the compounds prepared in the Examples of the present invention was measured using RT-qPCR gene expression analysis test, and the expression of NNMT gene in the tumor cell lines was measured respectively. The results were shown in FIG. 10.

Figure 10:
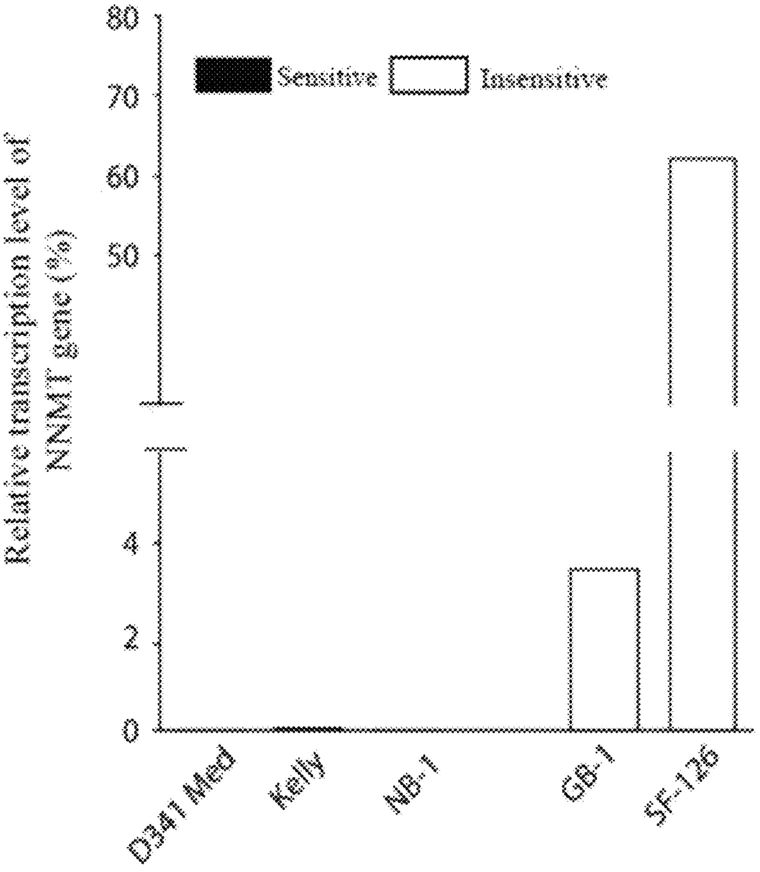
FIG. 10 shows the expression of NNMT gene in brain tumor cells sensitive and insensitive to the compounds prepared in the example.

As shown in FIG. 10, the mRNA transcription level of NNMT gene in three brain tumor cell lines (D341 Med, Kelly and NB-1) sensitive to the compounds prepared in the Examples of the present invention and two brain tumor cell lines (GB-1 and SF126) insensitive to the compounds prepared in the Examples of the present invention was measured using RT-qPCR gene expression analysis test, the results showed the expression of NNMT gene was low in sensitive cell lines (D341 Med, Kelly and NB-1), and the expression of NNMT gene was high in insensitive cell lines (GB-1 and SF126).

Therefore, the FIG. 10 showed that compared with brain tumor cell lines with high expression of NNMT gene, the inhibitory effect of the compounds prepared in the Examples of the present invention on brain tumor cell lines with low expression of NNMT gene was significantly enhanced, i.e, the expression of NNMT gene in brain tumor cell was negatively correlated with the sensitivity of brain tumor cell to the compounds prepared in the Examples of the present invention, therefor, the brain tumor with low expression of NNMT gene was highly sensitive to the compounds prepared in the Examples of the present invention, the compounds prepared in the Examples of the present invention has excellent precision treatment on the brain tumor with low expression of NNMT gene.

Example 172

The promoter region of NNMT gene, the region from 1050 bp before the transcription start site to 499 bp after the transcription start site in NNMT gene and the region from 1050 bp to 193 bp before the transcription start site in NNMT gene were subjected to bisulfite sequencing to measure methylation level of DNA CpG site in three brain tumor cell lines (D341 Med, Kelly and NB-1) sensitive to the compounds prepared in the Examples of the present invention and two brain tumor cell lines (GB-1 and SF126) insensitive to the compounds prepared in the Examples of the present invention. Firstly, genomic DNA was subjected to bisulfite, unmethylated cytosine was deamined to form uracil, and methylated cytosine could not be deamined, so the methylation sites could be determined by comparing the sequencing samples treated with bisulfite to the sequencing samples treated without bisulfite, and the result was shown in FIG. 11, FIG. 12, and FIG. 13.

Figure 11:
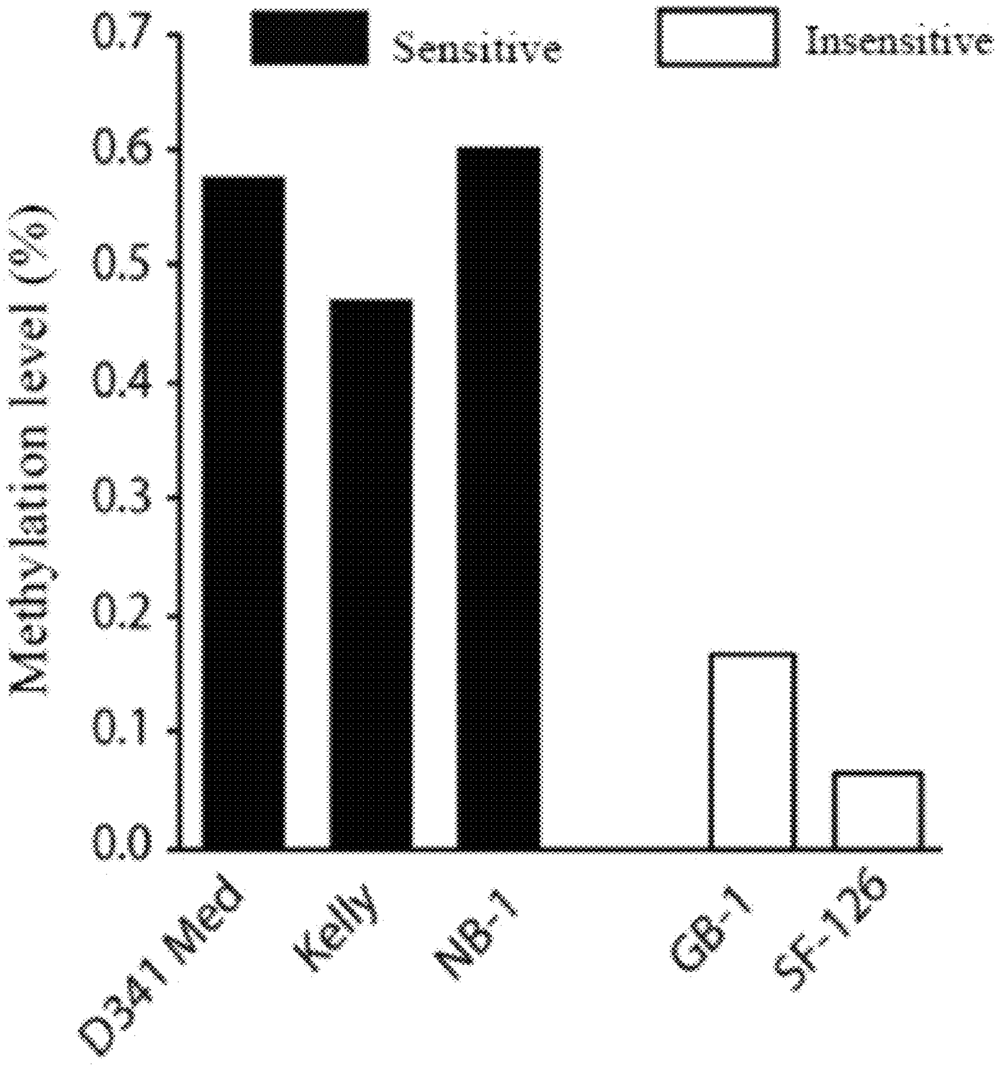
FIG. 11 shows the methylation level of DNA CpG site of promoter region of NNMT gene in brain tumor cells sensitive and insensitive to the compounds prepared in the example.
Figure 12:
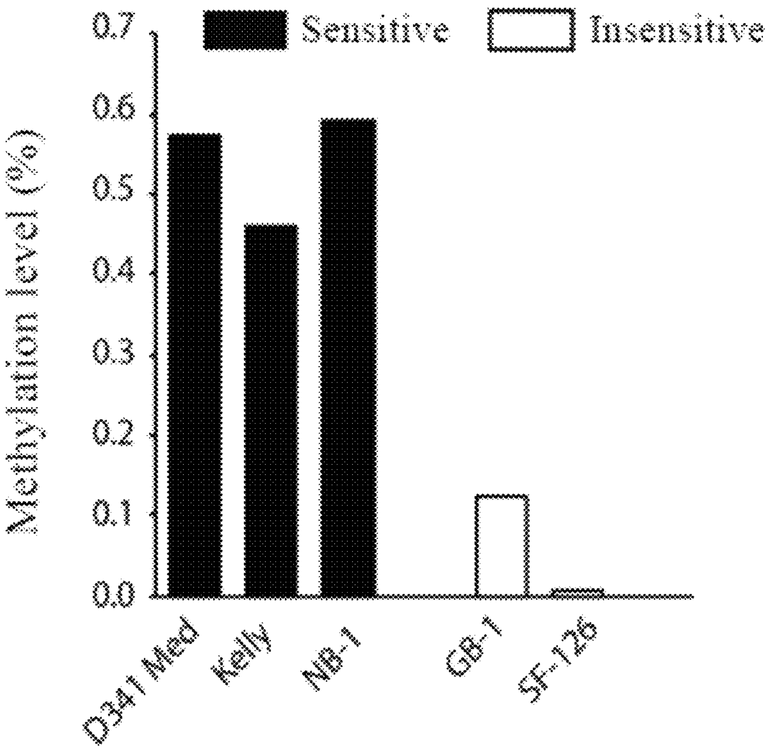
FIG. 12 shows the methylation level of DNA CpG sites from 1050 bp before the transcription start site to 499 bp after the transcription start site in NNMT gene in brain tumor cells sensitive and insensitive to the compounds prepared in the example.
Figure 13:
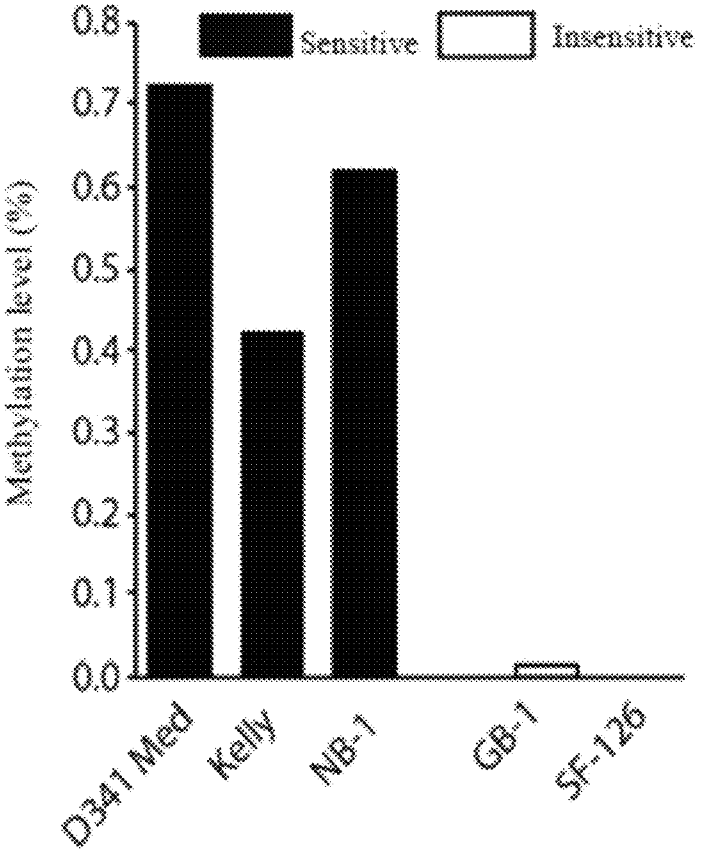
FIG. 13 shows the methylation level of DNA CpG sites from 1050 bp to 193 bp before the transcription start site in NNMT gene in brain tumor cells sensitive and insensitive to the compounds prepared in the example.

As shown in FIG. 11 (the promoter region of NNMT gene), FIG. 12 (the region from 1050 bp before the transcription start site to 499 bp after the transcription start site in NNMT gene) and FIG. 13 (the region from 1050 bp to 193 bp before the transcription start site in NNMT gene), the compounds prepared in the Examples of the present invention had significantly stronger inhibitory effect on brain tumor cells with high methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene, while the compounds prepared in the Examples of the present invention had significantly weaker inhibitory effect on brain tumor cells with low methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene, indicating the methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene was positively correlated with the sensitivity of brain tumor cell to the compounds prepared in the Examples of the present invention. Therefore, the brain tumor cells with high methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene were highly sensitive to the compounds prepared in the Examples of the present invention, the compounds prepared in the Examples of the present invention has excellent precision treatment on the tumor with high methylation level of DNA CpG site in the promoter region of NNMT gene, the region from 1050 bp before the transcription start site to 499 bp after the transcription start site in NNMT gene and the region from 1050 bp to 193 bp before the transcription start site in NNMT gene.

Example 173

The methylation level of DNA in cell was maintained by DNA methylation enzymes DNMT3a, DNMT3b and DNMT1. The original methylation of DNA was performed with DNMT3a and DNMT3b, DNMT1 could replicate and maintain methylated DNA with the help of protein UHRF1 (ubiquitin-like with PHD and ring finger domain 1). The correlation between the expression of NNMT and the expression of DNMT1, UHRF1, DNMT3a and DNMT3b in tumor was determined in the Example.

Experiment Method and Result:

The expression of NNMT gene, DNMT1, UHRF1, DNMT3a and DNMT3b in various cells were obtained from a public database (Cancer Cell Line Encyclopedia, CCLE, 1019 cells in total). Then, the correlation between expression of NNMT and the expression of DNMT1, UHRF1, DNMT3a and DNMT3b in these cells was analyzed using bioinformatics, and the correlation between the expression level of NNMT gene and the expression level of DNMT1, UHRF1, DNMT3a and DNMT3b in each cell was analyzed, the experiment result was shown in FIG. 14.

Figure 14:
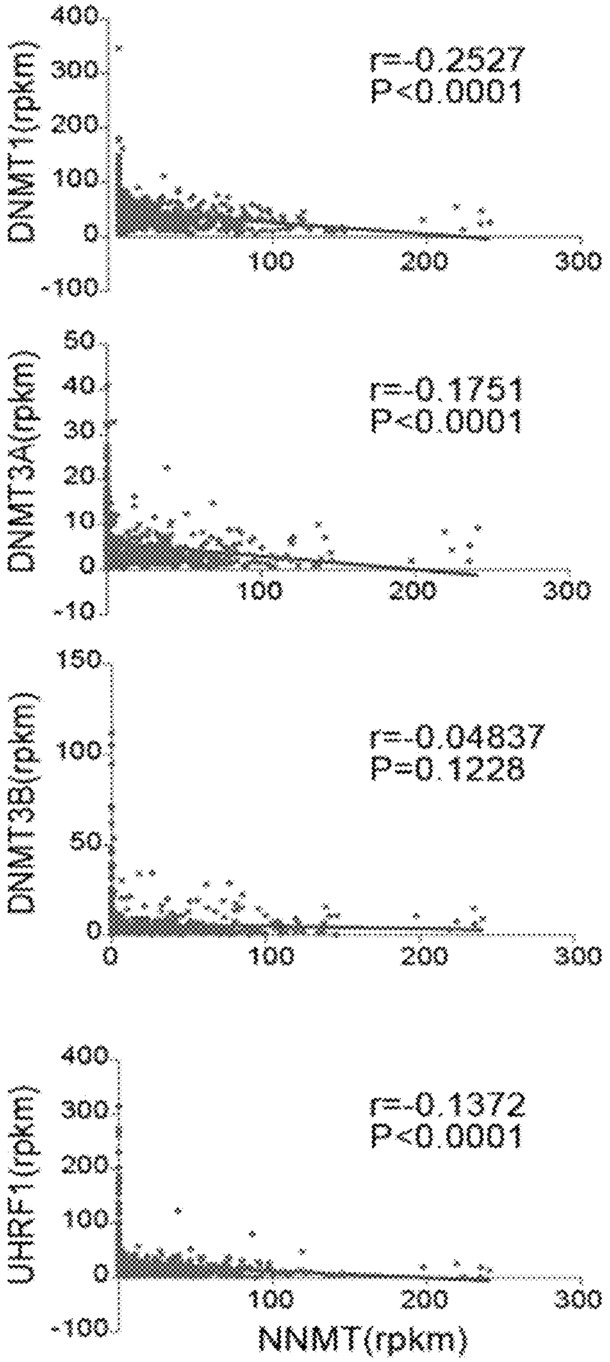
FIG. 14 shows the correlation between the expression of NNMT and the expression of DNMT1, UHRF1, DNMT3a and DNMT3b in tumor cells.

The FIG. 14 showed the expression of NNMT was negatively correlated with the expression of DNA methylase and UHRF1 in each cell. Therefore, the tumor with high expression of DNA methylase and UHRF1 was highly sensitive to the compounds prepared in the Examples of the present invention, the compounds prepared in the Examples of the present invention has excellent precision treatment on the tumor with high expression of DNA methylase and UHRF1.

The above is an embodiment designed for a specific case of the present invention. It should be understood for the skilled in the art the improvements can be made without departing from the principles of the present invention, and these improvements should also be considered as the scope of protection of the present invention.

The invention claimed is:

1. A compound of formula I, or an optical isomer thereof, or a racemate thereof, or a solvate thereof, or a pharmaceutically acceptable salt thereof, or a deuterated compound thereof;

I

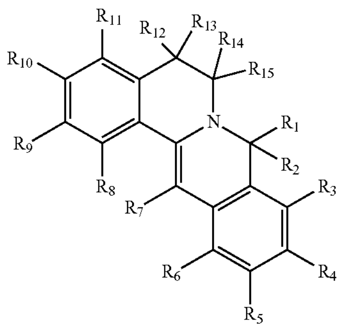

wherein, $R_1$ and $R_2$ are each independently hydrogen, deuterium, C1-C10 alkyl, cyclobutyl, cyclopentyl, cyclohexyl, cycloheptyl, cyclooctyl, C1-C10 haloalkyl, C6-C10 aryl, or 5-10 membered heteroaryl;

$R_3$ is halogen, $R_{17}$—O—, or $(R_{18}R_{19})N$—, wherein, $R_{17}$ is C1-C10 alkyl,

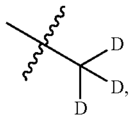

C3-C12 cycloalkyl-C2-C6 acyl-, C1-C10 haloalkyl, C6-C12 aryl-C1-C8 alkyl-, C6-C12 aryl-C6-C12 aryl-C1-C8 alkyl-, 5-12 membered heteroaryl-C1-C8 alkyl-, C6-C12 aryl-O-C1-C8 alkyl-, 5-12 membered heteroaryl-O-C1-C8 alkyl-, C2-C4 alkenyl-C1-C4 alkyl-C2-C4 alkenyl-C1-C4 alkyl-, C2-C4 alkenyl-C1-C4 alkyl-, or $(R_{20}R_{21})N$-C1-C10 alkyl-;

$R_4$is $R_{17}$—O—, wherein, $R_{17}$ is C1-C8 alkyl, or C1-C8 haloalkyl;

$R_5$ is hydrogen;

or $R_3$ and $R_4$, or $R_4$ and $R_5$ are connected to form

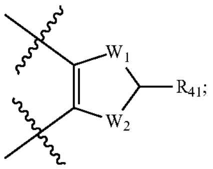

$R_6$ is hydrogen, or halogen;

$R_7$ is hydrogen, C1-C10 alkyl, C1-C10 haloalkyl, substituted or unsubstituted C6-C12 aryl-C1-C10 alkyl-, or substituted or unsubstituted 5-12 membered heteroaryl-C1-C10 alkyl-, wherein, each "substituted" means that 1, 2, 3, 4 or 5 hydrogen atoms on the group are independently substituted by substituent selected from the group consisting of C1-C6 alkyl, C1-C6 haloalkyl;

$R_8$, $R_{11}$, $R_{12}$, $R_{13}$, $R_{14}$ and $R_{15}$ are each independently hydrogen;

$R_9$ and $R_{10}$ are connected to form

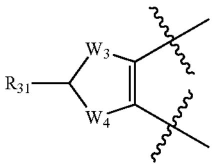

or

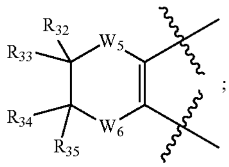

;

$R_{18}$ and $R_{19}$ are each independently hydrogen, or C6-C12 aryl-C1-C6 alkyl-; or $R_{18}$ and $R_{19}$ are connected to form a substituted or unsubstituted 3-10 membered heterocycloalkane ring, each "substituted" means that 1, 2 or 3 hydrogen atoms on the group are independently substituted by substituent selected from the group consisting of C1-C6 alkyl, C1-C6 haloalkyl, halogen, C1-C6 haloalkoxyl;

$R_{20}$ and $R_{21}$ are each independently hydrogen, or C2-C8 ester group; or $R_{20}$ and $R_{21}$ are connected to form a 3-10 membered heterocycloalkyl;

$R_{31}$, $R_{32}$, $R_{33}$, $R_{34}$ and $R_{35}$ are each independently hydrogen;

$R_{41}$ is hydrogen;

$W_1$ and $W_2$ are each independently O;

$W_3$, $W_4$, $W_5$ and $W_6$ are each independently O.

2. The compound of formula I, or an optical isomer thereof, or a racemate thereof, or a solvate thereof, or a pharmaceutically acceptable salt thereof, or a deuterated compound thereof of claim 1, wherein $R_1$ and $R_2$ are each independently hydrogen, deuterium, C1-C8 alkyl, cyclobutyl, cyclopentyl, cyclohexyl, cycloheptyl, cyclooctyl, C1-C8 haloalkyl, C6-C8 aryl, or 5-8 membered heteroaryl;

$R_3$ is halogen, $R_{17}$—O—, or $(R_{18}R_{19})N$—, wherein, $R_{17}$ is C1-C8 alkyl,

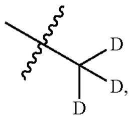

C3-C12 cycloalkyl-C2-C4 acyl-, C1-C8 haloalkyl, C6-C12 aryl-C1-C6 alkyl-, C6-C12 aryl-C6-C12 aryl-C1-C6 alkyl-, 5-12 membered heteroaryl-C1-C6 alkyl-, C6-C12 aryl-O-C1-C6 alkyl-, 5-12 membered heteroaryl-O-C1-C6 alkyl-, C2-C4 alkenyl-C1-C4 alkyl-C2-C4 alkenyl-C1-C4 alkyl-, C2-C4 alkenyl-C1-C4 alkyl-, or $(R_{20}R_{21})$N-C1-C8 alkyl-;

$R_4$is $R_{17}$—O—, wherein, $R_{17}$ is C1-C6 alkyl, or C1-C6 haloalkyl;

$R_5$ is hydrogen;

or $R_3$ and $R_4$, or $R_4$ and $R_5$ are connected to form

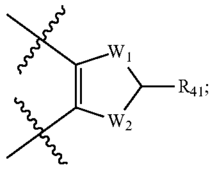

$R_6$ is hydrogen, or halogen;

$R_7$ is hydrogen, C1-C8 alkyl, C1-C8 haloalkyl, substituted or unsubstituted C6-C12 aryl-C1-C8 alkyl-, or substituted or unsubstituted 5-12 membered heteroaryl-C1-C8 alkyl-, wherein, each "substituted" means that 1, 2, 3, 4 or 5 hydrogen atoms on the group are independently substituted by substituent selected from the group consisting of C1-C4 alkyl, C1-C4 haloalkyl;

$R_8$, $R_{11}$, $R_{12}$, $R_{13}$, $R_{14}$ and $R_{15}$ are each independently hydrogen;

$R_9$ and $R_{10}$ are connected to form

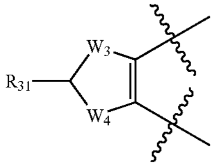

or

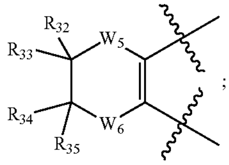

;

$R_{18}$ and $R_{19}$ are each independently hydrogen, or C6-C8 aryl-C1-C4 alkyl-; or $R_{18}$ and $R_{19}$ are connected to form

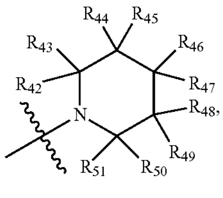

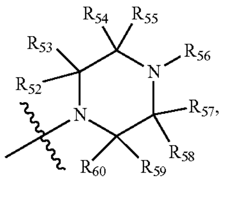

or azacycloheptane ring;

$R_{20}$ and $R_{21}$ are each independently hydrogen, or C2-C8 ester group; or $R_{20}$ and $R_{21}$ are connected to form a 3-8 membered heterocycloalkyl;

$R_{31}$, $R_{32}$, $R_{33}$, $R_{34}$ and $R_{35}$ are each independently hydrogen;

$R_{41}$ is hydrogen;

$R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, C1-C4 alkyl, C1-C4 haloalkyl, C1-C4 haloalkoxyl, or halogen;

$R_{52}$, $R_{53}$, $R_{54}$, $R_{55}$, $R_{56}$, $R_{57}$, $R_{58}$, $R_{59}$ and $R_{60}$ are each independently hydrogen, C1-C4 alkyl, C1-C4 haloalkyl, C1-C4 haloalkoxyl, or halogen;

$W_1$ and $W_2$ are each independently O;

$W_3$, $W_4$, $W_5$ and $W_6$ are each independently O.

3. The compound of formula I, or an optical isomer thereof, or a racemate thereof, or a solvate thereof, or a pharmaceutically acceptable salt thereof, or a deuterated compound thereof of claim 1, wherein $R_1$ and $R_2$ are each independently hydrogen, deuterium, C1-C6 alkyl, cyclobutyl, cyclopentyl, cyclohexyl, cycloheptyl, cyclooctyl, C1-C4 haloalkyl, C6-C8 aryl, or 5-8 membered heteroaryl;

$R_3$ is halogen, $R_{17}$—O—, or $(R_{18}R_{19})$N—, wherein, $R_{17}$ is C1-C6 alkyl,

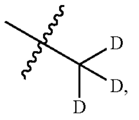

C6-C12 cycloalkyl-C2-C4 acyl-, C1-C6 haloalkyl, C6-C10 aryl-C1-C4 alkyl-, C6-C10 aryl-C6-C10 aryl-C1-C4 alkyl-, 5-10 membered heteroaryl-C1-C4 alkyl-, C6-C10 aryl-O-C1-C4 alkyl-, 5-10 membered heteroaryl-O-C1-C4 alkyl-, C2-C4 alkenyl-C1-C2 alkyl-C2-C4 alkenyl-C1-C2 alkyl-, C2-C4 alkenyl-C1-C2 alkyl-, or $(R_{20}R_{21})$N-C1-C8 alkyl-;

$R_4$is $R_{17}$—O—, wherein, $R_{17}$ is C1-C4 alkyl, or C1-C6 haloalkyl;

$R_5$ is hydrogen;

or $R_3$ and $R_4$, or $R_4$ and $R_5$ are connected to form

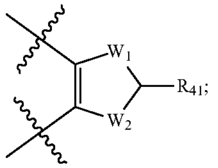

$R_6$ is hydrogen, or halogen;

$R_7$ is hydrogen, C1-C8 alkyl, C1-C8 haloalkyl, or

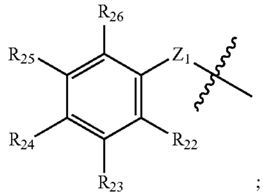

;

$R_8$, $R_{11}$, $R_{12}$, $R_{13}$, $R_{14}$ and $R_{15}$ are each independently hydrogen;

$R_9$ and $R_{10}$ are connected to form

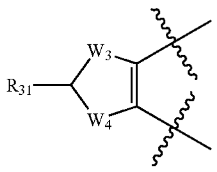

or

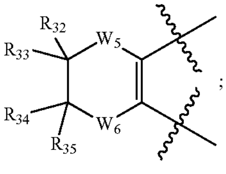

;

$R_{18}$ and $R_{19}$ are each independently hydrogen, or C6-C8 aryl-C1-C4 alkyl-; or $R_{18}$ and $R_{19}$ are connected to form

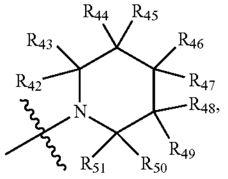

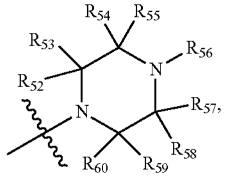

or azacycloheptane ring;

$R_{20}$ and $R_{21}$ are each independently hydrogen, or C3-C7 ester group; or $R_{20}$ and $R_{21}$ are connected to form a 5-8 membered heterocycloalkyl;

$R_{22}$, $R_{23}$, $R_{24}$, $R_{25}$ and $R_{26}$ are each independently hydrogen, C1-C6 alkyl, or C1-C6 haloalkyl;

$R_{31}$, $R_{32}$, $R_{33}$, $R_{34}$ and $R_{35}$ are each independently hydrogen;

$R_{41}$ is hydrogen;

$R_{42}$, $R_{43}$, $R_{44}$, $R_{45}$, $R_{46}$, $R_{47}$, $R_{48}$, $R_{49}$, $R_{50}$ and $R_{51}$ are each independently hydrogen, methyl, butyl, trifluoromethyl, trifluoromethoxyl, or halogen;

$R_{52}$, $R_{53}$, $R_{54}$, $R_{55}$, $R_{56}$, $R_{57}$, $R_{58}$, $R_{59}$ and $R_{60}$ are each independently hydrogen, methyl, butyl, trifluoromethyl, trifluoromethoxyl, or halogen;

$W_1$ and $W_2$ are each independently O;

$W_3$, $W_4$, $W_5$ and $W_6$ are each independently O;

$Z_1$ is methylidene, ethylidene, propylidene, butylidene, pentylidene, or hexylidene.

4. The compound of formula I, or an optical isomer thereof, or a racemate thereof, or a solvate thereof, or a pharmaceutically acceptable salt thereof, or a deuterated compound thereof of claim 1, wherein $R_1$ and $R_2$ are each independently hydrogen, deuterium, methyl, ethyl, propyl, butyl, pentyl, hexyl, heptyl, octyl, cyclobutyl, cyclopentyl, cyclohexyl, cycloheptyl, cyclooctyl, halomethyl, haloethyl, halopropyl, halobutyl, halopentyl, halohexyl, or phenyl;

$R_3$ is halogen, $R_{17}$—O—, or $(R_{18}R_{19})N$—, wherein, $R_{17}$ is methyl,

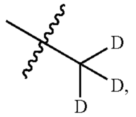

ethyl, propyl, butyl, pentyl, hexyl, cyclodecyl-acetyl-, haloethyl, halopropyl, halobutyl, halohexyl, phenyl-ethyl-, phenyl-propyl-, phenyl-butyl-, phenyl-phenyl-methyl-, phenyl-O-butyl-, butenyl-ethyl-propenyl-methyl-, ethylenyl-methyl-, $(R_{20}R_{21})N$-ethyl-, $(R_{20}R_{21})N$-butyl-, or $(R_{20}R_{21})$N-hexyl;

$R_4$ is $R_{17}$—O—, wherein, $R_{17}$ is methyl, ethyl, propyl, pentyl, hexyl, haloethyl, halopropyl, halobutyl, or halohexyl;

$R_5$ is hydrogen;

or $R_3$ and $R_4$, or $R_4$ and $R_5$ are connected to form

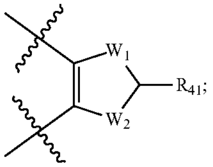

$R_6$ is hydrogen, or halogen;

$R_7$ is hydrogen, methyl, ethyl, propyl, butyl, pentyl, hexyl, heptyl, octyl, halohexyl, or

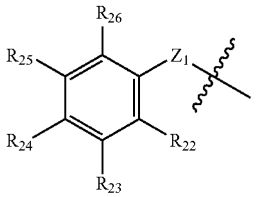

$R_8$, $R_{11}$, $R_{12}$, $R_{13}$, $R_{14}$ and $R_{15}$ are each independently hydrogen;

$R_9$ and $R_{10}$ are connected to form

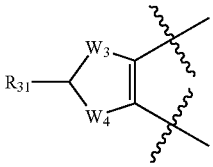

or

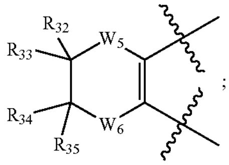

;

$R_{18}$ and $R_{19}$ are each independently hydrogen, or phenyl-ethyl-; or $R_{18}$ and $R_{19}$ are connected to form a methyl-piperazine ring, butyl-piperazine ring, trifluoromethyl-piperazine ring, trifluoromethoxyl-piperazine ring, halopiperazine ring, methyl-piperidine ring, trifluoromethyl-piperidine ring, trifluoromethoxyl-piperidine ring, halopiperidine ring, or azacycloheptane ring;

$R_{20}$ and $R_{21}$ are each independently hydrogen, or amyl ester group; or $R_{20}$ and $R_{21}$ are connected to form piperidine ring;

$R_{22}$, $R_{23}$, $R_{24}$, $R_{25}$ and $R_{26}$ are each independently hydrogen, trifluoromethoxyl, or propyl;

$R_{31}$, $R_{32}$, $R_{33}$, $R_{34}$ and $R_{35}$ are each independently hydrogen;

$R_{41}$ is hydrogen;

$W_1$ and $W_2$ are each independently O;

$W_3$, $W_4$, $W_5$ and $W_6$ are each independently O;

$Z_1$ is methylidene, ethylidene, propylidene, butylidene, pentylidene, or hexylidene.

5. The compound of formula I, or an optical isomer thereof, or a racemate thereof, or a solvate thereof, or a pharmaceutically acceptable salt thereof, or a deuterated compound thereof of claim 1, wherein Riis hydrogen, or deuterium;

$R_2$ is hydrogen, deuterium, methyl, propyl, butyl, pentyl, hexyl, cyclobutyl, cyclopentyl, cyclohexyl, trichloromethyl, or phenyl;

$R_3$ is Cl, Br, $R_{17}$—O—, or $(R_{18}R_{19})N$—, wherein, $R_{17}$ is methyl,

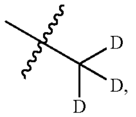

ethyl, propyl, butyl, pentyl, hexyl, cyclodecyl-acetyl-, fluoroethyl, bromoethyl, bromopropyl, chloropropyl, fluoropropyl, chlorobutyl, chlorohexyl, bromohexyl, phenyl-propyl-, phenyl-butyl-, phenyl-phenyl-methyl-, phenyl-O-butyl-, butenyl-ethyl-propenyl-methyl-, ethylenyl-methyl-, $(R_{20}R_{21})$N-ethyl-, $(R_{20}R_{21})$N-butyl-, or $(R_{20}R_{21})$N-hexyl-;

$R_4$ is $R_{17}$—O—, wherein, $R_{17}$ is methyl, or chloropropyl;

$R_5$ is hydrogen;

or $R_3$ and $R_4$, or $R_4$ and $R_5$ are connected to form

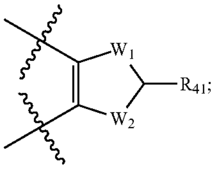

$R_6$ is hydrogen, or Br;

$R_7$ is hydrogen, ethyl, propyl, butyl, pentyl, hexyl, octyl, chlorohexyl, bromohexyl, or

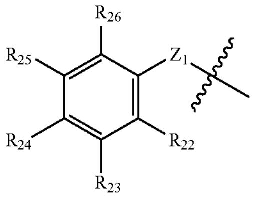

;

$R_8$, $R_{11}$, $R_{12}$, $R_{13}$, $R_{14}$ and $R_{15}$ are each independently hydrogen;

$R_9$ and $R_{10}$ are connected to form

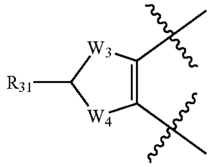

or

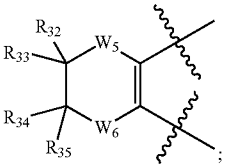

;

$R_{18}$ is hydrogen, $R_{19}$ is phenyl-ethyl-; or $R_{18}$ and $R_{19}$ are connected to form a methyl-piperazine ring, butyl-piperazine ring, trifluoromethyl-piperazine ring, trifluoromethoxyl-piperazine ring, chloropiperazine ring, methyl-piperidine ring, trifluoromethyl-piperidine ring, trifluoromethoxyl-piperidine ring, chloropiperidine ring, or azacycloheptane ring;

$R_{20}$ is hydrogen, $R_{21}$ is hydrogen, or amyl ester group; or $R_{20}$ and $R_{21}$ are connected to form piperidine ring;

$R_{22}$ is hydrogen;

$R_{23}$ is hydrogen;

$R_{24}$ is hydrogen, propyl, or trifluoromethoxyl;

$R_{25}$ is hydrogen;

$R_{26}$ is hydrogen;

$R_{31}$, $R_{32}$, $R_{33}$, $R_{34}$ and $R_{35}$ are each independently hydrogen;

$R_{41}$ is hydrogen;

$W_1$ and $W_2$ are each independently O;

$W_3$, $W_4$, $W_5$ and $W_6$ are each independently O;

$Z_1$ is methylidene, ethylidene, propylidene, or butylidene.

6. The compound of formula I, or an optical isomer thereof, or a racemate thereof, or a solvate thereof, or a pharmaceutically acceptable salt thereof, or a deuterated compound thereof of claim 1, wherein Riis hydrogen, or deuterium;

$R_2$ is hydrogen, deuterium, methyl, n-propyl, n-butyl, n-pentyl, n-hexyl, cyclobutyl, cyclopentyl, cyclohexyl, trichloromethyl, or phenyl;

$R_3$ is Cl, Br, $R_{17}$—O—, or $(R_{18}R_{19})$N—, wherein, $R_{17}$ is methyl,

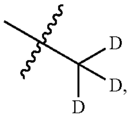

ethyl, n-propyl, n-butyl, n-pentyl,

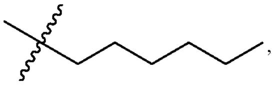,
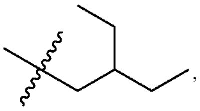,
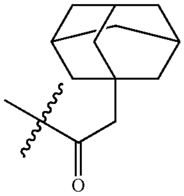,
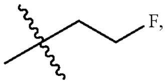
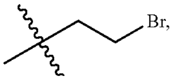
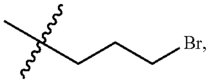
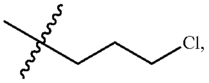 [SMILES: *CCCCl]
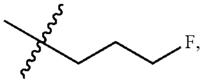
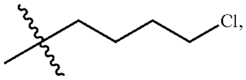
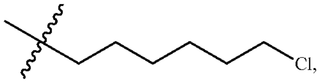
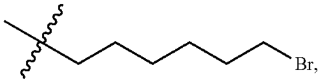
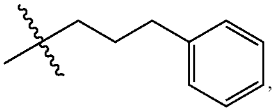,
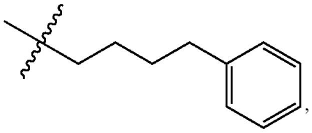,
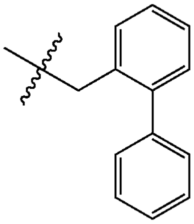, -continued

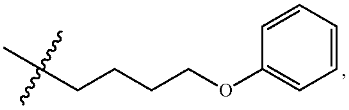

,

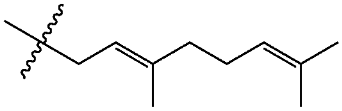

,

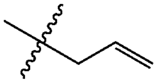

,

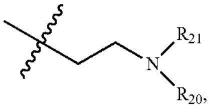

,

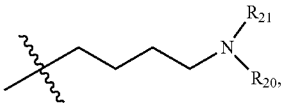

or

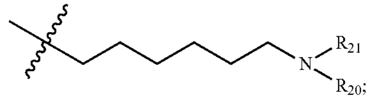

;

$R_4$is $R_{17}$—O—, wherein, $R_{17}$ is methyl, or

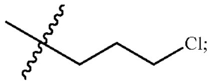

;

$R_5$ is hydrogen;

or $R_3$ and $R_4$, or $R_4$ and $R_5$ are connected to form

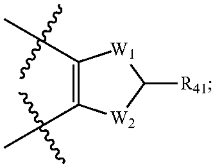

;

$R_6$ is hydrogen, or Br;

$R_7$ is hydrogen, ethyl, n-propyl, n-butyl, n-pentyl, n-hexyl,

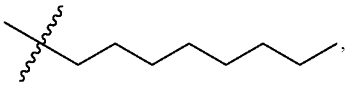

,

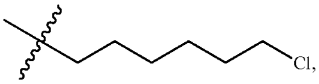

,

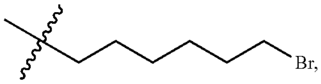

or

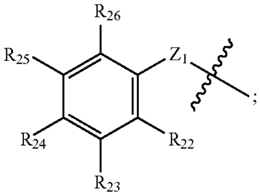

;

$R_8$, $R_{11}$, $R_{12}$, $R_{13}$, $R_{14}$ and $R_{15}$ are each independently hydrogen;

$R_9$ and $R_{10}$ are connected to form

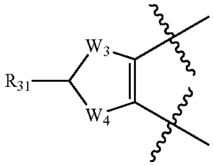

or

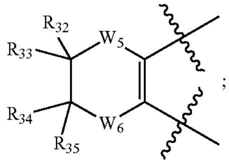

;

$R_{18}$ is hydrogen, $R_{19}$ is phenyl-ethyl-; or $R_{18}$ and $R_{19}$ are connected to form a

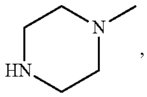

,

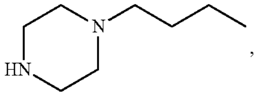

,

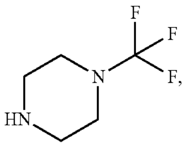

,

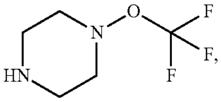

,

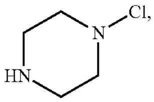

,

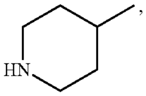

,

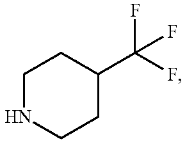

,

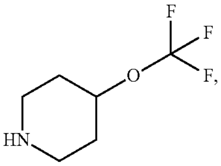

,

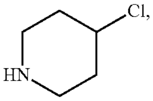

, or

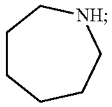

;

$R_{20}$ is hydrogen, $R_{21}$ is hydrogen,

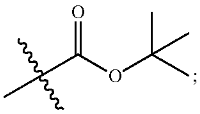 [SMILES: *C(=O)OC(C)(C)C]

;

or $R_{20}$ and $R_{21}$ are connected to form piperidine ring;

$R_{22}$ is hydrogen;

$R_{23}$ is hydrogen;

$R_{24}$ is hydrogen, isopropyl, or trifluoromethoxyl;

$R_{25}$ is hydrogen;

$R_{26}$ is hydrogen;

$R_{31}$, $R_{32}$, $R_{33}$, $R_{34}$ and $R_{35}$ are each independently hydrogen;

$R_{41}$ is hydrogen;

$W_1$ and $W_2$ are each independently O;

$W_3$, $W_4$, $W_5$ and $W_6$ are each independently O;

$Z_1$ is methylidene,

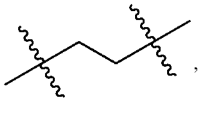

,

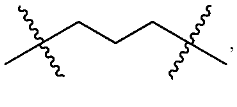

, or

-continued
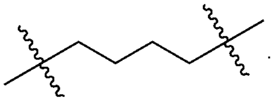
7. The compound of formula I, or an optical isomer thereof, or a racemate thereof, or a solvate thereof, or a pharmaceutically acceptable salt thereof, or a deuterated compound thereof of claim 1, wherein the compound is selected from the following group:
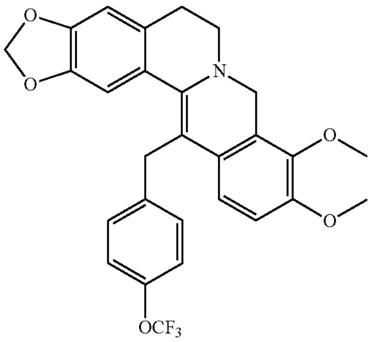
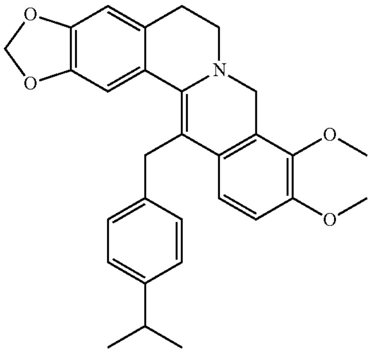
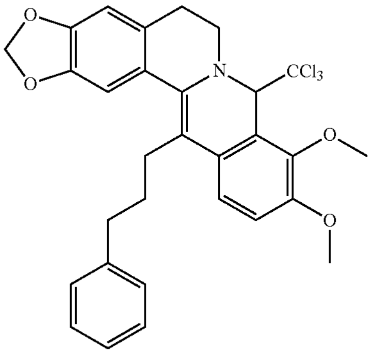
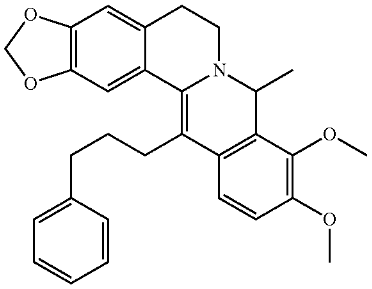
-continued
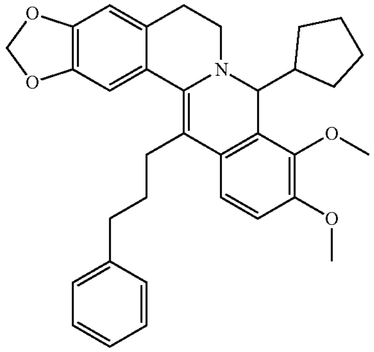
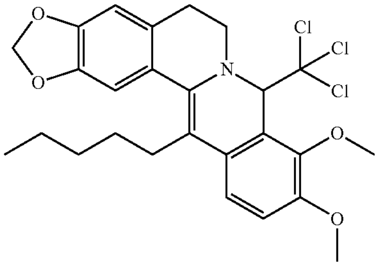 [SMILES: CCCCCC1=C2c3cc4c(cc3CCN2C(C(Cl)(Cl)Cl)c2c1ccc(OC)c2OC)OCO4]
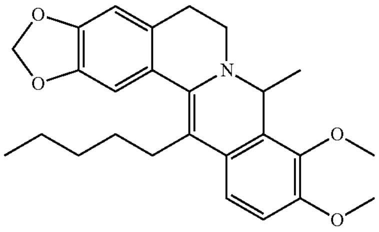
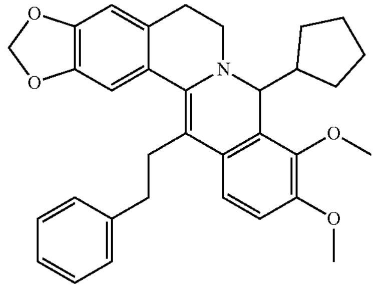
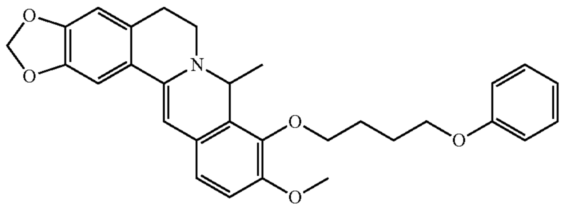
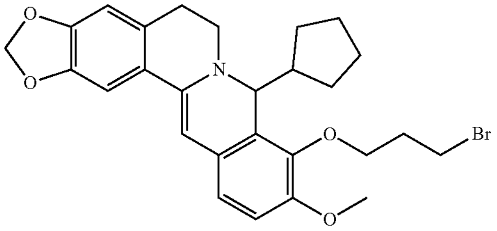

-continued
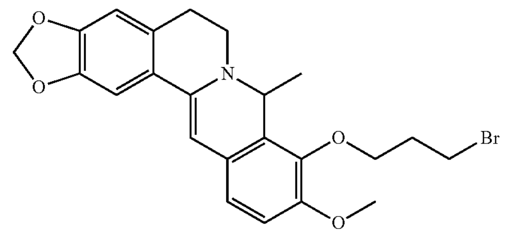
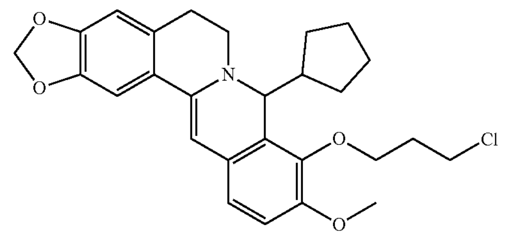
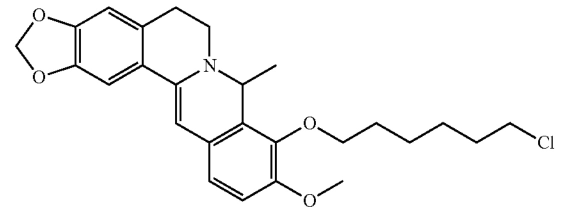
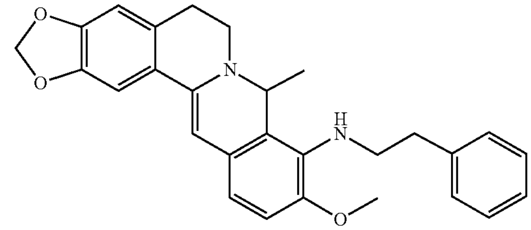
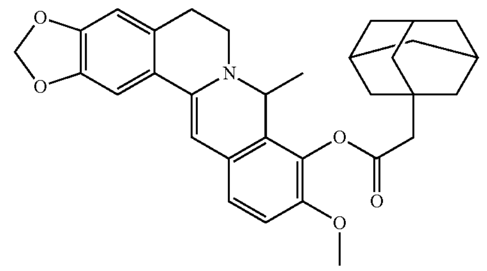
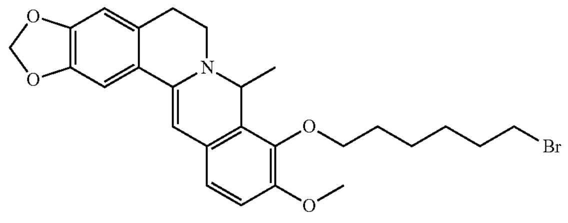
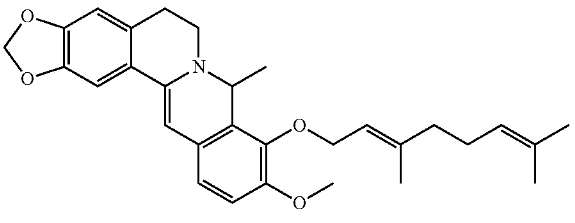
-continued
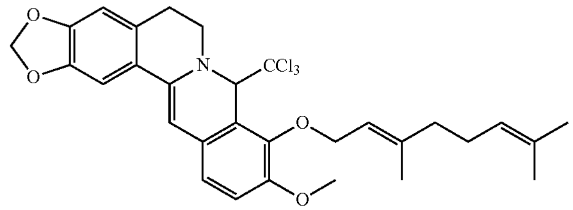
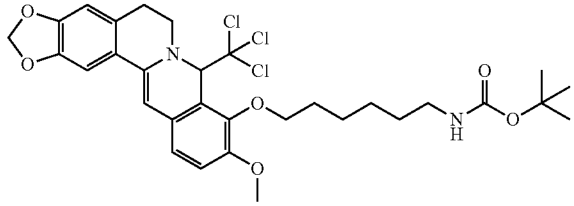
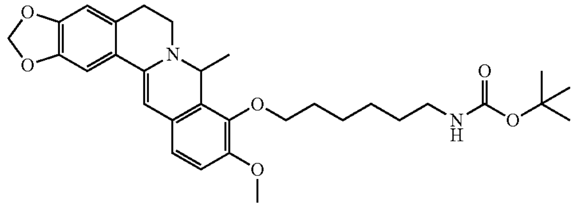
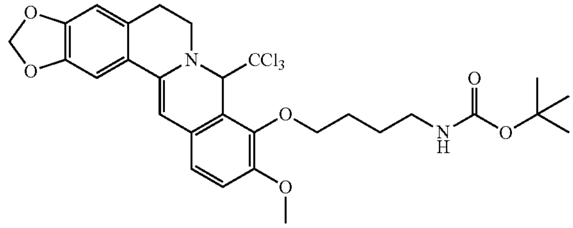
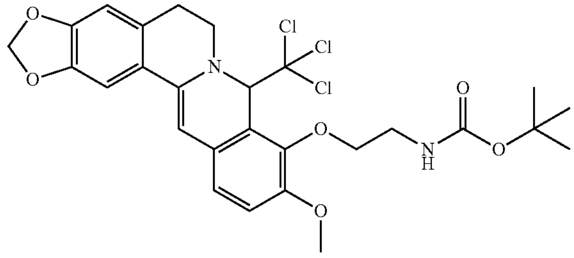
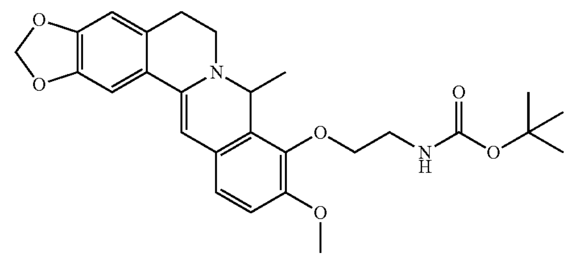
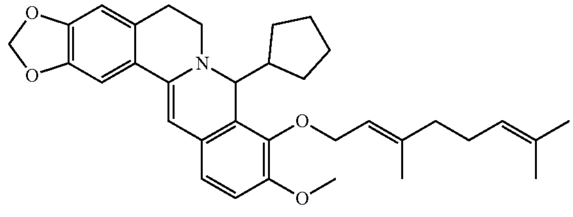

-continued
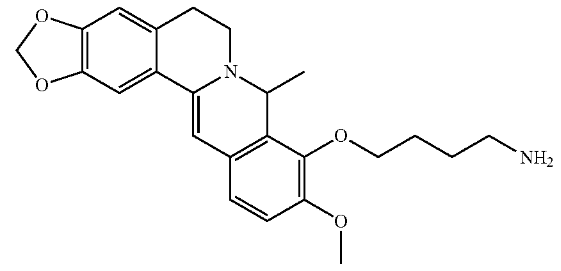
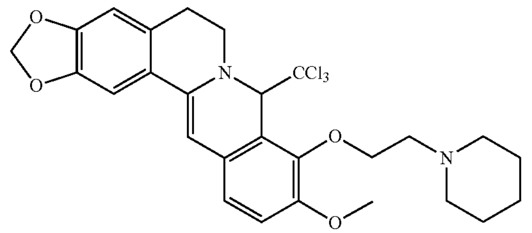
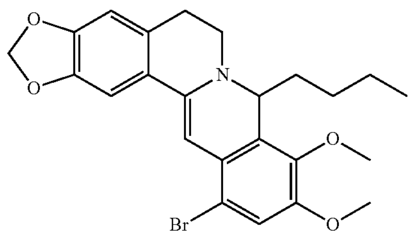
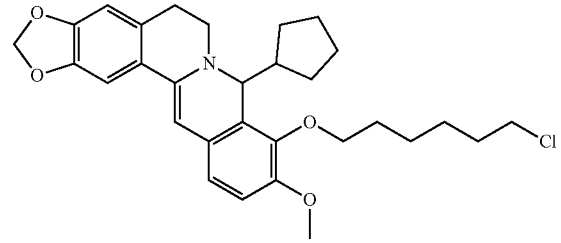
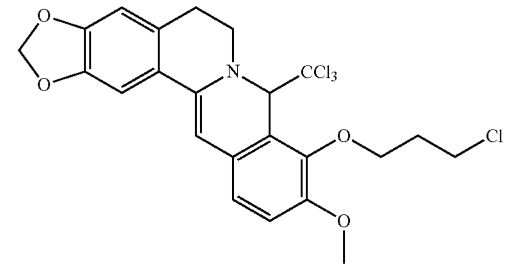
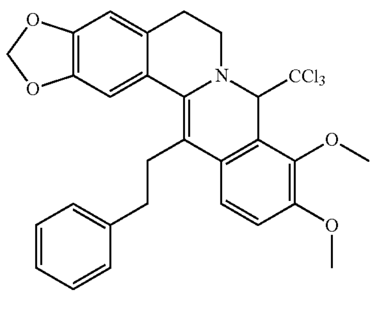
-continued
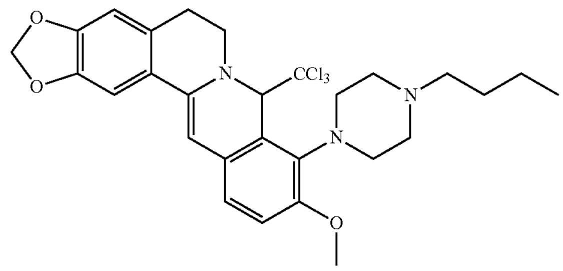
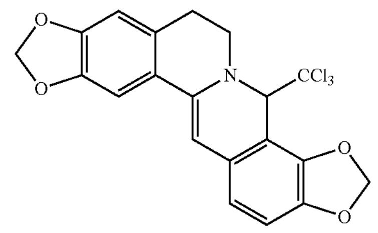
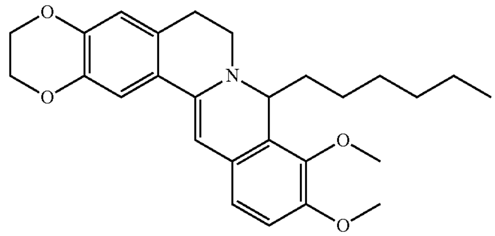
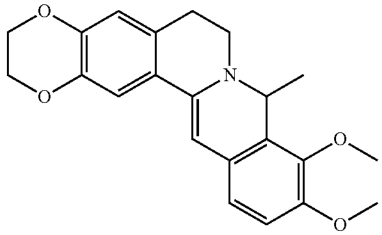
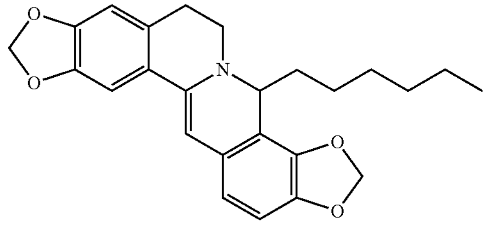
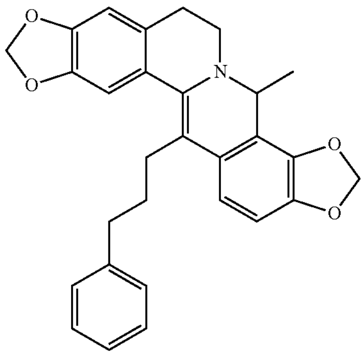

-continued
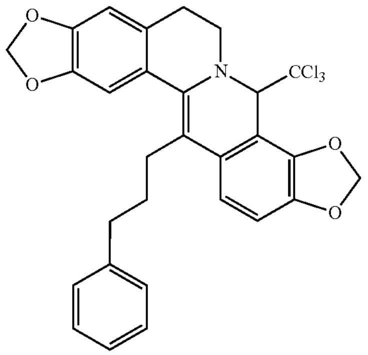
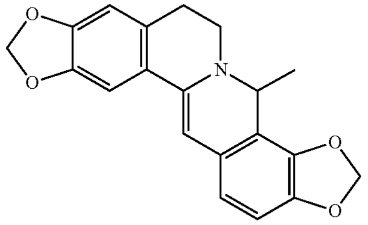
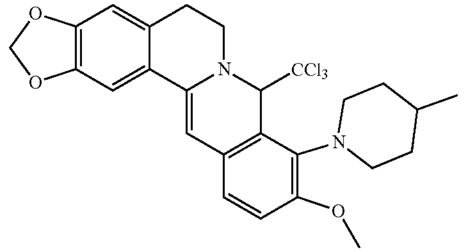
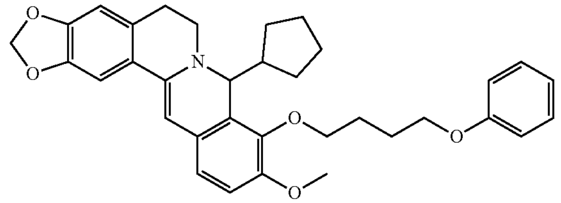
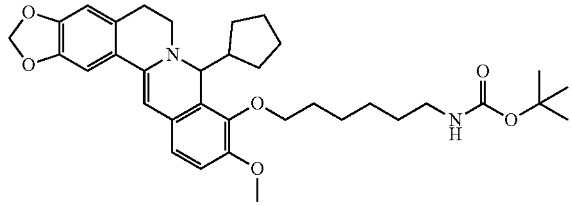
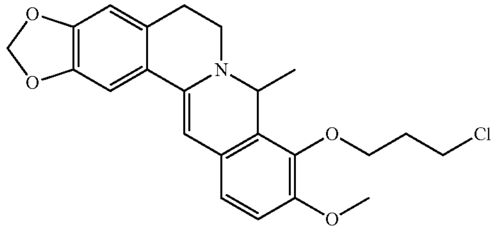
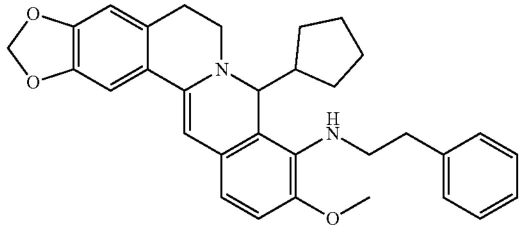
-continued
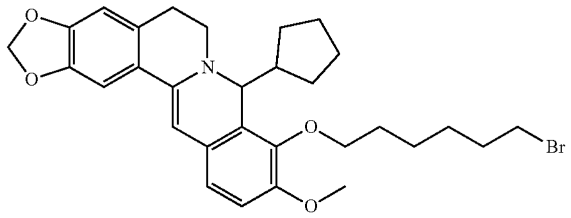
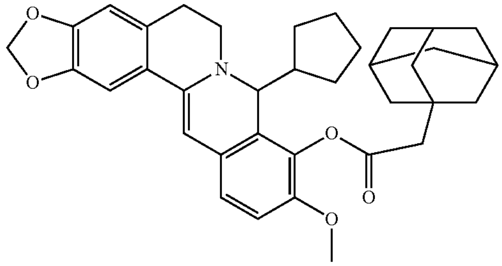
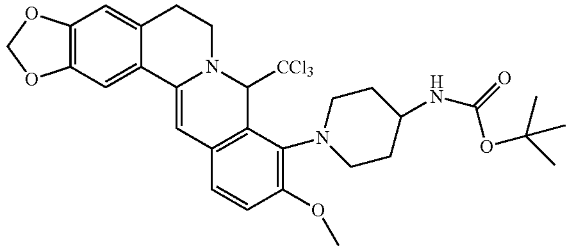
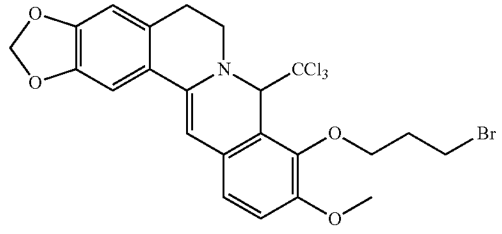
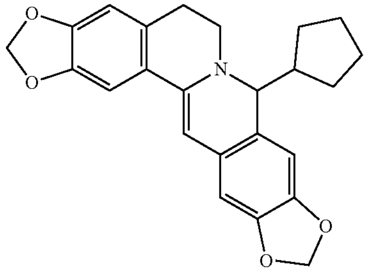
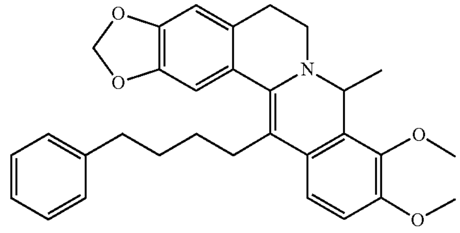
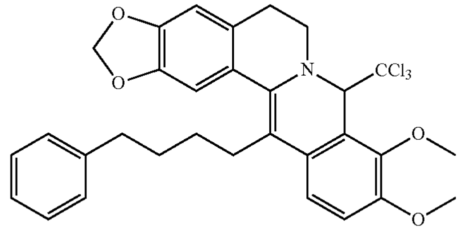

-continued
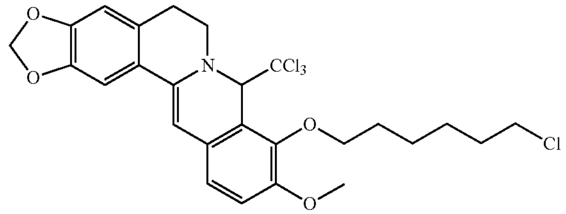
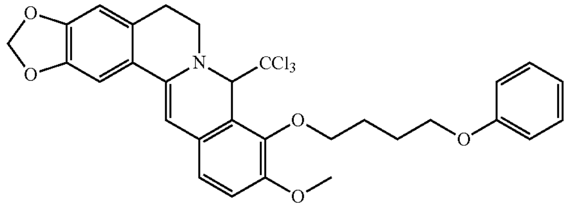
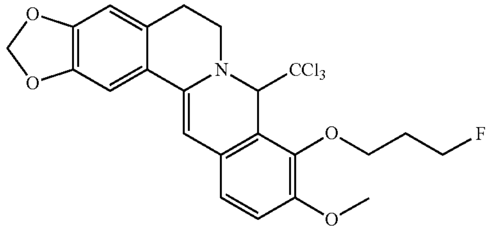
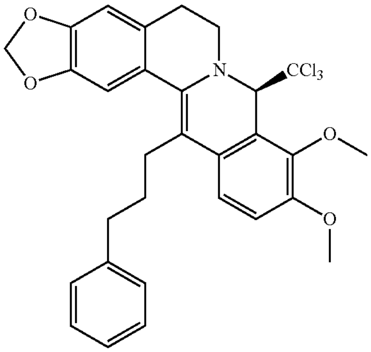
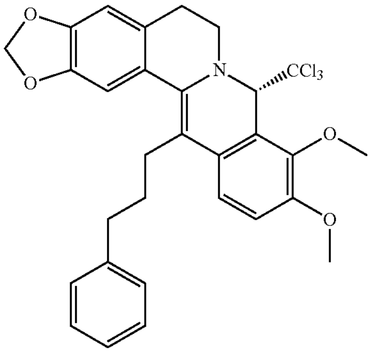
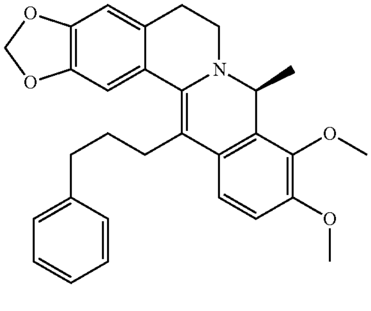
-continued
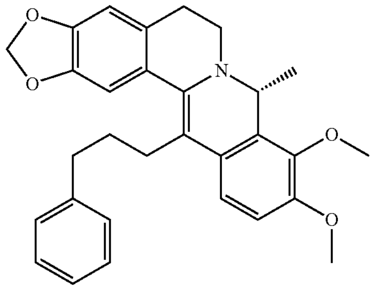
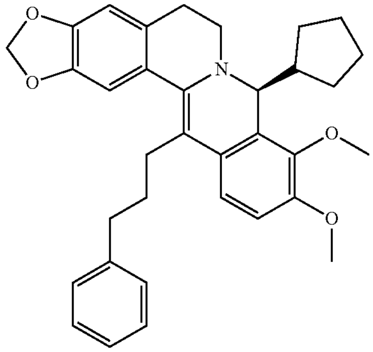
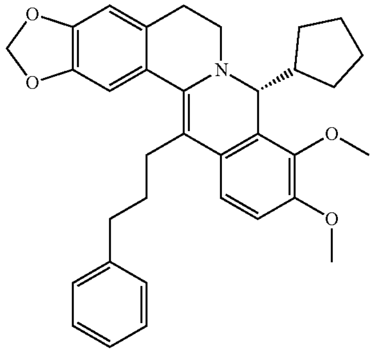 [SMILES: COc1ccc2c(c1OC)[C@@H](C1CCCC1)N1CCc3cc4c(cc3C1=C2CCCc1ccccc1)OCO4]
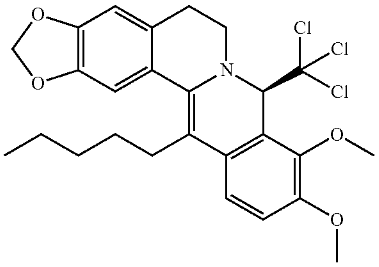
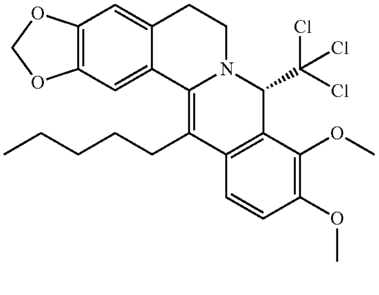

-continued
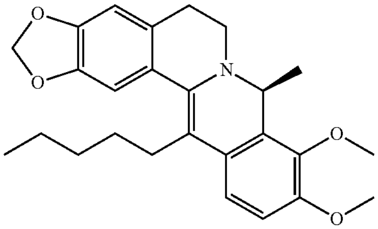
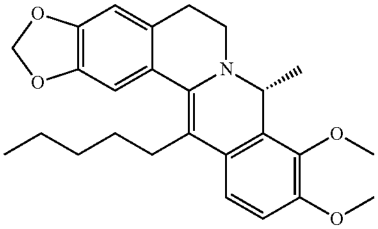
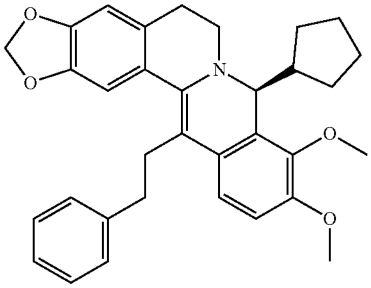
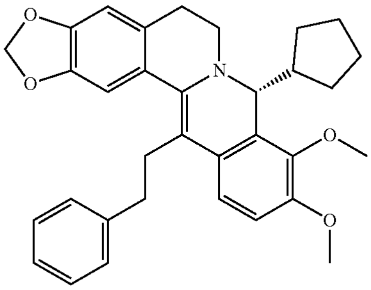
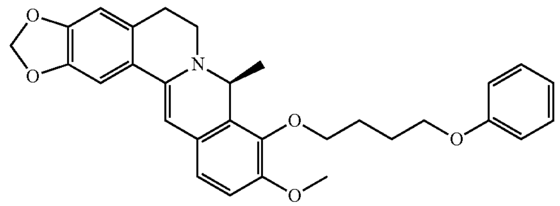
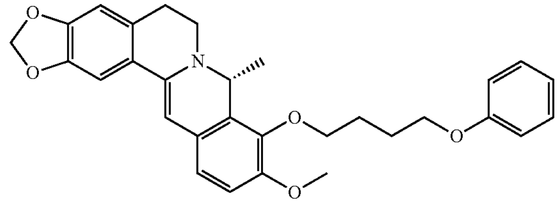
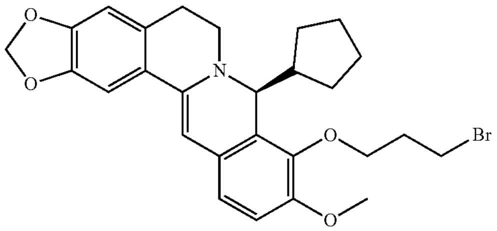
-continued
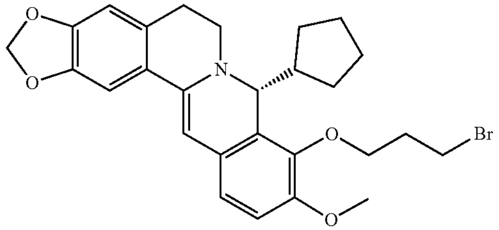
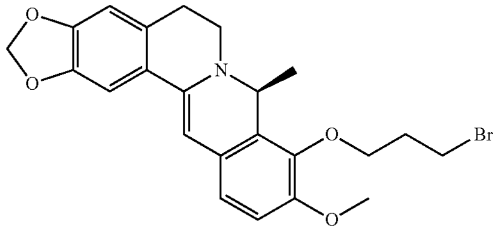
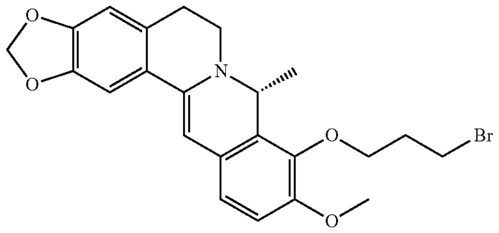
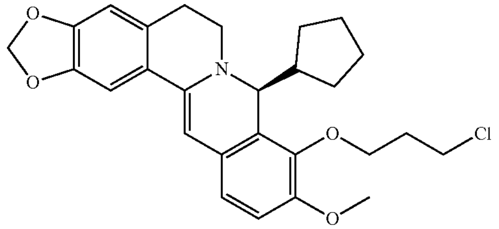
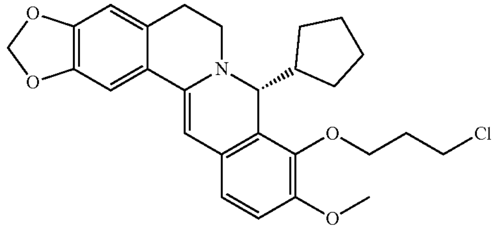
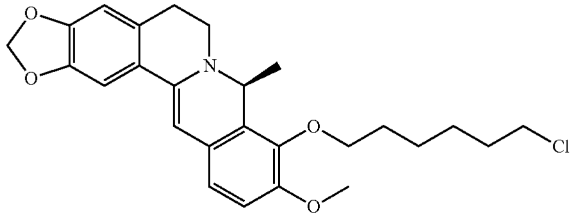
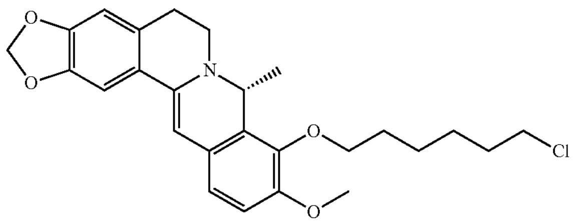

-continued
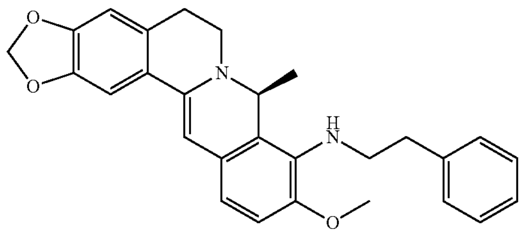
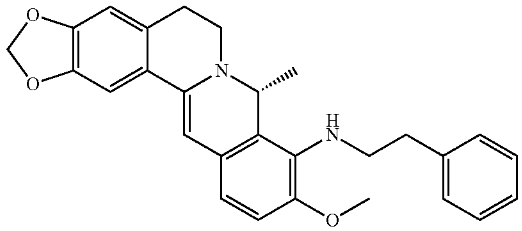
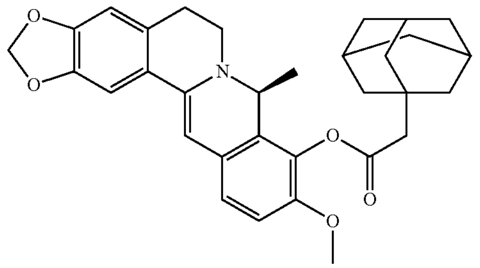
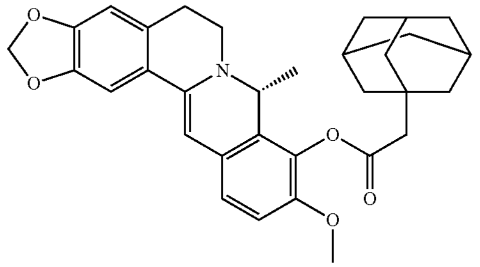
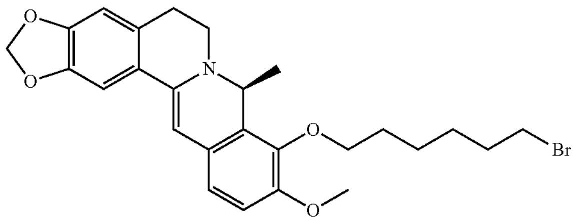
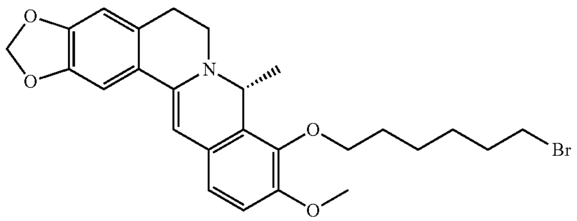
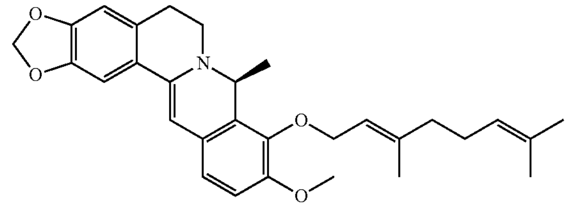
-continued
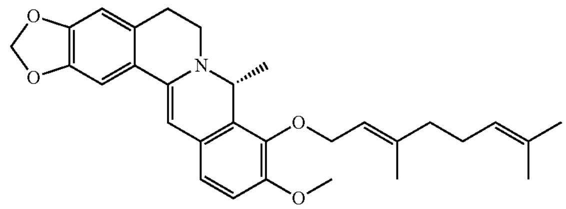
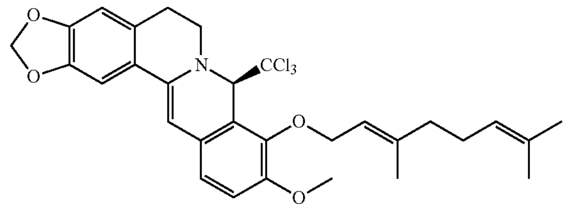
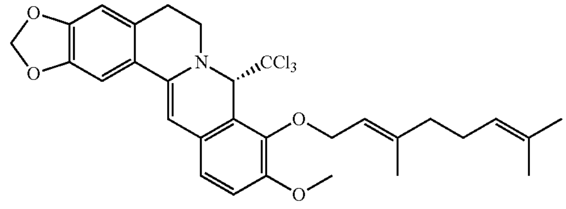
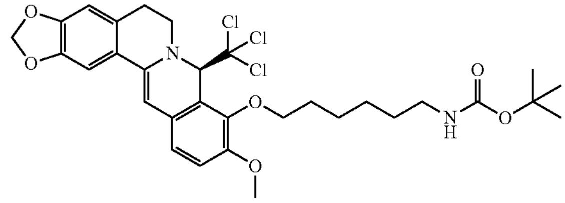
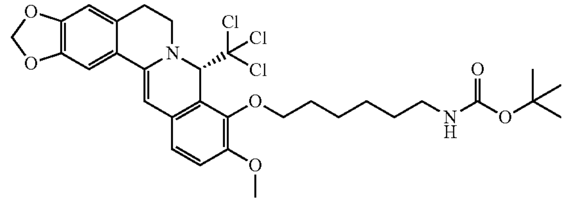
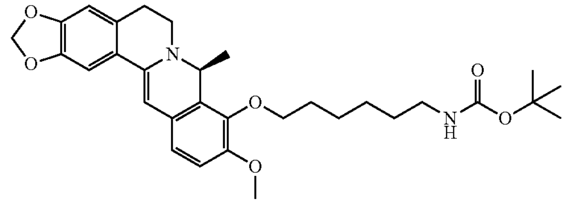
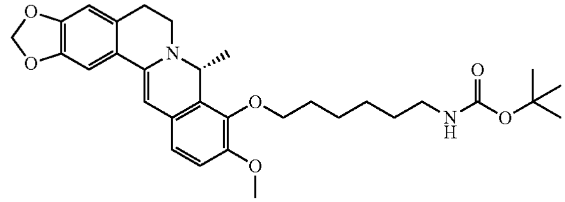
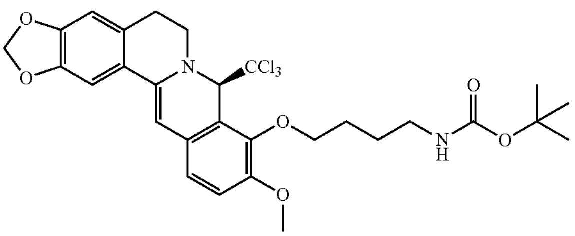

-continued
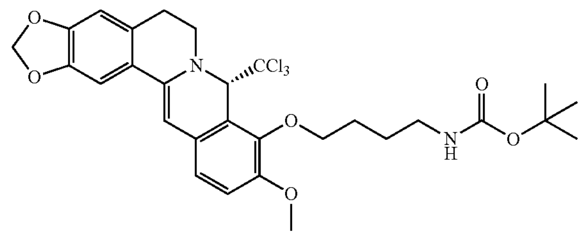
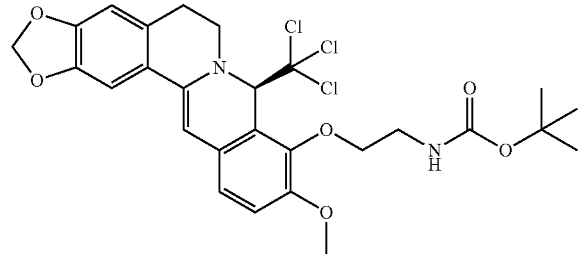
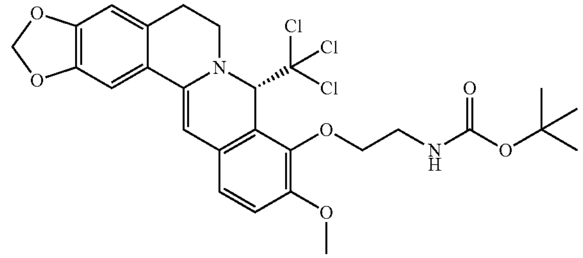
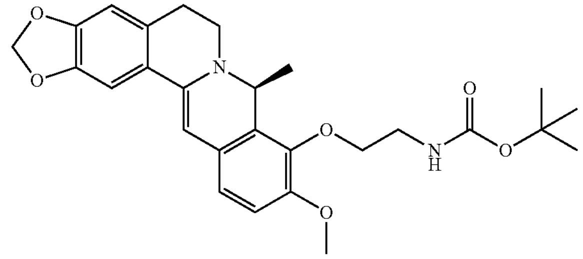
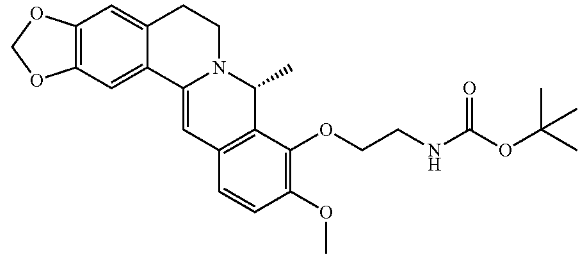
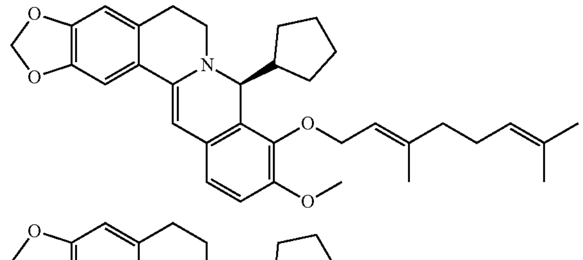
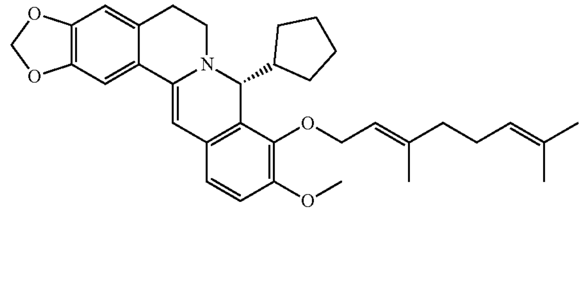
-continued
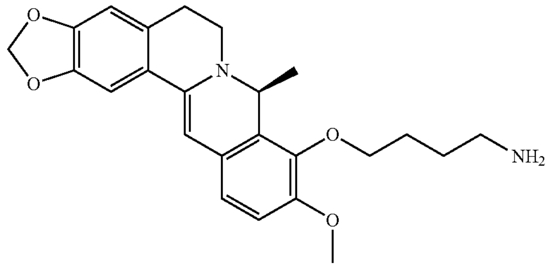
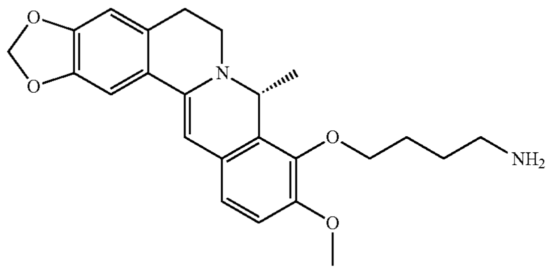
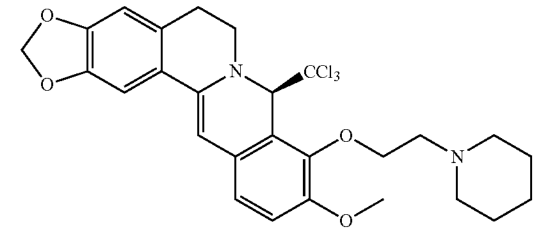
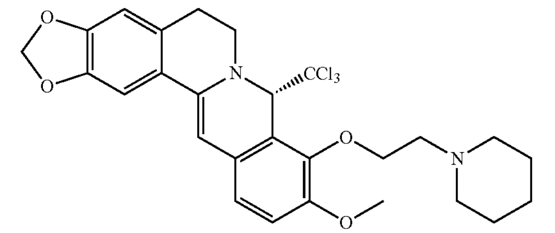
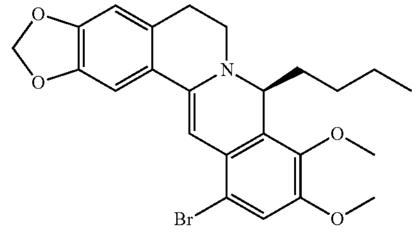
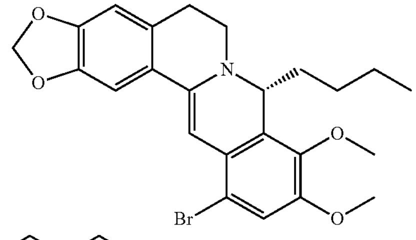
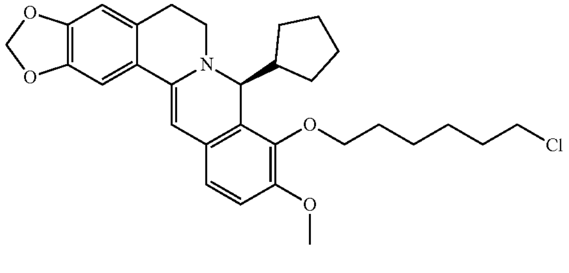

-continued
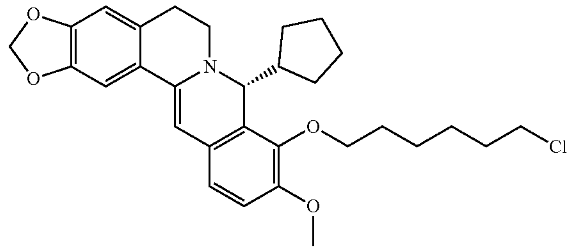
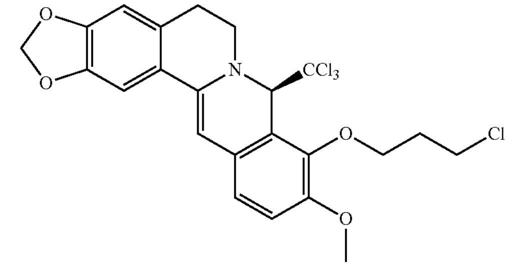
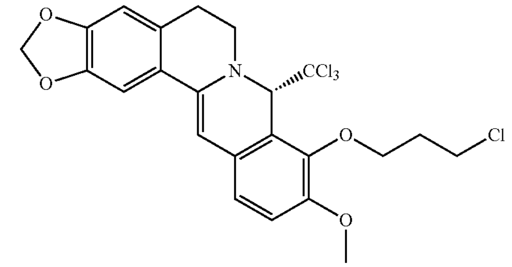
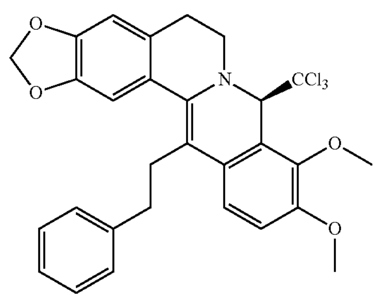
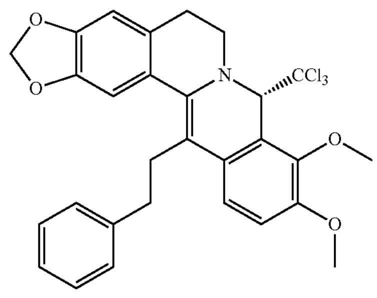
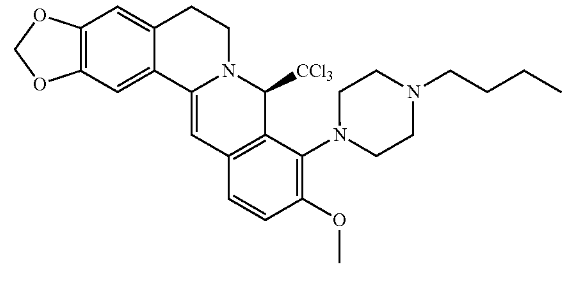
-continued
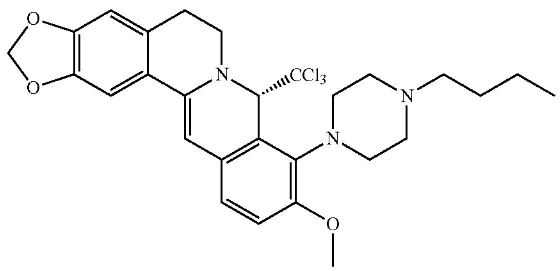
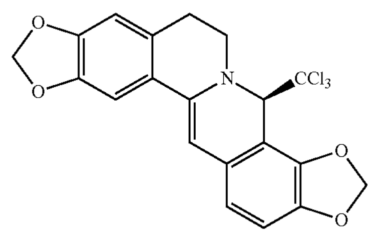
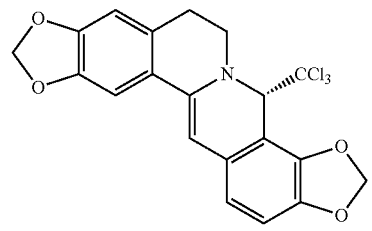
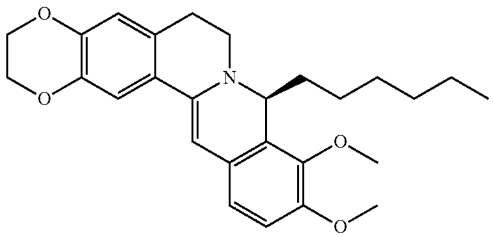
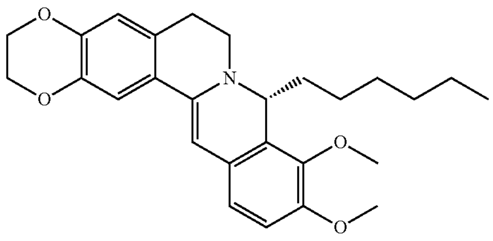
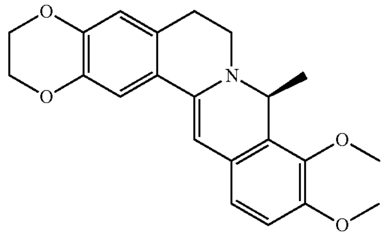
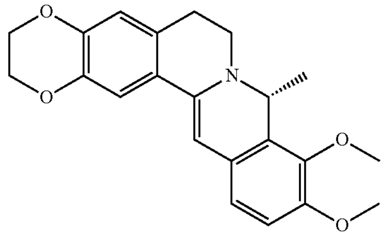

-continued
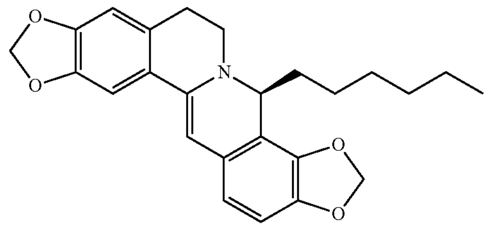
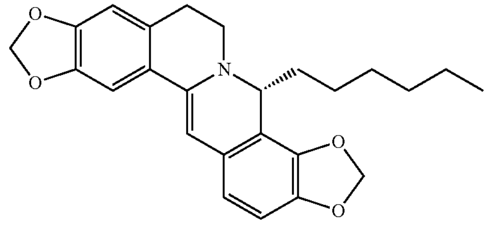
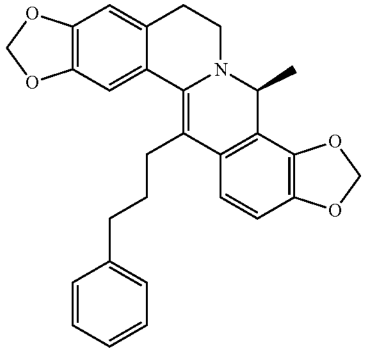
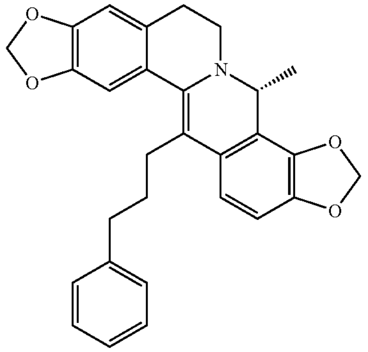
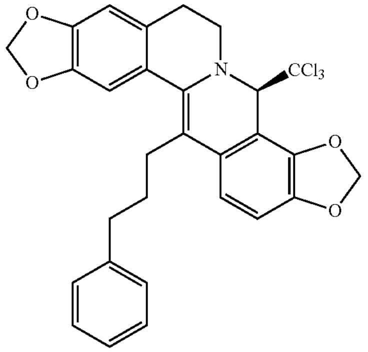
-continued
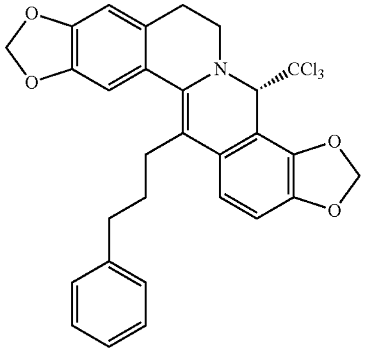
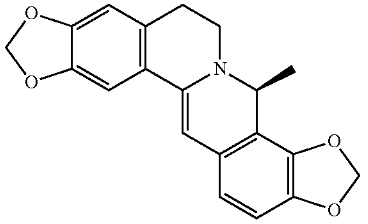
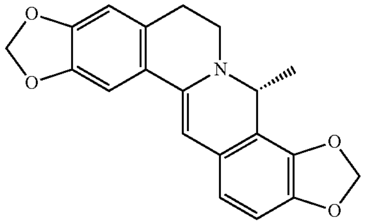
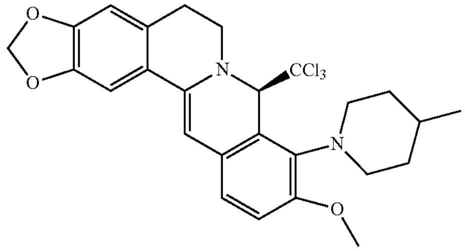
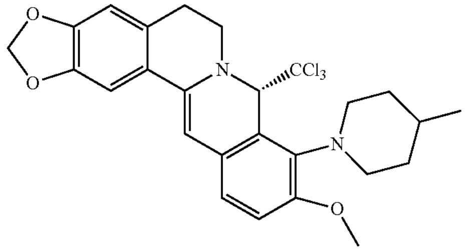
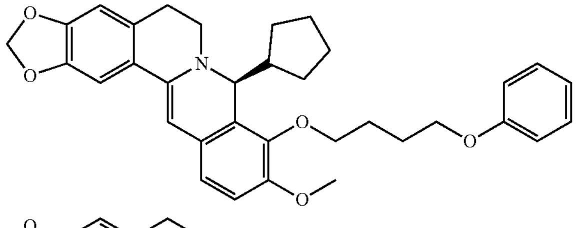
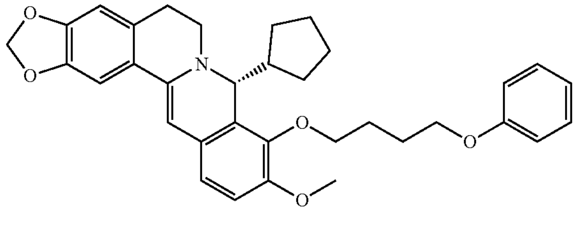

-continued
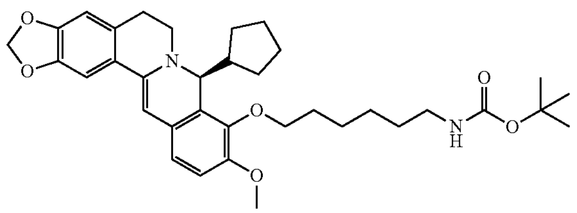
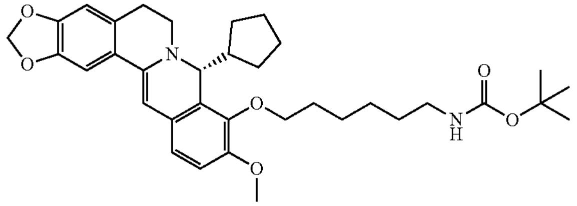
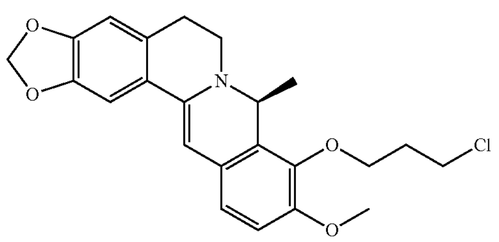
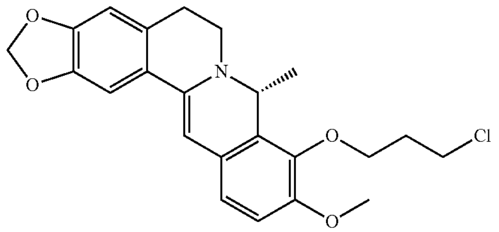
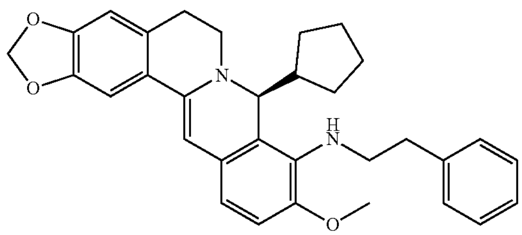
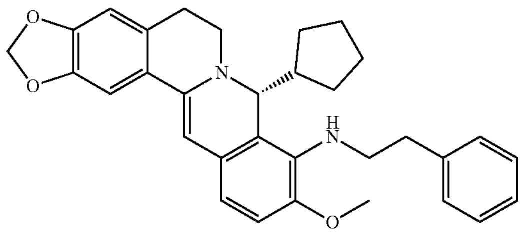
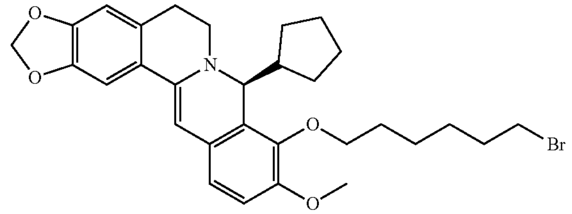
-continued
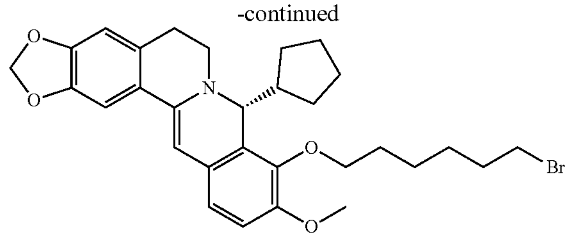
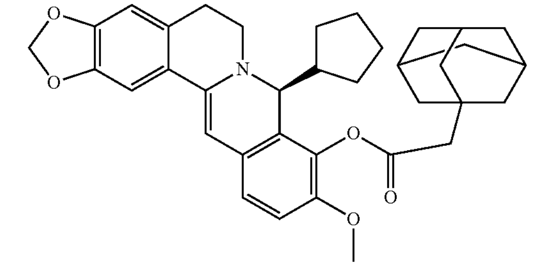
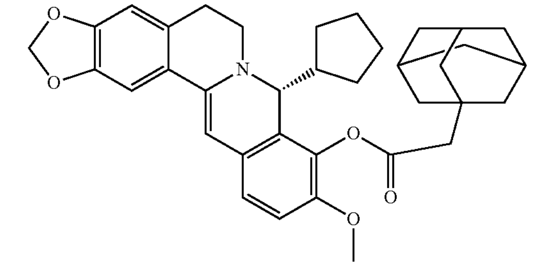
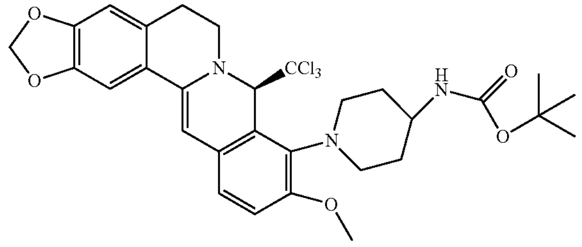
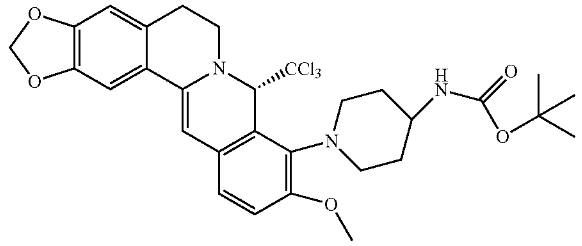
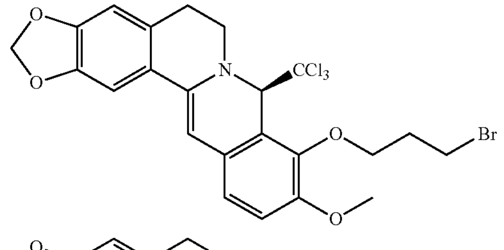
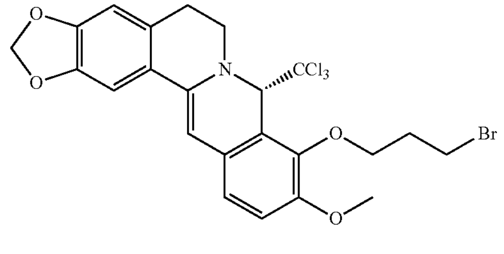

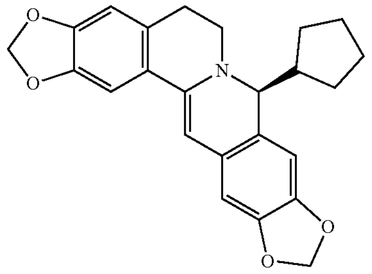
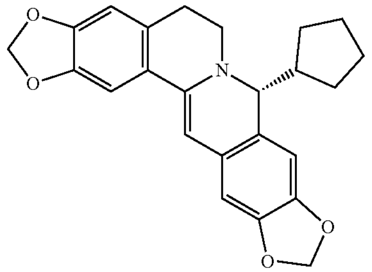
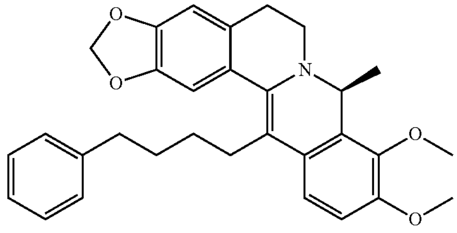
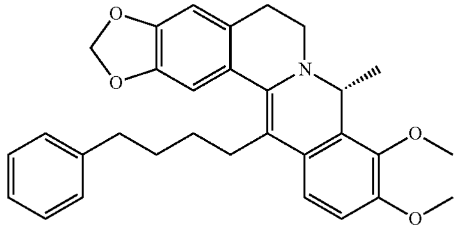
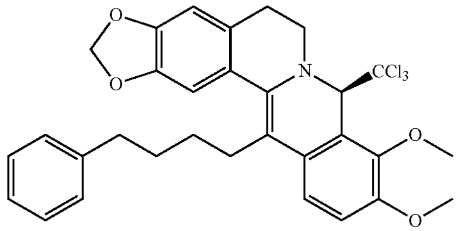
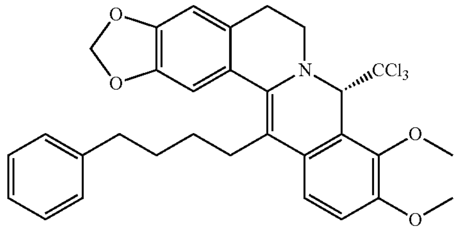
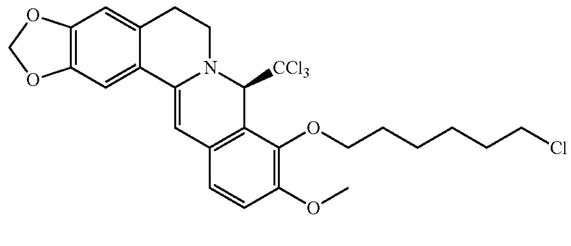
-continued
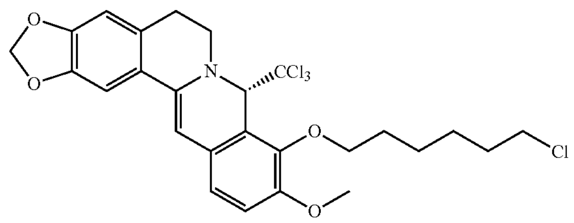
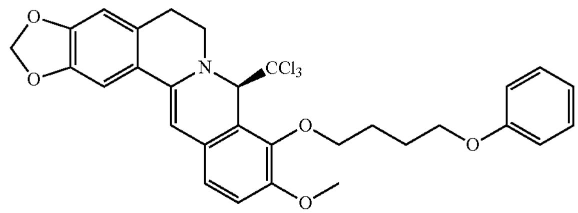
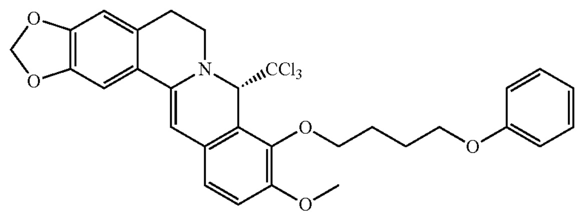
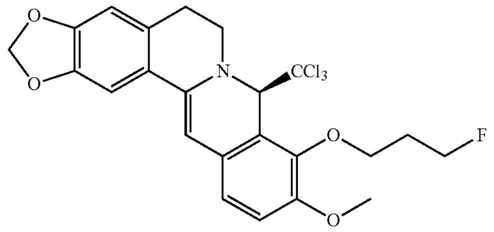
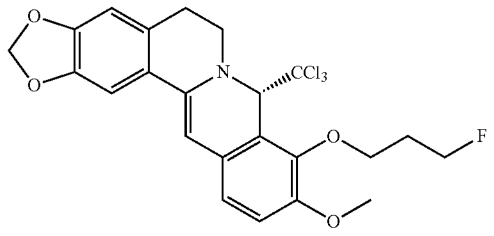
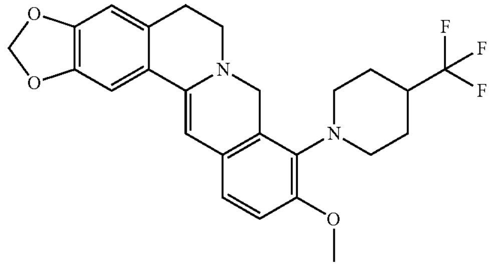
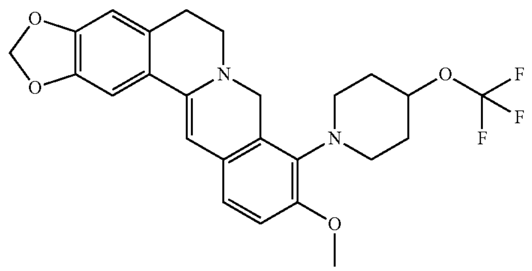

-continued
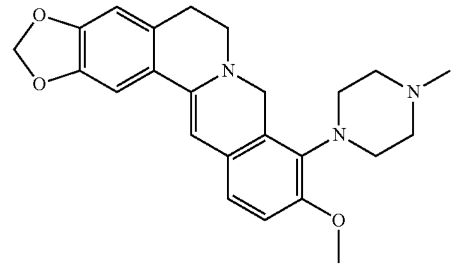
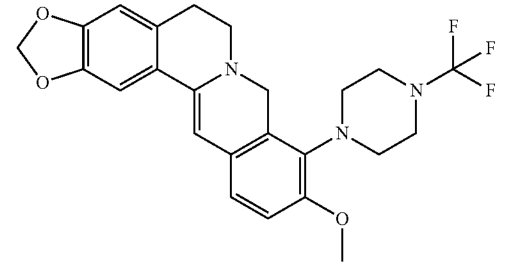
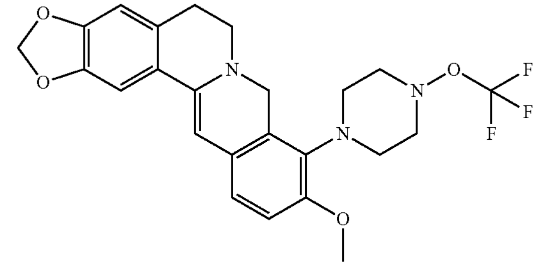
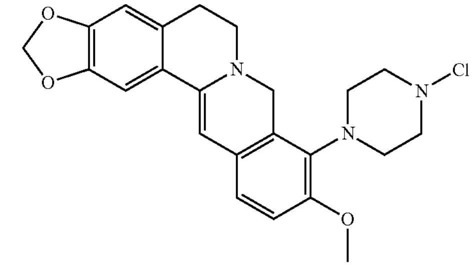
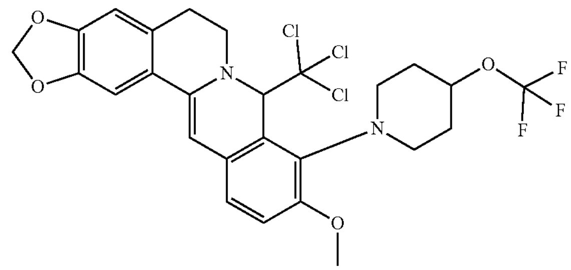
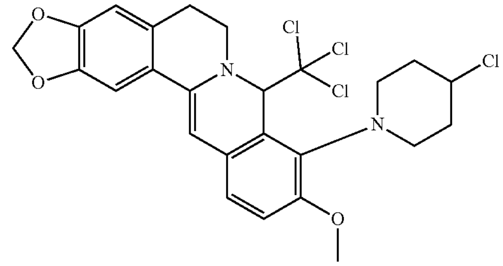
-continued
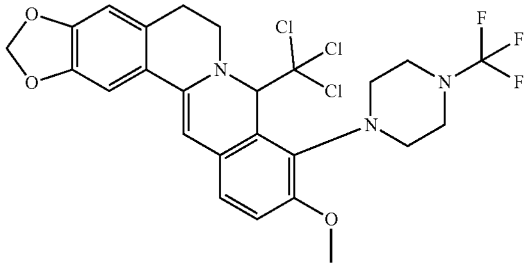
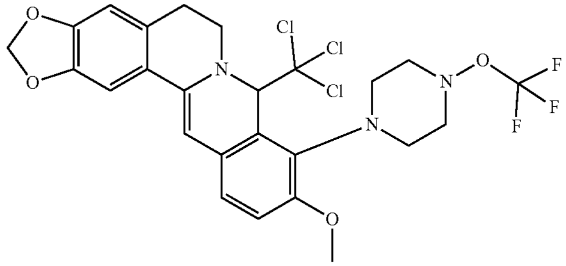
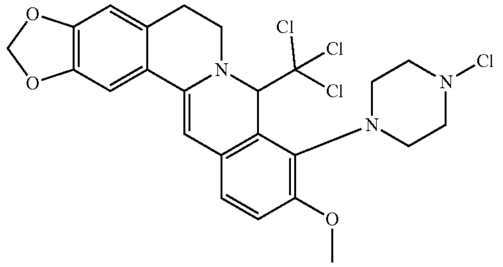
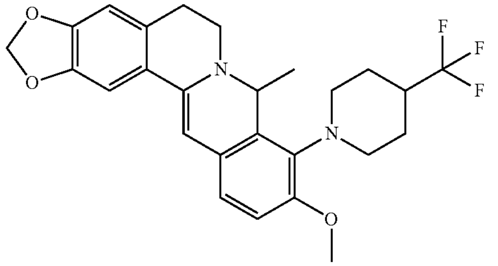
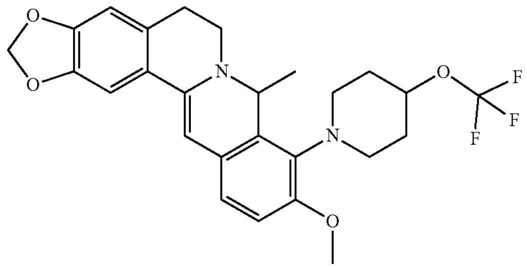
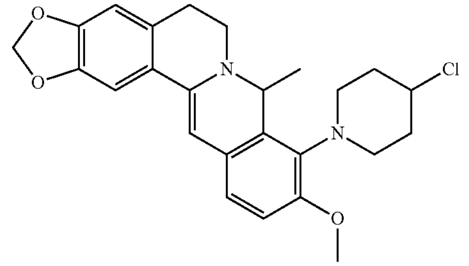

-continued
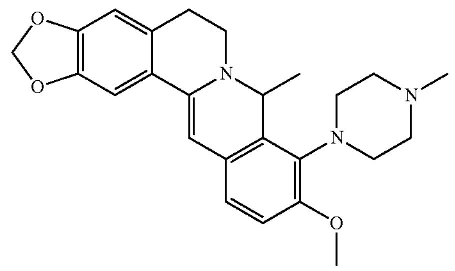
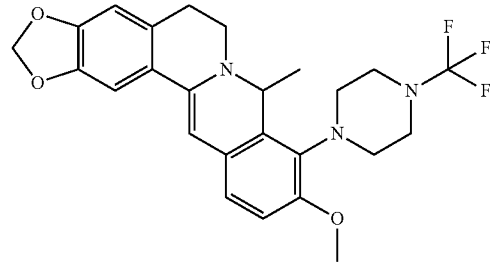
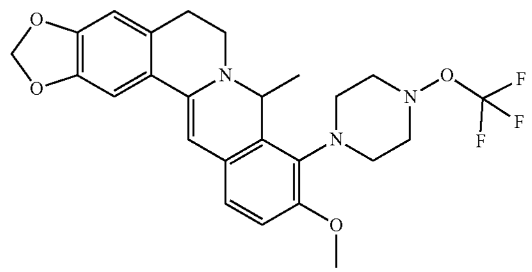
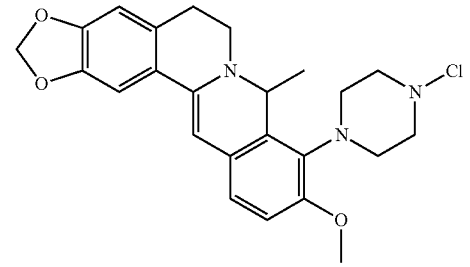
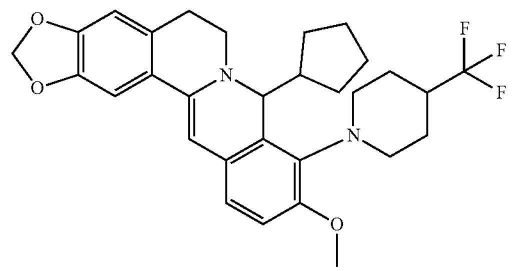
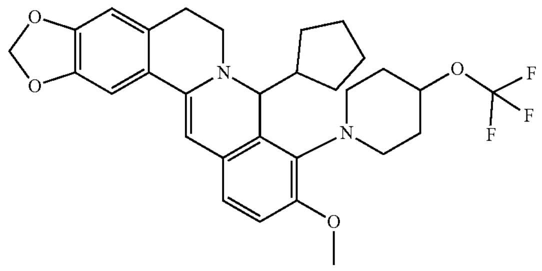
-continued
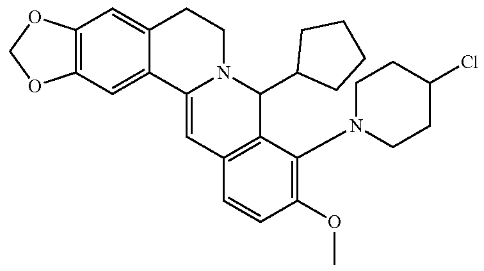
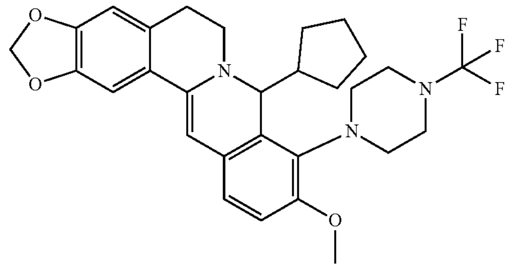
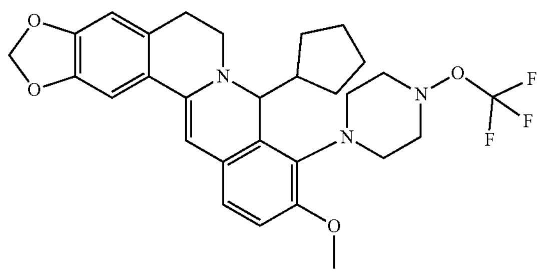
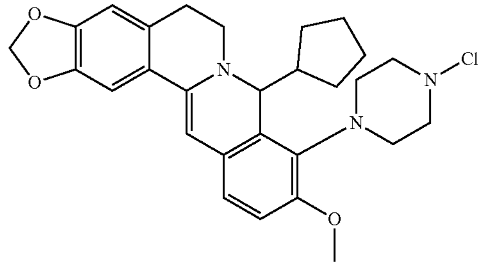
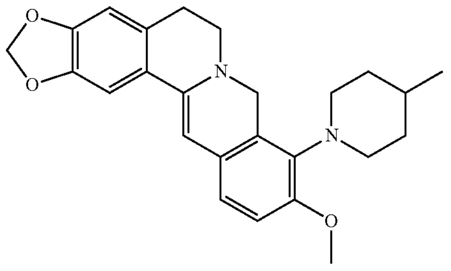
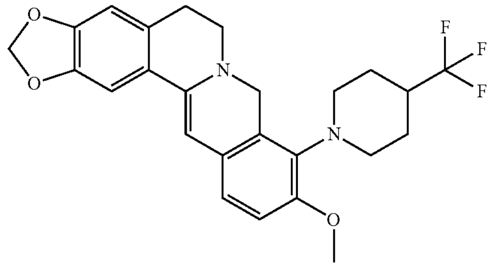

-continued
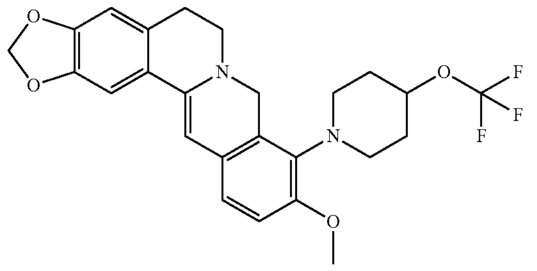
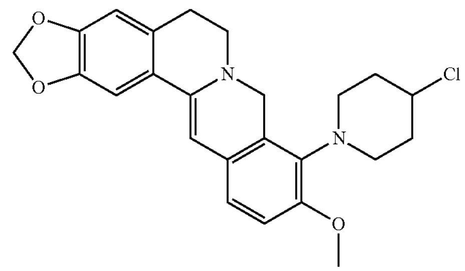
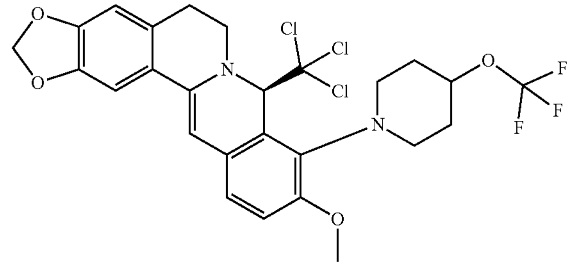
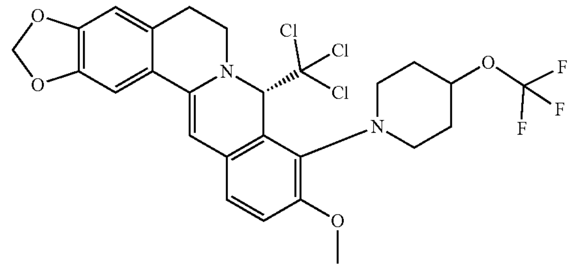
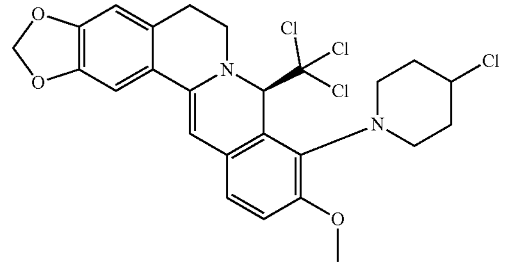
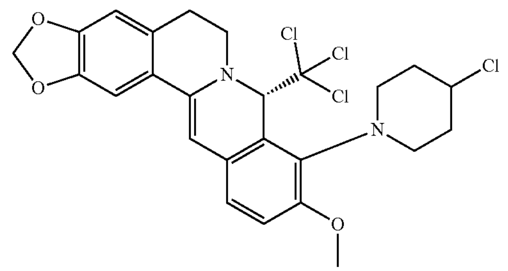
-continued
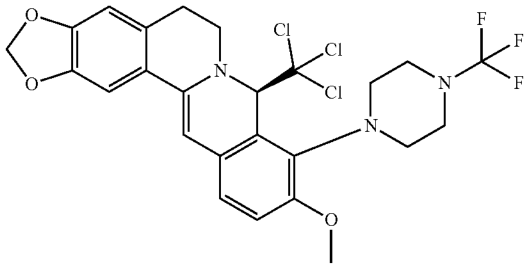
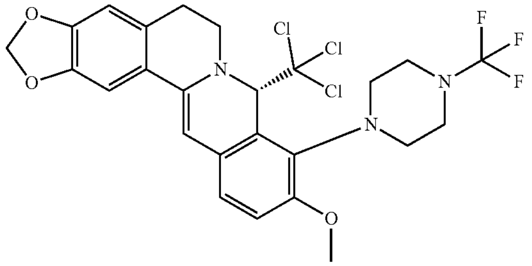
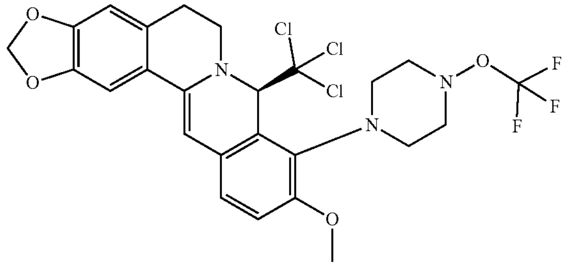
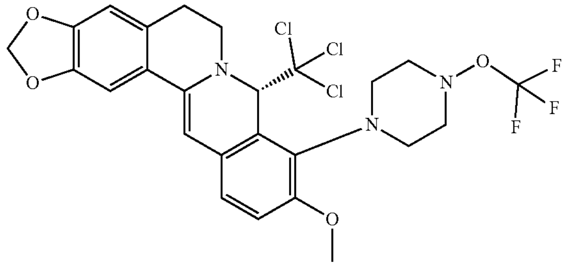
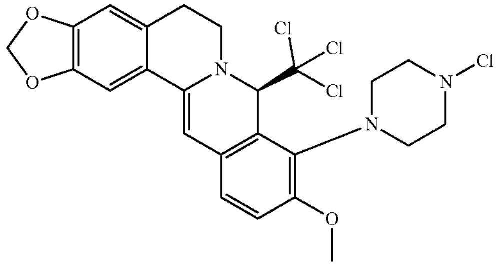
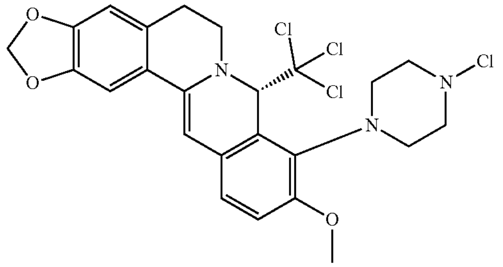

-continued
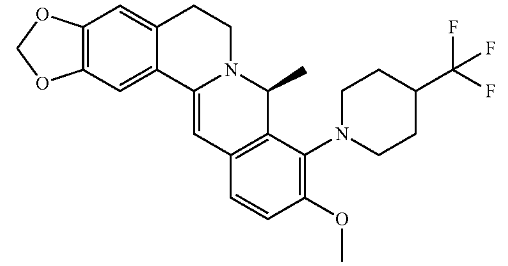
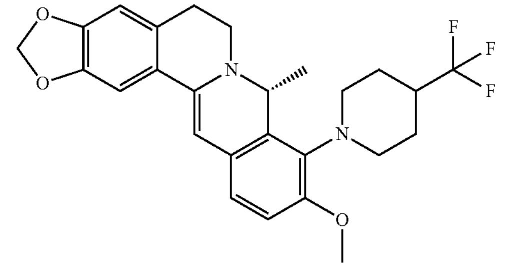
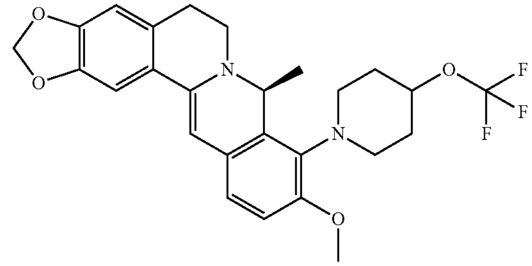
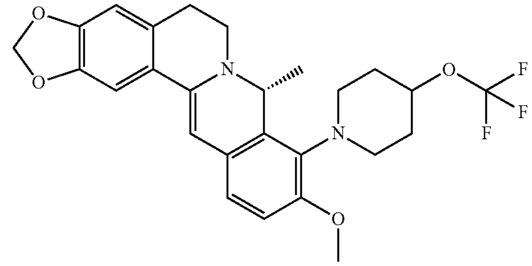
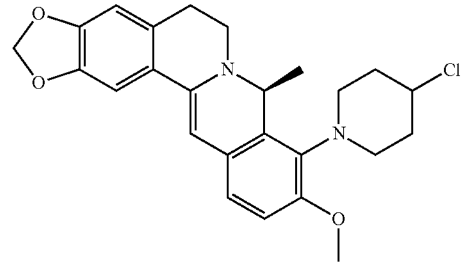
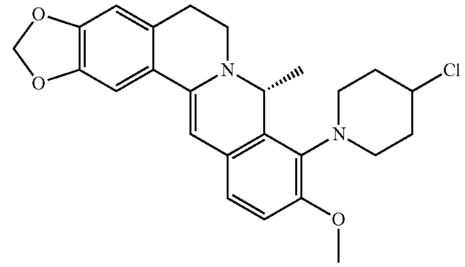
-continued
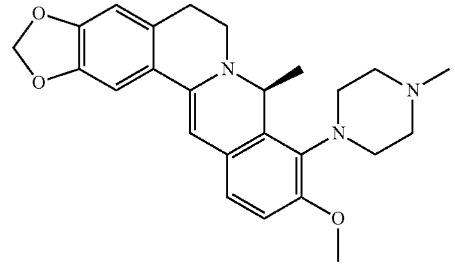
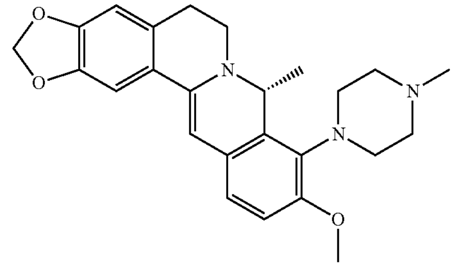
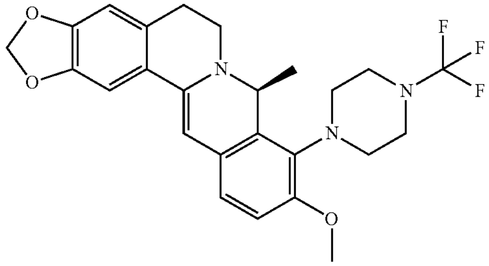
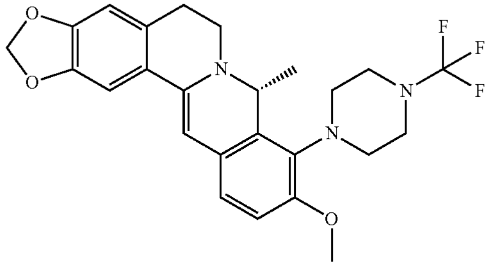
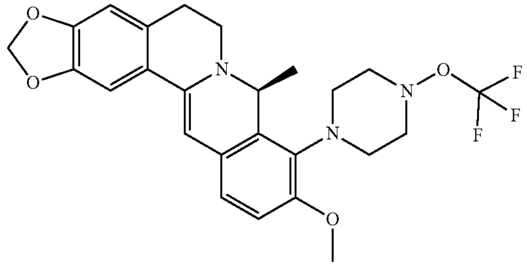
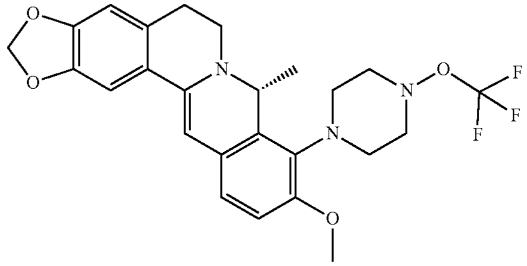

-continued
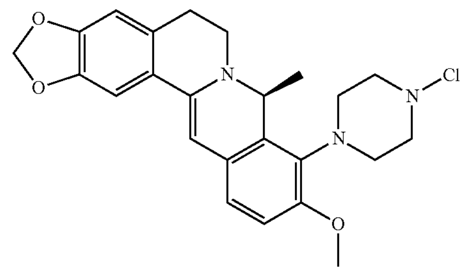
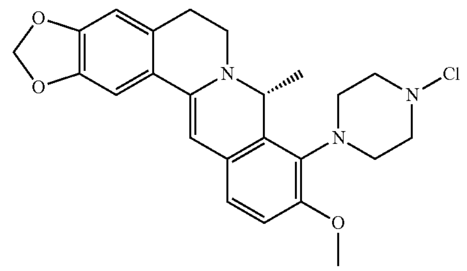
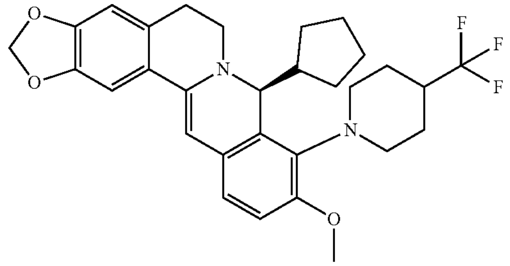
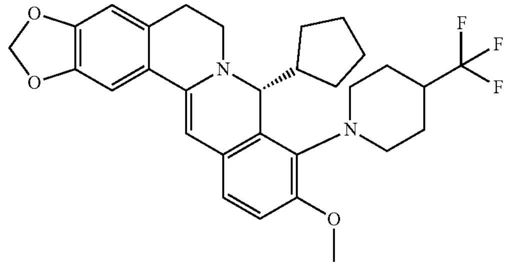
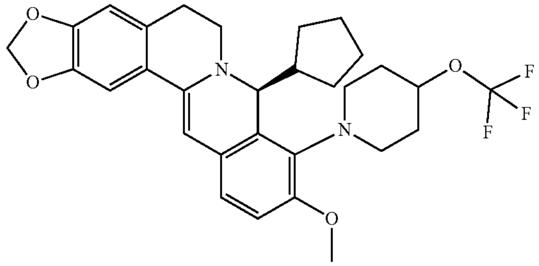
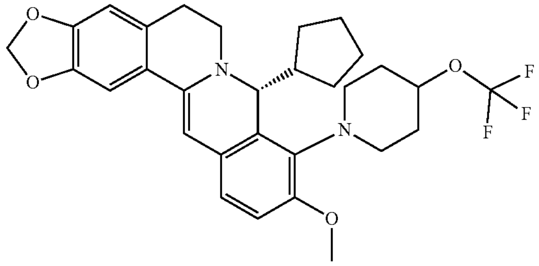
-continued
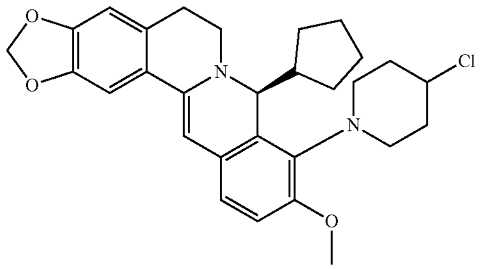
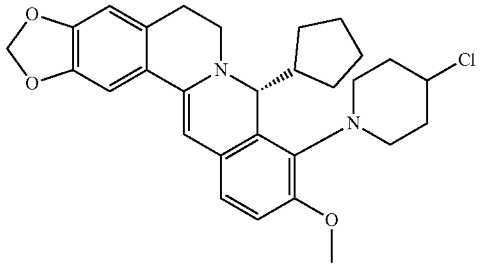
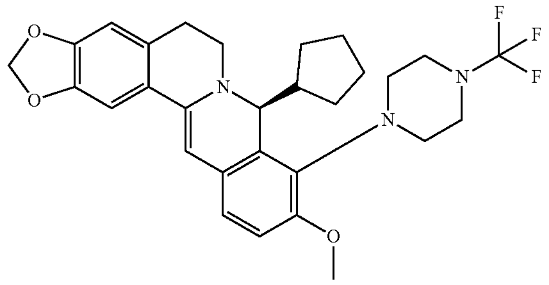
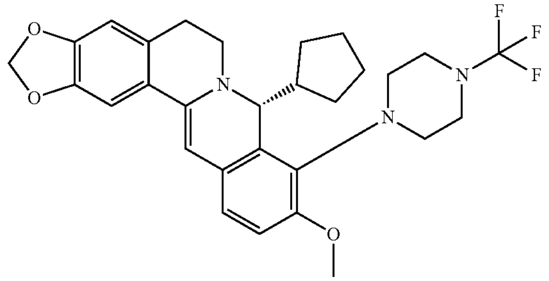
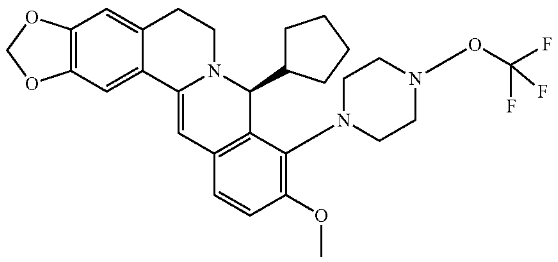
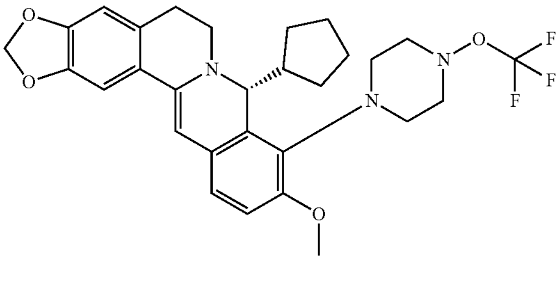

-continued
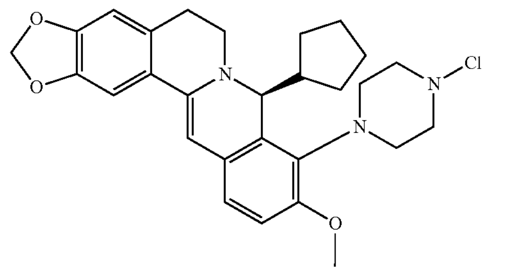
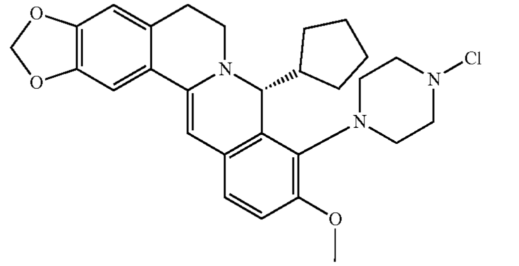
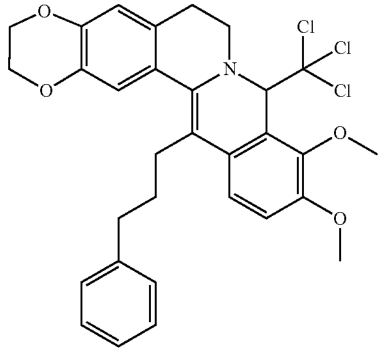
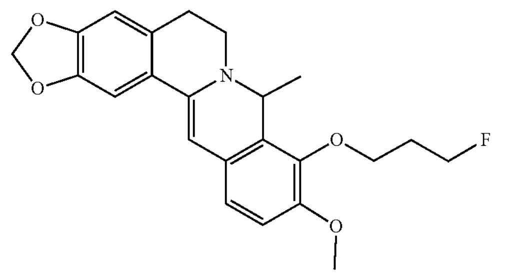
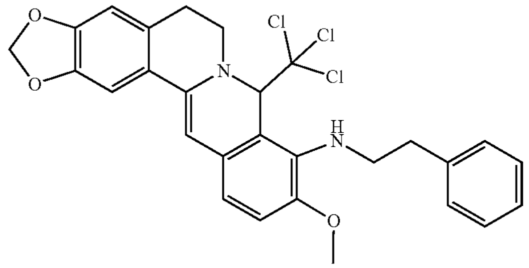
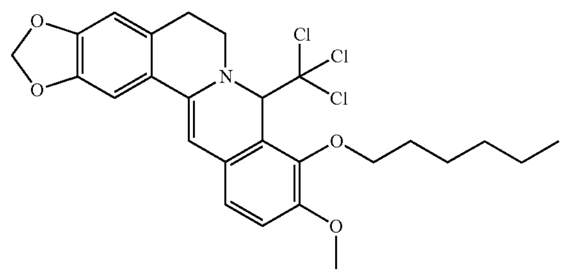
-continued
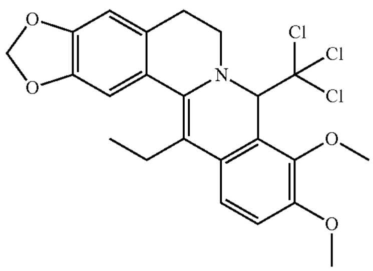
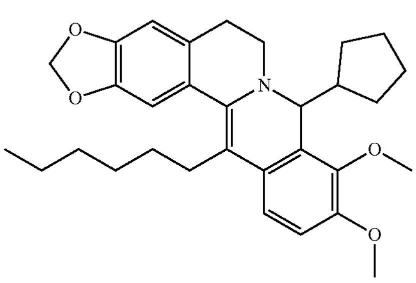
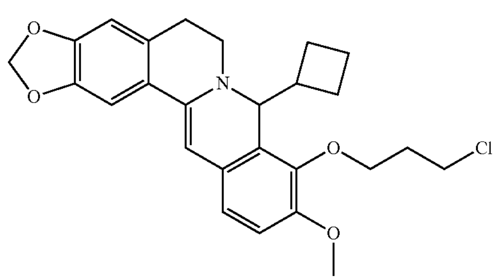
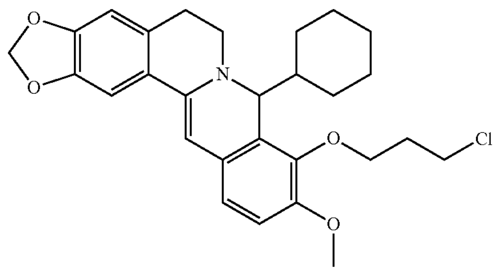
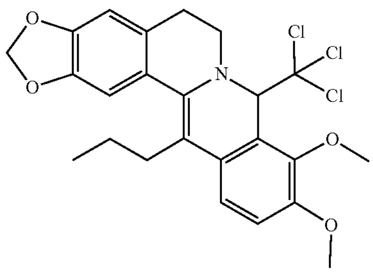
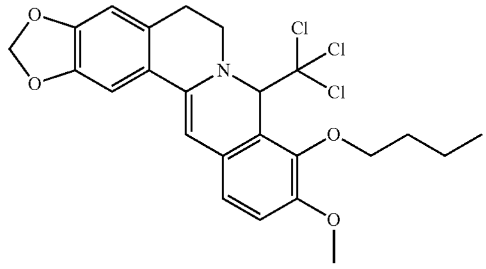

-continued
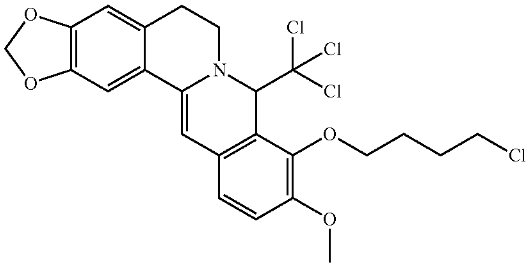
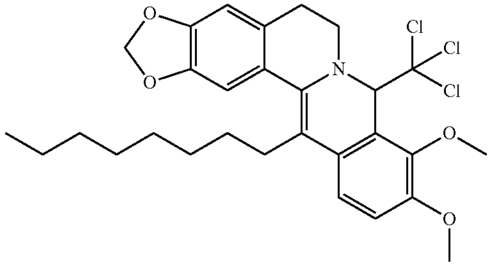
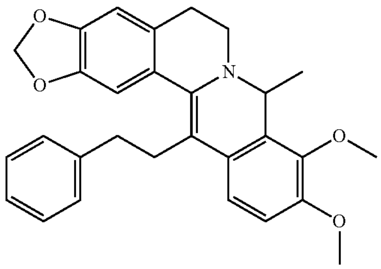
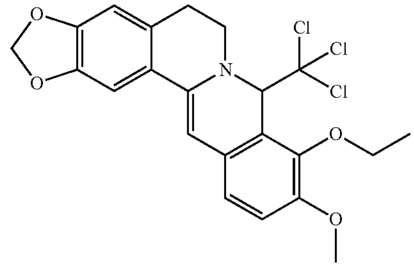
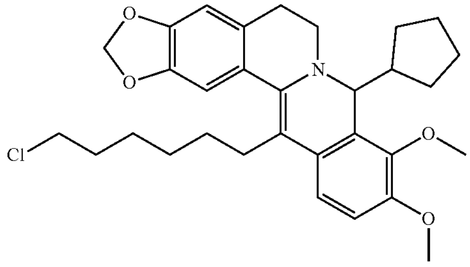
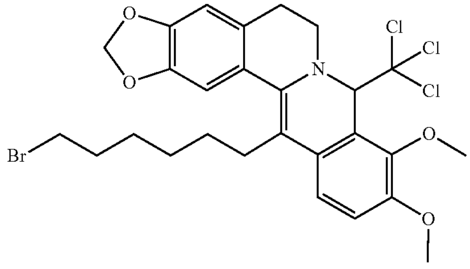
-continued
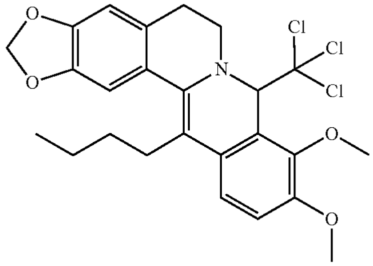
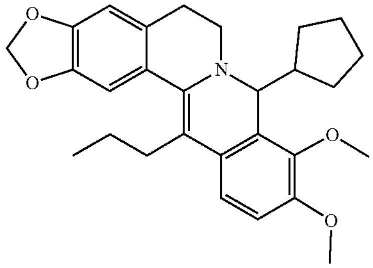
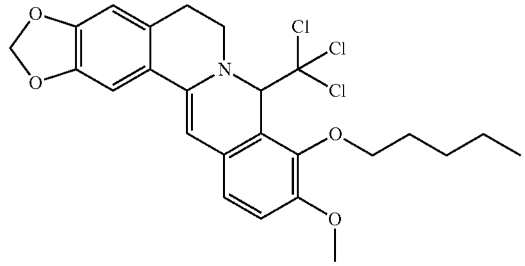
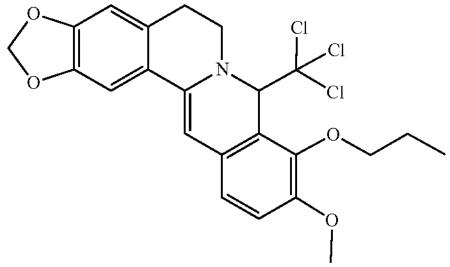
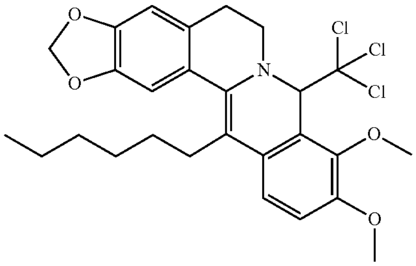
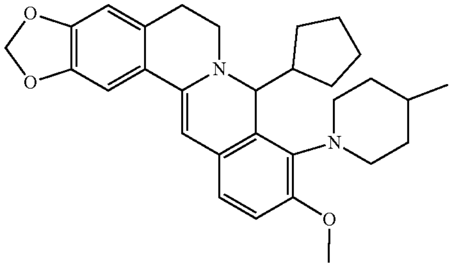

-continued
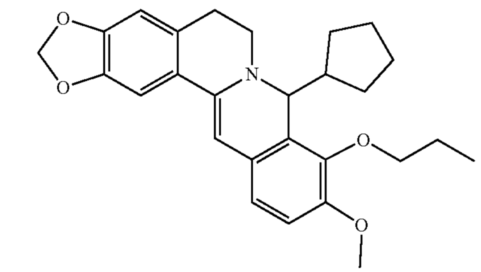
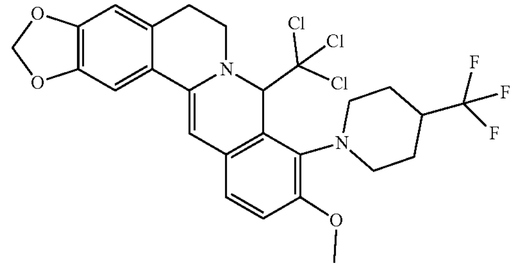
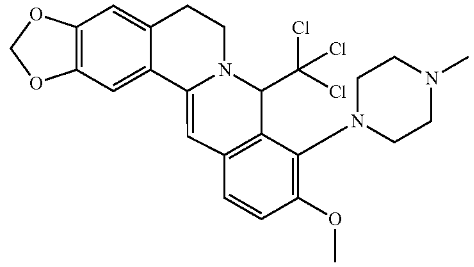
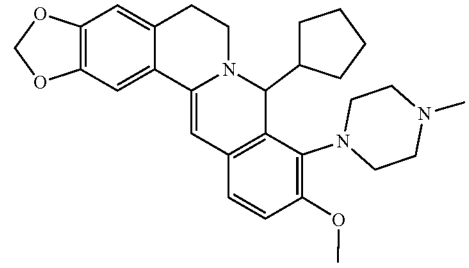
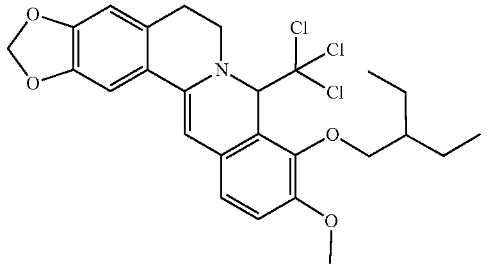
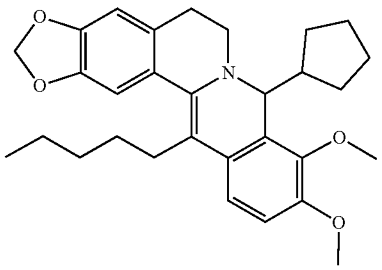
-continued
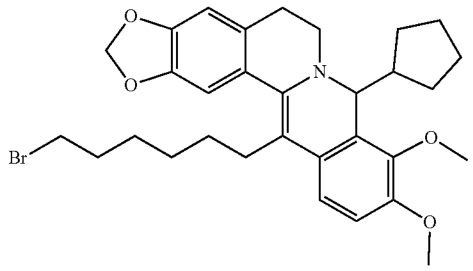
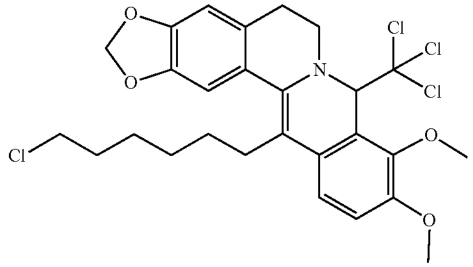
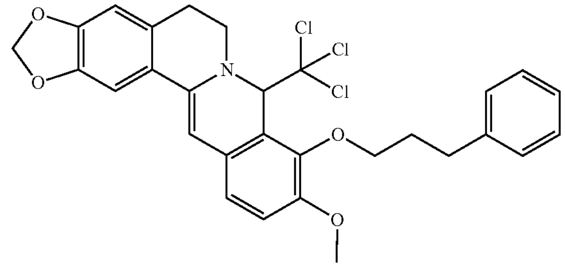
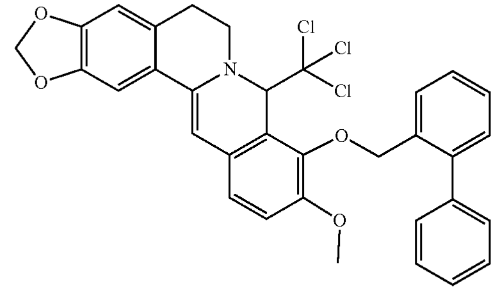
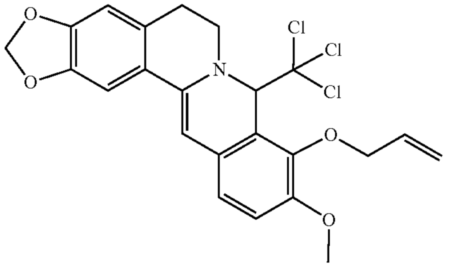
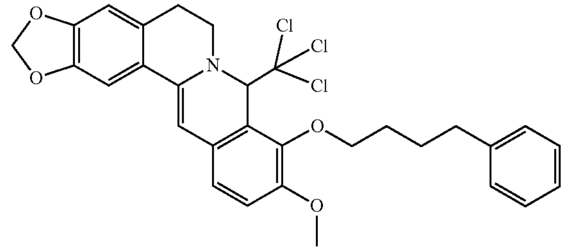

-continued
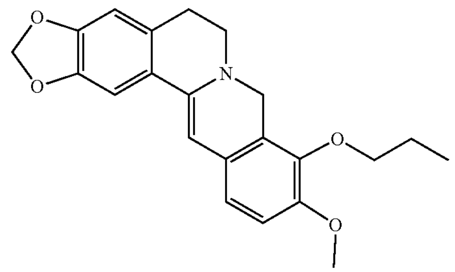
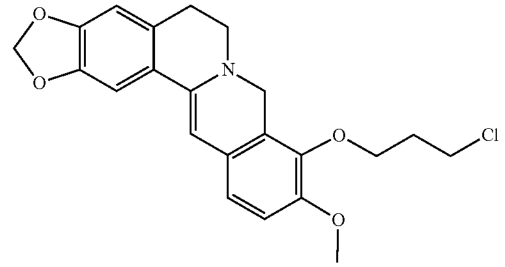
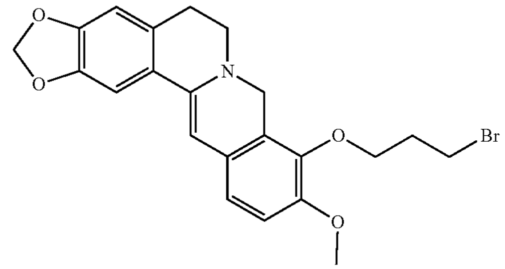
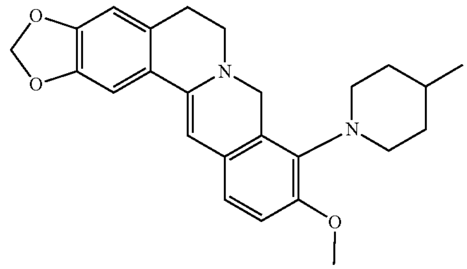
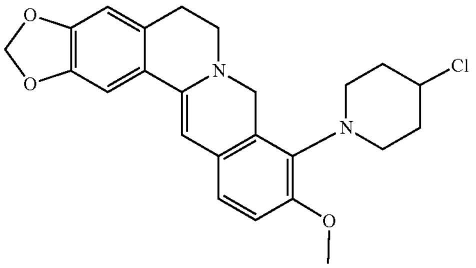
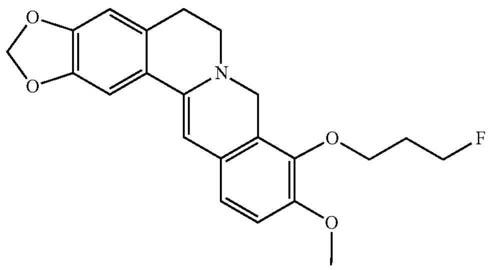
-continued
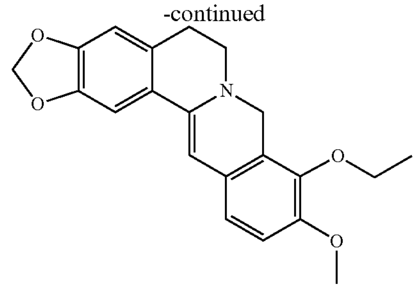
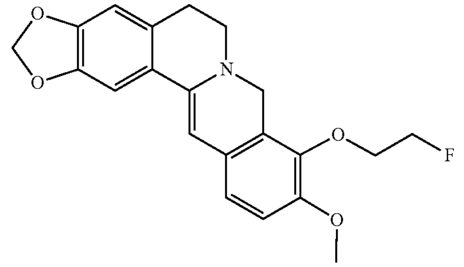
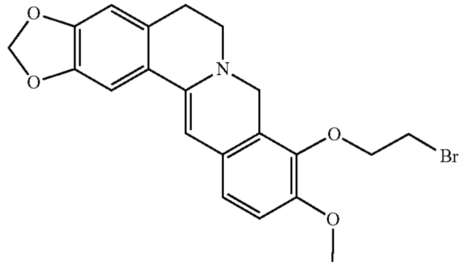
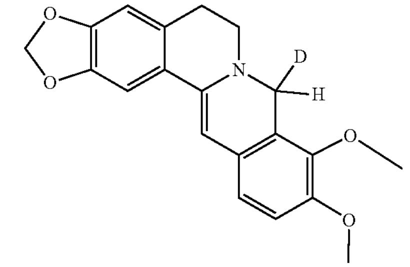
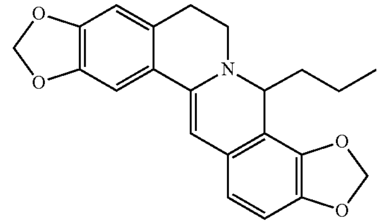
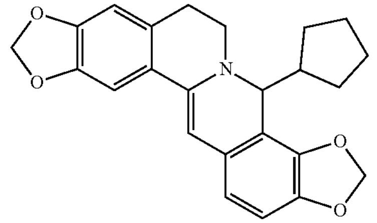
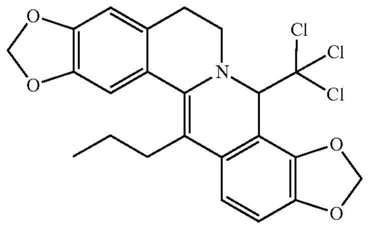

-continued
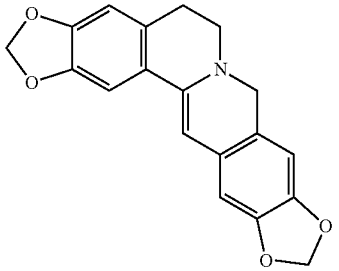
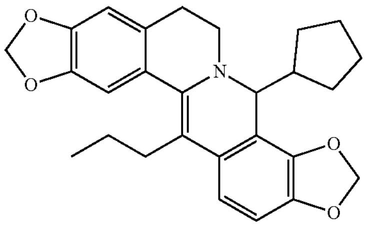
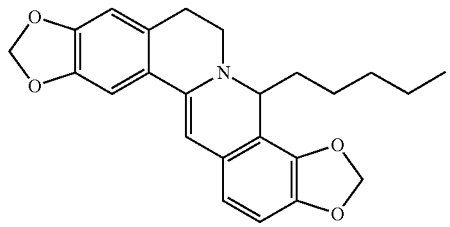
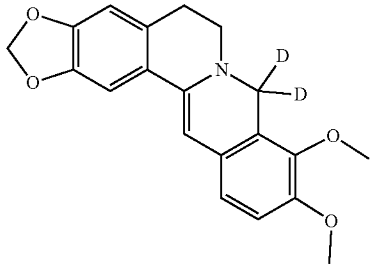
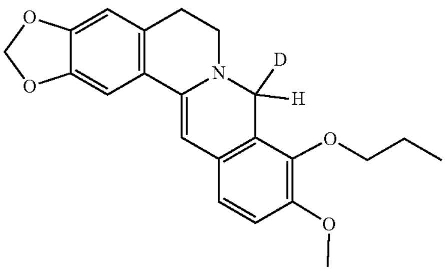
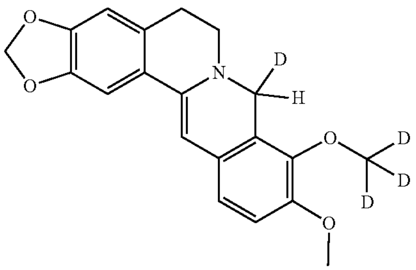
-continued
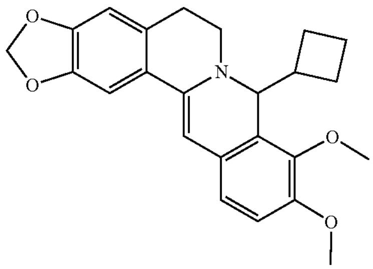
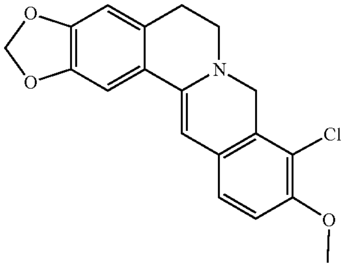
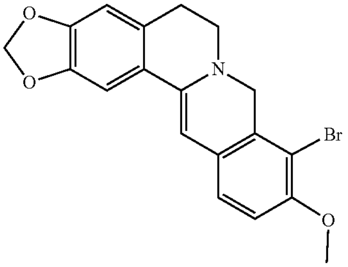
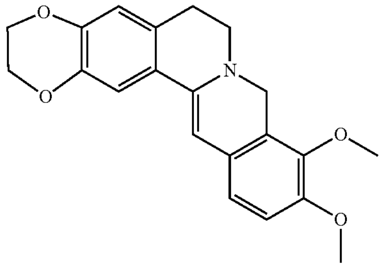
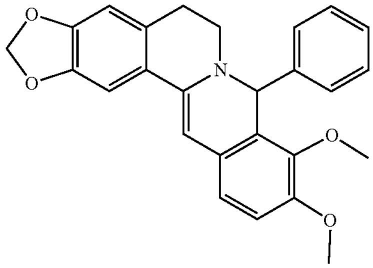
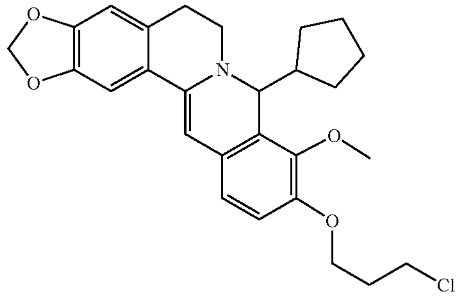

-continued
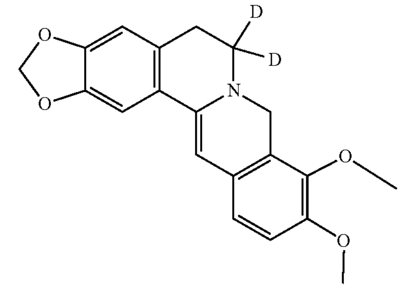
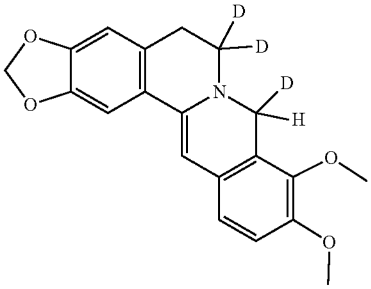
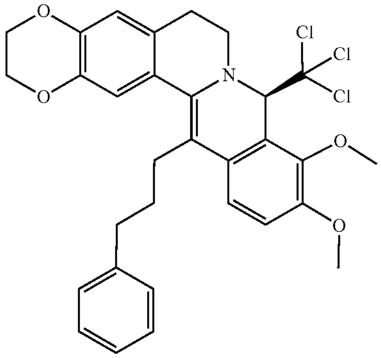
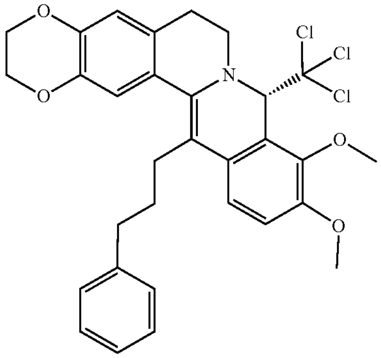
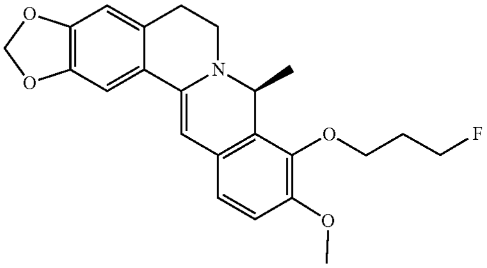
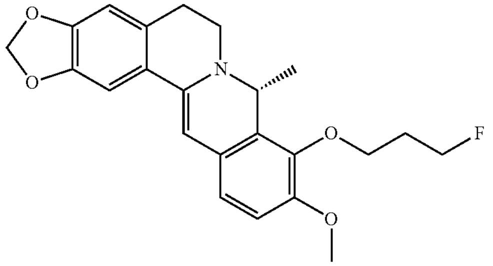
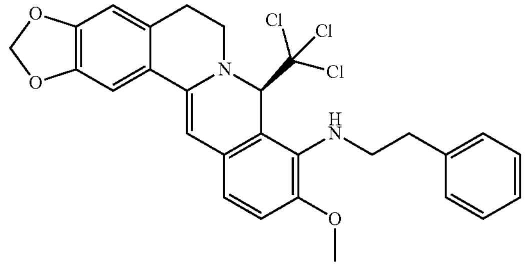
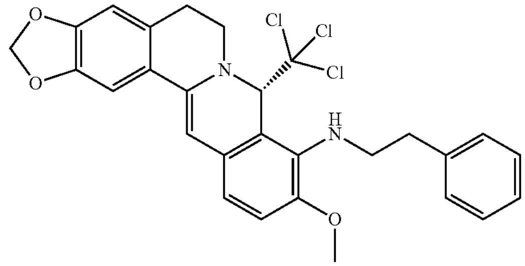
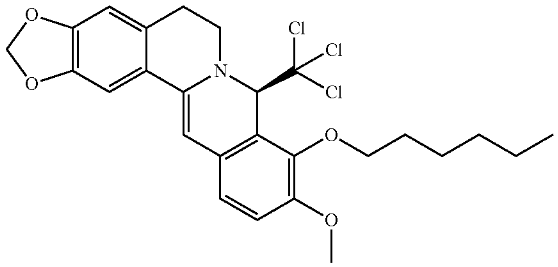
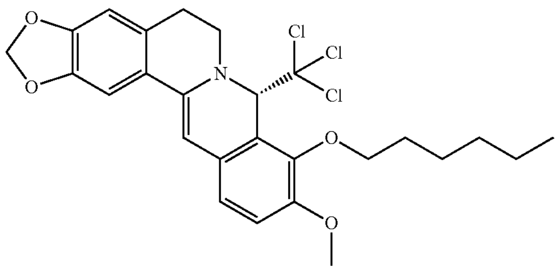
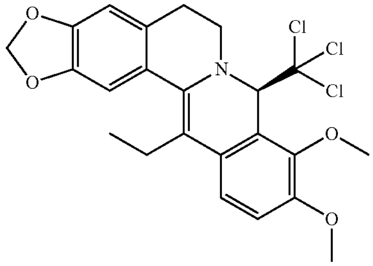

-continued
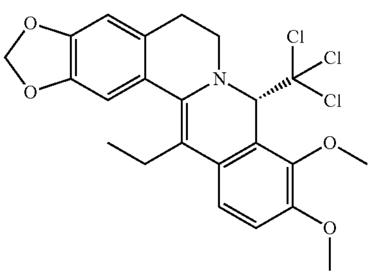
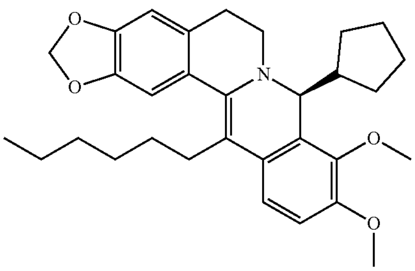
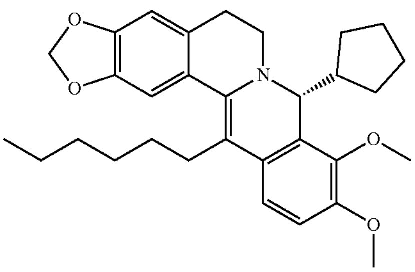
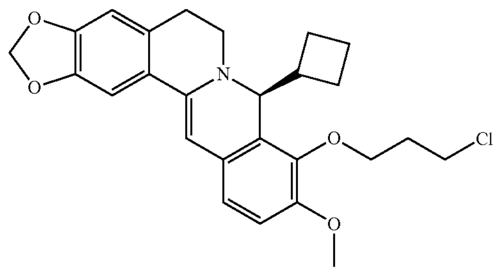
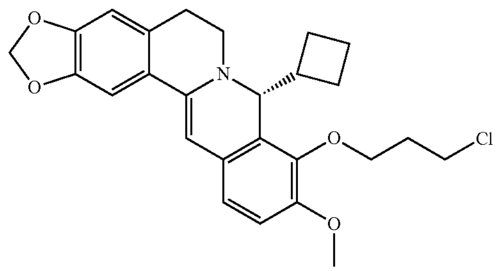
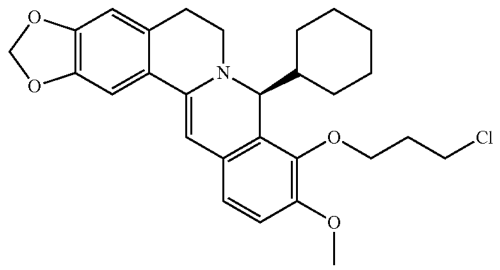
-continued
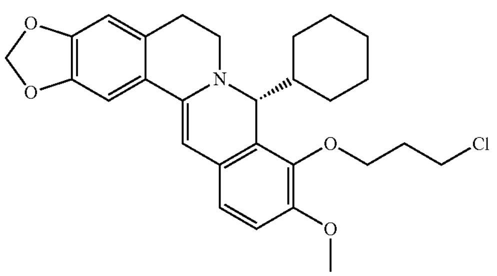
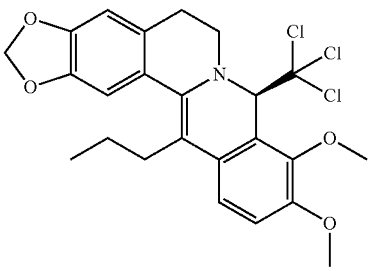
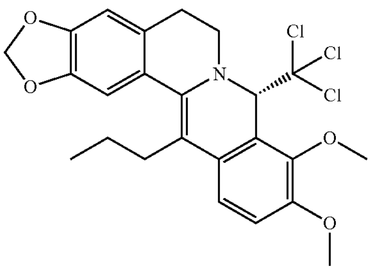
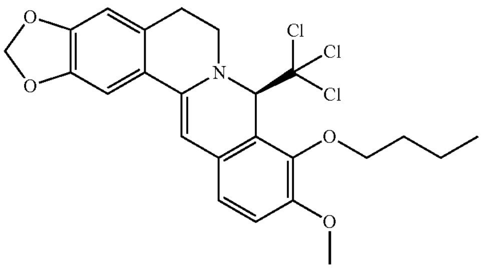
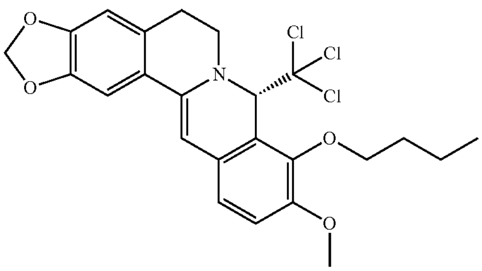
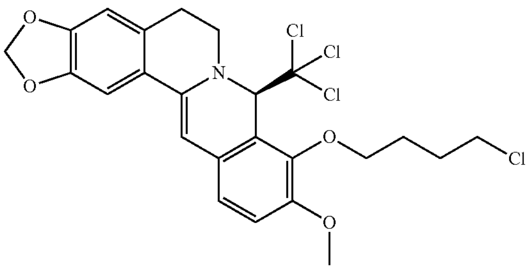

-continued
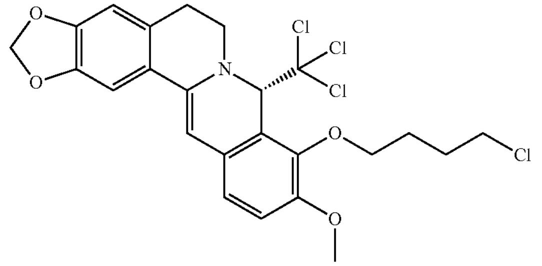
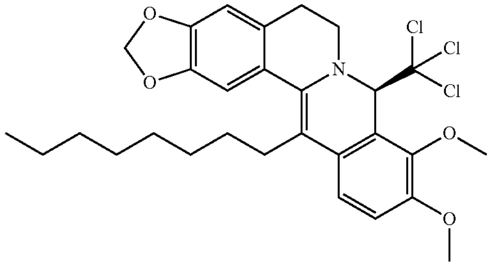
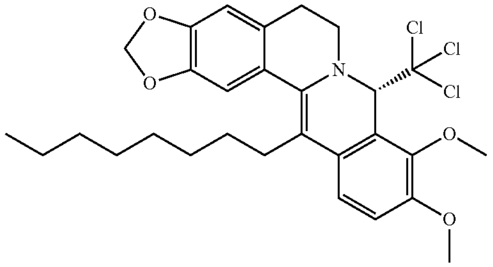
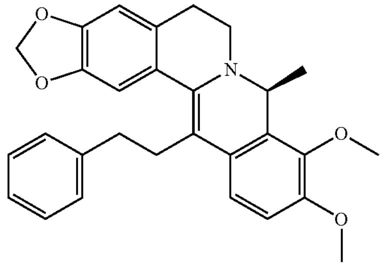
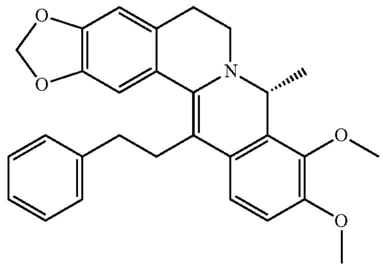
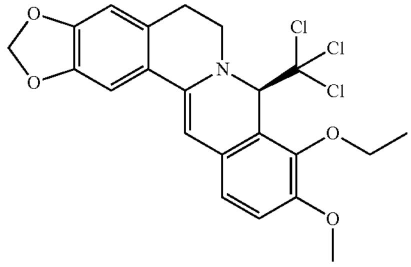
-continued
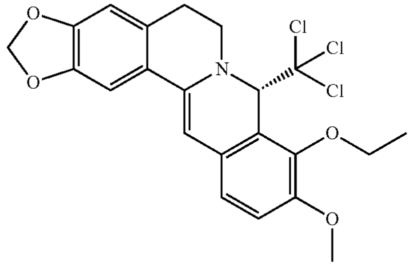
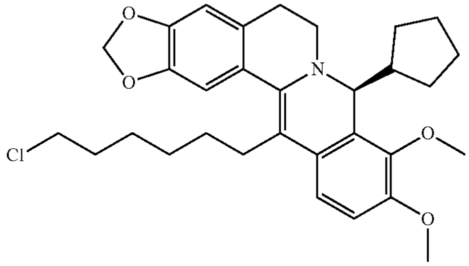
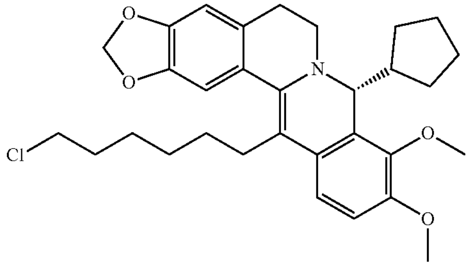
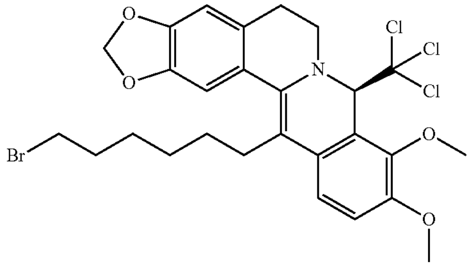
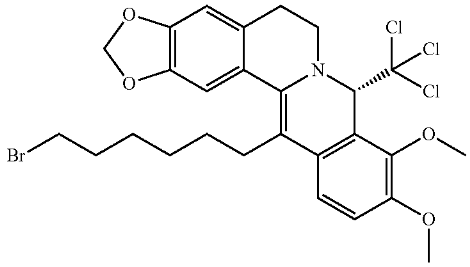
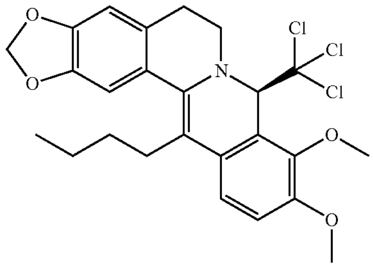

-continued
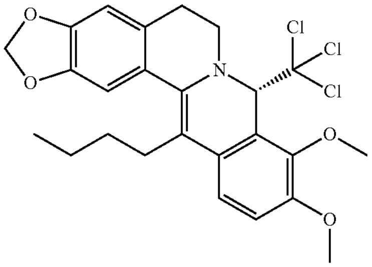
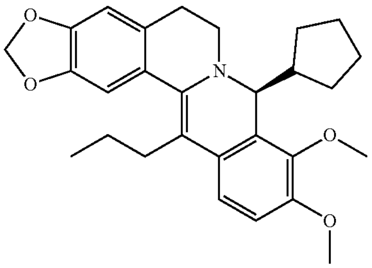
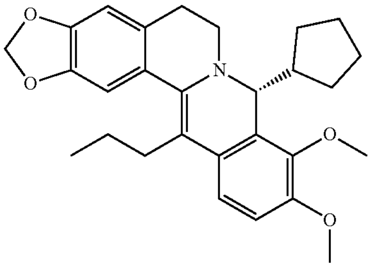
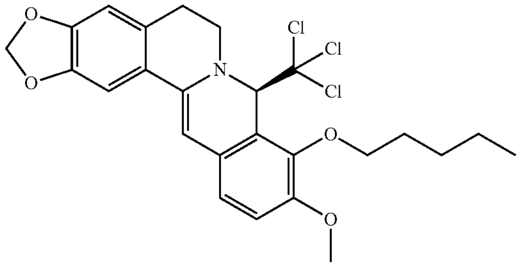
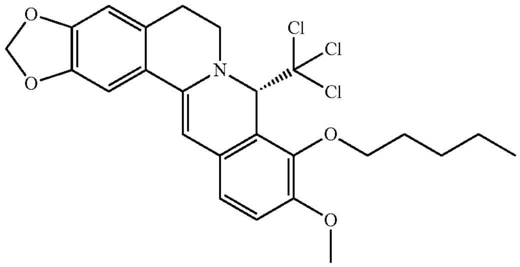
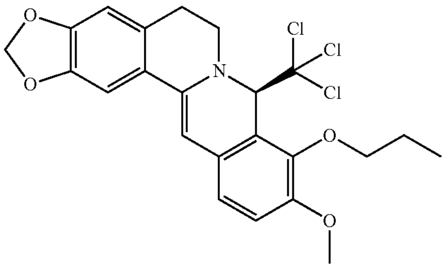
-continued
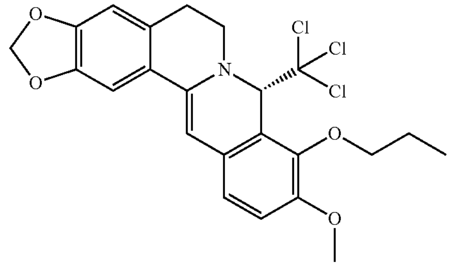
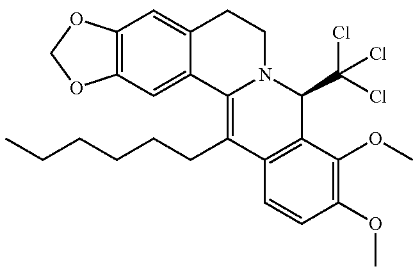
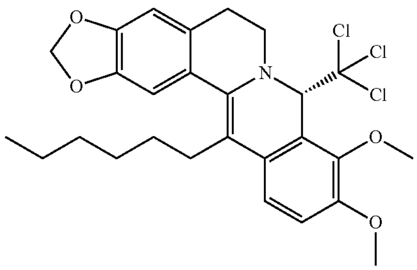
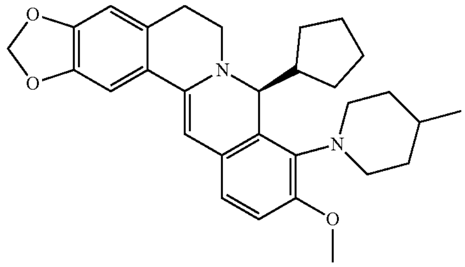
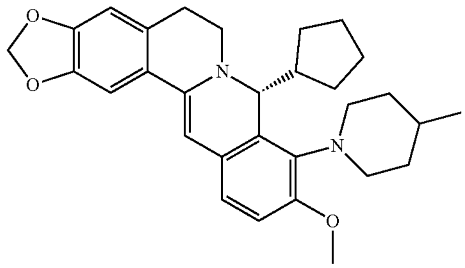
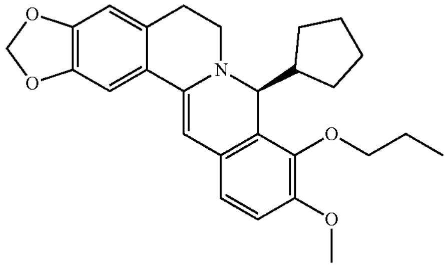

-continued
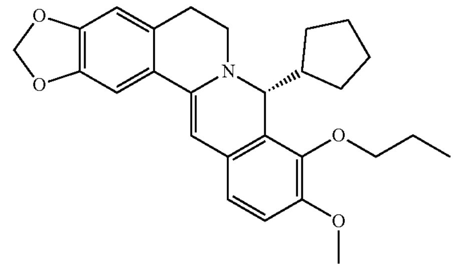
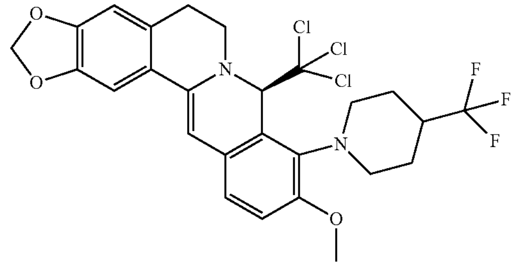
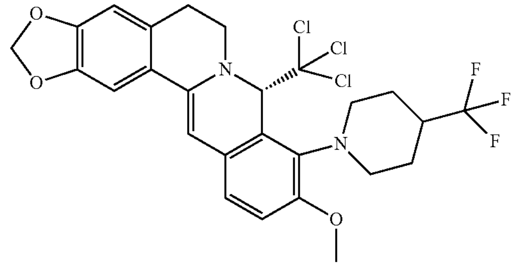
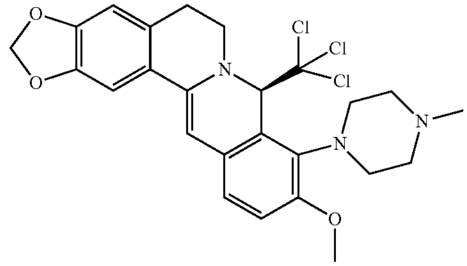
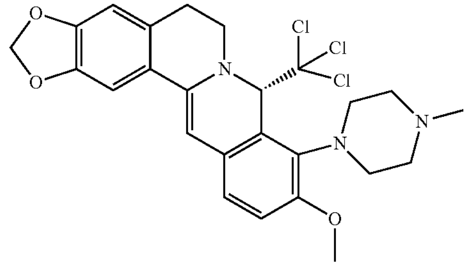
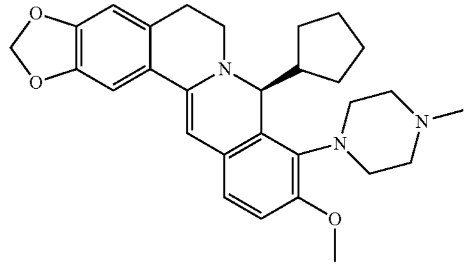
-continued
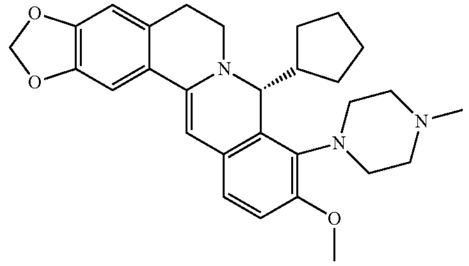
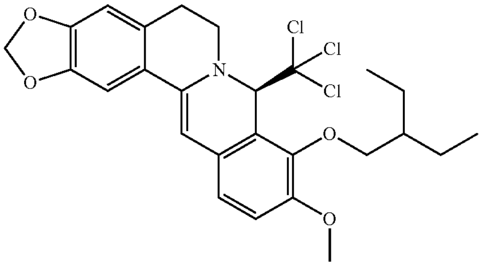
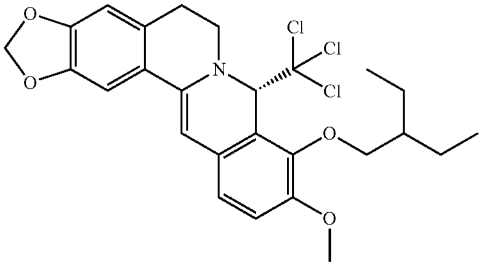
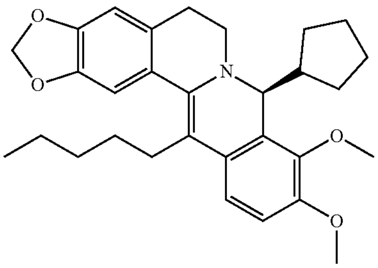
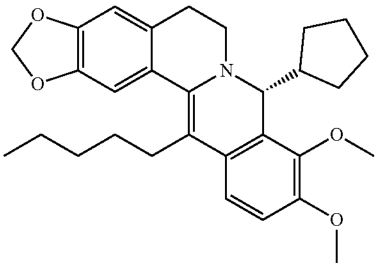
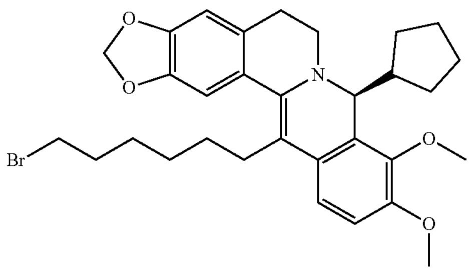

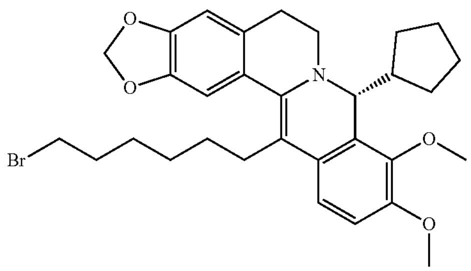
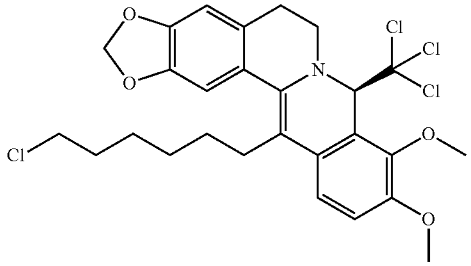
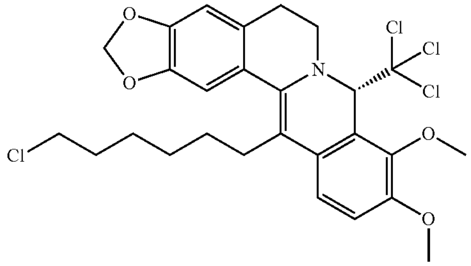
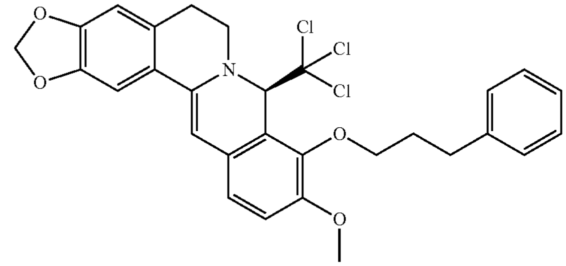
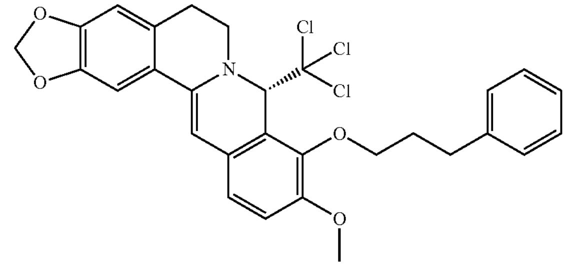
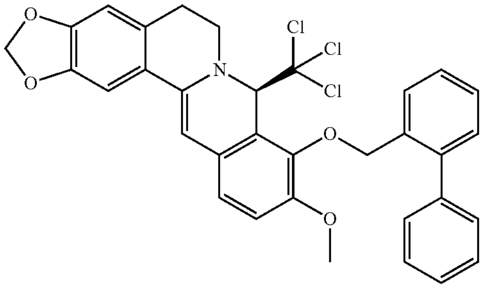
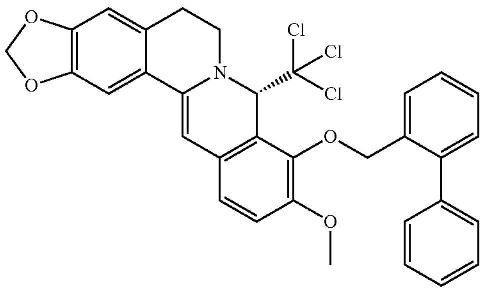
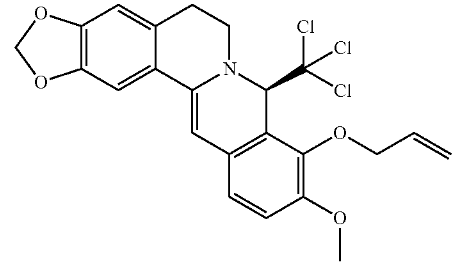
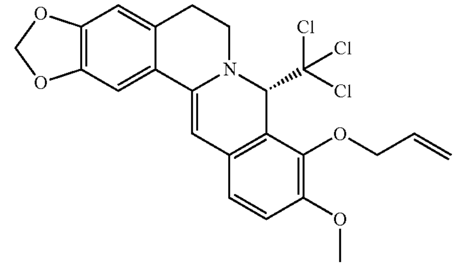
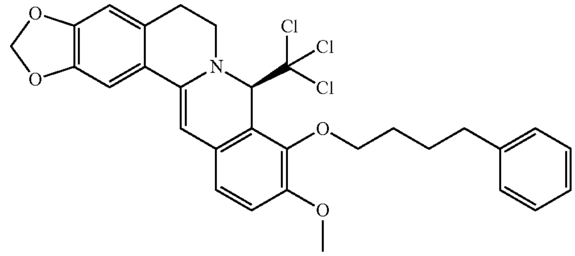
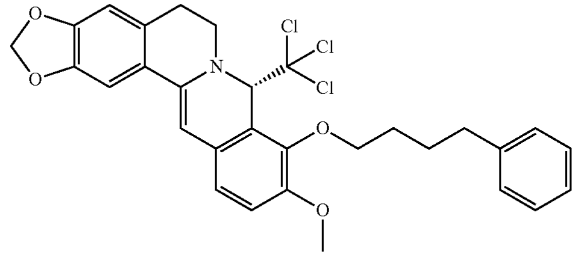
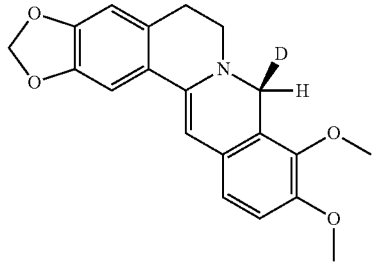

-continued
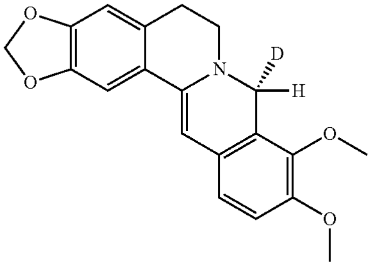
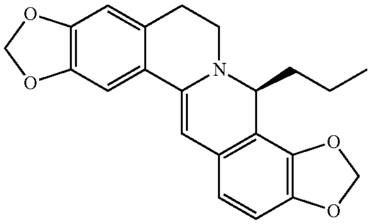
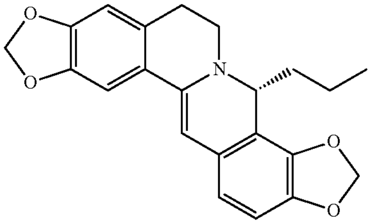
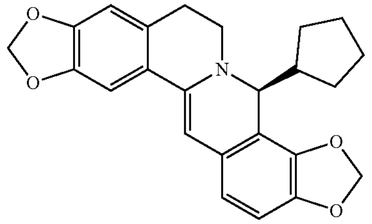
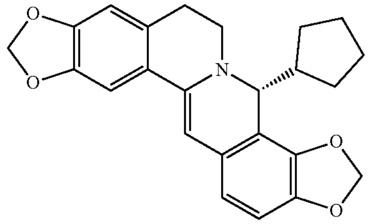
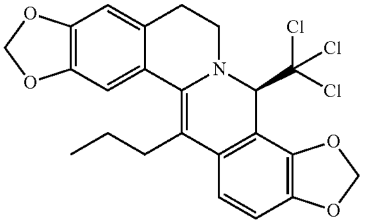
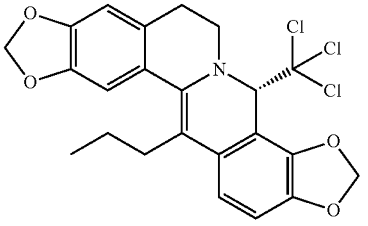
-continued
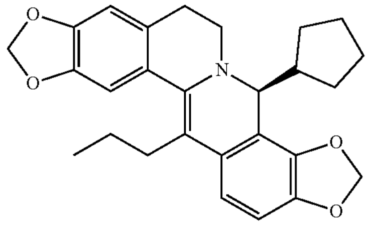
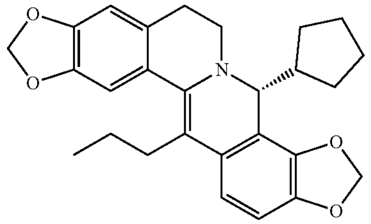
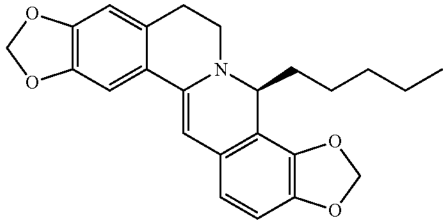
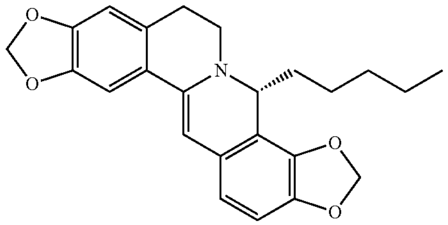
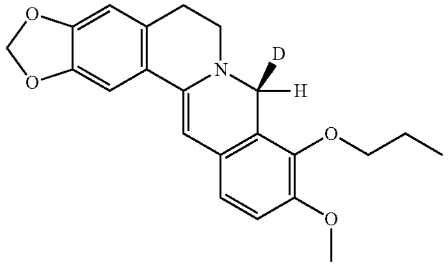
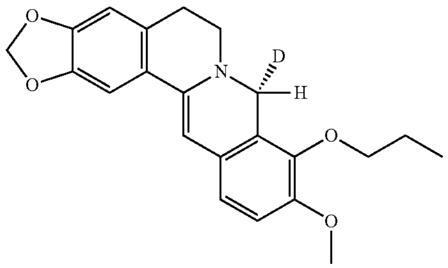
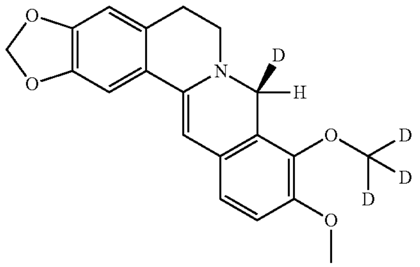

-continued
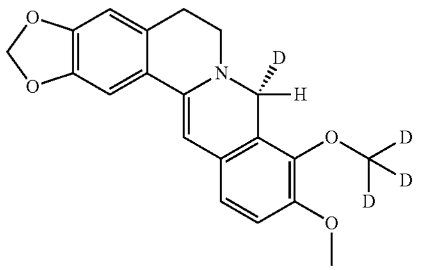
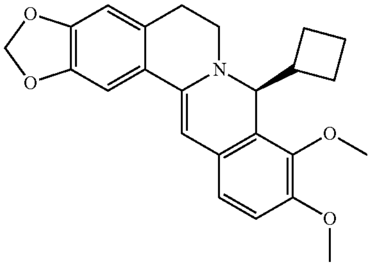
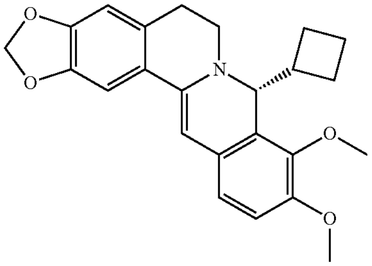
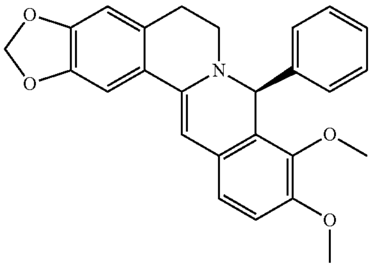
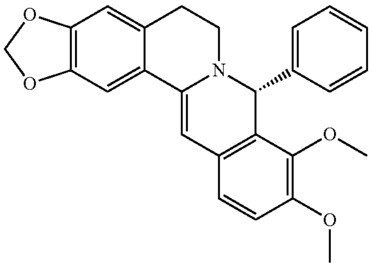
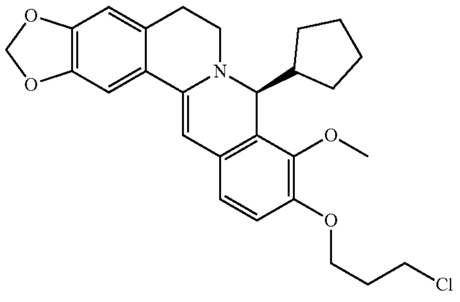
-continued
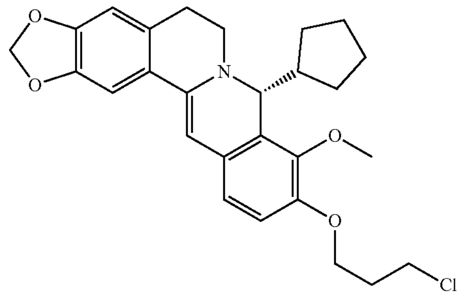
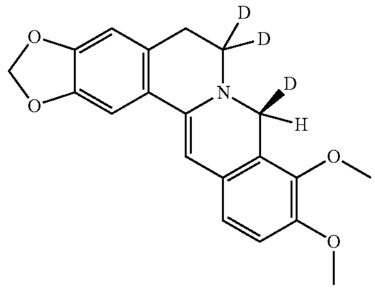
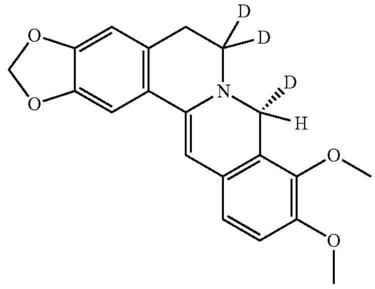
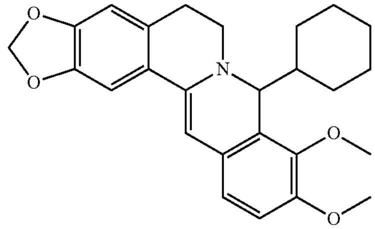
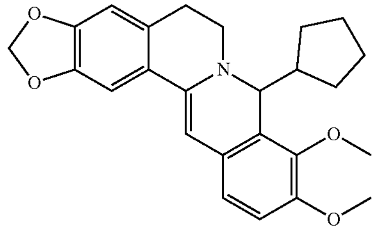
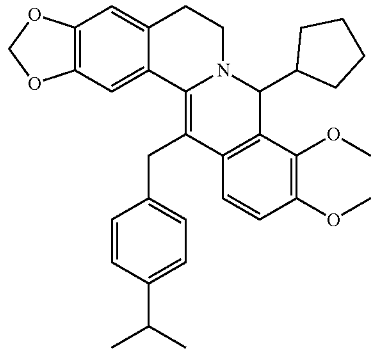

-continued
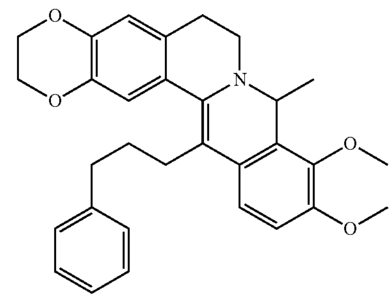
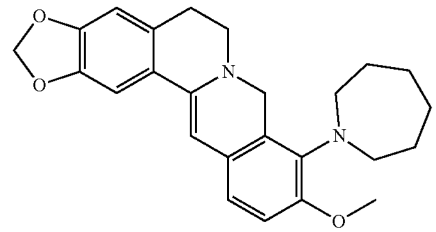
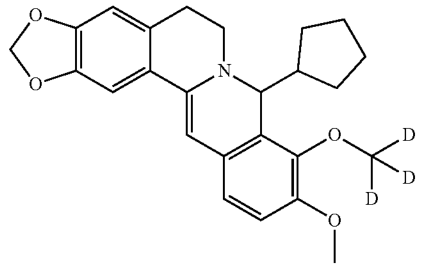
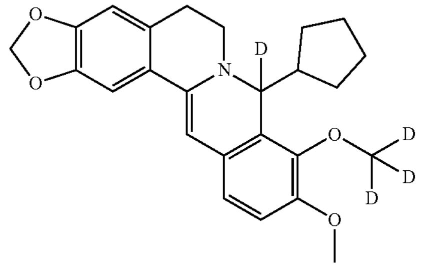
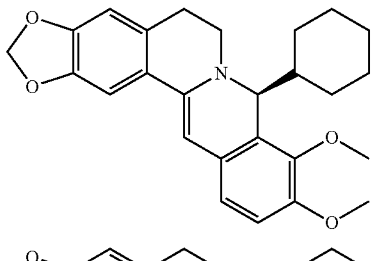
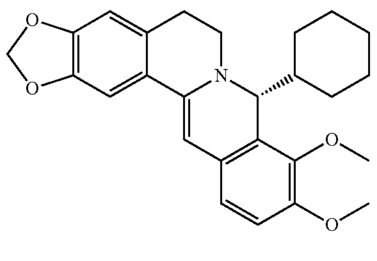
-continued
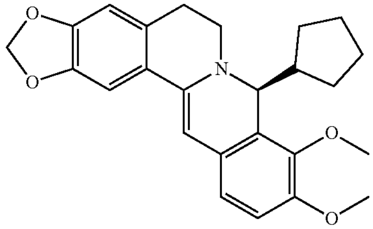
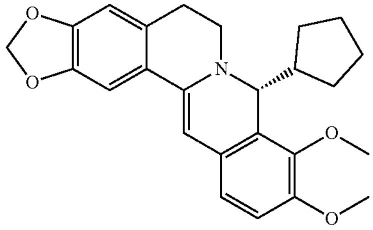
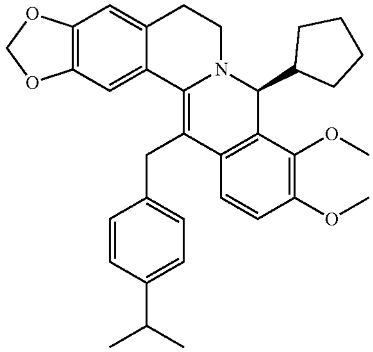
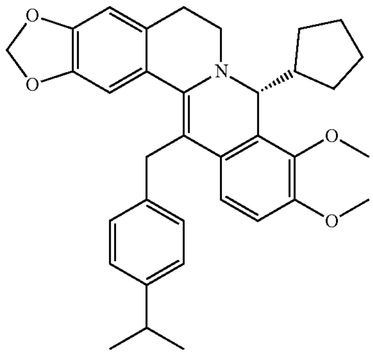
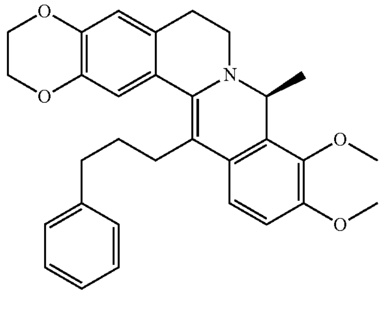

-continued

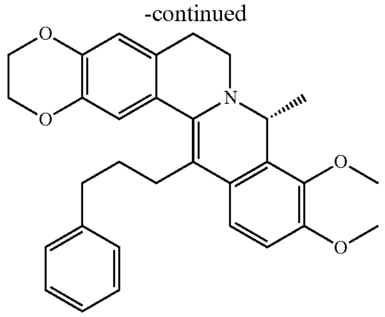

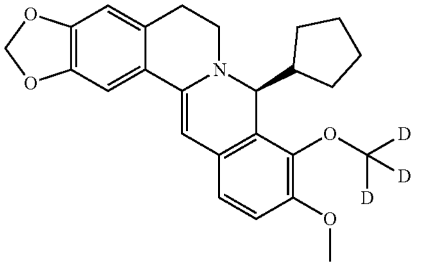

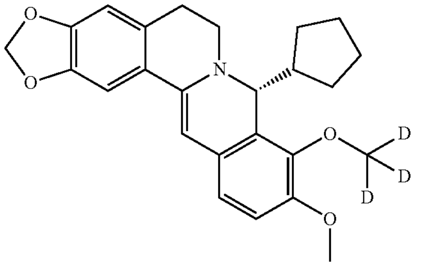

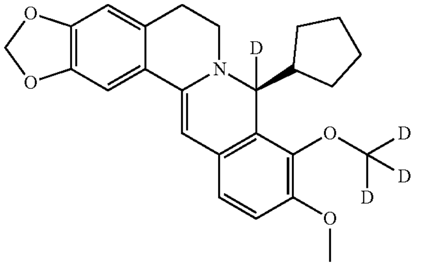

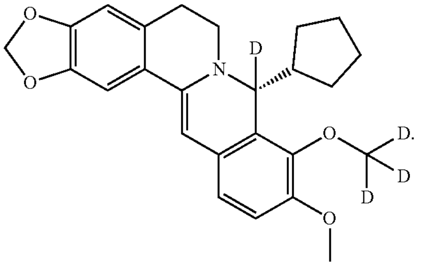

8. A composition, wherein the composition comprises (a) the compound of formula I, or an optical isomer thereof, or a racemate thereof, or a solvate thereof, or a pharmaceutically acceptable salt thereof, or a deuterated compound thereof of claim 1; and (b) a pharmaceutically acceptable carrier.

9. The composition of claim 8, wherein the composition is pharmaceutical composition;

the composition further comprises a pharmaceutically acceptable carrier;

the dosage form of the composition is a solid preparation, liquid preparation or semi-solid preparation; and/or the dosage form of the composition is oral preparation, external preparation or injection preparation.

10. A method for preventing and/or treating tumor, which comprises administering a compound of formula I, or an optical isomer thereof, or a racemate thereof, or a solvate thereof, or a pharmaceutically acceptable salt thereof, or a deuterated compound thereof of claim 1 to a subject in need.

11. The method of claim 10, wherein the tumor comprises tumor with low or no expression of NNMT gene; and/or the tumor comprises tumor with high expression of DNA methylase; and/or the tumor comprises tumor with high expression of UHRF1; and/or the tumor comprises tumor with high methylation level of nucleotide site of NNMT gene; and/or the tumor comprises tumor with high methylation level of DNA CpG site of NNMT gene.

12. The method of claim 11, wherein the NNMT gene is human NNMT gene;

the expression comprises protein expression and/or mRNA expression; and/or the DNA methylase is selected from the group consisting of DNMT1, DNMT3a, DNMT3b, and combinations thereof.

13. The method of claim 11, wherein the low or no expression of NNMT gene means the ratio (E1/E0) of the expression E1 of NNMT gene in the tumor cell to the expression E0 of NNMT gene in the same type of cell is <1.0;

the tumor with high expression of DNA methylase means the ratio (A1/A0) of the expression level Al of DNA methylase in the tumor cell to the expression level A0 of DNA methylase in the same type of cell is >1.0;

the tumor with high expression of UHRF1 means the ratio (F1/F0) of the expression level F1 of UHRF1 in the tumor cell to the expression level F0 of UHRF1 in the same type of cell is >1.0;

the high methylation level of nucleotide site of NNMT gene means the ratio (L1/L0) of the methylation level L1 of nucleotide site of NNMT gene in the tumor cell to the methylation level L0 of nucleotide site of NNMT gene in the same type of cell is >1.0; and/or the high methylation level of DNA CpG site of NNMT gene means the ratio (W1/W0) of the methylation level W1 of DNA CpG site of NNMT gene in the tumor cell to the methylation level W0 of DNA CpG site of NNMT gene in the same type of cell is >1.0.

14. The method of claim 13, wherein the same type of cell refers to the same type of tumor cell with normal or high expression of NNMT gene;

the same type of cell refers to the same type of tumor cell with normal or low expression of DNA methylase;

the same type of cell refers to the same type of tumor cell with normal or low expression of UHRF1;

the same type of cell refers to the same type of tumor cell with normal or low methylation level of nucleotide site of NNMT gene; and/or the same type of cell refers to the same type of tumor cell with normal or low methylation level of DNA CpG site of NNMT gene.

15. The method of claim 11, wherein the methylation level of nucleotide site of NNMT gene refers to the ratio of the number of methylated nucleotides to the number of all nucleotides in the NNMT gene;

the high methylation level of nucleotide site of NNMT gene means the methylation level of nucleotide site of NNMT gene in the tumor cell is ≥1%, the high methylation level of nucleotide site of NNMT gene means the methylation level (M %) of nucleotide site of NNMT gene in the tumor cell is ≥3% and ≤M1%, wherein M1 is any positive integer from 3 to 100;

the methylation level of nucleotide site of NNMT gene comprises the methylation level of nucleotide site in promoter region of NNMT gene;

the methylation level of nucleotide site of NNMT gene comprises the methylation level of nucleotide sites from 1050 bp before the transcription start site to 499 bp after the transcription start site in NNMT gene;

the methylation level of nucleotide site of NNMT gene comprises the methylation level of nucleotide sites from 1050 bp to 193 bp before the transcription start site in NNMT gene;

the methylation level of nucleotide site of NNMT gene comprises the methylation level of nucleotide sites from 840 bp to 469 bp before the transcription start site in NNMT gene;

the methylation level of nucleotide site of NNMT gene comprises the methylation level of nucleotide site between any two sites selected from group consisting of site 114165695, site 114165730, site 114165769, site 114165804, site 114165938, site 114166050 and site 114166066 on human chromosome 11;

the methylation level of nucleotide site of NNMT gene comprises the methylation level of nucleotide sites selected from group consisting of site 114165695 on human chromosome 11, site 114165730 on human chromosome 11, site 114165769 on human chromosome 11, site 114165804 on human chromosome 11, site 114165938 on human chromosome 11, site 114166050 on human chromosome 11, site 114166066 on human chromosome 11, and combinations thereof;

the methylation level of nucleotide site of NNMT gene comprises the methylation level of nucleotide site between any two sites selected from group consisting of site 1161, site 1196, site 1235, site 1270, site 1404, site 1516 and site 1532 in nucleotide sequence of SEQ ID NO: 1;

the methylation level of nucleotide site of NNMT gene comprises the methylation level of nucleotide site of one or more of site 1161, site 1196, site 1235, site 1270, site 1404, site 1516 and site 1532 in nucleotide sequence of SEQ ID NO: 1;

the methylation level of DNA CpG site of NNMT gene refers to the ratio of the number of methylated CpG nucleotides to the number of all nucleotides in the NNMT gene;

the methylation level of DNA CpG site of NNMT gene refers to the ratio of the number of methylated DNA CpG nucleotides to the number of all CpG nucleotides in the NNMT gene;

the high methylation level of DNA CpG site of NNMT gene means the methylation level of DNA CpG site of NNMT gene in the tumor cell is ≥1%;

the high methylation level of DNA CpG site of NNMT gene means the methylation level (M %) of DNA CpG site of NNMT gene in the tumor cell is ≥3% and ≤M2%, wherein M2 is any positive integer from 3 to 100;

the methylation level of DNA CpG site of NNMT gene comprises the methylation level of DNA CpG site in promoter region of NNMT gene;

the methylation level of DNA CpG site of NNMT gene comprises the methylation level of DNA CpG sites from 1050 bp before the transcription start site to 499 bp after the transcription start site in NNMT gene;

the methylation level of DNA CpG site of NNMT gene comprises the methylation level of the DNA CpG sites from 1050 bp to 193 bp before the transcription start site in NNMT gene;

the methylation level of DNA CpG site of NNMT gene comprises the methylation level of DNA CpG sites from 840 bp to 469 bp before the transcription start site in NNMT gene;

the methylation level of DNA CpG site of NNMT gene comprises the methylation level of DNA CpG site between any two sites selected from group consisting of site 114165695, site 114165730, site 114165769, site 114165804, site 114165938, site 114166050 and site 114166066 on human chromosome 11;

the methylation level of DNA CpG site of NNMT gene comprises the methylation level of sites selected from group consisting of site 114165695 on human chromosome 11, site 114165730 on human chromosome 11, site 114165769 on human chromosome 11, site 114165804 on human chromosome 11, site 114165938 on human chromosome 11, site 114166050 on human chromosome 11, site 114166066 on human chromosome 11, and combinations thereof;

the methylation level of DNA CpG site of NNMT gene comprises the methylation level of DNA CpG site between any two sites selected from group consisting of site 1161, site 1196, site 1235, site 1270, site 1404, site 1516 and site 1532 in nucleotide sequence of SEQ ID NO: 1; and/or the methylation level of DNA CpG site of NNMT gene comprises the methylation level of sites selected from group consisting of site 1161 in SEQ ID NO: 1, site 1196 in SEQ ID NO: 1, site 1235 in SEQ ID NO: 1, site 1270 in SEQ ID NO: 1, site 1404 in SEQ ID NO: 1, site 1516 in SEQ ID NO: 1, site 1532 in SEQ ID NO: 1, and combinations thereof.

16. The method of claim 15, wherein M1 is 5, 10, 15, 20, 25, 30, 35, 40, 45, 50, 55, 60, 65, 70, 80, 85, 90, 95 or 100;

M2 is 5, 10, 15, 20, 25, 30, 35, 40, 45, 50, 55, 60, 65, 70, 80, 85, 90, 95 or 100;

the nucleotide sequence of the promoter region of NNMT gene is as shown in SEQ ID NO: 1;

the sites from 1050 bp before the transcription start site to 499 bp after the transcription start site in NNMT gene is sites 951-2500 of nucleotide sequence as shown in SEQ ID NO: 1;

the sites from 1050 bp to 193 bp before the transcription start site in NNMT gene is sites 951-1808 of nucleotide sequence as shown in SEQ ID NO: 1; and/or the sites from 840 bp to 469 bp before the transcription start site in NNMT gene is sites 1161-1532 of nucleotide sequence as shown in SEQ ID NO: 1.

17. The method of claim 10, wherein the tumor is human tumor; and/or the tumor is selected from the group consisting of lung cancer, renal carcinoma, breast cancer, colon cancer, lymphoma, leukemia, pancreatic cancer, brain tumor, liver cancer, prostate cancer, and combinations thereof.

18. The method of claim 17, wherein the lung cancer is selected from the group consisting of non-small cell lung cancer, small cell lung cancer, and combinations thereof;

the colon cancer comprises colon adenocarcinoma;

the breast cancer comprises triple negative breast cancer;

the lymphoma is selected from the group consisting of B-cell lymphoma, skin T-cell lymphoma, and combinations thereof;

the brain tumor is selected from the group consisting of brain glioblastoma, neuroglioma, brain medulloblastoma, brain neuroblastoma, and combination thereof;

the renal carcinoma is selected from the group consisting of clear cell renal cell adenocarcinoma, renal carcinoma Wilms, and combination thereof;

the pancreatic cancer comprises pancreatic ductal carcinoma; and/or the leukemia is selected from the group consisting of T-lymphocyte leukemia, myeloid leukemia, and combinations thereof.

19. The method of claim 18, wherein the lymphoma comprises diffuse large B-cell lymphoma;

the brain medulloblastoma comprises cerebellar medulloblastoma;

the brain glioblastoma comprises glioblastoma multiforme;

the T-lymphocytic leukemia comprises acute T-lymphocytic leukemia;

the myeloid leukemia comprises type M4 of acute myeloid leukemia; and/or the myeloid leukemia comprises FAB type M4 of acute myeloid leukemia.

* * * * *

SEQUENCE LISTING

```
Sequence total quantity: 2
SEQ ID NO: 1           moltype = DNA  length = 2500
FEATURE                Location/Qualifiers
source                 1..2500
                       mol_type = other DNA
                       organism = synthetic construct
SEQUENCE: 1
tatccaagag ctatcagcac tcccatgttt attgtagcac tgttcacaat agccaagatt  60
tggaagtact ctaagtgtcc attagcagat gaatggataa agacaatgtg gtaatacaca  120
taatggagta ctattcagtc ataaagaaga attagatcct gtcatttgca ataacatgga  180
tggaactgga ggtcataatg ttgagtgaaa taaaccaggc acagaaagac aaactttgca  240
tgttctcact tatttatggg agctaaaaac taaaataact gaactcacag agatagagag  300
tagaaggatg gttacgagag gatgggaagg gtagcgaggt gggtaggggg gatgtgggga  360
tcattaatgg gtataaaaaa tagttagagg ccaggcgcag tggctcacgc ctgtaatccc  420
agcactttgg gaggccgagg taggcggaac acctgaggag ttcaagacca gcctggccaa  480
tatgatgaaa ccccgtctct actaaaaata caaaaattag ctgggcgtga tggtgtgcac  540
ctgtagtccc agctgcttgg gaggctgagg caggagaatc gctggaaccc aagaggtgaa  600
ggttgcagtg agctgagatc gcgtcactgc actccagcct gggtgacaga gtgagactcc  660
acatcaaaaa aaaaaaaaaa aagttagaaa gattgaataa gacctaatat ttgctagcac  720
aacagggtga atatagtaaa aaataattta tttgtacctt caaaaataac tagacaagta  780
taattgggtt gtttgtaaca cacaaaaaat aagtacttga agtggtggat accccattta  840
ccctgatgtg attattttgt attgcaggcc tctatcagaa tatctcatgt aacccataaa  900
tatatacacc tactctgtac ccacaaaaag tttttaaaaa gaaaaataaa tagcaaccga  960
aaaaaaaaga gagggagaaa agaaaaaaga aaaaaaaatc aagtgcctgg ctgggtagaa  1020
taaattctaa ggccacaatg ttactgacca tgggtttttt ggctctcagt gtatagaaat  1080
tgacacaagg ccaatagtct tcccaaacat gctttactgg aacttacgcc ctggcataag  1140
ggccacaaca aaagagagag cgaattctct ggcttgctga ctccttggaa aaaaccggta  1200
gggatttttt tattaggcaa agcacaggaa ttgacgtcag aggcaggatg tgctgctggg  1260
caaagcatac gagaagtggg gtatgcaggt cagcattact tggttgcaat ggttatcttg  1320
aggaatgggc caactggtgg tctggccagt ggcaacaagg ctgtaaatca attattcagc  1380
attccttccc aaggtgggac acccggcaac attgtttatc tcctaaggcc agttcctgga  1440
attaagtgaa aggatgacta atggacatgt tgtcagtgag gtagtggtgt gggttttgtg  1500
accagtggga atgcacgaaa gaatgcttta gcggggagtg agctgaagcc aagccccatc  1560
cctactctgt ctcaaagtga gttcagaaaa ggggatttaa agaattcttt tttttttttt  1620
tttttttttt gagacagagt cttgctctgt cgcccaggct ggagtgcagt ggcgccatct  1680
tggctcactg caagctccgc cccccgggtt catgccattc tcctgcctca gcctcccaag  1740
tagctgggac tgcaggtgcc taccaccaag cccagctaat tttttgtatt tttttttttag  1800
tagagacggg gtttcaccat gttagccagg atggtctcga tctcctgacc tcgtgatctg  1860
cccgccttag cctcccaaag tgctgggatt acaggcatga gcctccgccc ccggccttaa  1920
ataattctta aaggaagtaa agttaacttt gaaagaacta tcaggatttg gattgactga  1980
aaggagtggg gaagcttagg gaggaggtgc ttgccagaca ctgggtcatg gcagtggtcg  2040
gtgaagctgc agttgcctag ggcagggatg gagagagagt ctgggcatga ggagagggtc  2100
tcgggatgtt tggctggact agatttaca gaaagcctta tccaggcttt taaaattact  2160
ctttccagac ttcatctgag actccttctt cagccaacat tccttagccc tgaatacatt  2220
tcctatcctc atctttccct tctttttttt cctttctttt acatgtttaa atttaaacca  2280
ttcttcgtga cccctttct tgggagattc atggcaagaa cgagaagaat gatggtgctt  2340
gttaggggat gtcctgtctc tctgaacttt ggggtcctat gcattaaata attttcctga  2400
cgagctcaag tgctccctct ggtctacaat ccctggcggc tggccttcat cccttgggca  2460
agcattgcat acagctcatg gccctccctc taccataccc                        2500
```

-continued

```
SEQ ID NO: 2            moltype = DNA  length = 64
FEATURE                 Location/Qualifiers
source                  1..64
                        mol_type = other DNA
                        organism = synthetic construct
SEQUENCE: 2
gatccgggat gagtccatca aggaagattc aagagatctt ccttgatgga ctcatccttt  60
tttg                                                               64
```